(12) United States Patent
Lee et al.

(10) Patent No.: US 8,710,233 B2
(45) Date of Patent: Apr. 29, 2014

(54) VANILLOID RECEPTOR LIGANDS AND USE THEREOF FOR THE PRODUCTION OF PHARMACEUTICAL PREPARATIONS

(75) Inventors: Jeewoo Lee, Ansan-Si (KR); Hyung Chul Ryu, Ansan-Si (KR); Robert Frank, Aachen (DE); Gregor Bahrenberg, Aachen (DE); Jean De Vry, Stolberg (DE); Thomas Christoph, Aachen (DE); Derek John Saunders, Aachen (DE); Klaus Schiene, Düsseldorf (DE); Bernd Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/551,060

(22) Filed: Oct. 19, 2006

(65) Prior Publication Data
US 2007/0105861 A1 May 10, 2007

Related U.S. Application Data

(60) Provisional application No. 60/727,859, filed on Oct. 19, 2005.

(30) Foreign Application Priority Data

Oct. 19, 2005 (DE) .......................... 10 2005 050 408
Nov. 18, 2005 (DE) .......................... 10 2005 055 486

(51) Int. Cl.
*C07D 213/40* (2006.01)
*A61K 31/44* (2006.01)

(52) U.S. Cl.
USPC ............ 546/309; 546/337; 514/352; 514/357

(58) Field of Classification Search
USPC .......................... 514/357, 352; 546/309, 337
See application file for complete search history.

(56) References Cited

U.S. PATENT DOCUMENTS

| 6,821,992 B1 | 11/2004 | Cooke et al. |
| 2001/0037042 A1 | 11/2001 | Indolese et al. |
| 2007/0004772 A1 | 1/2007 | Sun et al. |
| 2007/0105861 A1 | 5/2007 | Lee et al. |

FOREIGN PATENT DOCUMENTS

| JP | 2004-506713 A | 3/2004 |
| WO | WO02/16318 A1 | 2/2002 |
| WO | WO 02/16318 A1 | 2/2002 |
| WO | WO 02/16319 A1 | 2/2002 |
| WO | WO 2005/003084 A1 | 1/2005 |
| WO | WO 2006/071940 | 7/2006 |
| WO | WO 2006/083673 A3 | 8/2006 |
| WO | WO2007/045462 A2 | 4/2007 |

OTHER PUBLICATIONS

Sigma-Aldrich website compound search, "https://www.sigmaaldrich.com/cgi-bin/hsrun/Suite7/Suite/HAHTpage/com. haht.escenario.foundation.SialUIHelperRunner.run" accessed Jun. 14, 2008.*
Dorwald F. A. Side Reactions in Organic Synthesis, 2005, Wiley: VCH, Weinheim p. IX of Preface p. 1-15.*
"Borane-dimethyl sulfide Complex (BDMS)" Product Bulletin BASF, 2005.*
Martin, Yvonne C. et. al. "Do Structurally Similar Molecules Have Similar Biological Activity?" Journal of Medicinal Chemistry 2002, 45, 4350-4358.*
Swanson et. al. "Identification and Biological Evaluation of 4-(3-Trifluoromethylpyridin-2-yl)piperazine-1-carboxylic Acid (5-Trifluoromethylpyridin-2-yl)amide, a High Affinity TRPV1 (VR1) Vanilloid Receptor Antagonist" Journal of Medicinal Chemistry 2005, 48, 1857-1872.*
West, Anthony R., Solid State Chemistry and its Applications, Wiley, New York, 1988, pp. 358 & 365.*
Alfonso R. Gennaro; "Remington's Pharmaceutical Science", Mack Publishing Company; 17$^{th}$ Edition, 1985 (Table of Contents).
Louis J. Ravin, PhD, "Preformulation", Chapter 76, pp. 1409-1423.
Anthony R. Disanto, PhD, "Bioavailability and Bioequivalency Testing", Chapter 77, pp. 1424-1431.
Adelbert M. Knevel, PhD, "Separation", Chapter 78, pp. 1432-1442.
G. Briggs Phillips, PhD, et al., "Sterilization", Chapter 79, pp. 1443-1454.
Frederick P. Siegel, PhD, "Tonicity, Osmoticity, Osmolality, and Osmolarity", Chapter 80, pp. 1455-1472.
Robert L. Giles, BA, et al., "Plastic Packaging Materials", Chapter 81, pp. 1473-1477.
Carl J. Lintner, PhD, "Stability of Pharmaceutical Products", Chapter 82, pp. 1478-1486.
Clyde R. Erskine, Jr., "Quality Assurance and Control", Chapter 83, pp. 1487-1491.
J. G. Nairn, PhD, "Solutions, Emulsions, Suspensions and Extractives", Chapter 84, pp. 1492-1517.
Kenneth E. Avis, DSc, "Parenteral Preparations", Chapter 85, pp. 1518-1541.
Salvatore J. Turco, PharmD, "Intravenous Admixtures", Chapter 86, pp. 1542-1552.
John D. Mullins, PhD, "Ophthalmic Preparations", Chapter 87, pp. 1553-1566.
Lawrence H. Block, PhD, "Medicated Applications", Chapter 88, pp. 1567-1584.
Edward G. Ripple, PhD, "Powders", Chapter 89, pp. 1585-1602.
Robert E. King, PhD, "Oral Solid Dosage Forms", Chapter 90, pp. 1603-1632.
Stuart C. Porter, PhD, "Coating of Pharmaceutical Dosage Forms", Chapter 91, pp. 1633-1643.
Mark A. Longer, et al., Sustained-Release Drug Delivery Systems, Chapter 92, pp. 1644-1661.
John J. Sclarra, PhD, et al., "Aerosols", Chapter 93, pp. 1662-1677.
Jeewoo Lee, et al., "Analysis of structure-activity relationships for the 'B-region' of N-(4-t-butylbenzyl)-N'-[4-(methylsulfonylamino)bensyl]-thiourea analogues as TRPV1 antagonists", Bioorganic & Medicinal Chemistry Letters, No. 15, 2005, pp. 4143-4150.
Yung-chi Cheng, et al, "Relationship Between the Inhibition Constant ($K_i$) and the Concentration of Inhibitor Which Causes 50 per cent Inhibition ($I_{50}$) of an Enzymatic Reaction", Biochemical Pharmacology, vol. 22, 1973, pp. 3099-3108.

(Continued)

*Primary Examiner* — David K O Dell
(74) *Attorney, Agent, or Firm* — Crowell & Moring LLP

(57) ABSTRACT

The present invention relates to novel vanilloid receptor ligands, to a process for the production thereof, to pharmaceutical preparations containing these compounds and to the use of these compounds for the production of pharmaceutical preparations.

22 Claims, No Drawings

(56) References Cited

OTHER PUBLICATIONS

L. C. Hendershot, et al., "Antagonism of the Frequency of Phenylquinone-Induced Writhing in the Mouse by Weak Analgesics and Nonanalgesics", J. Pharmacol. Exp. Ther., vol. 125, 1959, pp. 237-240.

David Dubuisson, et al., "The Formalin Test: A Quantitative Study of the Analgesic Effects of Morphine, Meperidine, and Brain Stem Stimulation in Rats and Cats", Pain, vol. 4, 1977, pp. 161-174.

Terence J. Coderre, et al., "Contribution of Central Neuroplasticity to pathological pain: review of clinical and experimental evidence", Pain, vol. 52, 1993, pp. 259-285.

Gary J. Bennett, et al., "A peripheral mononeuropathy in rat that produces disorders of pain sensation like those seen in man", Pain, No. 33, 1988, pp. 87-107.

Arnulf P. Hagen et al., "Reaction of Trifluoroacetic Acid with Alcohols, Phenols, Ethers, and Their Sulfur Analogues" J. Org. Chem. 1982, 47, pp. 1345-1347.

Elliot Bergman, "Decarbethoxylation of Perfuloracid Esters", J. Org. Chem., Mar. 23, 1958, vol. 23, pp. 476-477.

Otto Fischer et al. "Einwirkung von Phosphorpentachlorid auf N-Alkyl—Pyridone und—Chinolone" pp. 1307-1311.

Chrisopher G. Barber et al. "Selective Urokinase-Type Plasminogen Activator (uPA) Inhibitors. Part 1: 2-Pyridinyoluanidines" Biorganic & Medicinal Chemistry Letters 12, 2002, pp. 181-184.

Cover page of MX284520, published on Oct. 19, 2006 (one (1) page).

Laszlo E. Kiss et al., "Efficient Synthesis of 2-(Trifluoromethyl) nicotinic Acid Derivatives from Simple Fluorinated Precursors" Organic Letters, 2008 vol. 10, No. 9, pp. 1835-1837.

Gang Liu et al., "Aminopyridine carboxamides as c-Jun N-terminarl kinase inhibitors: Targeting the gatekeeper residue and beyond" Biorganic & Medicinal Chemistry Letters, 16, 2006, pp. 5723-5730.

Naomichi Furukawa et al., "Syntheses and Some Properties of Sulfoxides, Sulfilimines, Aminosulfonium Salts and Sulfoximines Containing Pyridine Nuclil Phosphorus and Sulfur" Jul. 1983, vol. 16, pp. 167-180.

John L. Kice et al., "The Effect of Ring Size on the Rate of Pyrolysis of Cycloalkyl Phenyl Sulfoxides", J. Org. Chem., May 1967, vol. 32, pp. 1631-1633.

Ernest L. Eliel et al., "The Stereochemistry and Reduction of the 1-Oxa-4-thia-8-t-butylspiro[4.5]decanes and -[5.5]undecanes", 1965, pp. 855-859.

Francesco Gasparrini et al., "A General Procedure for the Selectrive Oxidation of Sulfides to Sulfoxides by Nitric Acid: Tetrabromoaurate (III) Catalyst in a Biphasic System", J. Org. Chem, 55, 1990, pp. 1323-1334.

Peter Bakuzis et al., "Preparation of 1-(Phenylthio) cyclopentenes and 1-(Phenylthio) cyclohexenes by the Pummerer Reaction", J. Org. Chem., 50, 1985, pp. 2569-2573.

Teruo Umemoto et al., "Highly Selective Fluorinating Agents: A Counteranion-Bound N-Fluoropyridinium Salt System", J. Org. Chem., 60, 1995, pp. 6563-6570.

E. Besthorn und Bertha Geibelssrecht: Uber die, Apr. 1920, pp. 1017-1033.

Xiaohua Huang et al., "New Ammonia Equivalents for the Pd-Catalyzed Amination of Aryl Halides", Organic Letter, 2001, vol. 3, No. 21, pp. 3417-3419.

Ravin, "Preformulation,"Remington's Pharmaceutical Science, 1985, pp. 1409-1423 and 1418, Chapter 76, $17^{th}$ edition.

Disanto, "Bioavailability and Bioequivalency Testing," Remington's Pharmaceutical Science, 1985, pp. 1424-1431, Chapter 77, $17^{th}$ edition.

Knevel, "Separation," Remington's Pharmaceutical Science, 1985, pp. 1432-1442, Chapter 78, $17^{th}$ edition.

Phillips, "Sterilization," Remington's Pharmaceutical Science, 1985, pp. 1443-1454, Chapter 79, $17^{th}$ edition.

Siegel, "Tonicity, Osmoticity, Osmolality, and Osmolarity," Remington's Pharmaceutical Science, 1985, pp. 1455-1472, Chapter 80, $17^{th}$ edition.

Giles et al., "Plastic Packaging Materials," Remington's Pharmaceutical Science, 1985, pp. 1473-1477, Chapter 81, $17^{th}$ edition.

Lintner, "Stability of Pharmaceutical Products," Remington's Pharmaceutical Science, 1985, pp. 1478-1486, Chapter 82, $17^{th}$ edition.

Erskine, "Quality Assurance and Control, " Remington's Pharmaceutical Science, 1985, pp. 1487-1491, Chapter 83, $17^{th}$ edition.

Nairn, "Solutions, Emulsions, Suspensions and Extractives," Remington's Pharmaceutical Science, 1985, pp. 1492-1517, Chapter 84, $17^{th}$ edition.

Avis, "Parenteral Preparations," Remington's Pharmaceutical Science, 1985, pp. 1518-1541, Chapter 85, $17^{th}$ edition.

Turco, "Intravenous Admixtures," Remington's Pharmaceutical Science, 1985, pp. 1542-1552, Chapter 86, $17^{th}$ edition.

Mullins, "Ophthalmic Preparations," Remington's Pharmaceutical Science, 1985, pp. 1553-1566, Chapter 87, $17^{th}$ edition.

Block, "Medicated Applications," Remington's Pharmaceutical Science, 1985, pp. 1567-1584, Chapter 88, $17^{th}$ edition.

Ripple, "Powders," Remington's Pharmaceutical Science, 1985, pp. 1585-1602, Chapter 89, $17^{th}$ edition.

King, "Oral Solid Dosage Form," Remington's Pharmaceutical Science, 1985, pp. 1603-1632, Chapter 90, $17^{th}$ edition.

Porter, "Coating of Pharmaceutical Dosage Forms," Remington's Pharmaceutical Science, 1985, pp. 1633-1643, Chapter 91, $17^{th}$ edition.

Longer et al., "Sustained-Release Drug Delivery Systems," Remington's Pharmaceutical Science, 1985, pp. 1644-1661, Chapter 92, $17^{th}$ edition.

Sclarra et al., "AEROSOLS," Remington's Pharmaceutical Science, 1985, pp. 1662-1677, Chapter 93, $17^{th}$ edition.

Otto Fischer et al., "Einwirkung von Phosphorpentachlorid auf N-Alkyl-Pyridone und-Chinolone," Berichte der deutschen chemischen Gesellschaft, 1899, pp. 1307-1311, vol. 32, Issue 1.

* cited by examiner

VANILLOID RECEPTOR LIGANDS AND USE THEREOF FOR THE PRODUCTION OF PHARMACEUTICAL PREPARATIONS

The present invention relates to novel vanilloid receptor ligands, to a process for the production thereof, to pharmaceutical preparations containing these compounds and to the use of these compounds for the production of pharmaceutical preparations.

The treatment of pain, in particular of neuropathic pain, is of great significance in medicine. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

One suitable approach to the treatment of pain, in particular pain selected from the group consisting of acute pain, chronic pain, neuropathic pain and visceral pain, particularly preferably of neuropathic pain, is the vanilloid receptor subtype 1 (VR1/TRPV1), which is also frequently known as the capsaicin receptor. This receptor is stimulated inter alia by vanilloids such as for example capsaicin, heat and protons and plays a central role in the genesis of pain. It is furthermore of significance to numerous other physiological and pathophysiological processes, such as for example migraine; depression; neurodegenerative diseases; cognitive disorders; anxiety states; epilepsy; coughing; diarrhea; pruritus; inflammation; disorders of the cardiovascular system; disorders of food intake; dependency on medicines; abuse of medicines and in particular urinary incontinence.

One object of the present invention was accordingly to provide novel compounds which are in particular suitable as pharmacological active ingredients in pharmaceutical preparations, preferably in pharmaceutical preparations for the treatment of disorders or diseases which are at least in part mediated by vanilloid receptors 1 (VR1/TRPV1 receptors).

It has surprisingly now been found that the substituted compounds of the general formula I stated below exhibit excellent affinity for the vanilloid receptor subtype 1 (VR1/TRPV1 receptor) and are thus in particular suitable for the prevention and/or treatment of disorders or diseases which at least in part mediated by vanilloid receptors 1 (VR1/TRPV1). The substituted compounds of the general formulae A and I stated below also have an anti-inflammatory activity.

The present invention accordingly provides compounds of the general formula A,

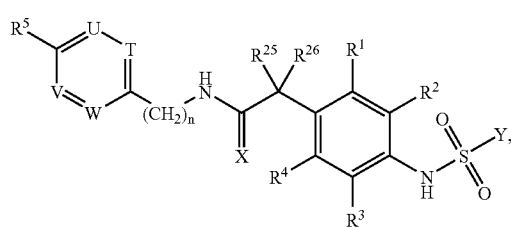

in which
X denotes O, S or N—C≡N;
Y denotes —NH$_2$; —NHR$^{30}$; —NR$^{31}$R$^{32}$ or denote a linear or branched, saturated or unsaturated, unsubstituted or at least monosubstituted aliphatic C$_{1-10}$ residue;
n denotes 0, 1, 2, 3 or 4;

R$^1$, R$^2$, R$^3$ and R$^4$, mutually independently, in each case denote H; F; Cl; Br; I; —SF$_5$; —NO$_2$; —CF$_3$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{24}$; —S(=O)$_2$—R$^{24}$ or denote a linear or branched, saturated or unsaturated, unsubstituted or at least monosubstituted aliphatic C$_{1-10}$ residue;

R$^5$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$—R$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$—C(=O)—OR$^{22}$; —C(=O)—R$^{23}$; —S(=O)$_2$—R$^{24}$; —S(=O)—R$^{24}$;

denotes a linear or branched, unsaturated or saturated, unsubstituted or at least monosubstituted aliphatic C$_{1-10}$ residue;

or denotes an unsaturated or saturated, unsubstituted or at least monosubstituted 3-, 4-, 5-, 6-, 7-, 8- or 9-membered cycloaliphatic residue, optionally comprising at least one heteroatom as a ring member, which residue is in each case attached to the parent structure via a carbon atom in the ring of the cycloaliphatic residue;

T denotes C—R$^6$ and U denotes C—R$^7$ and V denotes N and W denotes C—R$^8$
or
T denotes C—R$^6$ and U denotes N and V denotes C—R$^9$ and W denotes C—R$^8$
or
T denotes N and U denotes C—R$^7$ and V denotes C—R$^9$ and W denotes C—R$^8$
or
T denotes N and U denotes N and V denotes C—R$^9$ and W denotes C—R$^8$
or
T denotes N and U denotes C—R$^7$ and V denotes N and W denotes C—R$^8$
or
T denotes C—R$^6$ and U denotes N and V denotes N and W denotes C—R$^8$
or
T denotes C—R$^6$ and U denotes C—R$^7$ and V denotes C—R$^9$ and W denotes C—R$^{10}$;

R$^6$ and R$^7$, mutually independently, in each case denote H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$, —S(=O)$_2$—R$^{24}$; —S(=O)$_2$—R$^{24}$; or denote a linear or branched, saturated or unsaturated, unsubstituted or at least monosubstituted aliphatic C$_{1-10}$ residue;

or denote an unsubstituted or at least monosubstituted 6- or 10-membered aryl residue, which may be attached via a linear or branched, substituted or at least monosubstituted C$_{1-6}$ alkylene group or C$_{2-6}$ alkenylene group or C$_{2-6}$ alkynylene group;

R$^8$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$;

—C(=O)—OR$^{22}$; —C(=O)—R$^{23}$; —S(=O)—R$^{24}$; —S(=O)$_2$—R$^{24}$; —C(=NH)—NH$_2$; —C(=NH)—NH—R$^{27}$; —N=C(NH$_2$)$_2$; —N=C(NHR$^{28}$)(NHR$^{29}$);

denotes a linear or branched, saturated or unsaturated, unsubstituted or at least monosubstituted aliphatic C$_{1-10}$ residue;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

R$^9$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$NHR$^{19}$; —S(=O)$_2$—NR$^{20}$R$^{21}$; —C(=O)—OR$^{22}$; —C(=O)—R$^{23}$; —S(=O)—R$^{24}$; —S(=O)$_2$—R$^{24}$ or denotes a linear or branched, saturated or unsaturated, unsubstituted or at least monosubstituted aliphatic C$_{1-10}$ residue;

R$^{10}$ denotes —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$—C(=O)—R$^{23}$; —S(=O)—R$^{24}$; —S(=O)$_2$—R$^{24}$; —C(=NH)—NH$_2$; —C(=NH)—NH—R$^{27}$; —N=C(NH$_2$)$_2$; —N=C(NHR$^{28}$)(NHR$^{29}$);

denotes a linear or branched, saturated or unsaturated aliphatic C$_{1-10}$ residue, which is in each case substituted with optionally 1, 2, 3, 4, 5, 6, 7, 8 or 9 substituents mutually independently selected from the group consisting of —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$ and —SCF$_3$;

denotes an unsubstituted C$_{2-10}$ alkenyle residue or an unsubstituted C$_{2-10}$ alkynyle residue;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted C$_{1-6}$ alkylene group;

or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group;

R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{27}$, R$^{28}$ and R$^{29}$, mutually independently, in each case denote a linear or branched, saturated or unsaturated, unsubstituted or at least monosubstituted aliphatic C$_{1-10}$ residue;

denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be fused with a saturated or unsaturated, unsubstituted or at least monosubstituted mono- or polycyclic ring system and/or be attached via a linear or branched, unsubstituted or at least monosubstituted C$_{1-6}$ alkylene group or 2- to 6-membered heteroalkylene group;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or 2- to 6-membered heteroalkylene group;

or

R$^{12}$ and R$^{13}$, in each case together with the nitrogen atom joining them together as a ring member, form a saturated or unsaturated, unsubstituted or at least monosubstituted 4-, 5-, 6-, 7-, 8- or 9-membered heterocycloaliphatic residue, optionally comprising at least one further heteroatom as ring member, which may be fused with a saturated or unsaturated, unsubstituted or at least monosubstituted mono- or polycyclic ring system;

and

R$^{25}$ and R$^{26}$, mutually independently, in each case denote a hydrogen residue;

denote a linear or branched, saturated or unsaturated, unsubstituted or at least monosubstituted aliphatic C$_{1-10}$ residue;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

or denote an unsaturated or saturated, unsubstituted or at least monosubstituted, 3-, 4-, 5-, 6-, 7-, 8- or 9-membered cycloaliphatic residue optionally comprising at least one heteroatom as a ring member;

providing that R$^{25}$ and R$^{26}$ do not in each case denote a hydrogen residue;

or

R$^{25}$ and R$^{26}$, together with the carbon atom joining them together as a ring member, form a saturated or unsaturated, unsubstituted or at least monosubstituted 3-, 4-, 5- or 6-membered cycloaliphatic residue;

and R$^{30}$, R$^{31}$ and R$^{32}$, mutually independently, in each case denote a linear or branched, saturated or unsaturated, unsubstituted or at least monosubstituted aliphatic C$_{1-10}$ residue;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Unless otherwise stated, the above-stated aliphatic $C_{1-10}$ residues may preferably optionally in each case be substituted with 1, 2, 3, 4, 5, 6, 7, 8 or 9 substituents mutually independently selected from the group consisting of —C(=O)—O—$C_{1-5}$-alkyl, —O—C(=O)—$C_{1-5}$-alkyl, —O-phenyl, phenyl, F, Cl, Br, I, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —$OCF_3$ and —$SCF_3$.

The above-stated $C_{1-6}$ alkylene groups, $C_{2-6}$ alkenylene groups and $C_{2-6}$ alkynylene groups may preferably optionally in each case be substituted with 1, 2, 3, 4, 5, 6, 7, 8 or 9 substituents mutually independently selected from the group consisting of F, Cl, Br, I, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —$OCF_3$ and —$SCF_3$.

The term "heteroalkylene" denotes an alkylene group as stated above, wherein one or more carbon atoms are in each case replaced by a heteroatom mutually independently selected from the group consisting of oxygen, sulfur and nitrogen (NH). Heteroalkylene groups may preferably comprise 1, 2 or 3 heteroatom(s), more preferably one heteroatom, mutually independently selected from the group consisting of oxygen, sulfur and nitrogen (NH). Heteroalkylene groups may preferably be 2- to 6-membered, more preferably 2- or 3-membered. —$CH_2$—$CH_2$—O—$CH_2$—, —$CH_2$—CH($CH_3$)—O—$CH_2$—, —($CH_2$)—O—, —($CH_2$)$_2$—O—, —($CH_2$)$_3$—O—, —($CH_2$)$_4$—O—, —O—($CH_2$)—, —O—($CH_2$)$_2$—, —O—($CH_2$)$_3$—, —O—($CH_2$)$_4$—, —C($C_2H_5$)(H)—O—, —O—C($C_2H_5$)(H)—, —$CH_2$—O—$CH_2$—, —$CH_2$—S—$CH_2$—, —$CH_2$—NH—$CH_2$—, —$CH_2$—NH— and —$CH_2$—$CH_2$—NH—$CH_2$—$CH_2$ may be mentioned by way of example of heteroalkylene groups.

2- to 6-membered heteroalkylene groups may preferably optionally in each case be substituted with 1, 2, 3, 4, 5, 6, 7, 8 or 9 substituents mutually independently selected from the group consisting of F, Cl, Br, I, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —$OCF_3$ and —$SCF_3$.

The above-stated (hetero)cycloaliphatic residues may preferably optionally in each case be substituted with 1, 2, 3, 4 or 5 substituents mutually independently selected from the group consisting of —$C_{1-6}$-alkylene-OH, =$CH_2$, —O—$C_{1-5}$-alkylene-oxetanyl, —$C_{1-5}$-alkylene-O—$C_{1-5}$-alkylene-oxetanyl, —$CH_2$—NH—$C_{1-5}$-alkyl, —$CH_2$—N($C_{1-5}$-alkyl)$_2$, —N[C(=O)—$C_{1-5}$-alkyl]-phenyl, —$CH_2$—O—$C_{1-5}$-alkyl, oxo (=O), thioxo (=S), F, Cl, Br, I, —CN, —$CF_3$, —$SF_5$, —OH, —O—$C_{1-5}$-alkyl, —O—C(=O)—$C_{1-5}$-alkyl, —$NH_2$, —$NO_2$, —O—$CF_3$, —S—$CF_3$, —SH, —S—$C_{1-5}$-alkyl, —$C_{1-5}$-alkyl, —C(=O)—$C_{1-5}$-alkyl, —C(=O)—OH, —C(=O)—O—$C_{1-5}$alkly, —NH—$C_{1-5}$-alkyl, —N($C_{1-5}$-alkyl)$_2$, (4,5)-dihydroisoxazolyl, thiazolyl, (1,2,5)-thiadiazolyl, thiophenyl, phenethyl, —NH-phenyl, —N($C_{1-5}$-alkyl)-phenyl, cyclohexyl, cyclopentyl, piperidinyl, pyrrolidinyl, —($CH_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N[C(=O)—$C_{1-5}$-alkyl]-phenyl, —NH-phenyl, —N($C_{1-5}$-alkyl)-phenyl, —($CH_2$)-pyridinyl, pyridinyl, —O-phenyl, O-benzyl, phenyl and benzyl may optionally be substituted with 1, 2, 3, 4 or 5 substituents mutually independently selected from the group consisting of F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

The above-stated (hetero)cycloaliphatic residues may likewise preferably in each case optionally comprise 1, 2 or 3 (further) heteroatom(s) mutually independently selected from the group consisting of oxygen, nitrogen and sulfur.

The rings of the above-stated mono- or polycyclic ring systems may preferably optionally in each case be substituted with 1, 2, 3, 4 or 5 substituents mutually independently selected from the group consisting of oxo (=O), thioxo (=S), F, Cl, Br, I, —CN, —$CF_3$, —$SF_5$, —OH, —O—$C_{1-5}$-alkyl, —$NH_2$, —$NO_2$, —O—$CF_3$, —S—$CF_3$, —SH, —S—$C_{1-5}$-alkyl, —$C_{1-5}$-alkyl, —C(=O)—$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

The rings of the above-stated mono- or polycyclic ring systems are preferably in each case 5-, 6- or 7-membered and may in each case optionally comprise 1, 2, 3, 4 or 5 heteroatom(s) as ring member(s), which are mutually independently selected from the group consisting of oxygen, nitrogen and sulfur.

The above-stated aryl or heteroaryl residues may likewise preferably optionally in each case be substituted with 1, 2, 3, 4 or 5 substituents mutually independently selected from the group consisting of F, Cl, Br, I, —CN, —$CF_3$, —$SF_5$, —OH, —O—$C_{1-5}$-alkyl, —$NH_2$, —$NO_2$, —O—$CF_3$, —S—$CF_3$, —SH, —S—$C_{1-5}$-alkyl, —$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —NH—S(=O)$_2$—$C_{1-5}$-alkyl, —NH—C(=O)—O—$C_{1-5}$-alkyl, —C(=O)—H, —C(=O)—$C_{1-5}$-alkyl, —C(=O)—$NH_2$, —C(=O)—NH—$C_{1-5}$-alkyl, —C(=O)—N—($C_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

The above-stated heteroaryl residues likewise preferably in each case optionally comprise 1, 2, 3, 4 or 5 heteroatom(s) mutually independently selected from the group consisting of oxygen, nitrogen and sulfur as ring member(s).

If one or more of the above-stated residues denotes a saturated or unsaturated $C_{1-10}$ aliphatic residue, i.e. a $C_{10}$ alkyl, $C_{2-10}$ alkenyl or $C_{2-10}$ alkynyl residue, the latter may preferably be substituted with optionally 1, 2, 3, 4, 5, 6, 7, 8 or 9 substituents mutually independently selected from the group consisting of —O-phenyl, F, Cl, Br, I, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —C(=O)—O—$C_{1-5}$-alkyl, —$OCF_3$ and —$SCF_3$. $C_{2-10}$ alkenyl residues comprise at least one, preferably 1, 2, 3 or 4 C—C double bonds and $C_{2-10}$ alkynyl residues comprise at least one, preferably 1, 2, 3 or 4 C—C triple bonds.

alkyl residues are preferably selected from the group consisting of methyl, ethyl, n-propyl, isopropyl, n-butyl, sec-butyl, isobutyl, tert-butyl, n-pentyl, 3-methyl-but-1-yl, 2-pentyl, 3-pentyl, sec-pentyl, neo-pentyl, 4-methyl-pent-1-yl, (3,3)-dimethyl-but-1-yl, n-hexyl, n-heptyl, 2-heptyl, 3-heptyl, 4-heptyl, n-octyl, n-nonyl, 2-nonyl, 3-nonyl, 4-nonyl, 5-nonyl and (2,6)-dimethyl-hept-4-yl, which may optionally be substituted in each case with 1, 2, 3, 4, 5, 6, 7, 8 or 9 substituents mutually independently selected from the group consisting of —O-phenyl, —O—C(=O)—CH$_3$, —O—C(=O)—C$_2$H$_5$, —O—C(=O)—CH(CH$_3$)$_2$, —O—C(=O)—C(CH$_3$)$_3$, —C(=O)—O—CH$_3$, —C(=O)—O—C$_2$H$_5$, —C(=O)—O—CH(CH$_3$)$_2$, —C(=O)—O—C(CH$_3$)$_3$, F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Alkenyl residues which are likewise preferred are those selected from the group consisting of vinyl, 1-propenyl, 2-propenyl, 1-butenyl, 2-butenyl, 3-butenyl, 2-methyl-propen-1-yl, 3-methyl-but-2-en-1-yl, (3,3)-dimethyl-but-1-enyl, 2-methyl-buten-2-yl, 1-pentenyl, 2-pentenyl, 3-pentenyl, 4-pentenyl, 1-hexenyl, 1-heptenyl and 1-octenyl, which may optionally be substituted in each case with 1, 2 or 3 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Alkynyl residues which are furthermore preferred are those selected from the group consisting of (3,3)-dimethyl-but-1-ynyl, 4-methyl-pent-1-ynyl, 1-hexynyl, ethynyl, 1-propynyl, 2-propynyl, 1-butynyl, 2-butynyl, 3-butynyl, 1-pentynyl, 2-pentynyl, 3-pentynyl and 4-pentynyl, which may optionally be substituted in each case with 1, 2 or 3 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Particularly preferred optionally substituted C$_{1-10}$ aliphatic residues are those selected from the group consisting of methyl, —CF$_3$, —CHF$_2$, —CH$_2$F, —CF$_2$Cl, —CCl$_2$F, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CF$_2$—CH$_3$, —CHF—CF$_2$Cl, —CF$_2$—CFCl$_2$, —CFCl—CF$_2$Cl, —CFCl—CFCl$_2$, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$(C$_2$H$_5$)), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, —CH$_2$—CH$_2$—CH$_2$—CF$_3$, —CH$_2$—CH$_2$—CH$_2$—CH$_2$—CF$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, —CH$_2$—C(=O)—O—CH$_3$, —CH$_2$—C(=O)—O—C$_2$H$_5$, —CH$_2$—C(=O)—O—C(CH$_3$)$_3$, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, sec-butyl, isobutyl, tert-butyl, n-pentyl, sec-pentyl, neo-pentyl, n-hexyl, vinyl, 1-propenyl, 2-propenyl, 1-butenyl, 2-butenyl, 3-butenyl, 2-methyl-buten-2-yl, (1,1,2)-trifluor-1-butenyl, 1-pentenyl, 2-pentenyl, 3-pentenyl, 4-pentenyl, —CF=CF$_2$, —CCl=CCl$_2$, —CH$_2$—CF=CF$_2$, —CH$_2$—CCl=CCl$_2$, —C≡C—I, —C≡C—F and —C≡C—Cl.

If one or more of the above-stated substituents denotes a (hetero)cycloaliphatic residue, which may optionally be fused with a saturated or unsaturated, unsubstituted or at least monosubstituted mono- or polycyclic ring system, the latter may preferably be selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, (1,2,3,6)-tetrahydropyridinyl, azepanyl, azocanyl, diazepanyl, dithiolanyl, (1,3,4,5)-tetrahydropyrido[4,3-b]indolyl, (3,4)-dihydro-1H-isochinolinyl, (1,3,4,9)-tetrahydro-[b]-carbolinyl and (1,3)-thiazolidinyl.

(4,5,6,7)-tetrahydroisoxazolo[5,4-c]pyridinyl, (2,3)-dihydro-1H-indenyl, 3-aza-bicyclo[3.1.1]heptyl, 3-aza-bicyclo[3.2.1]octyl, 6-aza-bicyclo[3.3.1]heptyl, 8-aza-bicyclo[3.2.1]octyl, isoindolyl, indolyl, (1,2,3,4)-tetrahydrochinolinyl, (1,2,3,4)-tetrahydroisochinolinyl, (2,3)-dihydro-1H-isoindolyl, (1,2,3,4)-tetrahydronaphthyl, (2,3)-dihydro-benzo[1.4]dioxinyl, benzo[1.3]dioxolyl, (1,4)-benzodioxanyl, (2,3)-dihydrothieno[3,4-b][1,4]dioxinyl, (3,4)-dihydro-2H-benzo[1.4]oxazinyl, octahydro-1H-isoindolyl and octahydro-pyrrolo[3,4-c]pyrrolyl may be mentioned by way of example of unsubstituted or at least monosubstituted (hetero)cycloaliphatic residues which are fused with a saturated or unsaturated, unsubstituted or at least monosubstituted mono- or polycyclic ring system.

According to the present invention (hetero)cycloaliphatic residues can form a spirocyclic residue together with a further (hetero)cycloaliphatic residue via a common carbon atom in both rings.

6-aza-spiro[2.5]octyl, 8-azaspiro[4.5]decyl and 1-oxa-2,8-diaza-spiro[4.5]dec-2-enyl may be mentioned by way of example of spirocyclic residue.

The (hetero)cycloaliphatic residues may particularly preferably optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —CH$_2$—OH, —CH$_2$—CH$_2$—OH, =CH$_2$, —CH$_2$—O—CH$_2$-oxetanyl, —O—CH$_2$—oxetanyl, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH-phenyl, —N(CH$_3$)-phenyl, —N(C$_2$H$_5$)-phenyl, —N(C$_2$H$_5$)-phenyl, —O—CH$_2$—CH$_2$—CH$_2$—CH$_3$, (4,5)-dihydroisoxazolyl, thiazolyl, (1,2,5)-thiadiazolyl, thiophenyl, phenethyl, cyclohexyl, cyclopentyl, piperidinyl, pyrrolidinyl, —O—C(=O)—CH$_3$, —O—C(=O)—C$_2$H$_5$, —O—C(=O)—C(CH$_3$)$_3$, —(CH$_2$)- pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—$C_2H_5$]-phenyl, —N—[C(=O)—$CH_3$]-phenyl, —NH-phenyl, —N($CH_3$)-phenyl, —N($C_2H_5$)-phenyl, —($CH_2$)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—$CH(CH_3)_2$, —O—$C(CH_3)_3$, —O—$CF_3$, —S—$CF_3$, phenyl and —O-benzyl.

If one or more of the above-stated substituents denotes an aryl residue, the latter may preferably be selected from the group consisting of phenyl and naphthyl (1-naphthyl and 2-naphthyl).

If one or more of the above-stated substituents denotes a heteroaryl residue, the latter may preferably be selected from the group consisting of tetrazolyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, chinoxalinyl, chinolinyl and isochinolinyl.

isoindolyl, indolyl, (1,2,3,4)-tetrahydrochinolinyl, (1,2,3,4)-tetrahydroisochinolinyl, (2,3)-dihydro-1H-isoindolyl, (1,2,3,4)-tetrahydronaphthyl, (2,3)-dihydro-benzo[1.4]dioxinyl, (2,3)-dihydrothieno[3,4-b][1,4]dioxinyl, benzo[1.3]dioxolyl and (1,4)-benzodioxanyl may be mentioned by way of example of unsubstituted or at least monosubstituted aryl and heteroaryl residues which are fused with a saturated or unsaturated, unsubstituted or at least monosubstituted mono- or polycyclic ring system.

The aryl or heteroaryl residues may particularly preferably optionally in each case be substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —O—$CH(CH_3)_2$, —O—$C(CH_3)_3$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl, tert-butyl, n-pentyl, —C(=O)—OH, —C(=O)—O—$CH_3$, —C(=O)—O—$C_2H_5$, —C(=O)—O—$CH(CH_3)_2$, —C(=O)—O—$C(CH_3)_3$, —NH—$CH_3$, —NH—$C_2H_5$, —NH—$C(CH_3)_3$, —N($CH_3)_2$, —N($C_2H_5)_2$, —N($CH_3$)($CH_2H_5$), —NH—S(=O)$_2$—$CH_3$, —NH—S(=O$_2$)—$C_2H_5$, —NH—S(=O)$_2$—$CH(CH_3)_2$, —NH—C(=O)—O—$CH_3$, —NH—C(=O)—O—$C_2H_5$, —NH—C(=O)—O—$C(CH_3)_3$, —C(=O)—H, —C(=O)—$CH_3$, —C(=O)—$C_2H_5$, —C(=O)—$CH(CH_3)_2$, —C(=O)—$C(CH_3)_3$, —C(=O)—$NH_2$, —C(=O)—NH—$CH_3$, —C(=O)—NH—$C_2H_5$, —C(=O)—N($CH_3)_2$, —C(=O)—N($C_2H_5)_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

For the purposes of the present invention, a mono- or polycyclic ring system is taken to comprise mono- or polycyclic hydrocarbon residues which may be saturated or unsaturated and may optionally comprise 1, 2, 3, 4 or 5 heteroatom(s) as ring member(s), which are mutually independently selected from the group consisting of oxygen, nitrogen and sulfur. Such a mono- or polycyclic ring system may, for example, be fused (anellated) with an aryl residue or a heteroaryl residue.

If a polycyclic ring system, such as for example a bicyclic ring system, is present, the various rings may in each case mutually independently be of a different degree of saturation, i.e. be saturated or unsaturated. A polycyclic ring system is preferably a bicyclic ring system.

(1,3)-benzodioxolyl and (1,4)-benzodioxanyl may be mentioned by way of example of aryl residues which are fused with a mono- or polycyclic ring system.

If one or more of the above-stated substituents comprises a mono- or polycyclic ring system, the latter may preferably be substituted with 1, 2, 3, 4 or 5 substituents mutually independently selected from the group consisting of oxo (=O), thioxo (=S), F, Cl, Br, I, —CN, —$CF_3$, —$SF_5$, —OH, —O—$CH_3$, —O—$C_2H_5$, —O—$CH(CH_3)_2$, —O—$C(CH_3)_3$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl, tert-butyl, n-pentyl, —C(=O)—OH, —C(=O)—O—$CH_3$, —C(=O)—O—$C_2H_5$, —C(=O)—O—$CH(CH_3)_2$, —C(=O)—O—$C(CH_3)_3$, —NH—$CH_3$, —NH—$C_2H_5$, —NH—$C(CH_3)_3$, —N($CH_3)_2$, —N($C_2H_5)_2$, —N($CH_3$)($C_2H_5$), —NH—C(=O)—O—$CH_3$, —NH—C(=O)—O—$C_2H_5$, —NH—C(=O)—O—$C(CH_3)_3$, —C(=O)—H, —C(=O)—$CH_3$, —C(=O)—$C_2H_5$, —C(=O)—CH$(CH_3)_2$, —C(=O)—$C(CH_3)_3$, —C(=O)—$NH_2$, —C(=O)—NH—$CH_3$, —C(=O)—NH—$C_2H_5$, —C(=O)—N($CH_3)_2$, —C(=O)—N($C_2H_5)_2$, —O-phenyl, —O-benzyl, phenyl and benzyl, wherein in each case the cyclic moiety of the residues-O-phenyl, —O-benzyl, phenyl and benzyl may optionally be substituted with 1, 2, 3, 4 or 5 substituents mutually independently selected from the group consisting of F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

If one or more of the above-stated substituents comprises a linear or branched $C_{1-6}$ alkylene group, the latter may preferably be selected from the group consisting of —($CH_2$)—, —($CH_2$)$_2$—, —C(H)($CH_3$)—, —($CH_2$)$_3$—, —($CH_2$)$_4$—, —($CH_2$)$_5$—, —C(H)(C(H)($CH_3$)$_2$)— and —C($C_2H_5$)(H)—.

Preferred substituted compounds are those of the above-stated general formula A, in which X denotes O;

Y denotes —$NH_2$; —$NHR^{30}$; —$NR^{31}R^{32}$; or denotes an alkyl residue selected from the group consisting of —$CF_3$, —$CH_2$—$CF_3$, methyl, ethyl, n-propyl, isopropyl, tert-butyl, n-butyl, sec-butyl and isobutyl;

n denotes 1;

$R^1$, $R^3$ and $R^4$ in each case denote H;

$R^2$ denotes methyl; —O—$CH_3$; F; Cl; Br or I;

$R^5$ denotes a residue selected from the group consisting of methyl, ethyl, —$CF_3$, —$CCl_3$, —$CBr_3$, —$CHF_2$, —$CH_2F$, —$CF_2Cl$, —$CCl_2F$, —$C(CH_3)_2(CH_2OH)$, tert-butyl, —O—$CF_3$, —O—$CCl_3$, —O—$CBr_3$, —O—$CHF_2$, —O—$CH_2F$, —S—$CF_3$, —S—$CCl_3$, —S—$CBr_3$, —S—$CHF_2$ and —S—$CH_2F$;

T denotes CH and U denotes CH and V denotes N and W denotes C—$R^8$ or

T denotes CH and U denotes N and V denotes CH and W denotes C—$R^8$ or

T denotes N and U denotes CH and V denotes CH and W denotes C—$R^8$ or

T denotes N and U denotes N and V denotes CH and W denotes C—$R^8$ or

T denotes N and U denotes CH and V denotes N and W denotes C—R$^8$ or

T denotes CH and U denotes N and V denotes N and W denotes C—R$^8$ or

T denotes CH and U denotes CH and V denotes CH and W denotes C—R$^{10}$;

R$^8$ denotes H; F; Cl; Br; I; —CN; —OH; —NH$_2$; —NO$_2$; —NHR$^{11}$; —NR$^{12}$R$^{13}$; —OR$^{14}$; —SR$^{15}$;

or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —CH$_2$—CH$_2$—CH$_2$—CF$_3$, —CH$_2$—CH$_2$—CH$_2$—CH$_2$—CF$_3$, —CH$_2$—C(═O)—O—CH$_3$, —CH$_2$—C(═O)—C$_2$H$_5$, —CH$_2$—C(═O)—C(CH$_3$)$_3$, —CH$_2$—O—C(═O)—CH$_3$, —CH$_2$—O—C(═O)—C$_2$H$_5$, —CH$_2$—O—C(═O)—CH(CH$_3$)$_2$, —CH$_2$—O—C(═O)—C(CH$_3$)$_3$, n-butyl, methyl-but-1-yl, 4-methyl-pent-1-yl, n-pentyl, n-pentyl, n-hexyl, (3,3)-dimethyl-but-1-yl, (3,3)-dimethyl-but-1-ynyl, 4-methyl-pent-1-ynyl, 1-hexynyl, pentynyl, butynyl, propynyl, ethynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

or denotes a residues selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH═CH)—, —C≡C— or —C≡C—CH$_2$-group and in each case may optionally be substituted with 1, 2, 3, 4 or 5 substituents selected from the group consisting of —C(═O)—O—CH$_3$, —C(═O)—O—C$_2$H$_5$, —C(═O)—O—C(CH$_3$)$_3$, —C(═O)—CH$_3$, —C(═O)—C$_2$H$_5$, —C(═O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(═O)—C$_2$H$_5$]-phenyl, —N—[C(═O)—CH$_3$]-phenyl, oxo (═O), thioxo (═S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, (2,3)-dihydrothieno[3,4-b][1,4]dioxinyl, benzo[b]furanyl, indolyl, phenyl, naphthyl, oxazolyl, thiazolyl, imidazolyl, pyrimidinyl, thiophenyl, furanyl and pyridinyl, which may be in each case attached to the parent structure via a —(CH═CH)—, —C≡C—, —(CH$_2$)—, —(CH$_2$)$_2$— or —(CH$_2$)$_3$-group and/or in each case may optionally be substituted with 1, 2, 3, 4 or 5 selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(═O)$_2$—CH$_3$, —NH—S(═O$_2$)—C$_2$H$_5$, —NH—S(═O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{10}$ denotes —CN; —NH$_2$; —NO$_2$; —NHR$^{11}$; —NR$^{12}$R$^{13}$; —OR$^{14}$; —SR$^{15}$;

or a residue selected from the group consisting of phenyl, naphthyl, oxazolyl, thiazolyl, imidazolyl, pyrimidinyl, thiophenyl, furanyl and pyridinyl, which is in each case substituted with optionally 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11}$, R$^{12}$, R$^{13}$, R$^{14}$ and R$^{15}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—O—CH$_3$, ethenyl, propenyl, 2-butenyl, 3-butenyl, 2-bentenyl and 3-pentenyl;

or denote a residue selected from the group consisting of 2,3-dihydro-1H-indenyl, oxetanyl, piperidinyl, pyrrolidinyl, cyclopropyl, cyclobutyl, cyclopentyl and cyclohexyl, which may be in each case attached to the parent structure via a —CH$_2$—O—, —CH$_2$—CH$_2$—O—, —CH$_2$—CH$_2$—O—CH$_2$—, —CH$_2$—CH(CH$_3$)—O—CH$_2$, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(═O)—O—CH$_3$, —C(═O)—O—C$_2$H$_5$, —C(═O)—O—CH(CH$_3$)$_2$ and —C(═O)—O—C(CH$_3$)$_3$;

or denotes a radical selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, whereby the above-stated residues in each case may optionally be substituted with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

Or

R$^{12}$ and R$^{13}$, in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which may optionally in each case be substituted with 1, 2, 3, 4 or 5 substituents mutually independently selected from the group consisting of —CH$_2$—O—CH$_2$-oxetanyl, —O—CH$_2$-oxetanyl, —CH$_2$—OH, —CH$_2$—CH$_2$—OH, ═CH$_2$, —C(═O)—O—CH$_3$, —C(═O)—O—C$_2$H$_5$, —C(═O)—O—C(CH$_3$)$_3$, —C(═O)—CH$_3$, —C(═O)—C$_2$H$_5$, —C(═O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(═O)—C$_2$H$_5$]-phenyl, —N—[C(═O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (═O), thioxo (═S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, piperidinyl, pyrrolidinyl, —O-phenyl, —O—C(═O)—CH$_3$, —O—C(═O)—C$_2$H$_5$, —O—C(═O)—C(CH$_3$)$_3$, —(CH$_2$)-pyridinyl, pyridinyl, phenyl and benzyl, wherein in each case the cyclic moiety of the residues oxetanyl, —N—[C(═O)—C$_2$H$_5$]-phenyl, —N—[C(═O)—CH$_3$]-phenyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

And

R$^{25}$ denotes an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl or a residue selected from the group consisting of phenyl, benzyl, phenethyl, cyclopropyl, cyclobutyl, cyclopentyl and cyclohexyl; R$^{26}$ denotes a hydrogen residue or a residue selected from the group consisting of methyl, ethyl and n-propyl;

or

R$^{25}$ and R$^{26}$, in each case together with the carbon atom joining them together as a ring member, form a residue selected from the group consisting of cyclopropyl, cyclobutyl, cyclopentyl, cyclohexyl and cycloheptyl;

And R$^{30}$, R$^{31}$ and R$^{32}$, mutually independently, in each case denote an alkyl residue selected from the group consisting of —CF$_3$, —CH$_2$—CF$_3$, methyl, ethyl, n-propyl, isopropyl, tert-butyl, n-butyl, sec-butyl and isobutyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The present invention also provides compounds of general formula I,

I

In which

X denotes O, S or N—C≡N;

n denotes 0, 1, 2, 3 or 4;

R$^1$, R$^2$, R$^3$ and R$^4$, mutually independently, in each case denote H; F; Cl; Br; I; —SF$_5$; NO$_2$; —CF$_3$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$; —S(=O)—R$^{24}$; —S(=O)$_2$—R$^{24}$ or denote a linear or branched, saturated or unsaturated, unsubstituted or at least monosubstituted aliphatic C$_{1-10}$ residue;

R$^5$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$; —S(=O)$_2$—R$^{24}$; —S(=O)—R$^{24}$;

Denotes a linear or branched, unsaturated or saturated, unsubstituted or at least monosubstituted aliphatic C$_{1-10}$ residue;

or denotes an unsaturated or saturated, unsubstituted or at least monosubstituted 3-, 4-, 5-, 6-, 7-, 8- or 9-membered cycloaliphatic residue, optionally comprising at least one heteroatom as a ring member, which residue is in each case attached to the parent structure via a carbon atom in the ring of the cycloaliphatic residue;

T denotes C—R$^6$ and U denotes C—R$^7$ and V denotes N and W denotes C—R$^8$ or T denotes C—R$^6$ and U denotes N and V denotes C—R$^9$ and W denotes C—R$^8$ or T denotes N and U denotes C—R$^7$ and V denotes C—R$^9$ and W denotes C—R$^8$ or T denotes N and U denotes N and V denotes C—R$^9$ and W denotes C—R$^8$ or T denotes N and U denotes C—R$^7$ and V denotes N and W denotes C—R$^8$ or T denotes C—R$^6$ and U denotes N and V denotes N and W denotes C—R$^8$ Or T denotes C—R$^6$ and U denotes C—R$^7$ and V denotes C—R$^9$ and W denotes C—R$^{10}$;

R$^6$ and R$^7$, mutually independently, in each case denote H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$, S(=O)—R$^{24}$; —S(=O)$_2$—R$^{24}$; or denote a linear or branched, saturated or unsaturated, unsubstituted or at least monosubstituted aliphatic C$_{1-10}$ residue;

or denote an unsubstituted or at least monosubstituted 6- or 10-membered aryl residue, which may be attached via a linear or branched, substituted or at least monosubstituted C$_{1-6}$ alkylene group or C$_{2-6}$ alkenylene group or C$_{2-6}$ alkynylene group;

R$^8$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$; —S(=O)—R$^{24}$; —S(=O)$_2$—R$^{24}$; —C(=NH)—NH$_2$; —C(=NH)—NH—R$^{27}$; —N=C(NH$_2$)$_2$; —N=C(NHR$^{28}$)(NHR$^{29}$);

Denotes a linear or branched, saturated or unsaturated, unsubstituted or at least monosubstituted aliphatic C$_{1-10}$ residue;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

Or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

$R^9$ denotes H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; C(=O)—$OR^{22}$; —C(=O)—$R^{23}$; —S(=O)—$R^{24}$; —S(=O)$_2$—$R^{24}$ or denotes a linear or branched, saturated or unsaturated, unsubstituted or at least monosubstituted aliphatic $C_{1-10}$ residue;

$R^{10}$ denotes —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; $OR^{22}$; —C(=O)—$R^{23}$; —S(=O)—$R^{24}$; —S(=O)$_2$—$R^{24}$; —C(=NH)—$NH_2$; —C(=NH)—NH—$R^{27}$; —N=C(NH$_2$)$_2$; —N=C(NHR$^{28}$)(NHR$^{29}$);

denotes a linear or branched, saturated or unsaturated aliphatic $C_{1-10}$ residue, which is in each case substituted with optionally 1, 2, 3, 4, 5, 6, 7, 8 or 9 substituents mutually independently selected from the group consisting of —CN, —$NO_2$, —OH, —$NH_2$, —SH, —O($C_{1-5}$ alkyl), —S($C_{1-5}$ alkyl), —NH($C_{1-5}$ alkyl), —N($C_{1-5}$ alkyl)($C_{1-5}$ alkyl), —$OCF_3$ and —$SCF_3$;

Denotes an unsubstituted $C_{2-10}$ alkenyle residue or an unsubstituted $C_{2-10}$ alkynyle residue;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted $C_{1-6}$ alkylene group;

Or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group;

$R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{27}$, $R^{28}$ and $R^{29}$, mutually independently, in each case Denote a linear or branched, saturated or unsaturated, unsubstituted or at least monosubstituted aliphatic $C_{1-10}$ residue;

denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be fused with a saturated or unsaturated, unsubstituted or at least monosubstituted mono- or polycyclic ring system and/or be attached via a linear or branched, unsubstituted or at least monosubstituted $C_{1-6}$ alkylene group or 2- to 6-membered heteroalkylene group;

Or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or 2- to 6-membered heteroalkylene group;

Or $R^{12}$ and $R^{13}$, in each case together with the nitrogen atom joining them together as a ring member, form a saturated or unsaturated, unsubstituted or at least monosubstituted 4-, 5-, 6-, 7-, 8- or 9-membered heterocycloaliphatic residue, optionally comprising at least one further heteroatom as ring member, which may be fused with a saturated or unsaturated, unsubstituted or at least monosubstituted mono- or polycyclic ring system;

And $R^{25}$ and $R^{26}$, mutually independently, in each case denote a hydrogen residue;

Denote a linear or branched, saturated or unsaturated, unsubstituted or at least monosubstituted aliphatic $C_{1-10}$ residue;

Or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

Or denote an unsaturated or saturated, unsubstituted or at least monosubstituted, 3-, 4-, 5-, 6-, 7-, 8- or 9-membered cycloaliphatic residue optionally comprising at least one heteroatom as a ring member;

Providing that $R^{25}$ and $R^{26}$ do not in each case denote a hydrogen residue;

Or $R^{25}$ and $R^{26}$, together with the carbon atom joining them together as a ring member, form a saturated or unsaturated, unsubstituted or at least monosubstituted 3-, 4-, 5- or 6-membered cycloaliphatic residue;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred compounds are those of above-stated general formulae A and I, in which n, X, Y, T, U, V, W, $R^1$ to $R^7$, $R^9$ and $R^{11}$ to $R^{32}$ have the meaning as defined above;

$R^8$ denotes H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=)—$R^{23}$; —S(=O)—$R^{24}$; —S(=O)$_2$—$R^{24}$; —C(=NH)—$NH_2$; —C(=NH)—NH—$R^{27}$; —N=C(NH$_2$)$_2$; —N=C(NHR$^{28}$)(NHR$^{29}$);

denotes a saturated or unsaturated, unsubstituted or at least monosubstituted chain comprising 1 to 7 carbon atoms as chain members, wherein 1, 2 or 3 carbon atoms can be replaced by heteroatoms selected from the group consisting of oxygen, nitrogen (NH) and sulfur;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

and $R^{10}$ denotes —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)—$R^{24}$; —S(=O)$_2$—$R^{24}$; —C(=NH)—$NH_2$; —C(=NH)—NH—$R^{27}$; —N=C($NH_2$)$_2$; —N=C($NHR^{28}$)($NHR^{29}$);

denotes a saturated or unsaturated, unsubstituted or at least monosubstituted chain comprising 1 to 7 carbon atoms as chain members, wherein 1, 2 or 3 carbon atoms can be replaced by heteroatoms selected from the group consisting of oxygen, nitrogen (NH) and sulfur, which, in the absence of any heteroatoms as chain members, is substituted with optionally 1, 2, 3, 4, 5, 6, 7, 8 or 9 substituents mutually independently selected from the group consisting of —CN, —$NO_2$, —OH, —$NH_2$, —SH, —O($C_{1-5}$ alkyl), —S($C_{1-5}$ alkyl), —NH($C_{1-5}$ alkyl), —N($C_{1-5}$ alkyl)($C_{1-5}$ alkyl), —$OCF_3$ and —$SCF_3$;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted $C_{1-6}$ alkylene group;

or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group.

Preferably the chain comprises 5 to 7 carbon atoms as chain members, wherein 1, 2 or 3 carbon atoms can be replaced by heteroatoms selected from the group consisting of oxygen and sulfur.

If one or more of the above-stated residues denote a 1- to 7-membered chain or a 5- to 7-membered chain, the latter may preferably be substituted with optionally 1, 2, 3, 4, 5, 6, 7, 8 or 9 substitutents mutually independently selected from the group consisting of —$C_{1-5}$-alkyl, F, Cl, Br, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —$OCF_3$, —$SCF_3$, —O-phenyl, —S-phenyl, —NH-phenyl, oxetanyl, piperidinyl, pyrrolidinyl, cyclopropyl, cyclobutyl, cyclopentyl and cyclohexyl, wherein in each case the cyclic moiety of the residues may be substituted with optionally 1, 2, 3, 4 or 5 substituents mutually independently selected from the group consisting of F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—CH($CH_3$)$_2$, —O—C($CH_3$)$_3$, —O—$CF_3$, —S—$CF_3$, —C(=O)—$CH_2$, —C(=O)—$C_2H_5$, phenyl and —O-benzyl.

n-Pentyl, n-hexyl, 4-methyl-pent-1-ynyl, 1-hexynyl, pentynyl, 1-pentenyl, 1-heptenyl, 1-hexenyl, —O—$CH_2$—$CH_2$—$CH_2$—O—$CH_3$, —S—$CH_2$—$CH_2$—$CH_2$—O—$CH_3$, —S—$CH_2$—$CH_2$—$CH_2$—S—$CH_3$, —O—$CH_2$—CH($CH_3$)—O—$CH_2$-oxetanyl and —S—$CH_2$—CH($CH_3$)—O—$CH_2$-oxetanyl may be mentioned by way of example of 5- to 7-membered substituted or unsubstituted chains.

Preferred are those compounds of above-stated general formulae A and I, in which X, n, $R^1$ to $R^{29}$, T, U, V and W have the meaning defined above;

wherein unless otherwise stated, the above-stated aliphatic $C_{1-10}$ residues may optionally in each case be substituted with 1, 2, 3, 4, 5, 6, 7, 8 or 9 substituents mutually independently selected from the group consisting of F, Cl, Br, I, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —C(=O)—O—$C_{1-5}$-alkyl, —O—C(=O)—$C_{1-5}$-alkyl, —O-phenyl, phenyl, —$OCF_3$ and —$SCF_3$;

the above-stated 2- to 6-membered heteroalkylene groups, $C_{1-6}$-alkylene groups, $C_{2-6}$-alkenylene groups and $C_{2-6}$-alkynylene groups may optionally in each case be substituted with 1, 2, 3, 4, 5, 6, 7, 8 or 9 substituents mutually independently selected from the group consisting of F, Cl, Br, I, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —$OCF_3$ and —$SCF_3$;

the above-stated heteroalkylene groups may in each case optionally comprise 1, 2 or 3 heteroatom(s) mutually independently selected from the group consisting of oxygen, nitrogen (NH) and sulfur;

the above-stated (hetero)cycloaliphatic residues may optionally in each case be substituted with 1, 2, 3, 4 or 5 substituents mutually independently selected from the group consisting of —$C_{1-6}$-alkylene-OH, =$CH_2$, —O—$C_{1-5}$-alkylene-oxetanyl, —$C_{1-5}$-alkylene-O—$C_{1-5}$-alkylene-oxetanyl, —$CH_2$—NH—$C_{1-5}$-alkyl, —$CH_2$—N($C_{1-5}$-alkyl)$_2$, —N[C(=O)—$C_{1-5}$-alkyl]-phenyl, —$CH_2$—O—$C_{1-5}$-alkyl, oxo (=O), thioxo (=S), F, Cl, Br, I, —CN, —$CF_3$, —$SF_5$, —OH, —O—$C_{1-5}$-alkyl, —O—C(=O)—$C_{1-5}$-alkyl, —$NH_2$, —$NO_2$, —O—$CF_3$, —S—$CF_3$, —SH, —S—$C_{1-6}$-alkyl, —$C_{1-5}$-alkyl, —C(=O)—$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —NH-phenyl, —N($C_{1-5}$-alkyl)-phenyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —($CH_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N[C(=O)—$C_{1-5}$-alkyl]-phenyl, —NH-phenyl, —N($C_{1-5}$-alkyl)-phenyl, —($CH_2$)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl;

and the above-stated (hetero)cycloaliphatic residues may in each case optionally comprise 1, 2 or 3 (further) heteroatom(s) mutually independently selected from the group consisting of oxygen, nitrogen and sulfur;

the rings of the above-stated mono- or polycyclic ring systems may optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and the rings of the above-stated mono- or polycyclic ring systems are in each case 5-, 6- or 7-membered and may in each case optionally comprise 1, 2, 3, 4 or 5 heteroatom(s) as ring member(s), which are mutually independently selected from the group consisting of oxygen, nitrogen and sulfur;

and the above-stated aryl or heteroaryl residues may optionally in each case be substituted with 1, 2, 3, 4 or 5 substituents mutually independently selected from the group consisting of F, Cl, Br, —I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$alkyl, —N(C$_{1-5}$-alkyl)$_2$, —NH—S(=O)$_2$—C$_{1-5}$-alkyl, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, —C(=O)—N—(C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and the above-stated heteroaryl residues in each case optionally comprise 1, 2, 3, 4 or 5 heteroatom(s) mutually independently selected from the group consisting of oxygen, nitrogen and sulfur as ring member(s);

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The present invention also provides compounds of general formula B1,

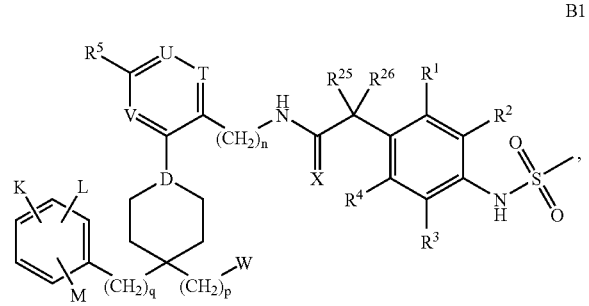

B1 in which
U, T, V, X, n, R$^1$, R$^2$, R$^3$, R$^4$, R$^5$, R$^{25}$ and R$^{26}$ have the meaning as defined above;

D denotes CH or N;
p denotes 0, 1, 2 or 3;
q denotes 0, 1, 2 or 3;
K, L and M, mutually independently, in each case denote H, F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —NH—S(=O)$_2$—C$_{1-5}$-alkyl, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, —C(=O)—N—(C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl;

W denotes —CN, —NR$^{34}$R$^{35}$, —C(=O)—R$^{36}$ or —C(=O)—OR$^{37}$;

and R$^{34}$, R$^{35}$, R$^{36}$ and R$^{37}$, mutually independently, in each case denote hydrogen or denote a linear or branched, saturated or unsaturated aliphatic C$_{1-10}$ residue denote an unsaturated or saturated, unsubstituted or at least monosubstituted 3-, 4-, 5-, 6-, 7-, 8- or 9-membered cycloaliphatic residue, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$-alkenylene group or C$_{2-6}$-alkynylene group.

The present invention also provides compounds of general formula B2,

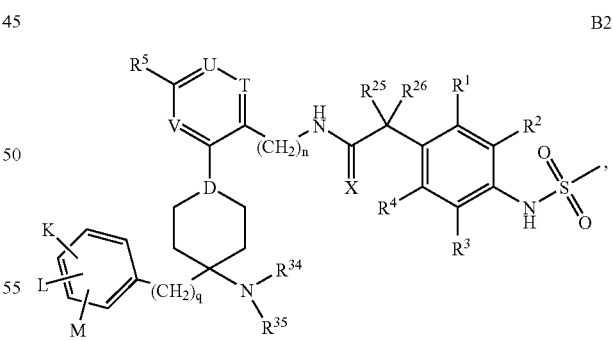

B2 in which
U, T, V, X, n, R$^1$, R$^2$, R$^3$, R$^4$, R$^5$, R$^{25}$ and R$^{26}$ have the meaning as defined above;
D denotes CH or N;
q denotes 0, 1, 2 or 3;
K, L and M, mutually independently, in each case denote H, F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$alkyl, —C(=O)—OH, —C(=O)—O—C$_{1-5}$- alkyl, —NH—$C_{1-5}$-alkyl, —N($C_{1-5}$-alkyl)$_2$, —NH—S(=O)$_2$—$C_{1-5}$-alkyl, —NH≤C(=O)—O—$C_{1-5}$-alkyl, —C(=O)—H, —C(=O)—$C_{1-5}$-alkyl, —C(=O)—NH$_2$, —C(=O)—NH—$C_{1-5}$-alkyl, —C(=O)—N—($C_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —$C_{1-5}$-alkyl, —O—$C_{1-5}$-alkyl, —O—CF$_3$, —S—CF$_3$, phenyl and —O-benzyl; and $R^{34}$ and $R^{35}$, mutually independently, in each case denote hydrogen or denote a linear or branched, saturated or unsaturated aliphatic $C_{1-10}$ residue;

denote an unsaturated or saturated, unsubstituted or at least monosubstituted 3-, 4-, 5-, 6-, 7-, 8- or 9-membered cycloaliphatic residue, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$-alkenylene group or $C_{2-6}$-alkynylene group.

Preferred compounds are those of above-stated general formulae I, B1 and B2, in which X denotes O, S or N—C=—N;

n denotes 0, 1, 2, 3 or 4;

$R^1$, $R^2$, $R^3$ and $R^4$, mutually independently, in each case denote H; F; Cl; Br; I; —SF$_5$; —NO$_2$; —CN; —CF$_3$; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$; —S(=S)—R$^{24}$; —S(=O)$_2$—R$^{24}$ or denote an alkyl residue selected from the group consisting of methyl, ethyl, n-propyl, isopropyl, tert-butyl, n-butyl, sec-butyl, isobutyl, n-pentyl, n-hexyl and n-heptyl;

$R^5$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$; —S(=O)—R$^{24}$; —S(=O)$_2$—R$^{24}$;

denotes an alkyl residue selected from the group consisting of methyl, ethyl, n-propyl, isopropyl, tert-butyl, n-butyl, sec-butyl, isobutyl, n-pentyl, n-hexyl and n-heptyl;

or denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues and may optionally in each case be substituted with 1, 2, 3, 4 or 5 substituents mutually independently selected from the group consisting of —CH$_2$—O—CH$_3$, —CH$_2$—O—CH$_2$—CH$_3$, oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH-phenyl, —N(CH$_3$)-phenyl, —N(C$_2$H$_5$)-phenyl, —N(C$_2$H$_5$)-phenyl, —O—CH$_2$—CH$_2$—CH$_2$—CH$_3$, piperidinyl, pyrrolidinyl, —O—C(=O)—CH$_3$, —O—C(=O)—C$_2$H$_5$, —O—C(=O)—C(CH$_3$)$_3$, —(CH$_2$)-pyridinyl, pyridinyl, —O-phenyl, —O-benzyl, phenyl and benzyl, wherein in each case the cyclic moiety of the residues —NH-phenyl, —N(CH$_3$)-phenyl, —N(C$_2$H$_5$)-phenyl, —(CH$_2$)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, iso-propyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl;

T denotes C—R$^6$ and U denotes C—R$^7$ and V denotes N and W denotes C—R$^8$ or T denotes C—R$^6$ and U denotes N and V denotes C—R$^9$ and W denotes C—R$^8$ or T denotes N and U denotes C—R$^7$ and V denotes C—R$^9$ and W denotes C—R$^8$ or T denotes N and U denotes N and V denotes C—R$^9$ and W denotes C—R$^8$ or T denotes N and U denotes C—R$^7$ and V denotes N and W denotes C—R$^8$ or T denotes C—R$^6$ and U denotes N and V denotes N and W denotes C—R$^8$ or T denotes C—R$^6$ and U denotes C—R$^7$ and V denotes C—R$^9$ and W denotes C—R$^{10}$;

$R^6$ and $R^7$, mutually independently, in each case denote H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$S(=O)$_2$—R$^{24}$; denote an alkyl residue selected from the group consisting of methyl, ethyl, n-propyl, isopropyl, tert-butyl, n-butyl, sec-butyl, isobutyl, n-pentyl, n-hexyl and n-heptyl or denote a phenyl residue, which may be attached via a —(CH=CH)—, —C≡C—, —(CH$_2$)—, —(CH$_2$)$_2$— or —(CH$_2$)$_3$-group and/or may optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl and n-pentyl;

$R^8$ denotes H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)—$R^{24}$; —S(=O)$_2$—$R^{24}$, —C(=NH)—$NH_2$; C(=NH)—NH—$R^{27}$; —N=C(NH$_2$)$_2$; —N=C(NHR$^{28}$)(NHR$^{29}$);

denotes an alkyl residue selected from the group consisting of methyl, ethyl, n-propyl, isopropyl, tert-butyl, n-butyl, sec-butyl, isobutyl, n-pentyl, 3-methyl-but-1-yl, 4-methyl-pent-1-yl, (3,3)-dimethyl-but-1-yl, n-hexyl and n-heptyl;

denotes an alkenyl residue selected from the group consisting of 2-methyl-propen-1-yl, 3-methyl-but-2-en-1-yl, (3,3)-dimethyl-but-1-enyl, ethenyl, propenyl, butenyl, 1-octenyl, 1-heptenyl, 1-hexenyl and 1-pentenyl;

denotes an alkynyl residue selected from the group consisting of ethynyl, propynyl, butynyl, (3,3)-dimethyl-but-1-ynyl, 4-methyl-pent-1-ynyl, 1-hexynyl and pentynyl;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH-phenyl, —N(CH$_3$)-phenyl, —N(C$_2$H$_5$)-phenyl, —N(C$_2$H$_5$)—phenyl, —O—CH$_2$—CH$_2$—CH$_2$—CH$_3$, piperidinyl, pyrrolidinyl, —O—C(=O)—CH$_3$, —O—C(=O)—C$_2$H$_5$, —O—C(=O)—C(CH$_3$)$_3$, —(CH$_2$)-pyridinyl, pyridinyl, —O-phenyl, —O-benzyl, phenyl and benzyl, wherein in each case the cyclic moiety of the residues —NH-phenyl, —N(CH$_3$)-phenyl, —N(C$_2$H$_5$)-phenyl, —(CH$_2$)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl;

or denotes a residue selected from the group consisting of tetrazolyl, phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, (2,3)-dihydrothieno[3,4-b][1,4]dioxinyl, benzo[b]thiophenyl, benzoxazolyl, benzisoxazolyl, thiazolyl, oxazolyl, isoxazolyl, pyridazinyl, pyrazinyl, pyrimidinyl, indazolyl, chinoxalinyl, chinolinyl and isochinolinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—S(=O)$_2$—CH$_3$, —NH—S(=O$_2$)—C$_2$H$_5$, —NH—S(=O)$_2$—CH(CH$_3$)$_2$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl;

$R^9$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$—C(=O)—OR$^{22}$; —C(=O)—R$^{23}$; —S(=O)—R$^{24}$; —S(=O)$_2$—R$^{24}$ or denotes an alkyl residue selected from the group consisting of methyl, ethyl, n-propyl, isopropyl, tert-butyl, n-butyl, sec-butyl, isobutyl, n-pentyl, n-hexyl and n-heptyl;

$R^{10}$ denotes —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^1$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$—C(=O)—R$^{23}$; —S(=O)—R$^{24}$; —S(=O)$_2$—R$^{24}$; —C(=NH)—NH$_2$; —C(=NH)—NH—R$^{27}$; —N=C(NH$_2$)$_2$; —N=C(NHR$^{28}$)(NHR$^{29}$);

denotes an alkyl residue selected from the group consisting of methyl, ethyl, n-propyl, isopropyl, tert-butyl, n-butyl, sec-butyl, isobutyl, n-pentyl, n-hexyl and n-heptyl which is in each case substituted with optionally 1, 2, 3, 4, 5, 6, 7, 8 or 9 substituents mutually independently selected from the group consisting of —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)=C$_2$H$_5$]-phenyl, —N—[C(=O)—CH$_3$]-phenyl, —CH$_2$—O—CH$_3$, —CH$_2$—O—CH$_2$—CH$_3$, oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH-phenyl, —N(CH$_3$)-phenyl, —N(C$_2$H$_5$)-phenyl, —N(C$_2$H$_5$)—phenyl, —O—CH$_2$—CH$_2$—CH$_3$, piperidinyl, pyrrolidinyl, —O—C(=O)—CH$_3$, —O—C(=O)—C$_2$H$_5$, —O—C(=O)—C(CH$_3$)$_3$, —(CH$_2$)-pyridinyl, pyridinyl, —O-phenyl, —O-benzyl, phenyl and benzyl, wherein in each case the cyclic moiety of the residues —NH-phenyl, —N(CH$_3$)-phenyl, —N(C$_2$H$_5$)-phenyl, —(CH$_2$)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl;

or denotes a residue selected from the group consisting of tetrazolyl, phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, (2,3)-dihydrothieno[3,4-b][1,4]dioxinyl, benzo[b]thiophenyl, benzoxazolyl, benzisoxazolyl, thiazolyl, oxazolyl, isoxazolyl, pyridazinyl, pyrazinyl, pyrimidinyl, indazolyl, chinoxalinyl, chinolinyl and isochinolinyl, wherein the residue may in each case be attached via a —(CH=CH)—, —C≡C—, —(CH$_2$)—, —(CH$_2$)$_2$— or —(CH$_2$)$_3$—group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—S(=O)$_2$—CH$_3$, —NH—S(=O$_2$)—C$_2$H$_5$, —NH—S(=O)$_2$—CH(CH$_3$)$_2$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl;

$R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{27}$, $R^{28}$ and $R^{29}$, mutually independently, in each case denote a residue selected from the group consisting of methyl, ethyl, n-propyl, isopropyl, tert-butyl, n-butyl, sec-butyl, isobutyl, n-pentyl, n-hexyl, n-heptyl, 3-pentyl, 4-heptyl, n-octyl, n-nonyl, 5-nonyl, (2,6)-dimethyl-hept-4-yl, 3-methyl-butyl, n-hexyl, (3,3)-dimethylbutyl, ethenyl, propenyl, 2-butenyl, 3-butenyl, 2-pentenyl and 3-pentenyl;

denote a residue selected from the group consisting of 2,3-dihydro-1H-indenyl, cyclopropyl, oxetanyl, cyclobutyl, cyclopentyl, cyclohexyl, cycloheptyl, cyclopentenyl, cyclohexenyl, Cycloheptenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, wherein the residue may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$, —(CH$_2$)—, —(CH$_2$)$_2$—CH—(CH$_2$)$_3$—group and/or in each case may optionally be substituted with 1, 2, 3, 4 or 5 substituents mutually independently selected from the group consisting of —CH$_2$—O—CH$_3$, —CH$_2$—O—CH$_2$—CH$_3$, oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH-phenyl, —N(CH$_3$)-phenyl, —N(C$_2$H$_5$)-phenyl, —N(C$_2$H$_5$)-phenyl, —O—CH$_2$—CH$_2$—CH$_2$—CH$_3$, piperidinyl, pyrrolidinyl, —O—C(=O)—CH$_3$, —O—C(=O)—C$_2$H$_5$, —O—C(=O)—C(CH$_3$)$_3$, —(CH$_2$)-pyridinyl, pyridinyl, —O-phenyl, —O-benzyl, phenyl and benzyl, wherein in each case the cyclic moiety of the residues —NH-phenyl, —N(CH$_3$)-phenyl, —N(C$_2$H$_5$)-phenyl, —(CH$_2$)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl;

or denote a residue selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, chinoxalinyl, chinolinyl and isochinolinyl, wherein the residue may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C (=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—CH(CH₃)₂, —C(=O)—C(CH₃)₃, —C(=O)—NH₂, —C(=O)—NH—CH₃, —C(=O)—NH—C₂H₅, —C(=O)—N(CH₃)₂, —C(=O)—N(C₂H₅)₂, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF₃, —SF₅, —CN, —NO₂, —C₁₋₅-alkyl, —O—C₁₋₅-alkyl, —O—CF₃, —S—CF₃, phenyl and —O-benzyl;

or

R¹² and R¹³ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,3,4,5)-tetrahydropyrido[4,3-b]indolyl, (3,4)-dihydro-1H-isochinolinyl, (1,3,4,9)-tetrahydro-[b]-carbolinyl, imidazolidinyl, (1,3)-thiazolidinyl, piperazinyl, morpholinyl, azepanyl, diazepanyl and thiomorpholinyl, which may optionally in each case be substituted with 1, 2, 3, 4 or 5 substituents mutually independently selected from the group consisting of —CH₂—O—CH₂-oxetanyl, —CH₂—OH, —CH₂—CH₂—OH, =CH₂, —O—CH₂-oxetanyl, (4,5)-dihydroisoxazolyl, thiazolyl, (1,2,5)-thiadiazolyl, thiophenyl, phenethyl, —CN, —CH₂—N(CH₃)₂, —CH₂—N(C₂H₅)₂, —CH₂—NH—CH₃, —CH₂—NH—C₂H₅, —N—[C(=O)—C₂H₅-]-phenyl, —N—[C(=O)—CH₃]-phenyl, —CH₂—O—CH₃, —CH₂—O—CH₂—CH₃, oxo (=O), thioxo (=S), F, Cl, Br, I, —CN, —CF₃, —SF₅, —OH, —O—CH₃, —O—C₂H₅, —CH(CH₃)₂, —O—C(CH₃)₃, —NH₂, —NO₂, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl, tert-butyl, n-pentyl, —C(=O)—CH₃, —C(=O)—C₂H₅, —C(=O)—CH(CH₃)₂, —C(=O)—C(CH₃)₃, —C(=O)—OH, —C(=O)—O—CH₃, —C(=O)—O—C₂H₅, —C(=O)—O—CH(CH₃)₂, —C(=O)—O—C(CH₃)₃, —NH—CH₃, —NH—C₂H₅, —NH—C(CH₃)₃, —N(CH₃)₂, —N(C₂H₅)₂, —N(CH₃)(C₂H₅), —NH-phenyl, —N(CH₃)-phenyl, —N(C₂H₅)-phenyl, —N(C₂H₅)-phenyl, —O—CH₂—CH₂—CH₂—CH₃, piperidinyl, pyrrolidinyl, cyclohexyl, cyclopentyl, —O—C(=O)—CH₃, —O—C(=O)—C₂H₅, —O—C(=O)—C(CH₃)₃, —(CH₂)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—C₂H₅]-phenyl, —N—[C(=O)—CH₃]-phenyl, —NH-phenyl, —N(CH₃)-phenyl, —N(C₂H₅)-phenyl, —(CH₂)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —CF₃, —SF₅, —CN, —NO₂, methyl, ethyl, n-propyl, isopropyl, n-butyl, sec-butyl, isobutyl, tert-butyl, —O—CH₃, —O—C₂H₅, —O—CH(CH₃)₂, —O—C(CH₃)₃, —O—CF₃, —S—CF₃, phenyl and —O-benzyl; and R²⁵ and R²⁶, mutually independently, in each case denote a hydrogen residue;

denote an alkyl residue selected from the group consisting of methyl, ethyl, n-propyl, isopropyl, tert-butyl, n-butyl, sec-butyl, isobutyl, n-pentyl, n-hexyl and n-heptyl;

denote a residue selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, chinoxalinyl, chinolinyl and isochinolinyl, wherein the residue may in each case be attached via a —(CH₂)—, —(CH₂)₂— or —(CH₂)₃—group and/or in each case may optionally be substituted with 1, 2, 3, 4 or 5 substituents selected from the group consisting of F, Cl, Br, I, —CN, —CF₃, —SF₅, —OH, —O—CH₃, —O—C₂H₅, —O—CH(CH₃)₂, —O—C(CH₃)₃, —NH₂, —NO₂, —O—CF₃, —S—CF₃, —SF₅, —OH, —CH₃, —S—C₂H₅, —S—CH(CH₃)₂, —S—C(CH₃)₃, methyl, ethyl, n-propyl, isopropyl, n-butyl, sec-butyl, isobutyl, tert-butyl and n-pentyl;

or denote a residue selected from the group consisting of cyclopropyl, cyclobutyl, cyclopentyl, cyclohexyl, cyclopentenyl and cyclohexenyl;

providing that R²⁵ and R²⁶ do not in each case denote a hydrogen residue;

or

R²⁵ and R²⁶ in each case together with the carbon atom joining them together as a ring member, form a residue selected from the group consisting of cyclopropyl, cyclobutyl, cyclopentyl, cyclohexyl, cyclopentenyl and cyclohexenyl;

wherein unless otherwise stated, the above-stated alkyl, alkenyl and alkynyl residues may in each case optionally be substituted with 1, 2, 3, 4, 5, 6, 7, 8 or 9 substituents mutually independently selected from the group consisting of alkenyl-C(=O)—O—CH₃, —C(=O)—O—C₂H₅, —C(=O)—O—C(CH₃)₃, —O—C(=O)—CH₃, —O—C(=O)—C₂H₅, —O—C(=O)—CH(CH₃)₂, —O—C(=O)—C(CH₃)₃, —O-phenyl, phenyl, F, Cl, Br, I, —CN, —NO₂, —OH, —NH₂, —SH, —O—CH₃, —O—C₂H₅, —O—CH(CH₃)₂, —O—C(CH₃)₃, —S—CH₃, —S—C₂H₅, —S—CH(CH₃)₂, —S—C(CH₃)₃, —NH—CH₃, —NH—C₂H₅, —NH—C(CH₃)₃, —N(CH₃)₂, —N(C₂H₅)₂, —N(CH₃)(C₂H₅), —OCF₃ and —SCF₃;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise preferred compounds are those of above-stated general formulae A, I, B1 and B2, in which X denotes O, S or N—C≡N;

Y denotes —NH₂; —NHR³⁰; —NR³¹R³²; denotes an alkyl residue selected from the group consisting of —CF₃, —CH₂—CF₃, methyl, ethyl, n-propyl, isopropyl, tert-butyl, n-butyl, sec-butyl and isobutyl;

n denotes 0, 1, 2, 3 or 4;

R¹, R², R³ and R⁴, mutually independently, in each case denote H; F; Cl; Br; I; —SF₅; —NO₂; —CN; —NH₂; —OH; —SH; —C(=O)—NH₂; —S(=O)₂—NH₂; —C(=O)—NH—OH; —C(=O)—OH; —C(=O)—H; —S(=O)₂—OH; —NHR¹¹; —NR¹²R¹³; —OR¹⁴; —SR¹⁵; —S(=O)—R²⁴; —S(=O)₂—R²⁴ or denote a residue selected from the group consisting of methyl, —CF₃, —CCl₃, —CBr₃, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, n-butyl, sec-butyl, isobutyl and tert-butyl;

R$^5$ denotes F; Cl; Br; I; —SF$_5$; —OR$^{14}$; —SR$^{15}$; —S(=O)—R$^{24}$; —S(=O)$_2$—R$^{24}$;

denotes a residue selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, n-butyl, sec-butyl, butyl, isobutyl, —C(CH$_3$)$_2$(CH$_2$OH), and tert-butyl;

or denotes a residue selected from the group consisting of cyclopropyl, cyclobutyl, cyclopentyl, cyclohexyl, cyclopentenyl and cyclohexenyl, which may optionally in each case be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl and n-pentyl;

T denotes C—R$^6$ and U denotes C—R$^7$ and V denotes N and W denotes C—R$^8$ or T denotes C—R$^6$ and U denotes N and V denotes C—R$^9$ and W denotes C—R$^8$ or T denotes N and U denotes C—R$^7$ and V denotes C—R$^9$ and W denotes C—R$^8$ or T denotes N and U denotes N and V denotes C—R$^9$ and W denotes C—R$^8$ or T denotes N and U denotes C—R$^7$ and V denotes N and W denotes C—R$^8$ or T denotes C—R$^6$ and U denotes N and V denotes N and W denotes C—R$^8$ or T denotes C—R$^6$ and U denotes C—R$^7$ and V denotes C—R$^9$ and W denotes C—R$^{10}$;

R$^6$ and R$^7$, mutually independently, in each case denote H; F; Cl; Br; I; —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—OR$^{22}$; —S(=O)—R$^{24}$; —S(=O)$_2$—R$^{24}$; denote a residue selected from the group consisting of —CH$_2$—OH, methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, n-butyl, sec-butyl, isobutyl and tert-butyl or denote a phenyl residue, which may optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl and n-pentyl;

R$^8$ denotes H; F; Cl; Br; I; —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—OR$^{22}$; —S(=O)—R$^{24}$; —S(=O)$_2$—R$^{24}$; —C(=NH)—NH$_2$; —C(=NH)—NH—R$^{27}$; —N=C(NH$_2$)$_2$; —N=C(NHR$^{28}$)(NHR$^{29}$);

or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, —CH$_2$—CH$_2$—CH$_2$—CF$_3$, —CH$_2$—CH$_2$—CH$_2$—CF$_3$, —CH$_2$—C(=O)—O—CH$_3$, —CH$_2$—C(=O)—C$_2$H$_5$, —CH$_2$—C(=O)—C(CH$_3$)$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, isopropyl, n-butyl, sec-butyl, isobutyl, tert-butyl, 3-methyl-but-1-yl, 4-methyl-pent-1-yl, n-pentyl, sec-pentyl, neo-pentyl, n-hexyl, 2-methyl-propen-1-yl, 3-methyl-but-2-en-1-yl, (3,3)-dimethyl-but-1-yl, (3,3)-dimethyl-but-1-enyl, ethenyl, propenyl, butenyl, 1-pentenyl, 1-octenyl, 1-heptenyl, 1-hexenyl, (3,3)-dimethyl-but-1-ynyl, 4-methyl-pent-1-ynyl, 1-hexynyl, ethynyl, propynyl, butynyl, pentynyl, —CF=CF$_2$, —CCl=Cl$_2$, —CH$_2$—CF=CF$_2$, —CH$_2$—CCl=CCl$_2$, —C≡C—I, —C≡C—F and —C≡C—Cl;

denotes a residue selected from the group consisting of cyclopropyl, cyclobutyl, cyclopentyl, cyclohexyl, cyclohexenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of (1,3)-benzodioxolyl, (1,4)-benzodioxanyl, tetrazolyl, (2,3)-dihydrothieno[3,4-b][1,4]dioxinyl, benzo[b]furanyl, phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, chinoxalinyl, chinolinyl and isochinolinyl, which may in each case be attached via a —(CH=CH)—, —C≡C—, —(CH$_2$)—, —(CH$_2$)$_2$— or —(CH$_2$)$_3$—groupand/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—S(=O)$_2$—CH$_3$, —NH—S(=O)$_2$—C$_2$H$_5$, —NH—S(=O)$_2$—CH(CH$_3$)$_2$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

R$^9$ denotes H; F; Cl; Br; I; —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —S(=O)—R$^{24}$; —S(=O)$_2$—R$^{24}$ or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, n-butyl, sec-butyl, isobutyl and tert-butyl;

R$^{10}$ denotes —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—OR$^{22}$; —S(=O)—R$^{24}$; —S(=O)$_2$—R$^{24}$; —C(=NH)—NH$_2$; —C(=NH)—NH—R$^{27}$; —N=C(NH$_2$)$_2$; —N⊙C(NHR$^{28}$)(NHR$^{29}$);

denotes a residue selected from the group consisting of cyclopropyl, cyclobutyl, cyclopentyl, cyclohexyl, cyclohexenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of (1,3)-benzodioxolyl, (1,4)-benzodioxanyl, tetrazolyl, (2,3)-dihydrothieno[3,4-b][1,4]dioxinyl, benzo[b]furanyl, phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, chinoxalinyl, chinolinyl and isochinolinyl, which may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—S(=O)$_2$—CH$_3$, —NH—S(=O)$_2$—C$_2$H$_5$, —NH—S(=O)$_2$—CH(CH$_3$)$_2$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

R$^{11}$, R$^{12}$, R$^{13}$, R$^{14}$, R$^{15}$, R$^{22}$, R$^{24}$, R$^{27}$, R$^{28}$ and R$^{29}$, mutually independently, in each case denote a residue selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl and isoxazolyl, which may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—

C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

or

R$^{12}$ and R$^{13}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl and thiomorpholinyl, which may optionally in each case be substituted with 1, 2, 3, 4 or 5 substituents mutually independently selected from the group consisting of —CH$_2$—O—CH$_2$-oxetanyl, —CH$_2$—OH, —CH$_2$—CH$_2$—OH, =CH$_2$, —O—CH$_2$—oxetanyl, (4,5)-dihydroisoxazolyl, thiazolyl, (1,2,5)-thiadiazolyl, thiophenyl, phenethyl, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$—N—[C(=O)—C$_2$H$_5$]-phenyl, phenyl, —N—[C(=O)—CH$_3$]-phenyl, —CH$_2$—O—CH$_3$, —CH$_2$—O—CH$_2$—CH$_3$, oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH-phenyl, —N(CH$_3$)-phenyl, —N(C$_2$H$_5$)-phenyl, —N(C$_2$H$_5$)-phenyl, —O—CH$_2$—CH$_2$—CH$_2$—CH$_3$, cyclohexyl, cyclopentyl, piperidinyl, pyrrolidinyl, —O—C(=O)—CH$_3$, —O—C(=O)—C$_2$H$_5$, —O—C(=O)—C(CH$_3$)$_3$, —(CH$_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—C$_2$H$_5$]-phenyl, —N—[C(=O)—CH$_3$]-phenyl, —NH-phenyl, —N(CH$_3$)-phenyl, —N(C$_2$H$_5$)-phenyl, —(CH$_2$)-pyridinyl, pyridinyl, —O-phenyl, —O-benzyl, phenyl and benzyl may optionally be substituted with 1, 2, 3, 4 or 5 substituents mutually independently selected from the group consisting of —CF$_3$, F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, O—CF$_3$, —S—CF$_3$, phenyl and —O-benzyl, and R$^{25}$ and R$^{26}$, mutually independently, in each case denote a hydrogen residue;

denote an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

denote a residue selected from the group consisting of phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, chinoxalinyl, chinolinyl and isochinolinyl, which may in each case be attached via a —(CH$_2$)—, —(CH$_2$)$_2$— or —(CH$_2$)$_3$-group in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl and n-pentyl;

or denote a residue selected from the group consisting of cyclopropyl, cyclobutyl, cyclopentyl and cyclohexyl;

providing that R$^{25}$ and R$^{26}$ do not in each case denote a hydrogen residue;

or

R$^{25}$ and R$^{26}$ in each case together with the carbon atom joining them together as a ring member, form a residue selected from the group consisting of cyclopropyl, cyclobutyl, cyclopentyl, cyclohexyl and cycloheptyl;

and R$^{30}$, R$^{31}$ and R$^{32}$, mutually independently, in each case denote an alkyl residue selected from the group consisting of —CF$_3$, —CH$_2$—CF$_3$, methyl, ethyl, n-propyl, isopropyl, tert-butyl, n-butyl, sec-butyl and isobutyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Further preferred compounds are those of above-stated general formulae A, I, B1 and B2, in which X denotes O, S or N—C≡N;

Y denotes —NH$_2$; —NHR$^{30}$; —NR$^{31}$R$^{32}$; denotes an alkyl residue selected from the group consisting of —CF$_3$, —CH$_2$—CF$_3$, methyl, ethyl, n-propyl, isopropyl, tert-butyl, n-butyl, sec-butyl and isobutyl;

n denotes 0, 1 or 2;

R$^1$, R$^3$ and R$^4$, mutually independently, in each case denote H; F; Cl; Br; or denote a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl and —CFCl—CF$_2$Cl;

R$^2$ denotes F; Cl; Br; I or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —O—CH$_3$, —O—CF$_3$, —O—CCl$_3$, —O—CBr$_3$, —O—CHF$_2$, —O—CH$_2$F, —O—CF$_2$Cl, —O—CCl$_2$F, —O—C$_2$H$_5$, —O—CF$_2$—CH$_3$, —O—CH$_2$—CF$_3$, —O—C$_2$F$_5$, —O—CH$_2$—CCl$_3$, —O—CH$_2$—CBr$_3$, —O—CHF—CF$_2$Cl, —O—CF$_2$—CF$_2$Cl, —O—CFCl—CF$_2$Cl, —O—CH$_2$—CH$_2$—CH$_3$, —O—CF$_2$—CF$_2$—CF$_3$, —O—CF(CF$_3$)$_2$, —O—C(CH$_3$)$_3$, —S—CH$_3$, —S—CF$_3$, —S—CCl$_3$, —S—CBr$_3$, —S—CHF$_2$, —S—CH$_2$F, —S—CF$_2$Cl, —S—CCl$_2$F, —S—C$_2$H$_5$, —S—CF$_2$—CH$_3$, —S—CH$_2$—CF$_3$, —S—C$_2$F$_5$, —S—CH$_2$—CCl$_3$, —S—CH$_2$—CBr$_3$, —S—CHF—CF$_2$Cl, —S—CF$_2$—CF$_2$Cl, —S—CFCl—CF$_2$Cl, —S—CH$_2$—CH$_2$—CH$_3$, —S—CF$_2$—CF$_2$—CF$_3$, —S—CF(CF$_3$)$_2$, —S—CH(CH$_3$)$_2$ and —S—C(CH$_3$)$_3$;

R$^5$ denotes F; Cl; Br; I; —SF$_5$;

or denotes a residue selected from the group consisting of methyl, ethyl, —CF$_3$, —CCl$_3$, —CBr$_3$, —CHF$_2$, —CH$_2$F, —CF$_2$Cl, —CCl$_2$F, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CF$_2$—CF$_2$—CF$_3$, —CF(CF$_3$)$_2$, sec-butyl, isobutyl, —C(CH$_3$)$_2$(CH$_2$OH), tert-butyl, —O—CF$_3$, —O—CCl$_3$, —O—CBr$_3$, —O—CHF$_2$, —O—CH$_2$F, —O—CF$_2$Cl, —O—CCl$_2$F, —O—CF$_2$—CH$_3$, —O—CH$_2$—CF$_3$, —O—C$_2$F$_5$, —O—CH$_2$—CCl$_3$, —O—CH$_2$—CBr$_3$, —O—CHF—CF$_2$Cl, —O—CF$_2$—CF$_2$Cl, —O—CFCl—CF$_2$Cl, —O—CF$_2$—CF$_2$—CF$_3$, —O—CF(CF$_3$)$_2$, —O—CH(CH$_3$)$_2$, —O—C(CH$_3$)$_3$, —S—CF$_3$, —S—CCl$_3$, —S—CBr$_3$, —S—CHF$_2$, —S—CH$_2$F, —S—CF$_2$Cl, —S—CCl$_2$F, —S—CF$_2$—CH$_3$, —S—CH$_2$—CF$_3$, —S—C$_2$F$_5$, —S—CH$_2$—CCl$_3$, —S—CH$_2$—CBr$_3$, —S—CHF—CF$_2$Cl, —S—CF$_2$—CF$_2$Cl, —S—CFCl—CF$_2$Cl, —S—CF$_2$—CF$_2$—CF$_3$, —S—CF(CF$_3$)$_2$, —S—CH(CH$_3$)$_2$, —S—C(CH$_3$)$_3$, —S(=O)$_2$—CF$_3$, —S(=O)$_2$—CCl$_3$, —S(=O)$_2$—CBr$_3$, —S(=O)$_2$—CHF$_2$, —S(=O)$_2$—CH$_2$F, —S(=O)$_2$—CF$_2$Cl, —S(=O)$_2$—CCl$_2$F, —S(=O)$_2$—CF$_2$—CH$_3$, —S(=O)$_2$—CH$_2$—CF$_3$, —S(=O)$_2$—C$_2$F$_5$, —S(=O)$_2$—CH$_2$—CCl$_3$, —S(=O)$_2$—CH$_2$—CBr$_3$, —S(=O)$_2$—CHF—CF$_2$Cl, —S(=O)$_2$—CF$_2$—CF$_2$Cl, —S(=O)$_2$—CFCl—CF$_2$Cl, —S(=O)$_2$—CF$_2$—CF$_2$—CF$_3$, —S(=O)$_2$—CF(CF$_3$)$_2$, —S(=O)$_2$—CH(CH$_3$)$_2$ and —S(=O)$_2$—C(CH$_3$)$_3$;

or denotes a residue selected from the group consisting of cyclopropyl, cyclobutyl, cyclopentyl, cyclohexyl, cyclopentenyl and cyclohexenyl;

T denotes C—R$^6$ and U denotes C—R$^7$ and V denotes N and W denotes C—R$^8$ or T denotes C—R$^6$ and U denotes N and V denotes C—R$^9$ and W denotes C—R$^8$ or T denotes N and U denotes C—R$^7$ and V denotes C—R$^9$ and W denotes C—R$^8$ or T denotes N and U denotes N and V denotes C—R$^9$ and W denotes C—R$^8$ or T denotes N and U denotes C—R$^7$ and V denotes N and W denotes C—R$^8$ or T denotes C—R$^6$ and U denotes N and V denotes N and W denotes C—R$^8$ or T denotes C—R$^6$ and U denotes C—R$^7$ and V denotes C—R$^9$ and W denotes C—R$^{10}$;

R$^6$ and R$^7$, mutually independently, in each case denote H; F; Cl; Br; I; —NO$_2$; —CN; —C(=O)—OCH$_3$; —C(=O)—OC$_2$H$_5$; or denote a residue selected from the group consisting of —CH$_2$—OH, methyl, —CF$_3$, —CCl$_3$, —CBr$_3$, —CHF$_2$, —CH$_2$F, —CF$_2$Cl, —CCl$_2$F, ethyl, n-propyl, isopropyl, sec-butyl, isobutyl and tert-butyl or denote a phenyl residue, which may optionally be substituted in each case with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl and n-pentyl;

R$^8$ denotes H; F; Cl; Br; I; —OH; —CN; —NH$_2$; —NO$_2$; —NHR$^{11}$; —NR$^{12}$R$^{13}$; —OR$^{14}$; —SR$^{15}$; —C(=O)—OR$^{22}$;

or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —CH$_2$—CH$_2$—CH$_2$—CF$_3$, —CH$_2$—CH$_2$—CH$_2$—CF$_3$, —CH$_2$—C(=O)—O—CH$_3$, —CH$_2$—C(=O)—C$_2$H$_5$, —CH$_2$—C(=O)—C(CH$_3$)$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, n-butyl, 3-methyl-but-1-yl, 4-methyl-pent-1-yl, n-pentyl, n-hexyl, (3,3)-dimethyl-but-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue selected from the group consisting of cyclopropyl, piperazinyl, azepanyl, diazepanyl, azocanyl and thiomorpholinyl, which is in each case attached to the parent structure via a carbon atom of the rings of the above-case attached to the parent structure via a carbon atom of the rings of the above-stated residues or via a —(CH=CH)—, —C≡C— or —C≡C—CH$_2$-group and may optionally in selected from the group consisting of —C(=O)—O—CH$_3$, —C(=O)—O—C$_2$H$_5$, —C(=O)—O-selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]—phenyl, oxo (=O), thioxo (=S), methyl, ethyl, n-propyl, isopropyl, n-butyl, sec-butyl, or denotes a residue selected from the group consisting of (1,3)-benzodioxolyl, (1,4)-benzodioxanyl, indolyl, tetrazolyl, (2,3)-dihydrothieno[3,4-b][1,4]dioxinyl, thiophenyl, furanyl and pyridinyl, which may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH$_3$, —NH—S(=O)$_2$—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^9$ denotes H; F; Cl; Br; I; —NO$_2$; —CN; or denotes a residue selected from the group consisting of methyl, —CF$_3$, —CCl$_3$, —CBr$_3$, —CHF$_2$, —CH$_2$F, —CF$_2$Cl, —CCl$_2$F, ethyl n-propyl, —CF$_2$—CF$_2$—CF$_3$, —CF(CF$_3$)$_2$, isopropyl, sec-butyl, isobutyl and tert-butyl;

R$^{10}$ denotes —CN; —OH; —NH$_2$; —NO$_2$; —NHR$^{11}$; —NR$^{12}$R$^{13}$; —OR$^{14}$; —SR$^{15}$; —C(=O)—OR$^{22}$;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—

$C_2H_5$, —N—[C(=O)—$C_2H_5$]-phenyl, —N—[C(=O)—$CH_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of (1,3)-benzodioxolyl, (1,4)-benzodioxanyl, indolyl, tetrazolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, which may in each case be attached via a —(CH=CH)—, —C≡C—, —($CH_2$)—, —($CH_2$)$_2$— or —($CH_2$)$_3$-group and/or in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —N($CH_3$)$_2$, —N($C_2H_5$)$_2$, —NH—S(=O)$_2$—$CH_3$, —NH—S(=O)$_2$)—$C_2H_5$, —NH—S(=O)$_2$—CH($CH_3$)$_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl and tert-butyl;

$R^{11}$, $R^{12}$, $R^{13}$, $R^{14}$, $R^{15}$ and $R^{22}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —$CH_2$—$CH_2$—O—$CH_3$, —$CH_2$—$CH_2$—O—$C_2H_5$, —$CH_2$—$CH_2$—O-phenyl, —$CH_2$—$CH_2$—$CH_2$—O—$CH_3$, ethenyl, propenyl, 2-butenyl, 3-butenyl, 2-pentenyl and 3-pentenyl;

denote a residue selected from the group consisting of 2,3-dihydro-1H-indenyl, cyclopropyl, oxetanyl, cyclobutyl, cyclopentyl, cyclohexyl, pyrrolidinyl, piperidinyl, morpholinyl, piperazinyl, azepanyl, diazepanyl, azocanyl and thiomorpholinyl, which may in each case be attached via a —$CH_2$—O—, —$CH_2$—$CH_2$—O—, —$CH_2$—$CH_2$—O—$CH_2$—, —$CH_2$—CH($CH_3$)—O—$CH_2$—, —($CH_2$)—, —($CH_2$)$_2$— or —($CH_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—$CH_3$, —C(=O)—O—$C_2H_5$, —C(=O)—O—CH($CH_3$)$_2$ and —C(=O)—O—C($CH_3$)$_3$;

or denote a residue selected from the group consisting of —($CH_2$)-pyridinyl, —($CH_2$)$_2$-pyridinyl, benzyl, phenethyl, phenyl, naphthyl, oxazolyl, thiazolyl, imidazolyl, pyrimidinyl, thiophenyl, furanyl, pyrrolyl and pyridinyl, which may optionally be substituted in each case with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl and tert-butyl;

or $R^{12}$ and $R^{13}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl and thiomorpholinyl, which may optionally in each case be substituted with 1, 2, 3, 4 or 5 substituents mutually independently selected from the group consisting of —$CH_2$—O—$CH_2$-oxetanyl, —O—$CH_2$-oxetanyl, —$CH_2$—OH, —$CH_2$—$CH_2$—OH, =$CH_2$, (4,5)-dihydroisoxazolyl, thiazolyl, (1,2,5)-thiadiazolyl, thiophenyl, phenethyl, —CN, —$CH_2$—N($CH_3$)$_2$, —$CH_2$—N($C_2H_5$)$_2$, —$CH_2$—NH—$CH_3$, —$CH_2$—NH—$C_2H_5$, —N—[C(=O)—$C_2H_5$]-phenyl, —N—[C(=O)—$CH_3$]-phenyl, —$CH_2$—O—$CH_3$, —$CH_2$—O—$CH_2$—$CH_3$, oxo (=O), thioxo (=S), F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl, tert-butyl, n-pentyl, —C(=O)—$CH_3$, —C(=O)—$C_2H_5$, —C(=O)—CH($CH_3$)$_2$, —C(=O)—C($CH_3$)$_3$, —C(=O)—OH, —C(=O)—O—$CH_3$, —C(=O)—O—$C_2H_5$, —C(=O)—O—CH($CH_3$)$_2$, —C(=O)—O—C($CH_3$)$_3$, —NH—$CH_3$, —NH—$C_2H_5$, —NH—C($CH_3$)$_3$, —N($CH_3$)$_2$, —N($C_2H_5$)$_2$, —N($CH_3$)($C_2H_5$), —NH-phenyl, —N($CH_3$)-phenyl, —N($C_2H_5$)-phenyl, —N($C_2H_5$)-phenyl, —O—$CH_2$—$CH_2$—$CH_2$—$CH_3$, cyclohexyl, cyclopentyl, piperidinyl, pyrrolidinyl, —O—C(=O)—$CH_3$, —O—C(=O)—$C_2H_5$, —O—C(=O)—C($CH_3$)$_3$, —($CH_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—$C_2H_5$]-phenyl, —N—[C(=O)—$CH_3$]-phenyl, —NH-phenyl, —N($CH_3$)-phenyl, —N($C_2H_5$)-phenyl, —($CH_2$)-pyridinyl, pyridinyl, —O-phenyl, —O-benzyl, N($CH_3$)-phenyl, —N($C_2H_5$)-phenyl, —($CH_2$)-pyridinyl, pyridinyl, —O-phenyl, —O-benzyl, phenyl and benzyl may optionally be substituted with 1, 2, 3, 4 or 5 substituents mutually independently selected from the group consisting of —$CF_3$, F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—CH($CH_3$)$_2$, —O—C($CH_3$)$_3$, —O—$CF_3$, —S—$CF_3$, phenyl and —O-benzyl;

and $R^{25}$ and $R^{26}$, mutually independently, in each case denote a hydrogen residue; denote an alkyl residue selected from the group consisting of —$CH_2$—OH, —$CH_2$—$CH_2$—OH, —$CH_2$—$CH_2$—$CH_2$—OH, —$CH_2$—$CH_2$—$CH_2$—$CH_2$—OH, isopropyl, n-butyl, sec-butyl, consisting of phenyl, benzyl, phenethyl, cyclopropyl, cyclobutyl, cyclopentyl and cyclohexyl; providing that $R^{25}$ and $R^{26}$ do not in each case denote a hydrogen residue;

providing that $R^{25}$ and $R^{26}$ do not in each case denote a hydrogen residue;

or $R^{25}$ and $R^{26}$ in each case together with the carbon atom joining them together as a cyclobutyl, cyclopentyl, cyclohexyl and cycloheptyl;

and $R^{30}$, $R^{31}$ and $R^{32}$, mutually independently, in each case denote an alkyl residue isopropyl, tert-butyl, n-butyl, sec-butyl and isobutyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise preferred compounds are those of above-stated general formulae I, B1 and B2, in which X denotes O or S;

n denotes 0, 1 or 2;

$R^1$, $R^3$ and $R^4$ in each case denote H;

$R^2$ denote F; Cl; Br; I or denote a residue selected from the group consisting of methyl, —$CF_3$, —$CCl_3$, —$CBr_3$, —CHF$_2$, —CH$_2$F, —O—CH$_3$, —O—CF$_3$, —O—CCl$_3$, —O—CBr$_3$, —O—CHF$_2$, —O—CH$_2$F, —S—CH$_3$, —S—CF$_3$, —S—CCl$_3$, —S—CBr$_3$, —S—CHF$_2$, —S—CH$_2$F, —S—CF$_2$Cl and S—CCl$_2$F;

R$^5$ denotes F; Cl; Br; I; —SF$_5$;

denotes a residue selected from the group consisting of methyl, ethyl, —CF$_3$, —CCl$_3$, —CBr$_3$, —CHF$_2$, —CH$_2$F, —CF$_2$Cl, —CCl$_2$F, —C(CH$_3$)$_2$(CH$_2$OH), tert-butyl, —O—CF$_3$, —O—CCl$_3$, —O—CBr$_3$, —O—CHF$_2$, —O—CH$_2$F, —O—CF$_2$Cl, —O—CCl$_2$F, —O—CF$_2$—CH$_3$, —S—CF$_3$, —S—CCl$_3$, —S—CBr$_3$, —S—CHF$_2$, —S—CH$_2$F, —S—CF$_2$Cl, —S—CCl$_2$F, —S—CF$_2$—CH$_3$, —S(=O)$_2$—CF$_3$, —S(=O)$_2$—CCl$_3$, —S(=O)$_2$—CBr$_3$, —S(=O)$_2$—CHF$_2$, —S(=O)$_2$—CH$_2$F and —S(=O)$_2$—CF$_2$Cl;

or denotes a residue selected from the group consisting of cyclopropyl, cyclobutyl, cyclopentyl, cyclohexyl, cyclopentenyl and cyclohexenyl;

T denotes C—R$^6$ and U denotes C—R$^7$ and V denotes N and W denotes C—R$^8$ or T denotes C—R$^6$ and U denotes N and V denotes C—R$^9$ and W denotes C—R$^8$ or T denotes N and U denotes C—R$^7$ and V denotes C—R$^9$ and W denotes C—R$^8$ or T denotes N and U denotes N and V denotes C—R$^9$ and W denotes C—R$^8$ or T denotes N and U denotes C—R$^7$ and V denotes N and W denotes C—R$^8$ or T denotes C—R$^6$ and U denotes N and V denotes N and W denotes C—R$^8$ or T denotes C—R$^6$ and U denotes C—R$^7$ and V denotes C—R$^9$ and W denotes C—R$^{10}$;

R$^6$ and R$^7$ in each case denote —CF$_3$; phenyl; —C(=O)—OCH$_3$; —C(=O)—OC$_2$H$_5$; methyl; —CH$_2$—OH; H; F; Cl; Br and I;

R$^8$ denotes H; F; Cl; Br; I; —CN; —OH; —NH$_2$; —NO$_2$; —NHR$^{11}$; —NR$^{12}$R$^{13}$; —OR$^{14}$; —SR$^{15}$; —C(=O)—OR$^{22}$;

denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$O, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —CH$_2$—CH$_2$—CH$_2$—CF$_3$, —CH$_2$—CH$_2$—CH$_2$—CH$_2$—CF$_3$, —CH$_2$—C(=O)—O—CH$_3$, —CH$_2$—C(=O)—C$_2$H$_5$, —CH$_2$—C(=O)—C(CH$_3$)$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, n-butyl, pentyl, n-hexyl, (3,3)-dimethyl-but-1-yl, 4-methyl-pent-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of (1,3)-benzodioxolyl, (1,4)-benzodioxanyl, indolyl, tetrazolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, which may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH$_3$, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^9$ denotes —CF$_3$; H; F; Cl; Br or I;

R$^{10}$ denotes —CN; —NH$_2$; —NO$_2$; —NHR$^{11}$; —NR$^{12}$R$^{13}$; —OR$^{14}$; —SR$^{15}$; —C(=O)—OR$^{22}$;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[(=O)—CH$_3$]-phenyl, phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of (1,3)-benzodioxolyl, (1,4)-benzodioxanyl, indolyl, tetrazolyl, (2,3)-dihydrothieno[3,4-b][1,4]dioxinyl, benzod ioxanyl, indolyl, tetrazolyl, (2,3)-dihydrothieno[3,4-b][1,4]dioxinyl, thiophenyl, furanyl and pyridinyl, which may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH$_3$, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11}$, R$^{12}$, R$^{13}$, R$^{14}$, R$^{15}$ and R$^{22}$, mutually independently, in each case denote a residue selected from the group consisting of methyl, ethyl, n-propyl, isopropyl, n-butyl, sec-butyl, isobutyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—

$CH_2$—O—$C_2H_5$, —$CH_2$—$CH_2$—O-phenyl, —$CH_2$—$CH_2$—$CH_2$—O—$CH_3$, ethenyl, propenyl, 2-butenyl, 3-butenyl, 2-pentenyl, 3-pentenyl and tert-butyl;

denote a residue selected from the group consisting of 2,3-dihydro-1H-indenyl, piperidinyl, pyrrolidinyl, cyclopropyl, oxetanyl, cyclobutyl, cyclopentyl and cyclohexyl, which may in each case be attached via a —$CH_2$—O—, —$CH_2$—$CH_2$—O—, —$CH_2$—$CH_2$—O—$CH_2$—, —$CH_2$—CH($CH_3$)—O—$CH_2$—, —($CH_2$)—, —($CH_2$)$_2$— or —($CH_2$)$_3$- group and/or in each case may optionally be substituted with 1, 2, 3, 4 or 5 substituents selected from the group consisting of methyl, ethyl, n-propyl, isopropyl, n-butyl, sec-butyl, —C(=O)—O—$CH_3$, —C(=O)—O—$C_2H_5$, —C(=O)—O—CH($CH_3$)$_2$ and —C(=O)—O—C($CH_3$)$_3$;

or denote a residue selected from the group consisting of —($CH_2$)-pyridinyl, —($CH_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF3, F, Cl, Br, —O—$CH_3$, —O—$C_2H_5$, methyl, ethyl, n-propyl, isopropyl, n-butyl, sec-butyl, isobutyl and tert-butyl;

or $R^{12}$ and $R^{13}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl and thiomorpholinyl, which may optionally in each case be substituted with 1 or 2 substituents mutually independently selected from the group consisting of —$CH_2$—O—$CH_2$-oxetanyl, —O—$CH_2$-oxetanyl, —$CH_2$—OH, —$CH_2$—$CH_2$—OH, =$CH_2$, (4,5)-dihydroisoxazolyl, thiazolyl, (1,2,5)-thiadiazolyl, thiophenyl, phenethyl, —CN, —$CH_2$—N($CH_3$)$_2$, —$CH_2$—N($C_2H_5$)$_2$, —$CH_2$—NH—$CH_3$, —$CH_2$—NH—$C_2H_5$, —N—[C(=O)—$C_2H_5$]-phenyl, —N—[C(=O)—$CH_3$]-phenyl, —$CH_2$—O—$CH_3$, —$CH_2$—O—$CH_2$—$CH_3$, oxo (=O), thioxo (=S), F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl, tert-butyl, n-pentyl, —C(=O)—$CH_3$, —C(=O)—$C_2H_5$, —C(=O)—CH($CH_3$)$_2$, —C(=O)—C($CH_3$)$_3$, —C(=O)—OH, —C(=O)—O—$CH_3$, —C(=O)—O—$C_2H_5$, —C(=O)—O—CH($CH_3$)$_2$, —C(=O)—O—C($CH_3$)$_3$, —NH—$CH_3$, —NH—$C_2H_5$, —NH—C($CH_3$)$_3$, —N($CH_3$)$_2$, —N($C_2H_5$)$_2$, —N($CH_3$)($C_2H_5$), —NH-phenyl, —N($CH_3$)-phenyl, —N($C_2H_5$)-phenyl, —N($C_2H_5$)-phenyl, —O—$CH_2$—$CH_2$—$CH_2$—$CH_3$, cyclohexyl, cyclopentyl, piperidinyl, pyrrolidinyl, —O—C(=O)—CH3, —O—C(=O)—$C_2H_5$, —O—C(=O)—C($CH_3$)$_3$, —($CH_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—$C_2H_5$]-phenyl, —N—[C(=O)—$CH_3$]-phenyl, —NH-phenyl, —N($CH_3$)-phenyl, —N($C_2H_5$)-phenyl, —($CH_2$)-pyridinyl, pyridinyl, —O-phenyl, —O-benzyl, phenyl and benzyl may optionally be substituted with 1, 2, 3, 4 or 5 substituents mutually independently selected from the group consisting of —$CF_3$, F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—CH($CH_3$)$_2$, —O—C($CH_3$)$_3$, —O—$CF_3$, —S—$CF_3$, phenyl and —O-benzyl;

and $R^{25}$ and $R^{26}$, mutually independently, in each case denote a hydrogen residue; denote an alkyl residue selected from the group consisting of —$CH_2$—OH, —$CH_2$—$CH_2$—OH, —$CH_2$—$CH_2$—$CH_2$—OH, —$CH_2$—$CH_2$—$CH_2$—$CH_2$—OH, isopropyl, n-butyl, sec-butyl, isobutyl, methyl, ethyl and n-propyl or denote a residue selected from the group consisting of phenyl, benzyl, phenethyl, cyclopropyl, cyclobutyl, cyclopentyl and cyclohexyl;

providing that $R^{25}$ and $R^{26}$ do not in each case denote a hydrogen residue;

or $R^{25}$ and $R^{26}$ in each case together with the carbon atom joining them together as a ring member, form a residue selected from the group consisting of cyclopropyl, cyclobutyl, cyclopentyl, cyclohexyl and cycloheptyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise preferred compounds are those of above-stated general formulae I, B1 and B2, in which X denotes O;

n denotes 1;

$R^1$, $R^3$ and $R^4$ in each case denote H; $R^2$ denote methyl; —O—$CH_3$; F; Cl; Br or I;

$R^5$ denote a residue selected from the group consisting of methyl, ethyl, —$CF_3$, —$CCl_3$, —$CBr_3$, —$CHF_2$, —$CH_2F$, —$CF_2Cl$, —$CCl_2F$, —C($CH_3$)$_2$($CH_2OH$), tert-butyl, —O—$CCl_3$, —O—$CBr_3$, —O—$CHF_2$, —O—$CH_2F$, —S—$CF_3$, —S—$CCl_3$, —S—$CBr_3$, —S—$CHF_2$ and —S—$CH_2F$;

or denote a residue selected from the group consisting of cyclopropyl, cyclobutyl, cyclopentyl, cyclohexyl, cyclopentenyl and cyclohexenyl;

T denotes CH and U denotes CH and V denotes N and W denotes C—$R^8$ or

T denotes CH and U denotes N and V denotes CH and W denotes C—$R^8$ or

T denotes N and U denotes CH and V denotes CH and W denotes C—$R^8$ or

T denotes N and U denotes N and V denotes CH and W denotes C—$R^8$ or

T denotes N and U denotes CH and V denotes N and W denotes C—$R^8$ or

T denotes CH and U denotes N and V denotes N and W denotes C—$R^8$ or

T denotes CH and U denotes CH and V denotes CH and W denotes C—$R^{10}$;

$R^8$ denotes H; F; Cl; Br; I; —CN; —OH; —$NH_2$; —$NO_2$; —$NHR^{11}$; —$NR^{12}R^{13}$; —$OR^{14}$; —$SR^{15}$;

or denotes a residue selected from the group consisting of methyl, —$CF_3$, —$CCl_3$, —$CBr_3$, —$CHF_2$, —$CH_2F$, —$CF_2Cl$, —$CCl_2F$, ethyl, —$CF_2$—$CH_3$, —$CH_2$—$CF_3$, —$C_2F_5$, —$CH_2$—$CCl_3$, —$CH_2$—$CBr_3$, —CHF—$CF_2Cl$, —$CF_2$—$CF_2Cl$, —CFCl—$CF_2Cl$, n-propyl, —$CF_2$—$CF_2$—

$CF_3$, —$CF(CF_3)_2$, isopropyl, sec-butyl, isobutyl, tert-butyl, —$CH_2$—$CH_2$—$CH_2$—$CF_3$, —$CH_2$—$CH_2$—$CH_2$—$CH_2$—$CF_3$, —$CH_2$—C(=O)—O—$CH_3$, —$CH_2$—C(=O)—$C_2H_5$, —$CH_2$—C(=O)—C($CH_3$)$_3$, —$CH_2$—O—C(=O)—$CH_3$, —$CH_2$—O—C(=O)—$C_2H_5$, —$CH_2$—O—C(=O)—CH($CH_3$)$_2$, —$CH_2$—O—C(=O)—C($CH_3$)$_3$, n-butyl, 3-methyl-but-1-yl, 4-methyl-pent-1-yl, n-pentyl, n-pentyl, n-hexyl, (3,3)-dimethyl-but-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

or denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—$CH_2$-group and may optionally in each case be substituted with 1, 2, 3, 4 or 5 substituents mutually independently selected from the group consisting of —C(=O)—O—$CH_3$, —C(=O)—O—$C_2H_5$, —C(=O)—O—C($CH_3$)$_3$, —C(=O)—$CH_3$, —C(=O)—$C_2H_5$, —C(=O)—C($CH_3$)$_3$, —CN, —$CH_2$—N($CH_3$)$_2$, —$CH_2$—N($C_2H_5$)$_2$, —$CH_2$—NH—$CH_3$, —$CH_2$—NH—$C_2H_5$, —N—[C(=O)—$C_2H_5$]-phenyl, —N—[(=O)—$CH_3$]-phenyl, phenyl, oxo (=O), thioxo (=S), methyl, ethyl, n-propyl, isopropyl, n-butyl, sec-butyl, isobutyl, tert-butyl and n-pentyl;

or denotes a radical selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, which may in each case be attached via a —(CH=CH)—, —C≡C—, —($CH_2$)—, —($CH_2$)$_2$— or —($CH_2$)$_3$-group and/or in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —N($CH_3$)$_2$, —N($C_2H_5$)$_2$, —NH—S(=O)$_2$—CH3, —NH—S(=O$_2$)—$C_2H_5$, —NH—S(=O)$_2$—CH($CH_3$)$_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl and tert-butyl;

$R^{10}$ denotes —CN; —$NH_2$; —$NO_2$; —$NHR^{11}$; —$NR^{12}R^{13}$; —$OR^{14}$; —$SR^{15}$;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—$CH_2$-group and may optionally in each case be substituted with 1, 2, 3, 4 or 5 substituents mutually independently selected from the group consisting of —C(=O)—O—$CH_3$, —C(=O)—O—$C_2H_5$, —C(=O)—O—C($CH_3$)$_3$, —C(=O)—$CH_3$, —C(=O)—$C_2H_5$, —C(=O)—C($CH_3$)$_3$, —CN, —$CH_2$—N($CH_3$)$_2$, —$CH_2$—N($C_2H_5$)$_2$, —$CH_2$—NH—$CH_3$, —$CH_2$—NH—$C_2H_5$, —N—[C(=O)—$C_2H_5$]-phenyl, —N—[(=O)—$CH_3$]-phenyl, phenyl, oxo (=O), thioxo (=S), methyl, ethyl, n-propyl, isopropyl, n-butyl, sec-butyl, isobutyl, tert-butyl and n-pentyl;

or denotes a radical selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, which may in each case be attached via a —(CH=CH)—, —C≡C—, —($CH_2$)—, —($CH_2$)$_2$— or —($CH_2$)$_3$-group and/or in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —N($CH_3$)$_2$, —N($C_2H_5$)$_2$, —NH—S(=O)$_2$—CH3, —NH—S(=O$_2$)—$C_2H_5$, —NH—S(=O)$_2$—CH($CH_3$)$_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl and tert-butyl substituted;

$R^{11}$, $R^{12}$, $R^{13}$, $R^{14}$ and $R^{15}$, mutually independently, in each case denotes a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —$CH_2$—$CH_2$—O—$CH_3$, —$CH_2$—$CH_2$—O—$C_2H_5$, —$CH_2$—$CH_2$—O-phenyl, —$CH_2$—$CH_2$—$CH_2$—O—$CH_3$, ethenyl, propenyl, 2-butenyl, 3-butenyl, 2-pentenyl and 3-pentenyl;

denotes a radical selected from the group consisting of 2,3-dihydro-1H-indenyl, piperidinyl, pyrrolidinyl, cyclopropyl, oxetanyl, cyclobutyl, cyclopentyl and cyclohexyl, which may in each case be attached via a —$CH_2$—O—, —$CH_2$—$CH_2$—O—, —$CH_2$—$CH_2$—O—$CH_2$—, —$CH_2$—CH($CH_3$)—$CH_2$—, —($CH_2$)—, —($CH_2$)$_2$— or —($CH_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—$CH_3$, —C(=O)—O—$C_2H_5$, —C(=O)—O—CH($CH_3$)$_2$ and —C(=O)—O—C($CH_3$)$_3$;

or denotes a radical selected from the group consisting of —($CH_2$)-pyridinyl, —($CH_2$)$_2$-pyridinyl, benzyl, phenethyl, phenyl, naphthyl, thiophenyl, furanyl, pyrrolyl and pyridinyl, which may in each case optionally be substituted with 1, 2, 3, 4 or 5 substituents selected from the group consisting of —CF3, F, Cl, Br, —O—$CH_3$, —O—$C_2H_5$, methyl, ethyl, n-propyl, isopropyl, n-butyl, sec-butyl, isobutyl and tert-butyl;

or $R^{12}$ and $R^{13}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which may optionally in each case be substituted with 1 or 2 substituents mutually independently selected from the group consisting of —$CH_2$—O—$CH_2$-oxetanyl, —O—$CH_2$-oxetanyl, —$CH_2$—OH, —$CH_2$—$CH_2$—OH, =$CH_2$, —C(=O)—O—$CH_3$, —C(=O)—O—$C_2H_5$, —C(=O)—O—C($CH_3$)$_3$, —C(=O)—$CH_3$, —C(=O)—$C_2H_5$, —C(=O)—C($CH_3$)$_3$, —CN, —$CH_2$—N($CH_3$)$_2$, —$CH_2$—N($C_2H_5$)$_2$, —$CH_2$—NH—$CH_3$, —$CH_2$—NH—$C_2H_5$, —N—[(=O)—$CH_5$]-phenyl, —N—[C(=O)—$CH_3$]-phenyl, —$CH_2$—O—$CH_3$, —$CH_2$—O—$CH_2$—$CH_3$, —$NH_2$, —NH—$CH_3$, —NH—$C_2H_5$, —N($CH_3$)$_2$, —N($C_2H_5$)$_2$, —NH-phenyl, —N($CH_3$)-phenyl, —N($C_2H_5$)-phenyl, oxo (=O), thioxo (=S), —OH, F, Cl, Br, —$CF_3$, —O—$CH_3$, —O—$C_2H_5$, —O—C($CH_3$)$_3$, —O—CH($CH_3$)$_2$, —O—$CH_2$—$CH_2$—$CH_2$—$CH_3$, methyl, ethyl, isopropyl, n-propyl, n-butyl, tert-butyl, sec-butyl, cyclohexyl, cyclopentyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, (4,5)-dihydroisoxazolyl, thiazolyl, (1,2,5)-thiadiazolyl, thiophenyl, phenethyl, pyridinyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—C$_2$H$_5$]-phenyl, —N—[C(=O)—CH$_3$]-phenyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

and

R$^{25}$ denotes an alkyl residue selected from the group consisting of —CH$_2$—OH, —CH$_2$—CH$_2$—OH, methyl, ethyl and n-propyl or denotes a residue selected from the group consisting of benzyl, phenyl, phenethyl, cyclopropyl, cyclobutyl, cyclopentyl and cyclohexyl;

R$^{26}$ denote a hydrogen residue or denote a residue selected from the group consisting of methyl, ethyl and n-propyl;

or

R$^{25}$ and R$^{26}$ in each case together with the carbon atom joining them together as a ring member, form a residue selected from the group consisting of cyclopropyl, cyclobutyl, cyclopentyl and cyclohexyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Ia1,

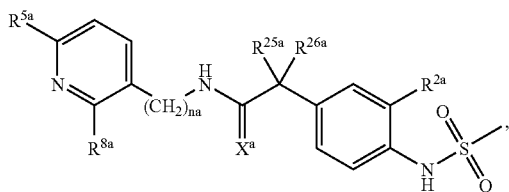

Ia1 in which

X$^a$ denotes O or S;

na denotes 0, 1 or 2;

R$^{2a}$ denotes F; Cl; Br; I or denotes a residue selected from the group consisting of methyl, —CF$_3$, —CCl$_3$, —CBr$_3$, —CHF$_2$, —CH$_2$F, —O—CH$_3$, —O—CF$_3$, —O—CCl$_3$, —O—CBr$_3$, —O—CHF$_2$, —O—CH$_2$F, —S—CH$_3$, —S—CF$_3$, —S—CCl$_3$, —S—CBr$_3$, —S—CHF$_2$, —S—CH$_2$F, —S—CF$_2$Cl and —S—-CCl$_2$F;

R$^{5a}$ denotes F; Cl; Br; I; —SF$_5$;

denotes a residue selected from the group consisting of methyl, ethyl, —CF$_3$, —CCl$_3$, —CBr$_3$, —CHF$_2$, —CH$_2$F, —CF$_2$Cl, —CCl$_2$F, —C(CH$_3$)$_2$—(CH$_2$OH), tert-butyl, —O—CF$_3$, —O—CCl$_3$, —O—CBr$_3$, —O—CHF$_2$, —O—CH$_2$F, —O—CF$_2$Cl, —O—CCl$_2$F, —O—CF$_2$—CH$_3$, —S—CF$_3$, —S—CCl$_3$, —S—CBr$_3$, —S—CHF$_2$, —S—CH$_2$F, —S—CF$_2$Cl, —S—CCl$_2$F, —S—CF$_2$—CH$_3$, —S(=O)$_2$—CF$_3$, —S(=O)$_2$—CCl$_3$, —S(=O)$_2$—CBr$_3$, —S(=O)$_2$—CHF$_2$, —S(=O)$_2$—CH$_2$F and —S(=O)$_2$—CF$_2$Cl;

or denotes a residue selected from the group consisting of cyclopropyl, cyclobutyl, cyclopentyl, cyclohexyl, cyclopentenyl and cyclohexenyl;

R$^{8a}$ denotes H; F; Cl; Br; I; —CN; —OH; —NH$_2$; —NO$_2$; —NHR$^{11a}$; —NR$^{12a}$R$^{13a}$; —OR$^{14a}$; —SR$^{15a}$; —C(=O)—OR$^{22a}$;

or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —CH$_2$—CH$_2$—CH$_2$—CF$_3$, —CH$_2$—CH$_2$—CH$_2$—CH$_2$—CF$_3$, —CH$_2$—C(=O)—O—CH$_3$, —CH$_2$—C(=O)—C$_2$H$_5$, —CH$_2$—C(=O)—C(CH$_3$)$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, n-butyl, 3-methyl-but-1-yl, 4-methyl-pent-1-yl, n-pentyl, n-hexyl, (3,3)-dimethyl-but-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzodioxolyl, (1,4)-benzodioxanyl, indolyl, (2,3)-dihydrothieno[3,4-b][1,4]dioxinyl, thiophenyl, furanyl and pyridinyl, which may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH3, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11a}$, R$^{12a}$, R$^{13a}$, R$^{14a}$, R$^{15a}$ and R$^{22a}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, piperidinyl, pyrrolidinyl, cyclopropyl, cyclobutyl, cyclopentyl and cyclohexyl, which may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which may optionally be substituted with 1, 2, 3, 4 or 5 substituents mutually independently selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or $R^{12a}$ and $R^{13a}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which may optionally in each case be substituted with 1 or 2 substituents mutually independently selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—C$_2$H$_5$]-phenyl, —N—[C(=O)—CH$_3$]-phenyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

$R^{25a}$ and $R^{26a}$, mutually independently, in each case denote a hydrogen residue; denote a residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

providing that $R^{25a}$ and $R^{26a}$ do not in each case denote a hydrogen residue;

or $R^{25a}$ and $R^{26a}$, in each case together with the carbon atom joining them together as a ring member, form a residue selected from the group consisting of cyclopropyl, cyclobutyl, cyclopentyl, cyclohexyl and cycloheptyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Ia,

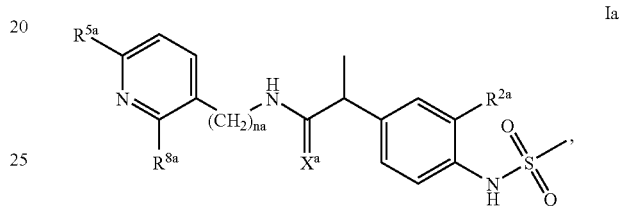

in which $X^a$, na, $R^{5a}$, $R^{8a}$ and $R^{2a}$ have the meaning as defined above;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise particularly preferred compounds are those of general formula Ia, in which $X^a$ denotes O or S;

na denotes 0, 1 or 2;

$R^{2a}$ denotes F; Cl; Br; I or denotes a residue selected from the group consisting of methyl, —CF$_3$, —CCl$_3$, —CBr$_3$, —CHF$_2$, —CH$_2$F, —O—CH$_3$, —O—CF$_3$, —O—CCl$_3$, —O—CBr$_3$, —O—CHF$_2$, —O—CH$_2$F, —S—CH$_3$, —S—CF$_3$, —S—CCl$_3$, —S—CBr$_3$, —S—CHF$_2$, —S—CH$_2$F, —S—CF$_2$Cl and S—CCl$_2$F;

$R^{5a}$ denotes F; Cl; Br; I; —SF$_5$;

denotes a residue selected from the group consisting of methyl, ethyl, —CF$_3$, —CCl$_3$, —CBr$_3$, —CHF$_2$, —CH$_2$F, —CF$_2$Cl, —CCl$_2$F, —C(CH$_3$)$_2$—(CH$_2$OH), tert-butyl, —O—CF$_3$, —O—CCl$_3$, —O—CBr$_3$, —O—CHF$_2$, —O—CH$_2$F, —O—CF$_2$Cl, —O—CCl$_2$F, —O—CF$_2$—CH$_3$, —S—CF$_3$, —S—CCl$_3$, —S—CBr$_3$, —S—CHF$_2$, —S—CH$_2$F, —S—CF$_2$Cl, —S—CCl$_2$F, —S—CF$_2$—CH$_3$, —S(=O)$_2$—CF$_3$, —S(=O)$_2$—CCl$_3$, —S(=O)$_2$—CBr$_3$, —S(=O)$_2$—CHF$_2$, —S(=O)$_2$—CH$_2$F and —S(=O)$_2$—CF$_2$Cl;

or denotes a residue selected from the group consisting of cyclopropyl, cyclobutyl, cyclopentyl, cyclohexyl, cyclopentenyl and cyclohexenyl;

$R^{8a}$ denotes H; F; Cl; Br; I; —CN; —OH; —NH$_2$; —NO$_2$; —NHR$^{11a}$; —NR$^{12a}$R$^{13a}$; —OR$^{14a}$; —SR$^{15a}$; —C(=O)—OR$^{22a}$;

or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —CH$_2$—CH$_2$—CH$_2$—CF$_3$, —CH$_2$—CH$_2$—CH$_2$—CF$_3$, —CH$_2$—C(=O)—O—CH$_3$, —CH$_2$—C(=O)—C$_2$H$_5$, —CH$_2$—C(=O)—C(CH$_3$)$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, n-butyl, 3-methyl-but-1-yl, 4-methyl-pent-1-yl, n-pentyl, n-hexyl, (3,3)-dimethyl-but-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

or denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[(=C)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, (2,3)-dihydrothieno[3,4-b][1,4]dioxinyl, benzo[b]furanyl, indolyl, phenyl, naphthyl, oxazolyl, thiazolyl, imidazolyl, pyrimidinyl, thiophenyl, furanyl and pyridinyl, which may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —H, —O—CH$_3$, —O—C$_2$H$_5$, —NH$_2$, —N(CH$_3$)$_2$, —N(C$_2$H$_5$)$_2$, —NH—S(=O)$_2$—CH3, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

$R^{11a}$, $R^{12a}$, $R^{13a}$, $R^{14a}$, $R^{15a}$ and $R^{22a}$, mutually independently, in each case denote a radical from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a radical selected from the group consisting of 2,3-dihydro-1H-indenyl, piperidinyl, pyrrolidinyl, cyclopropyl, cyclobutyl, oxetanyl, cyclopentyl and cyclohexyl, which may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or $R^{12a}$ and $R^{13a}$ in each case together with the nitrogen atom joining them together as a ring member, form a residue selected from the group consisting of

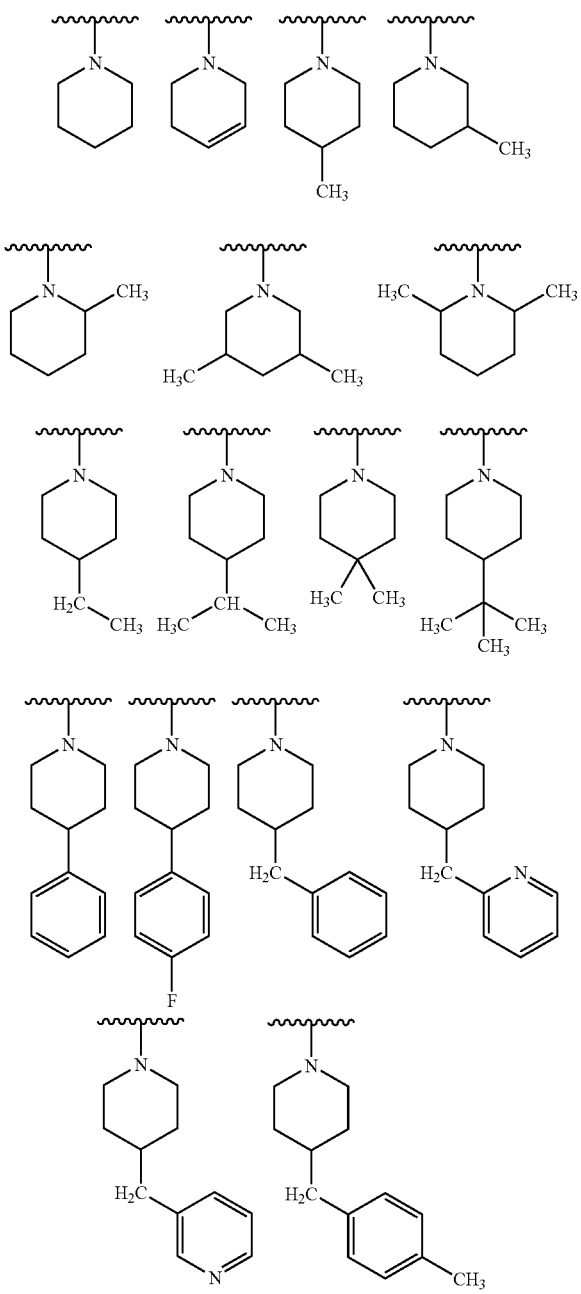

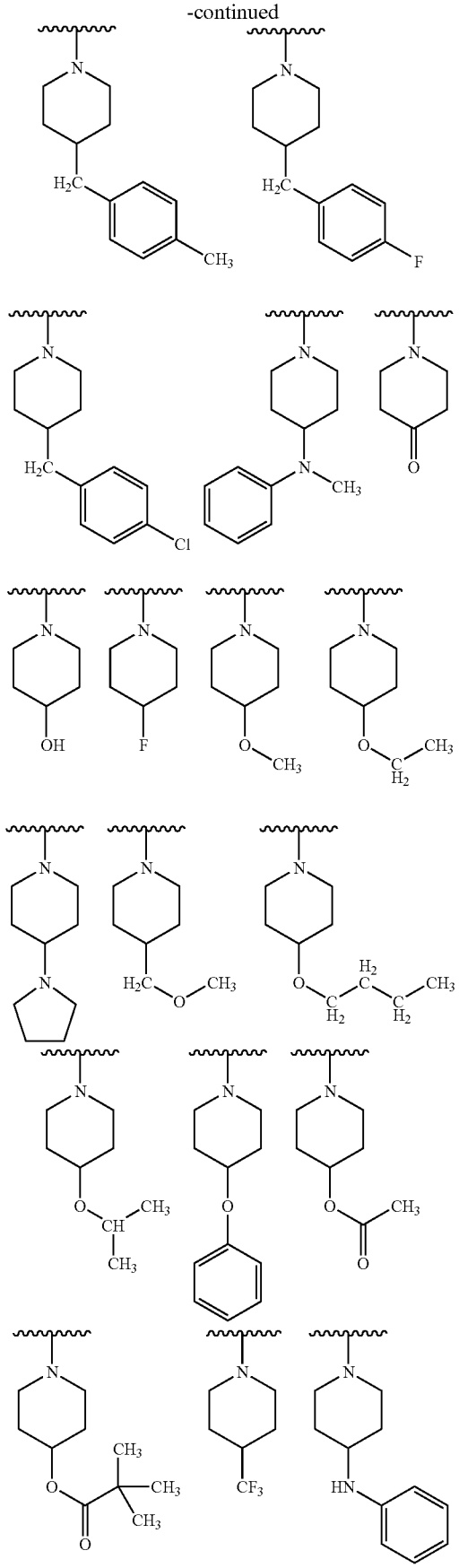
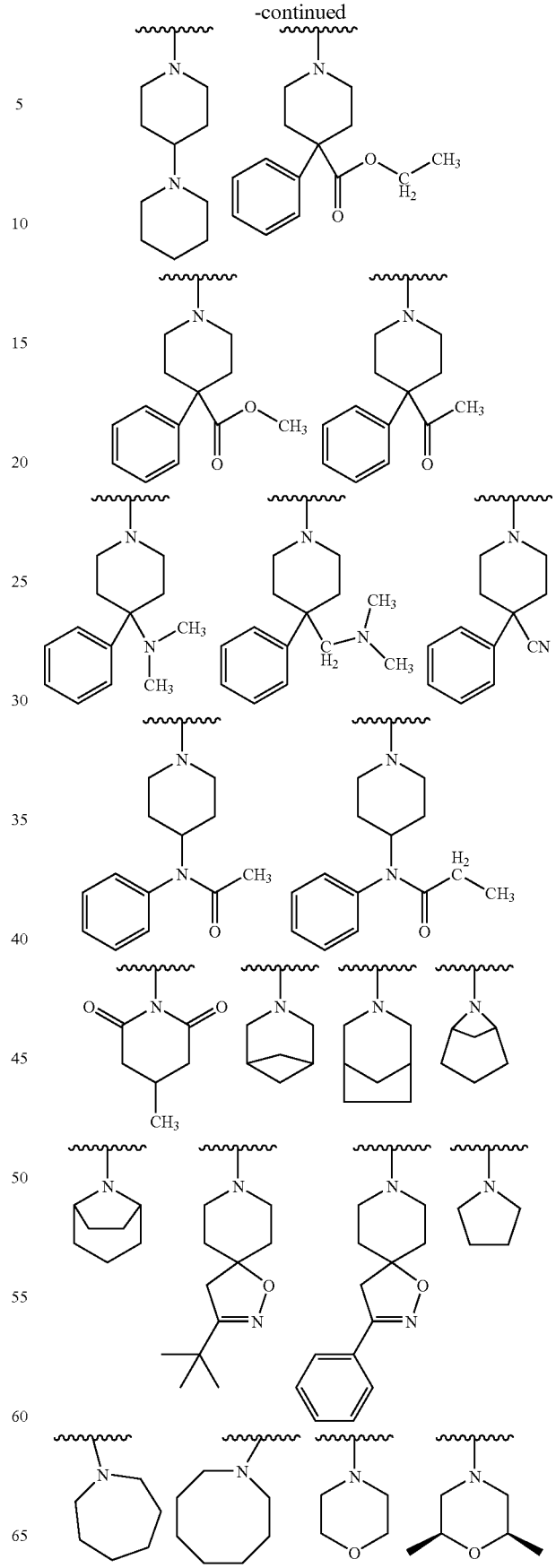

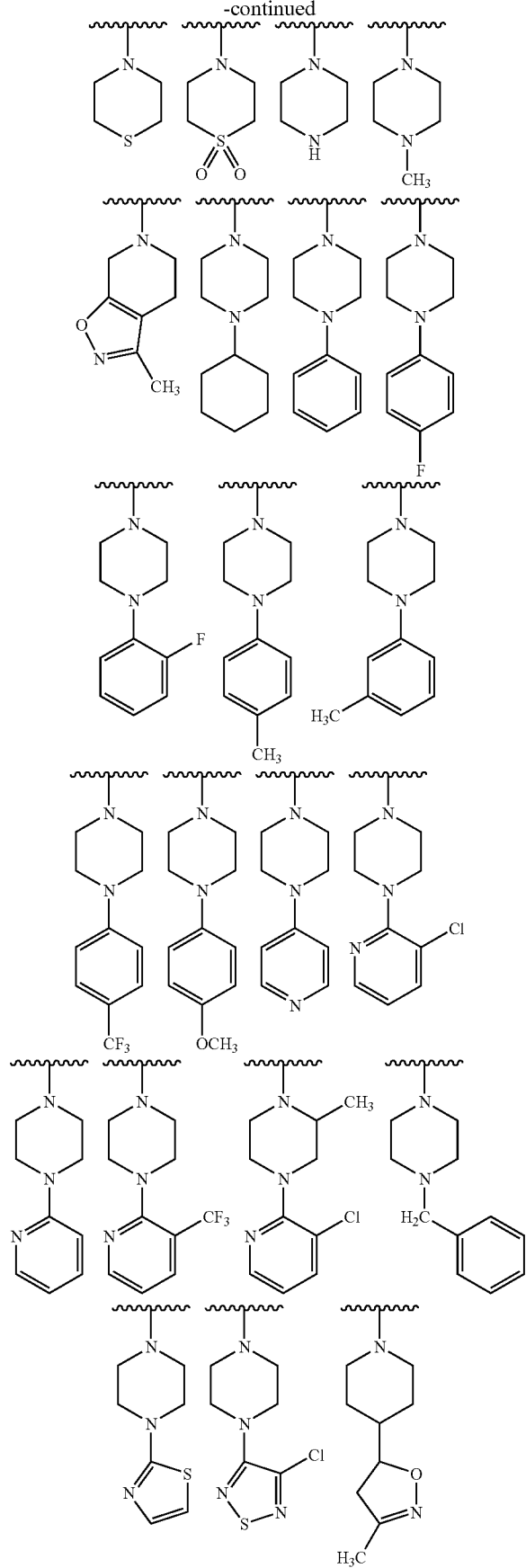
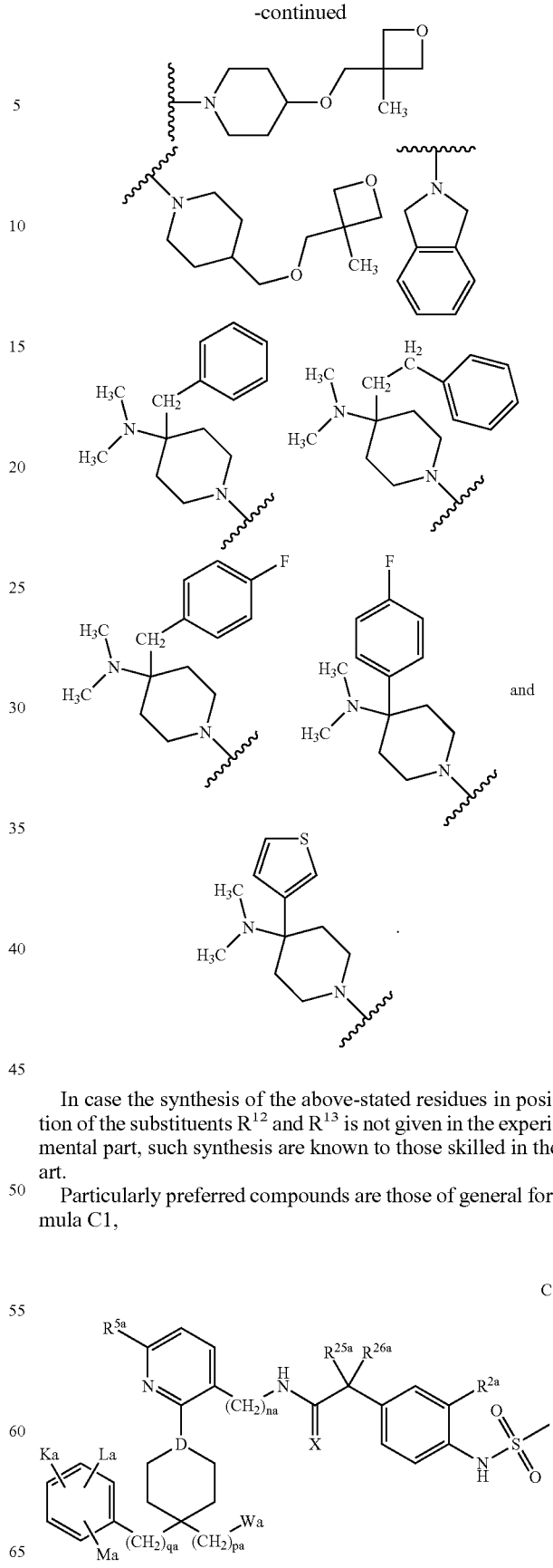
In case the synthesis of the above-stated residues in position of the substituents $R^{12}$ and $R^{13}$ is not given in the experimental part, such synthesis are known to those skilled in the art.
Particularly preferred compounds are those of general formula C1, in which na, $R^{2a}$, $R^{25a}$, $R^{26a}$, $R^{5a}$ and $X^a$ have the meaning as defined above;

D denotes CH or N;

pa denotes 0, qa denotes 0, 1 or 2;

Ka, La and Ma, mutually independently, in each case denote H, —$CF_3$, —OH, —O—$CH_3$, —O—$C_2H_5$, F, Cl, Br, methyl, ethyl, isopropyl, n-propyl, n-butyl, tert-butyl or sec-butyl;

Wa denotes $NR^{34a}R^{35a}$, —CN, —C(=O)—$R^{36a}$ or —C(=O)—$OR^{37a}$;

and $R^{34a}$, $R^{35a}$, $R^{36a}$ and $R^{37a}$, mutually independently, in each case denote H or denote a residue selected from the group consisting of methyl, ethyl, n-propyl, isopropyl, n-butyl, sec-butyl and isobutyl.

Likewise particularly preferred compounds are those of general formula C2,

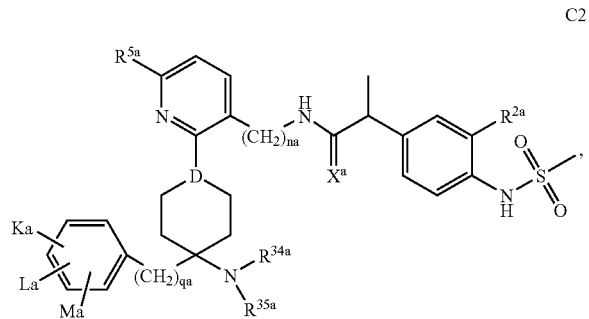

C2 in which na, $R^{2a}$, $R^{5a}$ and $X^a$ have the meaning as defined above;

D denotes CH or N;

qa denotes 0, 1 or 2;

Ka, La and Ma, mutually independently, in each case denote H, —$CF_3$, —OH, —O—$CH_3$, —O—$C_2H_5$, F, Cl, Br, methyl, ethyl, isopropyl, n-propyl, n-butyl, tert-butyl or sec-butyl;

and $R^{34a}$ and $R^{35a}$, mutually independently, in each case denote H or denote a residue selected from the group consisting of methyl, ethyl, n-propyl, isopropyl, n-butyl, sec-butyl and isobutyl.

Particularly preferred compounds are those of general formula Ib1,

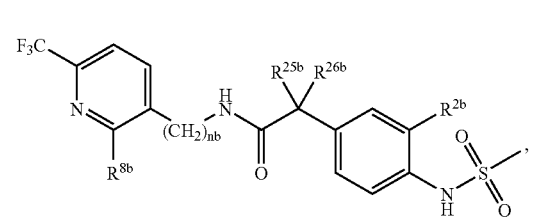

Ib1 in which nb denotes 0, 1 or 2;

$R^{2b}$ denotes methyl; —O—$CH_3$; F; Cl; Br or I;

$R^{8b}$ denotes H; F; Cl; Br; I; —CN; —OH; —$NH_2$; —$NO_2$; —$NHR^{11b}$; —$NR^{12b}R^{13b}$; —$OR^{14b}$; —$SR^{15b}$;

denotes a residue selected from the group consisting of methyl, —$CF_3$, —$CCl_3$, —$CBr_3$, —$CHF_2$, —$CH_2F$, —$CF_2Cl$, —$CCl_2F$, ethyl, —$CF_2$—$CH_3$, —$CH_2$—$CF_3$, —$C_2F_5$, —$CH_2$—$CCl_3$, —$CH_2$—$CBr_3$, —CHF—$CF_2Cl$, —$CF_2$—$CF_2Cl$, —CFCl—$CF_2Cl$, n-propyl, —$CF_2$—$CF_2$—$CF_3$, —$CF(CF_3)_2$, isopropyl, sec-butyl, isobutyl, tert-butyl, —$CH_2$—$CH_2$—$CH_2$—$CF_3$, —$CH_2$—$CH_2$—$CH_2$—$CH_2$—$CF_3$, —$CH_2$—C(=O)—O—$CH_3$, —$CH_2$—C(=O)—$C_2H_5$, —$CH_2$—C(=O)—C($CH_3$)$_3$, —$CH_2$—O—C(=O)—$CH_3$, —$CH_2$—O—C(=O)—$C_2H_5$, —$CH_2$—O—C(=O)—CH($CH_3$)$_2$, —$CH_2$—O—C(=O)—C($CH_3$)$_3$, n-butyl, n-pentyl, n-hexyl, (3,3)-dimethyl-but-1-yl, 3-methyl-but-1-yl, 4-methyl-pent-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—$CH_2$-group and may optionally in each case be substituted with 1, 2, 3, 4 or 5 substituents mutually independently selected from the group consisting —C(=O)—O—$CH_3$, —C(=O)—O—$C_2H_5$, —C(=O)—O—C($CH_3$)$_3$, —C(=O)—$CH_3$, —C(=O)—$C_2H_5$, —C(=O)—C($CH_3$)$_3$, —CN, —$CH_2$—N($CH_3$)$_2$, —$CH_2$—N($C_2H_5$)$_2$, —$CH_2$—NH—$CH_3$, —$CH_2$—NH—$C_2H_5$, —N—[C(=O)—$C_2H_5$]-phenyl, —N—[C(=O)—$CH_3$]-phenyl, oxo (=O), thioxo (=S), methyl ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzodioxolyl, (1,4)-benzodioxanyl, indolyl, (2,3)-dihydrothieno[3,4-b][1,4]dioxinyl, thiophenyl, furanyl and pyridinyl, which may in each case be attached via a —(CH=CH)—, —C≡C—, —($CH_2$)—, —($CH_2$)$_2$— or —($CH_2$)$_3$-group and/or in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —N($CH_3$)$_2$, —N($C_2H_5$)$_2$, —NH—S(=O)$_2$—CH3, —NH—S(=O$_2$)—$C_2H_5$, —NH—S(=O)$_2$—CH($CH_3$)$_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl and tert-butyl;

$R^{11b}$, $R^{12b}$, $R^{13b}$, $R^{14b}$ and $R^{15b}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —$CH_2$—$CH_2$—O—$CH_3$, —$CH_2$—$CH_2$—O—$C_2H_5$, —$CH_2$—$CH_2$—O-phenyl, —$CH_2$—$C_2$—$CH_2$—O—$CH_3$, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, which may in each case be attached via a —$CH_2$—O—, —$CH_2$—$CH_2$—O—, —$CH_2$—$CH_2$—O—$CH_2$—, —$CH_2$—CH($CH_3$)—O—$CH_2$—, —($CH_2$)—, —($CH_2$)$_2$— or —($CH_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(═O)—O—CH₃, —C(═O)—O—C₂H₅, —C(═O)—O—CH(CH₃)₂ and —C(═O)—O—C(CH₃)₃;

or denotes a residue selected from the group consisting of —(CH₂)-pyridinyl, —(CH₂)₂—pyridinyl, benzyl, phenethyl, phenyl, naphthyl, thiophenyl, furanyl, pyrrolyl and pyridinyl, which may optionally be substituted in each case with 1, 2, 3, 4 or 5 substituents selected from the group consisting of —CF3, F, Cl, Br, —O—CH₃, —O—C₂H₅, methyl, ethyl, n-propyl, isopropyl, n-butyl, sec-butyl, isobutyl and tert-butyl;

or $R^{12b}$ and $R^{13b}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which may optionally in each case be substituted with 1 or 2 substituents mutually independently selected from the group consisting of —CH₂—O—CH₂-oxetanyl, —O—CH₂-oxetanyl, —CH₂—OH, —CH₂—CH₂—OH, ═CH₂, —C(═O)—O—CH₃, —C(═O)—O—C₂H₅, —C(═O)—O—C(CH₃)₃, —C(═O)—CH₃, —C(═O)—C₂H₅, —C(═O)—C(CH₃)₃, —CN, —CH₂—N(CH₃)₂, —CH₂—N(C₂H₅)₂, —CH₂—NH—CH₃, —CH₂—NH—C₂H₅, —N—[C(═O)—C₂H₅]-phenyl, —N—[C(═O)—CH₃]-phenyl, —CH₂—O—CH₃, —CH₂—O—CH₂—CH₃, —NH₂, —NH—CH₃, —NH—C₂H₅, —N(CH₃)₂, —N(C₂H₅)₂, —NH-phenyl, —N(CH₃)-phenyl, —N(C₂H₅)-phenyl, oxo (═O), thioxo (═S), —OH, F, Cl, Br, —CF₃, —O—CH₃, —O—C₂H₅, —O—C(CH₃)₃, —O—CH(CH₃)₂, —O—CH₂—CH₂—CH₂—CH₃, methyl, ethyl, isopropyl, n-propyl, n-butyl, tert-butyl, sec-butyl, (4,5)-dihydroisoxazolyl, thiazolyl, (1,2,5)-thiadiazolyl, thiophenyl, phenethyl, cyclohexyl, cyclopentyl, piperidinyl, pyrrolidinyl, —O-phenyl, —O—C(═O)—CH₃, —O—C(═O)—C₂H₅, —O—C(═O)—C(CH₃)₃, —(CH₂)-pyridinyl, pyridinyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(═O)—C₂H₅]-phenyl, —N—[C(═O)—CH₃]-phenyl, —NH-phenyl, —N(CH₃)-phenyl, —N(C₂H₅)-phenyl, —(CH₂)-pyridinyl, pyridinyl, phenyl, —O-phenyl and benzyl may optionally be substituted with 1, 2, 3, 4 or 5 substituents mutually independently selected from the group consisting of —CF₃, —OH, —O—CH₃, —O—C₂H₅, F, Cl, Br, methyl, ethyl, isopropyl, n-propyl, n-butyl, tert-butyl and sec-butyl;

$R^{25b}$ and $R^{26b}$, mutually independently, in each case denote a hydrogen residue; denote an alkyl residue selected from the group consisting of —CH₂—OH, —CH₂—CH₂—OH, —CH₂—CH₂—CH₂—OH, —CH₂—CH₂—CH₂—CH₂—OH, isopropyl, n-butyl, sec-butyl, isobutyl, methyl, ethyl and n-propyl;

providing that $R^{25b}$ and $R^{26b}$ do not in each case denote a hydrogen residue;

or $R^{25b}$ and $R^{26b}$ in each case together with the carbon atom joining them together as a ring member, form a residue selected from the group consisting of cyclopropyl, cyclobutyl, cyclopentyl, cyclohexyl and cycloheptyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Ib,

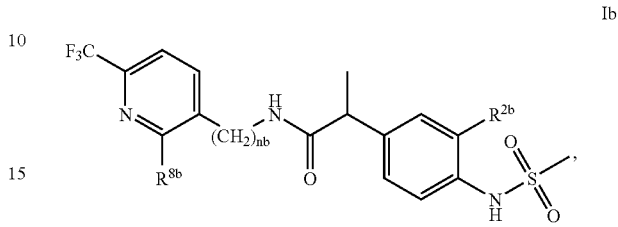

Ib in which nb, $R^{8b}$ and $R^{2b}$ have the meaning as defined above;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Ib, in which nb denotes 1;

$R^{2b}$ denotes F;

$R^{8b}$ denotes H; F; Cl; Br; I; —CN; —OH; —NH₂; —NO₂; —NHR^{11b}; —NR^{12b}R^{13b}; —OR^{14b}; SR^{15b};

denotes a residue selected from the group consisting of methyl, —CF₃, —CCl₃, —CBr₃, —CHF₂, —CH₂F, —CF₂Cl, —CCl₂F, ethyl, —CF₂—CH₃, —CH₂—CF₃, —C₂F₅, —CH₂—CBr₃, —CHF—CF₂Cl, —CF₂—CF₂Cl, —CFCl—CF₂Cl, n-propyl, —CF₂—CF₂—CF₃, —CF(CF₃)₂, isopropyl, sec-butyl, isobutyl, tert-butyl, —CH₂—CH₂—CH₂—CF₃, —CH₂—CH₂—CH₂—CH₂—CF₃, —CH₂—C(═O)—O—CH₃, —CH₂—C(═O)—C₂H₅, —CH₂—C(═O)—C(CH₃)₃, —CH₂—O—C(═O)—CH₃, —CH₂—O—C(═O)—C₂H₅, —CH₂—O—C(═O)—CH(CH₃)₂, —CH₂—O—C(═O)—C(CH₃)₃, n-butyl, n-pentyl, n-hexyl, (3,3)-dimethyl-but-1-yl, 3-methyl-but-1-yl, 4-methyl-pent-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH═CH)—, —C≡C— or —C≡C—CH₂-group and may optionally in each case be substituted with 1, 2, 3, 4 or 5 substituents mutually independently selected from the group consisting of —C(═O)—O—CH₃, —C(═O)—O—C₂H₅, —C(═O)—O—C(CH₃)₃, —C(═O)—CH₃, —C(═O)—C₂H₅, —C(═O)—C(CH₃)₃, —CN, —CH₂—N(CH₃)₂, —CH₂—N(C₂H₅)₂, —CH₂—NH—CH₃, —CH₂—NH—C₂H₅, —N—[C(═O)—C₂H₅]-phenyl, —N—[C(═O)—CH₃]-phenyl, oxo (═O), thioxo (═S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, which may in each case be attached via a —(CH═CH)—, —C≡C—, —(CH$_2$)—, —(CH$_2$)$_2$— or —(CH$_2$)$_3$-group and/or may optionally in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(═O)$_2$—CH3, —NH—S(═O$_2$)—C$_2$H$_5$, —NH—S(═O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

$R^{11b}$, $R^{12b}$, $R^{13b}$, $R^{14b}$ and $R^{15b}$, mutually independently, in each case denote a residue selected from the group consisting of —(CH$_2$)-pyridinyl, —(CH$_2$)$_2$-pyridinyl, methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, oxetanyl, piperidinyl, pyrrolidinyl, cyclopropyl, cyclobutyl, cyclopentyl and cyclohexyl, which may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(═O)—O—CH$_3$, —C(═O)—O—C$_2$H$_5$, —C(═O)—O—CH(CH$_3$)$_2$ and —C(═O)—O—C(CH$_3$)$_3$;

or denote a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or $R^{12b}$ and $R^{13b}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, ═CH$_2$, —C(═O)—O—CH$_3$, —C(═O)—O—C$_2$H$_5$, —C(═O)—O—C(CH$_3$)$_3$, —C(═O)—CH$_3$, —C(═O)—C$_2$H$_5$, —C(═O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(═O)—C$_2$H$_5$]-phenyl, —N—[C(═O)—CH$_3$]-phenyl, —CH$_2$—O—CH$_3$, —CH$_2$—O—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (═O), thioxo (═S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—Ch$_3$, methyl, ethyl, isopropyl, n-propyl, n-butyl, tert-butyl, sec-butyl, (4,5)-dihydroisoxazolyl, thiazolyl, (1,2,5)-thiadiazolyl, thiophenyl, phenethyl, cyclohexyl, cyclopentyl, piperidinyl, pyrrolidinyl, —O-phenyl, —O—C(═O)—CH$_3$, —O—C(═O)—C$_2$H$_5$, —O—C(═O)—C(CH$_3$)$_3$, —(CH$_2$)-pyridinyl, pyridinyl, phenyl and benzyl, wherein in each case the cyclic moiety of the residues oxetanyl, —N—[C(═O)—C$_2$H$_5$]-phenyl, —N—[C(═O)—CH$_3$]—phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Ic1,

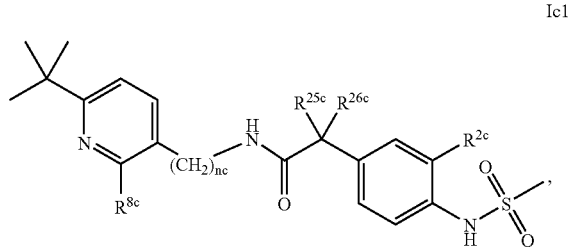

Ic1 in which nc denotes 0, 1 or 2;

$R^{2c}$ denotes methyl; —O—CH$_3$; F; Cl; Br or I;

$R^{8c}$ denotes H; F; Cl; Br; I; —CN; —OH; —NH$_2$; —NO$_2$; —NHR$^{11c}$; —NR$^{12c}$R$^{13c}$; —OR$^{14c}$; —SR$^{15c}$;

denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —CH$_2$—CH$_2$—CH$_2$—CF$_3$, —CH$_2$—CH$_2$—CH$_2$—CH$_2$—CF$_3$, —CH$_2$—C(═O)—O—CH$_3$, —CH$_2$—C(═O)—C$_2$H$_5$, —CH$_2$—C(═O)—C(CH$_3$)$_3$, —CH$_2$—O—C(═O)—CH$_3$, —CH$_2$—O—C(═O)—C$_2$H$_5$, —CH$_2$—O—C(═O)—CH(CH$_3$)$_2$, —CH$_2$—O—C(═O)—C(CH$_3$)$_3$, n-butyl, pentyl, n-hexyl, (3,3)-dimethyl-but-1-yl, 3-methyl-but-1-yl, 4-methyl-pent-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH═CH)—, —C≡C— or —C≡C—CH$_2$-group and in each case may optionally be substituted with 1, 2, 3, 4 or 5 substituents selected from the group consisting of —C(═O)—O—CH$_3$, —C(═O)—O—C$_2$H$_5$, —C(═O)—O—C(CH$_3$)$_3$, —C(═O)—CH$_3$, —C(═O)—C$_2$H$_5$, —C(═O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(═O)—C$_2$H$_5$]-phenyl, —N—[C(═O)—CH$_3$]-phenyl, oxo (═O), thioxo (═S), methyl, ethyl, n-propyl, isopropyl, n-butyl, sec-butyl, isobutyl, tert-butyl and n-pentyl;

or a residue selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, which may in each case be attached via a —(CH═CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(═O)$_2$—CH$_3$, —NH—S(═O$_2$)—C$_2$H$_5$, —NH—S(═O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

$R^{11c}$, $R^{12c}$, $R^{13c}$, $R^{14c}$ and $R^{15c}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, piperidinyl, pyrrolidinyl, cyclopropyl, cyclobutyl, oxetanyl, cyclopentyl and cyclohexyl, which may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(═O)—O—CH$_3$, —C(═O)—O—C$_2$H$_5$, —C(═O)—O—CH(CH$_3$)$_2$ and —C(═O)—O—C(CH$_3$)$_3$;

or denotes a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or $R^{12c}$ and $R^{13c}$ in each case together with the nitrogen atom joining them together as a ring member, form a residue selected from the group consisting of 3-aza-bicyclo[3.1.1]heptyl, 6-aza-aza-spiro[2.5]octyl, 3-aza-bicyclo[3.2.1]octyl, 6-aza-aza-bicyclo[3.3.1]heptyl, 8-aza-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, ═CH$_2$, —C(═O)—O—CH$_3$, —C(═O)—O—C$_2$H$_5$, —C(═O)—O—C(CH$_3$)$_3$, —C(═O)—CH$_3$, —C(═O)—C$_2$H$_5$, —C(═O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(═O)—C$_2$H$_5$]-phenyl, —N—[C(═O)—CH$_3$]-phenyl, phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (═O), thioxo (═S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(═O)—CH$_3$, —O—C(═O)—C$_2$H$_5$, —O—C(═O)—C(CH$_3$)$_3$, —(CH$_2$)-pyridinyl, pyridinyl, phenyl and benzyl, wherein in each case the cyclic moiety of the residues oxetanyl, —N—[C(═O)—C$_2$H$_5$]-phenyl, —N—[C(═O)—CH$_3$]-phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

$R^{25c}$ and $R^{26c}$, mutually independently, in each case denote a hydrogen residue; or denote a residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

providing that $R^{25c}$ and $R^{26c}$ do not in each case denote a hydrogen residue;

or $R^{25c}$ and $R^{26c}$ in each case together with the carbon atom joining them together as a ring member, form a residue selected from the group consisting of cyclopropyl, cyclobutyl, cyclopentyl, cyclohexyl and cycloheptyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Ic,

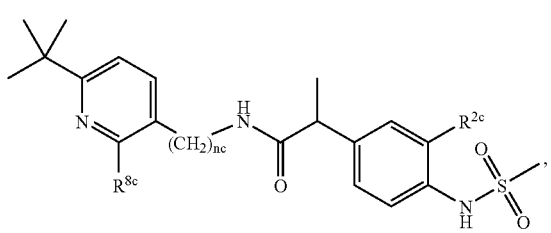

Ic in which nc, $R^{8c}$ and $R^{2c}$ have the meaning as defined above;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise particularly preferred compounds are those of general formula Ic, in which nc denotes 1;

$R^{2c}$ denotes F;

$R^{8c}$ denotes H; F; Cl; Br; I; —CN; —OH; —NH$_2$; —NO$_2$; —NHR$^{11c}$; —NR$^{12c}$R$^{13c}$; —OR$^{14c}$; SR$^{15c}$;

denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—Cl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —CH$_2$—CH$_2$—CH$_2$—CF$_3$, —CH$_2$—CH$_2$—CH$_2$—CH$_2$—CF$_3$, —CH$_2$—C(=O)—O—CH$_3$, —CH$_2$—C(=O)—C$_2$H$_5$, —CH$_2$—C(=O)—C(CH$_3$)$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, n-butyl, n-pentyl, n-hexyl, (3,3)-dimethyl-but-1-yl, 3-methyl-but-1-yl, 4-methyl-pent-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and in each case may optionally be substituted with 1, 2, 3, 4 or 5 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH3, —NH—S(=O$_2$)—C$_2$H$_5$, —NH—S(=O)$_2$—CH(CH$_3$)$_2$, NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

$R^{11c}$, $R^{12c}$, $R^{13c}$, $R^{14c}$ and $R^{15c}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, piperidinyl, pyrrolidinyl, cyclopropyl, cyclobutyl, oxetanyl, cyclopentyl and cyclohexyl, wherein the residue may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or $R^{12c}$ and $R^{13c}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_2$-oxetanyl, —O—CH$_2$-oxetanyl, —CH$_2$—OH, —CH$_2$—CH$_2$—OH, =CH$_2$, —CH$_2$—O—CH$_3$, —CH$_2$—O—CH$_2$—CH$_2$—OH, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, —N—[C(=O)—C$_2$H$_5$]-phenyl, —N—[C(=O)—CH$_3$]-phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Id1,

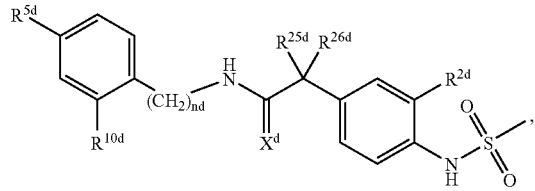

in which
$X^d$ denotes O or S;
nd denotes 0, 1 or 2;
$R^{2d}$ denotes F; Cl; Br; I or denotes a residue selected from the group consisting of methyl, —CF$_3$, —CCl$_3$, —CBr$_3$, —CHF$_2$, —CH$_2$F, —O—CH$_3$, —O—CF$_3$, —O—CCl$_3$, —O—CBr$_3$, —O—CHF$_2$, —O—CH$_2$F, —S—CH$_3$, —S—CF$_3$, —S—CCl$_3$, —S—CBr$_3$, —S—CHF$_2$, —S—CH$_2$F, —S—CF$_2$Cl and S—CCl$_2$F;

$R^{5d}$ denotes F; Cl; Br; I; —SF$_5$;
denotes a residue selected from the group consisting of methyl, ethyl, —CF$_3$, —CCl$_3$, —CBr$_3$, —CHF$_2$, —CH$_2$F, —CF$_2$Cl, —CCl$_2$F, —C(CH$_3$)$_2$—(CH$_2$OH), tert-butyl, —O—CF$_3$, —O—CCl$_3$, —O—CBr$_3$, —O—CHF$_2$, —O—CH$_2$F, —O—CF$_2$Cl, —O—CCl$_2$F, —O—CF$_2$—CH$_3$, —S—CF$_3$, —S—CCl$_3$, —S—CBr$_3$, —S—CHF$_2$, —S—CH$_2$F, —S—CF$_2$Cl, —S—CCl$_2$F, —S—CF$_2$—CH$_3$, —S(=O)$_2$—CF$_3$, —S(=O)$_2$—CCl$_3$, —S(=O)$_2$—CBr$_3$, —S(=O)$_2$—CHF$_2$, —S(=O)$_2$—CH$_2$F and —S(=O)$_2$—CF$_2$Cl;

or denotes a residue selected from the group consisting of cyclopropyl, cyclobutyl, cyclopentyl, cyclohexyl, cyclopentenyl and cyclohexenyl;

$R^{1d}$ denotes —CN; —OH; —NH$_2$; —NO$_2$; —NHR$^{11d}$; —NR$^{12d}$R$^{13d}$; —OR$^{14d}$; —SR$^{15d}$; —C(=O)—OR$^{22d}$;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and in each case may optionally be substituted with 1, 2, 3, 4 or 5 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, (2,3)-dihydrothieno[3,4-b][1,4]dioxinyl, benzodioxolyl, (1,4)-benzodioxanyl, (2,3)-dihydrothieno[3,4-b][1,4]dioxinyl, thiophenyl, furanyl and pyridinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH3, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

$R^{11d}$, $R^{12d}$, $R^{13d}$, $R^{14d}$, $R^{15d}$ and $R^{22d}$, mutually independently, in each case
denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, piperidinyl, pyrrolidinyl, cyclopropyl, cyclobutyl, oxetanyl, cyclopentyl and cyclohexyl, wherein the residue may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of —(CH$_2$)-pyridinyl, —(CH$_2$)$_2$-pyridinyl, phenyl, naphthyl, thiophenyl, furanyl, pyrrolyl and pyridinyl, which in each case may optionally be substituted with 1, 2, 3, 4 or 5 substituents selected from the group consisting of —CF3, F, Cl, Br, —O—CH$_3$, —O—C$_2$H$_5$, methyl, ethyl, n-propyl, isopropyl, n-butyl, sec-butyl, isobutyl and tert-butyl;

or
$R^{12d}$ and $R^{13d}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, —N—[C(=O)—C$_2$H$_5$]-phenyl, —N—[C(=O)—CH$_3$]-phenyl, (4,5)-dihydroisoxazolyl, thiazolyl, (1,2,5)-thiadiazolyl, thiophenyl, phenethyl, —NH-phenyl, —N(CH₃)-phenyl, —N(C₂H₅)-phenyl, —(CH₂)-pyridinyl, pyridinyl, phenyl, —O-phenyl and benzyl may optionally be substituted with 1, 2, 3, 4 or 5 substituents mutually independently selected from the group consisting of —CF₃, —OH, —O—CH₃, —O—C₂H₅, F, Cl, Br, methyl, ethyl, isopropyl, n-propyl, n-butyl, tert-butyl and sec-butyl;

$R^{25d}$ and $R^{26d}$, mutually independently, in each case denote a hydrogen residue; or denote an alkyl residue selected from the group consisting of —CH₂—OH, —CH₂—CH₂—OH, —CH₂—CH₂—CH₂—OH, —CH₂—CH₂—CH₂—CH₂—OH, isopropyl, n-butyl, sec-butyl, isobutyl, methyl, ethyl and n-propyl;

providing that $R^{25d}$ and $R^{26d}$ do not in each case denote a hydrogen residue;

or $R^{25d}$ and $R^{26d}$ in each case together with the carbon atom joining them together as a ring member, form a residue selected from the group consisting of cyclopropyl, cyclobutyl, cyclopentyl, cyclohexyl and cycloheptyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Id,

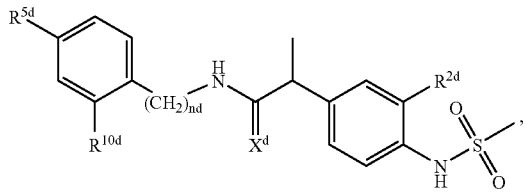

Id in which $X^d$, nd, $R^{2d}$, $R^{5d}$ and $R^{10d}$ have the meaning as defined above;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Ie1,

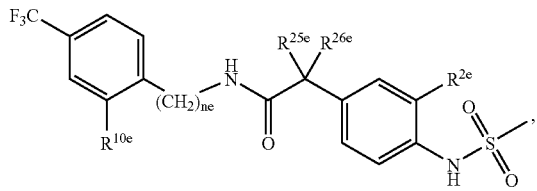

Ie1 in which ne denotes 0, 1 or;

$R^{2e}$ denotes methyl; —O—CH₃; F; Cl; Br or I;

$R^{10e}$ denotes —CN; —OH; —NH₂; —NO₂; —NHR$^{11e}$; —NR$^{12e}$R$^{13e}$; —OR$^{14e}$; —SR$^{15e}$;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH₂-group and in each case may optionally be substituted with 1, 2, 3, 4 or 5 substituents selected from the group consisting of —C(=O)—O—CH₃, —C(=O)—O—C₂H₅, —C(=O)—O—C(CH₃)₃, —C(=O)—CH₃, —C(=O)—C₂H₅, —C(=O)—C(CH₃)₃, —CN, —CH₂—N(CH₃)₂, —CH₂—N(C₂H₅)₂, —CH₂—NH—CH₃, —CH₂—NH—C₂H₅, —N—[C(=O)—C₂H₅]-phenyl, —N—[C(=O)—CH₃]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH₂)—, —(CH₂)₂— or —(CH₂)₃-group and/or in each case may optionally be substituted with 1, 2, 3, 4 or 5 substituents selected from the group consisting of F, Cl, Br, I, —CN, —CF₃, —SF₅, —OH, —O—CH₃, —O—C₂H₅, —NH₂, —N(CH₃)₂, —N(C₂H₅)₂, —NH—S(=O)₂—CH₃, —NH—S(=O)₂—C₂H₅, —NH—S(=O)₂—CH(CH₃)₂, —NO₂, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl and tert-butyl;

$R^{11e}$, $R^{12e}$, $R^{13e}$, $R^{14e}$ and $R^{15e}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH₂—CH₂—O—CH₃, —CH₂—CH₂—O—C₂H₅, —CH₂—CH₂—O-phenyl, —CH₂—CH₂—O—CH₃, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, wherein the residue may in each case be attached via a —CH₂—O—, —CH₂—CH₂—O—, —CH₂—CH₂—O—CH₂—, —CH₂—CH(CH₃)—O—CH₂—, —(CH₂)—, —(CH₂)₂— or —(CH₂)₃-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH₃, —C(=O)—O—C₂H₅, —C(=O)—O—CH(CH₃)₂ and —C(=O)—O—C(CH₃)₃;

or denote a residue selected from the group consisting of —(CH₂)-pyridinyl, —(CH₂)₂-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF3, F, Cl, Br, —O—CH₃, —O—C₂H₅, methyl, ethyl, n-propyl, isopropyl, n-butyl, sec-butyl, isobutyl and tert-butyl;

or $R^{12e}$ and $R^{13e}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, —N—[C(=O)—C$_2$H$_5$]-phenyl, —N—[C(=O)—CH$_3$]-phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

R$^{25e}$ and R$^{26e}$, mutually independently, in each denote a hydrogen residue;

or denote an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

providing that R$^{25e}$ and R$^{26e}$ do not in each case denote a hydrogen residue;

or

R$^{25e}$ and R$^{26e}$ in each case together with the carbon atom joining them together as a ring member, form a residue selected from the group consisting of cyclopropyl, cyclobutyl, cyclopentyl, cyclohexyl and cycloheptyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula Ie,

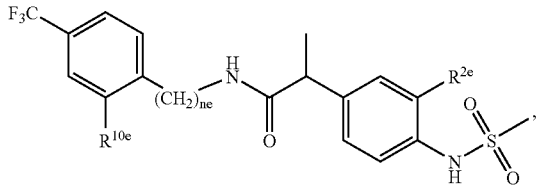

Ie in which ne, R$^{10e}$ and R$^{2e}$ have the meaning as defined above, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise particularly preferred compounds are those of general formula Ie, in which ne denotes 1;

R$^{2e}$ denotes F;

R$^{10e}$ denotes —CN; —OH; —NH$_2$; —NO$_2$; —NHR$^{11e}$; —NR$^{12e}$R$^{13e}$; —OR$^{14e}$; —SR$^{15e}$;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and in each case may optionally be substituted with 1, 2, 3, 4 or 5 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzodioxolyl, (1,4)-benzodioxanyl, indolyl, (2,3)-dihydrothieno[3,4-b][1,4]dioxinyl, thiophenyl, furanyl and pyridinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH$_3$, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11e}$, R$^{12e}$, R$^{13e}$, R$^{14e}$ and R$^{15e}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, wherein the residue may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH₃, —C(=O)—O—C₂H₅, —C(=O)—O—CH(CH₃)₂ and —C(=O)—O—C(CH₃)₃;

or denote a residue selected from the group consisting of —(CH₂)-pyridinyl, —(CH₂)₂-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF3, F, Cl, Br, —O—CH₃, —O—C₂H₅, methyl, ethyl, n-propyl, isopropyl, n-butyl, sec-butyl, isobutyl and tert-butyl;

or $R^{12e}$ and $R^{13e}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH₂—O—CH₂-oxetanyl, —O—CH₂-oxetanyl, —CH₂—OH, —CH₂—CH₂—OH, =CH₂, —C(=O)—O—CH₃, —C(=O)—O—C₂H₅, —C(=O)—O—C(CH₃)₃, —C(=O)—CH₃, —C(=O)—C₂H₅, —C(=O)—C(CH₃)₃, —CN, —CH₂—N(CH₃)₂, —CH₂—N(C₂H₅)₂, —CH₂—NH—CH₃, —CH₂—NH—C₂H₅, —N—[C(=O)—C₂H₅]-phenyl, —N—[C(=O)—CH₃]-phenyl, —CH₂—O—CH₃, —CH₂—O—CH₂—CH₃, —NH₂, —NH—CH₃, —NH—C₂H₅, —N(CH₃)₂, —N(C₂H₅)₂, —NH-phenyl, —N(CH₃)-phenyl, —N(C₂H₅)-phenyl, oxo (=O), thioxo (=S), —OH, F, Cl, Br, —CF₃, —O—CH₃, —O—C₂H₅, —O—C(CH₃)₃, —O—CH(CH₃)₂, —O—CH₂—CH₂—CH₂—CH₂—CH₃, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH₃, —O—C(=O)—C₂H₅, —O—C(=O)—C(CH₃)₃, —(CH₂)-pyridinyl, pyridinyl, phenyl and benzyl, wherein in each case the cyclic moiety of the residues oxetanyl, N—[C(=O)—C₂H₅]-phenyl, —N—[C(=O)—CH₃]-phenyl, (4,5)-dihydroisoxazolyl, thiazolyl, (1,2,5)-thiadiazolyl, thiophenyl, phenethyl, —NH-phenyl, —N(CH₃)-phenyl, —N(C₂H₅)-phenyl, —(CH₂)-pyridinyl, pyridinyl, phenyl, —O-phenyl and benzyl may optionally be substituted with 1, 2, 3, 4 or 5 substituents mutually independently selected from the group consisting of —CF₃, —OH, —O—CH₃, —O—C₂H₅, F, Cl, Br, methyl, ethyl, isopropyl, n-propyl, n-butyl, tert-butyl and sec-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula If1,

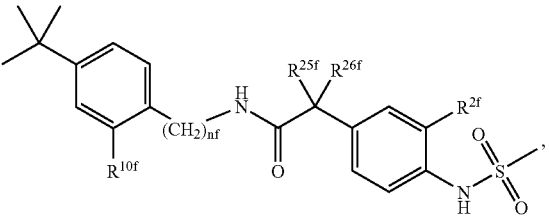

If1 in which nf denotes 0, 1 or 2;

$R^{2f}$ denotes methyl; —O—CH₃; F; Cl; Br or I;

$R^{10f}$ denotes —CN; —OH; —NH₂; —NO₂; —NHR$^{11f}$; —NR$^{12f}$R$^{13f}$; —OR$^{14f}$; —SR$^{15f}$;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH₂-group and in each case may optionally be substituted with 1, 2, 3, 4 or 5 substituents selected from the group consisting of —C(=O)—O—CH₃, —C(=O)—O—C₂H₅, —C(=O)—O—C(CH₃)₃, —C(=O)—CH₃, —C(=O)—C₂H₅, —C(=O)—C(CH₃)₃, —CN, —CH₂—N(CH₃)₂, —CH₂—N(C₂H₅)₂, —CH₂—NH—CH₃, —CH₂—NH—C₂H₅, —N—[C(=O)—C₂H₅]-phenyl, —N—[C(=O)—CH₃]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of (1,3)-benzodioxolyl, (1,4)-benzodioxanyl, indolyl, tetrazolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH₂)—, —(CH₂)₂— or —(CH₂)₃-group and/or in each case may optionally be substituted with 1, 2, 3, 4 or 5 substituents selected from the group consisting of F, Cl, Br, I, —CN, —CF₃, —SF₅, —OH, —O—CH₃, —O—C₂H₅, —NH₂, —N(CH₃)₂, —N(C₂H₅)₂, —NH—S(=O)₂—CH₃, —NH—S(=O)₂—C₂H₅, —NH—S(=O)₂—CH(CH₃)₂, —NO₂, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl and tert-butyl;

$R^{11f}$, $R^{12f}$, $R^{13f}$, $R^{14f}$ and $R^{15f}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH₂—CH₂—O—CH₃, —CH₂—CH₂—O—C₂H₅, —CH₂—CH₂—O-phenyl, —CH₂—CH₂—CH₂—O—CH₃, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, wherein the residue may in each case be attached via a —CH₂—O—, —CH₂—CH₂—O—, —CH₂—CH₂—O—CH₂—, —CH₂—CH(CH₃)—O—CH₂—, —(CH₂)—, —(CH₂)₂— or —(CH₂)₃-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF3, F, Cl, Br, —O—CH$_3$, —O—C$_2$H$_5$, methyl, ethyl, n-propyl, isopropyl, n-butyl, sec-butyl, isobutyl and tert-butyl;

or $R^{12f}$ and $R^{13f}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, —N—[C(=O)—C$_2$H$_5$]-phenyl, —N—[C(=O)—CH$_3$]-phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

$R^{25f}$ and $R^{26f}$, mutually independently, in each case denote a hydrogen residue;

or denote an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

providing that $R^{25f}$ and $R^{26f}$ do not in each case denote a hydrogen residue;

or $R^{25f}$ and $R^{26f}$ in each case together with the carbon atom joining them together as a ring member, form a residue selected from the group consisting of cyclopropyl, cyclobutyl, cyclopentyl, cyclohexyl and cycloheptyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of general formula If,

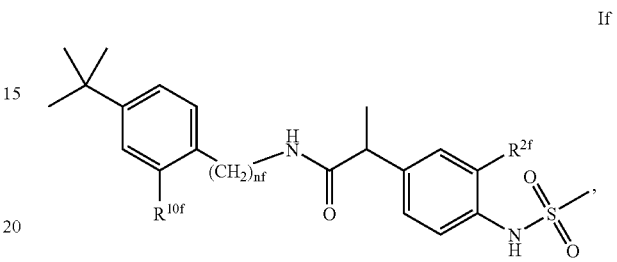

If in which nf, $R^{10f}$ and $R^{2f}$ have the meaning as defined above;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise particularly preferred compounds are those of general formula If, in which nf denotes 1;

$R^{2f}$ denotes F;

$R^{10f}$ denotes —CN; —OH; —NH$_2$; —NO$_2$; —NHR$^{11f}$; —NR$^{12f}$R$^{13f}$; —OR$^{14f}$; —SR$^{15f}$;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and in each case may optionally be substituted with 1, 2, 3, 4 or 5 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of (1,3)-benzodioxolyl, (1,4)-benzodioxanyl, indolyl, tetrazolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH$_3$, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11f}$, R$^{12f}$, R$^{13f}$, R$^{14f}$ and R$^{15f}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, wherein the residue may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, tert-butyl, n-pentyl, n-hexyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, isobutyl and tert-butyl;

or

R$^{12f}$ and R$^{13f}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —CH$_2$—O—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, cyclohexyl, cyclopentyl, (4,5)-dihydroisoxazolyl, thiazolyl, (1,2,5)-thiadiazolyl, thiophenyl, phenethyl, pyridinyl, phenyl and benzyl, wherein in each case the cyclic moiety of the residues oxetanyl, —N—[C(=O)—C$_2$H$_5$]-phenyl, —N—[C(=O)—CH$_3$]-phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl, and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of general formula Ig,

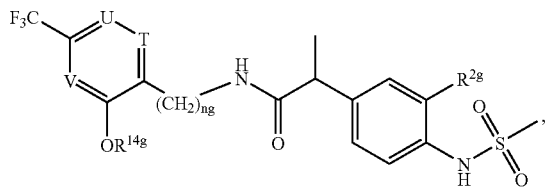

in which ng denotes 0, 1 or 2;

R$^{2g}$ denotes methyl; —O—CH$_3$; F; Cl; Br or I;

R$^{14g}$ denotes a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

T denotes CH and U denotes N and V denotes CH or

T denotes N and U denotes CH and V denotes CH or

T denotes N and U denotes N and V denotes CH or

T denotes N and U denotes CH and V denotes N or

T denotes CH and U denotes N and V denotes N;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise very particularly preferred compounds are those of general formula Ig, in which ng denotes 1;

R$^{2g}$ denotes F;

R$^{14g}$ denotes a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

T denotes CH and U denotes N and V denotes CH
or
T denotes N and U denotes CH and V denotes CH
or
T denotes N and U denotes N and V denotes CH
or
T denotes N and U denotes CH and V denotes N
or
T denotes CH and U denotes N and V denotes N;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Still further preferred compounds of the above-stated general formulae are those selected from the group consisting of

[1] 2-(3-fluoro-4-(methylsulfonamido)phenyl)-N-((2-methyl-6-(trifluoromethyl)pyridin-3-yl)methyl)propanamide

[2] 2-(3-fluoro-4-(methylsulfonamido)phenyl)-N-((2-(piperidin-1-yl)-6-(trifluoromethyl)pyridin-3-yl)methyl)propanamide

[3] 2-(3-fluoro-4-(methylsulfonamido)phenyl)-N-((2-piperidin-1-yl)-4-(trifluoromethyl)benzyl)propanamide

[4] 2-(3-fluoro-4-(methylsulfonamido)phenyl)-N-((2-fluoro-6-(trifluoromethyl)pyridin-3-yl)methyl)propanamide

[5] N-((2-chloro-6-(trifluoromethyl)pyridin-3-yl)methyl)-2-(3-fluoro-4-(methylsulfonamido)phenyl)propanamide

[6] N-((-bromo2-bromo-6-(trifluoromethyl)pyridin-3-yl)methyl)-2-(3-fluoro-4-(methylsulfonamido)phenyl)propanamide

[7] 2-(3-fluoro-4-(methylsulfonamido)phenyl)-N-((2-iodo-6-(trifluoromethyl)pyridin-3-yl)methyl)propanamide

[8] N-((2-tert-butyl-6-(trifluoromethyl)pyridin-3-yl)methyl)-2-(3-fluoro-4-(methylsulfonamido)phenyl)propanamide

[9] N-((2-cyano-6-(trifluoromethyl)pyridin-3-yl)methyl)-2-(3-fluoro-4-(methylsulfonamido)phenyl)propanamide

[10] (S)-2-(3-fluoro-4-(methylsulfonamido)phenyl)-N-((2-(piperidin-1-yl)-6-(trifluoromethyl)pyridin-3-yl)methyl)propanamide

[11] (R)-2-(3-fluoro-4-(methylsulfonamido)phenyl)-N-((2-(piperidin-1-yl)-6-(trifluoromethyl)pyridin-3-yl)methyl)propanamide

[12] 2-(3-fluoro-4-(methylsulfonamido)phenyl)-N-((2-morpholino-6-(trifluoromethyl)pyridin-3-yl)methyl)propanamide

[13] 2-(3-fluoro-4-(methylsulfonamido)phenyl)-N-((2-(pyrrolidin-1-yl)-6-(trifluoromethyl)pyridin-3-yl)methyl)propanamide

[14] N-((2-(dimethylamino)-6-(trifluoromethyl)pyridin-3-yl)methyl)-2-(3-fluoro-4-(methylsulfonamido)phenyl)propanamide

[15] N-((2-(diethylamino)-6-(trifluoromethyl)pyridin-3-yl)methyl)-2-(3-fluoro-4-(methylsulfonamido)phenyl)propanamide

[16] N-((2-(dipropylamino)-6-(trifluoromethyl)pyridin-3-yl)methyl)-2-(3-fluoro-4-(methylsulfonamido)phenyl)propanamide

[17] 2-(3-fluoro-4-(methylsulfonamido)phenyl)-N-((2-hydroxy-6-(trifluoromethyl)pyridin-3-yl)methyl)propanamide

[18] 2-(3-fluoro-4-(methylsulfonamido)phenyl)-N-((2-methoxy-6-(trifluoromethyl)pyridin-3-yl)methyl)propanamide

[19] N-((2-butoxy-6-(trifluoromethyl)pyridin-3-yl)methyl)-2-(3-fluoro-4-(methylsulfonamido)phenyl)propanamide

[20] 2-(3-fluoro-4-(methylsulfonamido)phenyl)-N-((2-isopropoxy-6-(trifluoromethyl)pyridin-3-yl)methyl)propanamide

[21] N-((2-cyclopentyloxy-6-(trifluoromethyl)pyridin-3-yl)methyl)-2-(3-fluoro-4-(methylsulfonamido)phenyl)propanamide

[22] 2-(3-fluoro-4-(methylsulfonamido)phenyl)-N-((2-phenyl-6-(trifluoromethyl)pyridin-3-yl)methyl)propanamide

[23] 2-(3-fluoro-4-(methylsulfonamido)phenyl)-N-((2-(4-fluoro-phenyl)-6-(trifluoromethyl)pyridin-3-yl)methyl)propanamide

[24] 2-(3-fluoro-4-(methylsulfonamido)phenyl)-N-((6-(trifluoromethyl)-2,2'-bipyridin-3-yl)methyl)propanamide

[25] 2-(3-fluoro-4-(methylsulfonamido)phenyl)-N-((6-(trifluoromethyl)-2,3'-bipyridin-3-yl)methyl)propanamide

[26] 2-(3-fluoro-4-(methylsulfonamido)phenyl)-N-((2-(pyrimidin-2-yl)-6-(trifluoromethyl)pyridin-3-yl)methyl)propanamide

[27] 2-(3-fluoro-4-(methylsulfonamido)phenyl)-N-((2-(thiazol-2-yl)-6-(trifluoromethyl)pyridin-3-yl)methyl)propanamide

[28] 2-(3-fluoro-4-(methylsulfonamido)phenyl)-N-((2-(oxazol-2-yl)-6-(trifluoromethyl)pyridin-3-yl)methyl)propanamide

[29] N-((2-(1H-imidazol-2-yl)-6-(trifluoromethyl)pyridin-3-yl)methyl)-2-(3-fluoro-4-(methylsulfonamido)phenyl)propanamide

[30] N-(2-cyano-4-(trifluoromethyl)benzyl)-2-(3-fluoro-4-(methylsulfonamido)phenyl)propanamide

[31] (S)-2-(3-fluoro-4-(methylsulfonamido)phenyl)-N-(2-(piperidin-1-yl)-4-(trifluoromethyl)benzyl)propanamide

[32] (R)-2-(3-fluoro-4-(methylsulfonamido)phenyl)-N-(2-(piperidin-1-yl)-4-(trifluoromethyl)benzyl)propanamide

[33] 2-(3-fluoro-4-(methylsulfonamido)phenyl)-N-(2-morpholino-4-(trifluoromethyl)benzyl)propanamide

[34] 2-(3-fluoro-4-(methylsulfonamido)phenyl)-N-(2-(pyrrolidin-1-yl)-4-(trifluoromethyl)benzyl)propanamide

[35] N-(2-(dimethylamino)-4-(trifluoromethyl)benzyl)-2-(3-fluoro-4-(methylsulfonamido)phenyl)propanamide

[36] N-(2-(diethylamino)-4-(trifluoromethyl)benzyl)-2-(3-fluoro-4-(methylsulfonamido)phenyl)propanamide

[37] N-(2-(dipropylamino)-4-(trifluoromethyl)benzyl)-2-(3-fluoro-4-(methylsulfonamido)phenyl)propanamide

[38] 2-(3-fluoro-4-(methylsulfonamido)phenyl)-N-(2-hydroxy-4-(trifluoromethyl)benzyl)propanamide

[39] 2-(3-fluoro-4-(methylsulfonamido)phenyl)-N-(2-methoxy-4-(trifluoromethyl)benzyl)propanamide

[40] N-(2-butoxy-4-(trifluoromethyl)benzyl)-2-(3-fluoro-4-(methylsuifonamido)phenyl)propanamide

[41] 2-(3-fluoro-4-(methylsulfonamido)phenyl)-N-(2-isopropoxy-4-(trifluoromethyl)benzyl)propanamide

[42] N-(2-cyclopentyloxy)-4-(trifluoromethyl)benzyl)-2-(3-fluoro-4-(methylsulfonamido)phenyl)propanamide

[43] 2-(3-fluoro-4-(methylsulfonamido)phenyl)-N-((5-(trifluoromethyl)biphenyl-2-yl)methyl)propanamide

[44] 2-(3-fluoro-4-(methylsulfonamido)phenyl)-N-((4'-fluoro-5-(trifluoromethyl)biphenyl-2-yl)methyl)propanamide

[45] 2-(3-fluoro-4-(methylsulfonamido)phenyl)-N-(2-(pyridin-2-yl)-4-(trifluoromethyl)benzyl)propanamide

[46] 2-(3-fluoro-4-(methylsulfonamido)phenyl)-N-(2-(pyridin-3-yl)-4-(trifluoromethyl)benzyl)propanamide

[47] 2-(3-fluoro-4-(methylsulfonamido)phenyl)-N-(2-(pyrimidin-2-yl)-4-(trifluoromethyl)benzyl)propanamide

[48] 2-(3-fluoro-4-(methylsulfonamido)phenyl)-N-(2-(thiazol-2-yl)-4-(trifluoromethyl)benzyl)propanamide
[49] 2-(3-fluoro-4-(methylsulfonamido)phenyl)-N-(2-(oxazol-2-yl)-4-(trifluoromethyl)benzyl)propanamide
[50] N-(2-(1H-imidazol-2-yl)-4-(trifluoromethyl)benzyl)-2-(3-fluoro-4-(methylsulfonamido)phenyl)propanamide
[51] N-((6-tert-butyl-2-(piperidin-1-yl)pyridin-3-yl)methyl)-2-(3-fluoro-4-(methylsufonamido)phenyl)propanamide
[52] 2-(3-fluoro-4-(methylsulfonamido)phenyl)-N-((4-(piperidin-1-yl)-6-(trifluoromethyl)pyridin-3-yl)methyl)propanamide
[53] 2-(3-fluoro-4-(methylsulfonamido)phenyl)-N-((3-(piperidin-1-yl)-5-(trifluoromethyl)pyridin-2-yl)methyl)propanamide
[54] 2-(3-fluoro-4-(methylsulfonamido)phenyl)-N-((4-(piperidin-1-yl)-2-(trifluoromethyl)pyrimidin-5-yl)methyl)propanamide
[55] 2-(3-fluoro-4-(methylsulfonamido)phenyl)-N-((3-(piperidin-1-yl)-5-(trifluoromethyl)pyrazin-2-yl)methyl)propanamide
[56] 2-(3-fluoro-4-(methylsulfonamido)phenyl)-N-((4-(piperidin-1-yl)-6-(trifluoromethyl)pyridazin-3-yl)methyl)propanamide
[57] 2-(3-fluoro-4-(methylsulfonamido)phenyl)-N-((2-piperidin-1-yl)-6-(trifluoromethyl)pyridin-3-yl)propanamide
[58] 2-(3-fluoro-4-(methylsulfonamido)phenyl)-N-((2-piperidin-1-yl)-4-(trifluoromethyl)phenyl)propanamide
[59] 2-(3-fluoro-4-(methylsulfonamido)phenyl)-N-(2-(2-(piperidin-1-yl)-6-(trifluoromethyl)pyridin-3-yl)ethyl)propanamide
[60] 2-(3-fluoro-4-(methylsulfonamido)phenyl)-N-(2-(piperidin-1-yl)-4-(trifluoromethyl)phenethyl)propanamide
[61] N-(2-amino-4-(trifluoromethyl)benzyl)-2-(3-fluoro-4-(methylsulfonamido)phenyl)propanamide
[62] 2-(3-fluoro-4-(methylsulfonamido)phenyl)-N-(2-nitro-4-(trifluoromethyl)benzyl)propanamide
[63] N-(4-tert-butyl-2-(piperidin-1-yl)benzyl)-2-(3-fluoro-4-(methylsulfonamido)phenyl)propanamide
[64] 2-(3-chloro-4-(methylsulfonamido)phenyl)-N-((2-(piperidin-1-yl)-6-(trifluoromethyl)pyridin-3-yl)methyl)propanamide
[65] 2-(3-chloro-4-(methylsulfonamido)phenyl)-N-((2-(pyrrolidin-1-yl)-6-(trifluoromethyl)pyridin-3-yl)methyl)propanamide
[66] 2-(3-chloro-4-(methylsulfonamido)phenyl)-N-(2-piperidin-1-yl)-4-(trifluoromethyl)benzyl)propanamide
[67] 2-(3-bromo-4-(methylsulfonamido)phenyl)-N-((2-piperidin-1-yl)-6-(trifluoromethyl)pyridin-3-yl)methyl)propanamide
[68] 2-(3-bromo-4-(methylsulfonamido)phenyl)-N-(2-piperidin-1-yl)-4-(trifluoromethyl)benzyl)propanamide
[69] 2-(3-bromo-4-(methylsulfonamido)phenyl)-N-(2-(pyrrolidin-1-yl)-4-(trifluoromethyl)benzyl)propanamide
[70] N-(4-tert-butyl-2-cyanobenzyl)-2-(3-fluoro-4-(methylsulfonamido)phenyl)propanamide
[71] N-((6-(chlorodiflouromethyl)-2-(piperidin-1-yl)pyridin-3-yl)methyl)-2-(3-fluoro-(4-methylsulfonamido)phenyl)propanamide
[72] (S)-2-(3-fluoro-4-(methylsulfonamido)phenyl)-N-((2-morpholino-6-(trifluoromethyl)pyridin-3-yl)methyl)propanamide
[73] N-((2-(4-benzylpiperazin-1-yl)-6-(trifluoromethyl)pyridin-3-yl)methyl)-2-(3-fluoro-4-(methylsulfonamido)phenyl)propanamide
[74] 2-(3-fluoro-4-(methylsulfonamido)phenyl)-N-((2-piperazin-1-yl)-6-(trifluoromethyl)pyridin-3-yl)methyl)propanamide;
[75] N-(2-chloro-4-(trifluoromethyl)benzyl)-2-(3-fluoro-4-(methylsulfonamido)phenyl)propanamide
[76] N-((2-(cyclohexyloxy)-6-(trifluoromethyl)pyridin-3-yl)methyl-2-(3-fluoro-4-methylsulfonamido)phenyl)propanamide
[77] N-((3-chloro-5-(trifluoromethyl)pyridin-2-yl)methyl-2-(3-fluoro-4-(methylsulfonamido)phenyl)propanamide
[78] 2-(3-fluoro-4-(methylsulfonamido)phenyl)-N-((3-(pyrrolidin-1-yl)-5-(trifluoromethyl)pyridin-2-yl)methyl)propanamide
[79] N-((2-(3,5-dimethylpiperidin-1-yl)-6-(trifluoromethyl)pyridin-3-yl)methyl)-2-(3-fluoro-4-(methylsulfonamido)phenyl)propanamide
[80] 2-(3-fluoro-4-(methylsulfonamido)phenyl)-N-((2-(4-methylpiperidin-1-yl)-6-(trifluoromethyl)pyridin-3-yl)methyl)propanamide
[81] N-((2-(azepan-1-yl)-6-(trifluoromethyl)pyridin-3-yl)methyl)-2-(3-fluoro-4-(methylsulfonamido)phenyl)propanamide
[82] 2-(3-fluoro-4-(methylsulfonamido)phenyl)-N-(2-(4-methylpiperidin-1-yl)-4-fluoromethyl)benzyl)propanamide;
83 (S)-2-(3-fluoro-4-methylsulfonamido-phenyl)-N-[2-(4-methyl-piperidin-1-yl)-4-trifluoromethyl-benzyl]-propionamide
84 (R)-2-(3-fluoro-4-methylsulfonamido-phenyl)-N-[2-(4-methyl-piperidin-1-yl)-4-trifluoromethyl-benzyl]-propionamide
85 N-(2-dimethylamino-6-trifluoromethyl-pyridin-3-ylmethyl)-2-(3-fluoro-4-ylsulfonamido-phenyl)-propionamide
87 2-(3-fluoro-4-methylsulfonamido-phenyl)-N-(2-imidazol-1-yl-6-trifluoromethyl-pyridin-3-ylmethyl)-propionamide
88 2-(3-fluoro-4-methylsulfonamido-phenyl)-N-(2-thiophen-2-yl-6-trifluoromethyl-pyridin-3-ylmethyl)-propionamide
89 2-(3-fluoro-4-methylsulfonamido-phenyl)-N-[2-(4-fluoro-phenyl)-6-trifluoromethyl-pyridin-3-ylmethyl]-propionamide
90 N-(2-cyclohexylamino-6-trifluoromethyl-pyridin-3-ylmethyl)-2-(3-fluoro-4-methylsulfonamido-phenyl)-propionamide
91 2-(3-fluoro-4-methylsulfonamido-phenyl)-N-(2-hexyloxy-6-trifluoromethyl-pyridin-3-ylmethyl)-propionamide
93 (S)-2-(3-fluoro-4-methylsulfonamido-phenyl)-N-(2-hexyloxy-6-trifluoromethyl-pyridin-3-ylmethyl)-propionamide
94 (R)-2-(3-fluoro-4-methylsulfonamido-phenyl)-N-(2-hexyloxy-6-trifluoromethyl-pyridin-3-ylmethyl)-propionamide
95 2-(3-fluoro-4-methylsulfonamido-phenyl)-N-(2-isobutoxy-6-trifluoromethyl-pyridin-3-ylmethyl)-propionamide
96 (S)-2-(3-fluoro-4-methylsulfonamido-phenyl)-N-(2-isobutoxy-6-trifluoromethyl-pyridin-3-ylmethyl)-propionamide
97 (R)-2-(3-fluoro-4-methylsulfonamido-phenyl)-N-(2-isobutoxy-6-trifluoromethyl-pyridin-3-ylmethyl)-propionamide
98 2-(3-fluoro-4-methylsulfonamido-phenyl)-N-(2-isobutoxy-4-trifluoromethyl-benzyl)-propionamide 99 (R)-2-(3-fluoro-4-methylsulfonamido-phenyl)-N-(2-isobutoxy-4-trifluoromethyl-benzyl)-propionamide
100 N-(2-cyclopropylmethoxy-6-trifluoromethyl-pyridin-3-ylmethyl)-2-(3-fluoro-4-methylsulfonamido-phenyl)-propionamide
101 N-(2-cyclobutylmethoxy-6-trifluoromethyl-pyridin-3-ylmethyl)-2-(3-fluoro-4-methylsulfonamido-phenyl)-propionamide
102 2-(3-chloro-4-methylsulfonamido-phenyl)-N-(2-pyrrolidin-1-yl-6-trifluoromethyl-pyridin-3-ylmethyl)-propionamide
103 2-(3-bromo-4-methylsulfonamido-phenyl)-N-(2-pyrrolidin-1-yl-6-trifluoromethyl-pyridin-3-ylmethyl)-propionamide
104 N-(4-benzyl-6'-trifluoromethyl-3,4,5,6-tetrahydro-2H-[1,2']bipyridinyl-3'-ylmethyl)-2-(3-fluoro-4-methylsulfonamido-phenyl)-propionamide
106 N-(2-benzyloxy-6-trifluoromethyl-pyridin-3-ylmethyl)-2-(3-fluoro-4-methylsulfonamido-phenyl)-propionamide
107 2-(3-fluoro-4-methylsulfonamido-phenyl)-N-[2-(3-methoxy-benzyloxy)-6-trifluoromethyl-pyridin-3-ylmethyl]-propionamide
108 N-(2-butoxy-4-tert-butyl-benzyl)-2-(3-fluoro-4-methylsulfonamido-phenyl)-propionamide
109 2-(3-fluoro-4-methylsulfonamido-phenyl)-N-[2-(4-phenyl-piperazin-1-yl)-6-trifluoromethyl-pyridin-3-ylmethyl]-propionamide
110 2-(3-fluoro-4-methylsulfonamido-phenyl)-N-(2-phenylamino-6-trifluoromethyl-pyridin-3-ylmethyl)-propionamide
111 2-(3-fluoro-4-methylsulfonamido-phenyl)-N-(2-propoxy-6-trifluoromethyl-pyridin-3-ylmethyl)-propionamide
112 2-(3-fluoro-4-methylsulfonamido-phenyl)-N-[2-(4-fluoro-phenylamino)-6-trifluoromethyl-pyridin-3-ylmethyl]-propionamide
113 N-[2-(4-chloro-phenylamino)-6-trifluoromethyl-pyridin-3-ylmethyl]-2-(3-fluoro-4-methylsulfonamido-phenyl)-propionamide
114 2-(3-fluoro-4-methylsulfonamido-phenyl)-N-(2-fluoro-4-trifluoromethyl-benzyl)-propionamide
115 N-(2-benzylamino-6-trifluoromethyl-pyridin-3-ylmethyl)-2-(3-fluoro-4-methylsulfonamido-phenyl)-propionamide
116 N-(2-butylamino-6-trifluoromethyl-pyridin-3-ylmethyl)-2-(3-fluoro-4-methylsulfonamido-phenyl)-propionamide
117 N-[2-(4-tert-butyl-phenyl)-6-trifluoromethyl-pyridin-3-ylmethyl]-2-(3-fluoro-4-methylsulfonamido-phenyl)-propionamide
118 N-[2-(3-chloro-4-fluoro-phenyl)-6-trifluoromethyl-pyridin-3-ylmethyl]-2-(3-fluoro-4-methylsulfonamido-phenyl)-propionamide
120 (S)—N-[2-(3-chloro-4-fluoro-phenyl)-6-trifluoromethyl-pyridin-3-ylmethyl]-2-(3-fluoro-4-methylsulfonamido-phenyl)-propionamide
121 (R)—N-[2-(3-chloro-4-fluoro-phenyl)-6-trifluoromethyl-pyridin-3-ylmethyl]-2-(3-fluoro-4-methylsulfonamido-phenyl)-propionamide
122 N-(2-butylsulfanyl-6-trifluoromethyl-pyridin-3-ylmethyl)-2-(3-fluoro-4-methylsulfonamido-phenyl)-propionamide
123 2-(3-fluoro-4-methylsulfonamido-phenyl)-N-[2-(3-methyl-butoxy)-6-trifluoromethyl-pyridin-3-ylmethyl]-propionamide
124 2-(3-fluoro-4-methylsulfonamido-phenyl)-N-[2-(2-methyl-cyclopropylmethoxy)-6-trifluoromethyl-pyridin-3-ylmethyl]-propionamide
125 N-[2-(3,3-dimethyl-butoxy)-6-trifluoromethyl-pyridin-3-ylmethyl]-2-(3-fluoro-4-methylsulfonamido-phenyl)-propionamide
126 N-(2-cyclohexylsulfanyl-6-trifluoromethyl-pyridin-3-ylmethyl)-2-(3-fluoro-4-methylsulfonamido-phenyl)-propionamide
127 2-(4-methylsulfonamido-3-methyl-phenyl)-N-(6'-tifluoronmethyl-3,4,5,6-tetrahydro-2H-[1,2']bipyridinyl-3'-yl-methyl)-propionamide
128 N-(2-azocan-1-yl-6-trifluoromethyl-pyridin-3-yl methyl)-2-(3-fluoro-4-methylsulfonamido-phenyl)-propionamide
129 2-(3-fluoro-4-methylsulfonamido-phenyl)-N-(2-pyrrolidin-1-yl-4-trifluoromethyl-benzyl)-thiopropionamide
130 2-(3-fluoro-4-methylsulfonamido-phenyl)-N-[2-(4-fluoro-phenyl)-6-trifluoromethyl-pyridin-3-ylmethyl]-thiopropionamide
131 N-[6'-(chloro-difluoro-methyl)-4-methyl-3,4,5,6-tetrahydro-2H-[1,2']bipyridinyl-3'-ylmethyl]-2-(3-fluoro-4-methylsulfonamido-phenyl)-propionamide
132 N-[2-azepan-1-yl-6-(chlor-difluor-methyl)-pyridin-3-ylmethyl]-2-(3-fluoro-4-methylsulfonamido-phenyl)-propionamide
133 N-(4-tert-butyl-2-isobutoxy-benzyl)-2-(3-fluoro-4-methylsulfonamido-phenyl)-propionamide
134 2-(3-fluoro-4-methylsulfonamido-phenyl)-N-[2-(4-methyl-piperazin-1-yl)-6-trifluoromethyl-pyridin-3-ylmethyl]-propionamide
135 N-[2-(3,4-dimethyl-phenylamino)-6-trifluoromethyl-pyridin-3-ylmethyl]-2-(3-fluoro-4-methylsulfonamido-phenyl)-propionamide
136 N-[2-(5-chloro-2-methyl-phenylamino)-6-trifluoromethyl-pyridin-3-ylmethyl]-2-(3-fluoro-4-methylsulfonamido-phenyl)-propionamide
137 2-(3-fluoro-4-methylsulfonamido-phenyl)-N-(4-phenyl-6'-trifluoromethyl-3,4,5,6-tetrahydro-2H-[1,2']bipyridinyl-3'-ylmethyl)-propionamide
138 2-(3-fluoro-4-methylsulfonamido-phenyl)-N-(4-fluoro-6'-trifluoromethyl-3,4,5,6-tetrahydro-2H-[1,2']bipyridinyl-3'-ylmethyl)-propionamide
139 2-(3-fluoro-4-methylsulfonamido-phenyl)-N-(6'-trifluoromethyl-3,6-dihydro-2H-[1,2']bipyridinyl-3'-ylmethyl)-propionamide
140 N-[2-butoxy-6-(chlor-difluor-methyl)-pyridin-3-ylmethyl]-2-(3-fluoro-4-methylsulfonamido-phenyl)-propionamide
142 2-(3-fluoro-4-methylsulfonamido-phenyl)-N-(2-pentyl-6-trifluoromethyl-pyridin-3-ylmethyl)-propionamide
144 (S)-2-(3-fluoro-4-methylsulfonamido-phenyl)-N-(2-pentyl-6-trifluoromethyl-pyridin-3-ylmethyl)-propionamide
145 (R)-2-(3-fluoro-4-methylsulfonamido-phenyl)-N-(2-pentyl-6-trifluoromethyl-pyridin-3-ylmethyl)-propionamide
147 N-[2-(4-chloro-phenyl)-6-trifluoromethyl-pyridin-3-ylmethyl]-2-(3-fluoro-4-methylsulfonamido-phenyl)-propionamide
148 2-(3-fluoro-4-methylsulfonamido-phenyl)-N-[2-(3-fluoro-phenyl)-6-trifluoromethyl-pyridin-3-ylmethyl]-propionamide
149 N-[2-(3-chloro-phenyl)-6-trifluoromethyl-pyridin-3-ylmethyl]-2-(3-fluoro-4-methylsulfonamido-phenyl)-propionamide 150 2-(3-fluoro-4-methylsulfonamido-phenyl)-N-[2-(2-fluoro-phenyl)-6-trifluoromethyl-pyridin-3-ylmethyl]-propionamide
151 2-(3-fluoro-4-methylsulfonamido-phenyl)-N-[2-(4-methoxy-phenyl)-6-trifluoromethyl-pyridin-3-ylmethyl]-propionamide
152 N-[4-tert-butyl-2-(2,2-dimethyl-propoxy)-benzyl]-2-(3-fluoro-4-methylsulfonamido-phenyl)-propionamide
153 N-(4-tert-butyl-2-pentyloxy-benzyl)-2-(3-fluoro-4-methylsulfonamido-phenyl)-propionamide
154 N-(4-tert-butyl-2-cyclohexyloxy-benzyl)-2-(3-fluoro-4-methylsulfonamido-phenyl)-propionamide
155 N-(4-tert-butyl-2-cyclopentyloxy-benzyl)-2-(3-fluoro-4-methylsulfonamido-phenyl)-propionamide
156 N-(2-cyclobutoxy-6-trifluoromethyl-pyridin-3-ylmethyl)-2-(3-fluoro-4-methylsulfonamido-phenyl)-propionamide
157 2-(3-fluoro-4-methylsulfonamido-phenyl)-N-[2-(4-methyl-cyclohexyloxy)-6-trifluoromethyl-pyridin-3-ylmethyl]-propionamide
158 acetic acid-3'-{[2-(3-fluoro-4-methylsulfonamido-phenyl)-propionylamino]-methyl}-6'-trifluoromethyl-3,4,5,6-tetrahydro-2H-[1,2']bipyridinyl-4-yl ester
159 2-(3-fluoro-4-methylsulfonamido-phenyl)-N-(4-methoxy-6'-trifluoromethyl-3,4,5,6-tetrahydro-2H-[1,2']bipyridinyl-3'-ylmethyl)-propionamide
160 N-(4-butoxy-6'-trifluoromethyl-3,4,5,6-tetrahydro-2H-[1,2']bipyridinyl-3'-ylmethyl)-2-(3-fluoro-4-methylsulfonamido-phenyl)-propionamide
161 N-(2-cyclopentylmethoxy-6-trifluoromethyl-pyridin-3-ylmethyl)-2-(3-fluoro-4-methylsulfonamido-phenyl)-propionamide
162 2-(3-fluoro-4-methylsulfonamido-phenyl)-N-(4-isopropoxy-6'-trifluoromethyl-3,4,5,6-tetrahydro-2H-[1,2']bipyridinyl-3'-ylmethyl)-propionamide
163 N-(2-ethoxy-6-trifluoromethyl-pyridin-3-ylmethyl)-2-(3-fluoro-4-methylsulfonamido-phenyl)-propionamide
164 2-(3-fluoro-4-methylsulfonamido-phenyl)-N-(6"-trifluoromethyl-3,4,5,6,3',4',5',6'-octahydro-2H,2'H-[1,4';1',2"]terpyridin-3"-ylmethyl)-propionamide
165 2-(3-fluoro-4-methylsulfonamido-phenyl)-N-(4-pyrrolidin-1-yl-6'-trifluoromethyl-3,4,5,6-tetrahydro-2H-[1,2']bipyridinyl-3'-ylmethyl)-propionamide
166 N-[6-(chloro-difluoro-methyl)-2-cyclopentyloxy-pyridin-3-ylmethyl]-2-(3-fluoro-4-methylsulfonamido-phenyl)-propionamide
167 N-[2-(butyl-methyl-amino)-6-trifluoromethyl-pyridin-3-ylmethyl]-2-(3-fluoro-4-methylsulfonamido-phenyl)-propionamide
168 N-[6-(chloro-difluoro-methyl)-2-cyclohexyloxy-pyridin-3-ylmethyl]-2-(3-fluoro-4-methylsulfonamido-phenyl)-propionamide
169 N-[2-benzyloxy-6-(chlor-difluor-methyl)-pyridin-3-ylmethyl]-2-(3-fluoro-4-methylsulfonamido-phenyl)-propionamide
170 N-[2-(4-tert-butyl-cyclohexyloxy)-6-trifluoromethyl-pyridin-3-ylmethyl]-2-(3-fluoro-4-methylsulfonamido-phenyl)-propionamide
171 N-[2-(4-ethyl-cyclohexyloxy)-6-trifluoromethyl-pyridin-3-ylmethyl]-2-(3-fluoro-4-methylsulfonamido-phenyl)-propionamide
172 2-(3-fluoro-4-methylsulfonamido-phenyl)-N-[2-(4-methyl-benzyloxy)-6-trifluoromethyl-pyridin-3-ylmethyl]-propionamide
173 N-[2-(4-chloro-benzylamino)-6-trifluoromethyl-pyridin-3-ylmethyl]-2-(3-fluoro-4-methylsulfonamido-phenyl)-propionamide
174 N-(2-azepan-1-yl-4-trifluoromethyl-benzyl)-2-(3-fluoro-4-methylsulfonamido-phenyl)-propionamide
175 N-[2-(4-fluoro-benzyloxy)-6-trifluoromethyl-pyridin-3-ylmethyl]-2-(3-fluoro-4-methylsulfonamido-phenyl)-propionamide
176 2-(3-fluoro-4-methylsulfonamido-phenyl)-N-[2-(4-pyridin-4-yl-piperazin-1-yl)-6-trifluoromethyl-pyridin-3-ylmethyl]-propionamide
177 2-(3-fluoro-4-methylsulfonamido-phenyl)-N-[2-(pyridin-4-ylmethoxy)-6-trifluoromethyl-pyridin-3-ylmethyl]-propionamide
178 2-(3-fluoro-4-methylsulfonamido-phenyl)-N-(2-phenethyloxy-6-trifluoromethyl-pyridin-3-ylmethyl)-propionamide
179 2-(3-fluoro-4-methylsulfonamido-phenyl)-N-{2-[4-(4-fluoro-phenyl)-piperazin-1-yl]-6-trifluoromethyl-pyridin-3-ylmethyl}-propionamide
180 N-[6-(chloro-difluoro-methyl)-2-hexyloxy-pyridin-3-ylmethyl]-2-(3-fluoro-4-methylsulfonamido-phenyl)-propionamide
181 N-[6-(chloro-difluoro-methyl)-2-(pyridin-3-ylmethoxy)-pyridin-3-ylmethyl]-2-(3-fluoro-4-methylsulfonamido-phenyl)-propionamide
182 N-[6-(chloro-difluoro-methyl)-2-(pyridin-2-ylmethoxy)-pyridin-3-ylmethyl]-2-(3-fluoro-4-methylsulfonamido-phenyl)-propionamide
183 N-(2-dibutylamino-6-trifluoromethyl-pyridin-3-ylmethyl)-2-(3-fluoro-4-methylsulfonamido-phenyl)-propionamide
184 2-(3-fluoro-4-methylsulfonamido-phenyl)-N-[6'-(4-fluoro-phenyl)-4-methyl-3,4,5,6-tetrahydro-2H-[1,2']bipyridinyl-3'-ylmethyl]-propionamide
185 N-[2-azepan-1-yl-6-(4-fluoro-phenyl)-pyridin-3-ylmethyl]-2-(3-fluoro-4-methylsulfonamido-phenyl)-propionamide
186 N-[6-(chloro-difluoro-methyl)-2-dipropylamino-pyridin-3-ylmethyl]-2-(3-fluoro-4-methylsulfonamido-phenyl)-propionamide
187 N-[6'-(chloro-difluoro-methyl)-3,5-dimethyl-3,4,5,6-tetrahydro-2H-[1,2']bipyridinyl-3'-ylmethyl]-2-(3-fluoro-4-methylsulfonamido-phenyl)-propionamide
188 N-[2-(1,3-dihydro-isoindol-2-yl)-6-trifluoromethyl-pyridin-3-ylmethyl]-2-(3-fluoro-4-methylsulfonamido-phenyl)-propionamide
189 3'-{[2-(3-fluoro-4-methylsulfonamido-phenyl)-propionylamino]-methyl}-4-phenyl-6'-trifluoromethyl-3,4,5,6-tetrahydro-2H-[1,2']bipyridinyl-4-carbonic acid ethylester
190 N-(4,6'-bis-trifluoromethyl-3,4,5,6-tetrahydro-2H-[1,2']bipyridinyl-3'-ylmethyl)-2-(3-fluoro-4-methylsulfonamido-phenyl)-propionamide
191 2-(3-fluoro-4-(methylsulfonamido)phenyl)-N-((2-styryl-6-(trifluoromethyl)pyridin-3-yl)methyl)propanamide
192 2-(3-fluoro-4-methylsulfonamido-phenyl)-N-(2-phenethyl-6-trifluoromethyl-pyridin-3-ylmethyl)-propionamide
193 N-{2-[4-(3-chloro-pyridin-2-yl)-piperazin-1-yl]-6-trifluoromethyl-pyridin-3-ylmethyl}-2-(3-fluoro-4-methylsulfonamido-phenyl)-propionamide
194 N-{2-[4-(3-chloro-pyridin-2-yl)-2-methyl-piperazin-1-yl]-6-trifluoromethyl-pyridin-3-ylmethyl}-2-(3-fluoro-4-methylsulfonamido-phenyl)-propionamide
195 N-(4,6'-bis-trifluoromethyl-3,4,5,6-tetrahydro-2H-[1,2']bipyridinyl-3'-ylmethyl)-2-(4-methylsulfonamido-3-methyl-phenyl)-propionamide 196 2-(4-methylsulfonamido-3-methyl-phenyl)-N-(4-methyl-6'-trifluoromethyl-3,4,5,6-tetrahydro-2H-[1,2']bipyridinyl-3'-ylmethyl)-propionamide 197 N-(4-ethyl-6'-trifluoromethyl-3,4,5,6-tetrahydro-2H-[1,2']bipyridinyl-3'-ylmethyl)-2-(3-fluoro-4-methylsulfonamido-phenyl)-propionamide 198 2-(3-fluoro-4-methylsulfonamido-phenyl)-N-(2-phenoxy-6-trifluoromethyl-pyridin-3-ylmethyl)-propionamide 199 2-(3-fluoro-4-methylsulfonamido-phenyl)-N-(4-methoxymethyl-6'-trifluoromethyl-3,4,5,6-tetrahydro-2H-[1,2']bipyridinyl-3'-ylmethyl)-propionamide 200 2-(3-fluoro-4-methylsulfonamido-phenyl)-N-[4-(4-fluoro-phenyl)-6'-trifluoromethyl-3,4,5,6-tetrahydro-2H-[1,2']bipyridinyl-3'-ylmethyl]-propionamide 201 2-(3-fluoro-4-methylsulfonamido-phenyl)-N-{2-[4-(2-fluoro-phenyl)-piperazin-1-yl]-6-trifluoromethyl-pyridin-3-ylmethyl}-propionamide 202 2-(3-fluoro-4-methylsulfonamido-phenyl)-N-[2-(pyridin-2-ylmethoxy)-6-trifluoromethyl-pyridin-3-ylmethyl]-propionamide 203 2-(4-methylsulfonamido-3-methyl-phenyl)-N-[2-(4-phenyl-piperazin-1-yl)-6-trifluoromethyl-pyridin-3-ylmethyl]-propionamide 204 N-(2-benzyloxy-6-trifluoromethyl-pyridin-3-ylmethyl)-2-(4-methylsulfonamido-3-methyl-phenyl)-propionamide 205 2-(3-fluoro-4-methylsulfonamido-phenyl)-N-[2-(methyl-phenyl-amino)-6-trifluoromethyl-pyridin-3-ylmethyl]-propionamide 206 2-(3-fluoro-4-methylsulfonamido-phenyl)-N-[4-trifluoromethyl-2-(4-trifluoromethyl-benzyloxy)-benzyl]-propionamide 207 N-[6-(chloro-difluoro-methyl)-2-(4-phenyl-piperazin-1-yl)-pyridin-3-ylmethyl]-2-(3-fluoro-4-methylsulfonamido-phenyl)-propionamide 208 N-[6-(chloro-difluoro-methyl)-2-isobutoxy-pyridin-3-ylmethyl]-2-(3-fluoro-4-methylsulfonamido-phenyl)-propionamide 209 N-(2-benzyloxy-4-trifluoromethyl-benzyl)-2-(3-fluoro-4-methylsulfonamido-phenyl)-propionamide 210 N-(4,4-dimethyl-6'-trifluoromethyl-3,4,5,6-tetrahydro-2H-[1,2']bipyridinyl-3'-ylmethyl)-2-(3-fluoro-4-methylsulfonamido-phenyl)-propionamide 211 2-(3-fluoro-4-methylsulfonamido-phenyl)-N-[2-(pyridin-3-ylmethoxy)-6-trifluoromethyl-pyridin-3-ylmethyl]-propionamide 212 2-(3-fluoro-4-methylsulfonamido-phenyl)-N-{6-trifluoromethyl-2-[4-(3-trifluoromethyl-pyridin-2-yl)-piperazin-1-yl]-pyridin-3-ylmethyl}-propionamide 213 2-(3-fluoro-4-methylsulfonamido-phenyl)-N-{6-trifluoromethyl-2-[4-(3-trifluoromethyl-pyridin-2-yl)-piperazin-1-yl]-pyridin-3-ylmethyl}-propionamide 214 2-(3-fluoro-4-methylsulfonamido-phenyl)-N-[2-(4-pyridin-2-yl-piperazin-1-yl)-6-trifluoromethyl-pyridin-3-ylmethyl]-propionamide 215 2-(3-fluoro-4-methylsulfonamido-phenyl)-N-(6-trifluoromethyl-pyridin-3-ylmethyl)-propionamide 216 2-(3-fluoro-4-methylsulfonamido-phenyl)-N-[2-(4-phenyl-piperazin-1-yl)-4-trifluoromethyl-benzyl]-propionamide 217 N-(2-azocan-1-yl-4-trifluoromethyl-benzyl)-2-(3-fluoro-4-methylsulfonamido-phenyl)-propionamide 218 N-[2-(4,4-dimethyl-piperidin-1-yl)-4-trifluoromethyl-benzyl]-2-(3-fluoro-4-methylsulfonamido-phenyl)-propionamide 219 2-(3-fluoro-4-methylsulfonamido-phenyl)-N-[2-(4-p-tolyl-piperazin-1-yl)-6-trifluoromethyl-pyridin-3-ylmethyl]-propionamide 220 2-(3-fluoro-4-methylsulfonamido-phenyl)-N-[2-(4-m-tolyl-piperazin-1-yl)-6-trifluoromethyl-pyridin-3-ylmethyl]-propionamide 221 2-(3-fluoro-4-methylsulfonamido-phenyl)-N-{2-[4-(4-methoxy-phenyl)-piperazin-1-yl]-6-trifluoromethyl-pyridin-3-ylmethyl}-propionamide 222 2-(3-fluoro-4-methylsulfonamido-phenyl)-N-{6-trifluoromethyl-2-[4-(4-trifluoromethyl-phenyl)-piperazin-1-yl]-pyridin-3-ylmethyl}-propionamide 223 N-(2-benzyloxy-4-hydroxymethyl-6-trifluoromethyl-pyridin-3-ylmethyl)-2-(3-fluoro-4-methylsulfonamido-phenyl)-propionamide 225 2-(3-fluoro-4-methylsulfonamido-phenyl)-N-(2-pentyloxy-6-trifluoromethyl-pyridin-3-ylmethyl)-propionamide 226 2,2-dimethyl-propionic acid-3'-{[2-(3-fluoro-4-methylsulfonamido-phenyl)-propionylamino]-methyl}-6'-trifluoromethyl-3,4,5,6-tetrahydro-2H-[1,2']bipyridinyl-4-yl ester 227 2-(3-fluoro-4-methylsulfonamido-phenyl)-N-(4-oxo-6'-trifluoromethyl-3,4,5,6-tetrahydro-2H-[1,2']bipyridinyl-3'-ylmethyl)-propionamide 228 N-(4-ethoxy-6'-trifluoromethyl-3,4,5,6-tetrahydro-2H-[1,2']bipyridinyl-3'-ylmethyl)-2-(3-fluoro-4-methylsulfonamido-phenyl)-propionamide 229 N-[2-(4-ethyl-piperidin-1-yl)-4-trifluoromethyl-benzyl]-2-(3-fluoro-4-methylsulfonamido-phenyl)-propionamide 230 2-(3-fluoro-4-methylsulfonamido-phenyl)-N-[4-trifluoromethyl-2-(4-trifluoromethyl-piperidin-1-yl)-benzyl]-propionamide 231 N-[2-(4-benzyl-piperidin-1-yl)-4-trifluoromethyl-benzyl]-2-(3-fluoro-4-methylsulfonamido-phenyl)-propionamide 233 N-(6-tert-butyl-2-cyclohexyloxy-pyridin-3-ylmethyl)-2-(3-fluoro-4-methylsulfonamido-phenyl)-propionamide 234 N-(6-tert-butyl-2-cyclopentyloxy-pyridin-3-ylmethyl)-2-(3-fluoro-4-methylsulfonamido-phenyl)-propionamide 235 N-(2-butoxy-6-tert-butyl-pyridin-3-ylmethyl)-2-(3-fluoro-4-methylsulfonamido-phenyl)-propionamide 236 N-(6-tert-butyl-2-hexyloxy-pyridin-3-ylmethyl)-2-(3-fluoro-4-methylsulfonamido-phenyl)-propionamide 237 N-(2-benzyloxy-6-tert-butyl-pyridin-3-ylmethyl)-2-(3-fluoro-4-methylsulfonamido-phenyl)-propionamide 238 N-(2-cyclohexyloxy-4-trifluoromethyl-benzyl)-2-(3-fluoro-4-methylsulfonamido-phenyl)-propionamide 239 (R)—N-(2-cyclohexyloxy-4-trifluoromethyl-benzyl)-2-(3-fluoro-4-methylsulfonamido-phenyl)-propionamide 240 N-(6-tert-butyl-2-pyrrolidin-1-yl-pyridin-3-ylmethyl)-2-(3-fluoro-4-methylsulfonamido-phenyl)-propionamide 241 N-(6'-tert-butyl-4-methyl-3,4,5,6-tetrahydro-2H-[1,2']bipyridinyl-3'-ylmethyl)-2-(3-fluoro-4-methylsulfonamido-phenyl)-propionamide 242 N-[2-(4-ethyl-benzyloxy)-6-trifluoromethyl-pyridin-3-ylmethyl]-2-(3-fluoro-4-methylsulfonamido-phenyl)-propionamide 243 N-[2-(4-butyl-benzyloxy)-6-trifluoromethyl-pyridin-3-ylmethyl]-2-(3-fluoro-4-methylsulfonamido-phenyl)-propionamide 244 N-[2-(4-tert-butyl-benzyloxy)-6-trifluoromethyl-pyridin-3-ylmethyl]-2-(3-fluoro-4-methylsulfonamido-phenyl)-propionamide 245 2-(3-fluoro-4-methylsulfonamido-phenyl)-N-[2-(indan-2-yloxy)-6-trifluoromethyl-pyridin-3-ylmethyl]-propionamide
246 2-(3-fluoro-4-methylsulfonamido-phenyl)-N-[2-(4-p-tolyl-piperazin-1-yl)-4-trifluoromethyl-benzyl]-propionamide
247 2-(3-fluoro-4-methylsulfonamido-phenyl)-N-[2-(4-m-tolyl-piperazin-1-yl)-4-trifluoromethyl-benzyl]-propionamide
248 2-(3-fluoro-4-methylsulfonamido-phenyl)-N-{4-trifluoromethyl-2-[4-(4-trifluoromethyl-phenyl)-piperazin-1-yl]-benzyl}-propionamide
249 2-(3-fluoro-4-methylsulfonamido-phenyl)-N-{2-[4-(4-methoxy-phenyl)-piperazin-1-yl]-4-trifluoromethyl-benzyl}-propionamide
250 N-[2-(3,4-dichloro-phenyl)-6-trifluoromethyl-pyridin-3-ylmethyl]-2-(3-fluoro-4-methylsulfonamido-phenyl)-propionamide
251 N-[2-(3-tert-butyl-1-oxa-2,8-diaza-spiro[4.5]dec-2-en-8-yl)-6-trifluoromethyl-pyridin-3-ylmethyl]-2-(3-fluoro-4-methylsulfonamido-phenyl)-propionamide
252 2-(3-fluoro-4-methylsulfonamido-phenyl)-N-[2-(3-phenyl-1-oxa-2,8-diaza-spiro[4.5]dec-2-en-8-yl)-6-trifluoromethyl-pyridin-3-ylmethyl]-propionamide
253 2-(3-fluoro-4-(pentafluorsulfanylsulfonamido)phenyl)-N-p-tolylpropanamid
254 2-(3-fluoro-4-methylsulfonamido-phenyl)-N-[2-(3-fluoro-4-methoxy-phenyl)-6-trifluoromethyl-pyridin-3-ylmethyl]-propionamide
255 2-(3-fluoro-4-methylsulfonamido-phenyl)-N-{2-[4-(4-fluoro-phenyl)-piperidin-1-yl]-4-trifluoromethyl-benzyl}-propionamide
256 N-(2-butoxy-6-trifluoromethyl-pyridin-3-ylmethyl)-2-(4-methylsulfonamido-3-methyl-phenyl)-propionamide
257 N-(2-hexyloxy-6-trifluoromethyl-pyridin-3-ylmethyl)-2-(4-methylsulfonamido-3-methyl-phenyl)-propionamide
258 N-[2-(4-chloro-benzyloxy)-6-trifluoromethyl-pyridin-3-ylmethyl]-2-(3-fluoro-4-methylsulfonamido-phenyl)-propionamide
259 N-(4-dimethylaminomethyl-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide
260 N-[2-(4-cyclohexyl-piperazin-1-yl)-6-trifluoromethyl-pyridin-3-ylmethyl]-2-(3-fluoro-4-methylsulfonamido-phenyl)-propionamide
261 N-(6-tert-butyl-2-cyclopentyloxy-4-hydroxymethyl-pyridin-3-ylmethyl)-2-(3-fluoro-4-methylsulfonamido-phenyl)-propionamide
262 2-(4-methylsulfonamido-phenyl)-N-(4-methyl-6'-trifluoromethyl-3,4,5,6-tetrahydro-2H-[1,2']bipyridinyl-3'-ylmethyl)-propionamide
263 N-[2-(3,3-dimethyl-butyl)-6-trifluoromethyl-pyridin-3-ylmethyl]-2-(3-fluoro-4-methylsulfonamido-phenyl)-propionamide
264 2-(3-fluoro-4-methylsulfonamido-phenyl)-N-[2-(2-p-tolyl-ethyl)-6-trifluoromethyl-pyridin-3-ylmethyl]-propionamide
265 N-[2-(2,3-dihydro-benzo[1,4]dioxin-6-yl)-6-trifluoromethyl-pyridin-3-ylmethyl]-2-(3-fluoro-4-methylsulfonamido-phenyl)-propionamide
266 N-(2-benzo[1,3]dioxol-5-yl-6-trifluoromethyl-pyridin-3-ylmethyl)-2-(3-fluoro-4-methylsulfonamido-phenyl)-propionamide
267 2-(3-fluoro-4-methylsulfonamido-phenyl)-N-(2-hexyl-6-trifluoromethyl-pyridin-3-ylmethyl)-propionamide
268 2-(3-fluoro-4-methylsulfonamido-phenyl)-N-[2-(4-methyl-pentyl)-6-trifluoromethyl-pyridin-3-ylmethyl]-propionamide
269 2-(3-fluoro-4-methylsulfonamido-phenyl)-N-(4-hydroxy-6'-trifluoromethyl-3,4,5,6-tetrahydro-2H-[1,2']bipyridinyl-3'-ylmethyl)-propionamide
270 N-(2-cyclohexylmethoxy-6-trifluoromethyl-pyridin-3-ylmethyl)-2-(3-fluoro-4-methylsulfonamido-phenyl)-propionamide
271 2-(3-fluoro-4-methylsulfonamido-phenyl)-N-[2-(4-methyl-cyclohexylmethoxy)-6-trifluoromethyl-pyridin-3-ylmethyl]-propionamide
272 2-(3-fluoro-4-methylsulfonamido-phenyl)-N-[2-(3-methylsulfonamido-phenyl)-6-trifluoromethyl-pyridin-3-ylmethyl]-propionamide
273 2-(3-fluoro-4-methylsulfonamido-phenyl)-N-[2-(2-methyl-propenyl)-6-trifluoromethyl-pyridin-3-ylmethyl]-propionamide
274 N-[2-(3,3-dimethyl-but-1-enyl)-6-trifluoromethyl-pyridin-3-ylmethyl]-2-(3-fluoro-4-methylsulfonamido-phenyl)-propionamide
275 2-(3-fluoro-4-methylsulfonamido-phenyl)-N-[2-(1H-indol-6-yl)-6-trifluoromethyl-pyridin-3-ylmethyl]-propionamide
276 2-(3-fluoro-4-methylsulfonamido-phenyl)-N-[2-(1H-indol-5-yl)-6-trifluoromethyl-pyridin-3-ylmethyl]-propionamide
277 N-[2-(4-chloro-3-fluoro-phenyl)-6-trifluoromethyl-pyridin-3-ylmethyl]-2-(3-fluoro-4-methylsulfonamido-phenyl)-propionamide
278 2-(3-fluoro-4-methylsulfonamido-phenyl)-N-[2-(4-fluoro-3-methyl-phenyl)-6-trifluoromethyl-pyridin-3-ylmethyl]-propionamide
279 N-[2-(2,2-dimethyl-cyclopropylmethoxy)-6-trifluoromethyl-pyridin-3-ylmethyl]-2-(3-fluoro-4-methylsulfonamido-phenyl)-propionamide
282 2-(3-fluoro-4-methylsulfonamido-phenyl)-N-(3-methyl-6'-trifluoromethyl-3,4,5,6-tetrahydro-2H-[1,2']bipyridinyl-3'-ylmethyl)-propionamide
283 2-(3-fluoro-4-methylsulfonamido-phenyl)-N-(2-methyl-6'-trifluoromethyl-3,4,5,6-tetrahydro-2H-[1,2']bipyridinyl-3'-ylmethyl)-propionamide
284 2-(3-fluoro-4-methylsulfonamido-phenyl)-N-[2-(4-methyl-6'-trifluoromethyl-3,4,5,6-tetrahydro-2H-[1,2']bipyridinyl-3'-yl)-ethyl]-propionamide
285 N-(4-cyano-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide
287 2-(4-ethanesulfonylamino-3-fluoro-phenyl)-N-(4-methyl-6'-trifluoromethyl-3,4,5,6-tetrahydro-2H-[1,2']bipyridinyl-3'-ylmethyl)-propionamide
288 2-(4-(N,N-dimethylsulfamoylamino)-3-fluorphenyl)-N-((2-(4-methylpiperidin-1-yl)-6-(trifluoromethyl)pyridin-3-yl)methyl)propanamide
289 2-(4-methylsulfonamido-3-methoxy-phenyl)-N-(4-methyl-6'-trifluoromethyl-3,4,5,6-tetrahydro-2H-[1,2']bipyridinyl-3'-ylmethyl)-propionamide
290 2-(3-fluoro-4-methylsulfonamido-phenyl)-N-(4-phenylamino-6'-trifluoromethyl-3,4,5,6-tetrahydro-2H-[1,2']bipyridinyl-3'-ylmethyl)-propionamide
291 N-(2-cyclohexyl-6-trifluoromethyl-pyridin-3-ylmethyl)-2-(3-fluoro-4-methylsulfonamido-phenyl)-propionamide
292 2-(3-fluoro-4-methylsulfonamido-phenyl)-N-(4-phenyl-6-trifluoromethyl-pyridin-3-methyl)-propionamide 293 2-(3-fluoro-4-methylsulfonamido-phenyl)-N-(4-methyl-6'-trifluoromethyl-3,4,5,6-tetrahydro-2H-[1,2']bipyridinyl-3'-ylmethyl)-thiopropionamide 294 N-(2-cyclohexylsulfanyl-6-trifluoromethyl-pyridin-3-ylmethyl)-2-(3-fluoro-4-methylsulfonamido-phenyl)-propionamide 295 2-(3-fluoro-4-methylsulfonamido-phenyl)-N-(4-phenyl-6'-trifluoromethyl-3,4,5,6-tetrahydro-2H-[1,2']bipyridinyl-3'-ylmethyl)-propionamide 296 N-(2-azepan-1-yl-6-tert-butyl-pyridin-3-ylmethyl)-2-(3-fluoro-4-methylsulfonamido-phenyl)-propionamide 297 N-(6-tert-butyl-2-dipropylamino-pyridin-3-ylmethyl)-2-(3-fluoro-4-methylsulfonamido-phenyl)-propionamide 298 N-(2-but-2-enyloxy-6-trifluoromethyl-pyridin-3-ylmethyl)-2-(3-fluoro-4-methylsulfonamido-phenyl)-propionamide 299 2-(3-fluoro-4-methylsulfonamido-phenyl)-N-(2-pent-2-enyloxy-6-trifluoromethyl-pyridin-3-ylmethyl)-propionamide 300 2-(3-fluoro-4-methylsulfonamido-phenyl)-N-(2-pent-1-enyl-6-trifluoromethyl-pyridin-3-ylmethyl)-propionamide 301 2-(3-fluoro-4-methylsulfonamido-phenyl)-N-(2-pent-1-enyl-6-trifluoromethyl-pyridin-3-ylmethyl)-propionamide 302 2-(3-fluoro-4-methylsulfonamido-phenyl)-N-(2-hexyloxy-4-methyl-6-trifluoromethyl-pyridin-3-ylmethyl)-propionamide 303 2-(3-fluoro-4-methylsulfonamido-phenyl)-N-{2-[2-(4-fluoro-phenyl)-ethyl]-6-trifluoromethyl-pyridin-3-ylmethyl}-propionamide 304 N-(4-acetyl-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide 307 2-(3-fluoro-4-methylsulfonamido-phenyl)-N-[4-(phenyl-propionyl-amino)-6'-trifluoromethyl-3,4,5,6-tetrahydro-2H-[1,2']bipyridinyl-3'-ylmethyl]-propionamide 308 N-[2-(4-dimethylamino-phenyl)-6-trifluoromethyl-pyridin-3-ylmethyl]-2-(3-fluoro-4-methylsulfonamido-phenyl)-propionamide 309 2-[3-fluoro-4-(propan-2-sulfonylamino)-phenyl]-N-(4-methyl-6'-trifluoromethyl-3,4,5,6-tetrahydro-2H-[1,2']bipyridinyl-3'-ylmethyl)-propionamide 310 2-[3-fluoro-4-(2,2,2-trifluor-ethansulfonylamino)-phenyl]-N-(4-methyl-6'-trifluoromethyl-3,4,5,6-tetrahydro-2H-[1,2']bipyridinyl-3'-ylmethyl)-propionamide 311 N-[2-(2,6-dimethyl-morpholin-4-yl)-6-trifluoromethyl-pyridin-3-ylmethyl]-2-(3-fluoro-4-methylsulfonamido-phenyl)-propionamide 312 2-(3-fluoro-4-trifluormethylsulfonamido-phenyl)-N-(4-methyl-6'-trifluoromethyl-3,4,5,6-tetrahydro-2H-[1,2']bipyridinyl-3'-ylmethyl)-propionamide 313 2-(3-fluoro-4-(sulfamoylamino)phenyl)-N-((2-(4-methylpiperidin-1-yl)-6-(trifluoromethyl)pyridin-3-yl)methyl)propanamide 314 N-[2-(1,1-dioxo-1l6-thiomorpholin-4-yl)-6-trifluoromethyl-pyridin-3-ylmethyl]-2-(3-fluoro-4-methylsulfonamido-phenyl)-propionamide 315 N-(6'-difluormethyl-4-methyl-3,4,5,6-tetrahydro-2H-[1,2']bipyridinyl-3'-ylmethyl)-2-(3-fluoro-4-methylsulfonamido-phenyl)-propionamide 316 N-(4,6'-dimethyl-3,4,5,6-tetrahydro-2H-[1,2']bipyridinyl-3'-ylmethyl)-2-(3-fluoro-4-methylsulfonamido-phenyl)-propionamide 317 2-(3-fluoro-4-methylsulfonamido-phenyl)-N-(4-phenyl-6'-trifluoromethyl-3,6-dihydro-2H-[1,2']bipyridinyl-3'-ylmethyl)-propionamide 318 N-(4,4'-dimethyl-6'-trifluoromethyl-3,4,5,6-tetrahydro-2H-[1,2']bipyridinyl-3'-ylmethyl)-2-(3-fluoro-4-methylsulfonamido-phenyl)-propionamide 319 N-[2-(4-cyclohexyl-piperazin-1-yl)-4-trifluoromethyl-benzyl]-2-(3-fluoro-4-methylsulfonamido-phenyl)-propionamide 320 N-(4'-tert-butyl-5-trifluoromethyl-biphenyl-2-ylmethyl)-2-(3-fluoro-4-methylsulfonamido-phenyl)-propionamide 321 2-(3-fluoro-4-methylsulfonamido-phenyl)-N-(4'-methoxy-5-trifluoromethyl-biphenyl-2-ylmethyl)-propionamide 322 N-(3'-chloro-5-trifluoromethyl-biphenyl-2-ylmethyl)-2-(3-fluoro-4-methylsulfonamido-phenyl)-propionamide 323 2-(3-fluoro-4-methylsulfonamido-phenyl)-N-(3'-fluoro-5-trifluoromethyl-biphenyl-2-ylmethyl)-propionamide 324 N-(3'-chloro-4'-fluoro-5-trifluoromethyl-biphenyl-2-ylmethyl)-2-(3-fluoro-4-methylsulfonamido-phenyl)-propionamide 325 N-(3',4'-dimethoxy-5-trifluoromethyl-biphenyl-2-ylmethyl)-2-(3-fluoro-4-methylsulfonamido-phenyl)-propionamide 326 N-[2-(3,4-dimethoxy-phenyl)-6-trifluoromethyl-pyridin-3-ylmethyl]-2-(3-fluoro-4-methylsulfonamido-phenyl)-propionamide 327 4-(3-{[2-(3-fluoro-4-methylsulfonamido-phenyl)-propionylamino]-methyl}-6-trifluoromethyl-pyridin-2-yloxymethyl)-piperidine-1-carbonic acid tert-butyl ester 328 N-(6-tert-butyl-2-pentyloxy-pyridin-3-ylmethyl)-2-(3-fluoro-4-methylsulfonamido-phenyl)-propionamide 329 N-[6-tert-butyl-2-(3-methyl-butoxy)-pyridin-3-ylmethyl]-2-(3-fluoro-4-methylsulfonamido-phenyl)-propionamide 330 N-(4-dimethylamino-4-phenyl-6'-trifluoromethyl-3,4,5,6-tetrahydro-2H-[1,2]bipyridinyl-3'-ylmethyl)-2-(3-fluoro-4-methylsulfonamido-phenyl)-propionamide 331 N-(2-dipropylamino-6-trifluoromethyl-pyridin-3-ylmethyl)-2-(4-methylsulfonamido-3-methyl-phenyl)-propionamide 332 2-(3-fluoro-4-methylsulfonamido-phenyl)-N-[4-(4-fluoro-phenyl)-6'-trifluoromethyl-3,6-dihydro-2H-[1,2']bipyridinyl-3'-ylmethyl]-propionamide 334 N-(2-cyclohex-1-enyl-6-trifluoromethyl-pyridin-3-ylmethyl)-2-(3-fluoro-4-methylsulfonamido-phenyl)-propionamide 335 N-[2-(1-ethyl-propoxy)-6-trifluoromethyl-pyridin-3-ylmethyl]-2-(3-fluoro-4-methylsulfonamido-phenyl)-propionamide 336 2-(3-fluoro-4-methylsulfonamido-phenyl)-N-[2-(1-propyl-butoxy)-6-trifluoromethyl-pyridin-3-ylmethyl]-propionamide 337 2-(3-fluoro-4-methylsulfonamido-phenyl)-N-[2-(1-isobutyl-3-methyl-butoxy)-6-trifluoromethyl-pyridin-3-ylmethyl]-propionamide 338 N-[2-(4,4-dimethyl-cyclohexyloxy)-6-trifluoromethyl-pyridin-3-ylmethyl]-2-(3-fluoro-4-methylsulfonamido-phenyl)-propionamide 339 2-(3-fluoro-4-methylsulfonamido-phenyl)-N-[6-trifluoromethyl-2-(4-trifluoromethyl-cyclohexyloxy)-pyridin-3-ylmethyl]-propionamide 340 2-(3-fluoro-4-methylsulfonamido-phenyl)-N-[6-trifluoromethyl-2-(4-trifluoromethyl-cyclohexyloxy)-pyridin-3-ylmethyl]-propionamide 341 4-(3-{[2-(3-fluoro-4-methylsulfonamido-phenyl)-propionylamino]-methyl}-6-trifluoromethyl-pyridin-2-yloxy)-piperidine-1-carbonic acid tert-butyl ester 342 4-[(3-{[2-(3-fluoro-4-methylsulfonamido-phenyl)-propionylamino]-methyl}-6-trifluoromethyl-pyridin-2-ylamino)-methyl]-piperidine-1-carbonic acid tert-butyl ester 343 2-(3-fluoro-4-methylsulfonamido-phenyl)-N-[2-(piperidin-4-ylmethoxy)-6-trifluoromethyl-pyridin-3-ylmethyl]-propionamide 344 2-(3-fluoro-4-methylsulfonamido-phenyl)-N-[2-(piperidin-4-yloxy)-6-trifluoromethyl-pyridin-3-ylmethyl]-propionamide 345 2-(3-fluoro-4-methylsulfonamido-phenyl)-N-(2-p-tolyloxy-6-trifluoromethyl-pyridin-3-ylmethyl)-propionamide 346 N-[2-(2-cyclohexyl-vinyl)-6-trifluoromethyl-pyridin-3-ylmethyl]-2-(3-fluoro-4-methylsulfonamido-phenyl)-propionamide 347 2-(3-fluoro-4-methylsulfonamido-phenyl)-N-(4-methyl-6'-trifluoromethyl-3,4,5,6-tetrahydro-2H-[1,2']bipyridinyl-3'-ylmethyl)-butyramide 348 N-[2-(3,5-dimethoxy-phenyl)-6-trifluoromethyl-pyridin-3-ylmethyl]-2-(3-fluoro-4-methylsulfonamido-phenyl)-propionamide 349 N-(2-cyclopentyloxy-4-methyl-6-trifluoromethyl-pyridin-3-ylmethyl)-2-(3-fluoro-4-methylsulfonamido-phenyl)-propionamide 350 N-(3',5'-dimethoxy-5-trifluoromethyl-biphenyl-2-ylmethyl)-2-(3-fluoro-4-methylsulfonamido-phenyl)-propionamide 351 ethyl 5-((2-(3-fluoro-4-(methylsulfonamido)phenyl)propanamido)methyl)-6-(4-methylpiperidin-1-yl)-2-(trifluoromethyl)nicotinat 352 2-(3-fluoro-4-(methylsulfonamido)phenyl)-N-((2-(nonan-5-yloxy)-6-(trifluoromethyl)pyridin-3-yl)methyl)propanamide 353 N-((6-tert-butyl-2-isobutoxypyridin-3-yl)methyl)-2-(3-fluoro-4-(methylsulfonamido)phenyl)propanamide 354 2-(3-fluoro-4-(methylsulfonamido)phenyl)-N-((2-(phenylethynyl)-6-(trifluoromethyl)pyridin-3-yl)methyl)propanamide 355 2-(3-fluoro-4-(methylsulfonamido)phenyl)-N-((2-(3-methoxypropoxy)-6-(trifluoromethyl)pyridin-3-yl)methyl)propanamide 356 N-((2-(4-benzylpiperidin-1-yl)-4-methyl-6-(trifluoromethyl)pyridin-3-yl)methyl)-2-(3-fluoro-4-(methylsulfonamido)phenyl)propanamide 357 2-(3-fluoro-4-methylsulfonamido-phenyl)-N-(4-methylene-6'-trifluoromethyl-3,4,5,6-tetrahydro-2H-[1,2']bipyridinyl-3'-ylmethyl)-propionamide 358 N-[2-(6-aza-spiro[2.5]oct-6-yl)-6-trifluoromethyl-pyridin-3-ylmethyl]-2-(3-fluoro-4-methylsulfonamido-phenyl)-propionamide 359 2-(3-fluoro-4-methylsulfonamido-phenyl)-N-[2-(3-methyl-but-2-enyloxy)-6-trifluoromethyl-pyridin-3-ylmethyl]-propionamide 360 N-[2-(3-cyclohexyl-propyl)-6-trifluoromethyl-pyridin-3-ylmethyl]-2-(3-fluoro-4-methylsulfonamido-phenyl)-propionamide 361 N-[2-(3-ethoxy-propoxy)-6-trifluoromethyl-pyridin-3-ylmethyl]-2-(3-fluoro-4-methylsulfonamido-phenyl)-propionamide 362 2-(3-fluoro-4-methylsulfonamido-phenyl)-N-[2-(2-phenoxy-ethoxy)-6-trifluoromethyl-pyridin-3-ylmethyl]-propionamide 363 N-[2-(3,5-dimethoxy-benzyloxy)-6-trifluoromethyl-pyridin-3-ylmethyl]-2-(3-fluoro-4-methylsulfonamido-phenyl)-propionamide 364 2-(3-fluoro-4-methylsulfonamido-phenyl)-N-(4-hydroxymethyl-6'-trifluoromethyl-3,4,5,6-tetrahydro-2H-[1,2']bipyridinyl-3'-ylmethyl)-propionamide 365 N-(6'-tert-butyl-4-phenyl-3,4,5,6-tetrahydro-2H-[1,2']bipyridinyl-3'-ylmethyl)-2-(3-fluoro-4-methylsulfonamido-phenyl)-propionamide 366 N-{6-tert-butyl-2-[4-(4-fluoro-phenyl)-piperazin-1-yl]-pyridin-3-ylmethyl}-2-(3-fluoro-4-methylsulfonamido-phenyl)-propionamide 367 2-(4-methylsulfonamido-3-methyl-phenyl)-N-(2-pyrrolidin-1-yl-6-trifluoromethyl-pyridin-3-ylmethyl)-propionamide

[368] N-((2-(1H-indol-4-yl)-6-(trifluoromethyl)pyridin-3-yl)methyl)-2-(3-fluoro-4-(methylsulfonamido)phenyl)propanamide,

[369] N-((6-tert-butyl-2-propoxypyridin-3-yl)methyl)-2-(3-fluoro-4-(methylsulfonamido)phenyl)propanamide,

[370] N-((6-tert-butyl-2-(3-methoxypropoxy)pyridin-3-yl)methyl)-2-(3-fluoro-4-(methylsulfonamido)phenyl)propanamide,

[371] N-((6-tert-butyl-2-(4-(dimethylamino)-4-phenylpiperidin-1-yl)pyridin-3-yl)methyl)-2-(3-fluoro-4-(methylsulfonamido)phenyl)propanamide,

[372] N-((6-tert-butyl-2-methoxypyridin-3-yl)methyl)-2-(3-fluoro-4-(methylsulfonamido)phenyl)propanamide,

[373] N-((6-tert-butyl-2-ethoxypyridin-3-yl)methyl)-2-(3-fluoro-4-(methylsulfonamido)phenyl)propanamide,

[374] N-((6-tert-butyl-2-isopropoxypyridin-3-yl)methyl)-2-(3-fluoro-4-(methylsulfonamido)phenyl)propanamide,

[375] 2-(3-fluoro-4-(methylsulfonamido)phenyl)-N-((2-(pentyloxy)-6-(trifluoromethyl)pyridin-3-yl)methyl)propanamide,

[376] 2-(3-fluoro-4-(methylsulfonamido)phenyl)-N-((2-(hexyloxy)-6-(trifluoromethyl)pyridin-3-yl)methyl)propanamide,

[377] N-((2-(3,5-dimethylcyclohexyloxy)-6-(trifluoromethyl)pyridin-3-yl)methyl)-2-(3-fluoro-4-(methylsulfonamido)phenyl)propanamide,

[378] N-((6-tert-butyl-2-(2-ethoxyethoxy)pyridin-3-yl)methyl)-2-(3-fluoro-4-(methylsulfonamido)phenyl)propanamide, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Further preferred are the compounds 126, 166, 174, 291, 83, 80, 89, 91, 104, 117, 118, 131, 137,140, 142, 149,160, 166, 167, 168, 172, 218, 235, 127, 196, 256, 257 and 204; still further preferred are the compounds 126, 166, 174, 291, 83, 80, 89, 91, 104,117, 118, 131, 137, 140, 142, 149, 160, 166, 167, 168, 172, 218 and 235; most preferred are the compounds 126, 166, 174 and 291.

The present invention accordingly provides compounds of the general formula I,

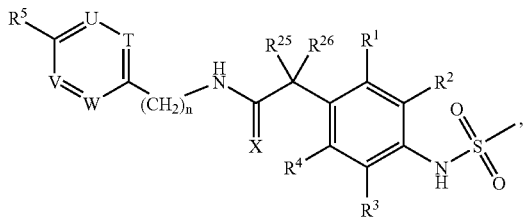

in which

X denotes O, S or N—C≡N;

n denotes 0, 1, 2, 3 or 4;

$R^1$, $R^2$, $R^3$ and $R^4$, mutually independently, in each case denote H; F; Cl; Br; I; —$SF_5$; —$NO_2$; —$CF_3$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$ or denote a linear or branched, saturated or unsaturated, unsubstituted or at least monosubstituted aliphatic $C_{1-10}$ residue;

$R^5$ denotes H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$;

denotes a linear or branched, saturated or unsaturated, unsubstituted or at least monosubstituted aliphatic $C_{1-10}$ residue;

or denotes an unsaturated or saturated, unsubstituted or at least monosubstituted 3-, 4-, 5-, 6-, 7-, 8- or 9-membered cycloaliphatic residue, optionally comprising at least one heteroatom as a ring member, which residue is in each case attached to the parent structure via a carbon atom in the ring of the cycloaliphatic residue;

T denotes C—$R^6$ and U denotes C—$R^7$ and V denotes N and W denotes C—$R^8$ or T denotes C—$R^6$ and U denotes N and V denotes C—$R^9$ and W denotes C—$R^8$ or T denotes N and U denotes C—$R^7$ and V denotes C—$R^9$ and W denotes C—$R^8$ or T denotes N and U denotes N and V denotes C—$R^9$ and W denotes C—$R^8$ or T denotes N and U denotes C—$R^7$ and V denotes N and W denotes C—$R^8$ or T denotes C—$R^6$ and U denotes N and V denotes N and W denotes C—$R^8$ or T denotes C—$R^6$ and U denotes C—$R^7$ and V denotes C—$R^9$ and W denotes C—$R^{10}$;

$R^6$ and $R^7$, mutually independently, in each case denote H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$ or denote a linear or branched, saturated or unsaturated, unsubstituted or at least monosubstituted aliphatic $C_{1-10}$ residue;

$R^8$ denotes H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$;

denotes a linear or branched, saturated or unsaturated, unsubstituted or at least monosubstituted aliphatic $C_{1-10}$ residue;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted $C_{1-6}$ alkylene group;

or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group;

$R^9$ denotes H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$ or denotes a linear or branched, saturated or unsaturated, unsubstituted or at least monosubstituted aliphatic $C_{1-10}$ residue;

$R^{10}$ denotes —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$;

denotes a linear or branched, saturated or unsaturated aliphatic $C_{1-10}$ residue, which is in each case substituted with optionally 1, 2, 3, 4, 5, 6, 7, 8 or 9 substituents mutually independently selected from the group consisting of —CN, —$NO_2$, —OH, —$NH_2$, —SH, —O($C_{1-5}$ alkyl), —S($C_{1-5}$ alkyl), —NH($C_{1-5}$ alkyl), —N($C_{1-5}$ alkyl)($C_{1-5}$ alkyl), —$OCF_3$ and —$SCF_3$;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted $C_{1-6}$ alkylene group;

or denotes an unsubstituted or at least monosubstituted 5- to 14-membered aryl or heteroaryl residue; which may be fused with a saturated or unsaturated, unsubstituted or at least monosubstituted mono- or polycyclic ring system and/or be attached via a linear or branched, unsubstituted or at least monosubstituted $C_{1-6}$ alkylene group;

$R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$, mutually independently, in each case denote a linear or branched, saturated or unsaturated, unsubstituted or at least monosubstituted aliphatic $C_{1-10}$ residue;

denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be fused with a saturated or unsaturated, unsubstituted or at least monosubstituted mono- or polycyclic ring system and/or be attached via a linear or branched, unsubstituted or at least monosubstituted $C_{1-6}$ alkylene group;

or denote an unsubstituted or at least monosubstituted 5- to 14-membered aryl or heteroaryl residue; which may be fused with a saturated or unsaturated, unsubstituted or at least monosubstituted mono- or polycyclic ring system and/or be attached via a linear or branched, unsubstituted or at least monosubstituted $C_{1-6}$ alkylene group;

or $R^{12}$ and $R^{13}$, in each case together with the nitrogen atom joining them together as a ring member, form a saturated or unsaturated, unsubstituted or at least monosubstituted 4-, 5-, 6-, 7-, 8- or 9-membered heterocycloaliphatic residue, which may be fused with a saturated or unsaturated, unsubstituted or at least monosubstituted mono- or polycyclic ring system;

and $R^{25}$ and $R^{26}$, mutually independently, in each case denote a hydrogen residue;

denote a linear or branched, saturated or unsaturated, unsubstituted or at least monosubstituted aliphatic $C_{1-10}$ residue;

or denote an unsaturated or saturated, unsubstituted or at least monosubstituted, 3-, 4-, 5-, 6-, 7-, 8- or 9-membered cycloaliphatic residue optionally comprising at least one heteroatom as a ring member;

providing that $R^{25}$ and $R^{26}$ do not in each case denote a hydrogen residue;

or $R^{25}$ and $R^{26}$, together with the carbon atom joining them together as a ring member, form a saturated or unsaturated, unsubstituted or at least monosubstituted 3-, 4-, 5- or 6-membered cycloaliphatic residue;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Unless otherwise stated, the above-stated aliphatic $C_{1-10}$ residues may preferably optionally in each case be substituted with 1, 2, 3, 4, 5, 6, 7, 8 or 9 substituents mutually independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$ and —SCF$_3$.

The above-stated $C_{1-6}$ alkylene groups may preferably optionally in each case be substituted with 1, 2, 3, 4, 5, 6, 7, 8 or 9 substituents mutually independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$ and —SCF$_3$.

The above-stated (hetero)cycloaliphatic residues may preferably optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, NO$_2$, —O—CF$_3$, —S—CF$_3$, —SH, —S—C$_{1-5}$ alkyl, —C$_{1-5}$ alkyl, alkyl, —C(=O)—OH, —C(=O)—O—C$_{1-5}$ alkyl, —NH(C$_{1-5}$ alkyl), —N(C$_{1-5}$ alkyl)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl —O-benzyl.

The above-stated (hetero)cycloaliphatic residues may likewise preferably in each case optionally comprise 1, 2 or 3 (further) heteroatom(s) mutually independently selected from the group consisting of oxygen, nitrogen and sulfur.

The rings of the above-stated mono- or polycyclic ring systems may preferably optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—C$_{1-5}$ alkyl, —C(=O)—OH, —C(=O)—O—C$_{1-5}$ alkyl, —NH(C$_{1-5}$ alkyl), —N(C$_{1-5}$ alkyl)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl.

The rings of the above-stated mono- or polycyclic ring systems are preferably in each case 5-, 6- or 7-membered and may in each case optionally comprise 1, 2, 3, 4 or 5 heteroatom(s) as ring member(s), which are mutually independently selected from the group consisting of oxygen, nitrogen and sulfur.

The above-stated aryl or heteroaryl residues may likewise preferably optionally in each case be substituted with 1, 2, 3, 4 or 5 substituents mutually independently selected from the group consisting of F, Cl, Br, I, —CN, —CF$_3$, —SF$_5$, —OH, —O—C$_{1-5}$ alkyl, —NH$_2$, —NO$_2$, —O—CF$_3$, —S—CF$_3$, —SH, —S—C$_{1-5}$ alkyl, —C$_{1-5}$ alkyl, —C(=O)—OH, —C(=O)—O—C$_{1-5}$ alkyl, —NH(C$_{1-5}$ alkyl), —N(C$_{1-5}$ alkyl)$_2$, —NH—C(=O)—O—C$_{1-5}$ alkyl, —C(=O)—H, —C(=O)—C$_{1-5}$ alkyl, —C(=O)—NH$_2$, —C(=O)—NH—C$_{1-5}$ alkyl, —C(=O)—N—(C$_{1-5}$ alkyl)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl.

The above-stated heteroaryl residues likewise preferably in each case optionally comprise 1, 2, 3, 4 or 5 heteroatom(s) mutually independently selected from the group consisting of oxygen, nitrogen and sulfur as ring member(s).

If one or more of the above-stated residues denotes a saturated or unsaturated $C_{1-10}$ aliphatic residue, i.e. a $C_{1-10}$ alkyl, $C_{2-10}$ alkenyl or $C_{2-10}$ alkynyl residue, the latter may preferably be substituted with optionally 1, 2, 3, 4, 5, 6, 7, 8 or 9 substituents mutually independently selected from the group consisting of F, Cl, Br, I, —CN, —NO$_2$, —OH, —NH$_2$, —SH, —O(C$_{1-5}$ alkyl), —S(C$_{1-5}$ alkyl), —NH(C$_{1-5}$ alkyl), —N(C$_{1-5}$ alkyl)(C$_{1-5}$ alkyl), —OCF$_3$ and —SCF$_3$. $C_{2-10}$ alkenyl residues comprise at least one, preferably 1, 2, 3 or 4

C—C double bonds and $C_{2-10}$ alkynyl residues comprise at least one, preferably 1, 2, 3 or 4 C—C triple bonds.

alkyl residues are preferably selected from the group consisting of methyl, ethyl, n-propyl, isopropyl, n-butyl, sec-butyl, isobutyl, tert-butyl, n-pentyl, sec-pentyl, neopentyl, n-hexyl and n-heptyl, which may optionally be substituted with 1, 2, 3, 4, 5, 6, 7, 8 or 9 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

alkenyl residues which are likewise preferred are those selected from the group consisting of vinyl, 1-propenyl, 2-propenyl, 1-butenyl, 2-butenyl, 3-butenyl, 2-methyl-2-butenyl, 1-pentenyl, 2-pentenyl, 3-pentenyl and 4-pentenyl, which may optionally be substituted with 1, 2 or 3 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Alkynyl residues which are furthermore preferred are those selected from the group consisting of ethynyl, 1-propynyl, 2-propynyl, 1-butynyl, 2-butynyl, 3-butynyl, 1-pentynyl, 2-pentynyl, 3-pentynyl and 4-pentynyl, which may optionally be substituted with 1, 2 or 3 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Particularly preferred optionally substituted $C_{1-10}$ aliphatic residues are those selected from the group consisting of methyl, —CF$_3$, —CHF$_2$, —CH$_2$F, —CF$_2$Cl, —CCl$_2$F, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CF$_2$—CH$_3$, —CHF—CF$_2$Cl, —CF$_2$—CFCl$_2$, —CFCl—CF$_2$Cl, —CFCl—CFCl$_2$, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methyl-2-butenyl, (1,1,2)-trifluoro-1-butenyl, 1-pentenyl, 2-pentenyl, 3-pentenyl, 4-pentenyl, —CF=CF$_2$, —CCl=CCl$_2$, —CH$_2$—CF=CF$_2$, —CH$_2$—CCl=CCl$_2$, —C≡C—I, —C≡C—F and —C≡C—Cl.

If one or more of the above-stated substituents denotes a (hetero)cycloaliphatic residue, which may optionally be fused with a saturated or unsaturated, unsubstituted or at least monosubstituted mono- or polycyclic ring system, the latter may preferably be selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, azocanyl, diazepanyl, dithiolanyl, (1,3,4,5)-tetrahydropyrido[4,3-b]indolyl, (3,4)-dihydro-1H-isoquinolinyl, (1,3,4,9)-tetrahydro-[b]-carbolinyl and (1,3)-thiazolidinyl.

The (hetero)cycloaliphatic residues may particularly preferably optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—F$_3$, —S—CF$_3$, phenyl and —O-benzyl.

If one or more of the above-stated substituents denotes an aryl residue, the latter may preferably be selected from the group consisting of phenyl and naphthyl (1-naphthyl and 2-naphthyl).

If one or more of the above-stated substituents denotes a heteroaryl residue, the latter may preferably be selected from the group consisting of thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, quinoxalinyl, quinolinyl and isoquinolinyl.

The aryl or heteroaryl residues may particularly preferably optionally in each case be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl, wherein in each case cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl.

For the purposes of the present invention, a mono- or polycyclic ring system is taken to comprise mono- or polycyclic hydrocarbon residues which may be saturated or unsaturated and may optionally comprise 1, 2, 3, 4 or 5 heteroatom(s) as ring member(s), which are mutually independently selected from the group consisting of oxygen, nitrogen and sulfur.

Such a mono- or polycyclic ring system may, for example, be fused (anellated) with an aryl residue or a heteroaryl residue.

If a polycyclic ring system, such as for example a bicyclic ring system, is present, the various rings may in each case mutually independently be of a different degree of saturation, i.e. be saturated or unsaturated. A polycyclic ring system is preferably a bicyclic ring system.

(1,3)-benzodioxolyl and (1,4)-benzodioxanyl may be mentioned by way of example of aryl residues which are fused with a mono- or polycyclic ring system.

If one or more of the above-stated substituents comprises a mono- or polycyclic ring system, the latter may preferably be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl.

If one or more of the above-stated substituents comprises a linear or branched C$_{1-6}$ alkylene group, the latter may preferably be selected from the group consisting of —(CH$_2$)—, —(CH$_2$)$_2$—, —C(H)(CH$_3$)—, —(CH$_2$)$_3$—, —(CH$_2$)$_4$—, —(CH$_2$)$_5$—, —C(H)(C(H)(CH$_3$)$_2$)— and —C(C$_2$H$_5$)(H)—.

Preferred substituted compounds are those of the above-stated general formula I, in which X denotes O, S or N—C≡N;

n denotes 0, 1, 2, 3 or 4;

R$^1$, R$^2$, R$^3$ and R$^4$, mutually independently, in each case denote H; F; Cl; Br; I; —SF$_5$; —NO$_2$; —CF$_3$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$; —S(=O)$_2$—R$^{24}$ or denote an alkyl residue selected from the group consisting of methyl, ethyl, n-propyl, isopropyl, tert-butyl, n-butyl, sec-butyl, isobutyl, n-pentyl, n-hexyl and n-heptyl;

R$^5$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$; —S(=O)$_2$—R$^{24}$;

denotes an alkyl residue selected from the group consisting of methyl, ethyl, n-propyl, isopropyl, tert-butyl, n-butyl, sec-butyl, isobutyl, n-pentyl, n-hexyl and n-heptyl;

or denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues and may optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl;

T denotes C—R$^6$ and U denotes C—R$^7$ and V denotes N and W denotes C—R$^8$ or T denotes C—R$^6$ and U denotes N and V denotes C—R$^9$ and W denotes C—R$^8$ or T denotes N and U denotes C—R$^7$ and V denotes C—R$^9$ and W denotes C—R$^8$ or T denotes N and U denotes N and V denotes C—R$^9$ and W denotes C—R$^8$ or T denotes N and U denotes C—R$^7$ and V denotes N and W denotes C—R$^8$ or T denotes C—R$^6$ and U denotes N and V denotes N and W denotes C—R$^8$ or T denotes C—R$^6$ and U denotes C—R$^7$ and V denotes C—R$^9$ and W denotes C—R$^{10}$;

R$^6$ and R$^7$, mutually independently in each case denote H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—OH; —C(=O)—H; —S(=O)$_2$—OH; —NHR$^{11}$; —NR$^{12}$R$^{13}$; —OR$^{14}$; —SR$^{15}$; —C(=O)—NHR$^{16}$; —C(=O)—NR$^{17}$R$^{18}$; —S(=O)$_2$—NHR$^{19}$; —S(=O)$_2$—NR$^{20}$R$^{21}$; —C(=O)—OR$^{22}$; —C(=O)—R$^{23}$; —S(=O)$_2$—R$^{24}$ or denote an alkyl residue selected from the group consisting of methyl, ethyl, n-propyl, isopropyl, tert-butyl, n-butyl, sec-butyl, isobutyl, n-pentyl, n-hexyl and n-heptyl;

$R^8$ denotes H; F; Cl; Br; I; —$SF_5$; —$CF_3$; —$CF_2Cl$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$;

denotes an alkyl residue selected from the group consisting of methyl, ethyl, n-propyl, isopropyl, tert-butyl, n-butyl, sec-butyl, isobutyl, n-pentyl, n-hexyl and n-heptyl;

denotes an alkenyl residue selected from the group consisting of ethenyl, propenyl, butenyl and pentenyl;

denotes an alkynyl residue selected from the group consisting of ethynyl, propynyl, butynyl and pentynyl;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues and may optionally in each case be substituted with 1, 2, 3, 4 or 5 substituents mutually independently selected from the group consisting of oxo (=O), thioxo (=S), F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl, tert-butyl, n-pentyl, —C(=O)—$CH_3$, —C(=O)—$C_2H_5$, —C(=O)—CH($CH_3$)$_2$, —C(=O)—C($CH_3$)$_3$, —C(=O)—OH, —C(=O)—O—$CH_3$, —C(=O)—O—$C_2H_5$, —C(=O)—O—CH($CH_3$)$_2$, —C(=O)—O—C($CH_3$)$_3$, —NH—$CH_3$, —NH—$C_2H_5$, —NH—C($CH_3$)$_3$, —N($CH_3$)$_2$, —N($C_2H_5$)$_2$, —N($CH_3$)($C_2H_5$), —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —$CF_3$, —$SF_5$, —CN, —$NO_2$, methyl, ethyl, n-propyl, isopropyl, n-butyl, sec-butyl, isobutyl, tert-butyl, —O—$CH_3$, —O—$C_2H_5$, —O—CH($CH_3$)$_2$, —O—C($CH_3$)$_3$, —O—$CF_3$, —S—$CF_3$, phenyl and —O-benzyl;

or denotes a residue selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, quinoxalinyl, quinolinyl and isoquinolinyl, which may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl, tert-butyl, n-pentyl, —C(=O)—OH, —C(=O)—O—$CH_3$, —C(=O)—O—$C_2H_5$, —C(=O)—O—CH($CH_3$)$_2$, —C(=O)—O—C($CH_3$)$_3$, —NH—$CH_3$, —NH—$C_2H_5$, —NH—C($CH_3$)$_3$, —N($CH_3$)$_2$, —N($C_2H_5$)$_2$, —N($CH_3$)($C_2H_5$), —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—CH($CH_3$)$_2$, —C(=O)—C($CH_3$)$_3$, —C(=O)—$NH_2$, —C(=O)—NH—$CH_3$, —C(=O)—NH—$C_2H_5$, —C(=O)—N($CH_3$)$_2$, —C(=O)—N($C_2H_5$)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —$CF_3$, —$SF_5$, —CN, —$NO_2$, —$C_{1-5}$ alkyl, —O—$C_{1-5}$ alkyl, —O—$CF_3$, —S—$CF_3$, phenyl and —O-benzyl;

$R^9$ denotes H; F; Cl; Br; I; —$SF_5$; —$NO_2$; —$CF_3$; —$CF_2Cl$; —(N; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$ or denotes an alkyl residue selected from the group consisting of methyl, ethyl, n-propyl, isopropyl, tert-butyl, n-butyl, sec-butyl, isobutyl, n-pentyl, n-hexyl and n-heptyl;

$R^{10}$ denotes —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{11}$; —$NR^{12}R^{13}$; —$OR^{14}$; —$SR^{15}$; —C(=O)—$NHR^{16}$; —C(=O)—$NR^{17}R^{18}$; —S(=O)$_2$—$NHR^{19}$; —S(=O)$_2$—$NR^{20}R^{21}$; —C(=O)—$OR^{22}$; —C(=O)—$R^{23}$; —S(=O)$_2$—$R^{24}$;

denotes an alkyl residue selected from the group consisting of methyl, ethyl, n-propyl, isopropyl, tert-butyl, n-butyl, sec-butyl, isobutyl, n-pentyl, n-hexyl and n-heptyl which is in each case substituted with optionally 1, 2, 3, 4, 5, 6, 7, 8 or 9 substituents mutually independently selected from the group consisting of —CN, —$NO_2$, —OH, —$NH_2$, —SH, —O—$CH_3$, —O—$C_2H_5$, —O—CH($CH_3$)$_2$, —O—C($CH_3$)$_3$, —S—$CH_3$, —S—$C_2H_5$, —S—CH($CH_3$)$_2$, —S—C($CH_3$)$_3$, —NH—$CH_3$, —NH—$C_2H_5$, —NH—C($CH_3$)$_3$, —N($CH_3$)$_2$, —N($C_2H_5$)$_2$, —N($CH_3$)($C_2H_5$), —$OCF_3$ and —$SCF_3$;

denotes an alkenyl residue selected from the group consisting of ethenyl, propenyl, butenyl and pentenyl;

denotes an alkynyl residue selected from the group consisting of ethynyl, propynyl, butynyl and pentynyl;

denotes a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues and may optionally in each case be substituted with 1, 2, 3, 4 or 5 substituents mutually independently selected from the group consisting of oxo (=O), thioxo (=S), F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec-butyl, isobutyl, tert-butyl, n-pentyl, —C(=O)—$CH_3$, —C(=O)—$C_2H_5$, —C(=O)—CH($CH_3$)$_2$, —C(=O)—C($CH_3$)$_3$, —C(=O)—OH, —C(=O)—O—$CH_3$, —C(=O)—O—$C_2H_5$, —C(=O)—O—CH($CH_3$)$_2$, —C(=O)—O—C($CH_3$)$_3$, —NH—$CH_3$, —NH—$C_2H_5$, —NH—C($CH_3$)$_3$, —N($CH_3$)$_2$, —N($C_2H_5$)$_2$, —N($CH_3$)($C_2H_5$), —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl;

or denotes a residue selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, quinoxalinyl, quinolinyl and isoquinolinyl, wherein the residue may in each case be attached via a —(CH$_2$)—, —(CH$_2$)$_2$— or —(CH$_2$)$_3$— group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl;

R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$ and R$^{24}$, mutually independently, in each case denote an alkyl residue selected from the group consisting of methyl, ethyl, n-propyl, isopropyl, tert-butyl, n-butyl, sec-butyl, isobutyl, n-pentyl, n-hexyl and n-heptyl;

denote a residue selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case be attached via a —(CH$_2$)—, —(CH$_2$)$_2$— or —(CH$_2$)$_3$-group and/or may optionally be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—OC(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl;

or denote a residue selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, quinoxalinyl, quinolinyl and isoquinolinyl, which may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$ alkyl, —O—CF$_3$, —S—CF$_3$, phenyl and —O-benzyl;

or

R$^{12}$ and R$^{13}$, in each case together with the nitrogen atom joining them together as a ring member, form a residue selected from the group consisting of pyrrolidinyl, piperidinyl, (1,3,4,5)-tetrahydropyrido[4,3-b]indolyl, (3,4)-dihydro-1H-isoquinolinyl, (1,3,4,9)-tetrahydro-[b]-carbolinyl, imidazolidinyl, (1,3)-thiazolidinyl, piperazinyl, morpholinyl, azepanyl, diazepanyl and thiomorpholinyl, which may optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec-butyl, isobutyl, tert-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl;

and $R^{25}$ and $R^{26}$, mutually independently, in each case denote a hydrogen residue;

denote an alkyl residue selected from the group consisting of methyl, ethyl, n-propyl, isopropyl, tert-butyl, n-butyl, sec-butyl, isobutyl, n-pentyl, n-hexyl and n-heptyl;

or denote a residue selected from the group consisting of cyclopropyl, cyclobutyl, cyclopentyl, cyclohexyl, cyclopentenyl and cyclohexenyl;

providing that $R^{25}$ and $R^{26}$ do not in each case denote a hydrogen residue;

or $R^{25}$ and $R^{26}$, in each case together with the carbon atom joining them together as a ring member, form a residue selected from the group consisting of cyclopropyl, cyclobutyl, cyclopentyl, cyclohexyl, cyclopentenyl and cyclohexenyl;

wherein unless otherwise stated, the above-stated alkyl, alkenyl and alkynyl residues may in each case optionally be substituted with 1, 2, 3, 4, 5, 6, 7, 8 or 9 substituents mutually independently selected from the group consisting of F, Cl, Br, I, —CN, —NO₂, —OH, —NH₂, —SH, —O—CH₃, —O—C₂H₅, —O—CH(CH₃)₂, —O—C(CH₃)₃, —S—CH₃, —S—C₂H₅, —S—CH(CH₃)₂, —S—C(CH₃)₃, —NH—CH₃, —NH—C₂H₅, —NH—C(CH₃)₃, —N(CH₃)₂, —NH—C₂H₅)₂, —N(CH₃)(C₂H₅), —OCF₃ and —SCF₃;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise preferred compounds are those of the above-stated general formula I, in which X denotes O, S or N—C≡N;

n denotes 0, 1, 2, 3 or 4;

$R^1$, $R^2$, $R^3$ and $R^4$, mutually independently, in each case denote H; F; Cl; Br; I; —SF₅; —NO₂; —CN; —NH₂; —OH; —SH; —C(=O)—NH₂; —S(=O)₂—NH₂; —C(=O)—NH—OH; —C(=O)—OH; —C(=O)—H; —S(=O)₂—OH; —NHR¹¹; —NR¹²R¹³; —OR¹⁴; —SR¹⁵; —S(=O)₂—R²⁴ or denote a residue selected from the group consisting of methyl, —CF₃, —CCl₃, —CBr₃, —CHF₂, —CH₂F, —CF₂Cl, —CCl₂F, ethyl, —CF₂—CH₃, —CH₂—CF₃, —C₂F₅, —CH₂—CCl₃, —CH₂—CBr₃, —CHF—CF₂Cl, —CF₂—CF₂Cl, —CFCl—CF₂Cl, n-propyl, —CF₂—CF₂—CF₃, —CF(CF₃)₂, isopropyl, sec-butyl, isobutyl and tert-butyl;

$R^5$ denotes F; Cl; Br; I; —SF₅; —OR¹⁴; —SR¹⁵; —S(=O)₂—R²⁴;

denotes a residue selected from the group consisting of methyl, —CF₃, —CCl₃, —CBr₃, —CHF₂, —CH₂F, —CF₂Cl, —CCl₂F, —CH₂—CN, —CH₂—O—CH₃, —CH₂—O—CF₃, —CH₂—SF₃, ethyl, —CF₂—CH₃, —CH₂—CF₃, —C₂F₅, —CH₂—CCl₃, —CH₂—CBr₃, —CHF—CF₂Cl, —CF₂CF₂Cl, —CFCl—CF₂Cl, —CH₂—CH₂—CN, n-propyl, —CF₂—CF₂—CF₃, —CF(CF₃)₂, isopropyl, —CH₂—CH₂—CH₂—CN, —CH₂—O—CH₂—CH₃, —CH₂—CH₂—SF₃, —CH₂—CH₂—OCF₃, —CH(CH₃)(O—CH₃), —CH(CH₃)(S—CH₃), n-butyl, —CF₂—CF₂—CF₂—CF₃, —CH₂—CH₂—CH₂—CH₂—CN, sec-butyl, isobutyl and tert-butyl;

or denotes a residue selected from the group consisting of cyclopropyl, cyclobutyl, cyclopentyl, cyclohexyl, cyclopentenyl and cyclohexenyl, which may optionally in each case be substituted with 1, 2, 3, 4 or 5 substituents mutually independently selected from the group consisting of oxo (=O), thioxo (=S), —OH, —O—CH₃, —O—C₂H₅, —O—CH(CH₃)₂, —O—C(CH₃)₃, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl, tert-butyl, and n-pentyl;

T denotes C—R⁶ and U denotes C—R⁷ and V denotes N and W denotes C—R⁸ or

T denotes C—R⁶ and U denotes N and V denotes C—R⁹ and W denotes C—R⁸ or

T denotes N and U denotes C—R⁷ and V denotes C—R⁹ and W denotes C—R⁸ or

T denotes N and U denotes N and V denotes C—R⁹ and W denotes C—R⁸ or

T denotes N and U denotes C—R⁷ and V denotes N and W denotes C—R⁸ or

T denotes C—R⁶ and U denotes N and V denotes N and W denotes C—R⁸ or

T denotes C—R⁶ and U denotes C—R⁷ and V denotes C—R⁹ and W denotes C—R¹⁰;

$R^6$ and $R^7$, mutually independently in each case denote H; F; Cl; Br; I; —SF₅; —NO₂; —CN; —NH₂; —OH; —SH; —C(=O)—NH₂; —S(=O)₂—NH₂; —C(=O)—NH—OH; —C(=O)—OH; —C(=O)—H; —S(=O)₂—OH; —NHR¹¹; —NR¹²R¹³; —OR¹⁴; —SR¹⁵; —S(=O)₂—R²⁴ or denote a residue selected from the group consisting of methyl, —CF₃, —CCl₃, —CBr₃, —CHF₂, —CH₂F, —CF₂Cl, —CCl₂F, ethyl, —CF₂—CH₃, —CH₂—CF₃, —C₂F₅, —CH₂—CCl₃, —CH₂—CBr₃, —CHF—CF₂Cl, —CF₂—CF₂Cl, —CFCl—CF₂Cl, n-propyl, —CF₂—CF₂—CF₃, —CF(CF₃)₂, isopropyl, sec-butyl, isobutyl and tert-butyl;

$R^8$ denotes H; F; Cl; Br; I; —SF₅; —NO₂; —CN; —NH₂; —OH; —SH; —C(=O)—NH₂; —S(=O)₂—NH₂; —C(=O)—NH—OH; —C(=O)—OH; —C(=O)—H; —S(=O)₂—OH; —NHR¹¹; —NR¹²R¹³; —OR¹⁴; —SR¹⁵; —C(=O)—OR²²; —S(=O)₂—R²⁴ or denotes a residue selected from the group consisting of methyl, —CF₃, —CCl₃, —CBr₃, —CHF₂, —CH₂F, —CF₂Cl, —CCl₂F, ethyl, —CF₂—CH₃, —CH₂—CF₃, —C₂F₅, —CH₂—CCl₃, —CH₂—CBr₃, —CHF—CF₂Cl, —CF₂—CF₂Cl, —CFCl—CF₂Cl, n-propyl, —CF₂—CF₂—CF₃, —CF(CF₃)₂, isopropyl, sec-butyl, isobutyl, tert-butyl, n-pentyl, sec-pentyl, neopentyl, n-hexyl, ethenyl, propenyl, butenyl, pentenyl, ethynyl, propynyl, butynyl, pentynyl, —CF=CF₂, —CCl=Cl₂, —CH₂—CF=CF₂, —CH₂—CCl=CCl₂, —C≡C—I, —C≡C—F and —C≡C—Cl;

denotes a residue selected from the group consisting of cyclopropyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues and may optionally in each case be substituted with 1, 2, 3, 4 or 5 substituents mutually independently selected from the group consisting of oxo (=O), thioxo (=S), —OH, —O—CH₃, —O—C₂H₅, —O—CH(CH₃)₂, —O—C(CH₃)₃, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl, tert-butyl, n-pentyl, —C(=O)—CH₃, —C(=O)—C₂H₅, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, quinoxalinyl, quinolinyl and isoquinolinyl, which may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, -SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

R$^9$ denotes H; F; Cl; Br; I; —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —S(=O)$_2$—R$^{24}$ or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;

R$^{10}$ denotes —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{11}$; —NR$^{12}$R$^{13}$; —OR$^{14}$; —SR$^{15}$; —C(=O)—OR$^{22}$; —S(=O)$_2$—R$^{24}$ or denotes a residue selected from the group consisting of ethenyl, propenyl, butenyl, pentenyl, ethynyl, propynyl, butynyl, pentynyl, —CF=CF$_2$, —CCl=Cl$_2$, —CH$_2$—CF=CF$_2$, —CH$_2$—CCl=CCl$_2$, —C≡C—I, —C≡C—F and —C≡C—Cl;

denotes a residue selected from the group consisting of cyclopropyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues and may optionally in each case be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, quinoxalinyl, quinolinyl and isoquinolinyl, which may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

R$^{11}$, R$^{12}$, R$^{13}$, R$^{14}$, R$^{15}$, R$^{22}$ and R$^{24}$, mutually independently, in each case denote a residue selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec-butyl, isobutyl and tert-butyl;

denote a residue selected from the group consisting of cyclopropyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which in each case may optionally be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl and isoxazolyl, wherein the residue may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

or

R$^{12}$ and R$^{13}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl, which may optionally in each case be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, and R$^{25}$ and R$^{26}$, mutually independently, in each case denote a hydrogen residue;

denote an alkyl residue selected from the group consisting of methyl, ethyl and n-propyl;

or denote a residue selected from the group consisting of cyclopropyl, cyclobutyl, cyclopentyl and cyclohexyl;

providing that R$^{25}$ and R$^{26}$ do not in each case denote a hydrogen residue;

or

R$^{25}$ and R$^{26}$, in each case together with the carbon atom joining them together as a ring member, form a residue selected from the group consisting of cyclopropyl, cyclobutyl, cyclopentyl and cyclohexyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Further preferred compounds are those of the above-stated general formula i, in which X denotes O, S or N—C≡N;

n denotes 0, 1 or 2;

R$^1$, R$^3$ and R$^4$, mutually independently, in each case denote H; F; Cl; Br; or denote a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl and —CFCl—CF$_2$Cl;

R$^2$ denotes F; Cl; Br; I or denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl, tert-butyl, —O—CH$_3$, —O—CF$_3$, —O—CCl$_3$, —O—CBr$_3$, —O—CHF$_2$, —O—CH$_2$F, —O—CF$_2$Cl, —O—CCl$_2$F, —O—C$_2$H$_5$, —O—CF$_2$—CH$_3$, —O—CH$_2$—CF$_3$, —O—C$_2$F$_5$, —O—CH$_2$—CCl$_3$, —O—CH$_2$—CBr$_3$, —O—CHF—CF$_2$Cl, —O—CF$_2$—CF$_2$Cl, —O—CFCl—CF$_2$Cl, —O—CH$_2$—CH$_2$—CH$_3$, —O—CF$_2$—CF$_2$—CF$_3$, —O—CF(CF$_3$)$_2$, —O—CH(CH$_3$)$_2$, —O—C(CH$_3$)$_3$, —S—CH$_3$, —S—CF$_3$, —S—CCl$_3$, —S—CBr$_3$, —S—CHF$_2$, —S—CH$_2$F, —S—CF$_2$Cl, —S—CCl$_2$F, —S—C$_2$H$_5$, —S—CF$_2$—CH$_3$, —S—CH$_2$—CF$_3$, —S—C$_2$F$_5$, —S—CH$_2$—CCl$_3$, —S—CH$_2$—CBr$_3$, —S—CHF—CF$_2$Cl, —S—CF$_2$—CF$_2$Cl, —S—CFCl—CF$_2$Cl, —S—CH$_2$—CH$_2$—CH$_3$, —S—CF$_2$—CF$_2$—CF$_3$, —S—CF(CF$_3$)$_2$, —S—CH(CH$_3$)$_2$ and —S—C(CH$_3$)$_3$;

R$^5$ denotes F; Cl; Br; I; —SF$_5$;

denotes a residue selected from the group consisting of —CF$_3$, —CCl$_3$, —CBr$_3$, —CHF$_2$, —CH$_2$F, —CF$_2$Cl, —CCl$_2$F, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CF$_2$—CF$_2$—CF$_3$, —CF(CF$_3$)$_2$, sec-butyl, isobutyl, tert-butyl, —O—CF$_3$, —O—CCl$_3$, —O—CBr$_3$, —O—CHF$_2$, —O—CH$_2$F, —O—CF$_2$Cl, —O—CCl$_2$F, —O—CF$_2$—CH$_3$, —O—CH$_2$—CF$_3$, —O—C$_2$F$_5$, —O—CH$_2$—CCl$_3$, —O—CH$_2$—CBr$_3$, —O—CHF—CF$_2$Cl, —O—CF$_2$—CF$_2$Cl, —O—CFCl—CF$_2$Cl, —O—CF$_2$—CF$_2$—CF$_3$, —O—CF(CF$_3$)$_2$, —O—CH(CH$_3$)$_2$, —O—C(CH$_3$)$_3$, —S—CF$_3$, —S—CCl$_3$, —S—CBr$_3$, —S—CHF$_2$, —S—CH$_2$F, —S—CF$_2$Cl, —S—CCl$_2$F, —S—CF$_2$—CH$_3$, —S—CH$_2$—CF$_3$, —S—C$_2$F$_5$, —S—CH$_2$—CCl$_3$, —S—CH$_2$—CBr$_3$, —S—CHF—CF$_2$Cl, —S—CF$_2$—CF$_2$Cl, —S—CFCl—CF$_2$Cl, —S—CF$_2$—CF$_2$—CF$_3$, —S—CF(CF$_3$)$_2$, —S—CH(CH$_3$)$_2$, —S—C(CH$_3$)$_3$, S(=O)$_2$—CF$_3$, —S(=O)$_2$—CCl$_3$, —S(=O)$_2$—CBr$_3$, —S(=O)$_2$—CHF$_2$, —S(=O)$_2$—CH$_2$F, —S(=O)$_2$—CF$_2$Cl, —S(=O)$_2$—CCl$_2$F, —S(=O)$_2$—CF$_2$—CH$_3$, —S(=O)$_2$—CH$_2$—CF$_3$, —S(=O)$_2$—C$_2$F$_5$, —S(=O)$_2$—CH$_2$—CCl$_3$, —S(=O)$_2$—CH$_2$—CBr$_3$, —S(=O)$_2$—CHF—CF$_2$Cl, —S(=O)$_2$—CF$_2$—CF$_2$Cl, —S(=O)$_2$—CFCl—CF$_2$Cl, —S(=O)$_2$—CF$_2$—CF$_2$—CF$_3$, —S(=O)$_2$—CF(CF$_3$)$_2$, —S(=O)$_2$—CH(CH$_3$)$_2$ and —S(=O)$_2$—C(CH$_3$)$_3$;

or denotes a residue selected from the group consisting of cyclopropyl, cyclobutyl, cyclopentyl, cyclohexyl, cyclopentenyl and cyclohexenyl;

T denotes C—R$^6$ and U denotes C—R$^7$ and V denotes N and W denotes C—R$^8$ or T denotes C—R$^6$ and U denotes N and V denotes C—R$^9$ and W denotes C—R$^8$ or T denotes N and U denotes C—R$^7$ and V denotes C—R$^9$ and W denotes C—R$^8$ or T denotes N and U denotes N and V denotes C—R$^9$ and W denotes C—R$^8$ or T denotes N and U denotes C—R$^7$ and V denotes N and W denotes C—R$^8$ or T denotes C—R$^6$ and U denotes N and V denotes N and W denotes C—R$^8$ or T denotes C—R$^6$ and U denotes C—R$^7$ and V denotes C—R$^9$ and W denotes C—R$^{10}$;

R$^6$ and R$^7$, mutually independently, in each case denote H; F; Cl; Br; I; —NO$_2$; —CN; or denote a residue selected from the group consisting of methyl, —CF$_3$, —CCl$_3$, —CBr$_3$, —CHF$_2$, —CH$_2$F, —CF$_2$Cl, —CCl$_2$F, ethyl, n-propyl, isopropyl, sec-butyl, isobutyl and tert-butyl;

R$^8$ denotes F; Cl; Br; I; —OH; —CN; —NH$_2$; —NO$_2$; —NHR$^{11}$; —NR$^{12}$R$^{13}$; —OR$^{14}$; —SR$^{15}$; —C(=O)—OR$^{22}$;

or denotes a residue selected from the group consisting of methyl, —$CF_3$, —$CCl_3$, —$CBr_3$, —$CHF_2$, —$CH_2F$, —$CF_2Cl$, —$CCl_2F$, ethyl, —$CF_2$—$CH_3$, —$CH_2$—$CF_3$, —$C_2F_5$, —$CH_2$—$CCl_3$, —$CH_2$—$CBr_3$, —$CHF$—$CF_2Cl$, —$CF_2$—$CF_2Cl$, —$CFCl$—$CF_2Cl$, n-propyl, —$CF_2$—$CF_2$—$CF_3$, —$CF(CF_3)_2$, isopropyl, sec-butyl, isobutyl and tert-butyl;

denotes a residue selected from the group consisting of cyclopropyl, cyclobutyl, cyclopentyl, cyclohexyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl and tert-butyl;

$R^9$ denotes H; F; Cl; Br; I; —$NO_2$; —CN; or denotes a residue selected from the group consisting of methyl, —$CF_3$, —$CCl_3$, —$CBr_3$, —$CHF_2$, —$CH_2F$, —$CF_2Cl$, —$CCl_2F$, ethyl, n-propyl, —$CF_2$—$CF_2$—$CF_3$, —$CF(CF_3)_2$, isopropyl, sec-butyl, isobutyl and tert-butyl;

$R^{10}$ denotes —CN; —OH; —$NH_2$; —$NO_2$; —$NHR^{11}$; —$NR^{12}R^{13}$; —$OR^{14}$; —$SR^{15}$; —C(=O)—$OR^{22}$;

denotes a residue selected from the group consisting of cyclopropyl, cyclobutyl, cyclopentyl, cyclohexyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues;

denotes a residue selected from the group consisting of cyclopropyl, cyclobutyl, cyclopentyl, cyclohexyl, pyrrolidinyl, piperidinyl, morpholinyl, piperazinyl, azepanyl, diazepanyl, azocanyl and thiomorpholinyl;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl and tert-butyl;

$R^{11}$, $R^{12}$, $R^{13}$, $R^{14}$, $R^{15}$ and $R^{22}$, mutually independently, in each case denote a residue selected from the group consisting of methyl, ethyl, n-propyl, isopropyl, n-butyl, sec-butyl, isobutyl and tert-butyl;

denote a residue selected from the group consisting of cyclopropyl, cyclobutyl, cyclopentyl, cyclohexyl, pyrrolidinyl, piperidinyl, morpholinyl, piperazinyl, azepanyl, diazepanyl, azocanyl and thiomorpholinyl;

or denote a residue selected from the group consisting of phenyl, naphthyl, thiophenyl, furanyl, pyrrolyl and pyridinyl, wherein the residue in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—CH$(CH_3)_2$, —S—$C(CH_3)_3$, methyl, ethyl, n-propyl, isopropyl, n-butyl, sec-butyl, isobutyl and tert-butyl;

or $R^{12}$ and $R^{13}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl, which may optionally in each case be substituted with 1, 2, 3, 4 or 5 substituents mutually independently selected from the group consisting of oxo (=O), thioxo (=S), methyl, ethyl, n-propyl, isopropyl, n-butyl, sec-butyl, isobutyl, tert-butyl, n-pentyl, —C(=O)—$CH_3$, —C(=O)—$C_2H_5$, —C(=O)—$CH(CH_3)_2$, —C(=O)—$C(CH_3)_3$, and $R^{25}$ and $R^{26}$, mutually independently, in each case denote a hydrogen residue or denote an alkyl residue selected from the group consisting of methyl, ethyl and n-propyl;

providing that $R^{25}$ and $R^{26}$ do not in each case denote a hydrogen residue;

or $R^{25}$ and $R^{26}$, in each case together with the carbon atom joining them together as a ring member, form a residue selected from the group consisting of cyclopropyl, cyclobutyl, cyclopentyl and cyclohexyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of the above-stated general formula I, in which X denotes O or S;

n denotes 0, 1 or 2;

$R^1$, $R^3$ and $R^4$ in each case denote H;

$R^2$ denotes F; Cl; Br; I or denotes a residue selected from the group consisting of methyl, —$CF_3$, —$CCl_3$, —$CBr_3$, —$CHF_2$, —$CH_2F$, —O—$CH_3$, —O—$CF_3$, —O—$CCl_3$, —O—$CBr_3$, —O—$CHF_2$, —O—$CH_2F$, —S—$CH_3$, —S—$CF_3$, —S—$CCl_3$, —S—$CBr_3$, —S—$CHF_2$, —S—$CH_2F$, —S—$CF_2Cl$ and —S—$CCl_2F$;

$R^5$ denotes F; Cl; Br; I; —$SF_5$;

denotes a residue selected from the group consisting of —$CF_3$, —$CCl_3$, —$CBr_3$, —$CHF_2$, —$CH_2F$, —$CF_2Cl$, —$CCl_2F$, tert-butyl, —O—$CF_3$, —O—$CCl_3$, —O—$CBr_3$, —O—$CHF_2$, —O—$CH_2F$, —O—$CF_2Cl$, —O—$CCl_2F$, —O—$CF_2$—$CH_3$, —S—$CF_3$, —S—$CCl_3$, —S—$CBr_3$, —S—$CHF_2$, —S—$CH_2F$, —S—$CF_2Cl$, —S—$Cl_2F$, —S—$CF_2$—$CH_3$, —S(=O)$_2$—$CF_3$, —S(=O)$_2$—$CCl_3$, —S(=O)$_2$—$CBr_3$, —S(=O)$_2$—$CHF_2$, —S(=O)$_2$—$CH_2F$ and —S(=O)$_2$—$CF_2Cl$;

or denotes a residue selected from the group consisting of cyclopropyl, cyclobutyl, cyclopentyl, cyclohexyl, cyclopentenyl and cyclohexenyl;

T denotes C—$R^6$ and U denotes C—$R^7$ and V denotes N and W denotes C—$R^8$ or T denotes C—$R^6$ and U denotes N and V denotes C—$R^9$ and W denotes C—$R^8$ or T denotes N and U denotes C—$R^7$ and V denotes C—$R^9$ and W denotes C—$R^8$ or T denotes N and U denotes N and V denotes C—$R^9$ and W denotes C—$R^8$ or T denotes N and U denotes C—$R^7$ and V denotes N and W denotes C—$R^8$ or T denotes C—$R^6$ and U denotes N and V denotes N and W denotes C—$R^8$ or T denotes C—$R^6$ and U denotes C—$R^7$ and V denotes C—$R^9$ and W denotes C—$R^{10}$;

$R^6$ and $R^7$ in each case denote H; F; Cl; Br and I;

$R^8$ denotes F; Cl; Br; I; —OH; —CN; —$NH_2$; —$NO_2$; —$NHR^{11}$; —$NR^{12}R^{13}$; —$OR^{14}$; —$SR^{15}$; —C(=O)—$OR^{22}$;

or denotes a residue selected from the group consisting of methyl, —$CF_3$, —$CCl_3$, —$CBr_3$, —$CHF_2$, —$CH_2F$, —$CF_2Cl$, —$CCl_2F$, ethyl, —$CF_2$—$CH_3$, —$CH_2$—$CF_3$, —$C_2F_5$, —$CH_2$—$CCl_3$, —$CH_2$—$CBr_3$, —CHF—$CF_2Cl$, —$CF_2$—$CF_2Cl$, —CFCl—$CF_2Cl$, n-propyl, —$CF_2$—$CF_2$—$CF_3$, —$CF(CF_3)_2$, isopropyl, sec-butyl, isobutyl and tert-butyl;

denotes a residue selected from the group consisting of cyclopropyl, cyclobutyl, cyclopentyl, cyclohexyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl and tert-butyl;

$R^9$ denotes H; F; Cl; Br or I;

$R^{10}$ denotes —CN; —OH; —$NH_2$; —$NO_2$; —$NHR^{11}$; —$NR^{12}R^{13}$; —$OR^{14}$; —$SR^{15}$; —C(=O)—$OR^{22}$;

denotes a residue selected from the group consisting of cyclopropyl, cyclobutyl, cyclopentyl, cyclohexyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl and tert-butyl;

$R^{11}$, $R^{12}$, $R^{13}$, $R^{14}$, $R^{15}$ and $R^{22}$, mutually independently, in each case denote a residue selected from the group consisting of methyl, ethyl, n-propyl, isopropyl, n-butyl, sec-butyl, isobutyl and tert-butyl;

denote a residue selected from the group consisting of cyclopropyl, cyclobutyl, cyclopentyl and cyclohexyl;

or denote a residue selected from the group consisting of phenyl, naphthyl, thiophenyl, furanyl, pyrrolyl and pyridinyl, wherein the residue in each case may optionally be substituted with 1, 2, 3, 4 or 5 substituents selected from the group consisting of F, Cl, Br, —O—$CH_3$, —O—$C_2H_5$, methyl, ethyl, n-propyl, isopropyl, n-butyl, sec-butyl, isobutyl and tert-butyl;

or $R^{12}$ and $R^{13}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl, and $R^{25}$ and $R^{26}$, mutually independently, in each case denote a hydrogen residue or denote an alkyl residue selected from the group consisting of methyl, ethyl and n-propyl;

providing that $R^{25}$ and $R^{26}$ do not in each case denote a hydrogen residue;

or $R^{25}$ and $R^{26}$, in each case together with the carbon atom joining them together as a ring member, form a residue selected from the group consisting of cyclopropyl, cyclobutyl, cyclopentyl and cyclohexyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those the above-stated general formula I, in which X denotes O;

n denotes 1;

$R^1$, $R^3$ and $R^4$ in each case denote H;

$R^2$ denotes F; Cl; Br or I;

$R^5$ denotes a residue selected from the group consisting of —$CF_3$, —$CCl_3$, —$CBr_3$, —$CHF_2$, —$CH_2F$, —$CF_2Cl$, —$CCl_2F$, tert-butyl, —O—$CF_3$, —O—$CCl_3$, —O—$CBr_3$, —O—$CHF_2$, —O—$CH_2F$, —S—$CF_3$, —S—$CCl_3$, —S—$CBr_3$, —S—$CHF_2$ and —S—$CH_2F$;

T denotes CH and U denotes CH and V denotes N and W denotes C—$R^8$ or

T denotes CH and U denotes N and V denotes CH and W denotes C—$R^8$ or

T denotes N and U denotes CH and V denotes CH and W denotes C—$R^8$ or

T denotes N and U denotes N and V denotes CH and W denotes C—$R^8$ or

T denotes N and U denotes CH and V denotes N and W denotes C—$R^8$ or

T denotes CH and U denotes N and V denotes N and W denotes C—$R^8$ or

T denotes CH and U denotes CH and V denotes CH and W denotes C—$R^{10}$;

$R^8$ denotes F; Cl; Br; I; —CN; —OH; —$NH_2$; —$NO_2$; —$NHR^{11}$; —$NR^{12}R^{13}$; —$OR^{14}$; —$SR^{15}$;

or denotes a residue selected from the group consisting of methyl, —$CF_3$, —$CCl_3$, —$CBr_3$, —$CHF_2$, —$CH_2F$, —$CF_2Cl$, —$CCl_2F$, ethyl, —$CF_2$—$CH_3$, —$CH_2$—$CF_3$, —$C_2F_5$, —$CH_2$—$CCl_3$, —$CH_2$—$CBr_3$, —CHF—$CF_2Cl$, —$CF_2$—$CF_2Cl$, —CFCl—$CF_2Cl$, n-propyl, —$CF_2$—$CF_2$—$CF_3$, —$CF(CF_3)_2$, isopropyl, sec-butyl, isobutyl and tert-butyl;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl and tert-butyl;

$R^{10}$ denotes —CN; —$NH_2$; —$NO_2$; —$NHR^{11}$; —$NR^{12}R^{13}$; —$OR^{14}$; —$SR^{15}$;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl and tert-butyl;

$R^{11}$, $R^{12}$, $R^{13}$, $R^{14}$ and $R^{15}$, mutually independently, in each case denote a residue selected from the group consisting of methyl, ethyl, n-propyl, isopropyl, n-butyl, sec-butyl, isobutyl and tert-butyl;

denote a residue selected from the group consisting of cyclopropyl, cyclobutyl, cyclopentyl and cyclohexyl;

or $R^{12}$ and $R^{13}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl, and $R^{25}$ denotes an alkyl residue selected from the group consisting of methyl, ethyl and n-propyl;

$R^{26}$ denotes a hydrogen residue;

or $R^{25}$ and $R^{26}$, in each case together with the carbon atom joining them together as a ring member, form a residue selected from the group consisting of cyclopropyl, cyclobutyl, cyclopentyl and cyclohexyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of the general formula Ia,

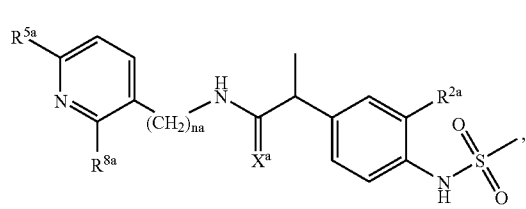

Ia in which
Xa denotes O or S;
na denotes 0, 1 or 2;

$R^{2a}$ denotes F; Cl; Br; I or denotes a residue selected from the group consisting of methyl, —$CF_3$, —$CCl_3$, —$CBr_3$, —$CHF_2$, —$CH_2F$, —O—$CH_3$, —O—$CF_3$, —O—$CCl_3$, —O—$CBr_3$, —O—$CHF_2$, —O—$CH_2F$, —S—$CH_3$, —S—$CF_3$, —S—$CCl_3$, —S—$CBr_3$, —S—$CHF_2$, —S—$CH_2F$, —S—$CF_2Cl$ and —S—$CCl_2F$;

$R^{5a}$ denotes F; Cl; Br; I; —$SF_5$;

denotes a residue selected from the group consisting of —$CF_3$, —$CCl_3$, —$CBr_3$, —$CHF_2$, —$CH_2F$, —$CF_2Cl$, —$CCl_2F$, tert-butyl, —O—$CF_3$, —O—$CCl_3$, —O—$CBr_3$, —O—$CHF_2$, —O—$CH_2F$, —O—$CF_2Cl$, —O—$CCl_2F$, —O—$CF_2$—$CH_3$, —S—$CF_3$, —S—$CCl_3$, —S—$CBr_3$, —S—$CHF_2$, —S—$CH_2F$, —S—$CF_2Cl$, —S—$CCl_2F$, —S—$CF_2$—$CH_3$, —$S(=O)_2$—$CF_3$, —$S(=O)_2$—$CCl_3$, —$S(=O)_2$—$CBr_3$, —$S(=O)_2$—$CHF_2$, —$S(=O)_2$—$CH_2F$ and —$S(=O)_2$—$CF_2Cl$;

or denotes a residue selected from the group consisting of cyclopropyl, cyclobutyl, cyclopentyl, cyclohexyl, cyclopentenyl and cyclohexenyl;

$R^{8a}$ denotes F; Cl; Br; I; —OH; —CN; —$NH_2$; —$NO_2$; —$NHR^{11a}$; —$NR^{12a}R^{13a}$; —$OR^{14a}$; —$SR^{15a}$; —C(=O)—$OR^{22a}$;

or denotes a residue selected from the group consisting of methyl, —$CF_3$, —$CCl_3$, —$CBr_3$, —$CHF_2$, —$CH_2F$, —$CF_2Cl$, —$CCl_2F$, ethyl, —$CF_2$—$CH_3$, —$CH_2$—$CF_3$, —$C_2F_5$, —$CH_2$—$CCl_3$, —$CH_2$—$CBr_3$, —CHF—$CF_2Cl$, —$CF_2$—$CF_2Cl$, —CFCl—$CF_2Cl$, n-propyl, —$CF_2$—$CF_2$—$CF_3$, —$CF(CF_3)_2$, isopropyl, sec-butyl, isobutyl and tert-butyl;

denotes a residue selected from the group consisting of cyclopropyl, cyclobutyl, cyclopentyl, cyclohexyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —$CF_3$, —$SF_5$, —OH, —O—$CH_3$, —O—$C_2H_5$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec-butyl, isobutyl and tert-butyl;

$R^{11a}$, $R^{12a}$, $R^{13a}$, $R^{14a}$, $R^{15a}$ and $R^{22a}$, mutually independently, in each case denote a residue selected from the group consisting of methyl, ethyl, n-propyl, isopropyl, n-butyl, sec-butyl, isobutyl and tert-butyl;

denote a residue selected from the group consisting of cyclopropyl, cyclobutyl, cyclopentyl and cyclohexyl;

or denote a residue selected from the group consisting of phenyl, naphthyl, thiophenyl, furanyl, pyrrolyl and pyridinyl, wherein the residue in each case may optionally be substituted with 1, 2, 3, 4 or 5 substituents selected from the group consisting of F, Cl, Br, —O—$CH_3$, —O—$C_2H_5$, methyl, ethyl, n-propyl, isopropyl, n-butyl, sec-butyl, isobutyl and tert-butyl;

or $R^{12a}$ and $R^{13a}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise very particularly preferred compounds are those of the general formula Ib, Ib in which
nb denotes 0, 1 or 2;
$R^{2b}$ denotes F; Cl; Br or I;
$R^{8b}$ denotes F; Cl; Br; I; —CN; —OH; —NH$_2$; —NO$_2$; —NHR$^{11b}$; —NR$^{12b}$R$^{13b}$; —OR$^{14b}$; SR$^{15b}$;
denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;
or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—C$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;
$R^{11b}, R^{12b}, R^{13b}, R^{14b}$ and $R^{15b}$, mutually independently, in each case
denote a residue selected from the group consisting of methyl, ethyl, n-propyl, isopropyl, n-butyl, sec-butyl, isobutyl and tert-butyl;
or denote a residue selected from the group consisting of cyclopropyl, cyclobutyl, cyclopentyl and cyclohexyl;
or
$R^{12b}$ and $R^{13b}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;
in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Further very particularly preferred compounds are those of the general formula Ib, in which
nb denotes 1;
$R^{2b}$ denotes F;
$R^{8b}$ denotes F; Cl; Br; I; —CN; —OH; —NH$_2$; —NO$_2$; —NHR$^{11b}$; —NR$^{12b}$R$^{13b}$; —OR$^{14b}$; —SR$^{15b}$;
denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;
or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;
$R^{11b}, R^{12b}, R^{13b}, R^{14b}$ and $R^{15b}$, mutually independently, in each case
denote a residue selected from the group consisting of methyl, ethyl, n-propyl, isopropyl, n-butyl, sec-butyl, isobutyl and tert-butyl;
or denote a residue selected from the group consisting of cyclopropyl, cyclobutyl, cyclopentyl and cyclohexyl;
or
$R^{12b}$ and $R^{13b}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;
in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Further very particularly preferred compounds are those of the general formula Ic, Ic in which
nc denotes 0, 1 or 2;
$R^{2c}$ denotes F; Cl; Br or I;
$R^{8c}$ denotes F; Cl; Br; I; —CN; —OH; —NH$_2$; —NO$_2$; —NHR$^{11c}$; —NR$^{12c}$R$^{13c}$; —OR$^{14c}$; —SR$^{15c}$;
denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;
or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11c}$, R$^{12c}$, R$^{13c}$, R$^{14c}$ and R$^{15c}$, mutually independently, in each case denote a residue selected from the group consisting of methyl, ethyl, n-propyl, isopropyl, n-butyl, sec-butyl, isobutyl and tert-butyl;

or denote a residue selected from the group consisting of cyclopropyl, cyclobutyl, cyclopentyl and cyclohexyl;

or

R$^{12c}$ and R$^{13c}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Further very particularly preferred compounds are those of the general formula Ic, in which nc denotes 1;

R$^{2c}$ denotes F;

R$^{8c}$ denotes F; Cl; Br; I; —CN; —OH; —NH$_2$; —NO$_2$; —NHR$^{11c}$; —NR$^{12c}$R$^{13c}$; —OR$^{14c}$; —SR$^{15c}$;

denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11c}$, R$^{12c}$, R$^{13c}$, R$^{14c}$ and R$^{15c}$, mutually independently, in each case denote a residue selected from the group consisting of methyl, ethyl, n-propyl, isopropyl, n-butyl, sec-butyl, isobutyl and tert-butyl;

or denote a residue selected from the group consisting of cyclopropyl, cyclobutyl, cyclopentyl and cyclohexyl;

or

R$^{12c}$ and R$^{13c}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of the general formula Id,

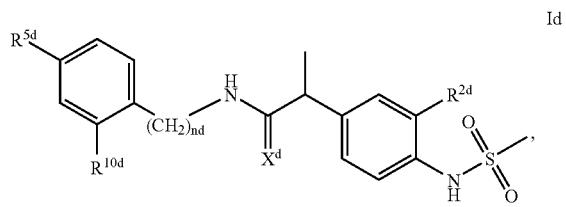

in which

X$^d$ denotes O or S;

nd denotes 0, 1 or 2;

R$^{2d}$ denotes F; Cl; Br; I or denotes a residue selected from the group consisting of methyl, —CF$_3$, —CCl$_3$, —CBr$_3$, —CHF$_2$, —CH$_2$F, —O—CH$_3$, —O—CF$_3$, —O—CCl$_3$, —O—CBr$_3$, —O—CHF$_2$, —O—CH$_2$F, —S—CH$_3$, —S—CF$_3$, —S—CCl$_3$, —S—CBr$_3$, —S—CHF$_2$, —S—CH$_2$F, —S—CF$_2$Cl and —S—CCl$_2$F;

R$^{5d}$ denotes F; Cl; Br; I; —SF$_5$;

denotes a residue selected from the group consisting of —CF$_3$, —CCl$_3$, —CBr$_3$, —CHF$_2$, —CH$_2$F, —CF$_2$Cl, —CCl$_2$F, tert-butyl, —O—CF$_3$, —O—CCl$_3$, —O—CBr$_3$, —O—CHF$_2$, —O—CH$_2$F, —O—CF$_2$Cl, —O—CCl$_2$F, —O—CF$_2$—CH$_3$, —S—CF$_3$, —S—CCl$_3$, —S—CBr$_3$, —S—CHF$_2$, —S—CH$_2$F, —S—CF$_2$Cl, —S—CCl$_2$F, —S—CF$_2$—CH$_3$, —S(=O)$_2$—CF$_3$, —S(=O)$_2$—CCl$_3$, —S(=O)$_2$—CBr$_3$, —S(=O)$_2$—CHF$_2$, —S(=O)$_2$—CH$_2$F and —S(=O)$_2$—CF$_2$Cl;

or denotes a residue selected from the group consisting of cyclopropyl, cyclobutyl, cyclopentyl, cyclohexyl, cyclopentenyl and cyclohexenyl;

R$^{10d}$ denotes —CN; —OH; —NH$_2$; —NO$_2$; —NHR$^{11d}$; —NR$^{12d}$R$^{13d}$; —OR$^{14d}$; —SR$^{15d}$; —C(=O)—OR$^{22d}$;

denotes a residue selected from the group consisting of cyclopropyl, cyclobutyl, cyclopentyl, cyclohexyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11d}$, R$^{12d}$, R$^{13d}$, R$^{14d}$, R$^{15d}$ and R$^{22d}$, mutually independently, in each case denote a residue selected from the group consisting of methyl, ethyl, n-propyl, isopropyl, n-butyl, sec-butyl, isobutyl and tert-butyl;

denote a residue selected from the group consisting of cyclopropyl, cyclobutyl, cyclopentyl and cyclohexyl;

or denote a residue selected from the group consisting of phenyl, naphthyl, thiophenyl, furanyl, pyrrolyl and pyridinyl, wherein the residue in each case may optionally be substituted with 1, 2, 3, 4 or 5 substituents selected from the group consisting of F, Cl, Br, —O—CH$_3$, —O—C$_2$H$_5$, methyl, ethyl, n-propyl, isopropyl, n-butyl, sec-butyl, isobutyl and tert-butyl;

or

R$^{12d}$ and R$^{13d}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise very particularly preferred compounds are those of the general formula Ie,

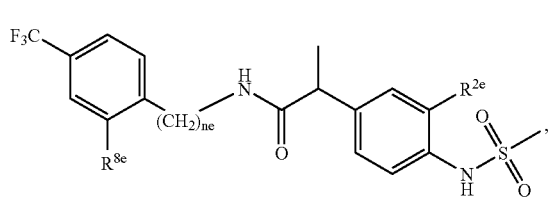

Ie in which ne denotes 0, 1 or 2;

R$^{2e}$ denotes F; Cl; Br or I;

R$^{10e}$ denotes F; Cl; Br; I; —CN; —OH; —NH$_2$; —NO$_2$; —NHR$^{11e}$; —NR$^{12e}$R$^{13e}$; —OR$^{14e}$; —SR$^{15e}$;

denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11e}$, R$^{12e}$, R$^{13e}$, R$^{14e}$ and R$^{15e}$, mutually independently, in each case denote a residue selected from the group consisting of methyl, ethyl, n-propyl, isopropyl, n-butyl, sec-butyl, isobutyl and tert-butyl;

or denote a residue selected from the group consisting of cyclopropyl, cyclobutyl, cyclopentyl and cyclohexyl;

or

R$^{12e}$ and R$^{13e}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise very particularly preferred compounds are those of the general formula Ie, in which ne denotes 1;

R$^{2e}$ denotes F;

R$^{10e}$ denotes F; Cl; Br; I; —CN; —OH; —NH$_2$; —NO$_2$; —NHR$^{11e}$; —NR$^{12e}$R$^{13e}$; —OR$^{14e}$; —SR$^{15e}$;

denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;

or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11e}$, R$^{12e}$, R$^{13e}$, R$^{14e}$ and R$^{15e}$, mutually independently, in each case denote a residue selected from the group consisting of methyl, ethyl, n-propyl, isopropyl, n-butyl, sec-butyl, isobutyl and tert-butyl;

or denote a residue selected from the group consisting of cyclopropyl, cyclobutyl, cyclopentyl and cyclohexyl;

or

R$^{12e}$ and R$^{13e}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise very particularly preferred compounds are those of the general formula If,

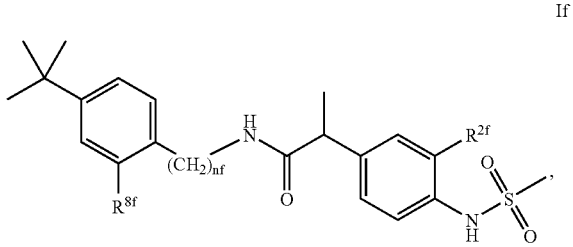

If in which
nf denotes 0, 1 or 2;
$R^{2f}$ denotes F; Cl; Br or I;
$R^{8f}$ denotes F; Cl; Br; I; —CN; —OH; —NH$_2$; —NO$_2$; —NHR$^{11f}$; —NR$^{12f}$R$^{13f}$; —OR$^{14f}$; —SR$^{15f}$;
denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;
or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;
$R^{11f}$, $R^{12f}$, $R^{13f}$, $R^{14f}$ and $R^{15f}$, mutually independently, in each case
denote a residue selected from the group consisting of methyl, ethyl, n-propyl, isopropyl, n-butyl, sec-butyl, isobutyl and tert-butyl;
or denote a residue selected from the group consisting of cyclopropyl, cyclobutyl, cyclopentyl and cyclohexyl;
or
$R^{12f}$ and $R^{13f}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;
in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise very particularly preferred compounds are those of the general formula If,
in which
nf denotes 1;
$R^{2f}$ denotes F;
$R^{8f}$ denotes F; Cl; Br; I; —CN; —OH; —NH$_2$; —NO$_2$; —NHR$^{11f}$; —NR$^{12f}$R$^{13f}$; —OR$^{14f}$; —SR$^{15f}$;
denotes a residue selected from the group consisting of methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, sec-butyl, isobutyl and tert-butyl;
or denotes a residue selected from the group consisting of phenyl, naphthyl, oxazolyl, thiazolyl, imidazolyl, pyrimidinyl, thiophenyl, furanyl and pyridinyl, which in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;
$R^{11f}$, $R^{12f}$, $R^{13f}$, $R^{14f}$ and $R^{15f}$, mutually independently, in each case
denote a residue selected from the group consisting of methyl, ethyl, n-propyl, isopropyl, n-butyl, sec-butyl, isobutyl and tert-butyl;
or denote a residue selected from the group consisting of cyclopropyl, cyclobutyl, cyclopentyl and cyclohexyl;
or
$R^{12f}$ and $R^{13f}$, in each case together with the nitrogen atom joining them together as a ring member, form a residue selected from the group consisting of pyrrolidinyl, piperidinyl, piperazinyl, morpholinyl, azepanyl, diazepanyl and thiomorpholinyl;
in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Further very particularly preferred compounds are those of the general formula Ig,

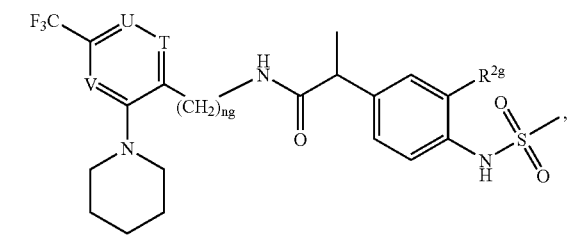

Ig in which
ng denotes 0, 1 or 2;
$R^{2g}$ denotes F; Cl; Br or I;
T denotes CH and U denotes N and V denotes CH
or
T denotes N and U denotes CH and V denotes CH
or
T denotes N and U denotes N and V denotes CH
or
T denotes N and U denotes CH and V denotes N
or
T denotes CH and U denotes N and V denotes N;
in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise very particularly preferred compounds are those of the general formula Ig,
in which
ng denotes 1;
$R^{2g}$ denotes F;
T denotes CH and U denotes N and V denotes CH
or
T denotes N and U denotes CH and V denotes CH
or
T denotes N and U denotes N and V denotes CH
or
T denotes N and U denotes CH and V denotes N or T denotes CH and U denotes N and V denotes N;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Still further preferred compounds of the above-stated general formula I are those selected from the group consisting of

[1] 2-(3-fluoro-4-(methylsulfonamido)phenyl)-N-((2-methyl-6-(trifluoromethyl)pyridin-3-yl)methyl)propanamide

[2] 2-(3-fluoro-4-(methylsulfonamido)phenyl)-N-((2-(piperidin-1-yl)-6-(trifluoromethyl)pyridin-3-yl)methyl)propanamide

[3] 2-(3-fluoro-4-(methylsulfonamido)phenyl)-N-(2-piperidin-1-yl)-4-(trifluoromethyl)benzyl)propanamide

[4] 2-(3-fluoro-4-(methylsulfonamido)phenyl)-N-((2-fluoro-6-(trifluoromethyl)pyridin-3-yl)methyl)propanamide

[5] N-((2-chloro-6-(trifluoromethyl)pyridin-3-yl)methyl)-2-(3-fluoro-4-(methylsulfonamido)phenyl)propanamide

[6] N-((2-bromo-6-(trifluoromethyl)pyridin-3-yl)methyl)-2-(3-fluoro-4-(methylsulfonamido)phenyl)propanamide

[7] 2-(3-fluoro-4-(methylsulfonamido)phenyl)-N-((2-iodo-6-(trifluoromethyl)pyridin-3-yl)methyl)propanamide

[8] N-((2-tert-butyl-6-(trifluoromethyl)pyridin-3-yl)methyl)-2-(3-fluoro-4-(methylsulfonamido)phenyl)propanamide

[9] N-((2-cyano-6-(trifluoromethyl)pyridin-3-yl)methyl)-2-(3-fluoro-4-(methylsulfonamido)phenyl)propanamide

[10] (S)-2-(3-fluoro-4-(methylsulfonamido)phenyl)-N-((2-(piperidin-1-yl)-6-(trifluoromethyl)pyridin-3-yl)methyl)propanamide

[11] (R)-2-(3-fluoro-4-(methylsulfonamido)phenyl)-N-((2-(piperidin-1-yl)-6-(trifluoromethyl)pyridin-3-yl)methyl)propanamide

[12] 2-(3-fluoro-4-(methylsulfonamido)phenyl)-N-((2-morpholino-6-(trifluoromethyl)pyridin-3-yl)methyl)propanamide

[13] 2-(3-fluoro-4-(methylsulfonamido)phenyl)-N-((2-(pyrrolidin-1-yl)-6-(trifluoromethyl)pyridin-3-yl)methyl)propanamide

[14] N-((2-(dimethylamino)-6-(trifluoromethyl)pyridin-3-yl)methyl)-2-(3-fluoro-4-(methylsulfonamido)phenyl)propanamide

[15] N-((2-(diethylamino)-6-(trifluoromethyl)pyridin-3-yl)methyl)-2-(3-fluoro-4-(methylsulfonamido)phenyl)propanamide

[16] N-((2-(dipropylamino)-6-(trifluoromethyl)pyridin-3-yl)methyl)-2-(3-fluoro-4-(methylsulfonamido)phenyl)propanamide

[17] 2-(3-fluoro-4-(methylsulfonamido)phenyl)-N-((2-hydroxy-6-(trifluoromethyl)pyridin-3-yl)methyl)propanamide

[18] 2-(3-fluoro-4-(methylsulfonamido)phenyl)-N-((2-methoxy-6-(trifluoromethyl)pyridin-3-yl)methyl)propanamide

[19] N-((2-butoxy-6-(trifluoromethyl)pyridin-3-yl)methyl)-2-(3-fluoro-4-(methylsulfonamido)phenyl)propanamide

[20] 2-(3-fluoro-4-(methylsulfonamido)phenyl)-N-((2-isopropoxy-6-(trifluoromethyl)pyridin-3-yl)methyl)propanamide

[21] N-((2-cyclopentyloxy-6-(trifluoromethyl)pyridin-3-yl)methyl)-2-(3-fluoro-4-(methylsulfonamido)phenyl)propanamide

[22] 2-(3-fluoro-4-(methylsulfonamido)phenyl)-N-((2-phenyl-6-(trifluoromethyl)pyridin-3-yl)methyl)propanamide

[23] 2-(3-fluoro-4-(methylsulfonamido)phenyl)-N-((2-(4-fluorophenyl)-6-(trifluoromethyl)pyridin-3-yl)methyl)propanamide

[24] 2-(3-fluoro-4-(methylsulfonamido)phenyl)-N-((6-(trifluoromethyl)-2,2'-bipyridin-3-yl)methyl)propanamide

[25] 2-(3-fluoro-4-(methylsulfonamido)phenyl)-N-((6-(trifluoromethyl)-2,3'-bipyridin-3-yl)methyl)propanamide

[26] 2-(3-fluoro-4-(methylsulfonamido)phenyl)-N-((2-(pyrimidin-2-yl)-6-(trifluoromethyl)pyridin-3-yl)methyl)propanamide

[27] 2-(3-fluoro-4-(methylsulfonamido)phenyl)-N-((2-(thiazol-2-yl)-6-(trifluoromethyl)pyridin-3-yl)methyl)propanamide

[28] 2-(3-fluoro-4-(methylsulfonamido)phenyl)-N-((2-(oxazol-2-yl)-6-(trifluoromethyl)pyridin-3-yl)methyl)propanamide

[29] N-((2-(1H-imidazol-2-yl)-6-(trifluoromethyl)pyridin-3-yl)methyl)-2-(3-fluoro-4-(methylsulfonamido)phenyl)propanamide

[30] N-(2-cyano-4-(trifluoromethyl)benzyl)-2-(3-fluoro-4-(methylsulfonamido)-phenyl)propanamide

[31] (S)-2-(3-fluoro-4-(methylsulfonamido)phenyl)-N-(2-(piperidin-1-yl)-4-(trifluoromethyl)benzyl)propanamide

[32] (R)-2-(3-fluoro-4-(methylsulfonamido)phenyl)-N-(2-(piperidin-1-yl)-4-(trifluoromethyl)benzyl)propanamide

[33] 2-(3-fluoro-4-(methylsulfonamido)phenyl)-N-(2-morpholino-4-(trifluoromethyl)benzyl)propanamide

[34] 2-(3-fluoro-4-(methylsulfonamido)phenyl)-N-(2-(pyrrolidin-1-yl)-4-(trifluoromethyl)benzyl)propanamide

[35] N-(2-(dimethylamino)-4-(trifluoromethyl)benzyl)-2-(3-fluoro-4-(methylsulfonamido)phenyl)propanamide

[36] N-(2-(diethylamino)-4-(trifluoromethyl)benzyl)-2-(3-fluoro-4-(methylsulfonamido)phenyl)propanamide

[37] N-(2-(dipropylamino)-4-(trifluoromethyl)benzyl)-2-(3-fluoro-4-(methylsulfonamido)phenyl)propanamide

[38] 2-(3-fluoro-4-(methylsulfonamido)phenyl)-N-(2-hydroxy-4-(trifluoromethyl)benzyl)propanamide

[39] 2-(3-fluoro-4-(methylsulfonamido)phenyl)-N-(2-methoxy-4-(trifluoromethyl)benzyl)propanamide

[40] N-(2-butoxy-4-(trifluoromethyl)benzyl)-2-(3-fluoro-4-(methylsulfonamido)phenyl)propanamide

[41] 2-(3-fluoro-4-(methylsulfonamido)phenyl)-N-(2-isopropoxy-4-(trifluoromethyl)benzyl)propanamide

[42] N-(2-(cyclopentyloxy)-4-(trifluoromethyl)benzyl)-2-(3-fluoro-4-(methylsulfonamido)phenyl)propanamide

[43] 2-(3-fluoro-4-(methylsulfonamido)phenyl)-N-((5-(trifluoromethyl)biphenyl-2-yl)methyl)propanamide

[44] 2-(3-fluoro-4-(methylsulfonamido)phenyl)-N-((4'-fluoro-5-(trifluoromethyl)biphenyl-2-yl)methyl)propanamide

[45] 2-(3-fluoro-4-(methylsulfonamido)phenyl)-N-(2-(pyridin-2-yl)-4-(trifluoromethyl)benzyl)propanamide

[46] 2-(3-fluoro-4-(methylsulfonamido)phenyl)-N-(2-(pyridin-3-yl)-4-(trifluoromethyl)benzyl)propanamide

[47] 2-(3-fluoro-4-(methylsulfonamido)phenyl)-N-(2-(pyrimidin-2-yl)-4-(trifluoromethyl)benzyl)propanamide

[48] 2-(3-fluoro-4-(methylsulfonamido)phenyl)-N-(2-(thiazol-2-yl)-4-(trifluoromethyl)benzyl)propanamide

[49] 2-(3-fluoro-4-(methylsulfonamido)phenyl)-N-(2-(oxazol-2-yl)-4-(trifluoromethyl)benzyl)propanamide

[50] N-(2-(1 H-imidazol-2-yl)-4-(trifluoromethyl)benzyl)-2-(3-fluoro-4-(methylsulfonamido)phenyl)propanamide

[51] N-((6-tert-butyl-2-(piperidin-1-yl)pyridin-3-yl)methyl)-2-(3-fluoro-4-(methylsufonamido)phenyl)propanamide

[52] 2-(3-fluoro-4-(methylsulfonamido)phenyl)-N-((4-(piperidin-1-yl)-6-(trifluoromethyl)pyridin-3-yl)methyl)propanamide
[53] 2-(3-fluoro-4-(methylsulfonamido)phenyl)-N-((3-(piperidin-1-yl)-5-(trifluoromethyl)pyridin-2-yl)methyl)propanamide
[54] 2-(3-fluoro-4-(methylsulfonamido)phenyl)-N-((4-(piperidin-1-yl)-2-(trifluoromethyl)pyrimidin-5-yl)methyl) propanamide
[55] 2-(3-fluoro-4-(methylsulfonamido)phenyl)-N-((3-(piperidin-1-yl)-5-(trifluoromethyl)pyrazin-2-yl)methyl)propanamide
[56] 2-(3-fluoro-4-(methylsulfonamido)phenyl)-N-((4-(piperidin-1-yl)-6-(trifluoromethyl)pyridazinyl-3-yl)methyl) propanamide
[57] 2-(3-fluoro-4-(methylsulfonamido)phenyl)-N-((2-piperidin-1-yl)-6-(trifluoromethyl)pyridin-3-yl)propanamide
[58] 2-(3-fluoro-4-(methylsulfonamido)phenyl)-N-((2-piperidin-1-yl)-4-(trifluoromethyl)phenyl)propanamide
[59] 2-(3-fluoro-4-(methylsulfonamido)phenyl)-N-(2-(2-(piperidin-1-yl)-6-(trifluoromethyl)pyridin-3-yl)ethyl) propanamide
[60] 2-(3-fluoro-4-(methylsulfonamido)phenyl)-N-(2-(piperidin-1-yl)-4-(trifluoromethyl)phenethyl)propanamide
[61] N-(2-amino-4-(trifluoromethyl)benzyl)-2-(3-fluoro-4-(methylsulfonamido)-phenyl)propanamide
[62] 2-(3-fluoro-4-(methylsulfonamido)phenyl)-N-(2-nitro-4-(trifluoromethyl)-benzyl)propanamide
[63] N-(4-tert-butyl-2-(piperidin-1-yl)benzyl)-2-(3-fluoro-4-(methylsulfonamido)-phenyl)propanamide
[64] 2-(3-chloro-4-(methylsulfonamido)phenyl)-N-((2-piperidin-1-yl)-6-(trifluoromethyl)pyridin-3-yl)methyl)propanamide
[65] 2-(3-chloro-4-(methylsulfonamido)phenyl)-N-((2-(pyrrolidin-1-yl)-6-(trifluoromethyl)pyridin-3-yl)methyl)propanamide
[66] 2-(3-chloro-4-(methylsulfonamido)phenyl)-N-(2-(piperidin-1-yl)-4-(trifluoromethyl)benzyl)propanamide
[67] 2-(3-bromo-4-(methylsulfonamido)phenyl)-N-((2-(piperidin-1-yl)-6-(trifluoromethyl)pyridin-3-yl)methyl)propanamide
[68] 2-(3-bromo-4-(methylsulfonamido)phenyl)-N-(2-(piperidin-1-yl)-4-(trifluoromethyl)benzyl)propanamide
[69] 2-(3-bromo-4-(methylsulfonamido)phenyl)-N-(2-(pyrrolidin-1-yl)-4-(trifluoromethyl)benzyl)propanamide
[70] N-(4-tert-butyl-2-cyanobenzyl)-2-(3-fluoro-4-(methylsulfonamido)-phenyl)propanamide
[71] N-((6-(chlorodiflouromethyl)-2-(piperidin-1-yl)pyridin-3-yl)methyl)-2-(3-fluoro-(4-methylsulfonamido)phenyl)propanamide
[72] (S)-2-(3-fluoro-4-(methylsulfonamido)phenyl)-N-((2-morpholino-6-(trifluoromethyl)pyridin-3-yl)methyl)propanamide
[73] N-((2-(4-benzylpiperazin-1-yl)-6-(trifluoromethyl)pyridin-3-yl)methyl)-2-(3-fluoro-4-(methylsulfonamido) phenyl)propanamide
[74] 2-(3-fluoro-4-(methylsulfonamido)phenyl)-N-((2-piperazin-1-yl)-6-(trifluoromethyl)pyridin-3-yl)methyl)propanamide;
[75] N-(2-chloro-4-(trifluoromethyl)benzyl)-2-(3-fluoro-4-(methylsulfonamido)phenyl)propanamide
[76] N-((2-(cyclohexyloxy)-6-(trifluoromethyl)pyridin-3-yl)methyl-2-(3-fluoro-4-methylsulfonamido)phenyl)propanamide
[77] N-((3-chloro-5-(trifluoromethyl)pyridin-2-yl)methyl-2-(3-fluoro-4-(methylsulfonamido)phenyl)propanamide
[78] 2-(3-fluoro-4-(methylsulfonamido)phenyl)-N-((3-(pyrrolidin-1-yl)-5-(trifluoromethyl)pyridin-2-yl)methyl)propanamide
[79] N-((2-(3,5-dimethylpiperidin-1-yl)-6-(trifluoromethyl) pyridin-3-yl)methyl)-2-(3-fluoro-4-(methylsulfonamido) phenyl)propanamide
[80] 2-(3-fluoro-4-(methylsulfonamido)phenyl)-N-((2-(4-methylpiperidin-1-yl)-6-(trifluoromethyl)pyridin-3-yl) methyl)propanamide
[81] N-((2-(azepan-1-yl)-6-(trifluoromethyl)pyridin-3-yl) methyl)-2-(3-fluoro-4-(methylsulfonamido)phenyl)propanamide
[82] 2-(3-fluoro-4-(methylsulfonamido)phenyl)-N-(2-(4-methylpiperidin-1-yl)-4-(trifluoromethyl)benzyl)propanamide;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Further preferred compounds of the general formulae A and I according to the invention are those which, in an FLIPR assay with CHO-K1 cells which have been transfected with the human gene VR1, in a concentration of less than 2000 nM, preferably of less than 1000 nM, particularly preferably of less then 300 nM, very particularly preferably of less than 100 nM, still more preferably of less than 70 nM, still even more preferably less than 50 nM, most preferably less than 10 nM, effect 50% displacement of capsaicin which is present in a concentration of 100 nM.

In this FLIPR assay, the influx of $Ca^{2+}$ is quantified with the assistance of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA) as described below.

The present invention also provides a process for production of compounds of the above-stated general formula I, in accordance with which at least one compound of the general formula II,

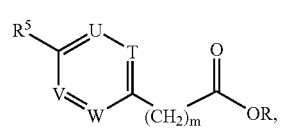

in which $R^5$, U, T, V and W have the above-stated meaning, m denotes 0, 1, 2 or 3 and R denotes hydrogen or denotes a $C_{1-6}$ alkyl residue, is reacted in a reaction medium, in the presence of at least one reducing agent, preferably in the presence of at least one reducing agent selected from the group consisting of sodium hydride, sodium, potassium hydride, lithium aluminum hydride, sodium borohydride, $BH_3 \times THF$ and di(isobutyl)aluminum hydride to yield at least one compound of the general formula III,

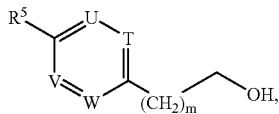

III in which $R^5$, U, T, V and W have the above-stated meaning and m denotes 0, 1, 2 or 3, and said compound is optionally purified and/or isolated, and at least one compound of the general formula III is reacted in a reaction medium in the presence of diphenylphosphoryl azide or in the presence of $HN_3$ to yield at least one compound of the general formula IV,

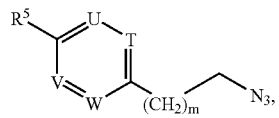

IV in which $R^5$, U, T, V and W have the above-stated meaning and m denotes 0, 1, 2 or 3, and said compound is optionally purified and/or isolated, and at least one compound of the general formula IV is reacted in a reaction medium in the presence of at least one reducing agent, preferably in the presence of at least one reducing agent selected from the group consisting of sodium hydride, potassium hydride, lithium aluminum hydride, sodium borohydride and di(isobutyl)aluminum hydride or in a reaction medium in the presence of a catalyst, preferably in the presence of a catalyst is based on platinum or palladium, particularly preferably in the presence of palladium on carbon, and in the presence of hydrogen or in the presence of hydrazine or in a reaction medium in the presence of triphenylphosphine to yield at least one compound of the general formula V,

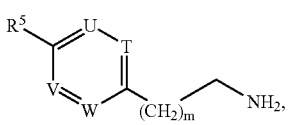

V in which $R^5$, U, T, V and W have the above-stated meaning and m denotes 0, 1, 2 or 3, and said compound is optionally purified and/or isolated, or at least one compound of the general formula VI,

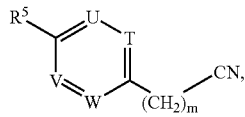

VI in which $R^5$, U, T, V, and W have the above-stated meaning and m denotes 0, 1, 2 or 3, is reacted in a reaction medium in the presence of at least one catalyst, preferably in the presence of at least one catalyst based on palladium or platinum, particularly preferably in the presence of palladium on carbon, optionally in the presence of at least one acid, preferably in the presence of hydrochloric acid, to yield at least one compound of the general formula V, optionally in the form of a corresponding salt, preferably in the form of a corresponding hydrochloride, and said compound is optionally purified and/or isolated, and at least one compound of the general formula V is reacted with at least one compound of the general formula VII,

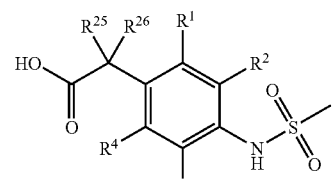

in which $R^1$, $R^2$, $R^3$, $R^4$, $R^{25}$ and $R^{26}$ have the above-stated meaning, in a reaction medium, optionally in the presence of at least one suitable coupling agent, optionally in the presence of at least one base, or with at least one compound of the general formula VIII,

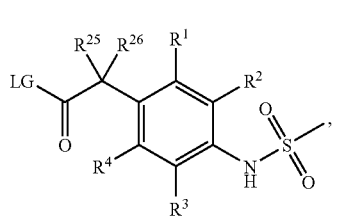

VIII in which $R^1$, $R^2$, $R^3$, $R^4$, $R^{25}$ and $R^{26}$ have the above-stated meaning and LG denotes a leaving group, preferably a chlorine or bromine atom, in a reaction medium, optionally in the presence of at least one base, to yield at least one compound of the general formula Ih,

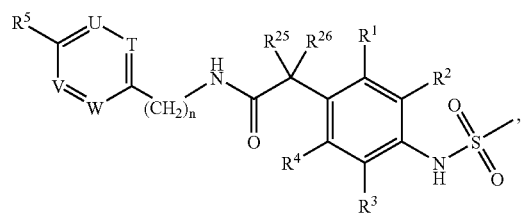

Ih in which T, U, V, W, $R^1$, $R^2$, $R^3$, $R^4$, $R^5$, $R^{25}$ and $R^{26}$ have the above-stated meaning and n denotes 1, 2, 3 or 4, and said compound is optionally purified and/or isolated, and optionally at least one compound of the general formula Ih is reacted in a reaction medium with at least one compound of the general formula IX,

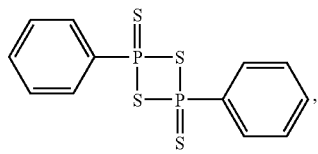

in which the phenyl residues are in each case substituted with 1 or 2 substituents mutually independently selected from the group consisting of methoxy, phenoxy, Cl, methyl and Br, preferably in each case with a phenoxy residue or methoxy residue, particularly preferably in each case with a methoxy residue in para position, or with phosphorus pentasulfide, to yield at least one compound of the general formula Ik,

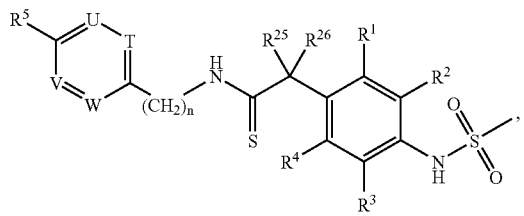

in which T, U, V, W, $R^1$, $R^2$, $R^3$, $R^4$, $R^5$, $R^{25}$ and $R^{26}$ have the above-stated meaning and n denotes 1, 2, 3 or 4, and said compound is optionally purified and/or isolated.

The present invention also provides a process for production of compounds of the above-stated general formula I, in accordance with which at least one compound of the general formula X,

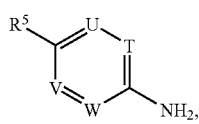

in which $R^5$, U, T, V, and W have the above-stated meaning, is reacted with at least one compound of the general formula VII,

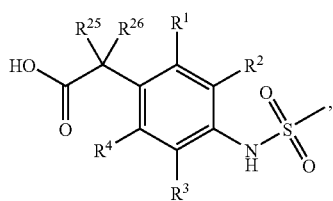

in which $R^1$, $R^2$, $R^3$, $R^4$, $R^{25}$ and $R^{26}$ have the above-stated meaning, in a reaction medium, optionally in the presence of at least one suitable coupling agent, optionally in the presence of at least one base, or with at least one compound of the general formula VIII,

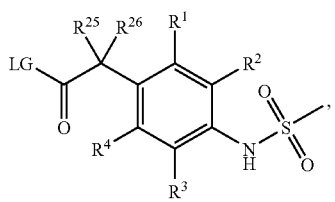

in which $R^1$, $R^2$, $R^3$, $R^4$, $R^{25}$ and $R^{26}$ have the above-stated meaning and LG denotes a leaving group, preferably a chlorine or bromine atom, in a reaction medium, optionally in the presence of at least one base, to yield at least one compound of the general formula Im,

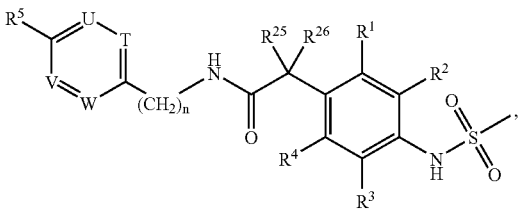

in which T, U, V, W, $R^1$, $R^2$, $R^3$, $R^4$, $R^5$, $R^{25}$ and $R^{26}$ have the above-stated meaning and said compound is optionally purified and/or isolated, and optionally at least one compound of the general formula Im is reacted in a reaction medium with at least one compound of the general formula IX,

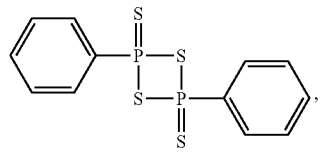

in which the phenyl residues are in each case substituted with 1 or 2 substituents mutually independently selected from the group consisting of methoxy, phenoxy, Cl, methyl and Br, preferably in each case with a phenoxy residue or methoxy residue, particularly preferably in each case with a methoxy residue in para position, or with phosphorus pentasulfide, to yield at least one compound of the general formula In,

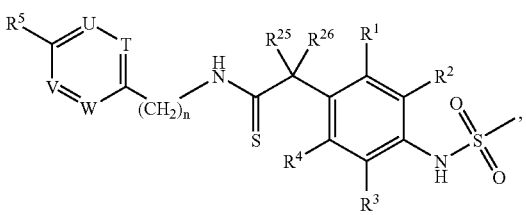

in which T, U, V, W, $R^1$, $R^2$, $R^3$, $R^4$, $R^5$, $R^{25}$ and $R^{26}$ have the above-stated meaning and said compound is optionally purified and/or isolated.

The reaction of compounds of the above-stated general formulae V or X with carboxylic acids of the above-stated general formula VII to yield compounds of the above-stated general formulae Ih or Im, respectively, preferably proceeds in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethyl-amino)-phosphonium hexafluorophosphate (BOP), dicyclohexylcarbodiimide (DCC), N'-(3-dimethylaminopropyl)-N-ethylcarbodiimide (EDCI), diisopropylcarbodiimide, 1,1'-carbonyl-diimidazole (CDI), N-[(dimethylamino)-1H-1,2,3-triazolo-[4,5-b]-pyridino-1-ylmethylene]-N-methyl-methaneaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluorborate (TBTU) and 1-hydroxy-7-azabenzotriazole (HOAt), optionally in the presence of at least one organic base, preferably selected from the group consisting of triethylamine, pyridine, dimethylaminopyridine, N-methylmorpholine and diisopropylethylamine, preferably at temperatures of −70° C. to 100° C.

Alternatively, the reaction of compounds of the above-stated general formulae V or X with carboxylic acid derivatives of the above-stated general formula VIII, in which LG denotes a leaving group, preferably a chlorine or bromine atom, to yield compounds of the above-stated general formulae Ih or Im proceeds in a reaction medium which is preferably selected from the group consisting of diethyl ether, tetrahydrofuran, acetonitrile, methanol, ethanol, dimethylformamide, dichloromethane and corresponding mixtures, optionally in the presence of an organic or inorganic base, preferably selected from the group consisting of triethylamine, dimethylaminopyridine, pyridine and diisopropylamine, at temperatures of −70° C. to 100° C.

The reaction of compounds of the general formulae Ih or Im to yield compounds of the general formulae Ik or In preferably proceeds in a reaction medium selected from the group consisting of toluene, para-xylene, ortho-xylene, meta-xylene, acetonitrile, dichloromethane, dimethylformamide and mixtures of the above-stated reaction media, with addition of a dithiaphosphetane, particularly preferably with addition of 2,4-bis(4-methoxyphenyl)-1,3,2,4-dithiadiphosphetane 2,4-disulfide (Lawesson's reagent), or with addition of phosphorus pentasulfide, at temperatures of 50 to 150° C.

The compounds of the above-stated formulae I, II, III, IV, V, VI, VIII, IX and X are in each case commercially obtainable and may also be produced using conventional methods known to the person skilled in the art.

The synthesis method for compounds of the general formula VII may be found in the document "4-(methylsulfonylamino)phenyl analogues as vanilloid antagonist showing excellent analgesic activity and the pharmaceutical compositions comprising the same" of J. W. Lee et al. [WO 2005/003084-A1]. The corresponding parts of the reference are hereby deemed to be part of the disclosure.

The above-described reactions may in each case be performed under the conventional conditions familiar to the person skilled in the art, for example with regard to pressure or the sequence of addition of the components. Optimum control of the process may optionally be established by the person skilled in the art by simple preliminary testing. The intermediate and final products obtained by the above-described reactions may in each case, if desired and/or necessary, be purified and/or isolated by conventional methods known to the person skilled in the art. Suitable purification methods are, for example, extraction methods and chromatographic methods such as column chromatography or preparative chromatography. All the above-described process steps and in each case also the purification and/or isolation of intermediate or final products may be performed in part or entirely under an inert gas atmosphere, preferably under a nitrogen atmosphere.

Those compounds of the above-stated general formulae I, Ia, Ia1, Ib, Ib1, Ic, Ic1, Id, Id1, Ie, Ie1, If, If1, Ig, Ih, Ik, Im, In, A, B1, B2, C1 and C2 in form of their (S)-enantiomer may be preferred. The (S)-enantiomer of compounds of general formula Ia is given by way of example.

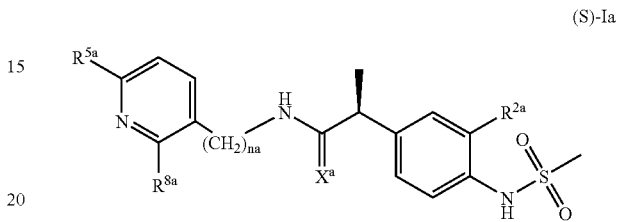

(S)-Ia

The substituted compounds according to the invention of the above-stated general formulae I, Ia, Ia1, Ib, Ib1, Ic, Ic1, Id, Id1, Ie, Ie1, If, If1, Ig, Ih, Ik, Im, In, A, B1, B2, C1 and C2, hereinafter designated only as compounds of the general formula I, and corresponding stereoisomers may be isolated both in the form of the free bases thereof, the free acids thereof and in the form of corresponding salts, in particular physiologically acceptable salts.

The free bases of the particular substituted compounds according to the invention of the above-stated general formula I and corresponding stereoisomers; in particular compounds of the above-stated general formula I which comprise a pyridinyl moiety or a basic moiety in place of the substituent $R^8$, may, for example, be converted into the corresponding salts, preferably physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The free bases of the respective substituted compounds of the above-stated general formula I and corresponding stereoisomers may likewise be converted into the corresponding physiologically acceptable salts with the free acid or a salt of a sugar substitute, such as for example saccharin, cyclamate or acesulfame.

The free acids of the substituted compounds of the above-stated general formula I and corresponding stereoisomers may correspondingly be converted into the corresponding physiologically acceptable salts by reaction with a suitable base. Alkali metal salts, alkaline earth metal salts or ammonium salts $[NH_xR_{4-x}]^+$, in which x=0, 1, 2, 3 or 4 and R denotes a linear or branched $C_{1-4}$ alkyl residue may be mentioned by way of example.

The substituted compounds according to the invention of the above-stated general formula I and corresponding stereoisomers may optionally, like the corresponding acids, the corresponding bases or salts of these compounds, also be obtained in the form of the solvates thereof, preferably in the form of the hydrates thereof, by conventional methods known to the person skilled in the art.

If the substituted compounds according to the invention of the above-stated general formula I are obtained after the production thereof in the form of the stereoisomers thereof, preferably in the form of the racemates thereof or other mixtures of their various enantiomers and/or diastereomers, these may be separated and optionally isolated by conventional methods known to the person skilled in the art. Examples which may be mentioned are chromatographic separation methods, in particular liquid chromatography methods at standard pressure or at elevated pressure, preferably MPLC and HPLC methods, and fractional crystallization methods. Individual enantiomers, e.g. diastereomeric salts formed by means of HPLC on a chiral stationary phase or by means of crystallization with chiral acids, such as (+)-tartaric acid, (−)-tartaric acid or (+)-10-camphorsulfonic acid, may here in particular be separated from one another.

The substituted compounds according to the invention of the above-stated general formula I and corresponding stereoisomers as well as in each case the corresponding acids, bases, salts and solvates are toxicologically safe and are therefore suitable as pharmaceutical active ingredients in pharmaceutical preparations.

The present invention accordingly also provides a pharmaceutical preparation containing at least one compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

These pharmaceutical preparations according to the invention are in particular suitable for regulating the vanilloid receptor 1 (VR1/TRPV1), preferably for inhibiting the vanilloid receptor 1 (VR1/TRPV1) and/or for stimulating the vanilloid receptor 1 (VR1/TRPV1).

The pharmaceutical preparations according to the invention are likewise preferably suitable for prevention and/or treatment of disorders or diseases which are at least in part mediated by vanilloid receptors 1.

The pharmaceutical preparation according to the invention is preferably suitable for the treatment and/or prevention of one or more diseases selected from the group consisting of pain selected from the group consisting of acute pain, chronic pain, neuropathic pain and visceral pain; joint pain; hyperalgesia; allodynia; causalgia; migraine; depression; neuropathy; nerve injury; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; epilepsy; airways diseases, preferably selected from the group consisting of asthma, bronchitis and pulmonary inflammation; coughing; urinary incontinence; an overactive bladder (OAB); diseases and/or injuries of the gastrointestinal tract; duodenal ulcers; gastric ulcers; irritable bowel syndrome; strokes; eye irritation; skin irritation; neurotic skin conditions; allergic skin diseases; psoriasis; vitiligo; herpes simplex; inflammation, preferably inflammation of the intestines, the eyes, the bladder, the skin or the nasal mucosa; diarrhea; pruritus; osteoporosis; arthritis; osteoarthritis; rheumatic diseases; disorders of food intake, preferably selected from the group consisting of bulimia, cachexia, anorexia and obesity; dependency on medicines; abuse of medicines; withdrawal symptoms associated with dependency on medicines; development of tolerance towards medicines, preferably towards natural or synthetic opioids; dependency on drugs; drug abuse; withdrawal symptoms associated with dependency on drugs; dependency on alcohol; alcohol abuse and withdrawal symptoms associated with dependency on alcohol; for diuresis; for antinatriuresis; for influencing the cardiovascular system; for increasing vigilance; for the treatment of wounds and/or burns; for the treatment of severed nerves; for increasing libido; for modulating locomotor activity; for anxiolysis; for local anaesthesia and/or for inhibiting undesired side-effects, preferably selected from the group consisting of hyperthermia, high blood pressure and constriction of the bronchial tubes, triggered by the administration of agonists of the vanilloid receptor 1 (VR1/TRPV1 receptors), preferably selected from the group consisting of capsaicin, resiniferatoxin, olvanil, arvanil, SDZ-249665, SDZ-249482, nuvanil and capsavanil The pharmaceutical preparation according to the invention is particularly preferably suitable for the treatment and/or prevention of one or more diseases selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; inflammation, preferably inflammation of the intestines, the eyes, the bladder, the skin or the nasal mucosa; urinary incontinence; an overactive bladder (OAB); dependency on medicines; abuse of medicines; withdrawal symptoms associated with dependency on medicines; development of tolerance towards medicines, preferably development of tolerance towards natural or synthetic opioids; dependency on drugs; drug abuse; withdrawal symptoms associated with dependency on drugs; dependency on alcohol; alcohol abuse and withdrawal symptoms associated with dependency on alcohol.

The pharmaceutical preparation according to the invention is very particularly preferably suitable for the treatment and/or prevention of pain, preferably of pain selected from the group consisting of acute pain, chronic pain, neuropathic pain and visceral pain, and/or urinary incontinence.

The present invention also provides the use of at least one compound according to the invention and optionally one or more pharmaceutically acceptable auxiliary substances for the production of a pharmaceutical preparation for regulating the vanilloid receptor 1 (VR1/TRPV1), preferably for inhibiting the vanilloid receptor 1 (VR1/TRPV1) and/or for stimulating the vanilloid receptor 1 (VR1/TRPV1).

It is preferred to use at least one substituted compound according to the invention and optionally one or more pharmaceutically acceptable auxiliary substances for the production of a pharmaceutical preparation for the prevention and/or treatment of disorders or diseases which are at least in part mediated by vanilloid receptors 1.

It is particularly preferred to use at least one compound according to the invention and optionally one or more pharmaceutically acceptable auxiliary substances for the production of a pharmaceutical preparation for the treatment and/or prevention of one or more diseases selected from the group consisting of pain, preferably of pain selected from the group consisting of acute pain, chronic pain, neuropathic pain and visceral pain and joint pain.

It is particularly preferred to use at least one compound according to the invention and optionally one or more pharmaceutically compatible auxiliary substances for the production of a pharmaceutical preparation for the treatment and/or prevention of one or more diseases selected from the group consisting of hyperalgesia; allodynia; causalgia; migraine; depression; neuropathy; nerve injury; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; epilepsy; airways diseases, preferably selected from the group consisting of asthma, bronchitis and pulmonary inflammation; coughing; urinary incontinence; an overactive bladder (OAB); diseases and/or injuries of the gastrointestinal tract; duodenal ulcers; gastric ulcers; irritable bowel syndrome; strokes; eye irritation; skin irritation; neurotic skin conditions; allergic skin diseases; psoriasis; vitiligo; herpes simplex; inflammation, preferably inflammation of the intestines, the eyes, the bladder, the skin or the nasal mucosa; diarrhea; pruritus; osteoporosis; arthritis; osteoarthritis; rheumatic diseases; disorders of food intake, preferably selected from the group consisting of bulimia, cachexia, anorexia and obesity; dependency on medicines; abuse of medicines; withdrawal symptoms associated with dependency on medicines; development of tolerance towards medicines, preferably towards natural or synthetic opioids; dependency on drugs; drug abuse; withdrawal symptoms associated with dependency on drugs; dependency on alcohol; alcohol abuse and withdrawal symptoms associated with dependency on alcohol; for diuresis; for antinatriuresis; for influencing the cardiovascular system; for increasing vigilance; for the treatment of wounds and/or burns; for the treatment of severed nerves; for increasing libido; for modulating locomotor activity; for anxiolysis; for local anaesthesia and/or for inhibiting undesired side-effects, preferably selected from the group consisting of hyperthermia, high blood pressure and constriction of the bronchial tubes, triggered by the administration of agonists of the vanilloid receptor 1 (VR1/TRPV1 receptors), preferably selected from the group consisting of capsaicin, resiniferatoxin, olvanil, arvanil, SDZ-249665, SDZ-249482, nuvanil and capsavanil.

It is very particularly preferred to use at least one substituted compound according to the invention and optionally one or more pharmaceutically acceptable auxiliary substances for the production of a pharmaceutical preparation for the treatment and/or prevention of one or more diseases selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; inflammation, preferably inflammation of the intestines, the eyes, the bladder, the skin or the nasal mucosa; urinary incontinence; an overactive bladder (OAB); dependency on medicines; abuse of medicines; withdrawal symptoms associated with dependency on medicines; development of tolerance towards medicines, preferably development of tolerance towards natural or synthetic opioids; dependency on drugs; drug abuse; withdrawal symptoms associated with dependency on drugs; dependency on alcohol; alcohol abuse and withdrawal symptoms associated with dependency on alcohol.

It is still further preferred to use at least one substituted compound according to the invention and optionally one or more pharmaceutically compatible auxiliary substances for the production of a pharmaceutical preparation for the treatment and/or prevention of pain, preferably selected from the group consisting of acute pain, chronic pain, neuropathic pain and visceral pain, and/or urinary incontinence.

The pharmaceutical preparation according to the invention is suitable for administration to adults and children including small children and babies.

The pharmaceutical preparation according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted compound of the above-stated general formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the pharmaceutical preparation according to the invention conventionally contains further physiologically acceptable pharmaceutical auxiliary substances, which are for example selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. The substituted compounds according to the invention used in the pharmaceutical preparation according to the invention in a depot in dissolved form or in a dressing, optionally with the addition of skin penetration promoters, are suitable percutaneous administration preparations. Orally or percutaneously administrable formulations may also release the particular substituted compound according to the invention in delayed manner.

Production of the pharmaceutical preparations according to the invention proceeds with the assistance of conventional means, devices, methods and processes known to the person skilled in the art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure. The quantity of the particular substituted compounds according to the invention of the above-stated general formula I to be administered to the patient may vary and is for example dependent on the weight or age of the patient and on the mode of administration, the indication and the severity of the complaint. Conventionally, 0.001 to 100 mg/kg, preferably 0.05 to 75 mg/kg, particularly preferably 0.05 to 50 mg/kg of patient body weight of at least one such compound according to the invention are administered.

Pharmacological Methods

I. Functional Investigation of the Vanilloid Receptor 1 (VR1/TRPV1 Receptor)

The agonistic or antagonistic action of the substances to be investigated on the vanilloid receptor 1 (VR1/TRPV1) of the rat species may be determined by the following assay. According to this assay, the influx of $Ca^{2+}$ through the receptor channel is quantified with the assistance of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA).

Method:

Complete medium: 50 mL HAMS F12 Nutrient Mixture (Gibco Invitrogen GmbH, Karlsruhe, Germany) with 10 vol. % FCS (foetal calf serum, Gibco Invitrogen GmbH, Karlsruhe, Germany, heat-inactivated);

2 mM L-glutamine (Sigma, Munich, Germany);

1 wt. % AA solution (antibiotic/antimycotic solution, PAA, Pasching, Austria)

and 25 ng/mL NGF medium (2.5 S, Gibco Invitrogen GmbH, Karlsruhe, Germany)

Cell culture plate: poly-D-lysine coated, black 96 well plates with a clear bottom (96 well black/clear plate, BD Biosciences, Heidelberg, Germany) are additionally coated with laminin (Gibco Invitrogen GmbH, Karlsruhe, Germany), by diluting laminin to a concentration of 100 µg/mL with PBS (Ca—Mg-free PBS, Gibco Invitrogen GmbH, Karlsruhe, Germany). Aliquots with a concentration of 100 µg/mL of laminin are taken and stored at −20° C. The aliquots are diluted with PBS in a 1:10 ratio to 10 µg/mL of laminin and a 50 µL portion is in each case pipetted into a well of the cell culture-plate. The cell culture-plates are incubated at 37° C. for at least two hours, the supernatant solution is aspirated and the wells are in each case washed twice with PBS. The coated cell culture-plates are stored with supernatant PBS, which is not removed until just before application of the cells.

Preparation of the Cells:

The spinal column is removed from decapitated rats and is placed directly in cold, i.e. located in an ice bath, HBSS buffer (Hank's buffered saline solution, Gibco Invitrogen GmbH, Karlsruhe, Germany) combined with 1 vol. % (percent by volume) of an AA solution (antibiotic/antimycotic solution, PAA, Pasching, Austria). The spinal column is cut open longitudinally and removed together with fasciae from the spinal canal. The dorsal root ganglia (DRGs) are then removed and in turn stored in cold HBSS buffer combined with 1 vol. % of an AA solution. The DRGs, from which all traces of blood and spinal nerves have been removed, are in each case transferred into 500 µL of cold collagenase type 2 (PAA, Pasching, Austria) and incubated for 35 minutes at 37° C. After addition of 2.5 vol. % of trypsin (PAA, Pasching, Austria), incubation is continued for a further 10 minutes at 37° C. Once incubation is complete, the enzyme solution is carefully removed by pipette and the DRGs, which are left behind, are in each case combined with 500 µL of complete medium.

The DRGs are in each case repeatedly suspended, drawn by means of a syringe through no. 1, no. 12 and no. 16 cannulas and transferred into 50 mL Falcon microtubes and each tube is made up to 15 mL with complete medium. The contents of each Falcon microtube are in each case filtered through a 70 µm Falcon filter insert and centrifuged for 10 minutes at 1200 revolutions and room temperature. The resultant pellet is in each case resuspended in 250 µL of complete medium and the cell count determined.

The number of cells in the suspension is adjusted to $3 \times 10^5$ per mL and a 150 µL portion of this suspension is in each case placed in a well of the cell culture plate which has been coated as described above. The plates are placed in an incubator at 37° C., 5 vol. % $CO_2$ and 95% relative atmospheric humidity for two to three days.

The cells are then loaded with 2 µM Fluo-4 and 0.01 vol. % Pluronic F127 (Molecular Probes Europe BV, Leiden, Netherlands) in HBSS buffer (Hank's buffered saline solution, Gibco Invitrogen GmbH, Karlsruhe, Germany) for 30 min at 37° C., washed 3× with HBSS buffer and, after a further 15 minutes' incubation at room temperature, used for $Ca^{2+}$ measurement in the FLIPR assay. $Ca^{2+}$-dependent fluorescence is here measured before and after the addition of substances ($\lambda ex=488$ nm, $\lambda em=540$ nm). Quantification proceeds by measuring the highest fluorescence intensity (FC, fluorescence counts) over time.

FLIPR Assay:

The FLIPR protocol comprises 2 additions of substance. The compounds to be tested (10 µM) are firstly pipetted onto the cells and $Ca^{2+}$ influx is compared with the control (capsaicin 10 µM). This provides the percentage activation relative to the $Ca^{2+}$ signal after addition of 10 µM of capsaicin (CP). After 5 minutes' incubation, 100 nM of capsaicin are added and the influx of $Ca^{2+}$ is again determined.

Desensitising agonists and antagonists result in suppression of $Ca^{2+}$ influx. The percentage inhibition in comparison with the maximum achievable inhibition with 10 µM capsaicin is calculated.

Triplicate determinations (n=3) are performed and these are repeated in at least 3 independent experiments (N=4).

On the basis of the percentage displacement by different concentrations of the compounds to be tested of the general formula I, $IC_{50}$ inhibition concentrations which bring about 50% displacement of capsaicin were calculated. $K_i$ values for the test substances were obtained by conversion using the Cheng-Prusoff equation (Cheng, Prusoff; Biochem. Pharmacopoeia. 22, 3099-3108,1973).

II. Functional Investigations on the Vanilloid Receptor (VR1)

The agonistic or antagonistic action of the substances to be investigated on the vanilloid receptor (VR1) may also be determined with the following assay. According to this assay, the influx of $Ca^{2+}$ through the channel is quantified with the assistance of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA).

Method:

Chinese hamster ovary cells (CHO K1 cells, European Collection of Cell Cultures (ECACC), Great Britain) are stably transfected with the VR1 gene. For functional investigations, these cells are plated out onto poly-D-lysine-coated, black 96 well plates with a clear bottom (BD Biosciences, Heidelberg, Germany) at a density of 25,000 cells/well. The cells are incubated overnight at 37° C. and 5% $CO_2$ in a culture medium (Ham's Nutrient Mixture F12, 10 vol. % FCS (foetal calf serum), 18 µg/mL L-proline). On the following day, the cells are incubated with Fluo-4 (Fluo-4 2 µM, Pluronic F127 0.01 vol. %, Molecular Probes in HBSS (Hank's buffered saline solution), Gibco Invitrogen GmbH, Karlsruhe, Germany) for 30 minutes at 37° C. The plates are then washed 3 times with HBSS buffer and, after a further 15 minutes' incubation at room temperature, used for $Ca^{2+0}$ measurement in the FLIPR. $Ca^{2+}$-dependent fluorescence is here measured before and after addition of the substances to be investigated (wavelength $\lambda_{ex}=488$ nm, $\lambda em=540$ nm). Quantification proceeds by measuring the highest fluorescence intensity (FC, fluorescence counts) over time.

FLIPR Assay:

The FLIPR protocol comprises 2 additions of substance. The substances to be tested (10 µM) are firstly pipetted onto the cells and $Ca^{2+}$ influx is compared with the control (capsaicin 10 µM) (% activation relative to the $Ca^{2+}$ signal after addition of 10 µM of capsaicin). After 5 minutes' incubation, 100 nM of capsaicin are added and the influx of $Ca^{2+}$ is again determined.

Desensitising agonists and antagonists resulted in suppression of $Ca^{2+}$ influx. The percentage inhibition in comparison with the maximum achievable inhibition with 10 µM capsaicin is calculated.

On the basis of the percentage displacement by different concentrations of the compounds to be tested of the general formula I, $IC_{50}$ inhibition concentrations which bring about 50% displacement of capsaicin were calculated. Ki values for the test substances were obtained by conversion using the Cheng-Prusoff equation (Cheng, Prusoff; Biochem. Pharmacopoeia. 22, 3099-3108,1973).

III. Formaldehyde Test in Mice

The investigation for determining the antinociceptive action of the compounds according to the invention is carried out by the formaldehyde test on male mice (NMRI, 20 to 30 g body weight, Iffa, Credo, Belgium).

In the formaldehyde test according to D. Dubuisson et al., Pain, 1977, 4, 161-174, a distinction is drawn between the first (early) phase (0-15 min after formaldehyde injection) and the second (late) phase (15-60 min after formaldehyde injection). The early phase, being a direct response to the formaldehyde injection, is considered to be a model of acute pain, while the late phase is considered to be a model of persistent (chronic) pain (T. J. Corre et al., Pain, 1993, 52, 259-285). The corresponding literature descriptions are hereby introduced as a reference and are deemed to be part of the disclosure.

The compounds according to the invention are investigated in the second phase of the formaldehyde test in order to obtain information concerning the effects of the substances on chronic/inflammatory pain.

The timing of the administration of the compounds according to the invention prior to the formaldehyde injection is selected as a function of the mode of administration of the compounds according to the invention. Intravenous administration of the test substances in an amount of 10 mg/kg of body weight proceeds 5 minutes before the formaldehyde injection. This is achieved by a single, subcutaneous formaldehyde injection (20 µL, 1% aqueous solution) into the dorsal side of the rear hind paw, such that a nociceptive reaction is induced in the freely mobile test animals, the reaction being expressed by distinct licking and biting of the affected paw.

Nociceptive behaviour is then continuously recorded by observing the animals for a period of three minutes in the second (late) phase of the formaldehyde test (21 to 24 minutes after the formaldehyde injection). Pain behaviour is quantified by summing the seconds for which the animals exhibit licking and biting of the affected paw over the investigation period.

The comparison is made in each case with control animals, which, instead of compounds according to the invention, received vehicle (0.9% aqueous sodium chloride solution) before administration of the formaldehyde. On the basis of the quantification of the pain behaviour, the action of the substance in the formaldehyde test is determined as a percentage change relative to the corresponding control.

After injection of substances which are antinociceptive in the formaldehyde test, the described behaviors of the animals, i.e. licking and biting, are reduced or eliminated.

IV. Investigation of Analgesic Efficacy by the Writing Test

Investigation of the compounds according to the invention of the general formula I for analgesic efficacy was performed by phenylquinone-induced writhing in the mouse, modified after I. C. Hendershot and J. Forsaith (1959) J. Pharmacol. Exp. Ther. 125, 237-240. The corresponding literature description is hereby introduced as a reference and is deemed to be part of the disclosure.

Male NMRI mice weighing from 25 to 30 g were used for this purpose. Groups of 10 animals per compound dose received, 10 minutes after intravenous administration of the compounds to be tested, 0.3 mL/mouse of a 0.02% aqueous solution of phenylquinone (phenylbenzoquinone, Sigma, Deisenhofen, Germany; solution prepared with addition of 5% of ethanol and stored in a water bath at 45° C.) administered intraperitoneally. The animals were placed individually in observation cages. A push button counter was used to record the number of pain-induced stretching movements (writhing reactions=straightening of the torso with stretching of the rear extremities) for 5-20 minutes after phenylquinone administration. The control was provided by animals which had received only physiological saline. All the compounds were tested at the standard dosage of 10 mg/kg.

V. Hypothermie Assay an der Maus

Male NMRI mice (weight 25-35 gram, supplier IFFA CREDO, Bruxelles, Belgium) are used in the hypothermie assay. The animals are kept under standardized conditions: light/darkness interval (6:00 to 18:00 light; 18:00 to 6:00 Uhr darkness), room temperature 19-22° C., relative humidity 35-70%, 15 times per hour change of compartment air, airflow <0.2 m/sec. The animals were fed on a standardized diet (ssniff diet, ssniff Spezialdiäten GmbH, Soest, Germany) and tap water. Water and diet were detracted during the experiment. All animals were used once in the experiment. The animals were allowed to adapt to the experimental conditions for at least 5 days.

The acute application of capsaicin (VR-1 agonist) leads to a decrease of the core body temperature in rat and mice via stimulation of heat sensors. Only compounds which act as specific VR-1-receptor antagonists can antagonize the capsaicin induced hypothermie. In contrast, morphine induced hypothermie is not antagonized by VR-1 antagonists. Thus, this experiment is suitable for the determination of compounds that act as VR1-antagonists via their effect on the core body temperature.

For the determination of the core body temperature a digital thermometer was used (Thermalert TH-5, physitemp, Clifton N.J., USA). The measuring head was inserted into the rectum.

The individual basis value is determined by measuring the body temperature twice in an interval of about half an hour. Subsequently a group of mice (n=6 to 10) is treated with capsaicin (3 mg/kg) intraperitoneally (i.p.). Another group of mice (n=6 to 10) is treated with capsaicin (3 mg/kg) intraperitoneally (i.p.) and the test compound (i.v. or p.o.). The test compound is given 10 min (i.v.) or 15 min (p.o.), respectively, before application of capsaicin. The body temperature is determined 7.5/15 and 30 min after application of capsaicin (i.v.+i.p.) or 15/30/60/90/120 min after application of capsaicin (p.o.+i.p.), respectively. In addition, another group of mice is only given the test compound or a vehicle control.

The measuring points are given as average values±S.E.M. of the absolute values. The antagonistic effect is given in percent of inhibition of capsaicin induced hypothermie.

VI. Neuropathic Pain in Mice

The efficacy of compounds of general formula I in the treatment of neuropathic pain is investigated by using the Bennet modell (chronic constriction injury; Bennett and Xie, 1988, Pain 33: 87-107.

NMRI mice (weight 16 to 18 g) under ketavet-rompun anaesthesia are supplied with three loose ligatures of the right nervus ischiaticus. The animals develop an oversensitivity to cold at the position of the pad that is innervated by the injured nerve which—after a recovery period of one week—is quantified over a period of three weeks by using a metal plate that is cooled to 4° C. (cold allodynia). The animals are observed for a period of 2 minutes on this plate and the number of brisk withdrawal reactions of the injured nerve is counted. The efficacy of the compounds is determined at different time points after administration of test compound (e.g. 15, 30, 45, and 60 min) relating to the value before substance application and the resulting area ander the curve (AUC) and/or blocking of cold allodynia at different time points is expressed either in percent efficacy relative to vehicle control (AUC) or relative to the initial value (time points). The group size is n=10, the stastical significance of efficacy against allodynia (*=p<0.05) is determined by analysis of variance with repeated measurements and post hoc analysis with Bonferroni adjustment.

The invention is illustrated below with the assistance of some Examples. These explanations are given merely by way of example and do not restrict the general concept of the invention.

EXAMPLES

The yields of the compounds produced have not been optimised.

All temperatures are uncorrected.

The term "equivalents" means molar equivalents, "RT" means room temperature, "M" and "N" are concentrations stated in mol/l, "aq." means aqueous, "sat." means saturated, "soln." means solution.

Further Abbreviations:

DMF N,N-dimethylformamide

EDCl N-ethyl-N'-(3-dimethylaminopropyl)-carbodiimide hydrochloride

EA ethyl acetate $H_2O$ water

MeOH methanol

The chemicals and solvents used were purchased from conventional suppliers (Acros, Avocado, Aldrich, Bachem, Fluka, Lancaster, Maybridge, Merck, Sigma, TCI, Oakwood etc.) or synthesised by conventional methods known to the person skilled in the art.

Silica gel 60 (0.0-0.063 mm) from E. Merck, Darmstadt, was used as the stationary phase for the column chromatography.

Thin-layer chromatography was performed with pre-coated silica gel 60 F 254 HPTLC plates from E. Merck, Darmstadt.

The mixture ratios of solvents, mobile solvents or for chromatographic investigations are always stated by volume/volume.

Analysis was carried out by mass spectroscopy and NMR.

1. General Method for the Preparation of Amines of the General Formula V-A

Amines of the general formula V-A are prepared as shown in scheme 1 below.

Scheme 1.

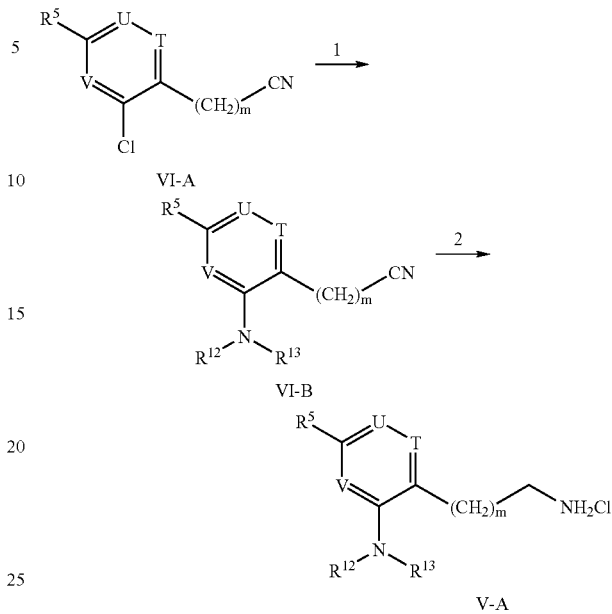

Stage 1:

Method A:

Compounds of the general formula VI-A (1 equivalent), in which $R^5$, U, T and V have the above-stated meaning and m denotes 0, 1, 2 or 3, are stirred with an amine of the general formula $HNR^{12}R^{13}$ (6 equivalents) for 48 hours at RT. The reaction mixture is combined with 1 N hydrochloric acid and repeatedly extracted with EA. The aqueous phase is saturated with NaCl and then extracted again with EA. The combined organic phases are washed with 1 N hydrochloric acid and with sat. aq. NaCl soln., dried over $MgSO_4$ and the solvent is removed under a vacuum.

The following compounds A-1 to A-6 were obtained according to the above-stated general method:

Compound A-1

2-(piperidin-1-yl)-6-(trifluoromethyl)nicotinonitrile

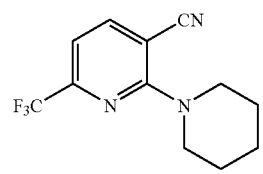 [SMILES: N#Cc1ccc(C(F)(F)F)nc1N1CCCCC1]

The compound was obtained in a yield of 86% as a pale yellow oil.

$^1$H NMR (300 MHz, $CDCl_3$) δ 7.87 (d, 1H, J=7.8 Hz), 6.95 (d, 1H, J=7.8 Hz), 3.78 (m, 4H), 1.71 (m, 6H)

IR (KBr) 2941, 2857, 2218, 1590, 1496, 1453, 1346, 1318, 1239, 1186 $cm^{-1}$

MS (FAB) m/z 256 (M+H)

Compound A-2

2-(morpholin-4-yl)-6-(trifluoromethyl)nicotinonitrile

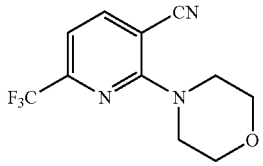 [SMILES: N#Cc1ccc(C(F)(F)F)nc1N1CCOCC1]

The compound was obtained in a yield of 78% as a pale yellow oil.

$^1$H NMR (300 MHz, CDCl$_3$) δ 7.94 (d, 1H, J=7.8 Hz), 7.05 (d, 1H, J=7.8 Hz), 3.84 (s, 8H)

IR (KBr) 3397, 2968, 1511, 1428, 1337, 1124 cm$^{-1}$

MS (FAB) m/z 258 (M+H)

Compound A-3

2-(pyrrolidin-1-yl)-6-(trifluoromethyl)nicotinonitrile

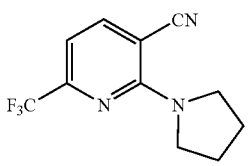 [SMILES: N#Cc1ccc(C(F)(F)F)nc1N1CCCC1]

The compound was obtained in a yield of 85% as a pale yellow oil.

$^1$H NMR (300 MHz, CDCl$_3$) δ 7.83 (d, 1H, J=7.8 Hz), 6.86 (d, 1H, J=7.8 Hz), 3.78-3.83 (m, 4H), 1.96-2.04 (m, 4H)

IR (KBr) 2976, 2880, 2216, 1591, 1502, 1457, 1344, 1303, 1247, 1181 cm$^{-1}$

MS (FAB) m/z 242 (M+H)

Compound A-4

2-(piperidin-1-yl)-4-(trifluoromethyl)benzonitrile

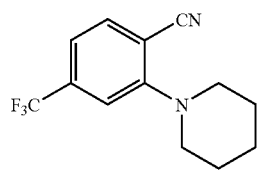 [SMILES: N#Cc1ccc(C(F)(F)F)cc1N1CCCCC1]

The compound was obtained in a yield of 74% as a pale yellow oil.

$^1$H NMR (300 MHz, CDCl$_3$) δ 7.63 (d, 1H, J=7.8 Hz), 7.1-7.19 (m, 2H), 3.22-3.25 (m, 4H), 1.60-1.80 (m, 6H)

Compound A-5

2-(morpholin-4-yl)-4-(trifluoromethyl)benzonitrile

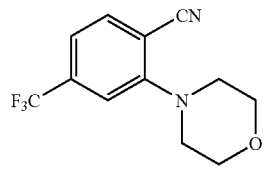 [SMILES: N#Cc1ccc(C(F)(F)F)cc1N1CCOCC1]

The compound was obtained in a yield of 80% as a pale yellow oil.

$^1$H NMR (300 MHz, CDCl$_3$) δ 8.31 (d, 1H, J=7.8 Hz), 7.85-7.88 (m, 2H), 4.36-4.39 (m, 4H), 3.76-3.79 (m, 4H)

IR (KBr) 2856, 1614, 2210, 1501, 1430, 1311, 1258, 1173, 1122, 1077 cm$^{-1}$

Compound A-6

2-(pyrrolidin-1-yl)-4-(trifluoromethyl)benzonitrile

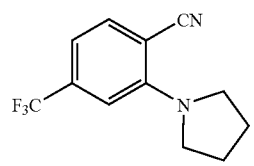 [SMILES: N#Cc1ccc(C(F)(F)F)cc1N1CCCC1]

The compound was obtained in a yield of 80% as a pale yellow oil.

$^1$H NMR (400 MHz, CDCl$_3$) δ 7.53 (d, 1H, J=8.8 Hz), 6.83-6.85 (m, 2H), 3.65 (t, 4H, J=6.4 Hz), 2.04 (t, 4H, J=6.4 Hz)

IR (KBr) 2972, 2212, 1619, 1561, 1504, 1454, 1306, 1169 cm$^{-1}$

Method B:

Compounds of the general formula VI-A (1 equivalent), in which R$^5$, U, T and V have the above-stated meaning and m denotes 0,1, 2 or 3, are stirred with an amine of the general formula HNR$^{12}$R$^{13}$ (2 equivalents) and DBU [1,8-diaza-bicyclo[5.4.0]andec-7-ene] (2 equivalents) in acetonitrile (7 mL per mmol of compound of general formula VI-A) for 18 hours at RT. The reaction mixture is repeatedly extracted with EA. The combined organic extracts are washed with sat. aq. NaCl soln., dried over MgSO$_4$ and the solvent is removed under a vacuum. The residue is purified by flash chromatography (SiO$_2$, different mixtures of hexanes and EA).

The following compounds A-7 to A-102 were obtained according to the above-stated general method:

Compound A-7: 6-(chlorodifluoromethyl)-2-(piperidin-1-yl)pyridine-3-carbonitrile

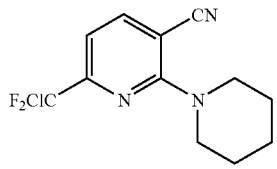

¹H NMR (300 MHz, CDCl₃) δ 7.87 (d, 1H, J=7.8 Hz), 6.94 (δ, 1H, J=7.8 Hz), 3.22-3.26 (m, 4H), 1.60-1.80 (m, 6H); IR (neat) 2939, 2857, 2217, 1588, 1493, 1451, 1296, 1235, 1109, 977, 917, 807 cm⁻¹; MS (FAB) m/z 272 (M+H)

A-8: 2-(4-benzylpiperazin-1-yl)-6-(trifluoromethyl)pyridine-3-carbonitrile

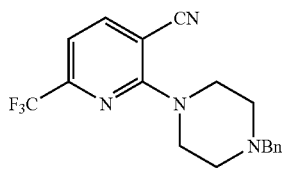 [SMILES: N#Cc1ccc(C(F)(F)F)nc1N1CCN(Cc2ccccc2)CC1]

¹H NMR (300 MHz, CDCl₃) δ 7.83 (d, 1H, J=7.8 Hz), 7.19-7.30 (m, 5H), 6.94 (d, 1H, J=7.8 Hz), 3.80-3.83 (m, 4H), 3.52 (s, 2H), 2.52-2.56 (m, 4H); IR (neat) 2813, 1590, 1498, 1451, 1321, 1239, 1143, 968, 824, 742 cm⁻¹; MS (FAB) m/z 347 (M+H)

A-9: 6-(trifluoromethyl)-2-(4-methylpiperidin-1-yl)pyridine-3-carbonitrile

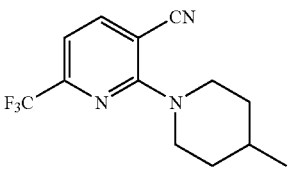 [SMILES: CC1CCN(c2nc(C(F)(F)F)ccc2C#N)CC1]

¹H NMR (300 MHz, CDCl₃) δ 7.87 (d, 1H, J=7.8 Hz), 6.95 (d, 1H, J=7.8 Hz), 4.53 (m, 2H), 3.05 (m, 2H), 1.78 (m, 2H), 1.64 (m, 1H), 1.29 (m, 2H), 1.00 (d, 3H, J=6.6 Hz); IR (neat) 2926, 2852, 2218, 1590, 1497, 1456, 1324, 1237, 1186, 1147, 1082, 963 cm⁻¹; MS (FAB) m/z 270 (M+H)

A-10: 6-(trifluoromethyl)-2-(3,5-dimethylpiperidin-1-yl)pyridine-3-carbonitrile

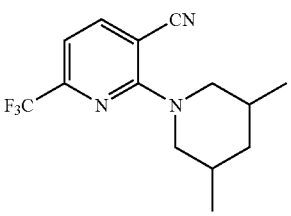 [SMILES: CC1CC(C)CN(c2nc(C(F)(F)F)ccc2C#N)C1]

¹H NMR (300 MHz, CDCl₃) δ 7.84 (d, 1H, J=7.8 Hz), 6.91 (d, 1H, J=7.8 Hz), 4.50 (m, 2H), 2.49 (m, 2H), 1.67-1.89 (m, 4H), 0.92 (d, 6H, J=6.6 Hz)
IR (neat) 2925, 2852, 2216, 1592, 1498, 1457, 1325, 1188, 1145, 1080, 962 cm⁻¹
MS (FAB) m/z 284 (M+H)

A-11: 2-azocan-1-yl-6-trifluoromethyl-nicotinonitrile

¹H NMR (300 MHz, CDCl₃) δ 7.86 (d, 1H, J=7.8 Hz), 6.87 (d, 1H, J=7.8 Hz), 3.88 (t, 4H, J=6.0 Hz), 1.87 (m, 4H), 1.55 (m, 4H); IR (KBr) 2929, 2857, 2213, 1592, 1563, 1510, 1455, 1327, 1235, 1188, 1145, 1080, 999, 816, 743 cm⁻¹; MS (FAB) m/z 284 (M+H)

A-12: 4-phenyl-6'-trifluoromethyl-3,4,5,6-tetrahydro-2H-[1,2']bipyridinyl-3'-carbonitrile

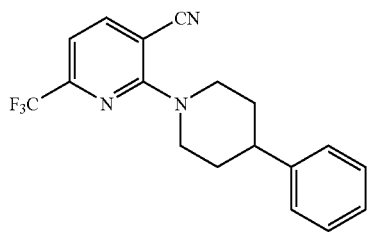 [SMILES: N#Cc1ccc(C(F)(F)F)nc1N1CCC(c2ccccc2)CC1]

¹H NMR (300 MHz, CDCl₃) δ 7.90 (dd, 1H, J=7.5, 0.9 Hz), 7.20-7.35 (m, 5H), 7.00 (d, 1H, J=7.5 Hz), 4.70 (dt, 2H, J=13.5, 1.8 Hz), 3.17 (dt, 2H, J=13.5, 3.3 Hz 2.82 (m, 1H), 1.95 (m, 2H), 1.87 (m, 2H); IR (KBr) 2938, 2852, 2217, 1590, 1566, 1376, 1190, 1145, 1081, 1012, 958, 824, 752 cm⁻¹; MS (FAB) m/z 332 (M+H)

A-13: 4-fluoro-6'-trifluoromethyl-3,4,5,6-tetrahydro-2H-[1,2']bipyridinyl-3'-carbonitrile

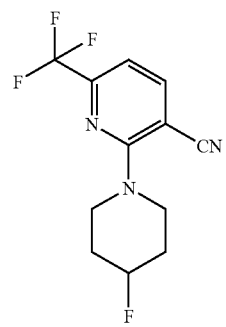 [SMILES: N#Cc1ccc(C(F)(F)F)nc1N1CCC(F)CC1]

¹H NMR (300 MHz, CDCl₃) δ 7.93 (dd, 1H, J=7.5, 0.9 Hz), 7.04 (d, 1H, J=7.5 Hz), 4.94 (dm, 1H, J=48.3 Hz), 3.98 (m, 2H), 3.81 (m, 1H), 1.90-2.13 (m, 4H)
MS (FAB) m/z 274 (M+H)

A-14: 6'-(chloro-difluoro-methyl)-4-methyl-3,4,5,6-tetrahydro-2H-[1,2']bipyridinyl-3'-carbonitrile

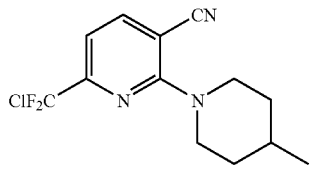

¹H NMR (300 MHz, CDCl₃) δ 7.86 (d, 1H, J=7.5 Hz), 6.93 (d, 1H, J=7.5 Hz), 4.53 (m, 2H), 3.05 (m, 2H), 1.62-1.80 (m, 3H), 1.23-1.27 (m, 2H), 0.99 (d, 3H, J=6.6 Hz); IR (KBr) 2925, 2217, 1589, 1559, 1497, 1455, 1336, 12231, cm⁻¹ MS (FAB) m/z 286 (M+H)

A-15: 2-azepan-1-yl-6-(chloro-difluoro-methyl)-nicotinonitrile

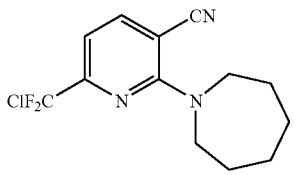

¹H NMR (300 MHz, CDCl₃) δ 7.85 (d, 1H, J=7.5 Hz), 6.85 (d, 1H, J=7.5 Hz), 3.87 (t, 4H, J=6.=Hz), 1.90 (m, 4H), 1.60 (m, 4H); IR (KBr) 2931, 2214, 1590, 1558, 1506, 1455,1339 cm⁻¹; MS (FAB) m/z 286 (M+H)

A-16: 6'-(4-fluoro-phenyl)-4-methyl-3,4,5,6-tetrahydro-2H-[1,2']bipyridinyl-3'-carbonitrile

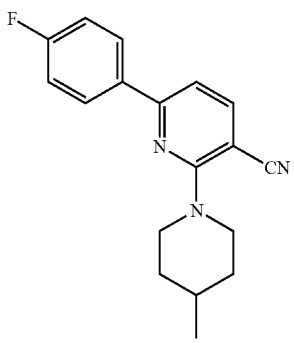 [SMILES: CC1CCN(c2nc(-c3ccc(F)cc3)ccc2C#N)CC1]

¹H NMR (300 MHz, CDCl₃) δ 8.00 (m, 2H), 7.77 (d, 1H, J=7.8 Hz), 7.07-7.17 (m, 3H), 4.51 (m, 2H), 3.05 (m, 2H), 1.77 (m, 2H), 1.66 (m, 1H), 1.35 (m, 2H), 0.99 (d, 3H, J=6.6 Hz); IR (KBr) 2935, 2210, 1576, 1508, 1449, 1329, 1233, 1156, 1116, 1021, 949 cm⁻¹; MS (FAB) m/z 296 (M+H)

A-17: 2-azepan-1-yl-6-(4-fluoro-phenyl)-nicotinonitrile

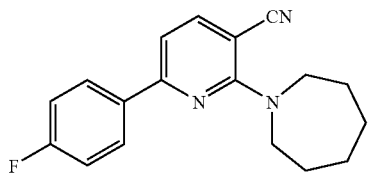 [SMILES: N#Cc1ccc(-c2ccc(F)cc2)nc1N1CCCCCC1]

¹H NMR (300 MHz, CDCl₃) δ 8.00 (m, 2H), 7.75 (d, 1H, J=7.8 Hz), 7.13 (dd, 1H, J=8.7, 8.7 Hz), 7.01 (d, 1H, J=7.8 Hz), 3.92 (t, 4H, J=6.=Hz), 1.92 (m, 4H), 1.60 (m, 4H); IR (KBr) 2930, 2855, 2206, 1577, 1504, 1452, 1338, 1277, 1234, 1155, 848, 805 cm⁻¹; MS (FAB) m/z 296 (M+H)

A-18: 6-(chloro-difluoro-methyl)-2-dipropylamino-nicotinonitrile

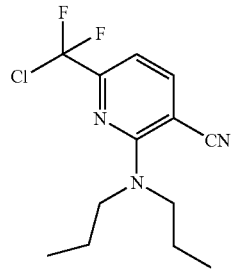 [SMILES: CCCN(CCC)c1nc(C(F)(F)Cl)ccc1C#N]

¹H NMR (300 MHz, CDCl₃) δ 7.82 (d, 1H, J=7.8 Hz), 6.83 (d, 1H, J=7.8 Hz), 3.63 (t, 4H, J=7.5 Hz), 1.73 (m, 4H), 0.96 (t, 6H, J=7.2 Hz); IR (KBr) 2968, 2214, 1590, 1455, 1374, 1232, 1108 cm⁻¹; MS (FAB) m/z 288 (M+H)

A-19: 2-(1,3-dihydro-isoindol-2-yl)-6-trifluoromethyl-nicotinonitrile

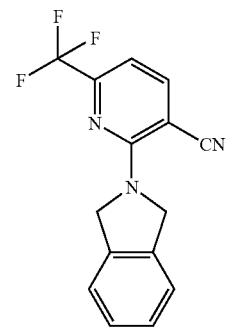 [SMILES: N#Cc1ccc(C(F)(F)F)nc1N1Cc2ccccc2C1]

$^1$H NMR (300 MHz, CDCl$_3$) δ 7.93 (d, 1H, J=7.8 Hz), 7.30-7.37 (m, 4H), 6.97 (d, 1H, J=7.8 Hz), 5.20 (s, 4H); IR (KBr) 2966, 2213, 1588, 1480, 1455, 1374, 1232, 1176 cm$^{-1}$; MS (FAB) m/z 290 (M+H)

A-20: 3'-cyano-4-phenyl-6'-trifluoromethyl-3,4,5,6-tetrahydro-2H-[1,2']bipyridinyl-4-carbonic acid ethylester

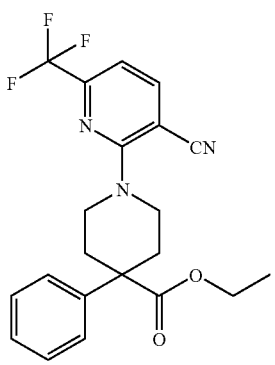 [SMILES: CCOC(=O)C1(c2ccccc2)CCN(c2nc(C(F)(F)F)ccc2C#N)CC1]

$^1$H NMR (300 MHz, CDCl$_3$) δ 8.22 (dd, 1H, J=8.1, 0.6 Hz), 7.90 (d, 1H, J=8.1 Hz), 7.24-7.42 (m, 5H), 4.41 (m, 2H), 4.16 (q, 2H, J=7.0 Hz), 3.38 (m, 2H), 2.73 (m, 2H), 2.08 (m, 2H), 1.21 (t, 3H, J=7.0 Hz); IR (neat) 2926, 2218, 1725, 1590, 1495, 1456, 1321, 1186, 1148, 1040, 963, 824, 738, 698 cm$^{-1}$; MS (FAB) m/z 404 (M+H)

A-21: 4,6'-bistrifluoromethyl-3,4,5,6-tetrahydro-2H-[1,2']bipyridinyl-3'-carbonitrile $^1$H NMR (300 MHz, CDCl$_3$) δ 7.94 (d, 1H, J=7.8 Hz), 7.07 (d, 1H, J=7.8 Hz), 4.62 (m, 2H), 3.07 (m, 2H), 2.35 (m, 1H), 2.03 (m, 2H), 1.70 (m, 2H)
IR (neat) 2964, 2221, 1591, 1495, 1456, 1394, 1342, 1254, 1147, 1084, 960, 827, 744, 697 cm$^{-1}$; MS (FAB) m/z 324 (M+H)

A-22: 4-methoxymethyl-6'-trifluoromethyl-3,4,5,6-tetrahydro-2H-[1,2']bipyridinyl-3'-carbonitrile

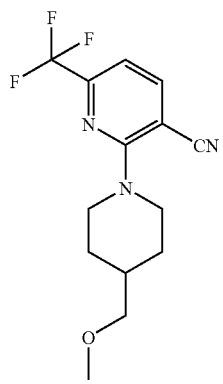 [SMILES: COCC1CCN(c2nc(C(F)(F)F)ccc2C#N)CC1]

$^1$H NMR (300 MHz, CDCl$_3$) δ 7.88 (d, 1H, J=7.8 Hz), 6.97 (d, 1H, J=7.8 Hz), 4.57 (m, 2H), 3.35 (s, 3H), 3.27 (d, 2H, J=6.0 Hz), 3.07 (m, 2H), 1.87 (m, 2H), 1.28-1.45 (m, 3H); IR (neat) 2951, 2237, 1590, 1465, 1431, 1349, 1269, 1188, 1150, 1117, 969, 842, 743 cm$^{-1}$; MS (FAB) m/z 300 (M+H)

A-23: 2-(4-p-tolyl-piperazin-1-yl)-6-trifluoromethyl-nicotinonitrile

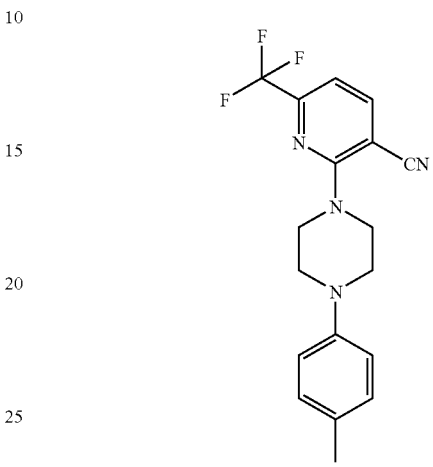

$^1$H NMR (300 MHz, CDCl$_3$) δ 7.93 (d, 1H, J=7.5 Hz), 7.11 (d, 2H, J=8.4 Hz), 7.05 (d, 1H, J=7.5 Hz), 6.88 (d, 2H, J=8.4 Hz), 4.00 (m, 4H), 3.28 (m, 4H), 2.28 (s, 3H); IR (neat) 2918, 2219, 1590, 1513, 1449, 1381, 1319, 1236, 1186, 1147, 1086, 1044, 970, 815, 743, 703 cm$^{-1}$; MS (FAB) m/z 347 (M+H)

A-24: 2-(4-m-tolyl-piperazin-1-yl)-6-trifluoromethyl-nicotinonitrile

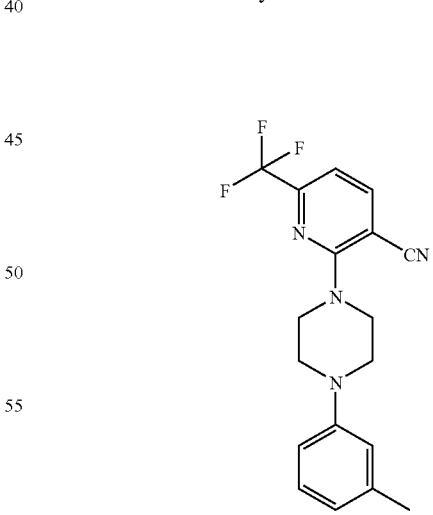

$^1$H NMR (300 MHz, CDCl$_3$) δ 7.94 (d, 1H, J=7.8 Hz), 7.19 (t, 1H, J=7.5 Hz), 7.06 (d, 1H, J=7.8 Hz), 6.72-6.78 (m, 3H), 4.00 (m, 4H), 3.33 (m, 4H), 2.34 (s, 3H)
IR (neat) 2830, 2214, 1591, 1487, 1320, 1345, 1184, 1140, 1088, 967, 816, 770, 694 cm$^{-1}$; MS (FAB) m/z 347 (M+H)

153

A-25: 2-[4-(4-methoxy-phenyl)-piperazin-1-yl]-6-trifluoromethyl-nicotinonitrile

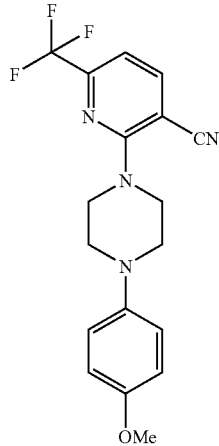 [SMILES: COc1ccc(N2CCN(c3nc(C(F)(F)F)ccc3C#N)CC2)cc1]

$^1$H NMR (300 MHz, CDCl$_3$) δ 7.93 (d, 1H, J=7.8 Hz), 7.05 (d, 1H, J=7.8 Hz), 6.94 (d, 2H, J=6.9 Hz), 6.86 (d, 2H, J=6.9 Hz), 4.00 (m, 4H), 3.77 (s, 3H), 3H), 3.21 (m, 4H); IR (neat) 2832, 2219, 1590, 1510, 1448, 1319, 1241, 1184, 1146, 1085, 1035, 970, 825, 743, 702 cm$^{-1}$; MS (FAB) m/z 363 (M+H)

A-26: 6-trifluoromethyl-2-[4-(4-trifluoromethyl-phenyl)-piperazin-1-yl]-nicotinonitrile

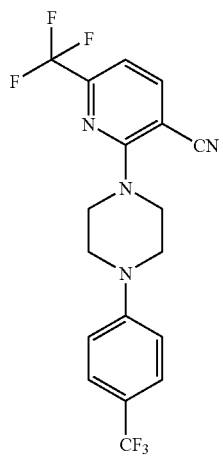 [SMILES: N#Cc1ccc(C(F)(F)F)nc1N1CCN(c2ccc(C(F)(F)F)cc2)CC1]

$^1$H NMR (300 MHz, CDCl$_3$) δ 7.96 (d, 1H, J=8.1 Hz), 7.52 (d, 2H, J=8.7 Hz), 7.09 (d, 1H, J=8.1 Hz), 6.94 (d, 2H, J=8.7 Hz), 4.01 (m, 4H), 3.46 (m, 4H);

IR (neat) 2923, 2220, 1685, 1594, 1509, 1455, 1344, 1318, 1233, 1186, 1147, 1089, 965, 818 cm$^{-1}$; MS (FAB) m/z 401 (M+H)

154

A-27: 6-trifluoromethyl-2-[4-(3-trifluoromethyl-pyridin-2-yl)-piperazin-1-yl]-nicotinonitrile

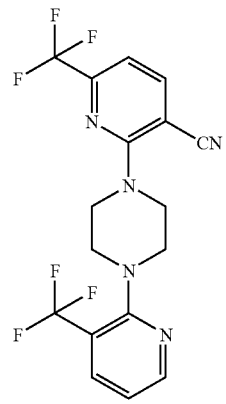 [SMILES: N#Cc1ccc(C(F)(F)F)nc1N1CCN(c2ncccc2C(F)(F)F)CC1]

$^1$H NMR (300 MHz, CDCl$_3$) δ 8.22 (d, 1H, J=3.3 Hz), 7.93 (d, 1H, J=7.5 Hz), 7.63 (d, 1H, J=7.5 Hz), 7.06 (d, 1H, J=9.0 Hz), 6.89 (m, 1H), 4.01 (m, 4H), 3.53 (m, 4H); IR (neat) 2856, 2216, 1589, 1441, 1375, 1344, 1312, 1234, 1148, 1097, 1023, 969, 832 cm$^{-1}$; MS (FAB) m/z 402 (M+H)

A-28: 2-imidazol-1-yl-6-trifluoromethyl-nicotinonitrile

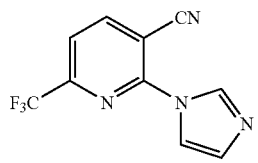 [SMILES: N#Cc1ccc(C(F)(F)F)nc1-n1ccnc1]

$^1$H NMR (300 MHz, CDCl$_3$) δ 8.62 (s, 1H), 8.38 (d, 1H, J=7.9 Hz), 8.00 (s, 1H), 7.76 (d, 1H, J=7.9 Hz), 7.29 (s, 1H); IR (neat) 3132, 2228, 1574, 1479, 1440, 1339, 1304, 1245, 1191, 1151, 1102, 1051, 985, 845, 744, 651 cm$^{-1}$; MS (FAB) m/z 239 (M+H)

A-29: 2-(4-(3-chloropyridin-2-yl)piperazin-1-yl)-6-(trifluoromethyl)nicotinonitrile

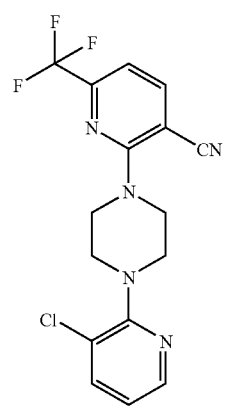 [SMILES: N#Cc1ccc(C(F)(F)F)nc1N1CCN(c2ncccc2Cl)CC1]

¹H NMR (300 MHz, CDCl₃) δ 8.46 (d, 1H, J=4.5 Hz), 7.89-7.95 (m, 2H), 7.04-7.07 (m, 2H), 3.99 (m, 4H), 3.44 (m, 4H); IR (neat) 2851, 2212, 1568, 1430, 1363, 1332, 1228, 1145, 1105, 962, 851 cm⁻¹; MS (FAB) m/z 372 (M+H)

A-30: 2-(4-cyclohexyl-piperazin-1-yl)-6-trifluoromethyl-nicotinonitrile

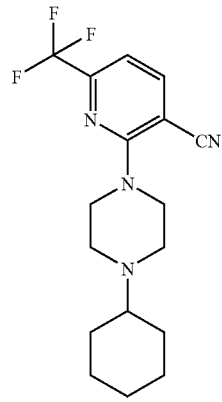 [SMILES: N#Cc1ccc(C(F)(F)F)nc1N1CCN(C2CCCCC2)CC1]

¹H NMR (300 MHz, CDCl₃) δ 7.90 (d, 1H, J=7.8 Hz), 6.98 (d, 1H, J=7.8 Hz), 3.86 (m, 4H), 2.70 (m, 4H), 2.31 (m, 1H), 1.80 (m, 4H), 1.20-1.28 (m, 6H); MS (FAB) m/z 339 (M+H)

A-31: 4-phenyl-6'-trifluoromethyl-3,4,5,6-tetrahydro-2H-[1,2']bipyridinyl-4,3'-dicarbonitrile

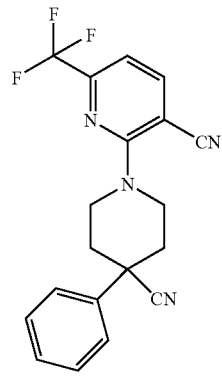 [SMILES: N#Cc1ccc(C(F)(F)F)nc1N1CCC(C#N)(c2ccccc2)CC1]

¹H NMR (300 MHz, CDCl₃) δ 7.97 (d, 1H, J=7.8 Hz), 7.33-7.53 (m, 5H), 7.13 (d, 1H, J=7.8 Hz), 4.66 (m, 2H), 3.55 (m, 2H), 2.15-2.31 (m, 4H); IR (neat) 2927, 2221, 1590, 1494, 1455, 1381, 1320, 1242, 1145, 1084, 1021, 963, 905, 829, 759, 699 cm⁻¹; MS (FAB) m/z 357 (M+H)

A-32: 4-phenylamino-6'-trifluoromethyl-3,4,5,6-tetrahydro-2H-[1,2']bipyridinyl-3'-carbonitrile

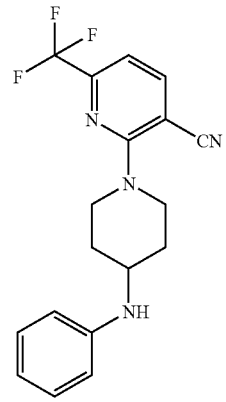 [SMILES: N#Cc1ccc(C(F)(F)F)nc1N1CCC(Nc2ccccc2)CC1]

¹H NMR (300 MHz, CDCl₃) δ 7.90 (d, 1H, J=7.8 Hz), 7.19 (m, 2H), 7.02 (d, 1H, J=7.8 Hz), 6.65 (m, 3H), 4.42 (m, 2H), 3.57 (m, 1H), 3.30 (m, 2H), 2.22 (m, 2H), 1.53 (m, 2H); MS (FAB) m/z 347 (M+H)

A-33: 2-azepan-1-yl-6-trifluoromethyl-nicotinonitrile

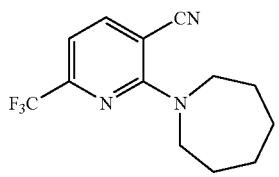 [SMILES: N#Cc1ccc(C(F)(F)F)nc1N1CCCCCC1]

¹H NMR (300 MHz, CDCl₃) δ 7.86 (d, 1H, J=7.1 Hz), 6.88 (d, 1H, J=7.7 Hz), 3.84-3.91 (m, 4H), 1.82-1.94 (m, 4H), 1.54-1.64 (m, 4H); IR (neat) 2930, 2215, 1593, 1563, 1508, 1458, 1327, 1246, 1144, 817 cm⁻¹; MS (FAB) m/z 270 (M+H)

A-34: N-(3'-cyano-6'-trifluoromethyl-3,4,5,6-tetrahydro-2H-[1,2']bipyridinyl-4-yl)-N-phenyl-propionamide

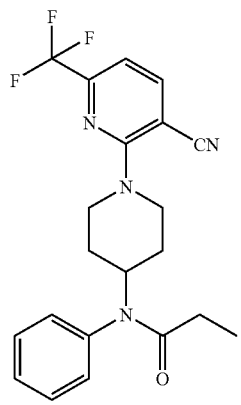 [SMILES: CCC(=O)N(c1ccccc1)C1CCN(c2nc(C(F)(F)F)ccc2C#N)CC1]

¹H NMR (300 MHz, CDCl₃) δ 7.85 (d, 1H, J=7.8 Hz), 7.41 (m, 3H), 7.11 (m, 2H), 6.95 (d, 2H, J=7.8 Hz), 4.96 (m, 1H), 4.61 (m, 2H), 3.14 (m, 2H), 1.96 (m, 4H), 1.46 (m, 2H), 1.03 (t, 3H, J=7.5 Hz); MS (FAB) m/z 403 (M+H)

A-35: 2-(4-dimethylamino-phenyl)-6-trifluoromethyl-nicotinonitrile

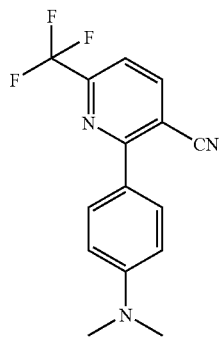 [SMILES: CN(C)c1ccc(-c2nc(C(F)(F)F)ccc2C#N)cc1]

¹H NMR (300 MHz, CDCl₃) δ 8.14 (d, 1H, J=8.1 Hz), 8.04 (d, 2H, J=8.7 Hz), 7.52 (d, 1H, J=7.8 Hz), 6.77 (d, 2H, J=8.7 Hz), 3.06 (s, 6H); IR (neat) 2969, 2215, 1571, 1522, 1463, 1409, 1341, 1254, 1132, 1108, 1024, 844, 790, 763 cm⁻¹; MS (FAB) m/z 292 (M+H)

A-36: 2-(2,6-dimethyl-morpholin-4-yl)-6-trifluoromethyl-nicotinonitrile

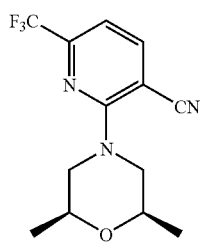 [SMILES: C[C@@H]1CN(c2nc(C(F)(F)F)ccc2C#N)C[C@H](C)O1]

¹H NMR (300 MHz, CDCl₃) δ 7.85 (d, 1H, J=7.5 Hz), 6.97 (d, 1H, J=7.5 Hz), 4.31 (m, 2H), 3.68 (m, 2H), 2.74 (m, 2H), 1.19 (d, 6H, J=6.3 Hz); IR (neat) 2979, 2867, 2220, 1591, 1566, 1452, 1330, 1297, 1240, 1146, 1080, 1008, 967, 828, 745 cm⁻¹;
MS (FAB) m/z 286 (M+H)

A-37: 2-(1,1-dioxo-thiomorpholin-4-yl)-6-trifluoromethyl-nicotinonitrile

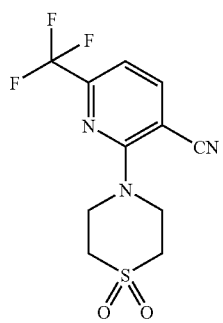 [SMILES: N#Cc1ccc(C(F)(F)F)nc1N1CCS(=O)(=O)CC1]

¹H NMR (300 MHz, CDCl₃) δ 8.06 (d, 1H, J=7.5 Hz), 7.27 (d, 1H, J=7.5 Hz), 4.32 (m, 4H), 3.23 (m, 4H); IR (neat) 2923, 2223, 1588, 1455, 1334, 1179, 1126, 1084, 865, 833 cm⁻¹; MS (FAB) m/z 306 (M+H)

A-38: 4,6'-dimethyl-3,4,5,6-tetrahydro-2H-[1,2']bipyridinyl-3'-carbonitrile

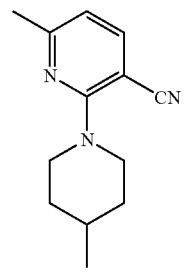 [SMILES: Cc1ccc(C#N)c(N2CCC(C)CC2)n1]

¹H NMR (300 MHz, CDCl₃) δ 7.60 (d, 1H, J=7.8 Hz), 6.53 (d, 1H, J=7.8 Hz), 4.39 (m, 2H), 2.96 (m, 2H), 2.41 (s, 3H), 1.60-1.76 (m, 3H), 1.35 (m, 2H), 0.98 (d, 3H, J=6.3 Hz); IR (neat) 2922, 2847, 2211, 1585, 1556, 1453, 1375, 1331, 1245, 1105, 965, 808, 764 cm⁻¹; MS (FAB) m/z 216 (M+H)

A-39: 4-(4-fluoro-phenyl)-6'-trifluoromethyl-3,6-dihydro-2H-[1,2']bipyridinyl-3'-carbonitrile

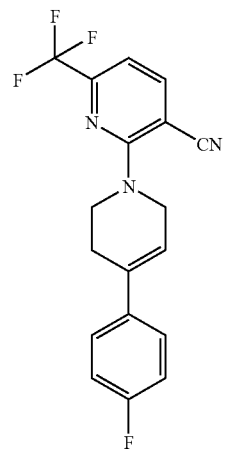 [SMILES: N#Cc1ccc(C(F)(F)F)nc1N1CC=C(c2ccc(F)cc2)CC1]

¹H NMR (300 MHz, CDCl₃) δ 7.92 (d, 1H, J=7.8 Hz), 7.33-7.40 (m, 2H), 6.99-7.06 (m, 3H), 6.07 (m, 1H), 4.43 (q, 2H, J=3.0 Hz), 4.08 (t, 2H, J=4.8 Hz), 2.72 (q, 2H, J=5.7 Hz); IR (neat) 2923, 2220, 1685, 1594, 1509, 1455, 1344, 1318, 1233, 1186, 1147, 1089, 965, 818 cm⁻¹; MS (FAB) m/z 348 (M+H)

A-40: 4-dimethylamino-4-phenyl-6'-trifluoromethyl-3,4,5,6-tetrahydro-2H-[1,2']bipyridinyl-3'-carbonitrile

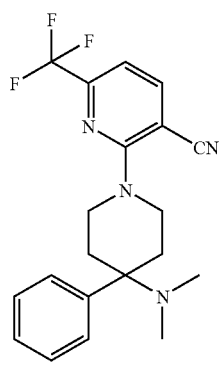 [SMILES: CN(C)C1(c2ccccc2)CCN(c2nc(C(F)(F)F)ccc2C#N)CC1]

$^1$H NMR (300 MHz, CDCl$_3$) δ 7.81 (d, 1H, J=8.1 Hz), 7.32-7.37 (m, 2H), 7.20-7.25 (m, 3H), 6.89 (d, 1H, J=8.1 Hz), 4.05 (m, 2H), 3.61 (m, 2H), 2.25 (m, 4H), 2.02 (s, 6H); IR (neat) 2945, 2867, 2784, 2217, 1590, 1497, 1452, 1321, 1240, 1146, 1082, 954, 913, 823, 736 cm$^{-1}$; MS (FAB) m/z 284 (M+H)

A-41: 2-(4-methyl-piperidin-1-yl)-4-trifluoromethyl-benzonitrile

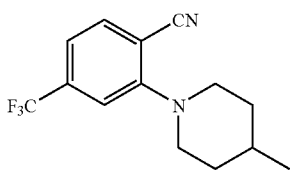

IR (neat) 2924, 2223, 1500, 1433, 1319, 1175, 1134, 1080, 1134, 829 cm$^{-1}$; MS (FAB) m/z 269 (M+H)

A-42: 2-butylamino-6-trifluoromethyl-nicotinonitrile

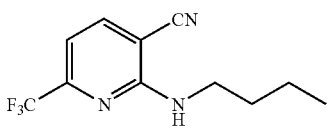 [SMILES: CCCCNc1nc(C(F)(F)F)ccc1C#N]

IR (neat) 3359, 2961, 2228, 1602, 1536, 1351, 1277, 1200, 1131, 821 cm$^{-1}$;
MS (FAB) m/z 244 (M+H)

A-43: 2,2-dimethyl-propionic acid-3'-cyano-6'-trifluoromethyl-3,4,5,6-tetrahydro-2H-[1,2']bipyridinyl-4-yl ester

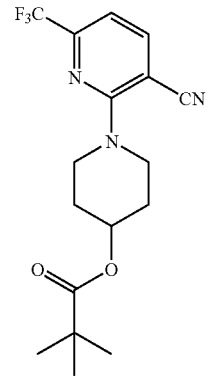 [SMILES: CC(C)(C)C(=O)OC1CCN(c2nc(C(F)(F)F)ccc2C#N)CC1]

$^1$H NMR (CDCl$_3$) δ 7.92 (dd, 1H, J=7.9, 0.8 Hz), 7.04 (d, 1H, J=7.7 Hz), 5.09-5.04 (m, 1H), 3.99-3.76 (m, 4H), 2.06-1.80 (m, 4H), 1.22 (s, 9H); IR (neat) 2969, 2232, 1727, 1592, 1459, 1325, 1156, 1029 cm$^{-1}$

A-44: acetic acid 3'-cyano-6'-trifluoromethyl-3,4,5,6-tetrahydro-2H-[1,2']bipyridinyl-4-yl ester

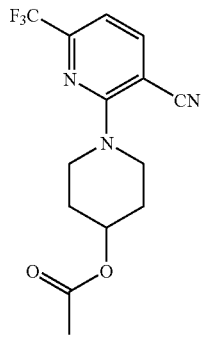 [SMILES: CC(=O)OC1CCN(c2nc(C(F)(F)F)ccc2C#N)CC1]

$^1$H NMR (CDCl$_3$) δ 7.92 (dd, 1H, J=7.9, 0.3 Hz), 7.05 (d, 1H, J=7.9 Hz), 5.06 (m, 1H), 4.11-4.03 (m, 2H), 3.70-3.62 (m, 2H), 2.10-2.00 (m, 2H), 2.09 (s, 3H), 1.87-1.76 (m, 2H); IR (neat) 2959, 2220, 1736, 1591, 1459, 1243, 1146, 1029 cm$^{-1}$

A-45: 4-methoxy-6'-trifluoromethyl-3,4,5,6-tetrahydro-2H-[1,2']bipyridinyl-3'-carbonitrile

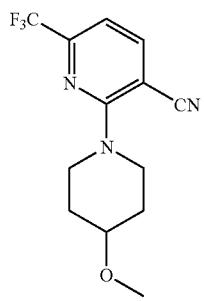 [SMILES: COC1CCN(c2nc(C(F)(F)F)ccc2C#N)CC1]

¹H NMR (CDCl₃) δ 7.90 (d, 1H, J=7.9 Hz), 7.00 (d, 1H, J=7.7 Hz), 4.12-4.05 (m, 2H), 3.65-3.49 (m, 3H), 3.39 (s, 3H), 2.04-1.97 (m, 2H), 1.80-1.73 (m, 2H); IR (neat) 2934, 2219, 1591, 1498, 1458, 1325, 1187, 1146 cm⁻¹

A-46: 4-butoxy-6'-trifluoromethyl-3,4,5,6-tetrahydro-2H-[1,2']bipyridinyl-3'-carbonitrile

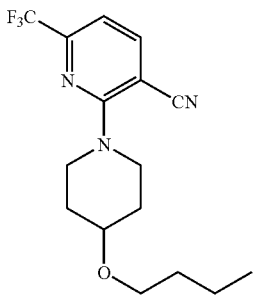 [SMILES: CCCCOC1CCN(c2nc(C(F)(F)F)ccc2C#N)CC1]

¹H NMR (CDCl₃) δ 7.89 (dd, 1H, J=7.7, 0.7 Hz), 6.99 (d, 1H, J=7.7 Hz), 4.13-4.05 (m, 2H), 3.64-3.55 (m, 3H), 3.48 (t, 2H, J=6.4 Hz), 2.02-1.93 (m, 2H), 1.79-1.68 (m, 2H), 1.62-1.53 (m, 2H), 1.45-1.33 (m, 2H), 0.93 (t, 3H, J=7.5 Hz); IR (neat) 2956, 2219, 1592, 1499, 1458, 1324, 1187, 1147, 959 cm⁻¹

A-47: 4-isopropoxy-6'-trifluoromethyl-3,4,5,6-tetrahydro-2H-[1,2']bipyridinyl-3'-carbonitrile

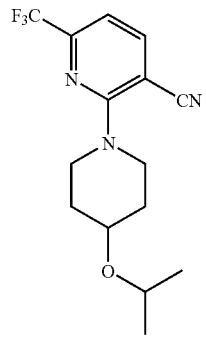 [SMILES: CC(C)OC1CCN(c2nc(C(F)(F)F)ccc2C#N)CC1]

¹H NMR (CDCl₃) δ 7.89 (dd, 1H, J=7.7, 0.7 Hz), 6.99 (d, 1H, J=7.9 Hz), 4.18-4.10 (m, 2H), 3.81-3.64 (m, 2H), 3.60-3.52 (m, 2H), 2.00-1.91 (m, 2H), 1.76-1.65 (m, 2H), 1.18 (d, 6H, J=6.1 Hz); IR (neat) 2971, 2220, 1592, 1499, 1458, 1324, 1236, 1185, 1147, 1039 cm⁻¹

A-48: 4-ethoxy-6'-trifluoromethyl-3,4,5,6-tetrahydro-2H-[1,2']bipyridinyl-3'-carbonitrile

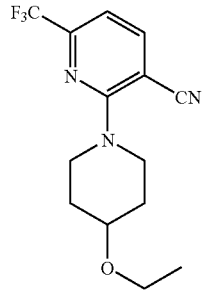 [SMILES: CCOC1CCN(c2nc(C(F)(F)F)ccc2C#N)CC1]

¹H NMR (CDCl₃) δ 7.89 (dd, 1H, J=7.9, 0.7 Hz), 6.99 (d, 1H, J=7.7 Hz), 4.18-4.10 (m, 2H), 3.64-3.51 (m, 5H), 2.04-1.95 (m, 2H), 1.79-1.68 (m, 2H), 1.23 (t, 3H, J=7.1 Hz); IR (neat) 2931, 2219, 1592, 1497, 1458, 1326, 1186, 1146, 1078 cm⁻¹

A-49: 4-methylene-6'-trifluoromethyl-3,4,5,6-tetrahydro-2H-[1,2']bipyridinyl-3'-carbonitrile

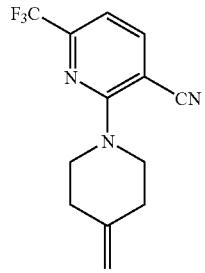 [SMILES: C=C1CCN(c2nc(C(F)(F)F)ccc2C#N)CC1]

¹H NMR (CDCl₃) δ 7.91 (d, 1H, J=7.9 Hz), 7.01 (d, 1H, J=7.9 Hz), 4.83 (s, 2H), 3.85 (t, 4H, J=5.7 Hz), 2.39 (t, 4H, J=5.9 Hz); IR (neat) 2946, 2220, 1591, 1495, 1458, 1333, 1238, 1191, 1147, 1088 cm⁻¹

A-50: 2-(6-aza-spiro[2.5]oct-6-yl)-6-trifluoromethyl-nicotinonitrile

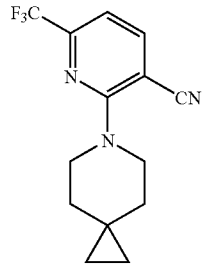 [SMILES: N#Cc1ccc(C(F)(F)F)nc1N1CCC2(CC1)CC2]

¹H NMR (CDCl₃) δ 7.88 (d, 1H, J=7.7 Hz), 6.97 (d, 1H, J=7.7 Hz), 3.87 (m, 4H), 1.53 (m, 4H), 0.40 (s, 4H); IR (neat) 2925, 2219, 1591, 1496, 1457, 1332, 1237, 1189, 1147, 960 cm⁻¹

A-51: 3-methyl-6'-trifluoromethyl-3,4,5,6-tetrahydro-2H-[1,2']bipyridinyl-3'-carbonitrile

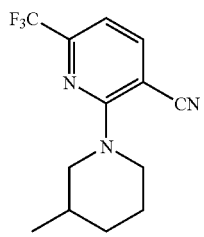 [SMILES: CC1CCCN(c2nc(C(F)(F)F)ccc2C#N)C1]

$^1$H NMR (CDCl$_3$) δ 7.87 (d, 1H, J=7.7 Hz), 6.95 (d, 1H, J=7.9 Hz), 4.47-4.36 (m, 2H), 3.09-3.00 (m, 1H), 2.79-2.71 (m, 1H), 1.92-1.60 (m, 4H), 1.27-1.14 (m, 1H), 0.97 (d, 3H, J=6.6 Hz); IR (neat) 2930, 2219, 1592, 1565, 1499, 1457, 1320, 1240, 1187, 1147 cm$^{-1}$ A-52: 2-methyl-6'-trifluoromethyl-3,4,5,6-tetrahydro-2H-[1,2']bipyridinyl-3'-carbonitrile

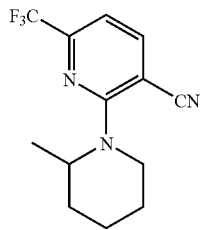 [SMILES: CC1CCCCN1c1nc(C(F)(F)F)ccc1C#N]

$^1$H NMR (CDCl$_3$) δ 7.87 (d, 1H, J=7.7 Hz), 6.93 (d, 1H, J=7.9 Hz), 4.85 (m, 1H), 4.34 (m, 1H), 3.23 (m, 1H), 1.80-1.55 (m, 6H), 1.33 (d, 3H, J=6.8 Hz);
IR (neat) 2941, 2218, 1592, 1485, 1343, 1189, 1147, 1074 cm$^{-1}$ A-53: 4-[(3-cyano-6-trifluoromethyl-pyridin-2-ylamino)-methyl]-piperidine-1-carbonic acid tert-butyl ester

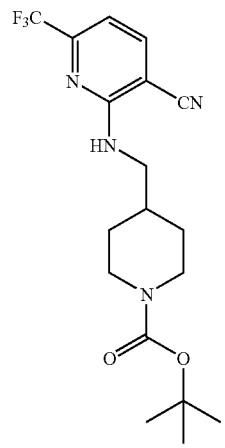 [SMILES: CC(C)(C)OC(=O)N1CCC(CNc2nc(C(F)(F)F)ccc2C#N)CC1]

$^1$H NMR (CDCl$_3$) δ 7.80 (d, 1H, J=7.7 Hz), 6.95 (d, 1H, J=7.7 Hz), 5.45 (m, 1H), 4.11 (m, 2H), 3.48 (m, 2H), 2.70 (m, 2H), 1.80-1.65 (m, 3H), 1.46 (s, 9H), 1.25-1.13 (m, 2H); IR (neat) 3369, 2926, 2223, 1685, 1599, 1533, 1424, 1281, 1178, 1146 cm$^{-1}$ A-54: 4-oxo-6'-trifluoromethyl-3,4,5,6-tetrahydro-2H-[1,2']bipyridinyl-3'-carbonitrile

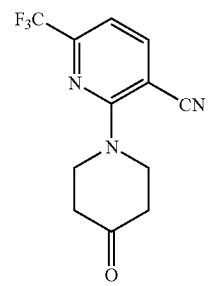

$^1$H NMR (CDCl$_3$) δ 8.00 (d, 1H, J=7.9 Hz), 7.15 d, 1H, J=7.9 Hz), 4.13 (t, 4H, J=6.0 Hz), 2.66 (t, 4H, J=6.2 Hz); IR (neat) 2976, 2221, 1713, 1567, 1460, 1338, 1236, 1187, 1143, 1099 cm$^{-1}$ A-55: 6"-trifluoromethyl-3,4,5,6,3',4',5',6'-octahydro-2H, 2'H-[1,4';1',2"]terpyridine-3"-carbonitrile

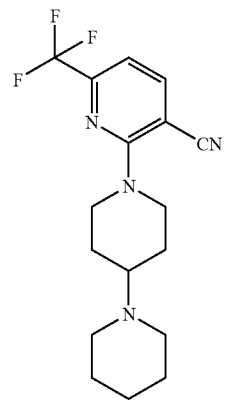 [SMILES: N#Cc1ccc(C(F)(F)F)nc1N1CCC(N2CCCCC2)CC1]

$^1$H NMR (300 MHz, CDCl$_3$) δ 7.88 (d, 1H, J=7.7 Hz), 6.98 (d, 1H, J=7.89 Hz), 4.61 (d, 2H, J=13 Hz), 3.08 (dd, 2H, J=13.4, 13.4 Hz), 2.58-2.51 (m, 5H, J=4.8 Hz), 1.97 (d, 2H, J=12.1 Hz), 1.72-1.56 (m, 6H), 1.45 (d, 2H, J=5.3 Hz); IR (neat) 2854, 2218, 1336, 1240, 958, 822 cm$^{-1}$; MS (FAB) m/z 339 (M+H)

A-56: 4-pyrrolidin-1-yl-6'-trifluoromethyl-3,4,5,6-tetrahydro-2H-[1,2']bipyridinyl-3'-carbonitrile

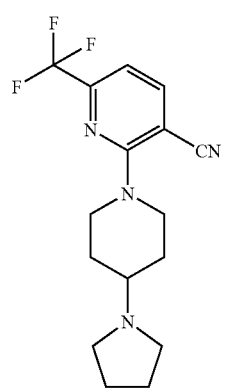 [SMILES: N#Cc1ccc(C(F)(F)F)nc1N1CCC(N2CCCC2)CC1]

$^1$H NMR (300 MHz, CDCl$_3$) δ 7.88 (d, 1H, J=7.9 Hz), 6.98 (d, 1H, J=7.9 Hz), 4.51 (d, 2H, J=13.0 Hz), 3.23-3.13 (m, 2H), 2.60 (s, 4H), 2.33-2.25 (m, 1H), 2.05-2.01 (m, 2H), 1.83-1.78 (m, 4H), 1.71-1.59 (m, 2H); IR (neat) 2959, 2219, 1238, 1083, 960, 824, 743 cm$^{-1}$; MS (FAB) m/z 325 (M+H)

A-57: 4-morpholin-4-yl-6'-trifluoromethyl-3,4,5,6-tetrahydro-2H-[1,2']bipyridinyl-3'-carbonitrile

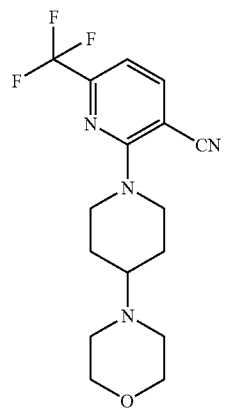 [SMILES: N#Cc1ccc(C(F)(F)F)nc1N1CCC(N2CCOCC2)CC1]

$^1$H NMR (300 MHz, CDCl$_3$) δ 7.91 (d, 1H, J=7.9 Hz), 7.01 (d, 1H, J=7.7 Hz), 4.58 (d, 2H, J=13.2 Hz), 3.75-3.70 (m, 5H), 3.15-3.06 (m, 2H), 2.61-2.45 (m, 4H), 2.01 (d, 2H, J=11.5 Hz), 1.69-1.56 (m, 2H); IR (neat) 2956, 2855, 2218, 1236, 1027, 958, 876 cm$^{-1}$; MS (FAB) m/z 341 (M+H)

A-58: 4-ethyl-6'-trifluoromethyl-3,4,5,6-tetrahydro-2H-[1,2']bipyridinyl-3'-carbonitrile

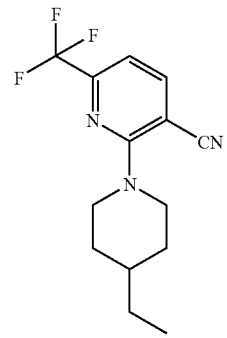 [SMILES: CCC1CCN(c2nc(C(F)(F)F)ccc2C#N)CC1]

$^1$H NMR (400 MHz, CDCl$_3$) δ 7.85 (d, 1H, J=7.6 Hz), 6.93 (d, 1H, J=7.6 Hz), 4.53 (d, 2H, J=13.2 Hz), 3.02 (dd, 2H, J=13.2, 13.2 Hz), 1.82 (d, 2H, J=12.4 Hz), 1.45-1.42 (m, 1H), 1.33-1.28 (m, 4H), 0.90 (t, 3H, J=7.2 Hz); IR (neat)) 2854, 2218, 1008, 911, 841, 744 cm$^{-1}$; MS (FAB) m/z 284 (M+H)

A-59: 4-benzyl-6'-trifluoromethyl-3,4,5,6-tetrahydro-2H-[1,2']bipyridinyl-3'-carbonitrile

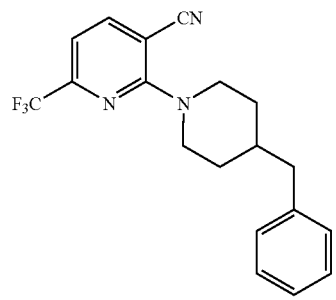 [SMILES: N#Cc1ccc(C(F)(F)F)nc1N1CCC(Cc2ccccc2)CC1]

$^1$H NMR (300 MHz, CDCl$_3$) δ 7.87 (d, 1H, J=7.9 Hz), 7.35-7.22 (m, 5H), 6.96 (d, 1H, J=7.7 Hz), 4.54 (m, 2H), 3.00 (td, 2H, J=6.7, 2.4 Hz), 2.59 (d, 2H, J=6.8 Hz), 1.88-1.83 (m, 3H), 1.39 (m, 2H); IR (neat) 2921, 2230, 1590, 1498, 1455, 1320, 1240, 1145, 958, 745, 701 cm$^{-1}$; MS (FAB) m/z 346 (M+H)

A-60: 2-(3,4-dimethyl-phenylamino)-6-trifluoromethyl-nicotinonitrile

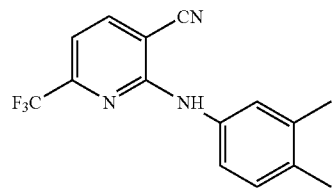 [SMILES: Cc1ccc(Nc2nc(C(F)(F)F)ccc2C#N)cc1C]

$^1$H NMR (300 MHz, CDCl$_3$), δ 7.92 (d, 1H, J=7.9 Hz), 7.43 (dd, 1H, J=8.1, 2.3 Hz), 7.38 (d, 1H, J=2.2 Hz), 7.14 (d, 1H, J=8.1 Hz), 7.10 (d, 1H, J=7.7 Hz), 2.28 (s, 3H), 2.26 (s, 3H);

IR (neat) 3315, 2922, 2228, 1595, 1532, 1453, 1428, 1350, 1271, 1199, 1141, 968, 820 cm$^{-1}$; MS (FAB) m/z 292 (M+H)

A-61: 2-(5-chloro-2-methyl-phenylamino)-6-trifluoromethyl-nicotinonitrile

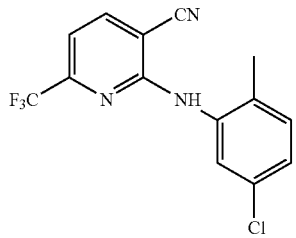 [SMILES: Cc1ccc(Cl)cc1Nc1nc(C(F)(F)F)ccc1C#N]

$^1$H NMR (300 MHz, CDCl$_3$) δ 8.12 (d, 1H, J=2.2 Hz), 7.98 (d, 1H, J=7.9 Hz), 7.18 (d, 2H, J=7.9 H), 7.10 (dd, 1H, J=8.1, 2.2 Hz), 2.32 (s, 3H); IR (neat) 3424, 2231, 1589, 1536, 1452, 1349, 1273, 1189, 1136, 960, 899, 837, 802 cm$^{-1}$; MS (FAB) m/z 312 (M+H)

A-62: 2-(4-chloro-benzylamino)-6-trifluoromethyl-nicotinonitrile

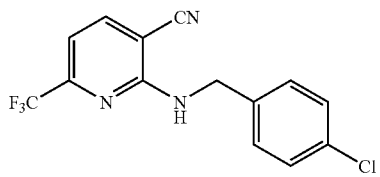 [SMILES: N#Cc1ccc(C(F)(F)F)nc1NCc1ccc(Cl)cc1]

$^1$H NMR (300 MHz, CDCl$_3$) δ 7.88 (d, 1H, J=7.7 Hz), 7.33 (s, 4H), 6.99 (d, 1H, J=7.8 Hz), 5.72 (bs, 1H), 4.69 (d, 2H, J=5.7 Hz); IR (neat) 3372, 2221, 1598, 1531, 1404, 1349, 1278, 1136, 907, 823, 793 cm$^{-1}$; MS (FAB) m/z 312 (M+H)

A-63: 2-(4-fluoro-phenylamino)-6-trifluoromethyl-nicotinonitrile

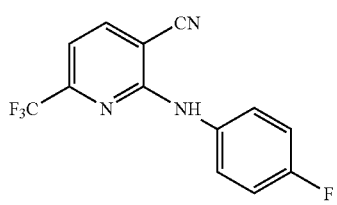 [SMILES: N#Cc1ccc(C(F)(F)F)nc1Nc1ccc(F)cc1]

$^1$H NMR (300 MHz, CDCl$_3$) δ 7.96 (d, 1H, J=7.9 Hz), 7.65-7.57 (m, 2H), 7.16-7.08 (m, 3H); IR (neat) 3362, 2226, 1619, 1592, 1546, 1508, 1463, 1435, 1350, 1271, 1194, 1142, 961, 831 cm$^{-1}$; MS (FAB) m/z 282 (M+H)

A-64: 2-(4-chloro-phenylamino)-6-trifluoromethyl-nicotinonitrile

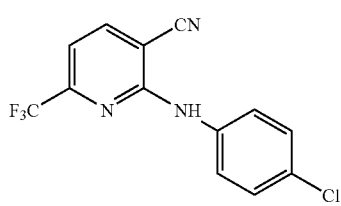 [SMILES: N#Cc1ccc(C(F)(F)F)nc1Nc1ccc(Cl)cc1]

$^1$H NMR (300 MHz, CD$_3$OD) δ 7.98 (d, 1H, J=7.9 Hz), 7.61 (d, 2H, J=9.0 Hz), 7.35 (d, 2H, J=8.8 Hz), 7.18 (d, 1H, J=7.9 Hz); IR (neat) 2230, 1614, 1538, 1490, 1435, 1312, 1262, 1173, 1138, 827, 696 cm$^{-1}$; MS (FAB) m/z 298 (M+H)

A-65: 2-phenylamino-6-trifluoromethyl-nicotinonitrile

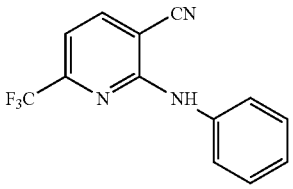 [SMILES: N#Cc1ccc(C(F)(F)F)nc1Nc1ccccc1]

$^1$H NMR (300 MHz, CD$_3$OD) δ 7.96 (d, 1H, J=7.7 Hz), 7.66 (d, 2H, J=8.8 Hz), 7.40 (t, 2H, J=7.5 Hz), 7.16 (m, 2H); IR (neat) 3341, 2230, 1611, 1539, 1496, 1446, 1413, 1350, 1271, 1195, 1139, 959, 828, 752, 691 cm$^{-1}$; MS (FAB) m/z 264 (M+H)

A-66: 2-azepan-1-yl-4-trifluoromethyl-benzonitrile

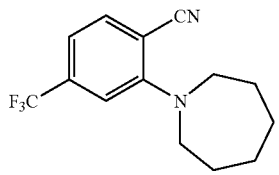 [SMILES: N#Cc1ccc(C(F)(F)F)cc1N1CCCCCC1]

$^1$H NMR (300 MHz, CDCl$_3$) δ 7.56 (d, 1H, J=8.1 Hz), 7.03 (s, 1H), 6.90 (d, 1H, J=8.1 Hz), 3.74-3.63 (m, 4H), 1.98-1.83 (m, 4H), 1.69-1.51 (m, 4H); IR (neat) 2931, 2213, 1616, 1560, 1503, 1444, 1316, 1171, 1131, 1081, 1001, 939, 859, 810 cm$^{-1}$;

MS (FAB) m/z 269 (M+H)

A-67: 2-(4-pyridin-4-yl-piperazin-1-yl)-6-trifluoromethyl-nicotinonitrile

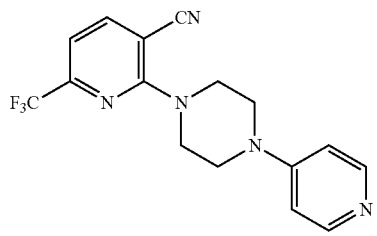 [SMILES: N#Cc1ccc(C(F)(F)F)nc1N1CCN(c2ccncc2)CC1]

¹H NMR (300 MHz, CDCl₃) δ 8.33 (d, 2H, J=6.4 Hz), 7.98 (d, 1H, J=7.9 Hz), 7.12 (d, 1H, J=7.9 Hz), 6.69 (d, 2H, J=6.6 Hz), 4.08-4.36 (m, 4H), 3.58-3.45 (m, 4H); IR (neat) 2917, 2230, 1592, 1481, 1445, 1390, 1321, 1236, 1139, 867, 804, 740 cm⁻¹;

MS (FAB) m/z 334 (M+H)

A-68: 2-[4-(4-fluoro-phenyl)-piperazin-1-yl]-6-trifluoromethyl-nicotinonitrile

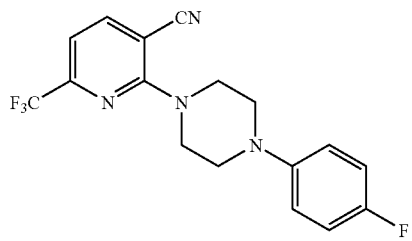 [SMILES: N#Cc1ccc(C(F)(F)F)nc1N1CCN(c2ccc(F)cc2)CC1]

¹H NMR (300 MHz, CDCl₃) δ 7.85 (d, 1H, J=7.7 Hz), 7.08 (d, 1H, J=7.7 Hz), 7.12-6.93 (m, 4H), 4.14-4.00 (m, 4H), 3.32-3.21 (m, 4H); IR (neat) 2828, 2219, 1590, 1509, 1449, 1319, 1234, 1185, 1147, 1086, 970, 824, 743, 704 cm⁻¹; MS (FAB) m/z 351 (M+H)

A-69: 2-[4-(2-fluoro-phenyl)-piperazin-1-yl]-6-trifluoromethyl-nicotinonitrile

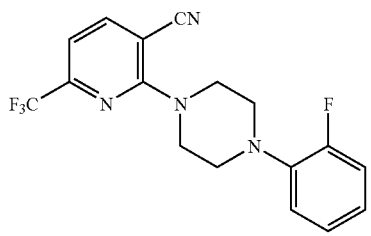 [SMILES: N#Cc1ccc(C(F)(F)F)nc1N1CCN(c2ccccc2F)CC1]

¹H NMR (300 MHz, CDCl₃) δ 7.95 (d, 1H, J=7.9 Hz), 7.07 (d, 1H, J=7.9 Hz), 7.06-6.96 (m, 4H), 4.12-4.01 (m, 4H), 3.34-3.22 (m, 4H); IR (neat) 2851, 2219, 1590, 1501, 1448, 1380, 1344, 1319, 1238, 1185, 1146, 1086, 970, 820, 754 cm⁻¹; MS (FAB) m/z 351 (M+H)

A-70: 2-(4-phenyl-piperazin-1-yl)-6-trifluoromethyl-nicotinonitrile

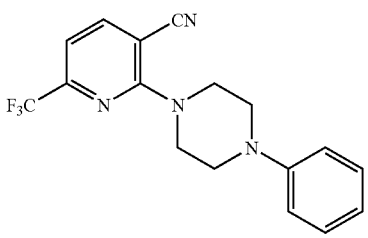 [SMILES: N#Cc1ccc(C(F)(F)F)nc1N1CCN(c2ccccc2)CC1]

¹H NMR (300 MHz, CDCl₃) δ 7.94 (d, 1H, J=7.7 Hz), 7.35-7.28 (m, 2H), 7.06 (d, 1H, J=7.9 Hz), 6.99-6.87 (m, 3H), 4.06-3.98 (m, 4H), 3.42-3.37 (m, 4H); IR (neat) 2850, 2219, 1591, 1496, 1448, 132, 1233, 1185, 1146, 1086, 970, 825, 759, 694 cm⁻¹; MS (FAB) m/z 333 (M+H)

A-71: 2-(methyl-phenyl-amino)-6-trifluoromethyl-nicotinonitrile

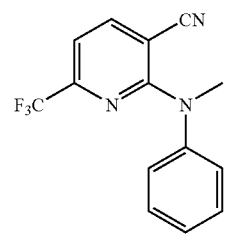 [SMILES: CN(c1ccccc1)c1nc(C(F)(F)F)ccc1C#N]

¹H NMR (300 MHz, CDCl₃) δ 7.79 (d, 1H, J=7.7 Hz), 7.47 (m, 2H), 7.29 (m, 2H), 7.03 (d, 1H, J=7.8 Hz), 6.78 (m, 1H), 3.54 (s, 3H); IR (neat) 2920, 2230, 1587, 1495, 1402, 1345, 1315, 1251, 1193, 1145, 942, 826, 745, 698 cm⁻¹; MS (FAB) m/z 278 (M+H)

A-72: 4,4-dimethyl-6'-trifluoromethyl-3,4,5,6-tetrahydro-2H-[1,2']bipyridinyl-3'-carbonitrile

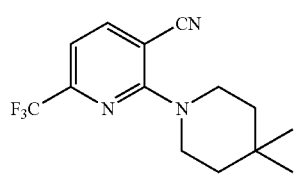 [SMILES: CC1(C)CCN(c2nc(C(F)(F)F)ccc2C#N)CC1]

¹H NMR (300 MHz, CDCl₃) δ 7.87 (d, 1H, J=7.9 Hz), 6.96 (d, 1H, J=7.9 Hz), 3.87-3.73 (m, 4H), 1.61-1.46 (m, 4H), 1.03

(s, 6H); IR (neat) 2924, 2218, 1591, 1566, 1498, 1463, 1346, 1320, 1241, 1182, 1147, 1082, 956, 823, 744 cm$^{-1}$; MS (FAB) m/z 284 (M+H)

A-73: 2-(4-p-tolyl-piperazin-1-yl)-4-trifluoromethyl-benzonitrile

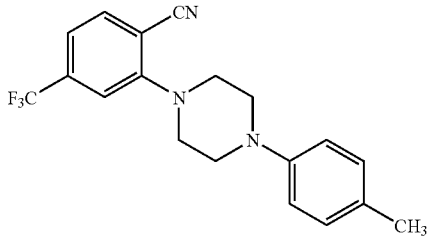 [SMILES: Cc1ccc(N2CCN(c3cc(C(F)(F)F)ccc3C#N)CC2)cc1]

$^1$H NMR (300 MHz, CDCl$_3$) δ 7.71 (d, 1H, J=8.1 Hz), 7.26 (d, 1H, J=7.9 Hz), 7.25 (s, 1H), 7.11 (d, 2H, J=8.4 Hz), 6.91 (d, 2H, J=8.6 Hz), 3.52-3.41 (m, 4H), 3.43-3.37 (m, 4H), 2.29 (s, 3H); IR (neat) 2838, 2227, 1615, 1517, 1432, 1308, 1240, 1178, 1121, 1079, 963, 809 cm$^{-1}$; MS (FAB) m/z 346 (M+H)

A-74: 2-(4-m-tolyl-piperazin-1-yl)-4-trifluoromethyl-benzonitrile

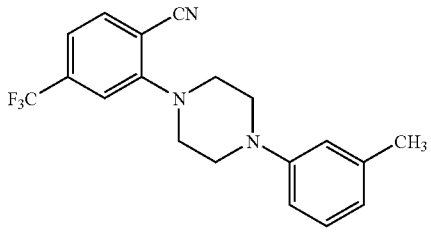 [SMILES: Cc1cccc(N2CCN(c3cc(C(F)(F)F)ccc3C#N)CC2)c1]

$^1$H NMR (300 MHz, CDCl$_3$) δ 7.71 (d, 1H, J=8.4 Hz), 7.26 (d, 1H, J=7.7 Hz), 7.24 (s, 1H), 7.19 (t, 1H, J=7.9 Hz), 6.81 (s, 1H), 6.80 (d, 1H, J=7.1 Hz), 6.74 (d, 1H, J=7.7 Hz), 3.49-3.31 (m, 8H), 2.34 (s, 3H); IR (neat) 2837, 2231, 1605, 1497, 1432, 1311, 1252, 1174, 1133, 1078, 964, 829, 777 cm$^{-1}$; MS (FAB) m/z 346 (M+H)

A-75: 4-trifluoromethyl-2-[4-(4-trifluoromethyl-phenyl)-piperazin-1-yl]-benzonitrile

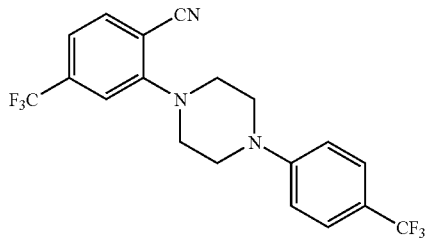 [SMILES: N#Cc1ccc(C(F)(F)F)cc1N1CCN(c2ccc(C(F)(F)F)cc2)CC1]

$^1$H NMR (300 MHz, CDCl$_3$) δ 7.72 (d, 1H, J=7.9 Hz), 7.53 (d, 2H, J=8.8 Hz), 7.29 (d, 1H, J=8.0 Hz), 7.25 (s, 1H), 6.99 (d, 2H, J=8.6 Hz), 3.57-3.41 (m, 8H); IR (neat) 2842, 2225, 1615, 1527, 1501, 1432, 1388, 1332, 1235, 1116, 1073, 962, 827, 735 cm$^{-1}$; MS (FAB) m/z 400 (M+H)

A-76: 2-[4-(4-methoxy-phenyl)-piperazin-1-yl]-4-trifluoromethyl-benzonitrile

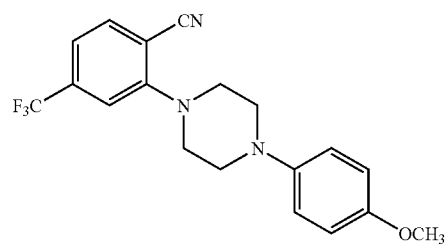 [SMILES: COc1ccc(N2CCN(c3cc(C(F)(F)F)ccc3C#N)CC2)cc1]

$^1$H NMR (300 MHz, CDCl$_3$) δ 7.63 (d, 1H, J=7.9 Hz), 7.19 (d, 1H, J=7.6 Hz), 7.18 (s, 1H), 6.93-6.82 (m, 4H), 3.72 (s, 3H), 3.43-3.35 (m, 4H), 3.28-3.21 (m, 4H); IR (neat) 2962, 2837, 2228, 1515, 1432, 1306, 1261, 1176, 1117, 1036, 962, 821 cm$^{-1}$;

MS (FAB) m/z 362 (M+H)

A-77: 2-[4-(4-fluoro-phenyl)-3,6-dihydro-2H-pyridin-1-yl]-4-trifluoromethyl-benzonitrile

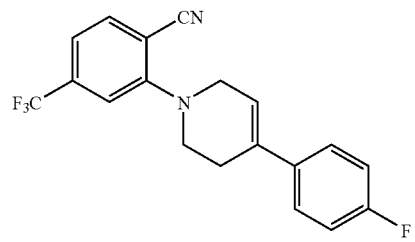 [SMILES: N#Cc1ccc(C(F)(F)F)cc1N1CC=C(c2ccc(F)cc2)CC1]

$^1$H NMR (300 MHz, CDCl$_3$) δ 7.68 (d, 1H, J=8.0 Hz), 7.40 (m, 2H), 7.22 (s, 1H), 7.18 (d, 1H, J=8.0 Hz), 7.05 (m, 2H), 6.11 (m, 1H), 3.98 (bq, 2H, J=3.1 Hz), 3.71 (t, 2H, J=5.5 Hz), 2.79 (m, 2H); IR (neat) 2919, 1683, 1601, 1509, 1440, 1332, 1229, 1173, 1134, 838 cm$^{-1}$; MS (FAB) m/z 347 (M+H)

A-78: 2-(butyl-methyl-amino)-6-trifluoromethyl-nicotinonitrile

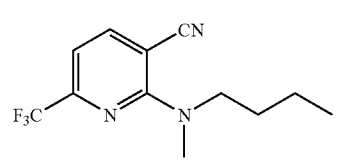 [SMILES: CCCCN(C)c1nc(C(F)(F)F)ccc1C#N]

$^1$H NMR (300 MHz, CDCl$_3$) δ 7.86 (d, 1H, J=7.9 Hz), 6.89 (d, 1H, J=7.7 Hz), 3.72 (t, 2H, J=7.7 Hz), 3.33 (s, 3H), 1.60-1.75 (m, 2H), 1.30-1.46 (m, 2H), 0.96 (t, 3H, J=7.4 Hz);

IR (neat) 2962, 2230, 1594, 1517, 1417, 1328, 1239, 1186, 1147, 818 cm$^{-1}$; MS (FAB) m/z 258 (M+H)

A-79: 2-(4-phenyl-piperazin-1-yl)-4-trifluoromethyl-benzonitrile

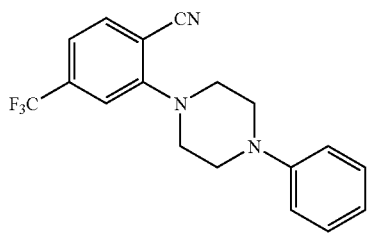 [SMILES: N#Cc1ccc(C(F)(F)F)cc1N1CCN(c2ccccc2)CC1]

$^1$H NMR (300 MHz, CDCl$_3$) δ 7.70 (d, 1H, J=8.2 Hz), 7.23-7.33 (m, 4H), 6.87-7.02 (m, 3H), 3.35-3.50 (m, 8H); IR (KBr) 2834, 2224, 1600, 1499, 1432, 1311, 1229, 1174, 1132, 1078, 962, 878, 828, 760 cm$^{-1}$; MS (FAB) m/z 332 (M+H)

A-80: 2-azocan-1-yl-4-trifluoromethyl-benzonitrile

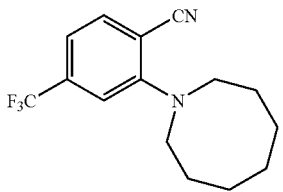 [SMILES: N#Cc1ccc(C(F)(F)F)cc1N1CCCCCCC1]

$^1$H NMR (300 MHz, CDCl$_3$) δ 7.56 (d, 1H, J=8.1 Hz), 7.00 (s, 1H), 6.86 (dd, 1H, J=8.2, 1.3 Hz), 3.71-3.79 (m, 4H), 1.79-1.91 (m, 4H), 1.50-1.69 (m, 6H); IR (neat) 2926, 2223, 2210, 1617, 1558, 1505, 1446, 1317, 1171, 1131, 1078, 989, 808 cm$^{-1}$; MS (FAB) m/z 283 (M+H)

A-81: 2-(4,4-dimethyl-piperidin-1-yl)-4-trifluoromethyl-benzonitrile

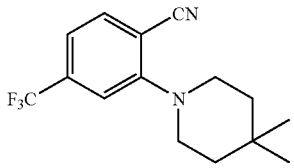

$^1$H NMR (300 MHz, CDCl$_3$) δ 7.64 (d, 1H, J=7.9 Hz), 7.21 (s, 1H), 7.16 (d, 1H, J=7.9 Hz), 3.22-3.29 (m, 4H), 1.55-1.64 (m, 4H), 1.03 (s, 6H); IR (neat) 2954, 2223, 1612, 1567, 1500, 1431, 1347, 1311, 1239, 1173, 1134, 1078, 952, 874, 825 cm$^{-1}$;
MS (FAB) m/z 283 (M+H)

A-82: 2-(4-ethyl-piperidin-1-yl)-4-trifluoromethyl-benzonitrile

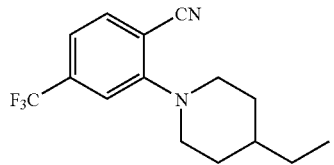 [SMILES: CCC1CCN(c2cc(C(F)(F)F)ccc2C#N)CC1]

$^1$H NMR (300 MHz, CDCl$_3$) δ 7.64 (d, 1H, J=7.9 Hz), 7.13-7.21 (m, 2H), 3.62-3.73 (m, 2H), 2.79-2.92 (m, 2H), 1.81-1.90 (m, 2H), 1.25-1.55 (m, 5H), 0.94 (t, 3H, J=7.0 Hz); IR (neat) 2930, 2224, 1612, 1567, 1500, 1433, 1312, 1247, 1216, 1174, 1133, 1078, 953, 877, 825 cm$^{-1}$; MS (FAB) m/z 283 (M+H)

A-83: 2-dipropylamino-4-trifluoromethyl-benzonitrile

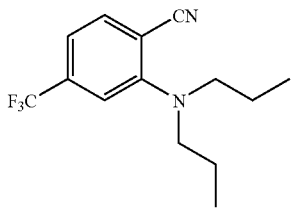 [SMILES: CCCN(CCC)c1cc(C(F)(F)F)ccc1C#N]

$^1$H NMR (300 MHz, CDCl$_3$) δ 7.58 (d, 1H, J=8.0 Hz), 7.04 (s, 1H), 6.97 (d, 1H, J=8.0 Hz), 3.35-3.42 (m, 4H), 1.58-1.72 (m, 4H), 0.89-0.97 (m, 6H) IR (neat) 2966, 2223, 1616, 1561, 1505, 1447, 1320, 1230, 1173, 1133, 1078, 992, 813 cm$^{-1}$; MS (FAB) m/z 271 (M+H)

A-84: 4-trifluoromethyl-2-(4-trifluoromethyl-piperidin-1-yl)-benzonitrile

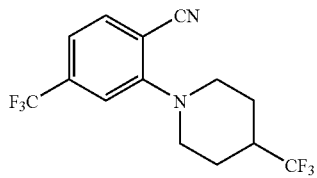

H NMR (300 MHz, CDCl$_3$) δ 7.69 (d, 1H, J=8.0 Hz), 7.18-7.29 (m, 2H), 3.69-3.79 (m, 2H), 2.83-2.93 (m, 2H), 2.22 (m, 1H), 1.99-2.10 (m, 2H), 1.81-1.99 (m, 2H); IR (neat) 2963, 2230, 1613, 1500, 1435, 1391, 1336, 1311, 1256, 1139, 1080, 955, 900, 830 cm$^{-1}$; MS (FAB) m/z 323 (M+H)

A-85: 2-(4-benzyl-piperidin-1-yl)-4-trifluoromethyl-benzonitrile

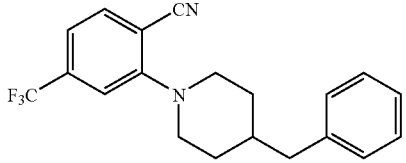 [SMILES: N#Cc1ccc(C(F)(F)F)cc1N1CCC(Cc2ccccc2)CC1]

¹H NMR (400 MHz, CDCl₃) δ 7.80 (dd, 1H, J=7.6, 7.6 Hz), 7.64 (d, 1H, J=8.4 Hz), 7.56 (d, 1H, J=8.4 Hz), 7.52 (d, 1H, J=8.4 Hz), 7.27-7.32 (m, 2H), 7.15-7.24 (m, 2H), 3.61-3.66 (m, 2H), 2.77-2.86 (m, 2H), 2.62 (d, 2H, J=7.2 Hz), 1.78-1.85 (m, 2 H), 1.72 (m, 1H), 1.49-1.60 (m, 2H); IR (neat) 2922, 2230, 1612, 1499, 1434, 1312, 1174, 1133, 1077, 953, 827, 746, 701 cm⁻¹; MS (FAB) m/z 345 (M+H)

A-86: 4-acetyl-4-phenyl-6'-trifluoromethyl-3,4,5,6-tetrahydro-2H-[1,2']bipyridinyl-3'-carbonitrile

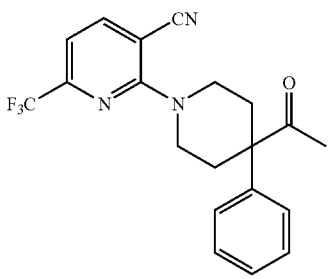 [SMILES: CC(=O)C1(c2ccccc2)CCN(c2nc(C(F)(F)F)ccc2C#N)CC1]

¹H NMR (300 MHz, CDCl₃) δ 7.90 (d, 1H, J=7.7 Hz), 7.25-7.44 (m, 5H), 7.01 (d, 1H, J=7.9 Hz), 4.10-4.25 (m, 2H), 3.51-3.63 (m, 2H), 2.50-2.62 (m, 2H), 2.13-2.27 (m, 2H), 1.97 (s, 3H); IR (neat) 2924, 2223, 1704, 1590, 1494, 1455, 1350, 1320, 1243, 1138, 959, 912, 743, 701 cm⁻¹; MS (FAB) m/z 374 (M+H)

A-87: 6-(chloro-difluoro-methyl)-2-(4-phenyl-piperazin-1-yl)-nicotinonitrile

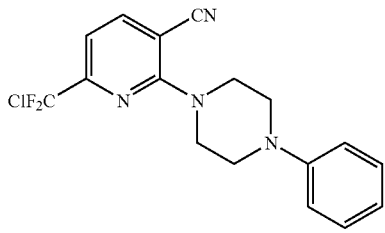

¹H NMR (300 MHz, CDCl₃) δ 7.94 (d, 1H, J=7.9 Hz), 7.24-7.34 (m, 2H), 7.04 (d, 1H, J=7.9 Hz), 6.87-7.00 (m, 3H), 4.00-4.06 (m, 4H), 3.32-3.39 (m, 4H); IR (neat) 2916, 2230, 2217, 1590, 1497, 1449, 1341, 1230, 1081, 986, 934, 812, 761, 693 cm⁻¹; MS (FAB) m/z 349 (M+H)

A-88: 2-dipropylamino-6-trifluoromethyl-nicotinonitrile

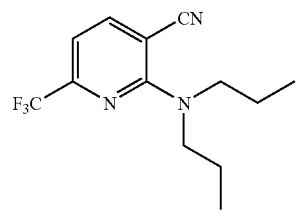 [SMILES: CCCN(CCC)c1nc(C(F)(F)F)ccc1C#N]

¹H NMR (300 MHz, CDCl₃) δ 7.74 (dd, 1H, J=7.8, 0.7 Hz), 6.75 (d, 1H, J=7.7 Hz), 3.53 (tt, 4H, J=7.7, 1.8 Hz), 1.70-1.66 (m, 4H), 0.86 (t, 4H, J=7.3 Hz); IR (neat) 2969, 2215, 1594, 1565, 1512, 1459, 1331 cm⁻¹; MS (FAB) m/z 272 (M+H)

A-89: 6'-tert-butyl-3,4,5,6-tetrahydro-2H-[1,2']bipyridinyl-3'-carbonitrile

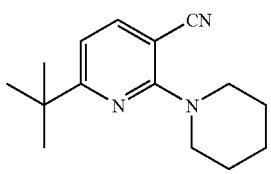 [SMILES: CC(C)(C)c1ccc(C#N)c(N2CCCCC2)n1]

¹H NMR (300 MHz, CDCl₃) δ 7.65 (d, 1H, J=7.9 Hz), 6.70 (d, 1H, J=7.9 Hz), 3.70-3.68 (bs, 4H), 1.65 (s, 6H), 1.30 (s, 9H); IR (neat) 2934, 2856, 2213, 1583, 1550, 1447, 1362 cm⁻¹; MS (FAB) m/z 244 (M+H)

A-90: 6-tert-butyl-2-pyrrolidin-1-yl-nicotinonitrile

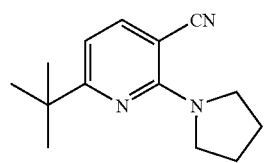 [SMILES: CC(C)(C)c1ccc(C#N)c(N2CCCC2)n1]

¹H NMR (300 MHz, CDCl₃) δ 7.61 (d, 1H, J=8.1 Hz), 6.59 (d, 1H, J=8.1 Hz), 3.80 (m, 4H), 2.00 (m, 4H), 1.28 (s, 9H); IR (neat) 3409, 2964, 2785, 2210, 1583, 1552, 1456 cm⁻¹; MS (FAB) m/z 230 (M+H)

A-91: 6'-tert-butyl-4-methyl-3,4,5,6-tetrahydro-2H-[1,2']bipyridinyl-3'-carbonitrile

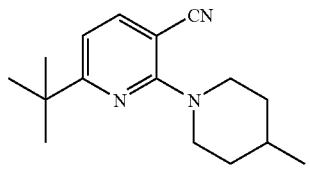 [SMILES: CC1CCN(c2nc(C(C)(C)C)ccc2C#N)CC1]

¹H NMR (300 MHz, CDCl₃) δ 7.57 (d, 1H, J=7.9 Hz), 6.63 (d, 1H, J=8 Hz), 4.37 (m, 2H), 2.90 (td, 2H, J=12.6, 2.4 Hz), 1.68-1.16 (m, 5H), 1.22 (s, 9H), 0.83 (d, 3H, J=7.5 Hz); IR (neat) 2956, 2869, 2213, 1582, 1550, 1452, 1367 cm$^{-1}$; MS (FAB) m/z 258 (M+H)

A-92: 6-tert-butyl-2-dipropylamino-nicotinonitrile

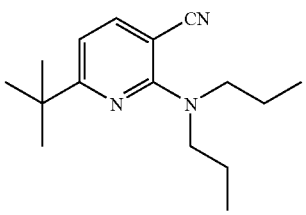 [SMILES: CCCN(CCC)c1nc(C(C)(C)C)ccc1C#N]

$^1$H NMR (300 MHz, CDCl$_3$) δ 7.61 (d, 1H, J=8.0 Hz), 6.59 (d, 1H, J=8.0 Hz), 3.58 (t, 4H, J=7.9 Hz), 1.68-1.64 (m, 4H), 1.28 (s, 9H), 0.95 (t, 6H, J=7.3 Hz); IR (neat) 2964, 2873, 2208, 1585, 1550, 1495, 1456 cm$^{-1}$; MS (FAB) m/z 320 (M+H)

A-93: 2-azepan-1-yl-6-tert-butyl-nicotinonitrile

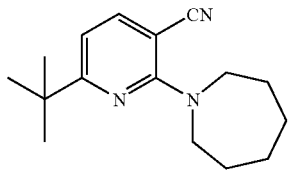 [SMILES: CC(C)(C)c1ccc(C#N)c(N2CCCCCC2)n1]

$^1$H NMR (300 MHz, CDCl$_3$) δ 7.60 (d, 1H, J=8.0 Hz), 6.60 (d, 1H, J=8.0 Hz), 3.90 (t, 4H, J=5.9 Hz), 1.89-1.85 (m, 4H), 1.59-1.43 (m, 4H), 1.28 (s, 9H); IR (neat) 2930, 2859, 2208, 1584, 1549, 1487, 1453 cm$^{-1}$; MS (FAB) m/z 258 (M+H)

A-94: 6'-tert-butyl-4-phenyl-3,4,5,6-tetrahydro-2H-[1,2']bipyridinyl-3'-carbonitrile

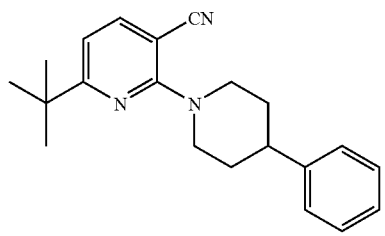 [SMILES: CC(C)(C)c1ccc(C#N)c(N2CCC(c3ccccc3)CC2)n1]

$^1$H NMR (300 MHz, CDCl$_3$) δ 7.69 (d, 1H, J=8.0 Hz), 7.38-7.19 (m, 5H), 6.76 (d, 1H, J=7.7 Hz), 4.60 (d, 2H, J=6.2 Hz), 3.10 (td, 2H, J=12.5, 2.8 Hz), 2.79 (m, 1H), 2.00-1.78 (m, 4H), 1.3 (s, 9H); IR (neat) 2959, 2213, 1583, 1550, 1452, 1368 1223 cm$^{-1}$, MS (FAB) m/z 320 (M+H)

A-95: 4-hydroxymethyl-6'-trifluoromethyl-3,4,5,6-tetrahydro-2H-[1,2']bipyridinyl-3'-carbonitrile

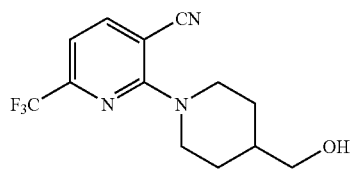 [SMILES: N#Cc1ccc(C(F)(F)F)nc1N1CCC(CO)CC1]

$^1$H NMR (300 MHz, CDCl$_3$) δ 7.89 (d, 1H, J=7.9 Hz), 6.99 (d, 1H, J=7.9 Hz), 4.58 (d, 1H, J=13.6 Hz), 3.57 (t, 2H, J=5.9 Hz), 3.01 (m, 2H), 1.92-1.87 (m, 3H), 1.41-1.34 (m, 2H); IR (neat) 2923, 2220, 1591, 1567, 1499, 1458, 1364 cm$^{-1}$; MS (FAB) m/z 286 (M+H)

A-96: 6-tert-butyl-2-[4-(4-fluoro-phenyl)-piperazin-1-yl]-nicotinonitrile

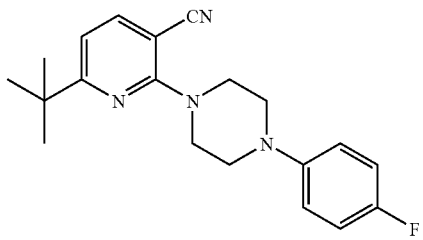 [SMILES: CC(C)(C)c1ccc(C#N)c(N2CCN(c3ccc(F)cc3)CC2)n1]

$^1$H NMR (300 MHz, CDCl$_3$) δ 7.70 (d, 1H, J=8.0 Hz), 7.02-6.89 (m, 4H), 6.81 (d, 1H, J=8.0 Hz), 3.92-3.88 (m, 4H), 3.26-3.23 (m, 4H), 1.30 (s, 9H); IR (neat) 2963, 2215, 1584, 1550, 1511, 1445, 1363 cm$^{-1}$; MS (FAB) m/z 339 (M+H)

A-97: 2-diethylamino-6-trifluoromethyl-nicotinonitrile

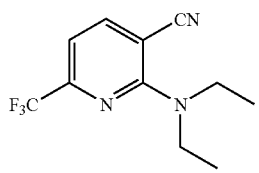

$^1$H NMR (300 MHz, CDCl$_3$) δ 7.86 (d, 1H, J=7.9 Hz), 7.07 (d, 1H, J=7.7 Hz), 3.74 (q, 4H, J=7.0 Hz), 1.30 (t, 6H, J=7.1

A-98: 2-dimethylamino-6-trifluoromethyl-nicotinonitrile

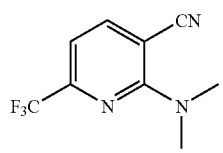

$^1$H NMR (300 MHz, CDCl$_3$) δ 7.87 (d, 1H, J=7.9 Hz), 6.92 (d, 1H, J=7.7 Hz), 3.35 (s, 4H); IR (KBr) 2940, 2218, 1595, 1525, 1411, 1320, 1265 cm$^{-1}$

MS (FAB) m/z 215 (M+H)

A-99: 2-dibutylamino-6-trifluoromethyl-nicotinonitrile

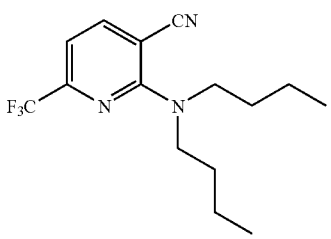 [SMILES: CCCCN(CCCC)c1nc(C(F)(F)F)ccc1C#N]

$^1$H NMR (300 MHz, CDCl$_3$) δ 7.84 (d, 1H, J=7.7 Hz), 6.85 (d, 1H, J=7.9 Hz), 3.66 (t, 4H, J=7.9 Hz), 1.72-1.60 (m, 4H), 1.45-1.32 (m, 4H), 0.97 (t, 6H, J=7.3 Hz); IR (KBr) 2962, 271, 2215, 1594, 1566, 1513, 1461 cm$^{-1}$; MS (FAB) m/z 300 (M+H)

A-100: 2-benzylamino-6-trifluoromethyl-nicotinonitrile

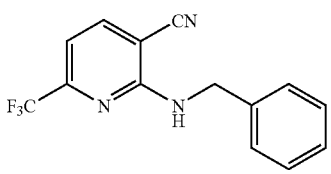

$^1$H NMR (300 MHz, CDCl$_3$) δ 7.87 (d, 1H, J=7.7 Hz), 7.40-7.26 (m, 5H), 6.97 (d, 1H, J=7.7 Hz); IR (KBr) 3357, 2228, 1560, 1534, 1424, 1343, 1282 cm$^{-1}$; MS (FAB) m/z 277 (M+H)

A-101: 4-benzyl-4'-methyl-6'-trifluoromethyl-3,4,5,6-tetrahydro-2H-[1,2']bipyridinyl-3'-carbonitrile $^1$H NMR (300 MHz, CDCl$_3$) δ 7.14-7.34 (m, 5H), 6.90 (bs, 1H), 4.39-4.49 (m, 2H), 2.90-3.02 (m, 2H), 2.59 (d, 2H, J=6.8 Hz), 2.52 (bs, 3H), 1.71-1.87 (m, 2H), 1.22-1.50 (m, 3H); IR (neat) 2922, 2850, 2214, 1577, 1494, 1452, 1391, 1243, 1182, 1143, 967, 913, 743, 701 cm$^{-1}$; MS (FAB) m/z 360 (M+H)

A-102: 4,4'-dimethyl-6'-trifluoromethyl-3,4,5,6-tetrahydro-2H-[1,2']bipyridinyl-3'-carbonitrile $^1$H NMR (300 MHz, CDCl$_3$) δ 6.89 (s, 1H), 4.42 (m, 2H), 3.02 (m, 2H), 2.52 (s, 3H), 1.65-1.79 (m, 3H), 1.33 (m, 2H), 0.99 (d, 3H, J=6.3 Hz); IR (neat) 2923, 2215, 1577, 1453, 1391, 1315, 1241, 1182, 1145, 1078, 969, 913, 847, 740 cm$^{-1}$; MS (FAB) m/z 284 (M+H)

Stage 2:
Method 1:
Compounds of the general formula VI-B (5 mmol), in which R$^5$, R$^{12}$, R$^{13}$, U, T and V have the above-stated meaning and m denotes 0, 1, 2 or 3, palladium on carbon (10%, 500 mg) and concentrated hydrochloric acid (3 mL) are dissolved in MeOH (30 mL) and exposed to a hydrogen atmosphere for 6 hours at RT. The reaction mixture is filtered through celite and the filtrate is evaporated under a vacuum. The residue is purified by means of flash chromatography (SiO$_2$, EA).

The following compounds B-1 to B-15 were obtained according to the above-stated general method:

Compound B-1

[2-(piperidin-1-yl)-6-(trifluoromethyl)-pyridin-3-yl]methylamine

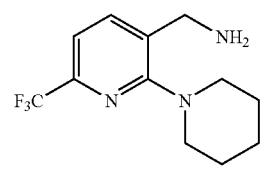 [SMILES: NCc1ccc(C(F)(F)F)nc1N1CCCCC1]

The compound was obtained in a yield of 50% as a pale yellow oil.

$^1$H NMR (300 MHz, CDCl$_3$) δ 7.86 (d, 1H, J=5.7 Hz), 7.26 (d, 1H, J=5.7 Hz), 4.01 (s, 2H), 3.11 (bs, 4H), 1.62-1.70 (m, 6H)

Compound B-2

[2-(morpholin-4-yl)-6-(trifluoromethyl)-pyridin-3-yl]methylamine

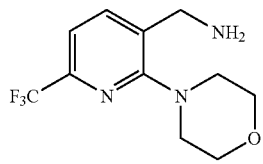 [SMILES: NCc1ccc(C(F)(F)F)nc1N1CCOCC1]

The compound was obtained in a yield of 28% as a pale yellow oil.

$^1$H NMR (400 MHz, CDCl$_3$) δ 7.86 (d, 1H, J=5.7 Hz), 7.31 (d, 1H, J=5.7 Hz), 3.93 (s, 2H), 3.85 (t, 4H, J=3.3 Hz), 3.23 (t, 4H, J=3.3 Hz)

Compound B-3

[2-(pyrrolidin-1-yl)-6-(trifluoromethyl)-pyridin-3-yl]methylamine

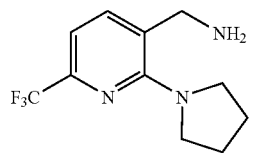

The compound was obtained in a yield of 60% as a pale yellow oil.

$^1$H NMR (300 MHz, CDCl$_3$) δ 7.58 (d, 1H, J=7.5 Hz), 6.98 (d, 1H, J=7.5 Hz), 3.93 (s, 2H), 3.55-3.60 (m, 4H), 1.93-1.97 (m, 4H)

Compound B-4

2-(piperidin-1-yl)-4-(trifluoromethyl)benzylamine

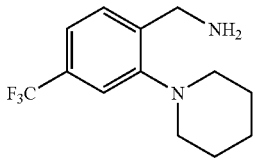 [SMILES: NCc1ccc(C(F)(F)F)cc1N1CCCCC1]

The compound was obtained in a yield of 50% as a pale yellow oil.

$^1$H NMR (300 MHz, CD$_3$OD) δ 7.59 (d, 1H, J=7.8 Hz), 7.52 (s, 1H), 7.47 (d, 1H, J=7.8 Hz), 4.28 (s, 2H), 2.89-2.93 (m, 4H), 1.63-1.82 (m, 6H)

Compound B-5

2-(morpholin-4-yl)-4-(trifluoromethyl)benzylamine

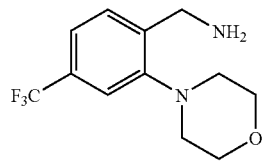 [SMILES: NCc1ccc(C(F)(F)F)cc1N1CCOCC1]

The compound was obtained in a yield of 38% as a pale yellow oil.

$^1$H NMR (300 MHz, CD$_3$OD) δ 7.61 (d, 1H, J=7.8 Hz), 7.55 (s, 1H), 7.50 (d, 1H, J=7.8 Hz), 4.26 (s, 2H), 3.87 (t, 4H, J=4.5 Hz), 2.95 (t, 4H, J=4.5 Hz)

Compound B-6

2-(pyrrolidin-1-yl)-4-(trifluoromethyl)benzylamine

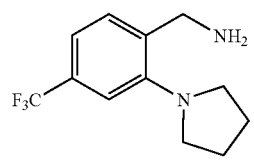

The compound was obtained in a yield of 55% as a pale yellow oil.

$^1$H NMR (300 MHz, CD$_3$OD) δ 7.83 (d, 1H, J=7.8 Hz), 7.25 (s, 1H), 7.18 (d, 1H, J=7.8 Hz), 4.21 (s, 2H), 3.15-3.19 (m, 4H), 1.95-1.99 (m, 4H)

B-7: C-[4-(4-fluoro-phenyl)-6'-trifluoromethyl-3,4,5,6-tetrahydro-2H-[1,2']bipyridinyl-3'-yl]-methylamine

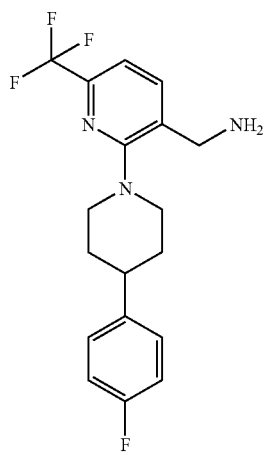 [SMILES: NCc1ccc(C(F)(F)F)nc1N1CCC(c2ccc(F)cc2)CC1]

$^1$H NMR (300 MHz, CDCl$_3$) δ 8.03 (d, 1H, J=7.5 Hz), 7.41 (d, 1H, J=7.5 Hz), 7.24 (m, 2H), 7.01 (dd, 1H, J=8.1, 8.4 Hz), 4.26 (s, 2H), 3.45 (m, 2H), 3.07 (m, 2H), 2.72 (m, 1H), 1.89-1.96 (m, 4H); IR (neat) 2913, 2846, 1593, 1512, 1469, 1422, 1368, 1225, 1190, 1152, 950, 839 cm$^{-1}$; MS (FAB) m/z 354 (M+H)

B-8: 4-(2,2-dimethyl-propionyloxy)-6'-trifluoromethyl-3,4,5,6-tetrahydro-2H-[1,2']bipyridinyl-3'-ylmethyl-ammonium acetate

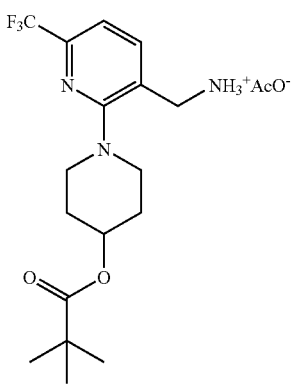

$^1$H NMR (CDCl$_3$) δ 7.81 (d, 1H, J=7.7 Hz), 7.31 (d, 1H, J=7.7 Hz), 4.98 (m, 1H), 4.35 (s, NH3+), 3.97 (s, 2H), 3.40-3.31 (m, 2H), 3.18-3.10 (m, 2H), 2.06-1.98 (m, 2H), 2.04 (s, 3H), 1.87-1.77 (m, 2H), 1.22 (s, 9H); IR (neat) 2970, 1724, 1593, 1462, 1419, 1168, 1033 cm$^{-1}$ B-9: 4-acetoxy-6'-trifluoromethyl-3,4,5,6-tetrahydro-2H-[1,2']bipyridinyl-3'-ylmethyl-ammonium acetate

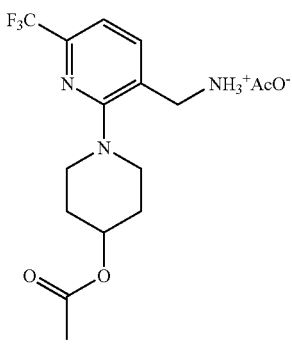

$^1$H NMR (CDCl$_3$) δ 7.81 (d, 1H, 7.7 Hz), 7.31 (d, 1H, 7.7 Hz), 4.97 (m, 1H), 4.03-3.93 (m, 5H), 3.45-3.35 (m, 2H), 3.14-3.05 (m, 1H), 2.08 (s, 3H), 2.10-1.98 (m, 2H), 1.88-1.77 (m, 2H); IR (neat) 2957, 1734, 1419, 1247, 1138, 1034 cm$^{-1}$ B-10: 4-methoxy-6'-trifluoromethyl-3,4,5,6-tetrahydro-2H-[1,2']bipyridinyl-3'-ylmethyl-ammonium acetate

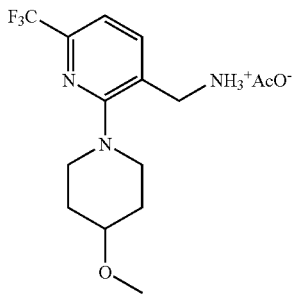

$^1$H NMR (CDCl$_3$) δ 7.80 (d, 1H, J=7.5 Hz), 7.29 (d, 1H, J=7.7 Hz), 4.28 (bs, NH3), 3.97 (s, 2H), 3.47-3.36 (m, 6H), 3.02-2.94 (m, 2H), 2.09-2.01 (m, 5H), 1.77-1.65 (m, 2H); IR (neat) 2930, 1542, 1461, 1418, 1335, 1178, 1137, 957 cm$^1$ B-11: 4-butoxy-6'-trifluoromethyl-3,4,5,6-tetrahydro-2H-[1,2']bipyridinyl-3'-ylmethyl-ammonium acetate

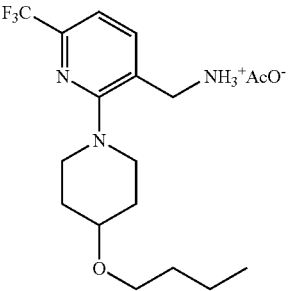

$^1$H NMR (CDCl$_3$) δ 7.80 (d, 1H, J=7.7 Hz), 7.29 (d, 1H, J=7.7 Hz), 4.03-3.98 (m, 5H, 2H+NH3), 3.49 (t, 2H, J=6.6 Hz), 3.47-3.37 (m, 3H), 3.01-2.93 (m, 2H), 2.07-1.97 (m, 2H), 1.98 (s, 3H), 1.77-1.65 (m, 2H), 1.62-1.55 (m, 2H), 1.45-1.33 (m, 2H), 0.92 (t, 3H, J=7.3 Hz); IR (neat) 2955, 1542, 1462, 1419, 1333, 1140, 1041 cm$^{-1}$ B-12: 4-ethoxy-6'-trifluoromethyl-3,4,5,6-tetrahydro-2H-[1,2']bipyridinyl-3'-ylmethyl-ammonium acetate

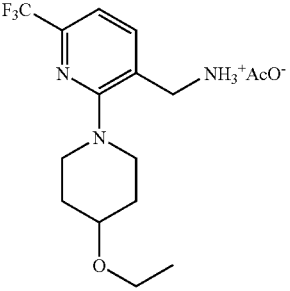

$^1$H NMR (CDCl$_3$) δ 7.80 (d, 1H, J=7.7 Hz), 7.29 (d, 1H, J=7.7 Hz), 5.30 (bs, NH3), 3.59-3.39 (m, 5H), 3.01-2.93 (m, 2H), 2.08-2.00 (m, 5H), 1.78-1.66 (m, 2H), 1.23 (t, 3H, J=7.0 Hz); IR (neat) 2927, 1593, 1419, 1333, 1241, 1178, 1139 cm$^{-1}$ B-13: C-(5'-trifluoromethyl-3,4,5,6-tetrahydro-2H-[1,3']bipyridinyl-2'-yl)-methylamine

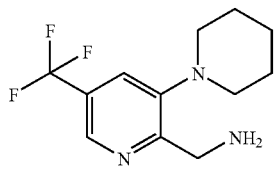

$^1$H NMR (300 MHz, D2O) δ 8.71 (s, 1H), 8.21 (s, 1H), 4.45 (s, 2H), 3.24 (d, 4H, J=4.6 Hz), 1.77 (s, 4H), 1.51 (s, 2H); MS (FAB) m/z 260 (M+H)

B-14: 2-(4-ethyl-piperidin-1-yl)-4-trifluoromethyl-benzylamine

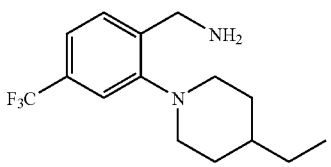 [SMILES: CCC1CCN(c2cc(C(F)(F)F)ccc2CN)CC1]

$^1$H NMR (400 MHz, CDCl$_3$) δ 7.43 (d, 1H, J=6.0 Hz), 7.27-7.33 (m, 2H), 3.92 (s, 2H), 3.04-3.12 (m, 2H), 2.63-2.72 (m, 2H), 1.78-1.85 (m, 2H), 1.24-1.43 (m, 5H), 0.93 (bt, 3H); IR (neat) 2925, 1423, 1337, 1311, 1242, 1165, 1123, 1080, 949, 826 cm$^{-1}$; MS (FAB) m/z 287 (M+H)

B-15: 4-isopropoxy-6'-trifluoromethyl-3,4,5,6-tetrahydro-2H-[1,2']bipyridinyl-3'-ylmethyl-ammonium acetate

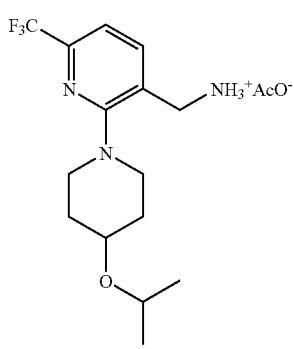

$^1$H NMR (CDCl$_3$) δ 7.78 (d, 1H, J=7.7 Hz), 7.28 (d, 1H), 4.26 (bs, NH3), 3.95 (s, 2H), 3.76 (m, 1H), 3.57-3.40 (m, 3H), 2.97 (m, 2H), 2.07 (s, 3H, AcO), 2.04-1.96 (m, 2H), 1.76-1.65 (m, 2H), 1.18 (d, 6H, J=6.2 Hz); IR (neat) 2972, 1593, 1462, 1419, 1333, 1177, 1140, 1041 cm$^{-1}$ Method 2:

Compounds of the general formula VI-B (2 mmol), in which R$^5$, R$^{12}$, R$^{13}$, U, T and V have the above-stated meaning and m denotes 0, 1, 2 or 3, are dissolved in THF (10 mL) and BH$_3$.S(CH$_3$)$_2$ [2.0 M in THF, 3 mL, 3 equivalents] is added.

The reaction mixture is heated to reflux for 8 hours, aq. HCl (2 N) is added and the reaction mixture is again heated to reflux for 30 minutes. Aq. NaOH soln. and EA are added. The combined organic extracts are washed with sat. aq. NaCl soln. and dried over MgSO$_4$. The solvent is evaporated under a vacuum and the residue is purified by flash chromatography (SiO$_2$, different mixtures of methylene chloride and methanol).

The following compounds B-16 to B-80 were obtained according to the above-stated general method:

B-16: (6-(chlorodifluoromethyl)-2-(piperidin-1-yl)pyridin-3-yl)methanamine

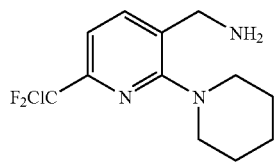

$^1$H NMR (300 MHz, CDCl$_3$) δ 7.78 (d, 1H, J=7.8 Hz), 7.22 (d, 1H, J=7.8 Hz), 3.90 (s, 2H), 3.12-3.16 (m, 4H), 1.60-1.70 (m, 6H) IR (neat) 2935, 2851, 1590, 1417, 1373, 1300, 1091, 972, 913, 827 cm$^{-1}$ MS (FAB) m/z 276 (M+H)

B-17: (2-(4-benzylpiperazin-1-yl)-6-(trifluoromethyl)pyridin-3-yl)methanamine

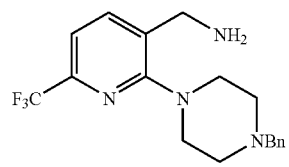 [SMILES: NCc1ccc(C(F)(F)F)nc1N1CCN(Cc2ccccc2)CC1]

$^1$H NMR (300 MHz, CDCl$_3$) δ 7.81 (d, 1H, J=7.8 Hz), 7.23-7.37 (m, 6H), 3.89 (s, 2H), 3.58 (s, 2H), 3.22-3.25 (m, 4H), 2.57-2.62 (m, 4H); IR (neat) 2814, 1592, 1417, 1324, 1176, 1135, 1005, 964, 836, 741, 700 cm$^{-1}$; MS (FAB) m/z 351 (M+H)

B-18: (6-(trifluoromethyl)-2-(4-methylpiperidin-1-yl)pyridin-3-yl)methanamine

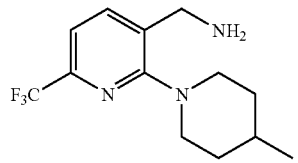 [SMILES: CC1CCN(c2nc(C(F)(F)F)ccc2CN)CC1]

$^1$H NMR (300 MHz, CDCl$_3$) δ 7.89 (d, 1H, J=7.8 Hz), 7.33 (d, 1H, J=7.8 Hz), 3.88 (s, 2H), 3.39 (m, 2H), 2.83 (m, 2H), 1.75 (m, 2H), 1.55 (m, 1H), 1.38 (m, 2H), 1.00 (d, 3H, J=6.6 Hz); MS (FAB) m/z 274 (M+H)

B-19: C-(4-fluoro-6'-trifluoromethyl-3,4,5,6-tetrahydro-2H-[1,2']bipyridinyl-3'-yl)-methylamine

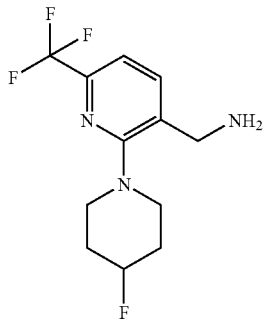 [SMILES: NCc1ccc(C(F)(F)F)nc1N1CCC(F)CC1]

$^1$H NMR (300 MHz, CDCl$_3$) δ 7.83 (d, 1H, J=7.8 Hz), 7.28 (d, 1H, J=7.8 Hz), 4.85 (dm, 1H, J=48.3 Hz), 3.92 (s, 2H), 3.39 (m, 2H), 3.14 (m, 2H), 2.01-2.28 (m, 4H);

MS (FAB) m/z 278 (M+H)

B-20: C-[6'-(chloro-difluoro-methyl)-4-methyl-3,4,5,6-tetrahydro-2H-[1,2']bipyridinyl-3'-yl]-methylamine

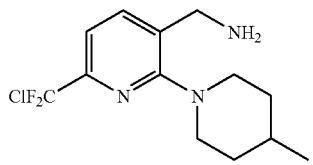

$^1$H NMR (300 MHz, CDCl$_3$) δ 7.72 (d, 1H, J=7.5 Hz), 7.13 (d, 1H, J=7.5 Hz), 3.84 (s, 2H), 3.37 (m, 2H), 2.77 (m, 2H), 1.68 (m, 2H), 1.48 (m, 1H), 1.24 (m, 2H), 0.89 (d, 3H, J=6.6 Hz); IR (neat) 2923, 1590, 1452, 1417, 1254, 1186 cm$^{-1}$; MS (FAB) m/z 290 (M+H)

B-21: C-[2-azepan-1-yl-6-(chloro-difluoro-methyl)-pyridin-3-yl]-methylamine

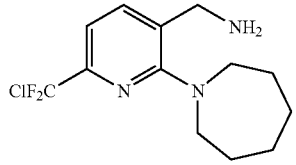

$^1$H NMR (300 MHz, CDCl$_3$) δ 7.69 (d, 1H, J=7.5 Hz), 6.97 (d, 1H, J=7.5 Hz), 3.98 (s, 2H), 3.37 (m, 4H), 1.71 (m, 4H), 1.51 (m, 4H); IR (neat) 3432, 2928, 2857, 1593, 1452, 1421, 1371, 1257 cm$^{-1}$; MS (FAB) m/z 290 (M+H)

B 22: C-[6'-(4-fluoro-phenyl)-4-methyl-3,4,5,6-tetrahydro-2H-[1,2']bipyridinyl-3'-yl]-methylamine

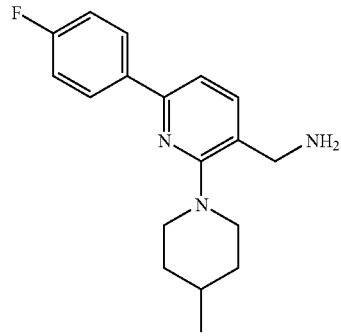 [SMILES: CC1CCN(c2nc(-c3ccc(F)cc3)ccc2CN)CC1]

$^1$H NMR (300 MHz, CDCl$_3$) d 8.00 (m, 2H), 7.66 (d, 1H, J=7.8 Hz), 7.30 (d, 1H, J=7.8 Hz), 7.10 (dd, 2H, J=8.7, 8.7 Hz), 3.90 (s, 2H), 3.43 (m, 2H), 2.89 (m, 2H), 1.74 (m, 2H), 1.53 (m, 1H), 1.38 (m, 2H), 0.99 (d, 3H, J=6.3 Hz); IR (neat) 2932, 2851, 1600, 1577, 1509, 1447, 1421, 1372, 1236, 1156, 1112, 1031 cm$^{-1}$; MS (FAB) m/z 300 (M+H)

B-23: C-[2-azepan-1-yl-6-(4-fluoro-phenyl)-pyridin-3-yl]-methylamine

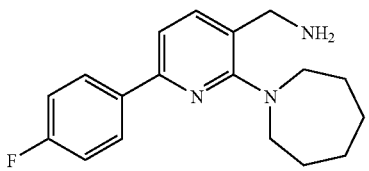 [SMILES: NCc1ccc(-c2ccc(F)cc2)nc1N1CCCCCC1]

$^1$H NMR (300 MHz, CDCl$_3$) δ 7.97 (m, 2H), 7.59 (d, 1H, J=7.8 Hz), 7.17 (d, 1H, J=7.8 Hz), 7.09 (dd, 2H, J=8.7, 8.7 Hz), 3.89 (s, 2H), 3.49 (t, 4H, J=6.0 Hz), 1.81 (m, 4H), 1.64 (m, 4H); IR (neat) 2925, 2853, 1576, 1508, 1448, 1373, 1230, 1154, 906 cm$^{-1}$; MS (FAB) m/z 300 (M+H)

B-24: [3-aminomethyl-6-(chloro-difluoro-methyl)-pyridin-2-yl]-dipropyl-amine

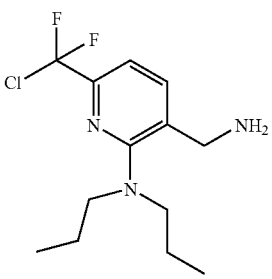 [SMILES: CCCN(CCC)c1nc(C(F)(F)Cl)ccc1CN]

$^1$H NMR (300 MHz, CDCl$_3$) δ 7.68 (d, 1H, J=7.8 Hz), 7.06 (d, 1H, J=7.8 Hz), 3.84 (s, 2H), 3.08 (t, 4H, J=7.5 Hz), 1.47 (m, 4H), 0.77 (t, 6H, J=7.2 Hz); IR (neat) 2964, 2874, 1591, 1462, 1418, 1372, 1257, 1091, 999 cm$^{-1}$ MS (FAB) m/z 292 (M+H)

B-25: C-[2-(1,3-dihydro-isoindol-2-yl)-6-trifluoromethyl-pyridin-3-yl]-methylamine

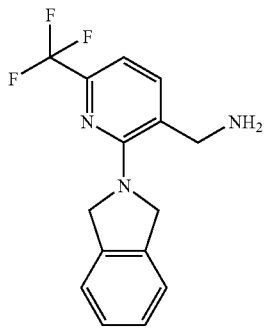 [SMILES: NCc1ccc(C(F)(F)F)nc1N1Cc2ccccc2C1]

$^1$H NMR (300 MHz, CDCl$_3$) δ 7.63 (d, 1H, J=7.8 Hz), 7.27-7.31 (m, 4H), 7.03 (d, 1H, J=7.8 Hz), 5.06 (s, 4H), 4.08 (s, 2H); IR (neat) 3365, 2926, 2857, 1598, 1457, 1363, 1263, 1177, 1132, 1013, 820 cm$^{-1}$; MS (FAB) m/z 294 (M+H)

B-26: 3'-aminomethyl-4-phenyl-6'-trifluoromethyl-3,4,5,6-tetrahydro-2H-[1,2']bipyridinyl-4-carbonic acid ethyl ester

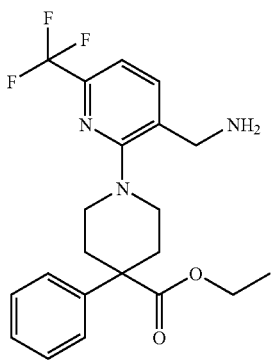 [SMILES: CCOC(=O)C1(c2ccccc2)CCN(c2nc(C(F)(F)F)ccc2CN)CC1]

$^1$H NMR (300 MHz, CDCl$_3$) δ 7.83 (d, 1H, J=7.5 Hz), 7.45 (m, 2H), 7.35 (m, 3H), 7.26 (d, 1H, J=8.1 Hz), 4.15 (q, 2H, J=7.2 Hz), 4.03 (s, 2H), 3.47 (m, 2H), 3.08 (m, 2H), 2.69 (m, 2H), 2.10 (m, 2H), 1.21 (t, 3H, J=7.2 Hz); MS (FAB) m/z 408 (M+H)

B-27: C-(4,6'-bis-trifluoromethyl-3,4,5,6-tetrahydro-2H-[1,2']bipyridinyl-3'-yl)-methylamine

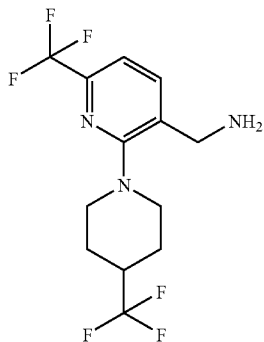 [SMILES: NCc1ccc(C(F)(F)F)nc1N1CCC(C(F)(F)F)CC1]

$^1$H NMR (300 MHz, CDCl$_3$) δ 7.80 (d, 1H, J=7.8 Hz), 7.23 (d, 1H, J=7.8 Hz), 3.83 (s, 2H), 3.48 (m, 2H), 2.79 (m, 2H), 2.15 (m, 1H), 1.88 (m, 2H), 1.65 (m, 2H); IR (neat) 2960, 1591, 121, 1378, 1337, 1255, 1141, 1084, 955, 901, 837, 698 cm$^{-1}$; MS (FAB) m/z 328 (M+H)

B-28: C-(4-methoxymethyl-6'-trifluoromethyl-3,4,5,6-tetrahydro-2H-[1,2']bipyridinyl-3'-yl)-methylamine

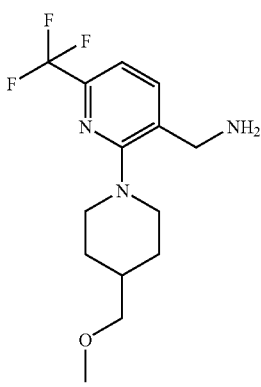 [SMILES: COCC1CCN(c2nc(C(F)(F)F)ccc2CN)CC1]

$^1$H NMR (300 MHz, CDCl$_3$) δ 7.81 (d, 1H, J=7.8 Hz), 7.26 (d, 1H, J=7.8 Hz), 3.91 (s, 2H), 3.36 (s, 3H), 3.29 (d, 2H, J=6.0 Hz), 2.87 (m, 2H), 2.37 (s, 2H), 1.71-1.86 (m, 4H), 1.34-1.47 (m, 3H); IR (neat) 2924, 1592, 1455, 1374, 1324, 1268, 1175, 1135, 950, 835 cm$^{-1}$; MS (FAB) m/z 304 (M+H)

B-29: C-[2-(4-p-tolyl-piperazin-1-yl)-6-trifluoromethyl-pyridin-3-yl]-methylamine

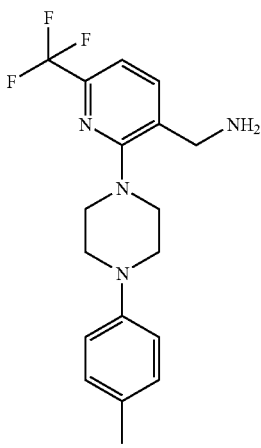 [SMILES: Cc1ccc(N2CCN(c3nc(C(F)(F)F)ccc3CN)CC2)cc1]

$^1$H NMR (300 MHz, CDCl$_3$) δ 7.85 (d, 1H, J=7.8 Hz), 7.30 (d, 1H, J=7.8 Hz), 7.09 (d, 2H, J=8.4 Hz), 6.88 (d, 2H, J=8.4 Hz), 3.94 (s, 2H), 3.37 (m, 4H), 3.26 (m, 4H), 2.27 (s, 3H); IR (neat) 3368, 2847, 1732, 1591, 1515, 117, 1333, 1235, 1176, 1137, 1051, 966, 916, 814, 755 cm$^{-1}$; MS (FAB) m/z 351 (M+H)

B-30: C-[2-(4-m-tolyl-piperazin-1-yl)-6-trifluoromethyl-pyridin-3-yl]-methylamine

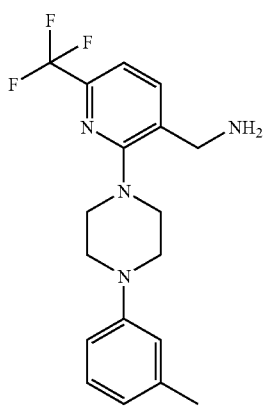 [SMILES: Cc1cccc(N2CCN(c3nc(C(F)(F)F)ccc3CN)CC2)c1]

¹H NMR (300 MHz, CDCl₃) δ 7.86 (d, 1H, J=7.8 Hz), 7.31 (d, 1H, J=7.8 Hz), 7.18 (t, 1H, J=7.5 Hz), 6.77-6.79 (m, 2H), 3.95 (s, 2H), 3.31-3.38 (m, 8H), 2.33 (s, 3H); IR (neat) 3367, 2845, 1595, 1493, 1418, 1335, 1240, 1335, 1137, 1045, 998, 967, 836, 775, 695 cm⁻¹; MS (FAB) m/z 351 (M+H)

B-31: C-{2-[4-(4-methoxy-phenyl)-piperazin-1-yl]-6-trifluoromethyl-pyridin-3-yl}-methylamine

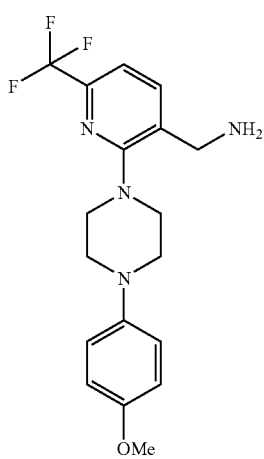 [SMILES: COc1ccc(N2CCN(c3nc(C(F)(F)F)ccc3CN)CC2)cc1]

¹H NMR (300 MHz, CDCl₃) δ 7.86 (d, 1H, J=7.8 Hz), 7.31 (d, 1H, J=7.8 Hz), 6.94 (d, 2H, J=6.9 Hz), (d, 2H, J=6.9 Hz), 3.95 (s, 2H), 3.77 (s, 3H), 3.39 (m, 4H), 3.22 (m, 4H); IR (neat) 2837, 1590, 1512, 1418, 1332, 1244, 1178, 1137, 1035, 967, 826 cm⁻¹; MS (FAB) m/z 367 (M+H)

B-32: C-{6-trifluoromethyl-2-[4-(4-trifluoromethyl-phenyl)-piperazin-1-yl]-pyridin-3-yl}-methylamine

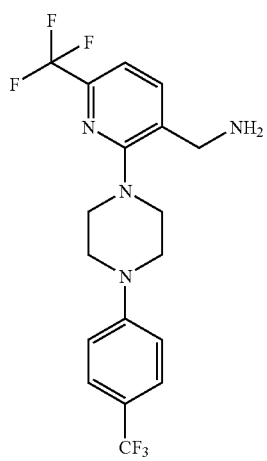 [SMILES: NCc1ccc(C(F)(F)F)nc1N1CCN(c2ccc(C(F)(F)F)cc2)CC1]

¹H NMR (300 MHz, CDCl₃) δ 7.89 (d, 1H, J=7.8 Hz), 7.50 (d, 2H, J=7.8 Hz), 7.32 (d, 1H, J=7.8 Hz), 6.97 (d, 2H, J=7.8 Hz), 4.09 (s, 2H), 3.40 (m, 8H), 2.27 (s, 2H); IR (neat) 2933, 1695, 1600, 1511, 1428, 1397, 1342, 1314, 1262, 1158, 1026, 835 cm⁻¹; MS (FAB) m/z 405 (M+H)

B-33: C-{6-trifluoromethyl-2-[4-(3-trifluoromethyl-pyridin-2-yl)-piperazin-1-yl]-pyridin-3-yl}-methylamine

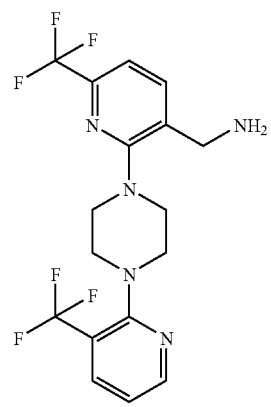 [SMILES: NCc1ccc(C(F)(F)F)nc1N1CCN(c2ncccc2C(F)(F)F)CC1]

¹H NMR (300 MHz, CDCl₃) δ 8.46 (d, 1H, J=3.3 Hz), 7.86-7.93 (m, 2H), 7.31 (d, 1H, J=7.5 Hz), 7.03 (m, 1H), 3.97 (s, 2H), 3.46 (m, 4H), 3.36 (m, 4H), 2.12 (bs, 2H); IR (neat) 3367, 2850, 1590, 1445, 1368, 1312, 1236, 1138, 1027, 966, 837 cm⁻¹;

MS (FAB) m/z 407 (M+H)

B-34: C-[2-(4-cyclohexyl-piperazin-1-yl)-6-trifluoromethyl-pyridin-3-yl]-methylamine

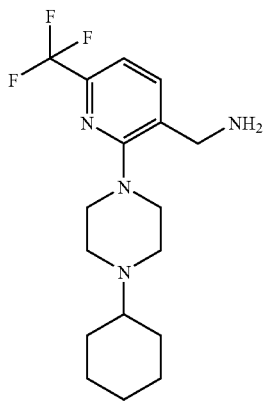 [SMILES: NCc1ccc(C(F)(F)F)nc1N1CCN(C2CCCCC2)CC1]

¹H NMR (300 MHz, CDCl₃) δ 7.80 (d, 1H, J=7.5 Hz), 7.27 (d, 1H, J=7.5 Hz), 3.90 (s, 2H), 3.25 (m, 4H), 2.73 (m, 4H), 2.16 (m, 1H), 1.70 (m, 4H), 1.19-1.28 (m, 6H); MS (FAB) m/z 343 (M+H)

B-35: 2-(4-methyl-6'-trifluoromethyl-3,4,5,6-tetrahydro-2H-[1,2']bipyridinyl-3'-yl)-ethylamine

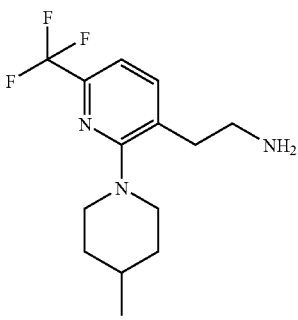 [SMILES: CC1CCN(c2nc(C(F)(F)F)ccc2CCN)CC1]

¹H NMR (300 MHz, CDCl₃) δ 7.46 (d, 1H, J=7.5 Hz), 7.12 (d, 1H, J=7.5 Hz), 3.32 (m, 2H), 2.95 (t, 2H, J=6.9 Hz), 2.75 (m, 4H), 1.55-1.63 (m, 5H), 0.91 (d, 3H, J=6.3 Hz); IR (neat) 3364, 2924, 1648, 1590, 1457, 1415, 1322, 1236, 1176, 1136, 1045, 944, 834 cm⁻¹; MS (FAB) m/z 288 (M+H)

B-36: (3'-aminomethyl-6'-trifluoromethyl-3,4,5,6-tetrahydro-2H-[1,2']bipyridinyl-4-yl)-phenyl-amine

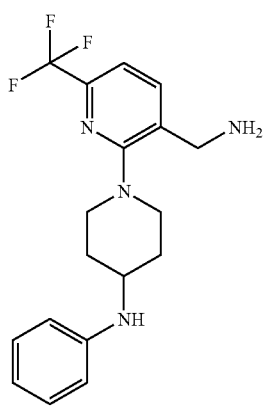 [SMILES: NCc1ccc(C(F)(F)F)nc1N1CCC(Nc2ccccc2)CC1]

¹H NMR (300 MHz, CDCl₃) δ 7.82 (d, 1H, J=7.5 Hz), 7.29 (d, 1H, J=7.5 Hz), 7.18 (m, 2H), 6.66 (m, 3H), 3.93 (s, 2H), 3.47 (m, 2H), 3.03 (m, 2H), 2.84 (bs, 2H), 2.18 (m, 2H), 1.58-1.66 (m, 3H); IR (neat) 3365, 2938, 1598, 1504, 1421, 1333, 1265, 1177, 1136, 1044, 953, 836, 752, 695 cm⁻¹; MS (FAB) m/z 351 (M+H)

B-37: C-[2-(2,6-dimethyl-morpholin-4-yl)-6-trifluoromethyl-pyridin-3-yl]-methylamine

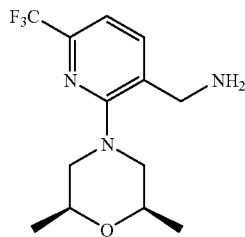 [SMILES: C[C@@H]1CN(c2nc(C(F)(F)F)ccc2CN)C[C@H](C)O1]

¹H NMR (300 MHz, CDCl₃) δ 7.77 (d, 1H, J=7.8 Hz), 7.20 (d, 1H, J=7.8 Hz), 3.84 (s, 2H), 3.73 (m, 2H), 3.25 (m, 2H), 2.60 (m, 2H), 1.70 (bs, 2H), 1.15 (d, 6H, J=6.3 Hz); IR (neat) 2976, 1591, 1459, 1418, 1249, 1175, 1006, 836 cm⁻¹; MS (FAB) m/z 290 (M+H)

B-38: C-[2-(1,1-dioxo-thiomorpholin-4-yl)-6-trifluoromethyl-pyridin-3-yl]-methylamine

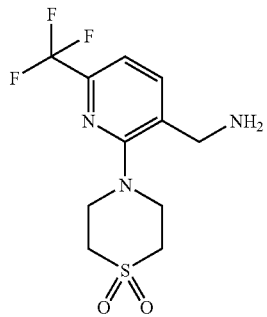 [SMILES: NCc1ccc(C(F)(F)F)nc1N1CCS(=O)(=O)CC1]

¹H NMR (300 MHz, CDCl₃) δ 7.94 (d, 1H, J=7.5 Hz), 7.38 (d, 1H, J=7.5 Hz), 3.82-3.91 (m, 6H), 3.20 (m, 4H), 1.52 (bs, 2H); IR (neat) 2929, 1709, 1591, 1465, 1334, 1280, 1178, 1126, 1029, 997, 864 cm⁻¹; MS (FAB) m/z 310 (M+H)

B-39: C-(2-imidazol-1-yl-6-trifluoromethyl-pyridin-3-yl)-methylamine

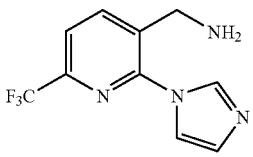 [SMILES: NCc1ccc(C(F)(F)F)nc1-n1ccnc1]

¹H NMR (300 MHz, CDCl₃) δ 8.17 (d, 1H, J=7.9 Hz), 8.11 (s, 1H), 7.67 (d, 1H, J=7.9 Hz), 7.49 (s, 1H), 7.14 (s, 1H), 3.93 (s, 2H); MS (FAB) m/z 243 (M+H)

B-40: C-(4,6'-dimethyl-3,4,5,6-tetrahydro-2H-[1,2']bipyridinyl-3'-yl)-methylamine

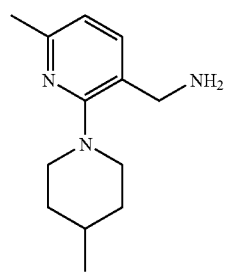 [SMILES: Cc1ccc(CN)c(N2CCC(C)CC2)n1]

¹H NMR (300 MHz, CDCl₃) δ 7.45 (d, 1H, J=6.6 Hz), 6.75 (d, 1H, J=6.5 Hz), 3.80 (s, 2H), 3.30 (m, 2H), 2.81 (m, 2H), 2.42 (s, 3H), 2.34 (bs, 2H), 1.72 (m, 2H), 1.51 (m, 1H), 1.33 (m, 2H), 0.98 (d, 3H, J=5.7 Hz); IR (neat) 3364, 2919, 1580, 1452, 1402, 1373, 1242, 1189, 1146, 1106, 1053, 962, 815 cm⁻¹; MS (FAB) m/z 220 (M+H)

B-41: (3-aminomethyl-6-trifluoromethyl-pyridin-2-yl)-cyclohexyl-amine

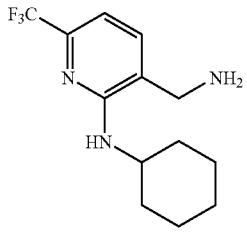 [SMILES: NCc1ccc(C(F)(F)F)nc1NC1CCCCC1]

¹H NMR (CDCl₃) δ 7.24 (d, 1H, J=7.4 Hz), 6.78 (d, 1H, J=7.1 Hz), 6.69 (bs, NH), 3.99 (m, 1H), 3.84 (s, 2H), 2.09-2.01 (m, 2H), 1.75-1.21 (m, 8H)

B-42: 3'-aminomethyl-6'-trifluoromethyl-3,4,5,6-tetrahydro-2H-[1,2']bipyridinyl-4-ol

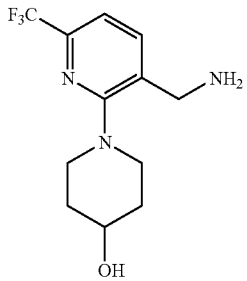 [SMILES: NCc1ccc(C(F)(F)F)nc1N1CCC(O)CC1]

¹H NMR (CDCl₃) δ 7.90 (d, 1H, J=7.7 Hz), 7.35 (d, 1H, J=7.7 Hz), 3.90 (s, 2H), 3.81-3.75 (m, 1H), 3.43-3.39 (m, 2H), 2.01-1.95 (m, 3H), 1.72-1.61 (m, 2H)

B-43: 6'-trifluoromethyl-3,4,5,6-tetrahydro-2H-[1,2']bipyridinyl-3'-ylamine

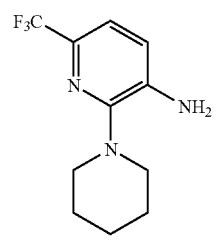 [SMILES: Nc1ccc(C(F)(F)F)nc1N1CCCCC1]

¹H NMR (CDCl₃) δ 7.17 (d, 1H, J=8.0 Hz), 6.92 (d, 1H, J=8.0 Hz), 4.02 (bs, NH), 3.07 (m, 4H), 1.74-1.56 (m, 6H); IR (neat) 2936, 1610, 1480, 1428, 1374, 1320, 1277, 1172, 1121 cm⁻¹

B-44: (3-aminomethyl-6-trifluoromethyl-pyridin-2-yl)-butyl-amine

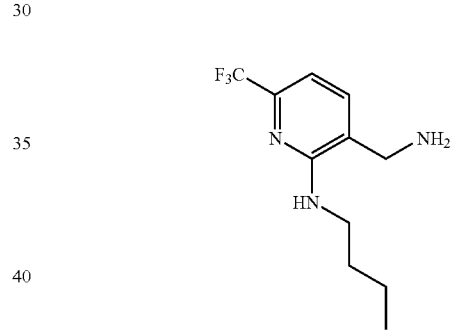

¹H NMR (CDCl₃) δ 7.24 (dd, 1H, J=7.3, 0.7 Hz), 6.80 (d, 1H, J=7.3 Hz), 6.78 (br, NH), 3.86 (s, 2H), 3.50-3.44 (m, 2H), 1.67-1.57 (m, 2H), 1.49-1.37 (m, 2H), 0.96 (t, 3H, J=7.1 Hz); IR (neat) 3301, 2929, 1611, 1532, 1458, 1309, 1175, 1133, 817 cm⁻¹

B-45: C-[2-(6-aza-spiro[2.5]oct-6-yl)-6-trifluoromethyl-pyridin-3-yl]-methylamine

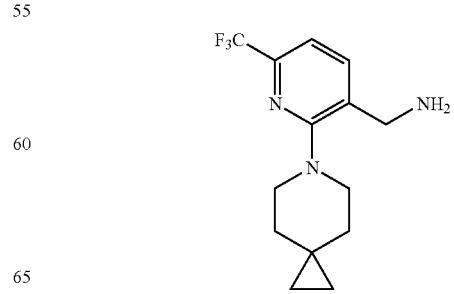

¹H NMR (CDCl₃) δ 7.82 (d, 1H, J=7.5 Hz), 7.26 (d, 1H, J=7.7 Hz), 3.93 (s, 2H), 3.22 (m, 4H), 1.52 (m, 4H), 0.36 (s, 4H); IR (neat) 2923, 1593, 1457, 1419, 1332, 1176, 1136, 956 cm⁻¹

B-46: C-(3-methyl-6'-trifluoromethyl-3,4,5,6-tetrahydro-2H-[1,2']bipyridinyl-3'-yl)-methylamine

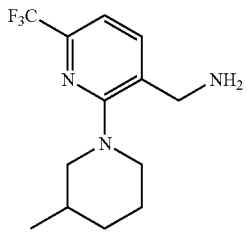 [SMILES: CC1CCCN(c2nc(C(F)(F)F)ccc2CN)C1]

¹H NMR (CDCl₃) δ 7.80 (dd, 1H, J=7.7, 0.7 Hz), 7.25 (d, 1H, J=7.5 Hz), 3.90 (s, 2H), 3.41-3.33 (m, 2H), 2.84-2.75 (m, 1H), 2.54-2.47 (m, 1H), 1.85-1.63 (m, 4H), 1.16-1.03 (m, 1H), 0.94 (d, 3H, J=6.6 Hz); IR (neat) 2927, 1593, 1458, 1418, 1176, 1136, 1001 cm⁻¹

B-47: C-(2-methyl-6'-trifluoromethyl-3,4,5,6-tetrahydro-2H-[1,2']bipyridinyl-3'-yl)-methylamine

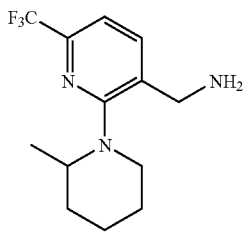 [SMILES: CC1CCCCN1c1nc(C(F)(F)F)ccc1CN]

¹H NMR (CDCl₃) δ 8.05 & 7.78 (d, 1H), 7.65 & 7.32 (d, 1H), 4.04 & 3.78 (m, 2H), 3.54 (m, 1H), 3.07 (m, 1H), 2.87 (m, 1H), 1.84-1.42 (m, 6H), 0.96 (d, 3H, J=6.2 Hz); IR (neat) 2933, 1539, 1459, 1412, 1337, 1178, 1139, 843 cm⁻¹

B-48: 4-[(3-aminomethyl-6-trifluoromethyl-pyridin-2-ylamino)-methyl]-piperidine-1-carbonic acid tert-butyl ester

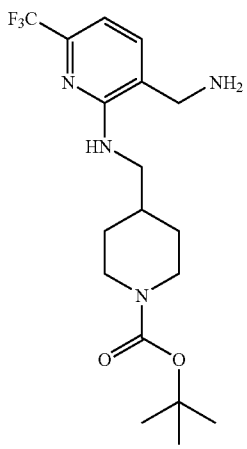 [SMILES: CC(C)(C)OC(=O)N1CCC(CNc2nc(C(F)(F)F)ccc2CN)CC1]

¹H NMR (CDCl₃) δ 7.26 (m, 2H), 6.79 (d, 1H, J=7.0 Hz), 4.11 (m, 2H), 3.89 (s, 2H), 3.39 (m, 2H), 2.69 (m, 2H), 1.85-1.65 (m, 5H), 1.43 (s, 9H); IR (neat) 3376, 2925, 1680, 1610, 1533, 1427, 1366, 1173, 1137 cm⁻¹

B-49: C-(4-benzyl-6'-trifluoromethyl-3,4,5,6-tetrahydro-2H-[1,2']bipyridinyl-3'-yl)-methylamine

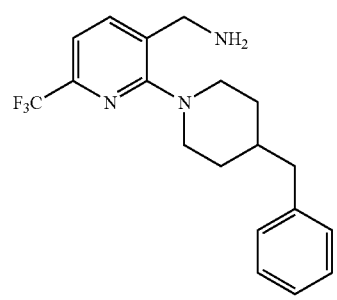 [SMILES: NCc1ccc(C(F)(F)F)nc1N1CCC(Cc2ccccc2)CC1]

¹H NMR (300 MHz, CDCl₃) δ 7.80 (d, 1H, J=7.7 Hz), 7.35-7.21 (m, 6H), 3.88 (s, 2H), 3.45 (m, 2H), 2.82 (m, 2H), 2.60 (d, 2H, J=6.6 Hz), 1.77-1.67 (m, 3H), 1.42 (m, 2H); IR (neat) 3385, 2921, 2847, 1592, 1454, 1418, 1373, 1320, 1267, 1174, 1134, 953, 834, 746, 701 cm⁻¹; MS (FAB) m/z 350 (M+H)

B-50: C-{2-[4-(4-fluoro-phenyl)-piperazin-1-yl]-6-trifluoromethyl-pyridin-3-yl}-methylamine

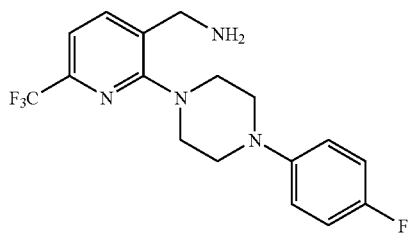 [SMILES: NCc1ccc(C(F)(F)F)nc1N1CCN(c2ccc(F)cc2)CC1]

¹H NMR (300 MHz, CDCl₃) δ 7.84 (d, 1H, J=8.0 Hz), 7.31 (d, 1H, J=7.6 Hz), 7.05-6.91 (m, 4H), 4.42 (s, 2H), 3.44-3.35 (m, 4H), 3.32-3.24 (m, 4H), 1.57 (bs, 2H); IR (neat) 2844, 1591, 1510, 1418, 1334, 1232, 1176, 1137, 1051, 966, 916, 825, 757 cm⁻¹; MS (FAB) m/z 355 (M+H)

B-51: C-{2-[4-(2-fluoro-phenyl)-piperazin-1-yl]-6-trifluoromethyl-pyridin-3-yl}-methylamine

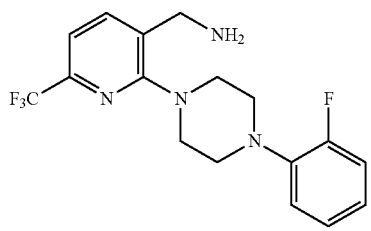 [SMILES: NCc1ccc(C(F)(F)F)nc1N1CCN(c2ccccc2F)CC1]

¹H NMR (300 MHz, CDCl₃) δ 7.87 (d, 1H, J=7.7 Hz), 7.31 (d, 1H, J=7.7 Hz), 7.21-7.03 (m, 4H), 3.96 (s, 2H), 3.48-3.35 (m, 4H), 3.29-3.15 (m, 4H)

IR (neat) 3384 m 2842 m 1571 m 1501 m 1453, 1416, 1372, 1337, 1236, 1176, 1136, 1052, 966, 822, 835, 754 cm⁻¹; MS (FAB) m/z 355 (M+H)

B-52: C-[2-(4-phenyl-piperazin-1-yl)-6-trifluoromethyl-pyridin-3-yl]-methylamine

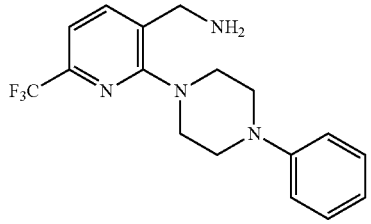 [SMILES: NCc1ccc(C(F)(F)F)nc1N1CCN(c2ccccc2)CC1]

¹H NMR (300 MHz, CDCl₃) δ 7.88 (d, 1H, J=7.7 Hz), 7.35-7.26 (m, 3H), 6.98 (d, 2H, J=7.9 Hz), 6.89 (m, 1H), 3.97 (s, 2H), 3.44-3.32 (m, 8H)

IR (neat) 2843, 1595, 1500, 1418, 1335, 1232, 1177, 1134, 966, 836, 759, 693 cm⁻¹;

MS (FAB) m/z 337 (M+H)

B-53: (3-aminomethyl-6-trifluoromethyl-pyridin-2-yl)-methyl-phenyl-amine

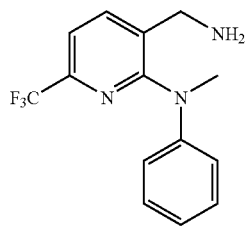 [SMILES: CN(c1ccccc1)c1nc(C(F)(F)F)ccc1CN]

¹H NMR (300 MHz, CDCl₃) δ 7.83 (d, 1H, J=7.5 Hz), 7.34 (d, 1H, J=7.7 Hz), 7.26 (m, 2H), 7.05 (m, 1H), 6.91 (m, 2H), 3.46 (s, 3H), 3.31 (s, 2H), 1.28 (bs, 2H); IR (neat) 2915, 1588, 1496, 1465, 1396, 1349, 1264, 1180, 1137, 930, 835, 756, 699 cm⁻¹; MS (FAB) m/z 282 (M+H)

B-54: C-(4,4-dimethyl-6'-trifluoromethyl-3,4,5,6-tetrahydro-2H-[1,2']bipyridinyl-3'-yl)-methylamine

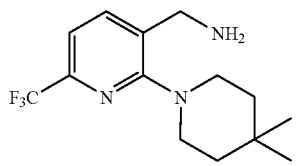

¹H NMR (300 MHz, CDCl₃) δ 7.81 (d, 1H, J=7.7 Hz), 7.25 (d, 1H, J=7.8 Hz), 3.89 (s, 2H), 3.22-3.13 (m, 4H), 1.59-1.46 (m, 4H), 1.01 (s, 6H); IR (neat) 2919, 1639, 1590, 1459, 1423, 1375, 1321, 1252, 1175, 1138, 1047, 954, 835 cm⁻¹; MS (FAB) m/z 288 (M+H)

B-55: 2-(4-p-tolyl-piperazin-1-yl)-4-trifluoromethyl-benzylamine

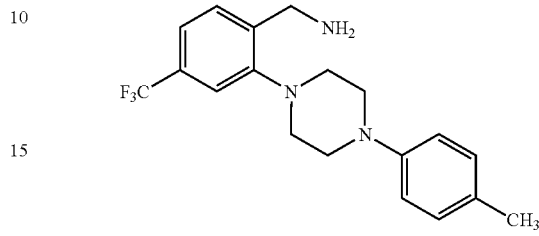

¹H NMR (300 MHz, CDCl₃) δ 7.51 (d, 1H, J=9.0 Hz), 7.37 (d, 1H, J=6.4 Hz), 7.36 (s, 1H), 7.11 (d, 2H, J=8.4 Hz), 6.90 (d, 2H, J=8.4 Hz), 3.99 (s, 2H), 3.10-3.02 (m, 4H), 3.17-3.07 (m, 4H), 2.29 (s, 3H); IR (neat) 2826, 1616, 1515, 1425, 1334, 1308, 1232, 1165, 1123, 1079, 959, 814 cm⁻¹; MS (FAB) m/z 350 (M+H)

B-56: 2-(4-m-tolyl-piperazin-1-yl)-4-trifluoromethyl-benzylamine

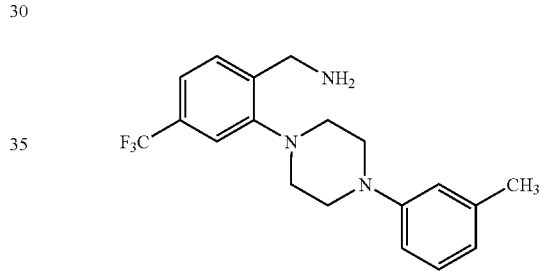

¹H NMR (300 MHz, CDCl₃) δ 7.51 (d, 1H, J=7.5 Hz), 7.37 (d, 1H, J=7.7 Hz), 7.36 (s, 1H), 7.19 (m, 1H), 6.81 (s, 1H), 6.80 (d, 1H, J=7.1 Hz), 6.73 (d, 1H, J=7.5 Hz), 3.99 (s, 2H), 3.51-3.42 (m, 4H), 3.17-3.06 (m, 4H), 2.34 (s, 3H), 1.67 (bs, 2H); IR (neat) 2828, 1604, 1498, 1425, 1336, 1310, 1250, 1166, 1123, 962, 777 cm⁻¹;

MS (FAB) m/z 350 (M+H)

B-57: 4-trifluoromethyl-2-[4-(4-trifluoromethyl-phenyl)-piperazin-1-yl]-benzylamine

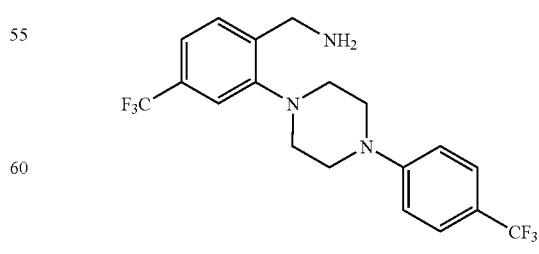

¹H NMR (300 MHz, CDCl₃) δ 7.59-7.42 (m, 3H), 7.38 (d, 1H, J=8.4 Hz), 7.35 (s, 1H), 6.99 (d, 2H, J=8.8 Hz), 4.00 (s, 2H), 3.49-3.35 (m, 4H), 3.19-3.05 (m, 4H); IR (neat) 2838, 1616, 1527, 1425, 1332, 1238, 1163, 1116, 1073, 960, 827 cm⁻¹; MS (FAB) m/z 404 (M+H)

B-58: 2-[4-(4-methoxy-phenyl)-piperazin-1-yl]-4-trifluoromethyl-benzylamine

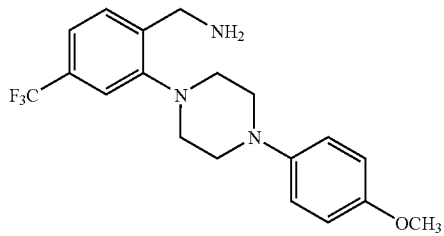 [SMILES: COc1ccc(N2CCN(c3cc(C(F)(F)F)ccc3CN)CC2)cc1]

¹H NMR (300 MHz, CDCl₃) δ 7.50 (d, 1H, J=8.0 Hz), 7.38 (d, 1H, J=7.6 Hz), 7.36 (s, 1H), 6.99-6.83 (m, 4H), 3.98 (s, 2H), 3.79 (s, 3H), 3.29-3.18 (m, 4H), 3.17-3.04 (m, 4H); IR (neat) 3395, 2831, 1511, 1426, 1307, 1244, 1167, 1123, 1078, 1037, 959, 826 cm⁻¹; MS (FAB) m/z 366 (M+H)

B-59: 2-[4-(4-fluoro-phenyl)-piperidin-1-yl]-4-trifluoromethyl-benzylamine

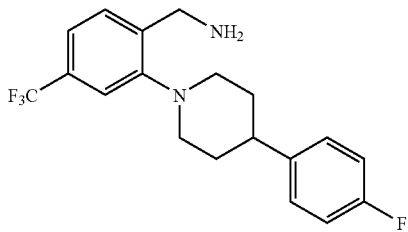 [SMILES: NCc1ccc(C(F)(F)F)cc1N1CCC(c2ccc(F)cc2)CC1]

¹H NMR (300 MHz, CDCl₃) δ 7.48 (d, 1H, J=8.0 Hz), 7.35 (s, 1H), 7.34 (d, 1H, J=7.6 Hz), 7.24 (m, 2H), 7.02 (m, 2H), 3.98 (s, 2H), 3.21 (bd, 2H, J=11.5 Hz), 2.86 (td, 2H, J=11.4, 2.9 Hz), 2.65 (m, 1H), 1.99-1.83 (m, 4H); IR (neat) 2921, 1608, 1509, 1425, 1321, 1224, 1164, 1123, 1079, 949, 884, 833, 732 cm⁻¹; MS (FAB) m/z 353 (M+H)

B-60: C-(6''-trifluoromethyl-3,4,5,6,3',4',5',6'-octahydro-2H,2'H-[1,4'; 1',2'']terpyridin-3''-yl)-methylamine

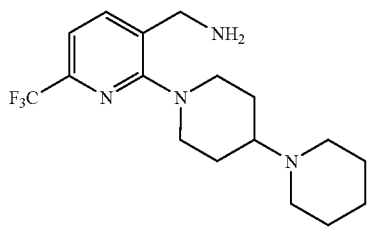 [SMILES: NCc1ccc(C(F)(F)F)nc1N1CCC(N2CCCCC2)CC1]

¹H NMR (300 MHz, CD₃OD) δ 7.91 (d, 1H, J=7.9 Hz), 7.35 (d, 1H, J=7.7 Hz), 3.87 (s, 2H), 3.52-3.56 (m, 2H), 2.82-2.90 (m, 2H), 2.49-2.64 (m, 5H), 1.97-2.01 (m, 2H), 1,50-1.51 (m, 8H); IR (neat) 2933, 2852, 1592, 1457, 14201339, 1135, 956 cm⁻¹; MS (FAB) m/z 343 (M+H)

B-61: C-(4-pyrrolidin-1-yl-6'-trifluoromethyl-3,4,5,6-tetrahydro-2H-[1,2']bipyridinyl-3'-yl)-methylamine

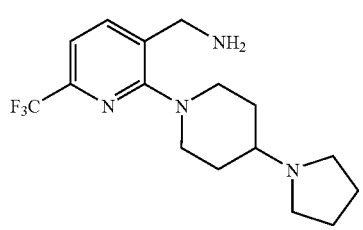 [SMILES: NCc1ccc(C(F)(F)F)nc1N1CCC(N2CCCC2)CC1]

¹H NMR (300 MHz, CD₃OD) δ 7.92 (d, 1H, J=7.7 Hz), 7.36 (d, 1H, J=7.7 Hz), 3.90 (s, 2H), 3.48-3.56 (m, 2H), 2.87-2.95 (m, 2H), 2.72-2.83 (m, 5H), 2.42 (m, 1H), 2.03-2.15 (m, 2H), 1.79-7.92 (m, 5H); IR (neat) 2959, 1592, 1459, 1421, 1339, 1240, 1176, 1135, 957, 834 cm⁻¹; MS (FAB) m/z 329 (M+H)

B-62: C-[6-(chloro-difluoro-methyl)-2-(4-phenyl-piperazin-1-yl)-pyridin-3-yl]-methylamine

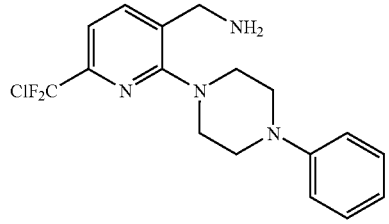

¹H NMR (300 MHz, CDCl₃) δ 7.86 (d, 1H, J=7.5 Hz), 7.26-7.34 (m, 3H), 6.95-7.03 (m, 2H), 6.89 (m, 1H), 3.96 (s, 2H), 3.30-3.46 (m, 8H); IR (neat) 2842, 1594, 1500, 1415, 1375, 1231, 1091, 980, 932, 900, 817, 759, 682 cm⁻¹; MS (FAB) m/z 353 (M+H)

B-63: 2-(4-phenyl-piperazin-1-yl)-4-trifluoromethyl-benzylamine

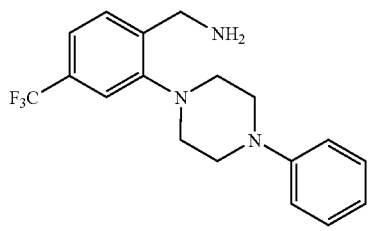 [SMILES: NCc1ccc(C(F)(F)F)cc1N1CCN(c2ccccc2)CC1]

¹H NMR (300 MHz, CDCl₃) δ 7.50 (d, 1H, J=8.3 Hz), 7.24-7.39 (m, 4H), 6.98 (d, 2H, J=8.1 Hz), 6.90 (dd, 1H, J=7.1, 7.1 Hz), 3.99 (s, 2H), 3.22-3.37 (m, 4H), 3.08-3.13 (m,

4H); IR (neat) 2826, 1599, 1500, 1423, 1334, 1308, 1232, 1163, 1121, 1079, 959, 882, 830, 760, 693 cm$^{-1}$; MS (FAB) m/z 336 (M+H)

B-64: 2-azocan-1-yl-4-trifluoromethyl-benzylamine

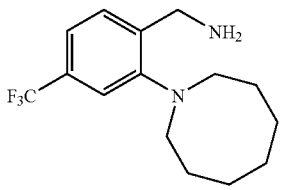

$^1$H NMR (300 MHz, CDCl$_3$) δ 7.46 (d, 1H, J=7.9 Hz), 7.41 (s, 1H), 7.30 (d, 1H, J=8.0 Hz), 4.03 (s, 2H), 3.02-3.14 (m, 4H), 2.44-2.56 (m, 3H), 1.61-1.81 (m, 7H); IR (neat) 2925, 1597, 1505, 1419, 1317, 1212, 1164, 1123, 1080, 982, 907, 827 cm$^{-1}$;

MS (FAB) m/z 287 (M+H)

B-65: 2-(4,4-dimethyl-piperidin-1-yl)-4-trifluoromethyl-benzylamine

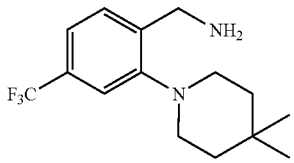 [SMILES: CC1(C)CCN(c2cc(C(F)(F)F)ccc2CN)CC1]

$^1$H NMR (300 MHz, CDCl$_3$) δ 7.44 (d, 1H, J=7.9 Hz), 7.27-7.36 (m, 2H), 3.92 (s, 2H), 2.82-2.84 (m, 4H), 1.46-1.60 (m, 4H), 1.01 (bs, 6H); IR (neat) 2919, 1424, 1337, 1309, 1227, 1166, 1124, 1079, 949, 827 cm$^{-1}$; MS (FAB) m/z 287 (M+H)

B-66: (2-aminomethyl-5-trifluoromethyl-phenyl)-dipropyl-amine

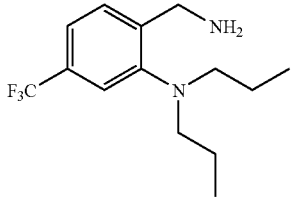 [SMILES: CCCN(CCC)c1cc(C(F)(F)F)ccc1CN]

$^1$H NMR (300 MHz, CDCl$_3$) δ 7.47 (d, 1H, J=7.7 Hz), 7.31-7.37 (m, 2H), 4.01 (s, 2H), 2.83-2.92 (m, 4H), 1.38-1.51 (m, 4H), 0.81-0.92 (m, 6H); IR (neat) 2964, 2875, 1463, 1422, 1327, 1220, 1166, 1125, 1079, 984, 891 cm$^{-1}$; MS (FAB) m/z 275 (M+H)

B-67: 4-trifluoromethyl-2-(4-trifluoromethyl-piperidin-1-yl)-benzylamine

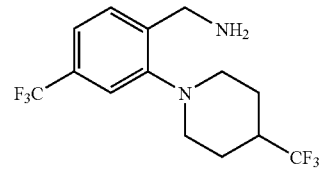

$^1$H NMR (300 MHz, CDCl$_3$) δ 7.50 (d, 1H, J=8.1 Hz), 7.36 (d, 1H, J=7.7 Hz), 7.29 (bs, 1H), 3.95 (s, 2H), 3.14-3.25 (m, 2H), 2.67-2.80 (m, 2H), 2.20 (m, 1H), 1.93-2.05 (m, 2H), 1.75-1.87 (m, 2H); IR (neat) 2958, 2820, 1424, 1333, 1306, 1254, 1128, 1081, 949, 899, 829, 734 cm$^{-1}$; MS (FAB) m/z 327 (M+H)

B-68: 3'-aminomethyl-4-methyl-6'-trifluoromethyl-3,4,5,6-tetrahydro-2H-[1,2']bipyridinyl-5'-carbonic acid ethyl ester

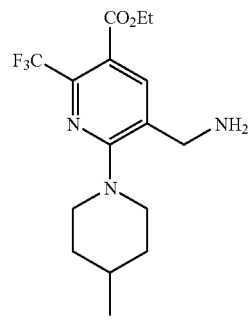 [SMILES: CCOC(=O)c1cc(CN)c(N2CCC(C)CC2)nc1C(F)(F)F]

$^1$H NMR (300 MHz, CDCl$_3$) δ 8.13 (s, 1H), 4.37 (q, 2H, J=7.1 Hz), 3.88 (s, 2H), 3.69 (m, 2H), 2.90 (t, 2H, J=11.5 Hz), 1.67 (m, 3H), 1.32 (m, 5H), 0.95 (d, 3H, J=13.7 Hz); IR (neat) 3391, 2924, 1542, 1452, 1373, 1024, 971, 794 cm$^{-1}$; MS (FAB) m/z 346 (M+H)

B-69: C-[6'-(chloro-difluoro-methyl)-3,5-dimethyl-3,4,5,6-tetrahydro-2H [1,2']bipyridinyl-3'-yl]-methylamine

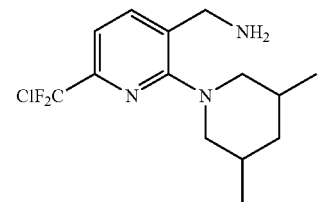

$^1$H NMR (300 MHz, CDCl$_3$) δ 7.75 (d, 1H, J=7.5 Hz), 7.18 (d, 1H, J=7.7 Hz), 3.89 (s, 2H), 3.18 (tt, 4H, J=7.3, 2.0 Hz), 1.60-1.48 (m, 4H), 0.86 (t, 6H, J=7.3 Hz); IR (neat) 3033, 2935, 1726, 1594, 1514, 1456, 1420 cm$^{-1}$; MS (FAB) m/z 304 (M+H)

B-70: (3-aminomethyl-6-trifluoromethyl-pyridin-2-yl)-dipropyl-amine

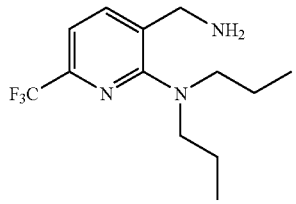 [SMILES: CCCN(CCC)c1nc(C(F)(F)F)ccc1CN]

$^1$H NMR (300 MHz, CDCl$_3$) δ 7.75 (d, 1H, J=7.5 Hz), 7.18 (d, 1H, J=7.7 Hz), 3.89 (s, 2H), 3.18 (tt, 4H, J=7.3, 2.0 Hz), 1.60-1.48 (m, 4H), 0.86 (t, 6H, J=7.3 Hz); IR (neat) 3367, 2966, 2875, 1593, 1465, 1419, 1338 cm$^{-1}$; MS (FAB) m/z 261 (M+H)

B-71: C-(6'-tert-butyl-3,4,5,6-tetrahydro-2H-[1,2']bipyridinyl-3'-yl)-methylamine

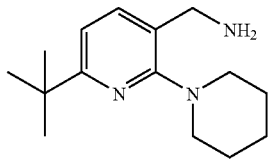 [SMILES: CC(C)(C)c1ccc(CN)c(N2CCCCC2)n1]

$^1$H NMR (300 MHz, CDCl$_3$) δ 7.48 (d, 1H, J=7.7 Hz), 6.90 (d, 1H, J=7.7 Hz), 3.83 (s, 2H), 3.08 (m, 4H), 1.70-1.50 (m, 6H), 1.30 (s, 9H); IR (neat) 2933, 2856, 1635, 1582, 1445, 1402, 1370 cm$^{-1}$; MS (FAB) m/z 248 (M+H)

B-72: C-(6-tert-butyl-2-pyrrolidin-1-yl-pyridin-3-yl)-methylamine

$^1$H NMR (300 MHz, CDCl$_3$) δ 7.36 (d, 1H, J=7.5 Hz), 6.70 (d, 1H, J=7.7 Hz), 3.86 (s, 2H), 3.53 (m, 4H), 1.96-1.90 (m, 4H), 1.30 (s, 9H); IR (neat) 2959, 2866, 1583, 1450, 1355, 1251, 1099 cm$^{-1}$; MS (FAB) m/z 234 (M+H)

B-73: C-(6'-tert-butyl-4-methyl-3,4,5,6-tetrahydro-2H-[1,2']bipyridinyl-3'-yl)-methylamine

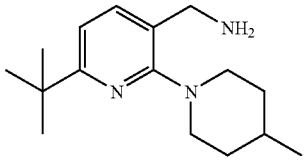 [SMILES: CC1CCN(c2nc(C(C)(C)C)ccc2CN)CC1]

$^1$H NMR (300 MHz, CDCl$_3$) δ 7.48 (d, 1H, J=7.7 Hz), 6.90 (d, 1H, J=7.9 Hz), 3.86 (s, 2H), 3.36 (m, 2H), 2.82 (m, 2H), 1.70-1.67 (m, 2H), 1.57-1.31 (m, 3H), 1.30 (s, 9H), 0.98 (d, 3H, J=6.4 Hz); IR (neat) 2954, 2921, 2869, 1635, 1583, 1451, 1403 cm$^{-1}$; MS (FAB) m/z 262 (M+H)

B-74: C-(2-azepan-1-yl-6-tert-butyl-pyridin-3-yl)-methylamine

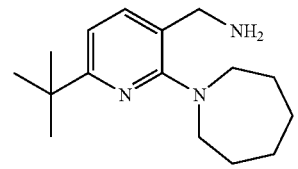 [SMILES: CC(C)(C)c1ccc(CN)c(N2CCCCCC2)n1]

$^1$H NMR (300 MHz, CDCl$_3$) δ 7.40 (d, 1H, J=7.7 Hz), 6.76 (d, 1H, J=7.7 Hz), 3.82 (s, 2H), 3.49-3.42 (m, 4H), 1.80 (m, 4H), 1.62 (m, 4H), 1.30 (s, 9H); IR (neat) 3396, 2925, 2856, 1643, 1582, 1454, 1364 cm$^{-1}$; MS (FAB) m/z 262 (M+H)

B-75: C-(6'-tert-butyl-4-phenyl-3,4,5,6-tetrahydro-2H-[1,2']bipyridinyl-3'-yl)-methylamine

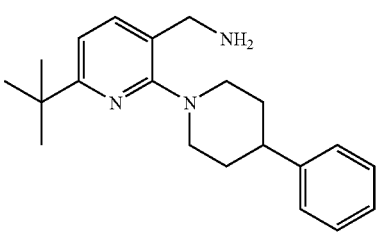 [SMILES: CC(C)(C)c1ccc(CN)c(N2CCC(c3ccccc3)CC2)n1]

$^1$H NMR (300 MHz, CDCl$_3$) δ 7.52 (d, 1H, J=7.7 Hz), 7.36-7.19 (m, 5H), 6.95 (d, 1H, J=7.7 Hz), 3.88 (s, 2H), 3.55-3.51 (m, 2H), 3.48 (s, 3H), 3.03-2.93 (m, 2H), 2.75-2.64 (m, 1H), 2.05-1.54 (m, 4H), 1.33 (s, 9H); IR (neat) 2957, 1644, 1578, 1452, 1401, 1370, 1231 cm$^{-1}$; MS (FAB) m/z 324 (M+H)

B-76: (3-aminomethyl-6-tert-butyl-pyridin-2-yl)-dipropyl-amine

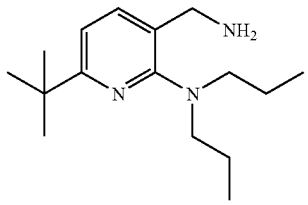 [SMILES: CCCN(CCC)c1nc(C(C)(C)C)ccc1CN]

$^1$H NMR (300 MHz, CDCl$_3$) δ 7.45 (d, 1H, J=7.7 Hz), 6.94 (d, 1H, J=7.7 Hz), 3.99 (s, 2H), 3.25-3.05 (m, 4H), 1.61-1.38 (m, 4H), 1.33 (s, 9H), 0.90-0.80 (m, 6H); IR (neat) 2961, 2871, 1634, 1583, 1460, 1369, 1243 cm$^{-1}$; MS (FAB) m/z 264 (M+H)

B-77: (3-aminomethyl-6-trifluoromethyl-pyridin-2-yl)-diethyl-amine

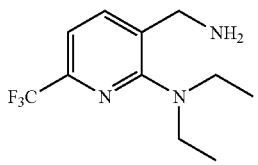 [SMILES: CCN(CC)c1nc(C(F)(F)F)ccc1CN]

$^1$H NMR (300 MHz, CDCl$_3$) δ 7.67 (d, 1H, J=7.5 Hz), 7.07 (d, 1H, J=7.7 Hz), 3.79 (s, 2H), 3.20-3.09 (q, 4H, J=7.0 Hz), 0.98 (t, 4H, J=7.0 Hz); IR (neat) 2924, 1588, 1429, 1332, 1219, 1170, 1129 cm$^{-1}$; MS (FAB) m/z 248 (M+H)

B-78: (3-aminomethyl-6-trifluoromethyl-pyridin-2-yl)-dimethyl-amine

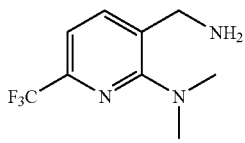

$^1$H NMR (300 MHz, CDCl$_3$) δ 7.72 (d, 1H, J=7.5 Hz), 7.12 (d, 1H, J=7.5 Hz), 4.01 (s, 2H), 2.85 (s, 4H); IR (neat) 2923, 1596, 1488 1394, 1350, 1272, 1175 cm$^{-1}$; MS (FAB) m/z 219 (M+H)

B-79: (3-aminomethyl-6-trifluoromethyl-pyridin-2-yl)-benzyl-amine

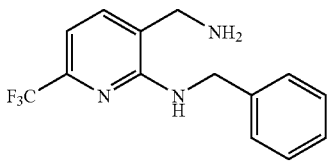 [SMILES: NCc1ccc(C(F)(F)F)nc1NCc1ccccc1]

$^1$H NMR (300 MHz, CDCl$_3$) δ 7.29-7.10 (m, 6H), 6.70 (d, 1H, J=7.4 Hz), 4.54 (d, 1H, J=2.0 Hz), 3.66 (s, 2H), 1.41 (bs, 2H); IR (neat) 3298, 2920, 1609, 1530, 1453, 1354 1309 cm$^{-1}$; MS (FAB) m/z 282 (M+H)

B-80: C-(4,4'-dimethyl-6'-trifluoromethyl-3,4,5,6-tetrahydro-2H-[1,2']bipyridinyl-3'-yl)-methylamine

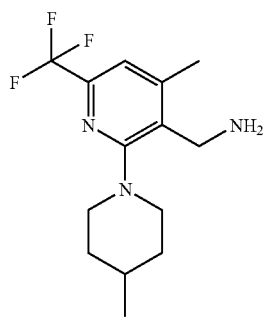 [SMILES: Cc1cc(C(F)(F)F)nc(N2CCC(C)CC2)c1CN]

$^1$H NMR (300 MHz, CDCl$_3$) δ 7.17 (s, 1H), 4.09 (s, 2H), 3.31 (m, 2H), 2.89 (m, 2H), 2.43 (s, 3H), 1.76 (m, 2H), 1.53 9 m, 1H), 1.37 (m, 2H), 1.44 (bs, 2H), 0.98 (d, 3H, J=6.3 Hz); IR (neat) 3380, 2952, 1598, 1567, 1465, 1373, 1311, 1276, 1176, 1138, 968, 916 cm$^{-1}$; MS (FAB) m/z 288 (M+H)

Method 3:

Compounds of the general formula VI-B (1.5 mmol), in which R$^5$, R$^{12}$, R$^{13}$, U, T and V have the above-stated meaning and m denotes 0, 1, 2 or 3, are dissolved in diethylether (3 mL) and a suspension of lithium aluminium hydride (3 mmol) in diethylether (5 mL) is slowly added. The reaction mixture is heated to reflux for 4 hours, and methanol and 1 N aq. NaOH soln. are slowly added at 0° C. The reaction mixture is diluted with methanol and filtered over celite. The solvent is evaporated under a vacuum and the residue is purified by flash chromatography (SiO$_2$, different mixtures of methylene chloride and methanol).

The following compound B-81 was prepared according to the above-stated procedure.

B-81: C-(4-methylene-6'-trifluoromethyl-3,4,5,6-tetrahydro-2H-[1,2']bipyridinyl-3'-yl)-methylamine

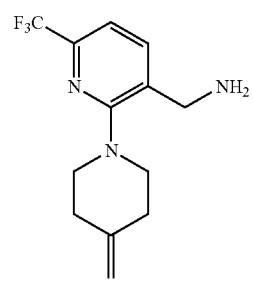 [SMILES: C=C1CCN(c2nc(C(F)(F)F)ccc2CN)CC1]

$^1$H NMR (CDCl$_3$) δ 7.84 (d, 1H, J=7.7 Hz), 7.27 (d, 1H, J=7.0 Hz), 4.76 (s, 2H), 3.94 (s, 2H), 3.25 (t, 4H, J=5.7 Hz), 2.38 (t, 4H, J=5.7 Hz)

Method 4:

Compounds of the general formula VI-B (0.39 mmol), in which $R^5$, $R^{12}$, $R^{13}$, U, T and V have the above-stated meaning and m denotes 0, 1, 2 or 3, are dissolved in methanol (8 mL) and $NiCl_2.H_2O$ (0.78 mmol) and sodium borohydride (1.56 mmol) are slowly added at 0° C. The reaction mixture is heated to reflux for 12 hours. The reaction mixture is diluted with methanol and filtered over celite. The solvent is evaporated under a vacuum and the residue is purified by flash chromatography ($SiO_2$, different mixtures of methylene chloride and methanol).

The following compounds B-82 to B-84 were obtained according to the above-stated general method:

B-82: (3-aminomethyl-6-trifluoromethyl-pyridin-2-yl)-butyl-methyl-amine

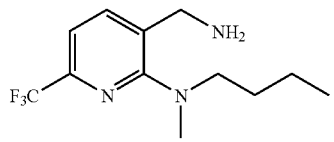 [SMILES: CCCCN(C)c1nc(C(F)(F)F)ccc1CN]

$^1$H NMR (300 MHz, $CDCl_3$) δ 7.75 (d, 1H, J=7.5 Hz), 7.18 (d, 1H, J=7.7 Hz), 3.91 (bs, 2H), 3.19 (bt, 2H), 2.89 (bs, 3H), 1.52-1.65 (m, 2H), 1.21-1.39 (m, 2H), 0.92 (t, 3H, J=7.3 Hz); IR (neat) 2961, 2868, 1594, 1465, 1400, 1334, 1176, 1136, 831 $cm^{-1}$; MS (FAB) m/z 262 (M+H)

B-83: C-(4-phenyl-6'-trifluoromethyl-3,6-dihydro-2H-[1,2']bipyridinyl-3'-yl)-methylamine

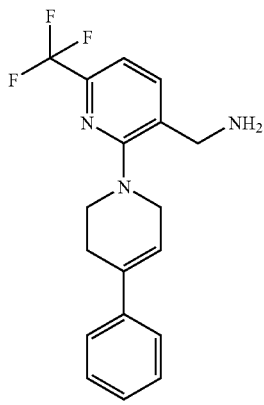 [SMILES: NCc1ccc(C(F)(F)F)nc1N1CC=C(c2ccccc2)CC1]

$^1$H NMR (300 MHz, $CDCl_3$) δ 7.85 (d, 1H, J=7.5 Hz), 7.43 (d, 1H, J=7.5 Hz), 7.22-7.35 (m, 5H), 6.20 (m, 1H), 3.97-4.01 (m, 4H), 3.41-3.46 (m, 4H), 2.74 (bs, 2H); IR (neat) 3395, 2922, 1593, 1422, 1372, 1338, 1267, 1175, 1135, 959, 833, 750, 697 $cm^{-1}$; MS (FAB) m/z 334 (M+H)

B-84: C-[4-(4-fluoro-phenyl)-6'-trifluoromethyl-3,6-dihydro-2H-[1,2']bipyridinyl-3'-yl]-methylamine

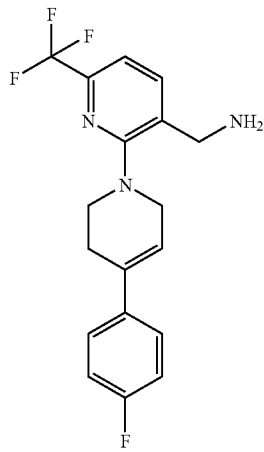 [SMILES: NCc1ccc(C(F)(F)F)nc1N1CC=C(c2ccc(F)cc2)CC1]

$^1$H NMR (300 MHz, $CDCl_3$) δ 7.86 (d, 1H, J=7.8 Hz), 7.40 (m, 3H), 7.03 (dd, 2H, J=9.0, 8.3 Hz), 6.14 (bs, 1H), 3.97-4.01 (m, 4H), 3.46 (m, 2H), 2.70 (m, 2H), 1.82 (bs, 2H); IR (neat) 3365, 2922, 1600, 1510, 1425, 1340, 1230, 1174, 1135, 963, 835 $cm^{-1}$; MS (FAB) m/z 334 (M+H)

3. General procedure for the preparation of amines of general formula V-Ba and V-Bb Amines of general formula V-Ba and VB-b are prepared as described in scheme 2. depicted below.

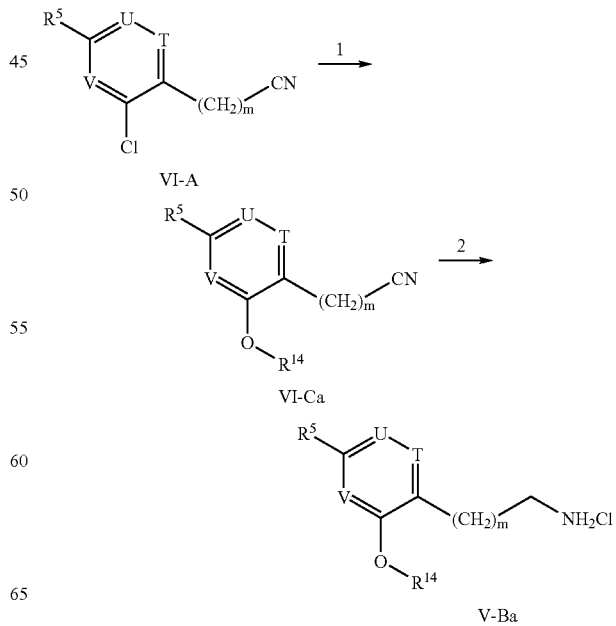

scheme 2.

-continued

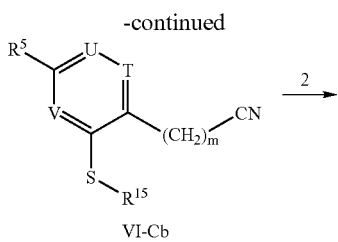
VI-Cb

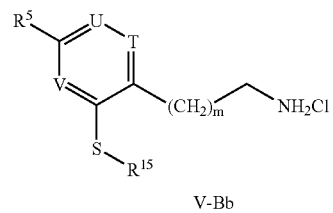
V-Bb

Stage 1: Preparation of nitrites of general formula VI-Ca and VI-Cb Compounds of general formula VI-A (1 equivalent), wherein $R^5$, U, T and V have the meaning as described above and m denotes 0, 1, 2 or 3, are treated with an alcohol of general formula HO—$R^{14}$ (3.5 equivalents) and DBU [1,8-diaza-bicyclo[5.4.0]andec-7-ene] (3.5 equivalents) in acetonitrile (7 mL per mmol of compound of general formula VI-A) for 12 hours at room temperature. The reaction mixture is extracted repeatedly with EA. The combined organic phases are washed with sat. aq. NaCl soln., dried over $MgSO_4$ and the solvent is removed under a vacuum. The residue is in each case purified via column chromatography ($SiO_2$, different mixtures of hexanes and EA).

Alternatively, compounds of general formula VI-Ca or VI-Cb (1 equivalent), wherein $R^5$, U, T and V have the meaning as described above, m denotes 0, 1, 2 or 3 and $R^{14}$ or $R^{15}$ denotes hydrogen, are treated with a compound of general formula $R^{14}$—Br or $R^{15}$—Br (4 equivalents), wherein $R^{14}$ and $R^{15}$ have the above-stated meaning and are different from hydrogen, in a mixture of acetonitrile and dimethyl formamide (1:2), optionally in the presence of 18-crown-6-ether as catalyst. The reaction mixture was refluxed for 12 h and allowed to cool to room temperature. The mixture was extracted with EA (30 mL). The organic phase was dried over $MgSO_4$, filtered, and concentrated in vacuo. The residue was purified by flash column chromatography on silica gel using EA/hexanes (1:1) as eluent.

The following compounds A-104 to A-173 were obtained according to the above-stated general method:

A-104: 2-(3-methyl-butoxy)-6-trifluoromethyl-nicotinonitrile

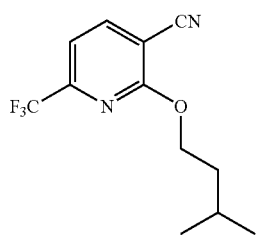 [SMILES: CC(C)CCOc1nc(C(F)(F)F)ccc1C#N]

$^1$H NMR (300 MHz, $CDCl_3$) δ 8.05 (d, 1H, J=7.8 Hz), 7.33 (d, 1H, J=7.8 Hz), 4.53 (t, 2H, J=6.9 Hz), 1.65-1.96 (m, 3H), 0.98 (d, 6H, J=6.3 Hz); MS (FAB) m/z 259 (M+H)

A-105: 2-(3,3-dimethyl-butoxy)-6-trifluoromethyl-nicotinonitrile

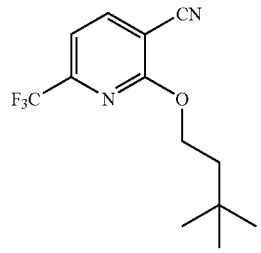 [SMILES: CC(C)(C)CCOc1nc(C(F)(F)F)ccc1C#N]

$^1$H NMR (300 MHz, $CDCl_3$) δ 8.05 (d, 1H, J=7.8 Hz), 7.33 (d, 1H, J=7.8 Hz), 4.56 (t, 2H, J=6.9 Hz), 1.77 (t, 2H, J=6.9 Hz), 1.01 (s, 9H); MS (FAB) m/z 273 (M+H)

A-106: 2-(2-methyl-cyclopropylmethoxy)-6-trifluoromethyl-nicotinonitrile

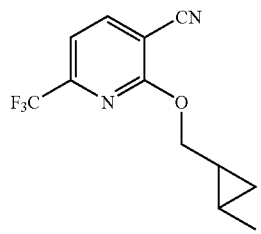 [SMILES: CC1CC1COc1nc(C(F)(F)F)ccc1C#N]

$^1$H NMR (300 MHz, $CDCl_3$) δ 8.05 (d, 1H, J=7.8 Hz), 7.32 (d, 1H, J=7.8 Hz), 4.33 (m, 2H), 1.06 (d, 3H, J=6.0 Hz), 1.02 (m, 1H), 0.85 (m, 1H), 0.56 (m, 1H), 0.46 (m, 1H); MS (FAB) m/z 257 (M+H)

A-107: 2-butoxy-6-(chloro-difluoro-methyl)-nicotinonitrile

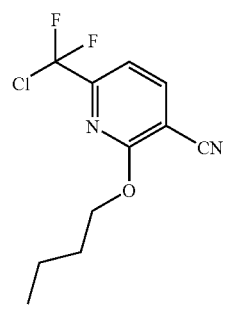 [SMILES: CCCCOc1nc(C(F)(F)Cl)ccc1C#N]

$^1$H NMR (300 MHz, $CDCl_3$) d 8.02 (d, 1H, J=7.8 Hz), 7.28 (d, 1H, J 0 7.8 Hz), 4.59 (t, 2H, J=7.2 Hz), 1.84 (m, 2H), 1.50 (m, 2H), 0.99 (t, 3H, J=6.9 Hz); IR (KBr) 2964, 2210, 1590, 1432, 1373, 1325, 1190 $cm^{-1}$; MS (FAB) m/z 265 (M+H)

A-108: 2-phenoxy-6-trifluoromethyl-nicotinonitrile

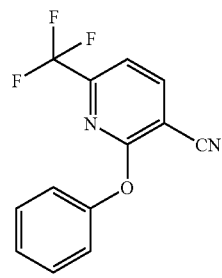 [SMILES: N#Cc1ccc(C(F)(F)F)nc1Oc1ccccc1]

$^1$H NMR (300 MHz, CDCl$_3$) δ 8.18 (d, 1H, J=7.8 Hz), 7.41-7.47 (m, 2H), 7.21-7.31 (m, 4H); IR (neat) 3100, 2950, 2210, 1580, 1490, 1462, 1411, 1194, 1271, 1150, 947 cm$^{-1}$; MS (FAB) m/z 265 (M+H)

A-109: 2-(1-butyl-pentyloxy)-6-trifluoromethyl-nicotinonitrile

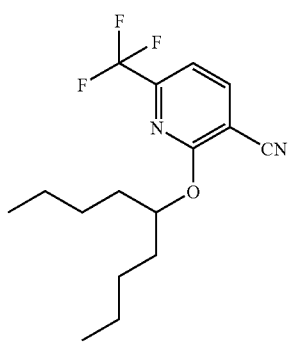 [SMILES: CCCCC(CCCC)Oc1nc(C(F)(F)F)ccc1C#N]

$^1$H NMR (300 MHz, CDCl$_3$) δ 8.03 (d, 1H, J=7.8 Hz), 7.29 (d, 1H, J=7.8 Hz), 5.36 (m, 1H), 1.65-1.78 (m, 4H), 1.32-1.39 (m, 8H), 0.90 (t, 6H, J=7.2 Hz) IR (neat) 2960, 2867, 2236, 1590, 1463, 1434, 1347, 1265, 1186, 1152, 1119, 966, 840, 743 cm$^{-1}$; MS (FAB) m/z 315 (M+H)

A-110: 2-(1-ethyl-propoxy)-6-trifluoromethyl-nicotinonitrile

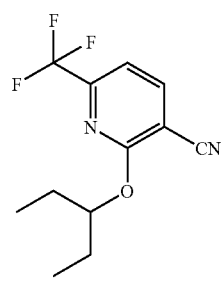 [SMILES: CCC(CC)Oc1nc(C(F)(F)F)ccc1C#N]

$^1$H NMR (300 MHz, CDCl$_3$) δ 7.96 (d, 1H, J=7.8 Hz), 7.29 (d, 1H, J=7.8 Hz), 5.15 (m, 1H), 1.72 (m, 4H), 0.89 (t, 6H, J=6.8 Hz); IR (neat) 2974, 2236, 1590, 1462, 1435, 1348, 1266, 1186, 1151, 1117, 967, 840 cm$^{-1}$; MS (FAB) m/z 259 (M+H)

A-111: 2-(1-propyl-butoxy)-6-trifluoromethyl-nicotinonitrile

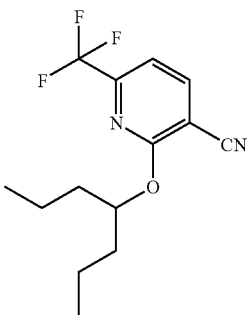 [SMILES: CCCC(CCC)Oc1nc(C(F)(F)F)ccc1C#N]

$^1$H NMR (300 MHz, CDCl$_3$) δ 8.04 (d, 1H, J=7.8 Hz), 7.20 (d, 1H, J=7.8 Hz), 5.41 (m, 1H), 1.69 (m, 4H), 1.43 (m, 4H), 0.93 (t, 6H, J=6.9 Hz) IR (neat) 2964, 2875, 2236, 1590, 1462, 1435, 1347, 1267, 1187, 1152, 1119, 979, 839, 744 cm$^{-1}$; MS (FAB) m/z 287 (M+H)

A-112: 2-(1-isobutyl-3-methyl-butoxy)-6-trifluoromethyl-nicotinonitrile

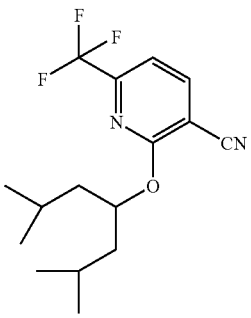 [SMILES: CC(C)CC(CC(C)C)Oc1nc(C(F)(F)F)ccc1C#N]

$^1$H NMR (300 MHz, CDCl$_3$) δ 7.97 (d, 1H, J=7.8 Hz), 7.23 (d, 1H, J=7.8 Hz), 5.49 (m, 1H), 1.60-1.78 (m, 6H), 0.84 (d, 12H, J=6.9 Hz); IR (neat) 3365, 2958, 2871, 2237, 1590, 1464, 1434, 1347, 1266, 1187, 1154, 964, 839 cm$^{-1}$; MS (FAB) m/z 315 (M+H)

A-113: 2-(4,4-dimethyl-cyclohexyloxy)-6-trifluoromethyl-nicotinonitrile

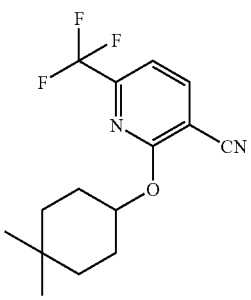 [SMILES: CC1(C)CCC(Oc2nc(C(F)(F)F)ccc2C#N)CC1]

¹H NMR (300 MHz, CDCl₃) δ 8.02 (d, 1H, J=7.8 Hz), 7.28 (d, 1H, J=7.8 Hz), 5.21 (m, 1H), 1.73-1.96 (m, 4H), 1.55 (m, 2H), 1.33 (m, 2H), 0.99 (s, 3H), 0.96 (s, 3H);

MS (FAB) m/z 299 (M+H)

A-114: 2-(3-methoxy-propoxy)-6-trifluoromethyl-nicotinonitrile

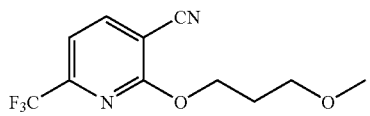 [SMILES: COCCCOc1nc(C(F)(F)F)ccc1C#N]

¹H NMR (300 MHz, CDCl₃) δ 8.06 (d, 1H, J=7.7 Hz), 7.35 (d, 1H, J=7.7 Hz), 4.59 (t, 2H, J=6.2 Hz), 3.59 (t, 2H, J=6.1 Hz), 3.37 (s, 3H), 2.07-2.17 (m, 2H); IR (neat) 2929, 2223, 1591, 1463, 1375, 1347, 1312, 1267, 1188, 1150, 1119, 977, 922, 742 cm⁻¹; MS (FAB) m/z 261 (M+H)

A-115: 2-(3-ethoxy-propoxy)-6-trifluoromethyl-nicotinonitrile

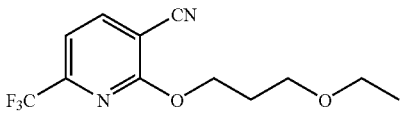

¹H NMR (300 MHz, CDCl₃) δ 8.05 (d, 1H, J=7.7 Hz), 7.34 (d, 1H, J=7.7 Hz), 4.60 (t, 2H, J=6.2 Hz), 3.62 (d, 2H, J=6.2 Hz), 3.50 (q, 2H, J=7.5 Hz), 2.04-2.16 (m, 2H), 1.99 (t, 3H, J=7.0 Hz); IR (neat) 2976, 2870, 2237, 1590, 1470, 1436, 1375, 1347, 1269, 1187, 1150, 1118, 994, 842, 743 cm⁻¹

MS (FAB) m/z 275 (M+H)

A-116: 2-(2-phenoxy-ethoxy)-6-trifluoromethyl-nicotinonitrile

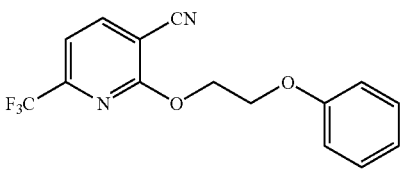 [SMILES: N#Cc1ccc(C(F)(F)F)nc1OCCOc1ccccc1]

¹H NMR (300 MHz, CDCl₃) δ 8.07 (d, 1H, J=7.7 Hz), 7.38 (d, 1H, J=7.7 Hz), 7.24-7.35 (m, 2H), 6.01-7.02 (m, 3H), 4.86 (t, 2H, J=5.0 Hz), 4.39 (t, 2H, J=5.0 Hz); IR (neat) 2235, 1589, 1429, 1348, 1241, 1193, 1142, 1112, 963, 840, 753, 692 cm⁻¹;

MS (FAB) m/z 309 (M+H)

A-117: 2-butoxy-6-trifluoromethyl-nicotinonitrile

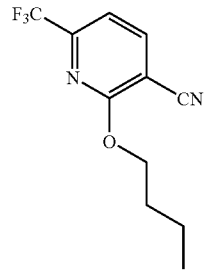 [SMILES: CCCCOc1nc(C(F)(F)F)ccc1C#N]

¹H NMR (CDCl₃) δ 8.04 (d, 1H, J=7.7 Hz), 7.33 (d, 1H, J=7.7 Hz), 4.50 (t, 2H, J=6.6 Hz), 1.87-1.78 (m, 2H), 1.58-1.45 (m, 2H), 0.99 (t, 3H, J=7.3 Hz)

IR (neat) 2965, 2240, 1591, 1468, 1436, 1349, 1270, 1189, 1151 cm⁻¹

A-118: 2-isopropoxy-6-trifluoromethyl-nicotinonitrile

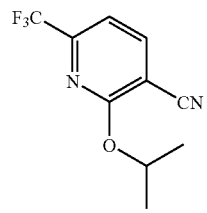 [SMILES: CC(C)Oc1nc(C(F)(F)F)ccc1C#N]

¹H NMR (CDCl₃) δ 8.04 (d, 1H, J=7.7 Hz), 7.30 (d, 1H, J=7.7 Hz), 5.46 (m, 1H), 1.43 (d, 6H, J=6.2 Hz)

IR (neat) 2988, 2237, 1591, 1435, 1343, 1269, 1187, 1150, 1115, 969 cm⁻¹

A-119: 2-cyclopentyloxy-6-trifluoromethyl-nicotinonitrile

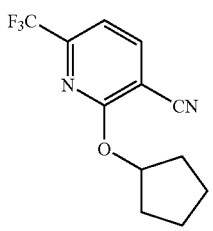 [SMILES: N#Cc1ccc(C(F)(F)F)nc1OC1CCCC1]

¹H NMR (CDCl₃) δ 8.02 (dd, 1H, J=7.7, 0.6 Hz), 7.30 (d, 1H, J=7.5 Hz), 5.60-5.54 (m, 1H), 2.09-1.57 (m, 8H)

IR (neat) 2969, 2236, 1590, 1435, 1350, 1268, 1187, 1150, 974 cm⁻¹

A-120: 2-cyclohexyloxy-6-trifluoromethyl-nicotinonitrile

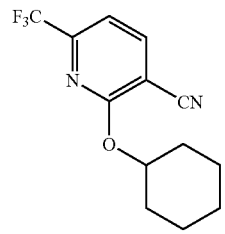 [SMILES: N#Cc1ccc(C(F)(F)F)nc1OC1CCCCC1]

$^1$H NMR (CDCl$_3$) δ 8.02 (d, 1H, J=7.7 Hz), 7.29 (d, 1H, J=7.7 Hz), 5.24 (m, 1H), 2.03-1.95 (m, 2H), 1.87-1.40 (m, 8H); IR (neat) 2940, 2862, 2236, 1591, 1436, 1348, 1269, 1188, 1150, 971 cm$^{-1}$

A-121: 2-methoxy-6-trifluoromethyl-nicotinonitrile

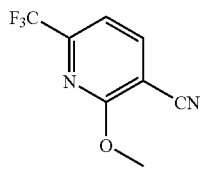

$^1$H NMR (CDCl$_3$) δ 8.06 (d, 1H, J=7.7 Hz), 7.37 (d, 1H, J=7.7 Hz), 4.13 (s, 3H); IR (neat) 2924, 2238, 1592, 1475, 1392, 1349, 1272, 1186, 1149, 1009 cm$^{-1}$

A-122: 2-hexyloxy-6-trifluoromethyl-nicotinonitrile

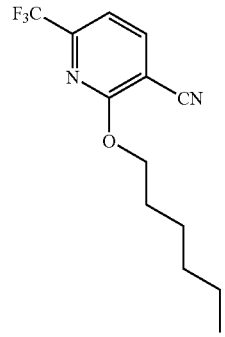 [SMILES: CCCCCCOc1nc(C(F)(F)F)ccc1C#N]

$^1$H NMR (CDCl$_3$) δ 8.04 (dd, 1H, J=7.7, 0.7 Hz), 7.33 (d, 1H, J=7.7 Hz), 4.49 (t, 2H, J=6.6 Hz), 1.89-1.79 (m, 2H), 1.50-1.30 (m, 6H), 0.91 (t, 3H); IR (neat) 2931, 1591, 1469, 1437, 1348, 1269, 1189, 1151 cm$^{-1}$

A-123: 2-isobutoxy-6-trifluoromethyl-nicotinonitrile

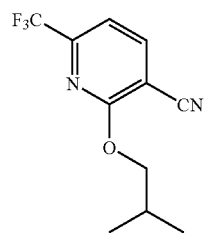 [SMILES: CC(C)COc1nc(C(F)(F)F)ccc1C#N]

$^1$H NMR (CDCl$_3$) δ 8.04 (d, 1H, J=7.7 Hz), 7.33 (d, 1H, J=7.7 Hz), 4.26 (d, 1H, J=6.6 Hz), 2.17 (m, 1H), 1.06 (d, 6H, J=6.8 Hz); IR (neat) 2968, 2237, 1592, 1469, 1436, 1347, 1268, 1188, 1151, 1119, 1000 cm$^{-1}$

A-124: 2-cyclopropylmethoxy-6-trifluoromethyl-nicotinonitrile

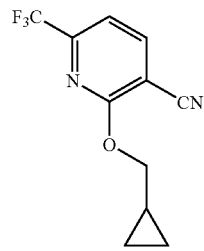 [SMILES: N#Cc1ccc(C(F)(F)F)nc1OCC1CC1]

$^1$H NMR (CDCl$_3$) δ 8.05 (d, 1H, J=7.7 Hz), 7.33 (d, 1H, J=7.7 Hz), 4.35 (d, 2H, J=7.1 Hz), 1.40-1.30 (m, 1H), 0.68-0.62 (m, 2H), 0.45-0.40 (m, 2H); IR (neat) 2960, 2240, 1592, 1468, 1438, 1391, 1355, 1266, 1187, 1149, 1119 cm$^{-1}$

A-125: 2-cyclobutylmethoxy-6-trifluoromethyl-nicotinonitrile

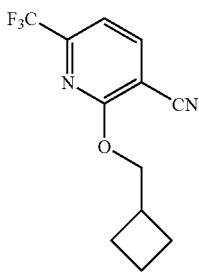 [SMILES: N#Cc1ccc(C(F)(F)F)nc1OCC1CCC1]

$^1$H NMR (CDCl$_3$) δ 8.04 (d, 1H, J=7.7 Hz), 7.33 (d, 1H, J=7.7 Hz), 4.46 (d, 2H, J=6.6 Hz), 2.88-2.78 (m, 1H), 2.20-1.85 (m, 6H); IR (neat) 2941, 2238, 1591, 1469, 1435, 1349, 1269, 1188, 1150, 1117, 988 cm$^{-1}$ A-126: 2-propoxy-6-trifluoromethyl-nicotinonitrile

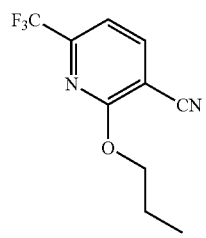 [SMILES: CCCOc1nc(C(F)(F)F)ccc1C#N]

$^1$H NMR (CDCl$_3$) δ 8.05 (dd, 1H), 7.33 (d, 1H, J=7.7 Hz), 4.46 (t, 2H, J=6.6 Hz), 1.93-1.82 (m, 2H), 1.06 (t, 3H, J=7.5 Hz)

IR (neat) 2974, 2238, 1592, 1437, 1346, 1271, 1190, 1151, 979 cm$^{-1}$

A-127: 2-pentyloxy-6-trifluoromethyl-nicotinonitrile

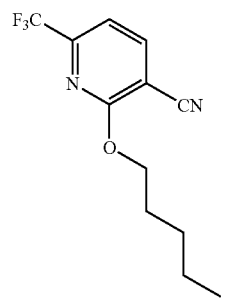 [SMILES: CCCCCOc1nc(C(F)(F)F)ccc1C#N]

$^1$H NMR (CDCl$_3$) δ 8.04 (dd, 1H), 7.33 (d, 1H, J=7.7 Hz), 4.49 (t, 2H, J=6.8 Hz), 1.89-1.80 (m, 2H), 1.51-1.35 (m, 4H), 0.94 (t, 3H, J=6.9 Hz); IR (neat) 2962, 2240, 1592, 1437, 1349, 1270, 1190, 1151 cm$^{-1}$ A-128: 2-cyclobutoxy-6-trifluoromethyl-nicotinonitrile

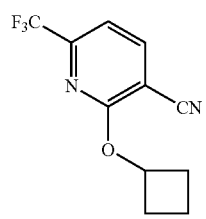 [SMILES: N#Cc1ccc(C(F)(F)F)nc1OC1CCC1]

$^1$H NMR (CDCl$_3$) δ 8.03 (dd, 1H, J=7.7, 0.7 Hz), 7.32 (d, 1H, J=7.7 Hz), 5.32 (m, 1H), 2.56-2.46 (m, 2H), 2.32-2.19 (m, 2H), 1.94-1.66 (m, 2H)

IR (neat) 2995, 2238, 1590, 1465, 1434, 1345, 1269, 1188, 1150 cm$^{-1}$

A-129: 2-(4-methyl-cyclohexyloxy)-6-trifluoromethyl-nicotinonitrile

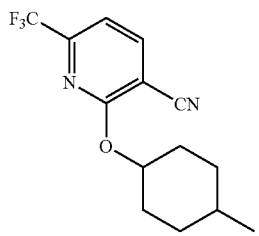 [SMILES: CC1CCC(Oc2nc(C(F)(F)F)ccc2C#N)CC1]

$^1$H NMR (CDCl$_3$) δ 8.02 (d, 1H, J=7.7 Hz), 7.29 (d, 1H, J=7.7 Hz), 5.11 (m, 1H), 2.20-2.12 (m, 2H), 1.85-1.75 (m, 2H), 1.63-1.43 (m, 3H), 1.20-1.05 (m, 2H), 0.94 (d, 3H, J=6.6 Hz); IR (neat) 2950, 2238, 1591, 1462, 1436, 1350, 1267, 1187, 1151, 993 cm$^{-1}$ A-130: 2-cyclopentylmethoxy-6-trifluoromethyl-nicotinonitrile

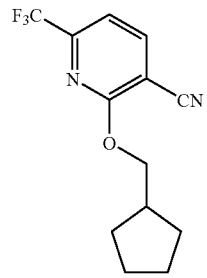 [SMILES: N#Cc1ccc(C(F)(F)F)nc1OCC1CCCC1]

$^1$H NMR (CDCl$_3$) δ 8.04 (dd, 1H, J=7.7, 0.5 Hz), 7.33 (d, 1H, J=7.7 Hz), 4.37 (d, 2H, J=6.9 Hz), 2.43 (m, 1H), 1.91-1.81 (m, 2H), 1.71-1.56 (m, 4H), 1.45-1.34 (m, 2H); IR (neat) 2957, 2236, 1592, 1436, 1346, 1269, 1188, 1150, 988 cm$^{-1}$ A-131: 2-ethoxy-6-trifluoromethyl-nicotinonitrile

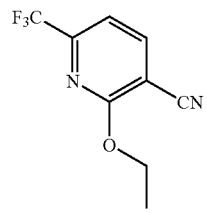

$^1$H NMR (CDCl$_3$) δ 8.05 (d, 1H, J=7.7 Hz), 7.33 (d, 1H, J=7.7 Hz), 4.57 (q, 2H, J=7.0 Hz), 1.47 (t, 3H, J=7.0 Hz); IR (neat) 2990, 2238, 1591, 1437, 1389, 1348, 1269, 1189, 1150, 1024 cm$^{-1}$ A-132: 2-(4-tert-butyl-cyclohexyloxy)-6-trifluoromethyl-nicotinonitrile

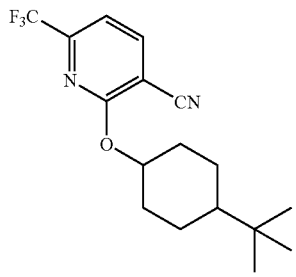 [SMILES: CC(C)(C)C1CCC(Oc2nc(C(F)(F)F)ccc2C#N)CC1]

$^1$H NMR (CDCl$_3$) δ 8.02 (d, 1H, J=7.7 Hz), 7.29 (d, 1H, J=7.7 Hz), 5.07 (m, 1H), 2.24-2.20 (m, 2H), 1.92-1.85 (m, 2H), 1.60-1.46 (m, 2H), 1.27-1.04 (m, 3H), 0.89 (s, 9H); IR (neat) 2954, 2237, 1591, 1435, 1350, 1269, 1188, 1151, 977 cm$^{-1}$ A-133: 2-(4-ethyl-cyclohexyloxy)-6-trifluoromethyl-nicotinonitrile

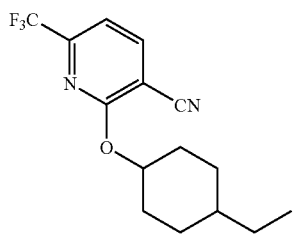 [SMILES: CCC1CCC(Oc2nc(C(F)(F)F)ccc2C#N)CC1]

$^1$H NMR (CDCl$_3$) δ 8.02 (d, 1H, J=7.0 Hz), 7.29 (d, 1H, J=7.7 Hz), 5.11 (m, 1H), 2.21-2.13 (m, 2H), 1.92-1.85 (m, 2H), 1.62-1.03 (m, 7H), 0.91 (t, 3H, J=7.0 Hz); IR (neat) 2934, 2237, 1591, 1435, 1350, 1269, 1188, 1151 cm$^{-1}$ A-134: 6-tert-butyl-2-cyclohexyloxy-nicotinonitrile

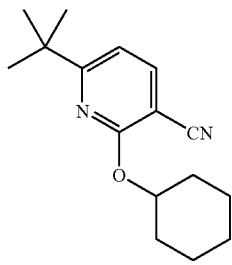 [SMILES: CC(C)(C)c1ccc(C#N)c(OC2CCCCC2)n1]

$^1$H NMR (CDCl$_3$) δ 7.76 (d, 1H, J=7.9 Hz), 6.91 (d, 1H, J=7.9 Hz), 5.16 (m, 1H), 2.03-1.35 (m, 10H), 1.32 (s, 9H); IR (neat) 2938, 2230, 1592, 1564, 1451, 1415, 1365, 1261 cm$^{-1}$ A-135: 6-tert-butyl-2-cyclopentyloxy-nicotinonitrile

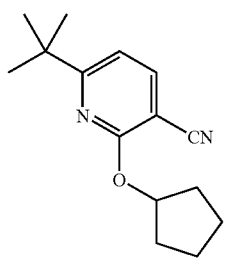 [SMILES: CC(C)(C)c1ccc(C#N)c(OC2CCCC2)n1]

$^1$H NMR (CDCl$_3$) δ 7.75 (d, 1H, J=7.9 Hz), 6.91 (d, 1H, J=7.9 Hz), 5.50 (m, 1H), 2.03-1.60 (m, 8H), 1.32 (s, 9H); IR (neat) 2964, 2230, 1592, 1564, 1451, 1414, 1353, 1262, 984 cm$^{-1}$ A-136: 2-butoxy-6-tert-butyl-nicotinonitrile

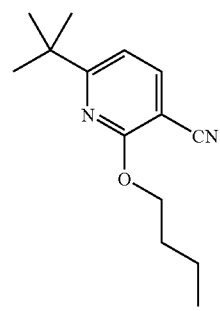 [SMILES: CCCCOc1nc(C(C)(C)C)ccc1C#N]

$^1$H NMR (CDCl$_3$) δ 7.77 (d, 1H, J=7.9 Hz), 6.94 (d, 1H, J=7.9 Hz), 4.44 (t, 2H, J=6.6 Hz), 1.80 (m, 2H), 1.49 (m, 2H), 1.32 (s, 9H), 0.98 (t, 3H, J=7.3 Hz); IR (neat) 2961, 2230, 1593, 1565, 1455, 1418, 1369, 1261, 1112 cm$^{-1}$ A-137: 6-tert-butyl-2-hexyloxy-nicotinonitrile

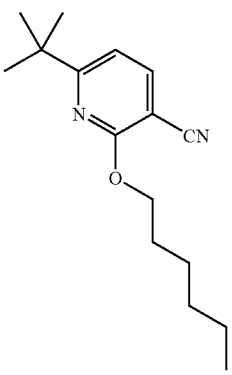 [SMILES: CCCCCCOc1nc(C(C)(C)C)ccc1C#N]

$^1$H NMR (CDCl$_3$), δ 7.77 (d, 1H, J=7.9 Hz), 6.94 (d, 1H, J=7.9 Hz), 4.43 (t, 2H, J=6.8 Hz), 1.81 (m, 2H), 1.50-1.30 (m, 6H), 1.32 (s, 9H), 0.90 (m, 3H);
IR (neat) 2929, 2230, 1593, 1565, 1455, 1418, 1369, 1261, 1112, 1000 cm$^{-1}$ A-138: 2-benzyloxy-6-tert-butyl-nicotinonitrile

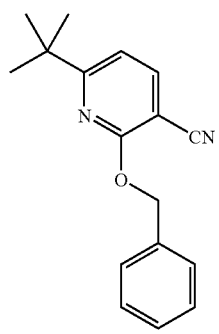 [SMILES: CC(C)(C)c1ccc(C#N)c(OCc2ccccc2)n1]

¹H NMR (CDCl₃) δ 7.79 (d, 1H, J=8.3 Hz), 7.50-7.30 (m, 5H), 6.97 (d, 1H, J=7.9 Hz), 5.53 (s, 2H), 1.31 (s, 9H); IR (neat) 2963, 2230, 1593, 1563, 1454, 1412, 1360, 1263, 1114, 999 cm⁻¹

A-139: 2-cyclohexylmethoxy-6-trifluoromethyl-nicotinonitrile

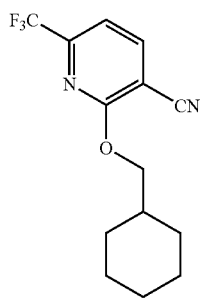 [SMILES: N#Cc1ccc(C(F)(F)F)nc1OCC1CCCCC1]

¹H NMR (CDCl₃) δ 8.04 (d, 1H, J=7.9 Hz), 7.32 (d, 1H, J=7.7 Hz), 4.28 (d, 2H, J=6.0 Hz), 1.90-1.70 (m, 6H), 1.35-1.05 (m, 5H); IR (neat) 2930, 2237, 1592, 1438, 1349, 1268, 1188, 1151, 994 cm⁻¹

A-140: 2-(4-methyl-cyclohexylmethoxy)-6-trifluoromethyl-nicotinonitrile

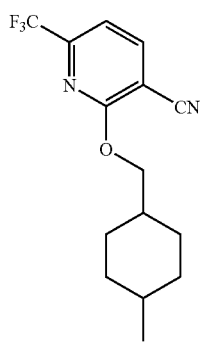 [SMILES: CC1CCC(COc2nc(C(F)(F)F)ccc2C#N)CC1]

¹H NMR (CDCl₃) δ 8.04 (d, 1H, J=7.7 Hz), 7.32 (d, 1H, J=7.7 Hz), 4.40 & 4.29 (d, 2H), 2.06-1.50 (m, 7H), 1.37-1.28 (m, 2H), 1.15-1.05 (m, 1H), 0.95 & 0.90 (d, 3H); IR (neat) 2924, 2237, 1592, 1437, 1349, 1268, 1188, 1151, 1118, 988 cm⁻¹

A-141: 4-(3-cyano-6-trifluoromethyl-pyridin-2-yloxymethyl)-piperidine-1-carbonic acid tert-butyl ester

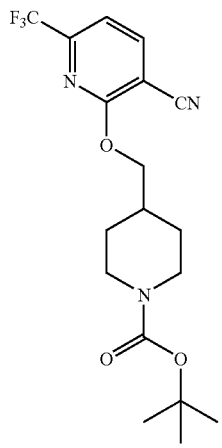 [SMILES: CC(C)(C)OC(=O)N1CCC(COc2nc(C(F)(F)F)ccc2C#N)CC1]

¹H NMR (CDCl₃) δ 8.06 (d, 1H, J=7.7 Hz), 7.36 (d, 1H, J=7.7 Hz), 4.34 (d, 2H), 4.23-4.12 (m, 2H), 2.81-2.70 (m, 2H), 2.04 (m, 1H), 1.87-1.81 (m, 2H), 1.47 (s, 9H), 1.37-1.23 (m, 2H); IR (neat) 2926, 2236, 1690, 1591, 1434, 1363, 1268, 1181, 1149, 986 cm⁻¹

A-142: 6-trifluoromethyl-2-(4-trifluoromethyl-cyclohexyloxy)-nicotinonitrile

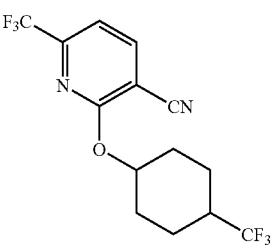 [SMILES: N#Cc1ccc(C(F)(F)F)nc1OC1CCC(C(F)(F)F)CC1]

¹H NMR (CDCl₃) δ 8.05 (d, 1H, J=7.7 Hz), 7.34 (d, 1H, J=7.7 Hz), 5.51 & 5.14 (m, 1H), 2.35-2.05 (m, 4H), 1.87-1.50 (m, 5H); IR (neat) 2957, 2237, 1591, 1463, 1436, 1346, 1270, 1186, 1150, 1014 cm⁻¹

A-143: 4-(3-cyano-6-trifluoromethyl-pyridin-2-yloxy)-piperidine-1-carbonic acid tert-butyl ester

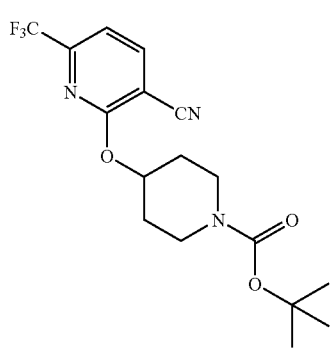 [SMILES: CC(C)(C)OC(=O)N1CCC(Oc2nc(C(F)(F)F)ccc2C#N)CC1]

¹H NMR (CDCl₃) δ 8.07 (d, 1H, J=7.7 Hz), 7.35 (d, 1H, J=7.7 Hz), 5.42 (m, 1H), 3.73 (m, 2H), 3.43 (m, 2H), 2.05-1.83 (m, 4H), 1.48 (s, 9H); IR (neat) 2975, 2237, 1693, 1591, 1430, 1350, 1273, 1236, 1181, 1022 cm⁻¹

A-144: 2-(3-methoxy-benzyloxy)-6-trifluoromethyl-nicotinonitrile

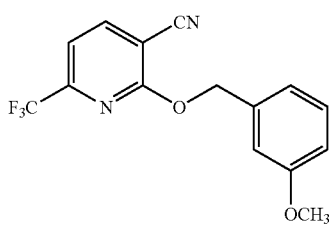 [SMILES: COc1cccc(COc2nc(C(F)(F)F)ccc2C#N)c1]

¹H NMR (300 MHz, CDCl₃) δ 8.06 (d, 1H, J=7.7 Hz), 7.36 (d, 1H, J=7.7 Hz), 7.29 (d, 1H, J=7.7 Hz), 7.10 (d, 1H, J=7.9 Hz), 7.09 (s, 1H), 6.88 (m, 1H), 5.54 (s, 2H), 3.82 (s, 3H); IR (neat) 2920, 2228, 1591, 1463, 1428, 1350, 1269, 1149, 980, 843, 781 cm⁻¹; MS (FAB) m/z 309 (M+H)

A-145: 2-(4-methyl-benzyloxy)-6-trifluoromethyl-nicotinonitrile

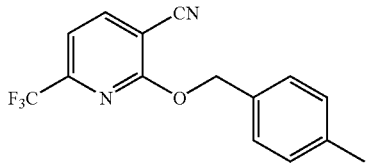 [SMILES: Cc1ccc(COc2nc(C(F)(F)F)ccc2C#N)cc1]

¹H NMR (300 MHz, CDCl₃) δ 8.05 (d, 1H, J=7.7 Hz), 7.42 (d, 2H, J=8.0 Hz), 7.32 (d, 1H, J=7.7 Hz), 7.19 (d, 2H, J=7.9 Hz), 5.52 (s, 2H), 2.36 (s, 3H)

IR (neat) 2923, 2236, 1590, 1464, 1432, 1348, 1270, 1186, 1149, 1117, 977, 842, 808, 745 cm⁻¹; MS (FAB) m/z 293 (M+H)

A-146: 2-(4-fluoro-benzyloxy)-6-trifluoromethyl-nicotinonitrile

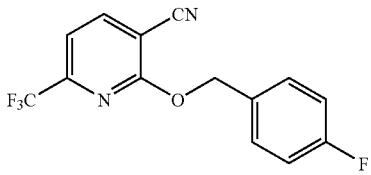 [SMILES: N#Cc1ccc(C(F)(F)F)nc1OCc1ccc(F)cc1]

¹H NMR (300 MHz, CDCl₃) δ 8.07 H, J=7.7 Hz), 7.52 (m, 2H), 7.37 (d, 1H, J=7.7 Hz), 7.07 (m, 2H), 5.52 (s, 2H); IR (neat) 2230, 1590, 1512, 1465, 1434, 1348, 1270, 1228, 1187, 1151, 1116, 979, 835, 745 cm⁻¹; MS (FAB) m/z 297 (M+H)

A-147: 2-(pyridin-4-ylmethoxy)-6-trifluoromethyl-nicotinonitrile

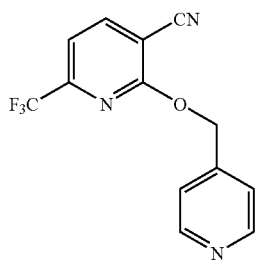 [SMILES: N#Cc1ccc(C(F)(F)F)nc1OCc1ccncc1]

¹H NMR (300 MHz, CDCl₃) δ 8.66 (s, 2H), 8.13 (d, 1H, J=7.7 Hz), 7.48-7.39 (m, 3H), 5.57 (s, 2H); IR (neat) 3028, 2218, 1591, 1466, 1427, 1358, 1275, 1176, 1145, 1021, 1145, 1021, 938, 865, 801, 772 cm⁻¹; MS (FAB) m/z 280 (M+H)

A-148: 2-phenethyloxy-6-trifluoromethyl-nicotinonitrile

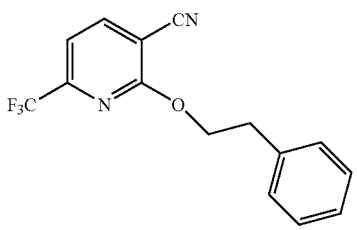 [SMILES: N#Cc1ccc(C(F)(F)F)nc1OCCc1ccccc1]

¹H NMR (300 MHz, CDCl₃) δ 8.03 (d, 1H, J=7.7 Hz), 7.41-7.26 (m, 6H), 4.67 (t, 2H, J=6.9 Hz), 3.15 (t, 2H, J=6.9 Hz); IR (neat) 3031, 2236, 1590, 1468, 1434, 1348, 1268, 1187, 1148, 1117, 996, 955, 842, 749, 701 cm⁻¹; MS (FAB) m/z 293 (M+H)

A-149: 2-(pyridin-2-ylmethoxy)-6-trifluoromethyl-nicotinonitrile

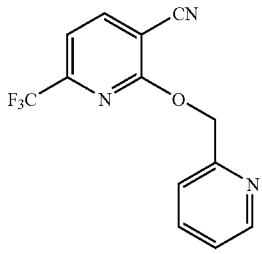 [SMILES: N#Cc1ccc(C(F)(F)F)nc1OCc1ccccn1]

$^1$H NMR (300 MHz, CDCl$_3$) δ 8.62 (m, 1H), 8.11 (d, 1H, J=7.7 Hz), 7.76 (td, 1H, J=7.7, 1.8 Hz), 7.57 (d, 1H, J=7.7 Hz), 7.41 (d, 1H, J=7.7 Hz), 7.27 (m, 1H), 5.66 (s, 2H); IR (neat) 2237, 1588, 1473, 1423, 1355, 1279, 1191, 1149, 1024, 937, 857, 768 cm$^{-1}$; MS (FAB) m/z 280 (M+H)

A-150: 2-benzyloxy-6-trifluoromethyl-nicotinonitrile

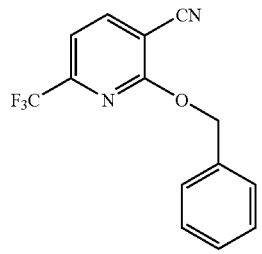 [SMILES: N#Cc1ccc(C(F)(F)F)nc1OCc1ccccc1]

$^1$H NMR (300 MHz, CDCl$_3$) δ 8.06 (d, 1H, J=7.7 Hz), 7.58-7.50 (m, 2H), 7.47-7.36 (m, 4H), 5.56 (s, 2H); IR (neat) 2237, 1590, 1464, 1429, 1350, 1271, 1180, 1149, 1115, 984, 842, 741, 699 cm$^{-1}$; MS (FAB) m/z 279 (M+H)

A-151: 2-benzyloxy-4-trifluoromethyl-benzonitrile

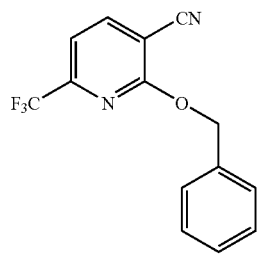 [SMILES: N#Cc1ccc(C(F)(F)F)nc1OCc1ccccc1]

$^1$H NMR (300 MHz, CDCl$_3$) δ 7.72 (d, 1H, J=7.9 Hz), 7.48-7.34 (m, 5H), 7.29 (d, 1H, J=8.0 Hz), 7.25 (s, 1H), 5.26 (s, 2H); IR (neat) 2229, 1504, 1431, 1371, 1328, 1243, 1121, 1078, 991, 877, 822, 738, 695 cm$^{-1}$; MS (FAB) m/z 278 (M+H)

A-152: 2-(pyridin-3-ylmethoxy)-6-trifluoromethyl-nicotinonitrile

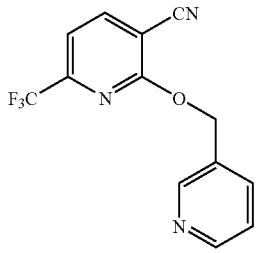 [SMILES: N#Cc1ccc(C(F)(F)F)nc1OCc1cccnc1]

$^1$H NMR (300 MHz, CDCl$_3$) δ 8.78 (s, 1H), 8.61 (d, 1H, J=4.8 Hz), 8.09 (d, 1H, J=7.7 Hz), 7.88 (dt, 1H, J=7.9 Hz), 7.39 (d, 1H, J=7.7 Hz), 7.34 (m, 1H), 5.58 (s, 2H); IR (neat) 2231, 1587, 1411, 1348, 1269, 1175, 1110, 1014, 936, 847, 790, 707 cm$^{-1}$; MS (FAB) m/z 280 (M+H)

A-153: 6-trifluoromethyl-2-(4-trifluoromethyl-benzyloxy)-nicotinonitrile

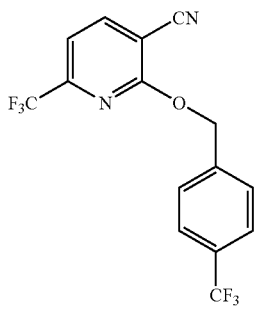 [SMILES: N#Cc1ccc(C(F)(F)F)nc1OCc1ccc(C(F)(F)F)cc1]

$^1$H NMR (300 MHz, CDCl$_3$) δ 8.09 (d, 1H, J=7.6 Hz), 7.76-7.61 (m, 4H), 7.39 (d, 1H, J=7.8 Hz), 5.61 (s, 2H); IR (neat) 2237, 1590, 1466, 1434, 1326, 1272, 1121, 1067, 1012, 845, 744 cm$^{-1}$; MS (FAB) m/z 347 (M+H)

A-154: 2-(4-ethyl-benzyloxy)-6-trifluoromethyl-nicotinonitrile

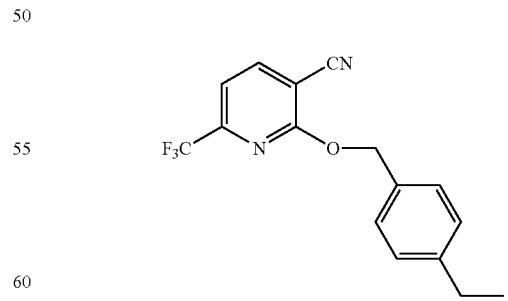

$^1$H NMR (300 MHz, CDCl$_3$) δ 8.04 (d, 1H, J=7.7 Hz), 7.45 (d, 2H, J=7.9 Hz), 7.34 (d, 1H, J=7.7 Hz), 7.22 (d, 2H, J=8.0 Hz), 5.53 (s, 2H), 2.66 (q, 2H, J=7.7 Hz), 1.24 (t, 3H, J=7.6 Hz); IR (neat) 2967, 2231, 1590, 1464, 1432, 1348, 1271, 1187, 1150, 1117, 977, 843 cm$^{-1}$; MS (FAB) m/z 307 (M+H)

A-155: 2-(4-butyl-benzyloxy)-6-trifluoromethyl-nicotinonitrile

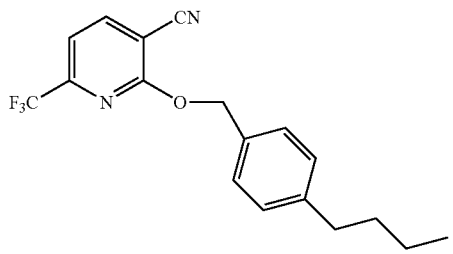 [SMILES: CCCCc1ccc(COc2nc(C(F)(F)F)ccc2C#N)cc1]

¹H NMR (300 MHz, CDCl₃) δ 8.05 (d, 1H, J=7.7 Hz), 7.43 (d, 2H, J=7.9 Hz), 7.34 (d, 1H, J=7.7 Hz), 7.20 (d, 2H, J=7.9 Hz), 5.52 (s, 2H), 2.61 (t, 2H, J=7.7 Hz), 1.60 (m, 2H), 1.35 (m, 2H), 0.92 (t, 3H, J=7.3 Hz); IR (neat) 2930, 2230, 1590, 1464, 1432, 1348, 1271, 1187, 1150, 1116, 976, 840 cm⁻¹; MS (FAB) m/z 335 (M+H)

A-156: 2-(4-tert-butyl-benzyloxy)-6-trifluoromethyl-nicotinonitrile

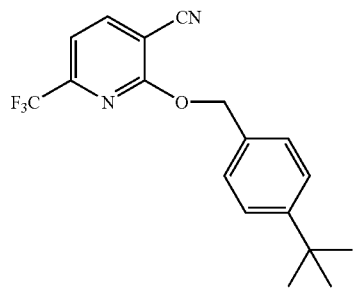 [SMILES: CC(C)(C)c1ccc(COc2nc(C(F)(F)F)ccc2C#N)cc1]

¹H NMR (300 MHz, CDCl₃) δ 8.05 (d, 1H, J=7.6 Hz), 7.57-7.40 (m, 4H), 7.35 (d, 1H, J=7.8 Hz), 5.53 (s, 2H), 1.33 (s, 9H); IR (neat) 2964, 2237, 1590, 1465, 1432, 1348, 1271, 1186, 1150, 1117, 975, 840, 744 cm⁻¹; MS (FAB) m/z 335 (M+H)

A-157: 2-(indan-2-yloxy)-6-trifluoromethyl-nicotinonitrile

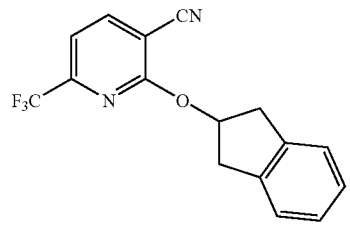 [SMILES: N#Cc1ccc(C(F)(F)F)nc1OC1Cc2ccccc2C1]

¹H NMR (300 MHz, CDCl₃) δ 8.05 (d, 1H, J=7.7 Hz), 7.36 (d, 1H, J=7.7 Hz), 7.29-7.17 (m, 4H), 5.91 (m, 1H), 3.52 (dd, 2H, J=16.9, 6.9 Hz), 3.14 (dd, 2H, J=16.9, 4.1 Hz); IR (neat) 2915, 2236, 1590, 1463, 1431, 1348, 1267, 1188, 1148, 1008, 972, 938, 841, 744 cm⁻¹; MS (FAB) m/z 305 (M+H)

A-158: 2-(4-chloro-benzyloxy)-6-trifluoromethyl-nicotinonitrile

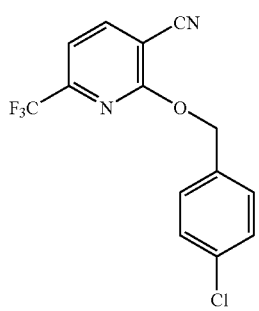 [SMILES: N#Cc1ccc(C(F)(F)F)nc1OCc1ccc(Cl)cc1]

¹H NMR (300 MHz, CDCl₃) d 8.07 (d, 1H, J=7.7 Hz), 7.49-7.32 (m, 4H), 7.37 (d, 1H, J=7.7 Hz), 5.52 (s, 2H); IR (neat) 2237, 1591, 1492, 1464, 1432, 1402, 1348, 1269, 1187, 1149, 1116, 987, 843, 809, 745 cm⁻¹; MS (FAB) m/z 313 (M+H)

The compounds A-159 and A-161 were obtained from the respective alkyne compounds by using the following procedure.

Triethylamine (11 mmol) and Lindlar's catalyst (7 wt-%, 1 mmol) were added to a solution of the alkyne (10 mmol) in DMF (25 mL). The reaction flask was evacuated, purged with hydrogen five times, and then stirred under a hydrogen atmosphere for 8 h. The reaction mixture was filtered over celite and washed with diethyl acetate (25 mL). The resulting solution was washed with 2 wt-% aq. NH₄Cl soln. (37 mL) and then twice with water (2×25 mL), dried over MgSO₄, filtered, and concentrated in vacuo. The residue was purified by flash column chromatography on silica gel using EA/hexanes (1:4) as eluent.

A-159: 2-but-2-enyloxy-6-trifluoromethyl-nicotinonitrile

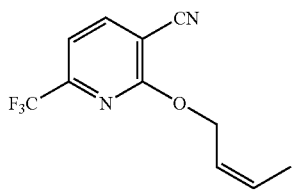 [SMILES: C/C=C\COc1nc(C(F)(F)F)ccc1C#N]

¹H NMR (300 MHz, CDCl₃) δ 8.05 (d, 1H, J=7.7 Hz), 7.34 (d, 1H, J=7.7 Hz), 5.81 (m, 1H), 5.72 (m, 1H), 5.09 (d, 2H, J=6.6 Hz), 1.81 (d, 3H, J=6.8 Hz)

IR (neat) 2919, 2237, 1591, 1466, 1433, 1335, 1267, 1188, 1150, 1118, 969, 842, 747 cm$^{-1}$; MS (FAB) m/z 243 (M+H)

A-160:
2-but-2-ynyloxy-6-trifluoromethyl-nicotinonitrile

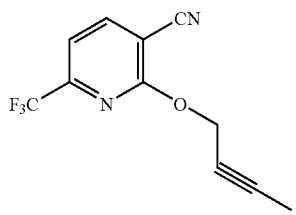 [SMILES: CC#CCOc1nc(C(F)(F)F)ccc1C#N]

$^1$H NMR (300 MHz, CDCl$_3$) δ 8.08 (d, 1H, J=7.5 Hz), 7.39 (d, 1H, J=7.7 Hz), 5.10 (q, 2H, J=2.4 Hz), 1.87 (t, 3H, J=2.3 Hz); IR (neat) 2924, 2239, 1590, 1460, 1429, 1348, 1271, 1189, 1151, 1117, 977, 931, 844, 745 cm$^{-1}$; MS (FAB) m/z 241 (M+H)

A-161:
2-pent-2-enyloxy-6-trifluoromethyl-nicotinonitrile

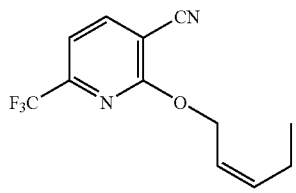 [SMILES: CC/C=C\COc1nc(C(F)(F)F)ccc1C#N]

$^1$H NMR (300 MHz, CDCl$_3$) δ 8.05 (d, 1H, J=7.7 Hz), 7.34 (d, 1H, J=7.7 Hz), 5.73-5.65 (m, 2H), 5.07 (d, 2H, J=6.0 Hz), 2.23 (m, 2H), 1.03 (t, 3H, J=7.6 Hz); IR (neat) 2967, 2237, 1590, 1465, 1431, 1405, 1342, 1267, 1187, 1151, 1118, 976, 842, 746 cm$^{-1}$; MS (FAB) m/z 257 (M+H)

A-162:
2-pent-2-ynyloxy-6-trifluoromethyl-nicotinonitrile

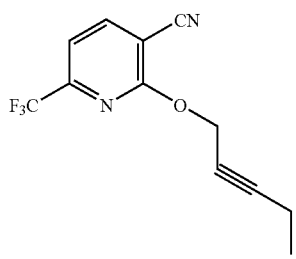 [SMILES: CCC#CCOc1nc(C(F)(F)F)ccc1C#N]

$^1$H NMR (300 MHz, CDCl$_3$) δ 8.08 (d, 1H, J=7.7 Hz), 7.39 (d, 1H, J=7.7 Hz), 5.11 (t, 2H, J=2.1 Hz), 2.23 (m, 2H), 1.14 (t, 3H, J=7.5 Hz); IR (neat) 2982, 2238, 1590, 1461, 1428, 1348, 1272, 1189, 1151, 1117, 979, 844 cm$^{-1}$; MS (FAB) m/z 255 (M+H)

A-163: 2-p-tolyloxy-6-trifluoromethyl-nicotinonitrile

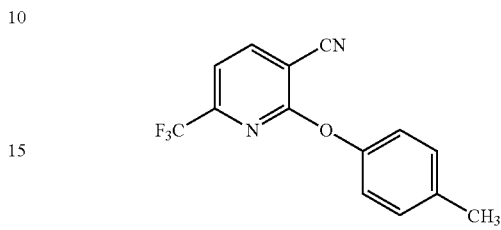

$^1$H NMR (300 MHz, CDCl$_3$) δ 8.17 (d, 1H, J=7.7 Hz), 7.44 (d, 1H, J=7.7 Hz), 7.22 (d, 2H, J=8.6 Hz), 7.10 (m, 2H), 2.39 (s, 3H); IR (neat) 2921, 2237, 1585, 1508, 1462, 1409, 1348, 1269, 1188, 1149, 1115, 947, 853 cm$^{-1}$; MS (FAB) mz 279 (M+H)

A-164:
2-cyclopentyloxy-4-trifluoromethyl-benzonitrile

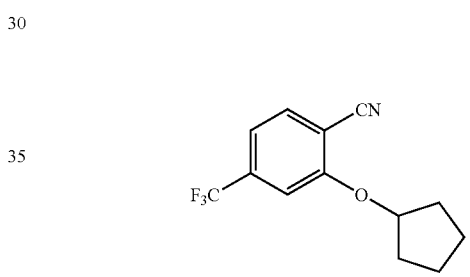

$^1$H NMR (300 MHz, CDCl$_3$) δ 7.67 (d, 1H, J=7.9 Hz), 7.23 (d, 1H, J=7.9 Hz), 7.17 (bs, 1H), 4.92 (m, 1H), 1.80-2.23 (m, 6H), 1.61-1.77 (m, 2H)

IR (neat) 2959, 2232, 1506, 1435, 1328, 1245, 1163, 1122, 1079, 877, 825 cm$^{-1}$ MS (FAB) m/z 256 (M+H)

A-165:
2-cyclohexyloxy-4-trifluoromethyl-benzonitrile

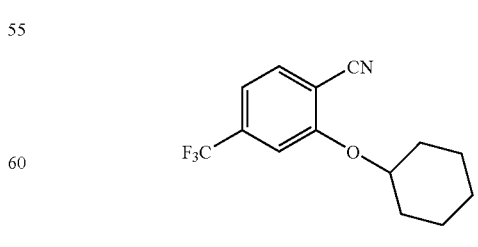

$^1$H NMR (300 MHz, CDCl$_3$) δ 7.68 (d, 1H, J=8.1 Hz), 7.23 (d, 1H, J=8.0 Hz), 7.17 (bs, 1H), 4.49 (m, 1H), 1.78-2.02 (m, 4H), 1.63-1.77 (m, 2H), 1.35-1.62 (m, 4H); IR (neat) 2939, 2862, 2233, 1615, 1503, 1430, 1328, 1247, 1176, 1132, 1075, 1018, 970, 904, 829 cm$^{-1}$; MS (FAB) m/z 270 (M+H)

A-166: 2-butoxy-4-trifluoromethyl-benzonitrile

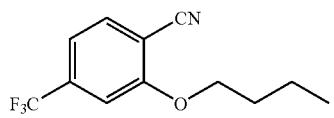 [SMILES: CCCCOc1cc(C(F)(F)F)ccc1C#N]

$^1$H NMR (300 MHz, CDCl$_3$) δ 7.68 (d, 1H, J=8.0 Hz), 7.14-7.30 (m, 2H), 4.13 (t, 2H, J=6.4 Hz), 1.81-1.93 (m, 2H), 1.49-1.62 (m, 2H), 1.01 (t, 3H, J=7.3 Hz); IR (neat) 2962, 2223, 1616, 1580, 1505, 1432, 1393, 1329, 1251, 1176, 1133, 1075, 975, 919, 865, 829 cm$^{-1}$; MS (FAB) m/z 244 (M+H)

A-167: 2-cyclopentyloxy-4-methyl-6-trifluoromethyl-nicotinonitrile

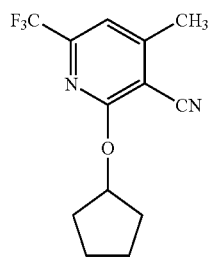 [SMILES: Cc1cc(C(F)(F)F)nc(OC2CCCC2)c1C#N]

$^1$H NMR (300 MHz, CDCl$_3$) δ 7.16 (s, 1H), 5.54 (m, 1H), 2.58 (s, 3H), 2.02 (m, 2H), 1.85 (m, 4H), 1.64 (m, 2H); IR (neat) 2967, 2232, 1576, 1348, 1314, 1075, 913, 865 cm$^{-1}$; MS (FAB) m/z 271 (M+H)

A-168: 2-butoxy-4-tert-butyl-benzonitrile

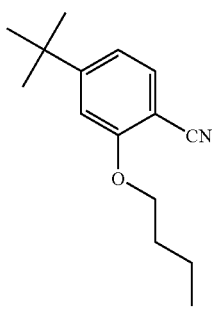 [SMILES: CCCCOc1cc(C(C)(C)C)ccc1C#N]

$^1$H NMR (300 MHz, CDCl$_3$) δ 7.40 (d, 1H, J=8.2 Hz), 7.0 (dd, 1H, J=1.6, 1.6 Hz), 6.90 (d, 1H, J=1.4 Hz), 4.0 (t, 2H, J=6.4 Hz), 1.88-1.74 (m, 2H), 1.61-1.50 (m, 2H), 1.3 (s, 9H), 0.9 (t, 3H, J=1.8 Hz)

IR (neat) 2963, 2224, 1604, 1412, 1237 cm$^{-1}$

A-169: 4-tert-butyl-2-isobutoxy-benzonitrile

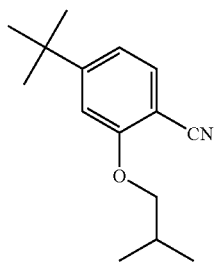 [SMILES: CC(C)COc1cc(C(C)(C)C)ccc1C#N]

$^1$H NMR (300 MHz, CDCl$_3$) δ 7.47 (d, 1H, J=8.2 Hz), 7.0 (dd, 1H, J=1.6, 1.6 Hz), 6.92 (d, 1H, J=1.4 Hz), 3.83 (d, 2H, J=6.4 Hz), 2.24-2.10 (m, 1H), 1.32 (s, 9H), 1.08 (d, 6H, J=6.8 Hz)

IR (neat) 2963, 2225, 1606, 1563, 1501, 1469 cm$^{-1}$

A-170: 4-tert-butyl-2-cyclohexyloxy-benzonitrile

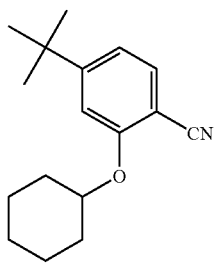 [SMILES: CC(C)(C)c1ccc(C#N)c(OC2CCCCC2)c1]

$^1$H NMR (300 MHz, CDCl$_3$) δ 7.46 (d, 1H, J=8.0 Hz), 7.0 (dd, 1H, J=1.6, 1.6 Hz), 6.95 (d, 1H, J=1.6 Hz), 4.43-4.39 (m, 1H), 2.0-1.77 (m, 4H), 1.77-1.60 (m, 4H), 1.48-1.37 (m, 2H), 1.31 (s, 9H)

IR (neat) 2934, 2858, 2225, 1741, 1604, 1563 cm$^{-1}$

A-171: 4-tert-butyl-2-(2,2-dimethyl-propoxy)-benzonitrile

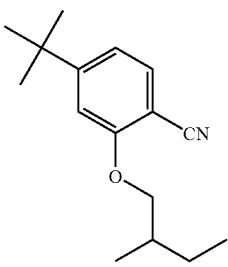 [SMILES: CCC(C)COc1cc(C(C)(C)C)ccc1C#N]

$^1$H NMR (300 MHz, CDCl$_3$) δ 7.46 (d, 1H, J=8.2 Hz), 7.0 (dd, 1H, J=1.6, 1.6 Hz), 6.91 (d, 1H, J=1.4 Hz), 3.70 (s, 2H), 1.32 (s, 9H), 1.09 (s, 9H)

IR (neat) 2963, 2225, 1605, 1564, 1500, 1468 cm$^{-1}$

A-172: 4-tert-butyl-2-cyclopentyloxy-benzonitrile

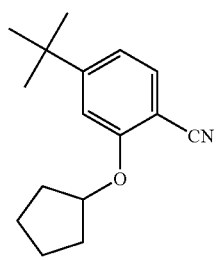 [SMILES: CC(C)(C)c1ccc(C#N)c(OC2CCCC2)c1]

$^1$H NMR (300 MHz, CDCl$_3$) δ 7.45 (d, 1H, J=8.0 Hz), 6.99-6.92 (m, 2H), 4.91-4.86 (m, 1H), 1.96-1.83 (m, 6H), 1.67-1.58 (m, 2H), 1.31 (s, 9H)

IR (neat) 2963, 2872, 2224, 1604, 1563, 1498 cm$^{-1}$

A-173: 4-tert-butyl-2-pentoxy-benzonitrile

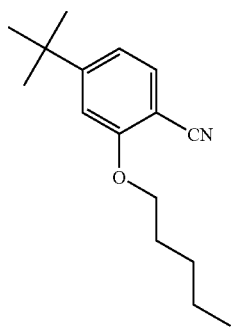 [SMILES: CCCCCOc1cc(C(C)(C)C)ccc1C#N]

$^1$H NMR (300 MHz, CDCl$_3$) δ 7.46 (d, 1H, J=8.0 Hz), 7.0 (dd, 1H, J=1.6, 1.6 Hz), 6.93 (d, 1H, J=1.6 Hz), 4.07 (t, 2H, J=6.4 Hz), 1.90-1.81 (m, 2H), 1.54-1.35 (m, 4H), 1.31 (s, 9H), 0.94 (t, 3H, J=6.9 Hz)

IR (neat) 2960, 2870, 2225, 1605, 1564, 1500 cm$^{-1}$

Stage 2:

Method 1:

Compounds of the general formula VI-Ca or VI-Cb (5 mmol), in which R$^5$, R$^4$, U, T and V have the above-stated meaning and m denotes 0, 1, 2 or 3, palladium on carbon (10%, 500 mg) and concentrated hydrochloric acid (3 mL) are dissolved in MeOH (30 mL) and exposed to a hydrogen atmosphere for 6 hours at RT. The reaction mixture is filtered through celite and the filtrate is evaporated under a vacuum. The residue is purified by means of flash chromatography (SiO$_2$, EA).

The following compounds B-85 to B-88 were obtained according to the above-stated general method:

B-85: 2-cyclopentylmethoxy-6-trifluoromethyl-pyridin-3-ylmethyl-ammonium acetate

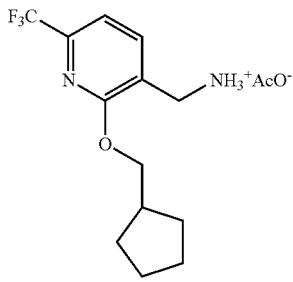

$^1$H NMR (CDCl$_3$) δ 7.68 (d, 1H, J=7.5 Hz), 7.23 (d, 1H, J=7.3 Hz), 4.95 (bs, NH3), 4.30 (d, 2H), 2.39 (m, 1H), 1.96 (s, 3H, AcO—), 1.88-1.75 (m, 2H), 1.68-1.54 (m, 4H), 1.42-1.30 (m, 2H); IR (neat) 2955, 2637, 2244, 1539, 1426, 1369, 1141, 997 cm$^{-1}$

B-86: 2-ethoxy-6-trifluoromethyl-pyridin-3-ylmethyl-ammonium acetate

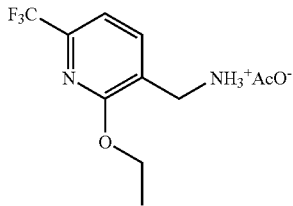

$^1$H NMR (CDCl$_3$) δ 7.66 (d, 1H, J=7.4 Hz), 7.23 (d, 1H, J=7.4 Hz), 5.66 (bs, NH$_3$), 4.48 (q, 2H, J=7.1 Hz), 3.91 (s, 2H), 2.00 (s, 3H, AcO), 1.42 (t, 3H, J=7.0 Hz); IR (neat) 2990, 1537, 1426, 1347, 1186, 1146, 1025 cm$^{-1}$

B-87: 2-(4-ethyl-cyclohexyloxy)-6-trifluoromethyl-pyridin-3-ylmethyl-ammonium acetate

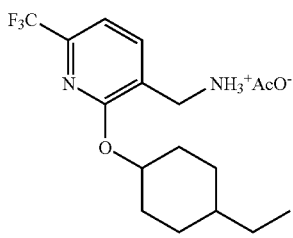

$^1$H NMR (CDCl$_3$) δ 7.62 (d, 1H, J=7.3 Hz), 7.19 (d, 1H, J=7.5 Hz), 5.45 (bs, NH3), 5.08 (m, 1H), 3.86 (s, 2H), 2.22-2.15 (m, 2H), 2.03 (s, 3H, AcO), 1.87-1.82 (m, 2H), 1.50-1.03 (m, 7H), 0.91 (t, 3H, J=6.8 Hz); IR (neat) 2926, 1572, 1421, 1355, 1275, 1186, 1141, 1010 cm$^{-1}$

B-88: 2-(4-tert-butyl-cyclohexyloxy)-6-trifluoromethyl-pyridin-3-ylmethyl-ammonium acetate

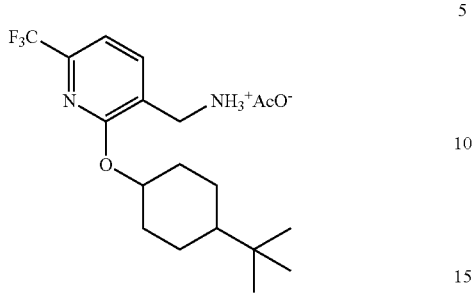

$^1$H NMR (CDCl$_3$) δ 7.62 (d, 1H, J=7.1 Hz), 7.19 (d, 1H, J=7.5 Hz), 5.04 (m, 1H), 4.13 (bs, NH3), 3.85 (s, 2H), 7.25-7.18 (m, 2H), 2.05 (s, 3H, AcO), 1.87-1.83 (m, 2H), 1.46-1.02 (m, 5H), 0.89 (s, 9H); IR (neat) 2951, 1545, 1468, 1424, 1357, 1272, 1183 cm$^{-1}$ Method 2:

Compounds of the general formula VI-Ca or VI-Cb (2 mmol), in which R$^5$, R$^{14}$, U, T and V have the above-stated meaning and m denotes 0, 1, 2 or 3, are dissolved in THF (10 mL) and BH$_3$.S(CH$_3$)$_2$ [2.0 M in THF, 3 mL, 3 equivalents] is added.

The reaction mixture is heated to reflux for 8 hours, aq. HCl (2 N) is added and the reaction mixture is again heated to reflux for 30 minutes. Aq. NaOH soln. and EA are added. The combined organic extracts are washed with sat. aq. NaCl soln. and dried over MgSO$_4$. The solvent is evaporated under a vacuum and the residue is purified by flash chromatography (SiO$_2$, different mixtures of methylene chloride and methanol).

The following compounds B-89 to B-144 were obtained according to the above-stated general method:

B-89: C-[2-(3-methyl-butoxy)-6-trifluoromethyl-pyridin-3-yl]-methylamine

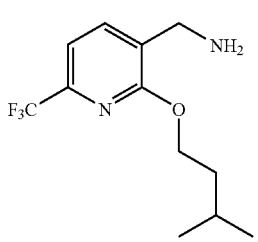 [SMILES: CC(C)CCOc1nc(C(F)(F)F)ccc1CN]

$^1$H NMR (300 MHz, CDCl$_3$) δ 7.63 (d, 1H, J=7.8 Hz), 7.21 (d, 1H, J=7.8 Hz), 4.43 (t, 1H, J=6.9 Hz), 3.84 (s, 2H), 2.43 (bs, 2H), 1.60-1.89 (m, 3H), 0.97 (d, 6H, J=6.6 Hz); MS (FAB) m/z 263 (M+H)

B-90: C-[2-(3,3-dimethyl-butoxy)-6-trifluoromethyl-pyridin-3-yl]-methylamine

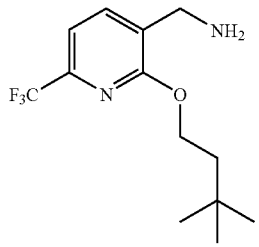 [SMILES: CC(C)(C)CCOc1nc(C(F)(F)F)ccc1CN]

$^1$H NMR (300 MHz, CDCl$_3$) δ 7.56 (d, 1H, J=7.8 Hz), 7.13 (d, 1H, J=7.8 Hz), 4.38 (t, 1H, J=6.9 Hz), 3.74 (s, 2H), 1.64 (t, 2H, J=6.9 Hz), 0.92 (s, 9H);

MS (FAB) m/z 277 (M+H)

B-91: C-[2-(2-methyl-cyclopropylmethoxy)-6-trifluoromethyl-pyridin-3-yl]-methylamine

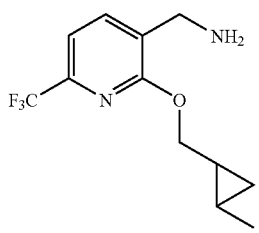 [SMILES: CC1CC1COc1nc(C(F)(F)F)ccc1CN]

$^1$H NMR (300 MHz, CDCl$_3$) δ 7.63 (d, 1H, J=7.8 Hz), 7.21 (d, 1H, J=7.8 Hz), 4.24 (m, 2H), 3.85 (s, 2H), 1.08 (d, 3H, J=6.0 Hz), 0.98 (m, 1H), 0.77 (m, 1H), 0.52 (m, 1H), 0.34 (m, 1H); MS (FAB) m/z 261 (M+H)

B-92: C-[2-butoxy-6-(chloro-difluoro-methyl)-pyridin-3-yl]-methylamine

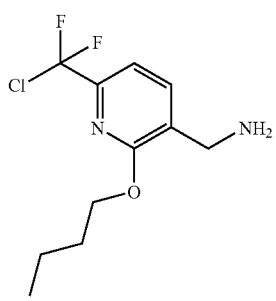 [SMILES: CCCCOc1nc(C(F)(F)Cl)ccc1CN]

$^1$H NMR (300 MHz, CDCl$_3$) δ 7.71 (d, 1H, J=7.8 Hz), 6.98 (d, 1H, J=7.8 Hz), 3.99 (s, 2H), 3.59 (t, 2H, J=7.2 Hz), 1.63 (m, 2H), 1.38 (m, 2H), 0.95 (t, 3H, J=6.9 Hz); IR (neat) 2960, 1599, 1422, 1353, 1264, 1094 cm$^{-1}$; MS (FAB) m/z 265 (M+H)

B-93: C-(2-phenoxy-6-trifluoromethyl-pyridin-3-yl)-methylamine

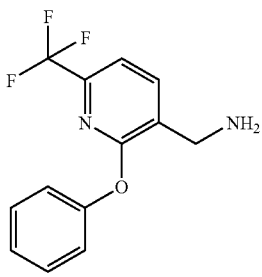 [SMILES: NCc1ccc(C(F)(F)F)nc1Oc1ccccc1]

$^1$H NMR (300 MHz, CDCl$_3$) δ 7.86 (dd, 1H, J=7.5, 1.5 Hz), 7.35-7.43 (m, 3H), 7.15-7.23 (m, 3H), 4.03 (s, 2H); IR (neat) 2922, 1589, 1490, 1468, 1405, 1257, 1186, 1138, 941, 839, 752, 691 cm$^{-1}$; MS (FAB) m/z 269 (M+H)

B-94: C-(2-butoxy-6-trifluoromethyl-pyridin-3-yl)-methylamine

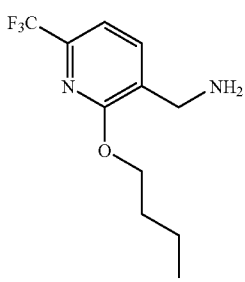

$^1$H NMR (CDCl$_3$), δ 7.65 (d, 1H, J=7.3 Hz), 7.21 (d, 1H, J=7.3 Hz), 4.41 (t, 2H, J=6.4 Hz), 3.84 (s, 2H), 1.78 (m, 2H), 1.50 (m, 2H), 0.98 (t, 3H, J=7.3 Hz); IR (neat) 2963, 1607, 1470, 1425, 1357, 1193, 1132 cm$^{-1}$ B-95: C-(2-isopropoxy-6-trifluoromethyl-pyridin-3-yl)-methylamine

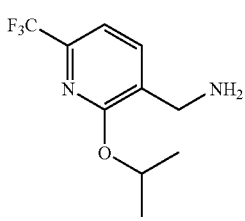 [SMILES: CC(C)Oc1nc(C(F)(F)F)ccc1CN]

$^1$H NMR (CDCl$_3$) δ 7.63 (d, 1H, J=7.3 Hz), 7.19 (d, 1H, J=7.3 Hz), 5.42 (m, 1H), 3.82 (s, 2H), 1.37 (d, 6H, J=6.2 Hz); IR (neat) 3370, 2983, 1602, 1467, 1421, 1341, 1268, 1178, 1141, 969 cm$^{-1}$ B-96: C-(2-cyclopentyloxy-6-trifluoromethyl-pyridin-3-yl)-methylamine

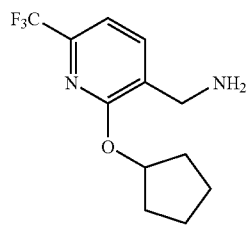 [SMILES: NCc1ccc(C(F)(F)F)nc1OC1CCCC1]

$^1$H NMR (CDCl$_3$) δ 7.62 (d, 1H, J=7.3 Hz), 7.19 (d, 1H, J=7.3 Hz), 5.53 (m, 1H), 3.81 (s, 2H), 2.05-1.95 (m, 2H), 1.82-1.63 (m, 6H)

B-97: C-(2-cyclohexyloxy-6-trifluoromethyl-pyridin-3-yl)-methylamine

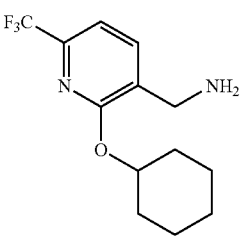 [SMILES: NCc1ccc(C(F)(F)F)nc1OC1CCCCC1]

$^1$H NMR (CDCl$_3$) δ 7.63 (d, 1H, J=7.3 Hz), 7.18 (d, 1H, J=7.5 Hz), 5.20 (m, 1H), 3.83 (s, 2H), 1.99-1.95 (m, 2H), 1.78-1.39 (m, 8H); IR (neat) 2937, 2860, 1603, 1462, 1421, 1362, 1264, 1140, 972 cm$^{-1}$ B-98: C-(2-hexyloxy-6-trifluoromethyl-pyridin-3-yl)-methylamine

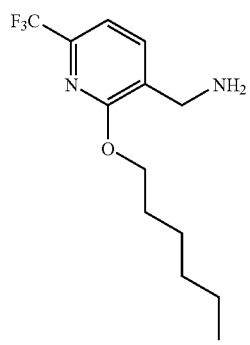 [SMILES: CCCCCCOc1nc(C(F)(F)F)ccc1CN]

$^1$H NMR (CDCl$_3$) δ 7.65 (d, 1H J=7.3 Hz), 7.22 (d, 1H, J=7.3 Hz), 4.40 (t, 2H, J=6.6 Hz), 3.85 (s, 2H), 1.84-1.74 (m,

2H), 1.50-1.30 (m, 6H), 0.90 (t, 3H, J=7.0 Hz); IR (neat) 2929, 1603, 1465, 1424, 1361, 1266, 1179, 1141 cm$^{-1}$ B-99: C-(2-isobutoxy-6-trifluoromethyl-pyridin-3-yl)-methylamine

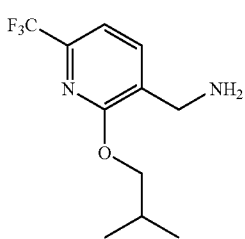 [SMILES: CC(C)COc1nc(C(F)(F)F)ccc1CN]

$^1$H NMR (CDCl$_3$) δ 7.66 (d, 1H, J=7.3 Hz), 7.22 (d, 1H, J=7.3 Hz), 4.18 (d, 2H, J=6.6 Hz), 3.86 (s, 2H), 2.12 (m, 1H), 1.04 (d, 6H, J=6.8 Hz)

IR (neat) 2964, 1603, 1465, 1424, 1362, 1266, 1178, 1140, 1011 cm$^{-1}$

B-100: C-(2-cyclopropylmethoxy-6-trifluoromethyl-pyridin-3-yl)-methylamine

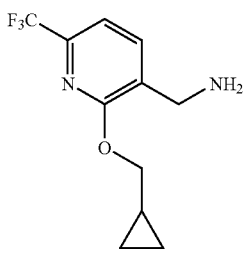 [SMILES: NCc1ccc(C(F)(F)F)nc1OCC1CC1]

$^1$H NMR (CDCl$_3$) δ 7.65 (d, 1H, J=7.5 Hz), 7.21 (d, 1H, J=7.3 Hz), 4.25 (d, 2H, J=7.1 Hz), 3.87 (s, 2H), 1.34-1.25 (m, 1H), 0.63-0.57 (m, 2H), 0.39-0.35 (m, 2H); IR (neat) 2948, 1603, 1465, 1427, 1388, 1263, 1177, 1138, 990 cm$^{-1}$ B-101: C-(2-cyclobutylmethoxy-6-trifluoromethyl-pyridin-3-yl)-methylamine

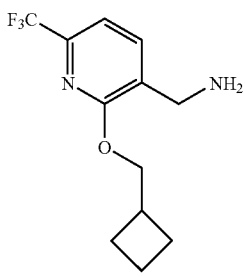 [SMILES: NCc1ccc(C(F)(F)F)nc1OCC1CCC1]

$^1$H NMR (CDCl$_3$) δ 7.64 (d, 1H, J=6.6 Hz), 7.22 (d, 1H, J=7.5 Hz), 4.37 (d, 2H, J=6.8 Hz), 3.85 (s, 2H), 2.85-2.75 (m, 1H), 2.17-1.85 (m, 6H); IR (neat) 2933, 1602, 1464, 1422, 1365, 1265, 1178, 1140, 998 cm$^{-1}$ B-102: 2-butoxy-4-trifluoromethyl-benzylamine

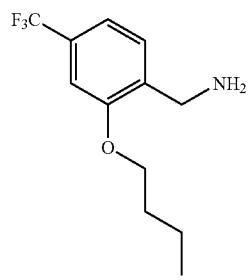

$^1$H NMR (CDCl$_3$) δ 7.33 (d, 1H, J=7.9 Hz), 7.18 (d, 1H, J=7.7 Hz), 7.05 (s, 1H), 4.04 (t, 2H, J=6.4 Hz), 3.87 (s, 2H), 1.83 (m, 2H), 1.51 (m, 2H), 1.00 (t, 3H, J=7.3 Hz); IR (neat) 3340, 2953, 1617, 1507, 1428, 1336, 1243, 1119 cm$^{-1}$ B-103: C-(2-propoxy-6-trifluoromethyl-pyridin-3-yl)-methylamine

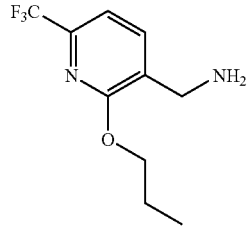 [SMILES: CCCOc1nc(C(F)(F)F)ccc1CN]

$^1$H NMR (CDCl$_3$) δ 7.65 (dd, 1H, J=7.3, 0.8 Hz), 7.22 (d, 1H, J=7.3 Hz), 4.37 (t, 2H, J=6.6 Hz), 3.85 (s, 2H), 1.88-1.77 (m, 2H), 1.04 (t, 3H, J=7.5 Hz); IR (neat) 2970, 1603, 1466, 1425, 1364, 1268, 1178, 1140 cm$^{-1}$ B-104: C-(2-pentyloxy-6-trifluoromethyl-pyridin-3-yl)-methylamine

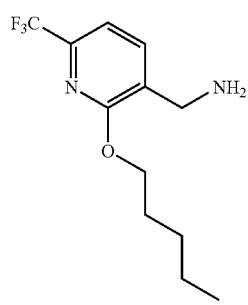 [SMILES: CCCCCOc1nc(C(F)(F)F)ccc1CN]

$^1$H NMR (CDCl$_3$) δ 7.65 (d, 1H, J=7.3 Hz), 7.22 (d, 1H, J=7.3 Hz), 4.40 (t, 2H, J=6.6 Hz), 3.85 (s, 2H), 1.91-1.67 (m,

2H), 1.46-1.35 (m, 4H), 0.93 (t, 3H, J=7.3 Hz); IR (neat) 2957, 1465, 1424, 1361, 1267, 1179, 1140 cm$^{-1}$

B-105: C-(2-cyclobutoxy-6-trifluoromethyl-pyridin-3-yl)-methylamine

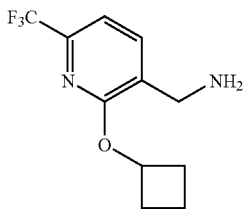 [SMILES: NCc1ccc(C(F)(F)F)nc1OC1CCC1]

$^1$H NMR (CDCl$_3$) δ 7.64 (d, 1H, J=7.5 Hz), 7.20 (d, 1H, J=7.4 Hz), 5.28 (m, 1H), 3.85 (s, 2H), 2.53-2.47 (m, 2H), 2.15-2.10 (m, 2H), 1.88-1.69 (m, 2H); IR (neat) 2990, 1602, 1466, 1420, 1346, 1265, 1178, 1139, 959 cm$^{-1}$

B-106: C-[2-(4-methyl-cyclohexyloxy)-6-trifluoromethyl-pyridin-3-yl]-methylamine

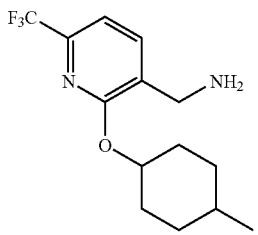 [SMILES: CC1CCC(Oc2nc(C(F)(F)F)ccc2CN)CC1]

$^1$H NMR (CDCl$_3$), δ 7.62 (d, 1H, J=7.4 Hz), 7.18 (d, 1H, J=7.4 Hz), 5.07 (m, 1H), 3.81 (s, 2H), 2.18-2.15 (m, 2H), 1.79-1.76 (m, 2H), 1.51-1.39 (m, 3H), 1.17-1.08 (m, 2H), 0.93 (d, 3H, J=6.5 Hz); IR (neat) 2929, 1603, 1462, 1420, 1356, 1266, 1178, 1140, 1005 cm$^{-1}$

B-107: C-(6-tert-butyl-2-cyclohexyloxy-pyridin-3-yl)-methylamine

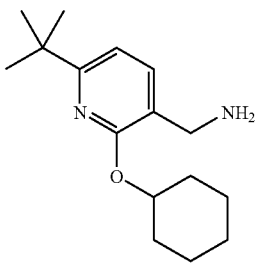 [SMILES: CC(C)(C)c1ccc(CN)c(OC2CCCCC2)n1]

$^1$H NMR (CDCl$_3$) δ 7.37 (d, 1H, J=7.5 Hz), 6.77 (d, 1H, J=7.5 Hz), 5.15 (m, 1H), 3.76 (bs, NH2), 3.48 (s, 2H), 2.30-1.39 (m, 10H), 1.30 (s, 9H);

IR (neat) 2935, 1582, 1452, 1406, 1363, 1254, 982 cm$^{-1}$

B-108: C-(6-tert-butyl-2-cyclopentyloxy-pyridin-3-yl)-methylamine

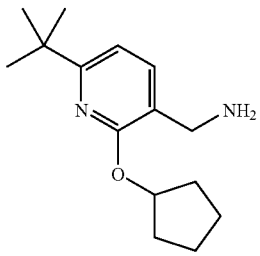 [SMILES: CC(C)(C)c1ccc(CN)c(OC2CCCC2)n1]

$^1$H NMR (CDCl$_3$) δ 7.36 (d, 1H, J=7.4 Hz), 6.78 (d, 1H, J=7.3 Hz), 5.50 (m, 1H), 3.73 (s, 2H), 2.11 (bs, NH2), 2.03-1.63 (m, 8H), 1.31 (s, 9H); IR (neat) 2960, 1583, 1454, 1406, 1350, 1255, 988 cm$^{-1}$

B-109: C-(2-butoxy-6-tert-butyl-pyridin-3-yl)-methylamine

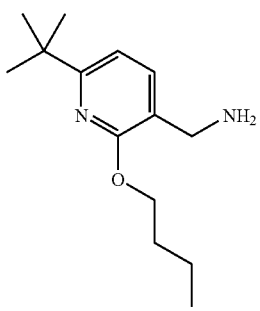 [SMILES: CCCCOc1nc(C(C)(C)C)ccc1CN]

$^1$H NMR (CDCl$_3$) δ 7.38 (d, 1H, J=7.5 Hz), 6.80 (d, 1H, J=7.5 Hz), 4.39 (t, 2H, J=6.6 Hz), 3.77 (s, 2H), 2.17 (bs, NH2), 1.77 (m, 2H), 1.49 (m, 2H), 1.31 (s, 9H), 0.98 (t, 3H, J=7.4 Hz); IR (neat) 2958, 1583, 1458, 1411, 1364, 1254 cm$^{-1}$

B-110: C-(6-tert-butyl-2-hexyloxy-pyridin-3-yl)-methylamine

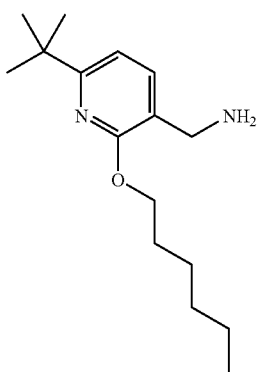 [SMILES: CCCCCCOc1nc(C(C)(C)C)ccc1CN]

$^1$H NMR (CDCl$_3$) δ 7.37 (d, 1H, J=7.3 Hz), 6.79 (d, 1H, J=7.5 Hz), 4.37 (t, 2H, J=6.6 Hz), 3.74 (s, 2H), 1.78 (m, 2H), 1.48-1.30 (m, 6H), 1.31 (s, 9H), 0.90 (m, 3H); IR (neat) 2956, 1582, 1458, 1411, 1361, 1253, 1016 cm$^{-1}$

B-111: C-(2-benzyloxy-6-tert-butyl-pyridin-3-yl)-methylamine

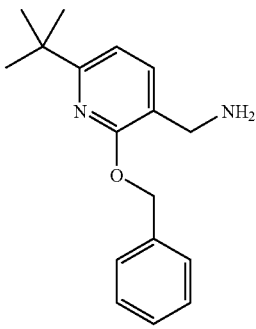 [SMILES: CC(C)(C)c1ccc(CN)c(OCc2ccccc2)n1]

¹H NMR (CDCl₃) δ 7.47-7.29 (m, 6H), 6.83 (d, 1H, J=7.5 Hz), 5.47 (s, 2H), 3.79 (s, 2H), 1.31 (s, 9H); IR (neat) 2957, 1582, 1454, 1405, 1357, 1253, 1009 cm⁻¹

B-112: C-(2-cyclohexylmethoxy-6-trifluoromethyl-pyridin-3-yl)-methylamine

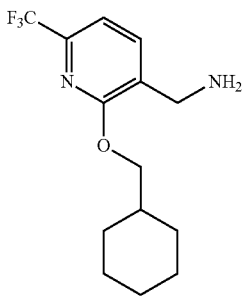 [SMILES: NCc1ccc(C(F)(F)F)nc1OCC1CCCCC1]

¹H NMR (CDCl₃) δ 7.64 (d, 1H, J=7.3 Hz), 7.21 (d, 1H, J=7.3 Hz), 4.20 (d, 2H), 3.85 (s, 2H), 1.86-1.67 (m, 5H), 1.32-1.00 (m, 6H)

B-113: C-[2-(4-methyl-cyclohexylmethoxy)-6-trifluoromethyl-pyridin-3-yl]-methylamine

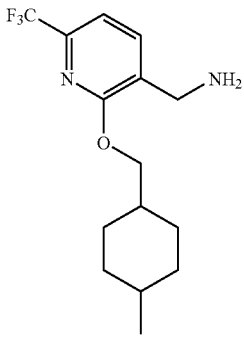 [SMILES: CC1CCC(COc2nc(C(F)(F)F)ccc2CN)CC1]

¹H NMR (CDCl₃) δ 7.78 & 7.64 (d, 1H), 7.21 (d, 1H, J=7.3 Hz), 4.40 & 3.85 (s, 2H), 4.31 & 4.20 (m, 2H), 2.00-1.50 (m, 7H), 1.40-1.00 (m, 3H), 0.95-0.87 (m, 3H); IR (neat) 2923, 1602, 1462, 1423, 1359, 1264, 1177, 1140, 1110 cm⁻¹

B-114: C-[2-(2,2-dimethyl-cyclopropylmethoxy)-6-trifluoromethyl-pyridin-3-yl]-methylamine

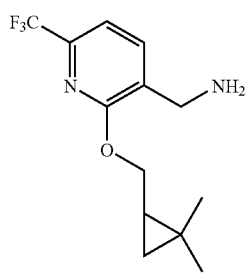 [SMILES: CC1(C)CC1COc1nc(C(F)(F)F)ccc1CN]

¹H NMR (CDCl₃) δ 7.64 (d, 1H, J=7.3 Hz), 7.21 (d, 1H, J=7.3 Hz), 4.63 (dd, 1H, J=11.5, 6.6 Hz), 4.20 (dd, 1H, J=11.6, 8.9 Hz), 3.86 (s, 2H), 1.14 (s, 3H), 1.10 (s, 3H), 0.88 (m, 1H), 0.58 (dd, 1H, J=8.6, 4.4 Hz), 0.30 (dd, 1H, J=4.8, 4.8 Hz); IR (neat) 2951, 1603, 1464, 1426, 1396, 1344, 1264, 1178, 1141, 987 cm⁻¹

B-115: 4-(3-aminomethyl-6-trifluoromethyl-pyridin-2-yloxymethyl)-piperidine-1-carbonic acid tert-butyl ester

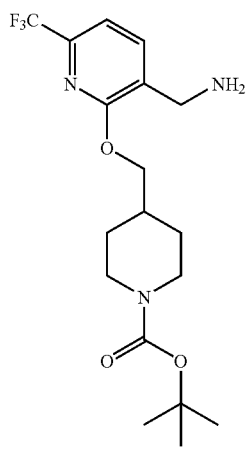 [SMILES: CC(C)(C)OC(=O)N1CCC(COc2nc(C(F)(F)F)ccc2CN)CC1]

¹H NMR (CDCl₃) δ 7.69 (d, 1H, J=7.5 Hz), 7.24 (d, 1H, J=7.5 Hz), 4.27 (d, 2H), 4.20-4.07 (m, 2H), 3.86 (s, 2H), 2.80-2.65 (m, 2H), 1.83-1.50 (m, 3H), 1.47 (s, 9H), 1.35-1.20 (m, 2H); IR (neat) 3392, 2926, 1688, 1424, 1361, 1268, 1174, 1142, 1017 cm⁻¹

B-116: C-[6-trifluoromethyl-2-(4-trifluoromethyl-cyclohexyloxy)-pyridin-3-yl]-methylamine

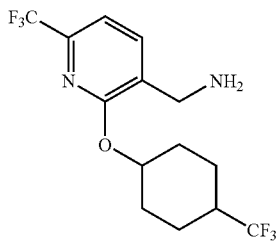

IR (neat) 2923, 1603, 1465, 1424, 1363, 1269, 1180, 1139 cm$^{-1}$

B-117: 4-(3-aminomethyl-6-trifluoromethyl-pyridin-2-yloxy)-piperidine-1-carbonic acid tert-butyl ester

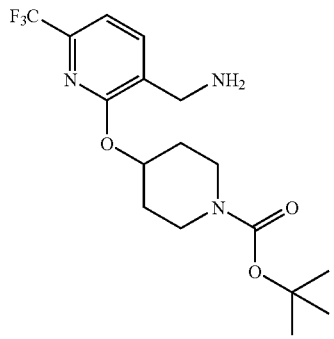 [SMILES: CC(C)(C)OC(=O)N1CCC(Oc2nc(C(F)(F)F)ccc2CN)CC1]

$^1$H NMR (CDCl$_3$) δ 7.69 (d, 1H, J=6.8 Hz), 7.24 (d, 1H, J=7.3 Hz), 5.36 (m, 1H), 3.85 (s, 2H), 3.68 (m, 2H), 3.40 (m, 2H), 2.05-1.60 (m, 4H), 1.48 (s, 9H)

IR (neat) 3393, 2928, 1688, 1421, 1363, 1272, 1237, 1173, 1139, 1028 cm$^{-1}$

B-118: C-[2-(pyridin-4-ylmethoxy)-6-trifluoromethyl-pyridin-3-yl]-methylamine

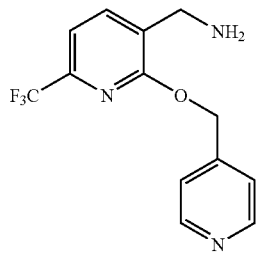 [SMILES: NCc1ccc(C(F)(F)F)nc1OCc1ccncc1]

$^1$H NMR (300 MHz, CDCl$_3$) δ 8.62 (d, 2H, J=6.0 Hz), 7.78 (d, 1H, J=7.2 Hz), 7.38 (d, 2H, J=6.2 Hz), 7.31 (d, 1H, J=7.6 Hz), 5.49 (s, 2H), 3.96 (s, 2H)

IR (neat) 3367, 1602, 1468, 1417, 1359, 1267, 1179, 1179, 1137, 1024, 936, 840, 801 cm$^{-1}$; MS (FAB) m/z 284 (M+H)

B-119: C-(2-phenethyloxy-6-trifluoromethyl-pyridin-3-yl)-methylamine

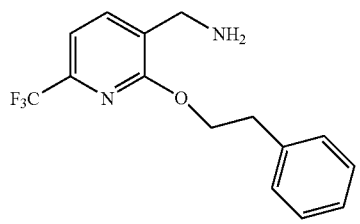 [SMILES: NCc1ccc(C(F)(F)F)nc1OCCc1ccccc1]

$^1$H NMR (300 MHz, CDCl$_3$) δ 7.63 (d, 1H, J=7.2 Hz), 7.38-7.21 (m, 6H), 4.63 (t, 2H, J=6.6 Hz), 3.78 (s, 2H), 3.11 (t, 2H, J=6.6 Hz), 1.61 (bs, 2H)

IR (neat) 3029, 2956, 1599, 1463, 1423, 1354, 1270, 1180, 1139, 1004, 951, 839, 747, 701 cm$^{-1}$; MS (FAB) m/z 297 (M+H)

B-120: C-[2-(pyridin-2-ylmethoxy)-6-trifluoromethyl-pyridin-3-yl]-methylamine

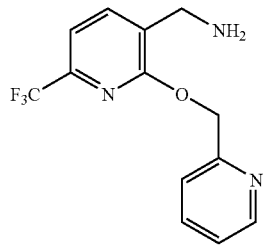 [SMILES: NCc1ccc(C(F)(F)F)nc1OCc1ccccn1]

$^1$H NMR (300 MHz, CDCl$_3$) δ 8.61 (d, 1H, J=4.9 Hz), 7.75 (d, 1H, J=7.7 Hz), 7.71 (td, 1H, J=7.7, 1.7 Hz), 7.48 (d, 1H, J=7.9 Hz), 7.26 (m, 2H), 5.61 (s, 2H), 3.98 (s, 2H), 2.13 (bs, 2H); IR (neat) 3395, 2920, 1598, 1417, 1355, 1274, 1181, 1137, 1002, 936, 840, 756 cm$^{-1}$; MS (FAB) m/z 284 (M+H)

B-121: C-(2-benzyloxy-6-trifluoromethyl-pyridin-3-yl)-methylamine

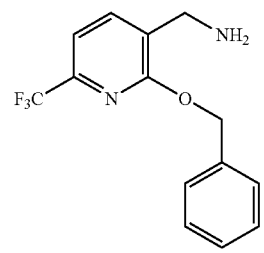 [SMILES: NCc1ccc(C(F)(F)F)nc1OCc1ccccc1]

$^1$H NMR (300 MHz, CDCl$_3$) δ 7.70 (d, 1H, J=7.3 Hz), 7.48 (m, 2H), 7.42-7.35 (m, 4H), 5.47 (s, 2H), 3.70 (s, 2H), 1.76

(bs, 2H); IR (neat) 2925, 1652, 1600, 1539, 1459, 1419, 1355, 1267, 1179, 1138, 992, 838, 741, 698 cm⁻¹; MS (FAB) m/z 283 (M+H)

B-122: 2-benzyloxy-4-trifluoromethyl-benzylamine

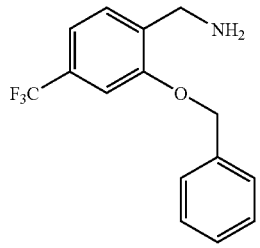 [SMILES: NCc1ccc(C(F)(F)F)cc1OCc1ccccc1]

¹H NMR (300 MHz, CDCl₃) δ 7.51-7.35 (m, 6H), 7.22 (d, 1H, J=7.7 Hz), 7.16 (s, 1H), 5.13 (s, 2H), 3.92 (s, 2H), 1.60 (bs, 2H); IR (neat) 2920, 1509, 1426, 1328, 1239, 1166, 1122, 1019, 917, 858, 740, 697 cm⁻¹; MS (FAB) m/z 282 (M+H)

B-123: C-[2-(pyridin-3-ylmethoxy)-6-trifluoromethyl-pyridin-3-yl]-methylamine

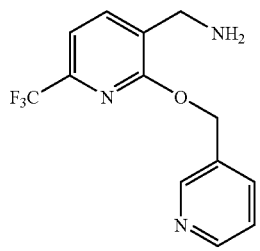 [SMILES: NCc1ccc(C(F)(F)F)nc1OCc1cccnc1]

¹H NMR (300 MHz, CDCl₃) δ 8.75 (s, 1H), 8.58 (d, 1H, J=4.4 Hz), 7.84 (d, 1H, J=7.7 Hz), 7.74 (d, 1H, J=7.5 Hz), 7.31 (d, 1H, J=4.9 Hz), 7.29 (d, 1H, J=7.3 Hz), 5.50 (s, 2H), 3.89 (s, 2H), 1.68 (bs, 2H); IR (neat) 2920, 1599, 1538, 1462, 1416, 1356, 1267, 1179, 1137, 997, 840 cm⁻¹; MS (FAB) m/z 284 (M+H)

B-124: C-[6-trifluoromethyl-2-(4-trifluoromethyl-benzyloxy)-pyridin-3-yl]-methylamine

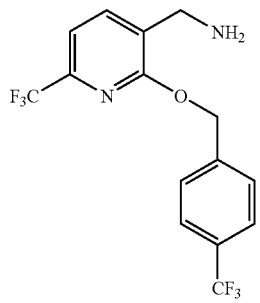 [SMILES: NCc1ccc(C(F)(F)F)nc1OCc1ccc(C(F)(F)F)cc1]

¹H NMR (300 MHz, CDCl₃) □7.74 (d, 1H, J=7.3 Hz), 7.69-7.54 (m, 4H), 7.29 (d, 1H, J=7.5 Hz), 5.53 (s, 2H), 3.91 (s, 2H), 1.50 (bs, 2H); IR (neat) 2919, 1600, 1467, 1419, 1356, 1326, 1267, 1131, 1067, 1014, 936, 826 cm⁻¹; MS (FAB) m/z 351 (M+H)

B-125: C-[2-(4-butyl-benzyloxy)-6-trifluoromethyl-pyridin-3-yl]-methylamine

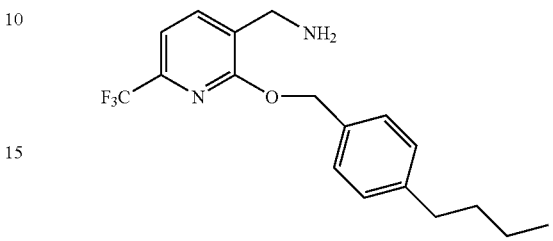

¹H NMR (300 MHz, CDCl₃) δ 7.68 (d, 1H, J=7.5 Hz), 7.39 (d, 2H, J=7.9 Hz), 7.25 (d, 1H, J=7.4 Hz), 7.19 (d, 2H, J=8.0 Hz), 5.43 (s, 2H), 3.87 (s, 2H), 2.61 (t, 2H, J=7.9 Hz), 1.60 (m, 2H), 1.36 (m, 2H), 0.93 (t, 3H, J=7.3 Hz)
IR (neat) 2929, 1599, 1463, 1420, 1353, 1267, 1180, 1141, 990, 836 cm⁻¹; MS (FAB) m/z 339 (M+H)

B-126: C-[2-(4-tert-butyl-benzyloxy)-6-trifluoromethyl-pyridin-3-yl]-methylamine

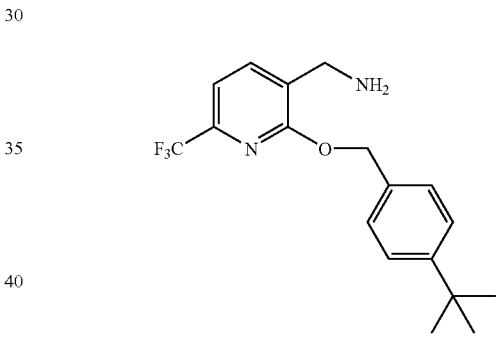

¹H NMR (300 MHz, CDCl₃) δ 7.68 (d, 1H, J=7.3 Hz), 7.49-7.34 (m, 4H), 7.25 (d, 1H, J=7.5 Hz), 5.44 (s, 2H), 3.87 (s, 2H), 1.52 (bs, 2H), 1.33 (s, 9H)
IR (neat) 2963, 1599, 1516, 1464, 1421, 1354, 1267, 1179, 1140, 990, 837 cm⁻¹; MS (FAB) m/z 339 (M+H)

B-127: C-[2-(indan-2-yloxy)-6-trifluoromethyl-pyridin-3-yl]-methylamine

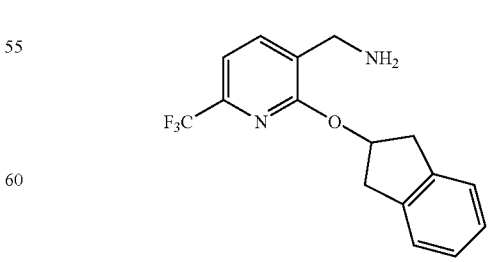

¹H NMR (300 MHz, CDCl₃) δ 7.66 (d, 1H, J=8.1 Hz), 7.25 (d, 1H, J=8.0 Hz), 7.24-7.15 (m, 4H), 5.91 (m, 1H), 3.76 (s, 2H), 3.48 (dd, 2H, J=17.0, 6.6 Hz), 3.14 (dd, 2H, J=16.9, 3.7

Hz), 1.43 (bs, 2H); IR (neat) 2953, 1676, 1596, 1464, 1418, 1348, 1266, 1186, 1139, 1012, 970, 935, 843, 743 cm$^{-1}$; MS (FAB) m/z 309 (M+H)

B-128: C-[2-(4-chloro-benzyloxy)-6-trifluoromethyl-pyridin-3-yl]-methylamine

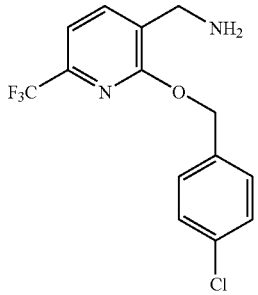 [SMILES: NCc1ccc(C(F)(F)F)nc1OCc1ccc(Cl)cc1]

$^1$H NMR (300 MHz, CDCl$_3$) δ 7.71 (d, 1H, J=7.3 Hz), 7.44-7.32 (m, 4H), 7.27 (d, 1H, J=7.3 Hz), 5.43 (s, 2H), 3.88 (s, 2H), 1.50 (bs, 2H); IR (neat) 2919, 1600, 1493, 1465, 1423, 1355, 1264, 1179, 1138, 1110, 997, 935, 839 cm$^{-1}$; MS (FAB) m/z 317 (M+H)

B-129: C-[6-(chloro-difluoro-methyl)-2-cyclopentyloxy-pyridin-3-yl]-methylamine

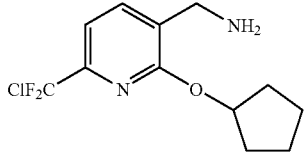

$^1$H NMR (300 MHz, CDCl$_3$) δ 7.60 (d, 1H, J=7.3 Hz), 7.16 (d, 1H, J=7.5 Hz), 5.52 (m, 1H), 3.81 (m, 2H), 1.95-2.10 (m, 2H), 1.60-1.90 (m, 6H); IR (neat) 3367, 2961, 1599, 1456, 1418, 1349, 1265, 1096, 991, 888, 827 cm$^{-1}$; MS (FAB) m/z 277 (M+H)

B-130: C-[6-(chloro-difluoro-methyl)-2-cyclohexyloxy-pyridin-3-yl]-methylamine

$^1$H NMR (400 MHz, CDCl$_3$) 7.61 (d, 1H, J=7.6 Hz), 7.15 (d, 1H, J=7.6 Hz), 5.19 (m, 1H), 3.83 (s, 2H), 1.93-2.04 (m, 2H), 1.70-1.82 (m, 2H), 1.52-1.66 (m, 6H); IR (neat) 2936, 2858, 1600, 1455, 1419, 1364, 1263, 1096, 989, 881 cm$^{-1}$; MS (FAB) m/z 291 (M+H)

B-131: C-[6-(chloro-difluoro-methyl)-2-(pyridin-3-ylmethoxy)-pyridin-3-yl]-methylamine

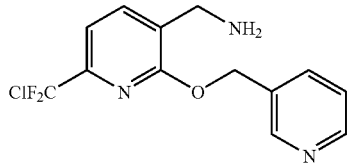

$^1$H NMR (300 MHz, CDCl$_3$) δ 8.76 (s, 1H), 8.57 (m, 1H), 7.85 (m, 1H), 7.72 (d, 1H, J=7.1 Hz), 7.31 (m, 1H), 7.25 (d, 1H, J=7.5 Hz), 5.51 (bs, 2H), 3.88 (s, 2H); IR (neat) 2922, 1598, 1456, 1414, 1357, 1096, 1005, 884, 829, 712 cm$^{-1}$; MS (FAB) m/z 300 (M+H)

B-132: C-[6-(chloro-difluoro-methyl)-2-(pyridin-2-ylmethoxy)-pyridin-3-yl]-methylamine

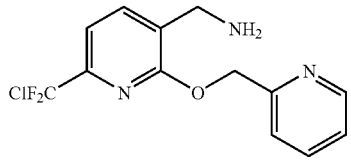

$^1$H NMR (300 MHz, CDCl$_3$) δ 8.59 (m, 1H), 7.68-7.84 (m, 2H), 7.47 (m, 1H), 7.21-7.26 (m, 2H), 5.66 (s, 2H), 4.09 (s, 2H); IR (neat) 2921, 1597, 1416, 1350, 1272, 1097, 1011, 969, 832, 763 cm$^{-1}$; MS (FAB) m/z 300 (M+H)

B-133: C-[6-(chloro-difluoro-methyl)-2-isobutoxy-pyridin-3-yl]-methylamine

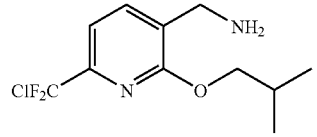

$^1$H NMR (300 MHz, CDCl$_3$) δ 7.63 (d, 1H, J=7.4 Hz), 7.19 (d, 1H, J=7.5 Hz), 4.15-4.23 (m, 2H), 3.86 (bs, 2H), 2.12 (m, 1H), 1.04 (d, 6H, J=6.7 Hz); IR (neat) 2963, 1599, 1460, 1422, 1361, 1264, 1184, 1095, 1012, 970, 880, 826 cm$^{-1}$; MS (FAB) m/z 265 (M+H)

B-134:
2-cyclopentyloxy-4-trifluoromethyl-benzylamine

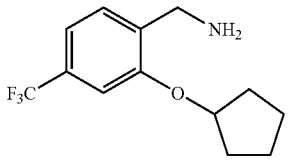 [SMILES: NCc1ccc(C(F)(F)F)cc1OC1CCCC1]

$^1$H NMR (300 MHz, CDCl$_3$) δ 7.32 (d, 1H, J=7.5 Hz), 7.15 (d, 1H, J=7.7 Hz), 7.04 (bs, 1H), 4.86 (m, 1H), 3.82 (s, 2H), 1.60-2.02 (m, 8H); IR (neat) 2962, 1590, 1507, 1427, 1331, 1238, 1167, 1122, 989, 916, 862 cm$^{-1}$; MS (FAB) m/z 260 (M+H)

B-135:
2-cyclohexyloxy-4-trifluoromethyl-benzylamine

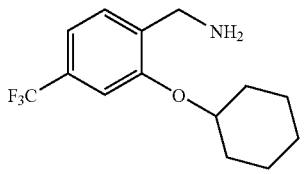 [SMILES: NCc1ccc(C(F)(F)F)cc1OC1CCCCC1]

$^1$H NMR (300 MHz, CDCl$_3$) δ 7.34 (d, 1H, J=7.9 Hz), 7.15 (d, 1H, J=7.7 Hz), 7.05 (bs, 1H), 4.39 (m, 1H), 3.86 (s, 2H), 1.90-2.00 (m, 4H), 1.70-1.89 (m, 2H), 1.51-1.69 (m, 2H), 1.32-1.51 (m, 2H); IR (neat) 2938, 2860, 1589, 1507, 1426, 1329, 1234, 1164, 1122, 1078, 1044, 973, 906, 862 cm$^{-1}$; MS (FAB) m/z 274 (M+H)

B-136: 2-butoxy-4-trifluoromethyl-benzylamine

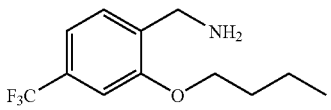

$^1$H NMR (300 MHz, CDCl$_3$) δ 7.34 (d, 1H, J=7.7 Hz), 7.18 (d, 1H, J=7.7 Hz), 7.05 (bs, 1H), 4.04 (t, 2H, J=6.2 Hz), 3.87 (s, 2H), 1.72-1.85 (m, 2H), 1.41-1.60 (m, 2H), 1.00 (t, 3H, J=7.3 Hz); IR (neat) 3304, 2957, 1507, 1427, 1382, 1330, 1239, 1159, 1114, 919, 861, 822 cm$^{-1}$; MS (FAB) m/z 248 (M+H)

B-137: C-(2-cyclopentyloxy-4-methyl-6-trifluoromethyl-pyridin-3-yl)-methylamine

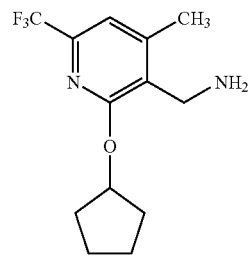 [SMILES: Cc1cc(C(F)(F)F)nc(OC2CCCC2)c1CN]

$^1$H NMR (300 MHz, CDCl$_3$) δ 7.04 (s, 1H), 5.51 (m, 1H), 3.82 (s, 2H), 2.38 (s, 3H), 2.01 (m, 2H), 1.75 (m, 6H); IR (neat) 2964, 1574, 1288, 1061, 993, 917, 865, 723 cm$^{-1}$; MS (FAB) m/z 275 (M+H)

B-138: C-[2-(1-butyl-pentyloxy)-6-trifluoromethyl-pyridin-3-yl]-methylamine

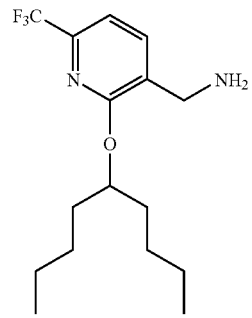 [SMILES: CCCCC(CCCC)Oc1nc(C(F)(F)F)ccc1CN]

$^1$H NMR (300 MHz, CDCl$_3$) δ 7.62 (d, 1H, J=7.3 Hz), 7.18 (d, 1H, J=7.5 Hz), 5.32 (m, 1H), 3.82 (s, 2H), 1.67~1.75 (m, 2H), 1.33 (m, 9H), 0.90 (m, 7H); IR (neat) 2932, 2865, 1601, 1464, 975, 835, 744, 701 cm$^{-1}$; MS (FAB) m/z 319 (M+H)

B-139: C-(2-p-tolyloxy-6-trifluoromethyl-pyridin-3-yl)-methylamine

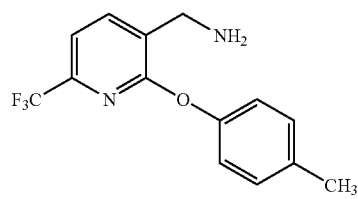 [SMILES: Cc1ccc(Oc2nc(C(F)(F)F)ccc2CN)cc1]

$^1$H NMR (300 MHz, CDCl$_3$) δ 7.84 (d, 1H, J=7.3 Hz), 7.35 (d, 1H, J=7.5 Hz), 7.19 (d, 2H, J=8.8 Hz), 7.06 (m, 2H), 4.02

(s, 2H), 2.37 (s, 3H); IR (neat) 2923, 1596, 1511, 1463, 1403, 1262, 1142, 943, 816 cm⁻¹; MS (FAB) m/z 283 (M+H)

B-140: C-(4-methyl-2-pentyloxy-6-trifluoromethyl-pyridin-3-yl)-methylamine

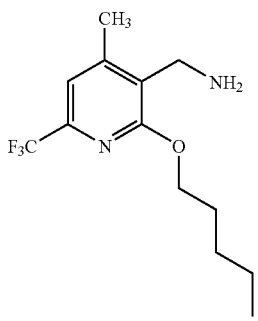 [SMILES: CCCCCOc1nc(C(F)(F)F)cc(C)c1CN]

¹H NMR (300 MHz, CDCl₃) δ 7.06 (s, 1H), 4.37 (t, 2H, J=6.6 Hz), 3.85 (s, 2H), 2.40 (s, 3H), 1.80 (m, 2H), 1.45 (m, 2H), 1.39-1.31 (m, 4H), 0.90 (m, 3H)

IR (neat) 2931, 1610, 1575, 1463, 1409, 1348, 1290, 1246, 1177, 1138, 1073, 917, 866, 721 cm⁻¹; MS (FAB) m/z 277 (M+H)

B-141: C-(2-methoxy-6-trifluoromethyl-pyridin-3-yl)-methylamine

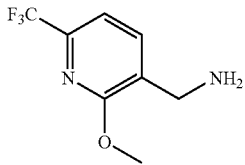

¹H NMR (CDCl₃) δ 7.67 (d, 1H, J=7.3 Hz), 7.25 (d, 1H), 4.03 (s, 3H), 3.85 (s, 2H); IR (neat) 3400, 2923, 1738, 1468, 1370, 1268, 1137 cm⁻¹

B-142: C-[2-(4-ethyl-benzyloxy)-6-trifluoromethyl-pyridin-3-yl]-methylamine

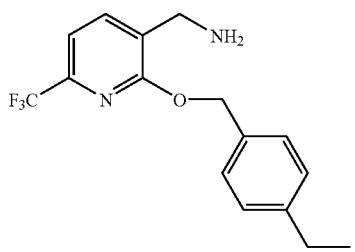 [SMILES: CCc1ccc(COc2nc(C(F)(F)F)ccc2CN)cc1]

¹H NMR (300 MHz, CDCl₃) δ 7.68 (d, 1H, J=7.3 Hz), 7.41 (d, 2H, J=7.9 Hz), 7.25 (d, 1H, J=7.2 Hz), 7.21 (d, 2H, J=7.9 Hz), 5.44 (s, 2H), 3.87 (s, 2H), 2.66 (q, 2H, J=7.5 Hz), 1.63 (bs, 2H), 1.24 (t, 3H, J=7.6 Hz); IR (neat) 2965, 1600, 1463, 1419, 1354, 1265, 1178, 1138, 1111, 990, 825 cm⁻¹; MS (FAB) m/z 311 (M+H)

B-143: C-[2-benzyloxy-6-(chloro-difluoro-methyl)-pyridin-3-yl]-methylamine

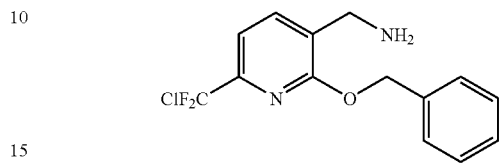

¹H NMR (400 MHz, CDCl₃) δ 7.67 (d, 1H, J=7.6 Hz), 7.45-7.52 (m, 2H), 7.28-7.40 (m, 3H), 7.22 (d, 1H, J=7.6 Hz), 5.48 (s, 2H), 3.88 (s, 2H); IR (neat) 2923, 1599, 1456, 1416, 1356, 1256, 1096, 1000, 883, 872, 698 cm⁻¹; MS (FAB) m/z 299 (M+H)

B-144: C-[6-(chloro-difluoro-methyl)-2-hexyloxy-pyridin-3-yl]-methylamine

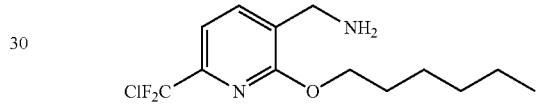

¹H NMR (300 MHz, CDCl₃) δ 7.62 (d, 1H, J=7.3 Hz), 7.18 (d, 1H, J=7.5 Hz), 4.34-4.44 (m, 2H), 3.80-3.85 (m, 2H), 1.70-1.84 (m, 2H), 1.21-1.52 (m, 6H), 0.85-0.95 (m, 3H); IR (neat) 2930, 1600, 1460, 1423, 1364, 1264, 1096, 1002, 879, 827 cm⁻¹; MS (FAB) m/z 293 (M+H)

Method 3:

Compounds of the general formula VI-Ca or VI-Cb (1.5 mmol), in which $R^5$, $R^{14}$, U, T and V have the above-stated meaning and m denotes 0, 1, 2 or 3, are dissolved in diethyl-ether (3 mL) and a suspension of lithium aluminium hydride (3 mmol) in diethylether (5 mL) is slowly added. The reaction mixture is heated to reflux for 4 hours, and methanol and 1 N aq. NaOH soln. are slowly added at 0° C. The reaction mixture is diluted with methanol and filtered over celite. The solvent is evaporated under a vacuum and the residue is purified by flash chromatography (SiO₂, different mixtures of methylene chloride and methanol).

The following compounds B-145 to B-150 were obtained according to the above-stated general method:

B-145: 2-butoxy-4-tert-butyl-benzylamine

¹H NMR (300 MHz, CDCl₃) δ 7.17 (d, 1H, J=7.8 Hz), 6.92 (dd, 1H, J=1.6, 1.6 Hz), 6.88 (d, 1H, J=1.6 Hz), 4.02 (t, 2H, J=6.4 Hz), 3.85 (bs, 2H), 1.85-1.76 (m, 2H), 1.57-1.44 (m, 2H), 1.3 (s, 9H), 0.98 (t, 3H, J=7.3 Hz)

IR (neat) 2959, 2869, 1612, 1576, 1507, 1468 cm⁻¹

B-146: 4-tert-butyl-2-isobutoxy-benzylamine

¹H NMR (300 MHz, CDCl₃) δ 7.18 (d, 1H, J=7.7 Hz), 6.92 (dd, 1H, J=1.6, 1.6 Hz), 6.86 (d, 1H, J=1.6 Hz), 4.15 (bs, 2H), 3.80 (s, 2H), 3.78 (d, 2H, J=6.4 Hz), 2.18-2.10 (m, 1H), 1.30 (s, 9H), 1.05 (d, 6H, J=6.6 Hz)

IR (neat) 2958, 1614, 1513, 1409, 1269, 1232 cm$^{-1}$

B-147: 4-tert-butyl-2-cyclohexyloxy-benzylamine $^1$H NMR (300 MHz, CDCl$_3$) δ 7.18 (d, 1H, J=7.5 Hz), 6.91-6.89 (m, 2H), 5.29 (bs, 2H), 4.43-4.30 (m, 1H), 3.88 (s, 2H), 2.03-1.25 (m, 10H), 1.29 (s, 9H)

IR (neat) 2932, 2875, 1611, 1504, 1455, 1412 cm$^{-1}$

B-148: 4-tert-butyl-2-(2,2-dimethyl-propoxy)-benzylamine $^1$H NMR (300 MHz, CDCl$_3$) δ 7.22 (d, 1H, J=7.8 Hz), 6.94 (dd, 1H, J=1.6, 1.6 Hz), 6.86 (s, 1H), 5.41 (bs, 2H), 3.95 (s, 2H), 3.60 (s, 2H), 1.30 (s, 9H), 1.06 (s, 9H)

IR (neat) 2958, 2867, 1613, 1577, 1475, 1410 cm$^{-1}$

B-149: 4-tert-butyl-2-cyclopentyloxy-benzylamine $^1$H NMR (300 MHz, CDCl$_3$) δ 7.12 (d, 1H, J=8.2 Hz), 6.90-6.88 (m, 2H), 4.86-4.80 (m, 1H), 3.75 (s, 2H), 2.94 (bs, 2H), 1.95-1.61 (m, 8H), 1.30 (s, 9H)

IR (neat) 2959, 1611, 1576, 1503, 1412, 1269 cm$^{-1}$

B-150: 4-tert-butyl-2-pentyloxy-benzylamine $^1$H NMR (300 MHz, CDCl$_3$) δ 7.18 (d, 1H, J=7.8 Hz), 6.94-6.87 (m, 2H), 4.73 (bs, 2H), 4.01 (t, 2H, J=6.4 Hz), 3.88 (s, 2H), 1.86-1.78 (m, 2H), 1.51-1.35 (m, 4H), 1.30 (s, 9H), 0.93 (t, 3H, J=6.9 Hz)

IR (neat) 2958, 2866, 1614, 1511, 1463, 1415 cm$^{-1}$

4. General Procedure for the Preparation of Amines of General Formula V-C

Amines of the general formula V-C are prepared as shown in scheme 3 below.

Scheme 3.

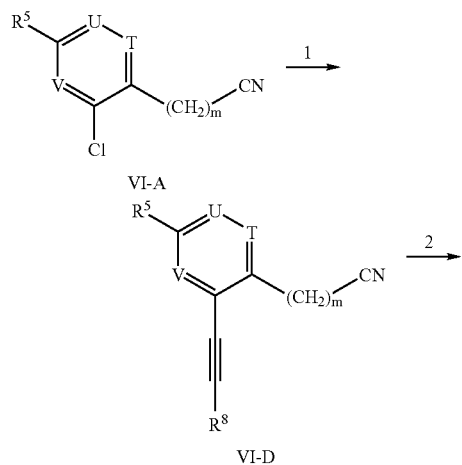

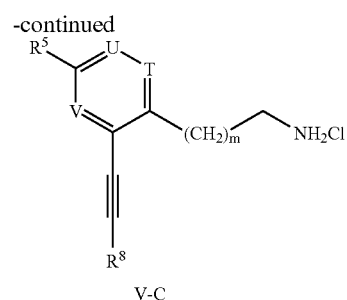

Stage 1: Preparation of Nitrites of General Formula VI-D

Compounds of general formula VI-A (1 equivalent), wherein $R^5$, U, T and V have the above-stated meaning and m denotes 0, 1, 2 or 3, are treated with bis(triphenylphosphine) palladium dichloride (7 mol-%) and copper(I)iodide (14 mol-%) in 1-methyl-2-pyrrolidinon (7 mL per mmol of compound of general formula VI-A). After 10 min the alkyne of general formula HC≡C—$R^8$ (3.5 equivalents) and N, N-diisopropylethylamine (2 equivalents) are added and the reaction mixture is stirred at a temperature between 90 and 110° C. for 12 hours. The reaction mixture is filtered over celite and repeatedly extracted with EA. The combined organic phases are washed with sat. aq. NaCl soln., dried over MgSO$_4$ and the solvent is removed under a vacuum. The residue is purified by flash chromatography (SiO$_2$, different mixtures of hexanes and EA).

The following compounds A-174 to A-180 were obtained according to the above-stated general method:

A-174: 2-pent-1-ynyl-6-trifluoromethyl-nicotinonitrile

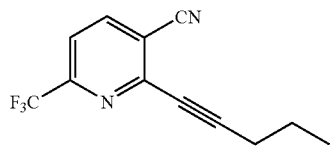 [SMILES: CCCC#Cc1nc(C(F)(F)F)ccc1C#N]

$^1$H NMR (300 MHz, CDCl$_3$) δ 8.13 (d, 1H, J=8.3 Hz), 7.68 (d, 1H, 8.3 Hz), 2.55 (t, 2H, J=7.1 Hz), 1.68-1.80 (m, 2H), 1.11 (t, 3H, J=7.3 Hz); IR (neat) 9969, 2230, 1569, 1406, 1341, 1197, 1153, 1086, 851 cm$^{-1}$; MS (FAB) m/z 239 (M+H)

A-175: 2-(3,3-dimethyl-but-1-ynyl)-6-trifluoromethyl-nicotinonitrile

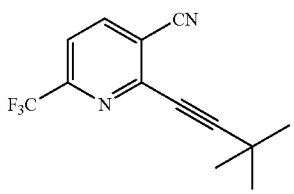 [SMILES: CC(C)(C)C#Cc1nc(C(F)(F)F)ccc1C#N]

$^1$H NMR (300 MHz, CDCl$_3$) δ 8.11 (d, 1H, J=8.3 Hz), 7.66 (d, 1H, J=8.3 Hz), 1.41 (bs, 9H); IR (neat) 2975, 2240, 2216, 1568, 1450, 1403, 1342, 1277, 1191, 1153, 1121, 1085, 850 cm⁻¹; MS (FAB) m/z 253 (M+H)

A-176: 2-p-tolylethynyl-6-trifluoromethyl-nicotinonitrile

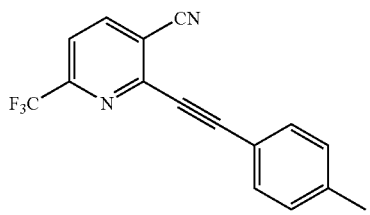 [SMILES: Cc1ccc(C#Cc2nc(C(F)(F)F)ccc2C#N)cc1]

¹H NMR (300 MHz, CDCl₃) δ 8.17 (d, 1H, J=8.1 Hz), 7.69 (d, 1H, J=8.1 Hz), 7.57-7.65 (m, 2H), 7.24-7.26 (m, 2H), 2.41 (s, 3H); IR (neat) 3079, 2216, 1567, 1413, 1343, 1286, 1184, 1143, 1112, 851, 819 cm⁻¹; MS (FAB) m/z 287 (M+H)

A-177: 2-hex-1-ynyl-6-trifluoromethyl-nicotinonitrile

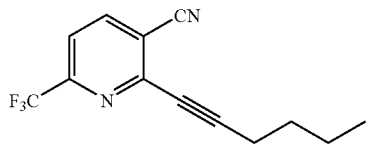 [SMILES: CCCCC#Cc1nc(C(F)(F)F)ccc1C#N]

¹H NMR (300 MHz, CDCl₃) δ 8.12 (d, 1H, J=7.7 Hz), 7.67 (d, 1H, J=8.1 Hz), 2.57 (d, 2H, J=7.0 Hz), 1.61-1.76 (m, 2H), 1.47-1.61 (m, 2H), 0.97 (t, 3H, J=7.3 Hz); IR (neat) 2962, 2234, 1570, 1449, 1406, 1342, 1198, 1153, 1124, 1085, 849, 742 cm⁻¹; MS (FAB) m/z 253 (M+H)

A-178: 2-(4-methyl-pent-1-ynyl)-6-trifluoromethyl-nicotinonitrile

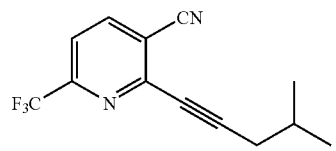 [SMILES: CC(C)CC#Cc1nc(C(F)(F)F)ccc1C#N]

¹H NMR (300 MHz, CDCl₃) δ 8.13 (d, 1H, J=8.1 Hz), 7.68 (d, 1H, J=8.1 Hz), 2.47 (d, 2H, J=6.4 Hz), 2.04 (m, 1H), 1.11 (d, 6H, J=6.6 Hz); IR (neat) 2964, 2233, 1571, 1450, 1405, 1341, 1198, 1153, 1086, 1017, 850, 743 cm⁻¹; MS (FAB) m/z 253 (M+H)

A-179: 2-(3-cyclohexyl-prop-1-ynyl)-6-trifluoromethyl-nicotinonitrile

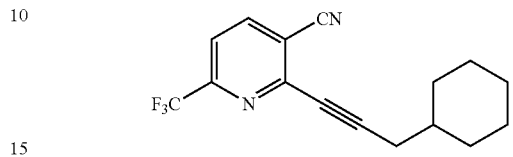

¹H NMR (300 MHz, CDCl₃) δ 8.12 (d, 1H, J=8.2 Hz), 7.66 (d, 1H, J=8.1 Hz), 2.47 (d, 2H, J=6.6 Hz), 1.39-1.94 (m, 5H), 0.88-1.40 (m, 6H); IR (neat) 2925, 2852, 2231, 1569, 1448, 1405, 1341, 1194, 1154, 1124, 1085, 847 cm⁻¹

MS (FAB) m/z 293 (M+H)

A-180: 2-(4-fluoro-phenylethynyl)-6-trifluoromethyl-nicotinonitrile

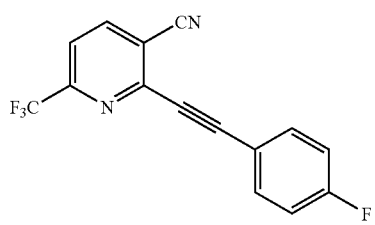 [SMILES: N#Cc1ccc(C(F)(F)F)nc1C#Cc1ccc(F)cc1]

¹H NMR (300 MHz, CDCl₃) δ 8.19 (d, 1H, J=8.0 Hz), 7.67-7.70 (m, 3H), 7.06-7.18 (m, 2H); IR (neat) 3077, 2233, 1562, 1507, 1445, 1409, 1341, 1288, 1233, 1157, 1111, 840 cm⁻¹; MS (FAB) m/z 291 (M+H)

5. General Procedure for the Preparation of Amines of General Formula V-D

Amines of the general formula V-D are prepared as shown in scheme 4 below.

Scheme 4.

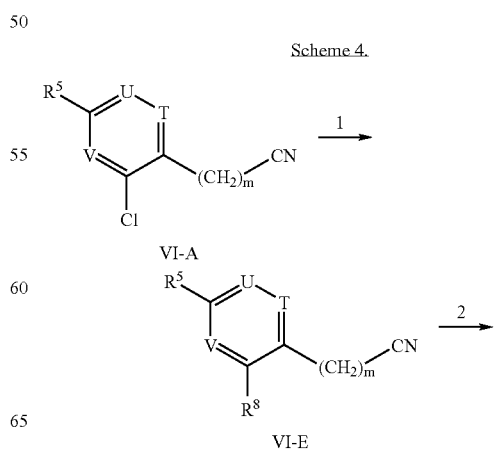

-continued

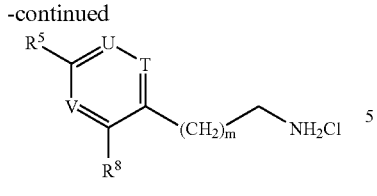

V-D

R⁸ = Aryl, Heteroaryl, Cycloalkenyl

Stage 1: Preparation of Nitrites of General Formula VI-E

Compounds of general formula VI-A (1 equivalent), wherein $R^5$, U, T and V have the above-stated meaning and m denotes 0, 1, 2 or 3, are treated with palladiumdichloride (5 mol-%) and a compound of general formula $R^8$—$B(OH)_2$ (2 equivalents) in a solvent mixture of toluene/dioxane/2 N aq. sodium carbonate soln. (20 mL per 1 mmol compound of general formula VI-A). The reaction mixture is heated to reflux for 12 hours and filtered over Celite. The combined organic extracts are dried over magnesium sulfate and the solvent is removed under a vacuum. The residue is purified by flash chromatography (SiO₂, different mixture of hexanes and EA).

The following compounds A-181 to A-201 were obtained according to the above-stated general method:

A-181: 2-(4-chloro-phenyl)-6-trifluoromethyl-nicotinonitrile

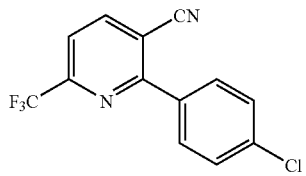 [SMILES: N#Cc1ccc(C(F)(F)F)nc1-c1ccc(Cl)cc1]

¹H NMR (300 MHz, CDCl₃) δ 8.29 (d, 1H, J=8.0 Hz), 7.98 (d, 2H, J=9.2 Hz), 7.76 (d, 1H, J=8.1 Hz), 7.54 (d, 2H, J=8.8 Hz); IR (neat) 2220, 1593, 1493, 1454, 1404, 1340, 1186, 1151, 1091, 1045, 1013, 841 cm⁻¹; MS (FAB) m/z 283 (M+H)

A-182: 6-(trifluoromethyl)-2-phenylpyridine-3-carbonitrile

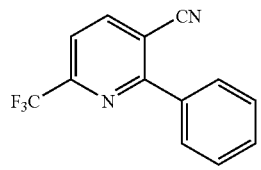 [SMILES: N#Cc1ccc(C(F)(F)F)nc1-c1ccccc1]

¹H NMR (300 MHz, CDCl₃) δ 7.50-7.55 (m, 3H), 7.72 (d, 1H, J=7.8 Hz), 7.95-8.01 (m, 2H), 8.24 (d, 1H, J=7.8 Hz); IR (neat) 2923, 2250, 1515, 1461, 1400, 1339, 1186, 1148 cm⁻¹; MS (FAB) m/z 249 (M+H)

A-183: 2-thiophen-2-yl-6-trifluoromethyl-nicotinonitrile

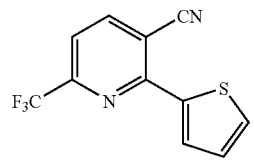 [SMILES: N#Cc1ccc(C(F)(F)F)nc1-c1cccs1]

¹H NMR (400 MHz, CDCl₃) δ 8.33 (d, 1H, J=2.7 Hz), 8.17 (d, 1H, J=6.0 Hz), 7.61 (dd, 1H, J=7.8, 0.6 Hz), 7.58 (d, 1H, J=6.0 Hz), 7.20 (t, 1H, J=2.7 Hz); MS (FAB) m/z 255 (M+H)

A-184: 2-(4-fluoro-phenyl)-6-trifluoromethyl-nicotinonitrile

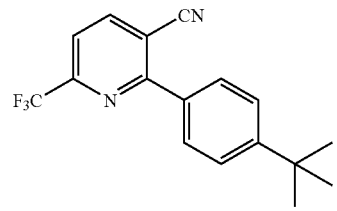 [SMILES: CC(C)(C)c1ccc(-c2nc(C(F)(F)F)ccc2C#N)cc1]

¹H NMR (300 MHz, CDCl₃) δ 8.27 (d, 1H, J=8.1 Hz), 8.04 (m, 2H), 7.74 (d, 1H, J=8.1 Hz), 7.24 (m, 2H); IR (neat) 3363, 2958, 1716, 1614, 1515, 1457, 1344, 1247, 1143, 1050, 833 cm⁻¹; MS (FAB) m/z 267 (M+H)

A-185: 2-(4-tert-butyl-phenyl)-6-trifluoromethyl-nicotinonitrile

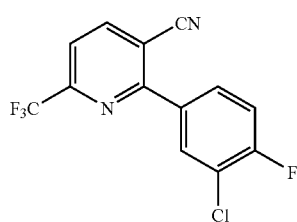 [SMILES: N#Cc1ccc(C(F)(F)F)nc1-c1ccc(F)c(Cl)c1]

¹H NMR (300 MHz, CDCl₃) δ 8.26 (d, 1H, J=8.1 Hz), 7.96 (d, 2H, J=9.0 Hz), 7.70 (d, 1H, J=8.1 Hz), 7.54 (d, 2H, J=9.0 Hz), 1.37 (s, 9H); IR (neat) 3267, 2920, 1731, 1604, 1510, 1413, 1345, 1229, 1141, 1094, 1049, 839, 749 cm⁻¹; MS (FAB) m/z 306 (M+H)

A-186: 2-(3-chloro-4-fluoro-phenyl)-6-trifluoromethyl-nicotinonitrile

¹H NMR (300 MHz, CDCl₃) δ 8.29 (d, 1H, J=7.8 Hz), 8.02 (dd, 1H, J=6.9, 2.1 Hz), 7.95 (m, 1H), 7.78 (d, 1H, J=7.8 Hz), 7.33 (t, 1H, J=8.4 Hz); MS (FAB) m/z 301 (M+H)

A-187: 2-(3-fluoro-phenyl)-6-trifluoromethyl-nicotinonitrile

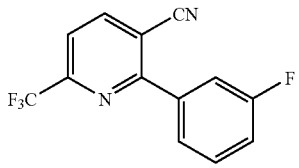 [SMILES: N#Cc1ccc(C(F)(F)F)nc1-c1cccc(F)c1]

¹H NMR (300 MHz, CDCl₃) δ 8.29 (d, 1H, J=8.0 Hz), 7.82 (m, 1H), 7.78 (d, 1H, J=8.0 Hz), 7.71 (m, 1H), 7.53 (m, 1H), 7.26 (m, 1H); IR (neat) 3424, 2235, 1584, 1463, 1398, 1340, 1278, 1189, 1153, 1093, 1051, 918, 850, 781, 707 cm⁻¹; MS (FAB) m/z 267 (M+H)

A-188: 2-cyclohex-1-enyl-6-trifluoromethyl-nicotinonitrile

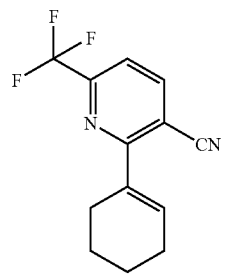 [SMILES: N#Cc1ccc(C(F)(F)F)nc1C1=CCCCC1]

¹H NMR (300 MHz, CDCl₃) δ 8.13 (d, 1H, J=8.1 Hz), 7.19 (d, 1H, J=8.1 Hz), 6.65 (m, 1H), 2.57 (m, 2H), 2.33 (m, 2H), 1.66-1.86 (m, 4H); MS (FAB) m/z 253 (M+H)

A-189: 4'-tert-butyl-5-trifluoromethyl-biphenyl-2-carbonitrile

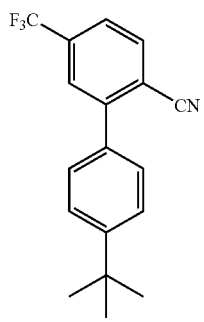 [SMILES: CC(C)(C)c1ccc(-c2cc(C(F)(F)F)ccc2C#N)cc1]

¹H NMR (300 MHz, CDCl₃) δ 7.89 (d, 1H, J=7.7 Hz), 7.78 (s, 1H), 7.68 (d, 1H, J=7.9 Hz), 7.54 (d, 4H, J=0.9 Hz), 1.38 (s, 9H); IR (neat) 2964, 2240, 1538, 1420, 1335, 1260, 1175, 1075, 838 cm⁻¹; MS (FAB) m/z 304 (M+H)

A-190: 4'-methoxy-5-trifluoromethyl-biphenyl-2-carbonitrile

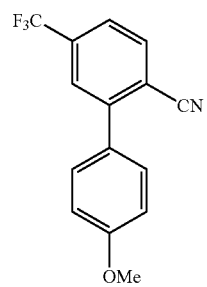 [SMILES: COc1ccc(-c2cc(C(F)(F)F)ccc2C#N)cc1]

¹H NMR (300 MHz, CDCl₃) δ 7.88 (d, 1H, J=8.2 Hz), 7.75 (s, 1H), 7.66 (d, 1H, J=8.0 Hz), 7.53 (dd, 2H, J=6.8 Hz, J=1.8 Hz), 7.05 (dd, 2H, J=6.6 Hz, J=2.0 Hz), 3.88 (s, 3H); IR (neat) 2958, 2240, 1610, 1517, 1294, 1076, 1040, 909, 831 cm⁻¹; MS (FAB) m/z 277 (M+H)

A-191: 3'-chloro-5-trifluoromethyl-biphenyl-2-carbonitrile

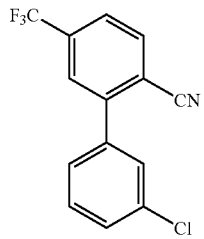 [SMILES: N#Cc1ccc(C(F)(F)F)cc1-c1cccc(Cl)c1]

¹H NMR (300 MHz, CDCl₃) δ 7.93 (d, 1H, J=8.3 Hz), 7.75 (d, 2H, J=7.7 Hz), 7.53 (m, 1H), 7.45 (m, 3H); IR (neat) 3068, 2232, 1567, 1411, 1252, 1041, 839, 698 cm⁻¹; MS (FAB) m/z 282 (M+H)

A-192: 3'-fluoro-5-trifluoromethyl-biphenyl-2-carbonitrile

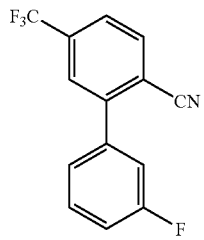 [SMILES: N#Cc1ccc(C(F)(F)F)cc1-c1cccc(F)c1]

¹H NMR (300 MHz, CDCl₃) δ 7.92 (dd, 1H, J=7.9 Hz, J=0.6 Hz), 7.75 (m, 2H), 7.52 (m, 1H), 7.37 (d, 1H, J=6.0 Hz), 7.20 (m, 2H); IR (neat) 2238, 1588, 1489, 1450, 1292, 907, 841, 791, 701 cm$^{-1}$; MS (FAB) m/z 265 (M+H)

A-193: 3'-chloro-4'-fluoro-5-trifluoromethyl-biphenyl-2-carbonitrile

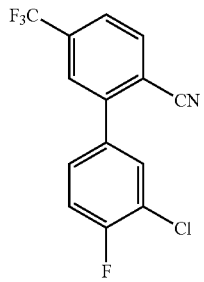 [SMILES: N#Cc1ccc(C(F)(F)F)cc1-c1ccc(F)c(Cl)c1]

$^1$H NMR (300 MHz, CDCl$_3$) δ 7.93 (d, 1H, J=8.2 Hz), 7.76 (d, 2H, J=7.1 Hz), 7.61 (dd, 1H, J=6.8 Hz, J=2.4 Hz), 7.48 (m, 1H), 7.32 (m, 1H); IR (neat) 2238, 1490, 1416, 1333, 1263, 1177, 1075, 888, 835 cm$^{-1}$; MS (FAB) m/z 299 (M+H)

A-194: 3',4'-dimethoxy-5-trifluoromethyl-biphenyl-2-carbonitrile

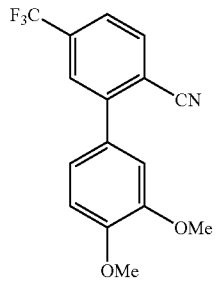 [SMILES: COc1ccc(-c2cc(C(F)(F)F)ccc2C#N)cc1OC]

$^1$H NMR (300 MHz, CDCl$_3$) δ 7.88 (d, 1H, J=8.3 Hz), 7.78 (s, 1H), 7.67 (d, 1H, J=8.0 Hz), 7.14 (m, 2H), 7.01 (d, 1H, J=8.3 Hz), 3.97 (s, 3H), 3.96 (s, 3H), IR (neat) 2940, 2238, 1604, 1521, 1420, 1217, 1075, 1025, 838 cm$^{-1}$; MS (FAB) m/z 308 (M+H)

A-195: 2-pyridin-3-yl-4-trifluoromethyl-benzonitrile

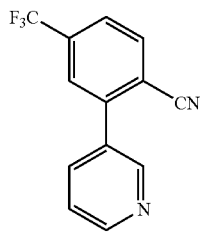 [SMILES: N#Cc1ccc(C(F)(F)F)cc1-c1cccnc1]

$^1$H NMR (300 MHz, CDCl$_3$) δ 8.81 (d, 1H, J=2.2 Hz), 8.77 (dd, 1H, J=5.0 Hz, J=1.7 Hz), 7.96 (m, 2H), 7.80 (d, 2H, J=5.7

Hz), 7.50 (m, 1H); IR (neat) 3031, 2238, 2229, 1569, 1415, 1015, 929, 839, 808 cm$^{-1}$; MS (FAB) m/z 249 (M+H)

A-196: 2-(3,4-dimethoxy-phenyl)-6-trifluoromethyl-nicotinonitrile

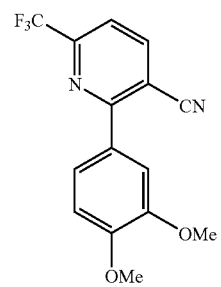 [SMILES: COc1ccc(-c2nc(C(F)(F)F)ccc2C#N)cc1OC]

$^1$H NMR (300 MHz, CDCl$_3$) δ 8.19 (d, 1H, J=7.9 Hz), 7.62 (m, 3H), 6.98 (d, 1H, J=8.4 Hz), 3.95 (s, 3H), 3.92 (s, 3H); IR (neat) 2969, 2238, 1569, 1462, 1340, 1088, 1024, 845, 762 cm$^{-1}$; MS (FAB) m/z 309 (M+H)

A-197: 2-(3,5-dimethoxy-phenyl)-6-trifluoromethyl-nicotinonitrile

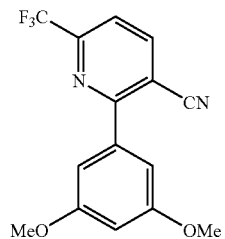 [SMILES: COc1cc(OC)cc(-c2nc(C(F)(F)F)ccc2C#N)c1]

$^1$H NMR (300 MHz, CDCl$_3$) δ 8.23 (d, 1H, J=8.1 Hz), 7.71 (d, 1H, J=8.1 Hz), 7.10 (s, 2H), 6.61 (s, 1H), 3.85 (s, 6H); IR (neat) 2233, 1598, 1458, 1400, 920, 859, 831, 790 cm$^{-1}$; MS (FAB) m/z 309 (M+H)

A-198: 3',5'-dimethoxy-5-trifluoromethyl-biphenyl-2-carbonitrile

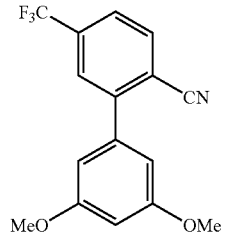 [SMILES: COc1cc(OC)cc(-c2cc(C(F)(F)F)ccc2C#N)c1]

$^1$H NMR (300 MHz, CDCl$_3$) δ 7.80 (m, 2H), 6.95 (d, 1H, J=2.4 Hz), 6.73 (m, 2H), 6.57 (m, 1H), 3.86 (s, 3H), 3.85 (s,

A-199: 2-(3-chloro-phenyl)-6-trifluoromethyl-nicotinonitrile

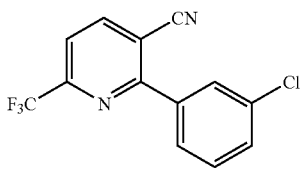 [SMILES: N#Cc1ccc(C(F)(F)F)nc1-c1cccc(Cl)c1]

$^1$H NMR (300 MHz, CDCl$_3$) δ 8.29 (d, 1H, J=8.1 Hz), 7.96 (m, 1H), 7.90 (m, 1H), 7.78 (d, 1H, J=8.0 Hz), 7.46-7.55 (m, 2H); IR (neat) 3394, 2231, 1566, 1337, 1194, 1134, 1089, 850 cm$^{-1}$; MS (FAB) m/z 283 (M+H)

A-200: 2-(2-fluoro-phenyl)-6-trifluoromethyl-nicotinonitrile

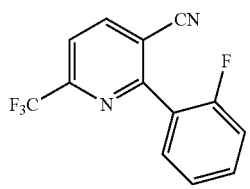 [SMILES: N#Cc1ccc(C(F)(F)F)nc1-c1ccccc1F]

$^1$H NMR (300 MHz, CDCl$_3$) δ 8.29 (d, 1H, J=8.1 Hz), 7.83 (d, 1H, J=8.1 Hz), 7.65 (m, 1H), 7.57 (m, 1H), 7.36 (dd, 1H, J=7.5, 1.1 Hz), 7.30 (m, 1H); IR (neat) 2230, 1617, 1463, 1401, 1340, 1186, 1149, 852, 762 cm$^{-1}$; MS (FAB) m/z 267 (M+H)

A-201: 2-(4-methoxy-phenyl)-6-trifluoromethyl-nicotinonitrile

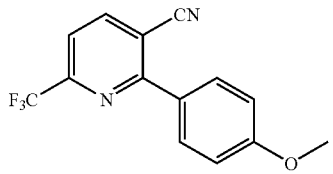 [SMILES: COc1ccc(-c2nc(C(F)(F)F)ccc2C#N)cc1]

$^1$H NMR (300 MHz, CDCl$_3$) δ 8.23 1H, J=8.0 Hz), 8.04 (d, 2H, J=9.0 Hz), 7.67 (d, 1H, J=8.0 Hz), 7.06 (d, 2H, J=9.0 Hz), 3.90 (s, 3H); IR (neat) 2239, 1608, 1398, 1340, 1259, 1181, 1148, 1087, 841 cm$^{-1}$; MS (FAB) m/z 279 (M+H)

Stage 2:
Method 1

Compounds of the general formula VI-E (5 mmol), in which R$^5$, R$^8$, U, T and V have the above-stated meaning and m denotes 0, 1, 2 or 3, palladium on carbon (10%, 500 mg) and concentrated hydrochloric acid (3 mL) are dissolved in MeOH (30 mL) and exposed to a hydrogen atmosphere for 6 hours at RT. The reaction mixture is filtered through celite and the filtrate is evaporated under a vacuum. The residue is purified by means of flash chromatography (SiO$_2$, EA).

The following compounds B-151 to B-152 were obtained according to the above-stated general method:

B-151: C-(2-cyclohexyl-6-trifluoromethyl-pyridin-3-yl)-methylamine

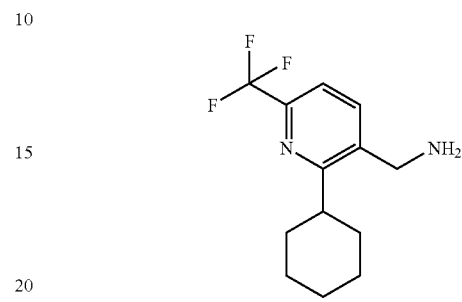

$^1$H NMR (300 MHz, CDCl$_3$) δ 7.81 (d, 1H, J=7.8 Hz), 7.45 (d, 1H, J=7.8 Hz), 3.99 (s, 2H), 2.87 (m, 1H), 1.72-1.88 (m, 6H), 1.44 (bs, 2H), 1.34-1.37 (m, 4H); IR (neat) 2928, 2855, 1588, 1453, 1405, 1343, 1257, 1179, 1137, 1011, 917, 841 cm$^{-1}$;

MS (FAB) m/z 259 (M+H)

B-152: C-(4-phenyl-6-trifluoromethyl-pyridin-3-yl)-methylamine

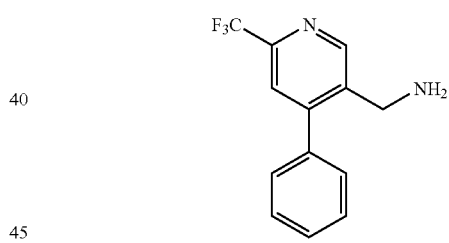

$^1$H NMR (300 MHz, CD$_3$OD) δ 7.76 (s, 1H), 7.18-7.55 (m, 6H), 4.27 (s, 2H) IR (neat) 398, 2948, 1595, 1491, 1404, 1332, 1220, 1140, 1084, 919, 769, 701 cm$^{-1}$;

MS (FAB) m/z 253 (M+H)

Method 2:

Compounds of the general formula VI-E (2 mmol), in which R$^5$, R$^8$, U, T and V have the above-stated meaning and m denotes 0, 1, 2 or 3, are dissolved in THF (10 mL) and BH$_3$.S(CH$_3$)$_2$ [2.0 M in THF, 3 mL, 3 equivalents] is added.

The reaction mixture is heated to reflux for 8 hours, aq. HCl (2 N) is added and the reaction mixture is again heated to reflux for 30 minutes. Aq. NaOH soln. and EA are added. The combined organic extracts are washed with sat. aq. NaCl soln. and dried over MgSO$_4$. The solvent is evaporated under a vacuum and the residue is purified by flash chromatography (SiO$_2$, different mixtures of methylene chloride and methanol).

The following compounds B-153 to B-171 were obtained according to the above-stated general method:

B-153: (6-(trifluoromethyl)-2-phenylpyridin-3-yl) methanamine

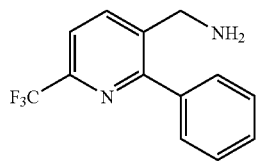 [SMILES: NCc1ccc(C(F)(F)F)nc1-c1ccccc1]

¹H NMR (300 MHz, CDCl₃) d 8.07 (d, 1H, J=7.8 Hz), 7.67 (d, 1H, J=7.8 Hz), 7.43-7.55 (m, 5H), 3.97 ((s, 2H); IR (neat) 2924, 1402, 1344, 1179, 1136, 844, 768, 702 cm⁻¹; MS (FAB) m/z 253 (M+H)

B-154: (2-bromo-6-(trifluoromethyl)pyridin-3-yl) methanamine

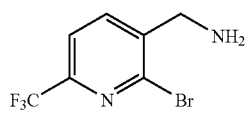

¹H NMR (300 MHz, CDCl₃) δ 7.91 (d, 1H, J=7.8 Hz), 7.61 (d, 1H, J=7.8 Hz), 3.95 (s, 2H); MS (FAB) m/z 256 (M+H)

B-155: C-[2-(4-tert-butyl-phenyl)-6-trifluoromethyl-pyridin-3-yl]-methylamine

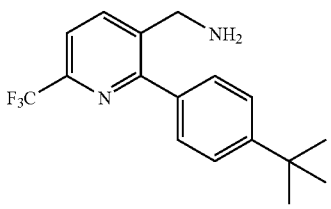 [SMILES: CC(C)(C)c1ccc(-c2nc(C(F)(F)F)ccc2CN)cc1]

¹H NMR (300 MHz, CDCl₃+CD₃OD) d 8.26 (d, 1H, J=7.8 Hz), 7.63 (d, 1H, J=7.8 Hz), 7.40 (d, 2H, J=8.1 Hz), 7.29 (d, 2H, J=8.1 Hz), 4.51 (s, 2H), 1.25 (s, 9H); MS (FAB) m/z 309 (M+H)

B-156: C-[2-(3-chloro-4-fluoro-phenyl)-6-trifluoromethyl-pyridin-3-yl]-methylamine

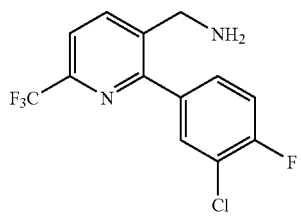 [SMILES: NCc1ccc(C(F)(F)F)nc1-c1ccc(F)c(Cl)c1]

¹H NMR (300 MHz, CDCl₃) δ 8.14 (d, 1H, J=7.8 Hz), 7.65-7.71 (m, 2H), 7.46 (m, 1H), 7.23 (t, 1H, J=8.4 Hz), 3.96 (s, 2H); MS (FAB) m/z 305 (M+H)

B-157: [4-(3-aminomethyl-6-trifluoromethyl-pyridin-2-yl)-phenyl]-dimethyl-amine

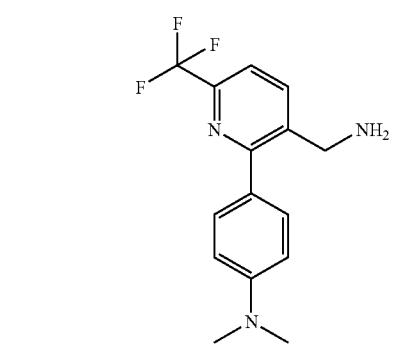 [SMILES: CN(C)c1ccc(-c2nc(C(F)(F)F)ccc2CN)cc1]

¹H NMR (300 MHz, CDCl₃) δ 8.03 (d, 1H, J=7.5 Hz), 7.56 (d, 1H, J=7.5 Hz), 7.47 (d, 2H, J=9.0 Hz), 6.77 (d, 2H, J=9.0 Hz), 4.06 (s, 2H), 3.01 (s, 6H), 2.36 (bs, 2H); IR (neat) 3396, 2921, 1610, 1518, 1401, 1344, 1176, 944, 824 cm⁻¹; MS (FAB) m/z 296 (M+H)

B-158: C-[2-(4-chloro-phenyl)-6-trifluoromethyl-pyridin-3-yl]-methylamine

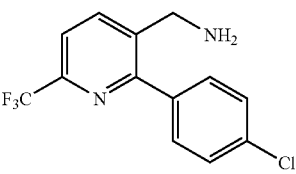 [SMILES: NCc1ccc(C(F)(F)F)nc1-c1ccc(Cl)cc1]

¹H NMR (300 MHz, CDCl₃) δ 8.11 (d, 1H, J=8.0 Hz), 7.66 (m, 1H), 7.52 (d, 2H, J=8.2 Hz), 7.44 (d, 2H, J=8.4 Hz), 3.96 (s, 2H); IR (neat) 2921, 1595, 1460, 1407, 1344, 1178, 1138, 1093, 835 cm⁻¹; MS (FAB) m/z 287 (M+H)

B-159: C-[2-(3-fluoro-phenyl)-6-trifluoromethyl-pyridin-3-yl]-methylamine

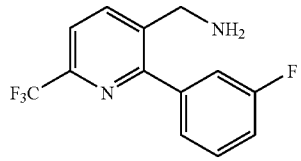 [SMILES: NCc1ccc(C(F)(F)F)nc1-c1cccc(F)c1]

¹H NMR (300 MHz, CDCl₃) δ 8.12 (d, 1H, J=8.1 Hz), 7.70 (d, 1H, 8.1 Hz), 7.45 (m, 1H), 7.27-7.35 (m, 2H), 7.09 (m,

1H), 3.98 (s, 2H); IR (neat) 2922, 1587, 1463, 1400, 1344, 1272, 1183, 1136, 845, 792, 708 cm$^{-1}$; MS (FAB) m/z 271 (M+H)

B-160: C-[2-(3-chloro-phenyl)-6-trifluoromethyl-pyridin-3-yl]-methylamine

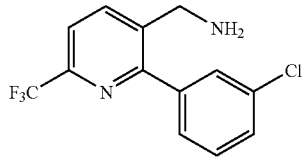 [SMILES: NCc1ccc(C(F)(F)F)nc1-c1cccc(Cl)c1]

$^1$H NMR (300 MHz, CDCl$_3$) δ 8.11 (d, 1H, J=8.0 Hz), 7.70 (d, 1H, J=8.0 Hz), 7.56 (m, 1H), 7.37-7.46 (m, 3H), 3.97 (s, 2H); IR (neat) 2922, 1586, 1344, 1179, 1138, 1099, 888, 845 cm$^{-1}$; MS (FAB) m/z 287 (M+H)

B-161: C-[2-(2-fluoro-phenyl)-6-trifluoromethyl-pyridin-3-yl]-methylamine

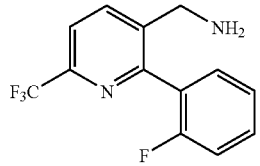 [SMILES: NCc1ccc(C(F)(F)F)nc1-c1ccccc1F]

$^1$H NMR (300 MHz, CDCl$_3$) δ 8.14 (d, 1H, J=8.0 Hz), 7.74 (d, 1H, J=8.1 Hz), 7.42-7.48 (m, 2H), 7.30 (m, 1H), 7.17 (m, 1H), 3.86 (s, 2H); IR (neat) 2924, 1617, 1456, 1345, 1179, 1138, 762 cm$^{-1}$; MS (FAB) m/z 271 (M+H)

B-162: C-[2-(4-methoxy-phenyl)-6-trifluoromethyl-pyridin-3-yl]-methylamine

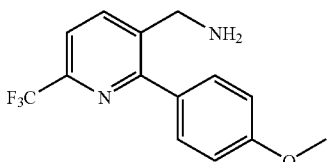

$^1$H NMR (300 MHz, CDCl$_3$) δ 8.06 (d, 1H, J=7.9 Hz), 7.63 (d, 1H, J=7.9 Hz), 7.52 (d, 2H, J=8.8 Hz), 7.00 (d, 2H, J=8.8 Hz), 4.01 (s, 2H), 3.87 (bs, 3H); IR (neat) 2926, 1611, 1515, 1345, 1251, 1178, 1135, 837 cm$^{-1}$; MS (FAB) m/z 283 (M+H)

B-163: C-(4'-tert-butyl-5-trifluoromethyl-biphenyl-2-yl)-methylamine

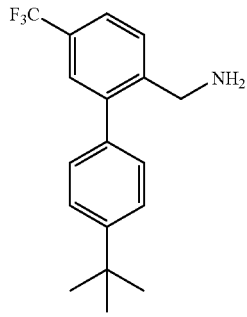 [SMILES: CC(C)(C)c1ccc(-c2cc(C(F)(F)F)ccc2CN)cc1]

$^1$H NMR (300 MHz, CDCl$_3$) δ 7.60 (s, 2H), 7.47 (m, 3H), 7.26 (m, 2H), 3.87 (s, 2H), 1.37 (s, 9H); IR (neat) 2963, 1514, 1419, 1259, 1167, 1078, 1036, 836 cm$^{-1}$; MS (FAB) m/z 308 (M+H)

B-164: C-(4'-methoxy-5-trifluoromethyl-biphenyl-2-yl)-methylamine

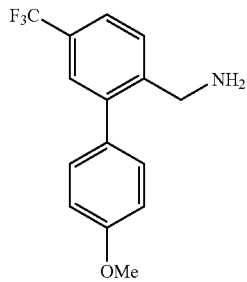 [SMILES: COc1ccc(-c2cc(C(F)(F)F)ccc2CN)cc1]

$^1$H NMR (300 MHz, CDCl$_3$) δ 7.59 (s, 2H), 7.48 (s, 1H), 7.25 (m, 2H), 6.98 (dd, 2H, J=8.6 Hz, J=2.0 Hz), 3.86 (s, 3H); IR (neat) 3328, 2914, 1610, 1516, 1464, 1418, 1042, 904 cm$^{-1}$; MS (FAB) m/z 282 (M+H)

B-165: C-(3'-chloro-5-trifluoromethyl-biphenyl-2-yl)-methylamine

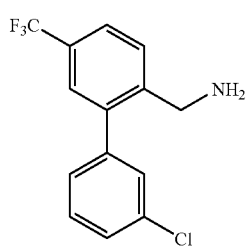 [SMILES: NCc1ccc(C(F)(F)F)cc1-c1cccc(Cl)c1]

¹H NMR (300 MHz, CDCl₃) δ 7.65 (s, 2H), 7.47 (s, 1H), 7.39 (m, 2H), 7.35 (m, 1H), 7.22 (m, 1H), 3.84 (s, 2H); IR (neat) 2921, 1565, 1419, 1256, 1040, 835, 791, 701 cm⁻¹; MS (FAB) m/z 286 (M+H)

B-166: C-(3'-fluoro-5-trifluoromethyl-biphenyl-2-yl)-methylamine

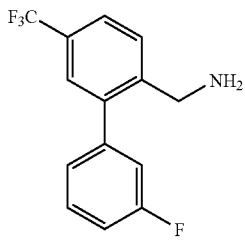 [SMILES: NCc1ccc(C(F)(F)F)cc1-c1cccc(F)c1]

¹H NMR (300 MHz, CDCl₃) δ 7.64 (d, 2H, J=1.3 Hz), 7.48 (s, 1H), 7.41 (m, 1H), 7.09 (m, 3H), 3.85 (s, 2H); IR (neat) 2920, 1615, 1485, 1444, 1274, 902, 791, 705 cm⁻¹; MS (FAB) m/z 270 (M+H)

B-167: C-(3'-chloro-4'-fluoro-5-trifluoromethyl-biphenyl-2-yl)-methylamine

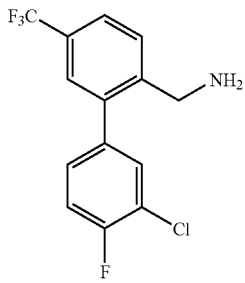 [SMILES: NCc1ccc(C(F)(F)F)cc1-c1ccc(F)c(Cl)c1]

¹H NMR (300 MHz, CDCl₃) δ 7.65 (s, 2H), 7.43 (m, 2H), 7.24 (m, 2H), 3.83 (s, 2H); IR (neat) 2921, 1494, 1419, 1168, 1078, 886, 828 cm⁻¹; MS (FAB) m/z 304 (M+H)

B-168: C-(3',4'-dimethoxy-5-trifluoromethyl-biphenyl-2-yl)-methylamine

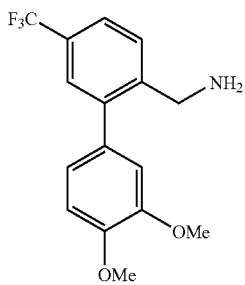 [SMILES: COc1ccc(-c2cc(C(F)(F)F)ccc2CN)cc1OC]

¹H NMR (300 MHz, CDCl₃) δ 7.60 (d, 2H, J=1.3 Hz), 7.50 (s, 1H), 6.94 (m, 1H), 6.88 (m, 2H), 3.94 (s, 3H), 3.90 (s, 3H), 3.69 (m, 2H); IR (neat) 3367, 2938, 1518, 1421, 1170, 1078, 1026, 816 cm⁻¹; MS (FAB) m/z 312 (M+H)

B-169: C-[2-(3,4-dimethoxy-phenyl)-6-trifluoromethyl-pyridin-3-yl]-methylamine

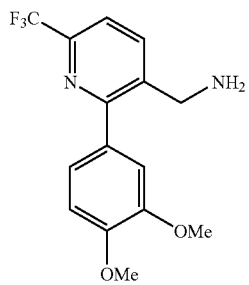 [SMILES: COc1ccc(-c2nc(C(F)(F)F)ccc2CN)cc1OC]

¹H NMR (300 MHz, CDCl₃) δ 8.06 (d, 1H, J=7.9 Hz), 7.64 (d, 1H, J=7.9 Hz), 7.16 (d, 1H, J=2.0 Hz), 7.12 (dd, 1H, J=8.1 Hz, J=2.0 Hz), 6.96 (d, 1H, J=8.3 Hz), 4.01 (s, 2H), 3.94 (s, 3H), 3.93 (s, 3H); IR (neat) 2937, 1604, 1463, 1415, 1253, 1175, 1026, 819 cm⁻¹; MS (FAB) m/z 313 (M+H)

B-170: C-[2-(3,5-dimethoxy-phenyl)-6-trifluoromethyl-pyridin-3-yl]-methylamine

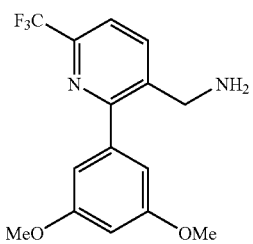 [SMILES: COc1cc(OC)cc(-c2nc(C(F)(F)F)ccc2CN)c1]

¹H NMR (300 MHz, CDCl₃) δ 8.07 (d, 1H, J=8.0 Hz), 7.67 (d, 1H, J=8.0 Hz), 6.65 (d, 2H, J=1.8 Hz), 6.53 (t, 1H, J=2.2 Hz), 3.96 (s, 2H), 3.82 (s, 6H); IR (neat) 2942, 1597, 1460, 1401, 1345, 1098, 1040, 841 cm⁻¹; MS (FAB) m/z 313 (M+H)

B-171: C-(3',5'-dimethoxy-5-trifluoromethyl-biphenyl-2-yl)-methylamine

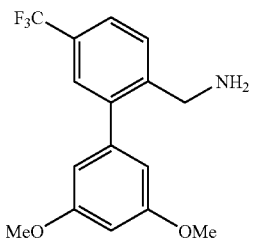 [SMILES: COc1cc(OC)cc(-c2cc(C(F)(F)F)ccc2CN)c1]

¹H NMR (300 MHz, CDCl₃) δ 7.60 (s, 2H), 7.50 (s, 1H), 6.50 (t, 1H, J=2.4 Hz), 6.46 (d, 2H, J=2.4 Hz), 3.87 (s, 2H), 3.82 (s, 6H); IR (neat) 2940, 1458, 1417, 1332, 1207, 1077, 903, 837 cm⁻¹; MS (FAB) m/z 312 (M+H)

6. General Procedure for the Preparation of Carbonic Acids of General Formula VIIa Carbonic Acides of the General Formula VIIa are Prepared as Shown in Scheme 5 Below.

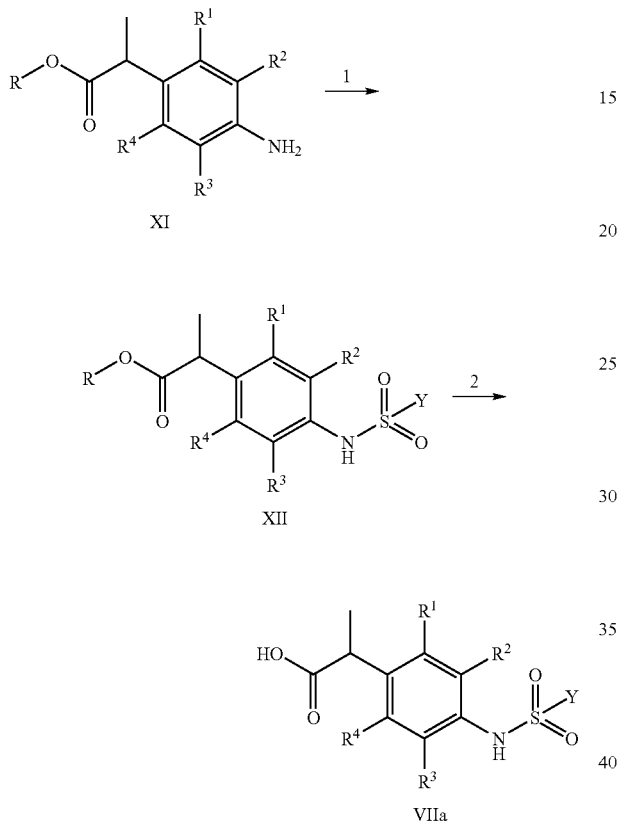

Stage 1:
Compounds of general formula XI (7 mmol), wherein $R^1$, $R^2$, $R^3$, $R^4$ and Y have the above-stated meaning and R denotes a linear or branched $C_{1-6}$-alkyl residue, are treated with a compound of general formula Cl—S(=O)$_2$—Y (8 mmol), wherein Y has the above-stated meaning. The reaction mixture is stirred for 10 min at 0° C. and subsequently for 3 hours at room temperature in pyridine (10 mL). The reaction mixture is taken up in methylene choride and aq. HCl (1 N). The organic phase is separated and the solvent is removed under a vacuum. The residue is in each case crystallized from mixtures of methylene chloride and hexanes.

Stage 2:
Compounds of general formula XII (5 mmol), wherein $R^1$, $R^2$, $R^3$, $R^4$ and Y have the above-stated meaning and R denotes a linear or branched $C_{1-6}$-alkyl residue, are treated with lithiumhydroxide monohydrate (15 mmol) in a solvent mixture of water and tetrahydrofuran (1:2, 24 mL) for 4 hours at 40° C. The reaction mixture is taken up in dichloromethane and water, treated with aq. HCl (1 N), and repeatedly extracted with dichloromethane. The combined organic extracts are washed with sat. aq. NaCl soln. and dried over sodium sulfate. The solvent is removed under a vacuum and the residue is in each case crystallized from mixtures of methylene chloride and hexanes.

D-1: 2-(4-dimethylaminosulfonylamino-3-fluoro-phenyl)-propionic acid ethylester

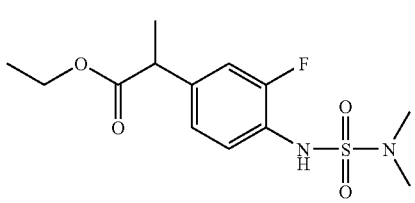 [SMILES: CCOC(=O)C(C)c1ccc(NS(=O)(=O)N(C)C)c(F)c1]

$^1$H NMR (300 MHz, CDCl$_3$) δ 7.44 (dd, 1H, J=8.1, 8.1 Hz), 6.94-7.05 (m, 2H), 6.78 (bs, 1H), 4.07 (m, 2H), 3.62 (q, 1H, J=6.9 Hz), 2.76 (s, 6H), 1.39 (d, 3H, J=6.9 Hz), 1.39 (t, 3H, J=7.2 Hz), 1.17 (t, 3H, J=7.5 Hz)

MS (FAB) m/z 319 (M+H)

D-2: 2-(4-dimethylaminosulfonylamino-3-fluoro-phenyl)-propionic acid

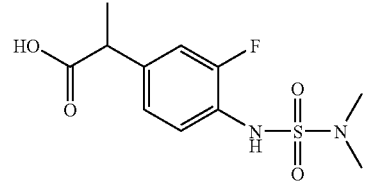 [SMILES: CC(C(=O)O)c1ccc(NS(=O)(=O)N(C)C)c(F)c1]

$^1$H NMR (300 MHz, CDCl$_3$) δ 750 (dd, 1H, J=8.1, 8.1 Hz), 7.05-7.12 (m, 2H), 6.69 (bs, 1H), 3.71 (q, 1H, J=6.9 Hz), 2.82 (s, 6H), 1.49 (d, 3H, J=6.9 Hz)

MS (FAB) m/z 291 (M+H)

D-3: 2-[3-fluoro-4-(2,2,2-trifluoro-ethansulfony-lamino)-phenyl]-propionic acid ethyl ester

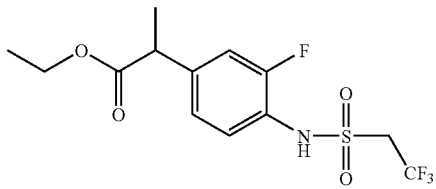 [SMILES: CCOC(=O)C(C)c1ccc(NS(=O)(=O)CC(F)(F)F)c(F)c1]

$^1$H NMR (300 MHz, CDCl$_3$) δ 7.50 (dd, 1H, J=8.1, 8.1 Hz), 7.11-7.18 (m, 2H), 7.00 (bs, 1H), 4.14 (m, 2H), 3.87 (q, 2H, J=9.0 Hz), 3.70 (q, 1H, J=6.9 Hz), 1.49 (d, 3H, J=6.9 Hz), 1.23 (t, 3H, J=6.9 Hz)

MS (FAB) m/z 358 (M+H)

D-4: 2-[3-fluoro-4-(2,2,2-trifluoro-ethansulfonylamino)-phenyl]-propionic acid

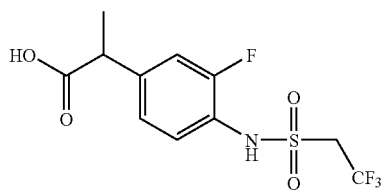 [SMILES: CC(C(=O)O)c1ccc(NS(=O)(=O)CC(F)(F)F)c(F)c1]

MS (FAB) m/z 330 (M+H)

D-5: 2-(3-fluoro-4-trifluoromethylsulfonamido-phenyl)-propionic acid ethyl ester

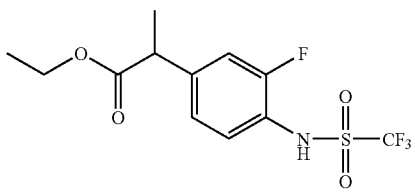 [SMILES: CCOC(=O)C(C)c1ccc(NS(=O)(=O)C(F)(F)F)c(F)c1]

$^1$H NMR (300 MHz, CDCl$_3$) δ 7.45 (dd, 1H, J=8.1, 8.1 Hz), 7.09-7.16 (m, 2H), 7.00 (bs, 1H), 4.14 (m, 2H), 3.70 (q, 1H, J=6.9 Hz), 1.49 (d, 3H, J=6.9 Hz), 1.22 (t, 3H, J=7.2 Hz); MS (FAB) m/z 344 (M+H)

D-6: 2-(4-aminosulfonylamino-3-fluoro-phenyl)-propionic acid

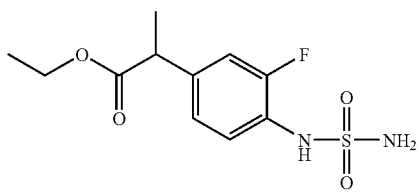 [SMILES: CCOC(=O)C(C)c1ccc(NS(N)(=O)=O)c(F)c1]

$^1$H NMR (300 MHz, CDCl$_3$) δ 7.49 (dd, 1H, J=8.1, 8.1 Hz), 7.04-7.12 (m, 2H), 6.68 (bs, 1H), 5.05 (bs, 2H), 4.14 (m, 2H), 3.68 (q, 1H, J=6.9 Hz), 1.46 (d, 3H, J=6.9 Hz), 1.23 (t, 3H, J=7.2 Hz)
MS (FAB) m/z 291 (M+H)

D-7: 2-[3-fluoro-4-(2,2,2-trifluoro-ethansulfonylamino)-phenyl]-propionic acid

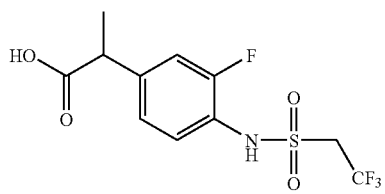 [SMILES: CC(C(=O)O)c1ccc(NS(=O)(=O)CC(F)(F)F)c(F)c1]

MS (FAB) m/z 330 (M+H)

D-8: 2-[3-fluoro-4-(propan-2-sulfonylamino)-phenyl]-propionic acid ethylester

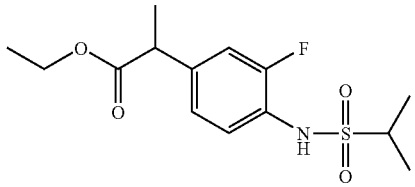 [SMILES: CCOC(=O)C(C)c1ccc(NS(=O)(=O)C(C)C)c(F)c1]

$^1$H NMR (300 MHz, CDCl$_3$) δ 7.55 (dd, 1H, J=8.1, 8.1 Hz), 7.05-7.12 (m, 2H), 6.71 (bs, 1H), 4.15 (m, 2H), 3.67 (q, 1H, J=6.9 Hz), 3.07 (m, 1H), 1.47 (d, 3H, J=6.9 Hz), 1.40 (d, 6H, J=6.9 Hz), 1.22 (t, 3H, J=7.2 Hz)

MS (FAB) m/z 318 (M+H)

D-9: 2-(4-ethanesulfonylamino-3-fluoro-phenyl)-propionic acid ethylester

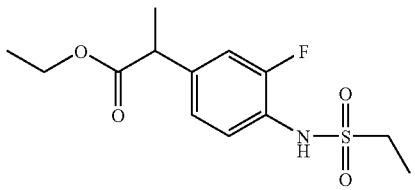 [SMILES: CCOC(=O)C(C)c1ccc(NS(=O)(=O)CC)c(F)c1]

$^1$H NMR (300 MHz, CDCl$_3$) δ 7.52 (dd, 1H, J=8.1, 8.1 Hz), 7.06-7.14 (m, 2H), 6.62 (bs, 1H), 4.13 (m, 2H), 3.66 (q, 1H, J=6.9 Hz), 3.12 (q, 2H, J=7.2 Hz), 1.47 (d, 3H, J=6.9 Hz), 1.39 (t, 3H, J=7.2 Hz), 1.25 (t, 3H, J=7.2 Hz)

MS (FAB) m/z 304 (M+H)

D-10: 2-(4-ethanesulfonylamino-3-fluoro-phenyl)-propionic acid

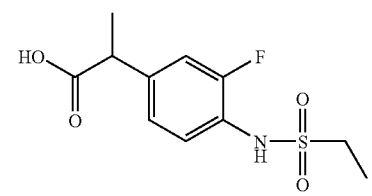 [SMILES: CCS(=O)(=O)Nc1ccc(C(C)C(=O)O)cc1F]

$^1$H NMR (300 MHz, CDCl$_3$) δ 7.53 (dd, 1H, J=8.1, 8.1 Hz), 7.08-7.15 (m, 2H), 6.76 (bs, 1H), 3.71 (q, 1H, J=6.9 Hz), 3.12 (q, 2H, J=7.5 Hz), 1.50 (d, 3H, J=6.9 Hz), 1.39 (t, 3H, J=7.5 Hz)

MS (FAB) m/z 276 (M+H)

Compounds of general formula VIIa, in which R$^2$ denotes methyl, can be prepared according to the following procedures.

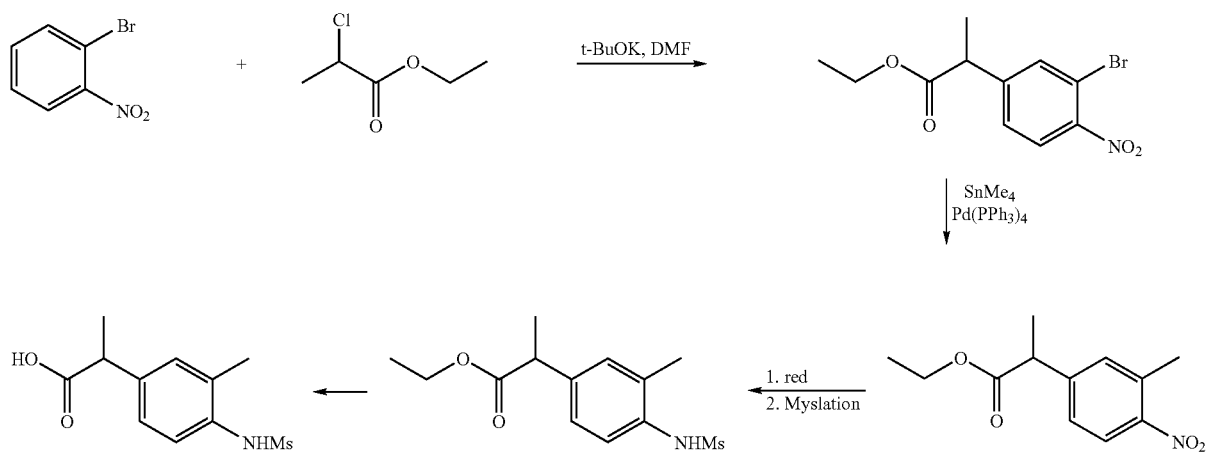

To a stirred solution of potassium t-butoxide (125.7 g, 1.12 mol) in DMF (600 mL) was added a mixture of 1-bromo-2-nitrobenzene (56.5 g, 0.28 mol) and ethyl 2-chloropropionate (38.7 g, 0.28 mol) at −30° C. within 3 min. After being stirred for 2 min at −30° C., more ethyl 2-chloropropionate (3.87 g, 0.028 mol) was added. After being stirred for 5 min at −30° C. the mixture was poured into cooled 10% aq. HCl soln., diluted with water and extracted with EA several times. The combined organic layers were washed with water and brine, dried over MgSO₄, and concentrated in vacuo. The residue was purified by flash column chromatography on silica gel using EA:hexanes (1:10) as eluent. I To a stirred solution of ethyl 2-(3-bromo-4-nitrophenyl) propanoate (3.76 g, 0.012 mol) in DMF (20 mL) under nitrogen was added a Pd(PPh₃)₄ (0.77 g, 5 mol %) and tetramethyltin (6.68 g, 0.037 mol) at rt. After being stirred for 8 hrs at 120° C. the mixture was cooled to rt and then filtered through Celite. The filtrate was diluted with water and extracted with EA several times. The combined organic layers were washed with water and brine, dried over MgSO₄, and concentrated in vacuo. The residue was purified by flash column chromatography on silica gel using EA:hexanes (1:10) as eluent.

A suspension of ethyl 2-(3-methyl-4-nitrophenyl)propanoate (1.76 g, 0.007 mol) and 10% Pd on carbon (200 mg) in MeOH (30 mL) was hydrogenated under a balloon of hydrogen for 6 hrs and filtered through celite. The filtrate was concentrated in vacuo and the residue was purified by flash column chromatography on silica gel using EA/hexanes (1:4) as eluent. The compound thus obtained (1.43 g, 0.007 mol) and methanesulfonyl chloride (0.95 g, 0.008 mol) in pyridine (10 mL) were stirred at 0° C. for 10 min then stirred for 3 hrs at rt. After removing pyridine by 1 N HCl/dichloromethane workup, the organic layer was concentrated in vacuo. The residue was purified by recrystallization with dichloromethane/n-hexane.

7. General Method for Reacting Amines of the General Formulae V or X with Carboxylic Acids of the General Formula VII The acid of the general formula VII (1 equivalent), the amine of the general formulae V or X (1.2 equivalents) and EDCI (1.2 equivalents) are stirred in DMF (10 mmol acid in 20 mL) for 12 hours at RT and water is then added. The reaction mixture is repeatedly extracted with EA, the aqueous phase is saturated with NaCl and then extracted again with EA. The combined organic phases are washed with 1 N hydrochloric acid and sat. aq. NaCl soln., dried over MgSO₄ and the solvent is removed under a vacuum. The residue is purified by means of flash chromatography (SiO₂, EA/hexane 1:2).

The following example compounds 1, 2, 3, 10, 12, 13, 33 and 34 were obtained according to the above-stated general method:

Example 2

2-(3-fluoro-4-(methylsulfonamido)phenyl)-N-((2-(piperidin-1-yl)-6-(trifluoromethyl)pyridin-3-yl)methyl)propanamide

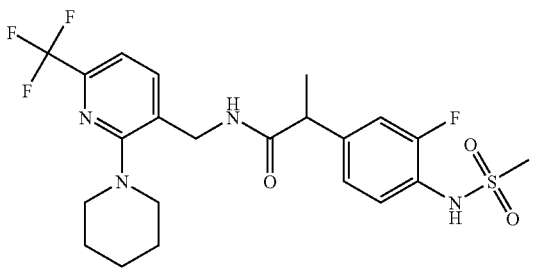 [SMILES: CC(C(=O)NCc1ccc(C(F)(F)F)nc1N1CCCCC1)c1ccc(NS(C)(=O)=O)c(F)c1]

The compound was obtained in a yield of 88% as a white solid with a melting point of 75-79° C.

$^1$H NMR (300 MHz, CDCl₃) δ 7.47-7.55 (m, 2H, Ar), 7.07-7.22 (m, 3H, Ar), 6.33 (bt, 1H, NHCO), 4.47 (d, 2H, J=5.7 Hz, ArCH₂NH), 3.54 (q, 1H, J=6.9 Hz, CHCH₃), 3.00-3.05 (m, 7H, piperidine, SO₂CH₃), 1.61 (m, 6H, piperidine), 1.52 (d, 3H, J=6.9 Hz, CHCH₃)

IR (KBr) 3741, 3281, 2935, 1652, 1512, 1419, 1334, 1248 cm$^{-1}$

MS (FAB) m/z 503 (M+H)

Example 10

(S)-2-(3-fluoro-4-(methylsulfonamido)phenyl)-N-((2-(piperidin-1-yl)-6-(trifluoromethyl)pyridin-3-yl)methyl)propanamide

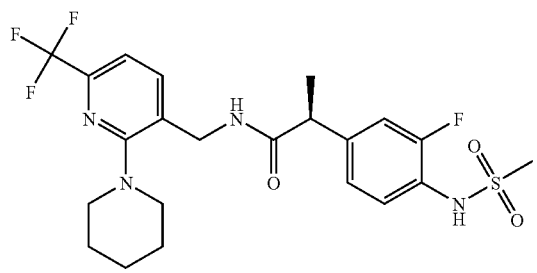 [SMILES: C[C@H](C(=O)NCc1ccc(C(F)(F)F)nc1N1CCCCC1)c1ccc(NS(C)(=O)=O)c(F)c1]

The compound was obtained in a yield of 65% as a white solid with a melting point of 75-79° C.

$^1$H NMR (300 MHz, CDCl$_3$) δ 7.47-7.55 (m, 2H, Ar), 7.07-7.22 (m, 3H, Ar), 6.33 (bt, 1H, NHCO), 4.47 (d, 2H, J=5.7 Hz, ArCH$_2$NH), 3.54 (q, 1H, J=6.9 Hz, CHCH$_3$), 3.00-3.05 (m, 7H, piperidine, SO$_2$CH$_3$), 1.52 (d, 3H, J=6.9 Hz, CHCH$_3$), 1.61 (m, 6H, piperidine)

IR (KBr) 3289, 2935, 2853, 1655, 1591, 1512, 1419, 1335 cm$^{-1}$

MS (FAB) m/z 503 (M+H)

Example 12

2-(3-fluoro-4-(methylsulfonamido)phenyl)-N-((2-morpholino-6-(trifluoromethyl)pyridin-3-yl)methyl)propanamide

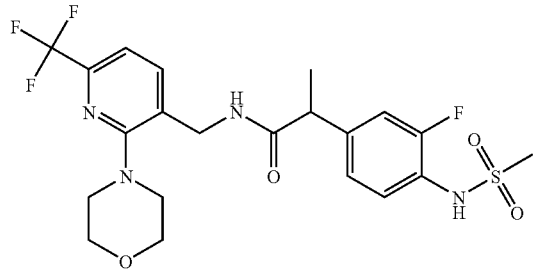 [SMILES: CC(C(=O)NCc1ccc(C(F)(F)F)nc1N1CCOCC1)c1ccc(NS(C)(=O)=O)c(F)c1]

The compound was obtained in a yield of 60% as a white solid.

$^1$H NMR (300 MHz, CDCl$_3$) δ 7.49-7.56 (m, 2H, Ar), 7.26 (d, 1H, J=7.5 Hz, Ar), 7.08-7.17 (m, 2H, Ar), 6.53 (bs, 1H, NHSO$_2$), 6.06 (bt, 1H, NHCO), 4.48 (d, 2H, J=5.7 Hz, ArCH$_2$NH), 3.76 (m, 4H, Morpholin), 3.57 (q, 1H, J=6.9 Hz, CHCH$_3$), 3.13 (m, 4H, morpholine), 3.04 (s, 3H, SO$_2$CH$_3$), 1.55 (d, 3H, J=6.9 Hz, CHCH$_3$)

IR (KBr) 3741, 1645, 1512, 1416, 1334, 1157 cm$^{-1}$

MS (FAB) m/z 505 (M+H)

Example 13

2-(3-fluoro-4-(methylsulfonamido)phenyl)-N-((2-(pyrrolidin-1-yl)-6-(trifluoromethyl)pyridin-3-yl)methyl)propanamide

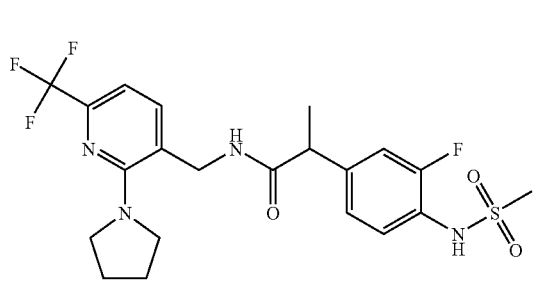 [SMILES: CC(C(=O)NCc1ccc(C(F)(F)F)nc1N1CCCC1)c1ccc(NS(C)(=O)=O)c(F)c1]

The product was obtained in a yield of 80%.

$^1$H NMR (300 MHz, CDCl$_3$) δ 7.51 (t, 1H, J=8.3 Hz, H-5), 7.38 (d, 2H, J=7.5 Hz Ar), 7.13 (dd, 1H, J=11.1, 2.0 Hz, Ar), 7.07 (dd, 1H, J=7.8, 1.8 Hz, Ar), 6.94 (d, 1H, J=7.5 Hz, Ar), 5.72 (bt, 1H, NHCO), 4.47 (d, 2H, J=5.3 Hz, ArCH$_2$NH), 3.52 (q, 1H, J=6.9 Hz, CHCH$_3$), 3.42-3.46 (m, 4H, pyrrolidine), 3.02 (s, 3H, SO$_2$CH$_3$), 1.82-1.89 (m, 4H, pyrrolidine), 1.50 (d, 3H, J=6.9 Hz, CHCH$_3$)

Example 1

2-(3-fluoro-4-(methylsulfonamido)phenyl)-N-((2-methyl-6-(trifluoromethyl)pyridin-3-yl)methyl)propanamide

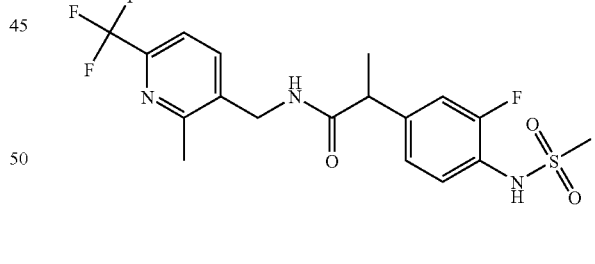

The compound was obtained in a yield of 78% as a white solid with a melting point of 149-152° C.

$^1$H NMR (300 MHz, CDCl$_3$) δ 7.54 (d, 1H, J=7.8 Hz, Ar), 7.41-7.46 (m, 2H, Ar), 7.14 (dd, 1H, J=11.1, 2.0 Hz, Ar), 7.07 (dd, 1H, J=7.8, 1.8 Hz, Ar), 6.87 (bs, 1H, NHSO$_2$), 6.16 (bt, 1H, NHCO), 4.43 (d, 2H, J=5.1 Hz, ArCH$_2$NH), 3.58 (q, 1H, J=6.9 Hz, CHCH$_3$), 3.01 (s, 3H, SO$_2$CH$_3$), 2.50 (s, 3H, ArCH$_3$), 1.50 (d, 3H, J=6.9 Hz, CHCH$_3$)

IR (KBr) 3741, 1649, 1513, 1338, 1153, 756 cm$^{-1}$

MS (FAB) m/z 434 (M+H)

Example 3

2-(3-fluoro-4-(methylsulfonamido)phenyl)-N-(2-piperidin-1-yl)-4-(trifluoromethyl)benzyl)propanamide

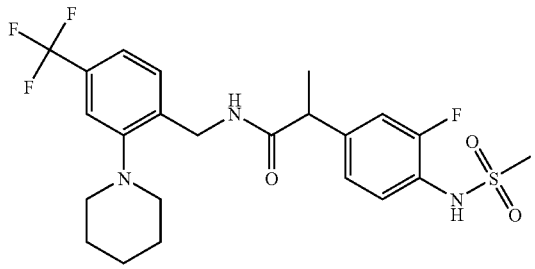 [SMILES: CC(C(=O)NCc1ccc(C(F)(F)F)cc1N1CCCCC1)c1ccc(NS(C)(=O)=O)c(F)c1]

The compound was obtained in a yield of 78% as a pale yellow solid with a melting point of 126-127° C.

$^1$H NMR (300 MHz, CDCl$_3$) δ 7.48 (t, 1H, J=8.3 Hz, H-5), 7.32 (bd, 2H, Ar), 7.05-7.15 (m, 4H, Ar), 6.81 (bs, 1H, NHSO$_2$), 6.66 (bt, 1H, NHCO), 4.52 (d, 2H, J=5.1 Hz, ArCH$_2$NH), 3.55 (q, 1H, J=6.9 Hz, CHCH$_3$), 3.00 (s, 3H, SO$_2$CH$_3$), 2.79 (bs, 4H, piperidine), 1.49-1.64 (m, 7H, piperidine, CHCH$_3$), 1.25 (m, 2H, piperidine)

IR (KBr) 3289, 2934, 1652, 1511, 1423, 1337, 1220, 1160 cm$^{-1}$

MS (FAB) m/z 502 (M+H)

Example 33

2-(3-fluoro-4-(methylsulfonamido)phenyl)-N-(2-morpholino-4-(trifluoromethyl)benzyl)propanamide

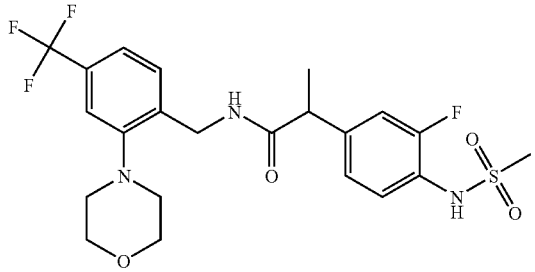 [SMILES: CC(C(=O)NCc1ccc(C(F)(F)F)cc1N1CCOCC1)c1ccc(NS(C)(=O)=O)c(F)c1]

The compound was obtained in a yield of 60% as a white solid.

$^1$H NMR (300 MHz, CDCl$_3$) δ 7.43 (t, 1H, J=8.3 Hz, Ar), 7.16-7.24 (m, 3H, Ar), 7.09 (dd, 1H, J=11.1, 2.0 Hz, Ar), 7.01 (dd, 1H, J=7.8, 1.8 Hz, Ar), 6.70 (bs, 1H, NHSO$_2$), 6.15 (bt, 1H, NHCO), 4.47 (d, 2H, J=5.4 Hz, ArCH$_2$NH), 3.70 (t, 4H, J=4.2 Hz, morpholine), 3.50 (q, 1H, J=7.2 Hz, CHCH$_3$), 2.95 (s, 3H, SO$_2$CH$_3$), 2.78 (t, 4H, J=4.2 Hz, morpholine), 1.45 (d, 3H, J=7.2 Hz, CHCH$_3$)

IR (KBr) 2921, 1650, 1512, 1423, 1336, 1159 cm$^{-1}$

MS (FAB) m/z 504 (M+H)

Example 34

2-(3-fluoro-4-(methylsulfonamido)phenyl)-N-(2-(pyrrolidin-1-yl)-4-(trifluoromethyl)benzyl)propanamide

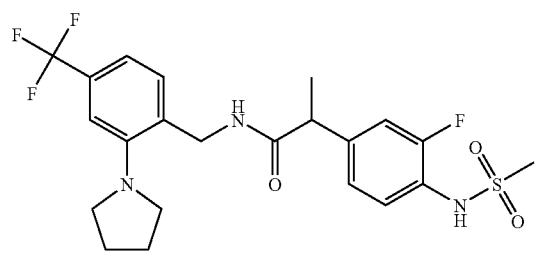 [SMILES: CC(C(=O)NCc1ccc(C(F)(F)F)cc1N1CCCC1)c1ccc(NS(C)(=O)=O)c(F)c1]

The product was obtained in a yield of 70%.

$^1$H NMR (300 MHz, CDCl$_3$) δ 7.49 (t, 1H, J=8.1 Hz, Ar), 7.05-7.19 (m, 5H, Ar), 6.79 (bs, 1H, NHSO$_2$), 6.26 (bt, 1H, NHCO), 4.49 (d, 2H, J=4.8 Hz, ArCH$_2$NH), 3.54 (q, 1H, J=7.2 Hz, CHCH$_3$), 3.08-3.12 (m, 4H, pyrrolidine), 3.01 (s, 3H, SO$_2$CH$_3$), 1.86-1.90 (m, 4H, pyrrolidine), 1.50 (d, 3H, J=7.2 Hz, CHCH$_3$)

The compounds listed in Table 1 may also be obtained as described above. The starting compounds required for this purpose are known to the person skilled in the art.

TABLE 1

| | |
|---|---|
| [4] | 2-(3-fluoro-4-(methylsulfonamido)phenyl)-N-((2-fluoro-6-(trifluoromethyl)-pyridin-3-yl)methyl)propanamide |
| [5] | N-((2-chloro-6-(trifluoromethyl)pyridin-3-yl)methyl)-2-(3-fluoro-4-(methylsulfonamido)phenyl)propanamide |
| [6] | N-((2-bromo-6-(trifluoromethyl)pyridin-3-yl)methyl)-2-(3-fluoro-4-(methylsulfonamido)phenyl)propanamide |
| [7] | 2-(3-fluoro-4-(methylsulfonamido)phenyl)-N-((2-iodo-6-(trifluoromethyl)pyridin-3-yl)methyl)propanamide |
| [8] | N-((2-tert-butyl-6-(trifluoromethyl)pyridin-3-yl)methyl)-2-(3-fluoro-4-(methylsulfonamido)phenyl)propanamide |
| [9] | N-((2-cyano-6-(trifluoromethyl)pyridin-3-yl)methyl)-2-(3-fluoro-4-(methylsulfonamido)phenyl)propanamide |
| [11] | (R)-2-(3-fluoro-4-(methylsulfonamido)phenyl)-N-((2-(piperidin-1-yl)-6-(trifluoromethyl)pyridin-3-yl)methyl)propanamide |
| [14] | N-((2-(dimethylamino)-6-(trifluoromethyl)pyridin-3-yl)methyl)-2-(3-fluoro-4-(methylsulfonamido)phenyl)propanamide |
| [15] | N-((2-(diethylamino)-6-(trifluoromethyl)pyridin-3-yl)methyl)-2-(3-fluoro-4-(methylsulfonamido)phenyl)propanamide |
| [16] | N-((2-(dipropylamino)-6-(trifluoromethyl)pyridin-3-yl)methyl)-2-(3-fluoro-4-(methylsulfonamido)phenyl)propanamide |
| [17] | 2-(3-fluoro-4-(methylsulfonamido)phenyl)-N-((2-hydroxy-6-(trifluoromethyl)pyridin-3-yl)methyl)propanamide |

TABLE 1-continued

[18] 2-(3-fluoro-4-(methylsulfonamido)phenyl)-N-((2-methoxy-6-(trifluoromethyl)pyridin-3-yl)methyl)propanamide
[19] N-((2-butoxy-6-(trifluoromethyl)pyridin-3-yl)methyl)-2-(3-fluoro-4-(methylsulfonamido)phenyl)propanamide
[20] 2-(3-fluoro-4-(methylsulfonamido)phenyl)-N-((2-isopropoxy-6-(trifluoromethyl)pyridin-3-yl)methyl)propanamide
[21] N-((2-cyclopentyloxy-6-(trifluoromethyl)pyridin-3-yl)methyl)-2-(3-fluoro-4-(methylsulfonamido)phenyl)propanamide
[22] 2-(3-fluoro-4-(methylsulfonamido)phenyl)-N-((2-phenyl-6-(trifluoromethyl)pyridin-3-yl)methyl)propanamide
[23] 2-(3-fluoro-4-(methylsulfonamido)phenyl)-N-((2-(4-fluorophenyl)-6-(trifluoromethyl)pyridin-3-yl)methyl)propanamide
[24] 2-(3-fluoro-4-(methylsulfonamido)phenyl)-N-((6-(trifluoromethyl)-2,2'-bipyridin-3-yl)methyl)propanamide
[25] 2-(3-fluoro-4-(methylsulfonamido)phenyl)-N-((6-(trifluoromethyl)-2,3'-bipyridin-3-yl)methyl)propanamide
[26] 2-(3-fluoro-4-(methylsulfonamido)phenyl)-N-((2-(pyrimidin-2-yl)-6-(trifluoromethyl)pyridin-3-yl)methyl)propanamide
[27] 2-(3-fluoro-4-(methylsulfonamido)phenyl)-N-((2-(thiazol-2-yl)-6-(trifluoromethyl)pyridin-3-yl)methyl)propanamide
[28] 2-(3-fluoro-4-(methylsulfonamido)phenyl)-N-((2-(oxazol-2-yl)-6-(trifluoromethyl)pyridin-3-yl)methyl)propanamide
[29] N-((2-(1H-imidazol-2-yl)-6-(trifluoromethyl)pyridin-3-yl)methyl)-2-(3-fluoro-4-(methylsulfonamido)phenyl)propanamide
[30] N-(2-cyano-4-(trifluoromethyl)benzyl)-2-(3-fluoro-4-(methylsulfonamido)-phenyl)propanamide
[31] (S)-2-(3-fluoro-4-(methylsulfonamido)phenyl)-N-(2-(piperidin-1-yl)-4-(trifluoromethyl)benzyl)propanamide
[32] (R)-2-(3-fluoro-4-(methylsulfonamido)phenyl)-N-(2-(piperidin-1-yl)-4-(trifluoromethyl)benzyl)propanamide
[35] N-(2-(dimethylamino)-4-(trifluoromethyl)benzyl)-2-(3-fluoro-4-(methylsulfonamido)phenyl)propanamide
[36] N-(2-(diethylamino)-4-(trifluoromethyl)benzyl)-2-(3-fluoro-4-(methylsulfonamido)phenyl)propanamide
[37] N-(2-(dipropylamino)-4-(trifluoromethyl)benzyl)-2-(3-fluoro-4-(methylsulfonamido)phenyl)propanamide
[38] 2-(3-fluoro-4-(methylsulfonamido)phenyl)-N-(2-hydroxy-4-(trifluoromethyl)benzyl)propanamide
[39] 2-(3-fluoro-4-(methylsulfonamido)phenyl)-N-(2-methoxy-4-(trifluoromethyl)benzyl)propanamide
[40] N-(2-butoxy-4-(trifluoromethyl)benzyl)-2-(3-fluoro-4-(methylsulfonamido)-phenyl)propanamide
[41] 2-(3-fluoro-4-(methylsulfonamido)phenyl)-N-(2-isopropoxy-4-(trifluoromethyl)benzyl)propanamide
[42] N-(2-(cyclopentyloxy)-4-(trifluoromethyl)benzyl)-2-(3-fluoro-4-(methylsulfonamido)phenyl)propanamide
[43] 2-(3-fluoro-4-(methylsulfonamido)phenyl)-N-((5-(trifluoromethyl)biphenyl-2-yl)methyl)propanamide
[44] 2-(3-fluoro-4-(methylsulfonamido)phenyl)-N-((4'-fluoro-5-(trifluoromethyl)-biphenyl-2-yl)methyl)propanamide
[45] 2-(3-fluoro-4-(methylsulfonamido)phenyl)-N-(2-(pyridin-2-yl)-4-(trifluoromethyl)benzyl)propanamide
[46] 2-(3-fluoro-4-(methylsulfonamido)phenyl)-N-(2-(pyridin-3-yl)-4-(trifluoromethyl)benzyl)propanamide
[47] 2-(3-fluoro-4-(methylsulfonamido)phenyl)-N-(2-(pyrimidin-2-yl)-4-(trifluoromethyl)benzyl)propanamide
[48] 2-(3-fluoro-4-(methylsulfonamido)phenyl)-N-(2-(thiazol-2-yl)-4-(trifluoromethyl)benzyl)propanamide
[49] 2-(3-fluoro-4-(methylsulfonamido)phenyl)-N-(2-(oxazol-2-yl)-4-(trifluoromethyl)benzyl)propanamide
[50] N-(2-(1H-imidazol-2-yl)-4-(trifluoromethyl)benzyl)-2-(3-fluoro-4-(methylsulfonamido)phenyl)propanamide
[51] N-((6-tert-butyl-2-(piperidin-1-yl)pyridin-3-yl)methyl)-2-(3-fluoro-4-(methylsufonamido)phenyl)propanamide
[52] 2-(3-fluoro-4-(methylsulfonamido)phenyl)-N-((4-(piperidin-1-yl)-6-(trifluoromethyl)pyridin-3-yl)methyl)propanamide
[53] 2-(3-fluoro-4-(methylsulfonamido)phenyl)-N-((3-(piperidin-1-yl)-5-(trifluoromethyl)pyridin-2-yl)methyl)propanamide
[54] 2-(3-Fluoro-4-(methylsulfonamido)phenyl)-N-((4-(piperidin-1-yl)-2-(trifluoromethyl)pyrimidin-5-yl)methyl)propanamide
[55] 2-(3-fluoro-4-(methylsulfonamido)phenyl)-N-((3-(piperidin-1-yl)-5-(trifluoromethyl)pyrazin-2-yl)methyl)propanamide
[56] 2-(3-fluoro-4-(methylsulfonamido)phenyl)-N-((4-(piperidin-1-yl)-6-(trifluoromethyl)pyridazinyl-3-yl)methyl)propanamide
[57] 2-(3-fluoro-4-(methylsulfonamido)phenyl)-N-((2-piperidin-1-yl)-6-(trifluoromethyl)pyridin-3-yl)propanamide
[58] 2-(3-fluoro-4-(methylsulfonamido)phenyl)-N-((2-piperidin-1-yl)-4-(trifluoromethyl)phenyl)propanamide
[59] 2-(3-fluoro-4-(methylsulfonamido)phenyl)-N-(2-(2-(piperidin-1-yl)-6-(trifluoromethyl)pyridin-3-yl)ethyl)propanamide
[60] 2-(3-fluoro-4-(methylsulfonamido)phenyl)-N-(2-(piperidin-1-yl)-4-(trifluoromethyl)phenethyl)propanamide
[61] N-(2-amino-4-(trifluoromethyl)benzyl)-2-(3-fluoro-4-(methylsulfonamido)-phenyl)propanamide
[62] 2-(3-fluoro-4-(methylsulfonamido)phenyl)-N-(2-nitro-4-(trifluoromethyl)-benzyl)propanamide TABLE 1-continued

- [63] N-(4-tert-butyl-2-(piperidin-1-yl)benzyl)-2-(3-fluoro-4-(methylsulfonamido)-phenyl)propanamide
- [64] 2-(3-chloro-4-(methylsulfonamido)phenyl)-N-((2-(piperidin-1-yl)-6-(trifluoromethyl)pyridin-3-yl)methyl)propanamide
- [65] 2-(3-chloro-4-(methylsulfonamido)phenyl)-N-((2-(pyrrolidin-1-yl)-6-(trifluoromethyl)pyridin-3-yl)methyl)propanamide
- [66] 2-(3-chloro-4-(methylsulfonamido)phenyl)-N-(2-(piperidin-1-yl)-4-(trifluoromethyl)benzyl)propanamide
- [67] 2-(3-bromo-4-(methylsulfonamido)phenyl)-N-((2-(piperidin-1-yl)-6-(trifluoromethyl)pyridin-3-yl)methyl)propanamide
- [68] 2-(3-bromo-4-(methylsulfonamido)phenyl)-N-(2-(piperidin-1-yl)-4-(trifluoromethyl)benzyl)propanamide
- [69] 2-(3-bromo-4-(methylsulfonamido)phenyl)-N-(2-(pyrrolidin-1-yl)-4-(trifluoromethyl)benzyl)propanamide
- [70] N-(4-tert-butyl-2-cyanobenzyl)-2-(3-fluoro-4-(methylsulfonamido)-phenyl)propanamide
- [4] 2-(3-Fluor-4-(methylsulfonamido)phenyl)-N-((2-fluoro-6-(trifluoromethyl)pyridin-3-yl)methyl)propanamide
- [5] N-((2-chloro-6-(trifluoromethyl)pyridin-3-yl)methyl)-2-(3-fluoro-4-(methylsulfonamido)phenyl)propanamide
- [6] N-((-bromo2-bromo-6-(trifluoromethyl)pyridin-3-yl)methyl)-2-(3-fluoro-4-(methylsulfonamido)phenyl)propanamide
- [7] 2-(3-Fluor-4-(methylsulfonamido)phenyl)-N-((2-iodo-6-(trifluoromethyl)pyridin-3-yl)methyl)propanamide
- [8] N-((2-tert-butyl-6-(trifluoromethyl)pyridin-3-yl)methyl)-2-(3-fluoro-4-(methylsulfonamido)phenyl)propanamide
- [9] N-((2-cyano-6-(trifluoromethyl)pyridin-3-yl)methyl)-2-(3-fluoro-4-(methylsulfonamido)phenyl)propanamide
- [11] (R)-2-(3-Fluor-4-(methylsulfonamido)phenyl)-N-((2-(piperidin-1-yl)-6-(trifluoromethyl)pyridin-3-yl)methyl)propanamide
- [14] N-((2-(dimethylamino)-6-(trifluoromethyl)pyridin-3-yl)methyl)-2-(3-fluoro-4-(methylsulfonamido)phenyl)propanamide
- [15] N-((2-(diethylamino)-6-(trifluoromethyl)pyridin-3-yl)methyl)-2-(3-fluoro-4-(methylsulfonamido)phenyl)propanamide
- [16] N-((2-(dipropylamino)-6-(trifluoromethyl)pyridin-3-yl)methyl)-2-(3-fluoro-4-(methylsulfonamido)phenyl)propanamide
- [17] 2-(3-Fluor-4-(methylsulfonamido)phenyl)-N-((2-hydroxy-6-(trifluoromethyl)pyridin-3-yl)methyl)propanamide
- [18] 2-(3-Fluor-4-(methylsulfonamido)phenyl)-N-((2-methoxy-6-(trifluoromethyl)pyridin-3-yl)methyl)propanamide
- [19] N-((2-butoxy-6-(trifluoromethyl)pyridin-3-yl)methyl)-2-(3-fluoro-4-(methylsulfonamido)phenyl)propanamide
- [20] 2-(3-Fluor-4-(methylsulfonamido)phenyl)-N-((2-isopropoxy-6-(trifluoromethyl)pyridin-3-yl)methyl)propanamide
- [21] N-((2-cyclopentyloxy-6-(trifluoromethyl)pyridin-3-yl)methyl)-2-(3-fluoro-4-(methylsulfonamido)phenyl)propanamide
- [22] 2-(3-Fluor-4-(methylsulfonamido)phenyl)-N-((2-phenyl-6-(trifluoromethyl)pyridin-3-yl)methyl)propanamide
- [23] 2-(3-Fluor-4-(methylsulfonamido)phenyl)-N-((2-(4-fluoro-phenyl)-6-(trifluoromethyl)pyridin-3-yl)methyl)propanamide
- [24] 2-(3-Fluor-4-(methylsulfonamido)phenyl)-N-((6-(trifluoromethyl)-2,2'-bipyridin-3-yl)methyl)propanamide
- [25] 2-(3-Fluor-4-(methylsulfonamido)phenyl)-N-((6-(trifluoromethyl)-2,3'-bipyridin-3-yl)methyl)propanamide
- [26] 2-(3-Fluor-4-(methylsulfonamido)phenyl)-N-((2-(pyrimidin-2-yl)-6-(trifluoromethyl)pyridin-3-yl)methyl)propanamide
- [27] 2-(3-Fluor-4-(methylsulfonamido)phenyl)-N-((2-(thiazol-2-yl)-6-(trifluoromethyl)pyridin-3-yl)methyl)propanamide
- [28] 2-(3-Fluor-4-(methylsulfonamido)phenyl)-N-((2-(oxazol-2-yl)-6-(trifluoromethyl)pyridin-3-yl)methyl)propanamide
- [29] N-((2-(1H-imidazol-2-yl)-6-(trifluoromethyl)pyridin-3-yl)methyl)-2-(3-fluoro-4-(methylsulfonamido)phenyl)propanamide
- [30] N-(2-cyano-4-(trifluoromethyl)benzyl)-2-(3-fluoro-4-(methylsulfonamido)phenyl)propanamide
- [31] (S)-2-(3-Fluor-4-(methylsulfonamido)phenyl)-N-(2-(piperidin-1-yl)-4-(trifluoromethyl)benzyl)propanamide
- [32] (R)-2-(3-Fluor-4-(methylsulfonamido)phenyl)-N-(2-(piperidin-1-yl)-4-(trifluoromethyl)benzyl)propanamide
- [35] N-(2-(dimethylamino)-4-(trifluoromethyl)benzyl)-2-(3-fluoro-4-(methylsulfonamido)phenyl)propanamide
- [36] N-(2-(diethylamino)-4-(trifluoromethyl)benzyl)-2-(3-fluoro-4-(methylsulfonamido)phenyl)propanamide
- [37] N-(2-(dipropylamino)-4-(trifluoromethyl)benzyl)-2-(3-fluoro-4-(methylsulfonamido)phenyl)propanamide
- [38] 2-(3-Fluor-4-(methylsulfonamido)phenyl)-N-(2-hydroxy-4-(trifluoromethyl)benzyl)propanamide
- [39] 2-(3-Fluor-4-(methylsulfonamido)phenyl)-N-(2-methoxy-4-(trifluoromethyl)benzyl)propanamide
- [40] N-(2-butoxy-4-(trifluoromethyl)benzyl)-2-(3-Fluoro-4-(methylsulfonamido)phenyl)propanamide
- [41] 2-(3-Fluor-4-(methylsulfonamido)phenyl)-N-(2-isopropoxy-4-(trifluoromethyl)benzyl)propanamide
- [42] N-(2-(cyclopentyloxy)-4-(trifluoromethyl)benzyl)-2-(3-fluoro-4-(methylsulfonamido)phenyl)propanamide TABLE 1-continued

[43] 2-(3-Fluor-4-(methylsulfonamido)phenyl)-N-((5-(trifluoromethyl)biphenyl-2-yl)methyl)propanamide
[44] 2-(3-Fluor-4-(methylsulfonamido)phenyl)-N-((4'-fluoro-5-(trifluoromethyl)biphenyl-2-yl)methyl)propanamide
[45] 2-(3-Fluor-4-(methylsulfonamido)phenyl)-N-(2-(pyridin-2-yl)-4-(trifluoromethyl)benzyl)propanamide
[46] 2-(3-Fluor-4-(methylsulfonamido)phenyl)-N-(2-(pyridin-3-yl)-4-(trifluoromethyl)benzyl)propanamide
[47] 2-(3-Fluor-4-(methylsulfonamido)phenyl)-N-(2-(pyrimidin-2-yl)-4-(trifluoromethyl)benzyl)propanamide
[48] 2-(3-Fluor-4-(methylsulfonamido)phenyl)-N-(2-(thiazol-2-yl)-4-(trifluoromethyl)benzyl)propanamide
[49] 2-(3-Fluor-4-(methylsulfonamido)phenyl)-N-(2-(oxazol-2-yl)-4-(trifluoromethyl)benzyl)propanamide
[50] N-(2-(1H-imidazol-2-yl)-4-(trifluoromethyl)benzyl)-2-(3-fluoro-4-(methylsulfonamido)phenyl)propanamide
[51] N-((6-tert-butyl-2-(piperidin-1-yl)pyridin-3-yl)methyl)-2-(3-fluoro-4-(methylsufonamido)phenyl)propanamide
[52] 2-(3-Fluor-4-(methylsulfonamido)phenyl)-N-((4-(piperidin-1-yl)-6-(trifluoromethyl)pyridin-3-yl)methyl)propanamide
[53] 2-(3-Fluor-4-(methylsulfonamido)phenyl)-N-((3-(piperidin-1-yl)-5-(trifluoromethyl)pyridin-2-yl)methyl)propanamide
[54] 2-(3-Fluor-4-(methylsulfonamido)phenyl)-N-((4-(piperidin-1-yl)-2-(trifluoromethyl)pyrimidin-5-yl)methyl)propanamide
[55] 2-(3-Fluor-4-(methylsulfonamido)phenyl)-N-((3-(piperidin-1-yl)-5-(trifluoromethyl)pyrazin-2-yl)methyl)propanamide
[56] 2-(3-Fluor-4-(methylsulfonamido)phenyl)-N-((4-(piperidin-1-yl)-6-(trifluoromethyl)pyridazin-3-yl)methyl)propanamide
[57] 2-(3-Fluor-4-(methylsulfonamido)phenyl)-N-((2-piperidin-1-yl)-6-(trifluoromethyl)pyridin-3-yl)propanamide
[58] 2-(3-Fluor-4-(methylsulfonamido)phenyl)-N-((2-piperidin-1-yl)-4-(trifluoromethyl)phenyl)propanamide
[59] 2-(3-Fluor-4-(methylsulfonamido)phenyl)-N-(2-(2-(piperidin-1-yl)-6-(trifluoromethyl)pyridin-3-yl)ethyl)propanamide
[60] 2-(3-Fluor-4-(methylsulfonamido)phenyl)-N-(2-(piperidin-1-yl)-4-(trifluoromethyl)phenethyl)propanamide
[61] N-(2-amino-4-(trifluoromethyl)benzyl)-2-(3-fluoro-4-(methylsulfonamido)phenyl)propanamide
[62] 2-(3-Fluor-4-(methylsulfonamido)phenyl)-N-(2-nitro-4-(trifluoromethyl)benzyl)propanamide
[63] N-(4-tert-butyl-2-(piperidin-1-yl)benzyl)-2-(3-fluoro-4-(methylsulfonamido)phenyl)propanamide
[64] 2-(3-chloro-4-(methylsulfonamido)phenyl)-N-((2-(piperidin-1-yl)-6-(trifluoromethyl)pyridin-3-yl)methyl)propanamide
[65] 2-(3-chloro-4-(methylsulfonamido)phenyl)-N-((2-(pyrrolidin-1-yl)-6-(trifluoromethyl)pyridin-3-yl)methyl)propanamide
[66] 2-(3-chloro-4-(methylsulfonamido)phenyl)-N-(2-(piperidin-1-yl)-4-(trifluoromethyl)benzyl)propanamide
[67] 2-(3-bromo-4-(methylsulfonamido)phenyl)-N-((2-(piperidin-1-yl)-6-(trifluoromethyl)pyridin-3-yl)methyl)propanamide
[68] 2-(3-bromo-4-(methylsulfonamido)phenyl)-N-(2-(piperidin-1-yl)-4-(trifluoromethyl)benzyl)propanamide
[69] 2-(3-bromo-4-(methylsulfonamido)phenyl)-N-(2-(pyrrolidin-1-yl)-4-(trifluoromethyl)benzyl)propanamide
[70] N-(4-tert-butyl-2-cyanobenzyl)-2-(3-fluoro-4-(methylsulfonamido)phenyl)propanamide
[71] N-((6-(chlorodiflouromethyl)-2-(piperidin-1-yl)pyridin-3-yl)methyl)-2-(3-fluoro-(4-methylsulfonamido)phenyl)propanamide
[72] (S)-2-(3-Fluor-4-(methylsulfonamido)phenyl)-N-((2-morpholino-6-(trifluoromethyl)pyridin-3-yl)methyl)propanamide
[73] N-((2-(4-benzylpiperazin-1-yl)-6-(trifluoromethyl)pyridin-3-yl)methyl)-2-(3-fluoro-4-(methylsulfonamido)phenyl)propanamide
[74] 2-(3-Fluor-4-(methylsulfonamido)phenyl)-N-((2-piperazin-1-yl)-6-(trifluoromethyl)pyridin-3-yl)methyl)propanamide
[75] N-(2-chloro-4-(trifluoromethyl)benzyl)-2-(3-fluoro-4-(methylsulfonamido)phenyl)propanamide
[76] N-((2-(cyclohexyloxy)-6-(trifluoromethyl)pyridin-3-yl)methyl-2-(3-fluoro-4-(methylsulfonamido)phenyl)propanamide
[77] N-((3-chloro-5-(trifluoromethyl)pyridin-2-yl)methyl-2-(3-fluoro-4-(methylsulfonamido)phenyl)propanamide
[78] 2-(3-Fluor-4-(methylsulfonamido)phenyl)-N-((3-(pyrrolidin-1-yl)-5-(trifluoromethyl)pyridin-2-yl)methyl)propanamide
[79] N-((2-(3,5-dimethylpiperidin-1-yl)-6-(trifluoromethyl)pyridin-3-yl)methyl)-2-(3-fluoro-4-(methylsulfonamido)phenyl)propanamide
[80] 2-(3-Fluor-4-(methylsulfonamido)phenyl)-N-((2-(4-methylpiperidin-1-yl)-6-(trifluoromethyl)pyridin-3-yl)methyl)propanamide
[81] N-((2-(azepan-1-yl)-6-(trifluoromethyl)pyridin-3-yl)methyl)-2-(3-fluoro-4-(methylsulfonamido)phenyl)propanamide
[82] 2-(3-Fluor-4-(methylsulfonamido)phenyl)-N-(2-(4-methylpiperidin-1-yl)-4-(trifluoromethyl)benzyl)propanamide Example compounds 8, 9, 23, 24, 25, 26, 27, 28, 29, 30, 35, 36, 38, 39, 47, 48, 49, 50, 52, 54 55, 56, 59 and 60 can be obtained by those above-stated methods.

Example 81

N-(2-azepan-1-yl-6-trifluoromethyl-pyridin-3-ylmethyl)-2-(3-fluoro-4-methylsulfonamido-phenyl)-propionamide

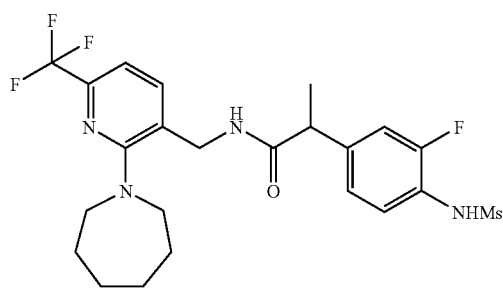

$^1$H NMR (300 MHz, CDCl$_3$) δ 7.52 (dd, 1H, J=8.1, 8.1 Hz), 7.40 (d, 1H, J=7.5 Hz), 7.14 (dd, 1H, J=8.1, 1.8 Hz), 7.08 (d, 1H, J=8.1 Hz), 7.03 (d, 1H, J=7.5 Hz), 5.86 (bt, 1H), 4.43 (d, 2H, J=5.7 Hz), 3.54 (q, 1H, J=6.9 Hz), 3.38 (m, 4H), 3.03 (s, 3H), 1.75 (m, 4H), 1.57 (m, 4H), 1.52 (d, 3H, J=6.9 Hz); IR (KBr) 3291, 2928, 1652, 1593, 1511, 1422, 1333, 1275, 1214, 1159, 972, 822, 759 cm$^{-1}$; MS (FAB) m/z 531 (M+H)

Example 80

2-(3-fluoro-4-methylsulfonamido-phenyl)-N-(2-4-methylpiperidin-1-yl-6-trifluoromethyl-pyridin-3-ylmethyl)-propionamide

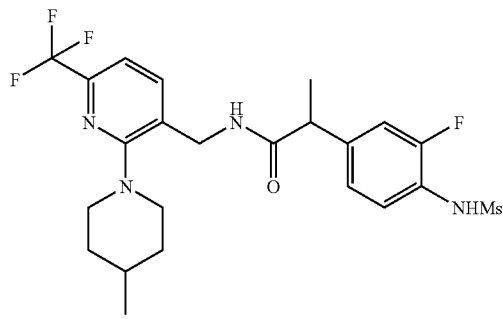

$^1$H NMR (300 MHz, CDCl$_3$) δ 7.47-7.55 (m, 2H), 7.07-7.22 (m, 3H), 6.29 (bt, 1H), 4.47 (d, 2H, J=5.7 Hz), 3.54 (q, 1H, J=6.9 Hz), 3.30 (m, 2H), 3.03 (s, 3H), 2.82 (m, 2H), 1.71 (m, 2H), 1.52 (d, 3H, J=6.9 Hz), 1.24 (m, 3H), 0.97 (d, 3H, J=6.6 Hz); IR (KBr) 3290, 2924, 1655, 1592, 1512, 1456, 1419, 1334, 1157, 970, 834, 758 cm$^{-1}$; MS (FAB) m/z 517 (M+H)

Example 79

2-(3-fluoro-4-methylsulfonamido-phenyl)-N-(2-3,5 dimethylpiperidin-1-yl-6-trifluoromethyl-pyridin-3-ylmethyl)-propionamide

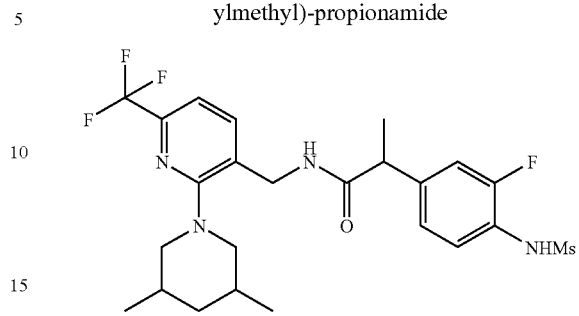

$^1$H NMR (300 MHz, CDCl$_3$) δ 7.47-7.54 (m, 2H), 7.21 (d, 1H, J=7.8 Hz), 7.13 (dd, 1H, J=8.1, 1.8 Hz), 7.07 (d, 1H, J=8.1 Hz), 6.48 (bs, 1H), 6.28 (bt, 1H), 4.47 (d, 2H, J=5.7 Hz), 3.54 (q, 1H, J=6.9 Hz), 3.23 (m, 2H), 3.03 (s, 3H), 2.35 (m, 2H), 1.54-1.76 (m, 2H), 1.52 (d, 3H, J=6.9 Hz), 0.90 (d, 3H, J=5.7 Hz), 0.88 (d, 3H, J=5.7 Hz); IR (KBr) 3289, 2957, 1655, 1591, 1512, 1458, 1419, 1336, 1247, 1158, 1013, 970, 831, 757 cm$^{-1}$; MS (FAB) m/z 531 (M+H)

The following compounds were also prepared according to the above-stated method.

Example 85

N-(2-dimethylamino-6-trifluoromethyl-pyridin-3-ylmethyl)-2-(3-fluoro-4-methylsulfonamido-phenyl)-propionamide

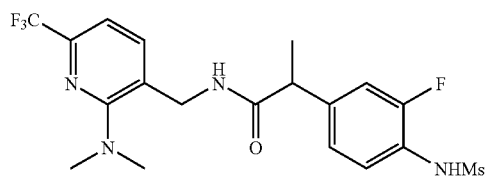

$^1$H NMR (300 MHz, CDCl$_3$) δ 7.46-7.40 (m, 2H), 7.20-7.00 (m, 3H), 6.60 (bt, 1H), 4.50 (bd, 2H), 3.60 (m, 1H), 3.00 (s, 3H), 2.80 (s, 6H), 1.49 (d, 3H, J=7.0 Hz); IR (KBr) 3284, 2936, 1656, 1594, 1511, 1395, 1335 cm$^{-1}$; MS (FAB) m/z 463 (M+H)

Example 87

2-(3-fluoro-4-methylsulfonamido-phenyl)-N-((6-(trifluoromethyl)-2-(1H-imidazol-1-yl)pyridin-3-yl)methyl)-propionamide

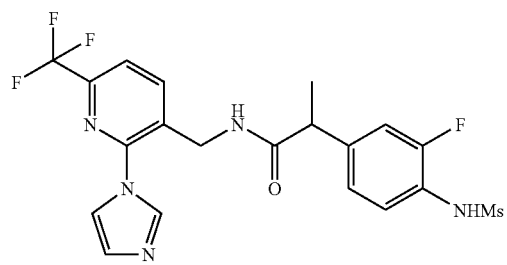

¹H NMR (300 MHz, CDCl₃) δ 7.98 (d, 1H, J=8.4 Hz), 7.82 (s, 1H), 7.70 (d, 1H, J=8.4 Hz), 7.49 (dd, 1H, J=8.1, 8.1 Hz), 7.30 (s, 1H), 7.18 (s, 1H), 7.04-7.08 (m, 2H), 6.15 (bt, 1H), 4.45 (d, 2H, J=5.1 Hz), 3.53 (q, 1H, J=6.9 Hz), 3.04 (s, 3H), 1.47 (d, 3H, J=6.9 Hz); IR (KBr) 2923, 1665, 1511, 1424, 1337, 1154, 973, 760 cm⁻¹; MS (FAB) m/z 487 (M+H)

Example 88

2-(3-fluoro-4-methylsulfonamido-phenyl)-N-((6-(trflluoromethyl)-2-(thiophen-2-yl)pyridin-3-yl)methyl)-propionamide

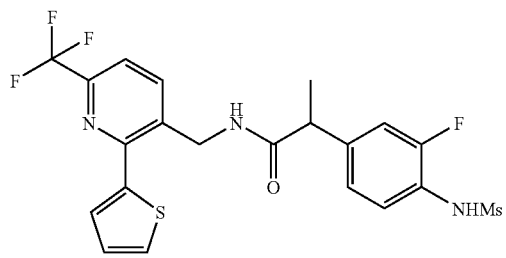

¹H NMR (300 MHz, CDCl₃) δ 7.74 (d, 1H, J=8.7 Hz), 7.47-7.5 (m, 3H), 7.35 (dd, 1H, 3.6, 1.2 Hz), 7.02-7.11 (m, 3H), 6.51 (bs, 1H), 5.79 (bt, 1H), 4.70 (d, 2H, J=5.1 Hz), 3.53 (q, 1H, J=6.9 Hz), 3.02 (s, 3H), 1.51 (d, 3H, J=6.9 Hz); IR (KBr) 2920, 1737, 1644, 1509, 1428, 1328, 1148, 979, 768 cm⁻¹; MS (FAB) m/z 502 (M+H)

Example 89

2-(3-fluoro-4-methylsulfonamido-phenyl)-N-((2-(trifluoromethyl)-6-phenylpyridin-4-yl)methyl)-propionamide

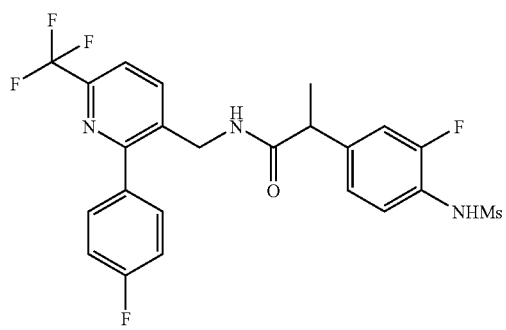

¹H NMR (300 MHz, CDCl₃) δ 7.77 (d, 1H, J=8.1 Hz), 7.61 (d, 1H, J=8.1 Hz), 7.50 (dd, 1H, J=8.1, 8.1 Hz), 7.40-7.45 (m, 2H), 6.99-7.16 (m, 4H), 6.57 (bs, 1H), 5.63 (bt, 1H), 4.49 (d, 2H, J=5.7 Hz), 3.47 (q, 1H, J=6.9 Hz), 3.02 (s, 3H), 1.49 (d, 3H, J=6.9 Hz); IR (KBr) 3296, 1657, 1513, 1457, 1411, 1340, 1156, 1048, 973, 842, 757 cm⁻¹; MS (FAB) m/z 514 (M+H)

Example 90

N-(2-cyclohexylamino-6-trifluoromethyl-pyridin-3-ylmethyl)-2-(3-fluoro-4-methylsulfonamido-phenyl)-propionamide

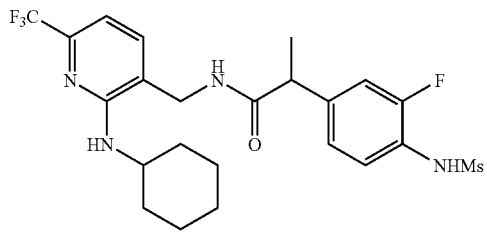

¹H NMR (CDCl₃) δ 7.51 (dd, 1H, J=6.6, 6.6 Hz), 7.22 (d, 1H, J=5.8 Hz), 7.18 (dd, 1H, J=8.9, 1.5 Hz), 7.08 (d, 2H, J=6.6 Hz), 6.74 (d, 1H, J=5.8 Hz), 6.47 (bs, NH), 5.84 (bd, NH), 5.67 (bt, NH), 4.32 (m, 2H), 3.91 (m, 1H), 3.48 (q, 1H, J=5.7 Hz), 3.03 (s, 3H), 1.98-1.61 (m, 5H), 1.52 (d, 3H, J=5.7 Hz), 1.42-1.07 (m, 5H); IR (neat) 3337, 2930, 2854, 1647, 1514, 1453, 1334, 1159, 909 cm⁻¹; MS (FAB) m/z 517 (M+H)

Example 91

2-(3-fluoro-4-methylsulfonamido-phenyl)-N-(2-hexyloxy-6-trifluoromethyl-pyridin-3-ylmethyl)-propionamide

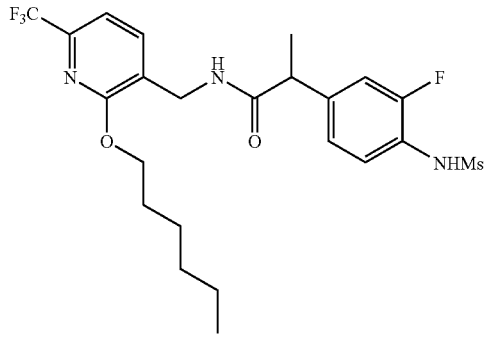

¹H NMR (CDCl₃) δ 7.57 (d, 1H, J=7.1 Hz), 7.52 (dd, 1H, J=8.3, 8.3 Hz), 7.19 (d, 1H, J=7.3 Hz), 7.12-7.05 (m, 2H), 6.48 (bs, NH), 5.99 (bt, NH), 4.38-4.29 (m, 4H), 3.51 (q, 1H, J=7.1 Hz), 3.03 (s, 3H), 1.75-1.68 (m, 2H), 1.49 (d, 3H, J=7.1 Hz), 1.38-1.30 (m, 6H), 0.91 (t, 3H); IR (neat) 3292, 2930, 1654, 1514, 1463, 1425, 1338, 1269, 1155, 973 cm⁻¹; MS (FAB) m/z 520 (M+H)

Example 95

2-(3-fluoro-4-methylsulfonamido-phenyl)-N-(2-isobutoxy-6-trifluoromethyl-pyridin-3-ylmethyl)-propionamide

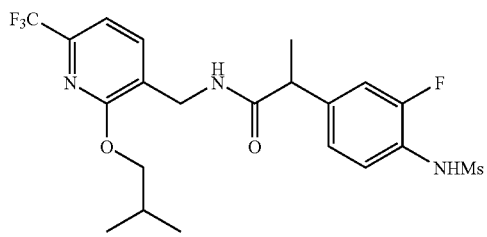

¹H NMR (CDCl₃) δ 7.58 (d, 1H, J=7.3 Hz), 7.51 (dd, 1H, J=8.4, 8.4 Hz), 7.19 (d, 1H, J=7.5 Hz), 7.12-7.05 (m, 2H), 6.50 (bs, NH), 5.95 (bt, NH), 4.41-4.37 (m, 2H), 4.17-4.06 (m, 2H), 3.51 (q, 1H, J=7.1 Hz), 3.03 (s, 3H), 2.05 (m, 1H), 1.49 (d, 3H, J=7.1 Hz), 0.99 (d, 6H, J=6.8 Hz); IR (neat) 3295, 2966, 1655, 1514, 1463, 1425, 1336, 1157 cm⁻¹; MS (FAB) m/z 492 (M+H)

Example 100

N-(2-cyclopropylmethoxy-6-trifluoromethyl-pyridin-3-ylmethyl)-2-(3-fluoro-4-methylsulfonamido-phenyl)-propionamide

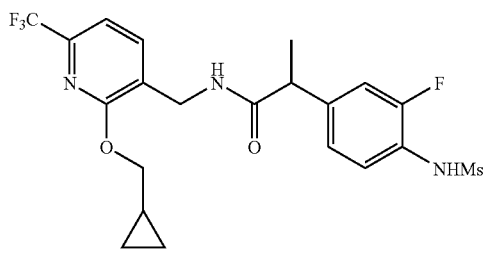

¹H NMR (CDCl₃) δ 7.59 (d, 1H, J=7.3 Hz), 7.51 (dd, 1H, J=8.3, 8.3 Hz), 7.19 (d, 1H, J=7.5 Hz), 7.13-7.06 (m, 2H), 6.49 (bs, NH), 6.08 (bt, NH), 4.42-4.39 (m, 2H), 4.24-4.11 (m, 2H), 3.52 (q, 1H, J=7.1 Hz), 3.03 (s, 3H), 1.59 (d, 3H, J=7.0 Hz), 1.25-1.15 (m, 1H), 0.62-0.56 (m, 2H), 0.36-0.33 (m, 2H); IR (neat) 3288, 1655, 1513, 1427, 1376, 1335, 1158, 984 cm⁻¹; MS (FAB) m/z 490 (M+H)

Example 101

N-(2-cyclobutylmethoxy-6-trifluoromethyl-pyridin-3-ylmethyl)-2-(3-fluoro-4-methylsulfonamido-phenyl)-propionamide

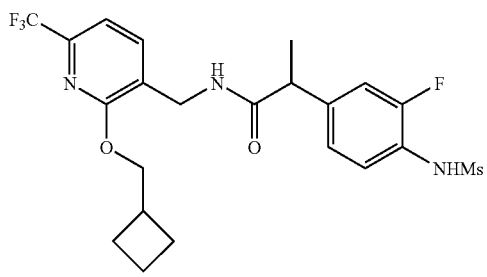

¹H NMR (CDCl₃) δ 7.57 (d, 1H, J=7.5 Hz), 7.50 (dd, 1H, J=8.2, 8.2 Hz), 7.19 (d, 1H, J=7.3 Hz), 7.12-7.04 (m, 2H), 6.64 (bs, NH), 6.02 (bt, NH), 4.45-4.26 (m, 4H), 3.51 (q, 1H, J=7.1 Hz), 3.03 (s, 3H), 2.71 (m, 1H), 2.13-1.79 (m, 6H), 1.48 (d, 3H, J=7.1 Hz); IR (neat) 3289, 2940, 1656, 1513, 1424, 1335, 1157, 993 cm⁻¹; MS (FAB) m/z 504 (M+H)

Example 102

2-(3-chloro-4-methylsulfonamido-phenyl)-N-(2-pyrrolidin-1-yl-6 trifluoromethyl-pyridin-3-ylmethyl)-propionamide

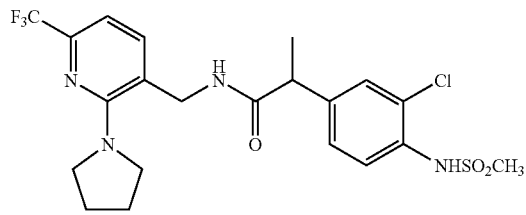

¹H NMR (300 MHz, CDCl₃) δ 7.60 (d, 1H, J=8.4 Hz), 7.41 (s, 1H) 7.39 (d, 1H, J=7.9 Hz), 7.22 (d, 1H, J=8.4 Hz), 6.95 (d, 1H, J=7.5 Hz), 6.79 (bs, 1H), 5.74 (bt, 1H), 4.47 (d, 2H, J=5.1 Hz), 3.52 (q, 1H, J=7.1 Hz), 3.48-3.41 (m, 4H), 3.01 (s, 3 H), 1.89-1.82 (m, 4H), 1.51 (d, 3H, J=7.0 Hz); IR (neat) 3291, 2974, 1651, 1598, 1497, 1431, 1333, 1159, 971, 913, 733 cm⁻¹; MS (FAB) m/z 505 (M+H)

Example 103

2-(3-bromo-4-methylsulfonamido-phenyl)-N-(2-pyrrolidin-1-yl-6-trifluoromethyl-pyridin-3-ylmethyl)-propionamide

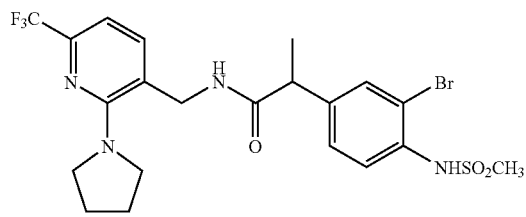

¹H NMR (300 MHz, CDCl₃) δ 7.60 (d, 1H, J=8.4 Hz), 7.56 (d, 1H, J=2.0 Hz), 7.39 (d, 1H, J=7.5 Hz), 7.27 (dd, 1H, J=8.3, 2.2 Hz), 6.95 (d, 1H, J=7.5 Hz), 6.77 (bs, 1H), 5.77 (bt, 1H), 4.47 (d, 2H, J=5.1 Hz), 3.51 (q, 1H, J=7.1 Hz), 3.47-3.41 (m, 4H), 3.01 (s, 3H), 1.89-1.83 (m, 4H), 1.51 (d, 3H, J=7.1 Hz); IR (neat) 3294, 2973, 1651, 1598, 1494, 1431, 1333, 1159, 971, 912, 733 cm⁻¹; MS (FAB) m/z 549 (M+H)

Example 104

N-(4-benzyl-6'-trifluoromethyl-3,4,5,6-tetrahydro-2H-[1,2']bipyridinyl-3'-ylmethyl)-2-(3-fluoro-4-methylsulfonamido-phenyl)-propionamide

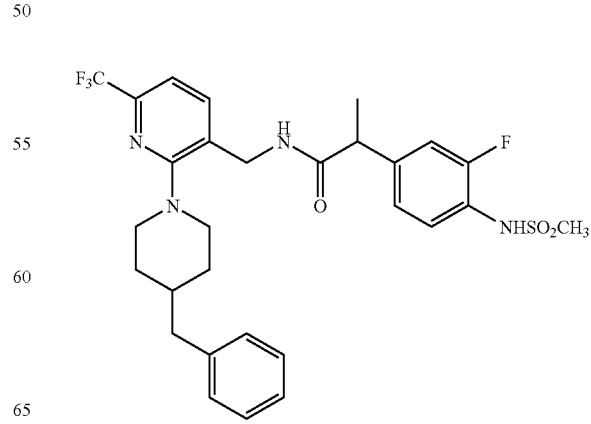

¹H NMR (300 MHz, CDCl₃) δ 7.53 (dd, 1H, J=8.2, 8.2 Hz), 7.48 (d, 1H, J=7.9 Hz), 7.29-7.14 (m, 7H), 7.07 (d, 1H, J=8.1 Hz), 6.49 (bs, 1H), 6.23 (bt, 1H), 4.46 (d, 2H, J=5.7 Hz), 3.54 (q, 1H, J=7.0 Hz), 3.31 (m, 2H), 3.02 (s, 3H), 2.78 (m, 2H), 2.59 (d, 2H, J=6.6 Hz), 1.78-1.71 (m, 3H), 1.52 (d, 3H, J=7.1 Hz), 1.30 (m, 2H); IR (neat) 3292, 2923, 1655, 1592, 1512, 1420, 1335, 1158, 968, 939, 734 cm⁻¹; MS (FAB) m/z 593 (M+H)

Example 106

N-(2-benzyloxy-6-trifluoromethyl-pyridin-3-ylmethyl)-2-(3-fluoro-4-methylsulfonamido-phenyl)-propionamide

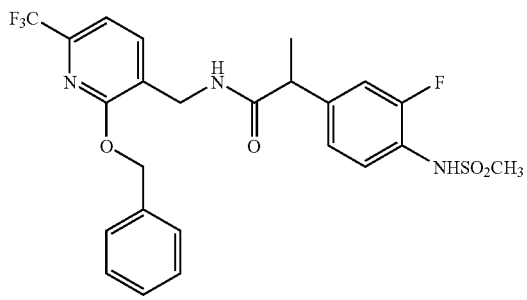

¹H NMR (300 MHz, CDCl₃) δ 7.62 (d, 1H, J=7.1 Hz), 7.47 (dd, 1H, J=8.4, 8.4 Hz), 7.44-7.36 (m, 5H), 7.24 (d, 1H, J=7.5 Hz), 7.04 (dd, 1H, J=11.2, 1.8 Hz), 6.97 (d, 1H, J=8.4 Hz), 6.42 (bs, 1H), 5.96 (bt, 1H), 5.41 (m, 2H), 4.39 (m, 2H), 3.41 (q, 1H, J=7.1 Hz), 3.01 (s, 3H), 1.42 (d, 3H, J=7.1 Hz); IR (neat) 3295, 1655, 1512, 1419, 1353, 1267, 1156, 977, 907, 737 cm⁻¹; MS (FAB) m/z 526 (M+H)

Example 107

2-(3-fluoro-4-methylsulfonamido-phenyl)-N-[2-(3-methoxy-benzyloxy)-6-trifluoromethyl-pyridin-3-ylmethyl]-propionamide

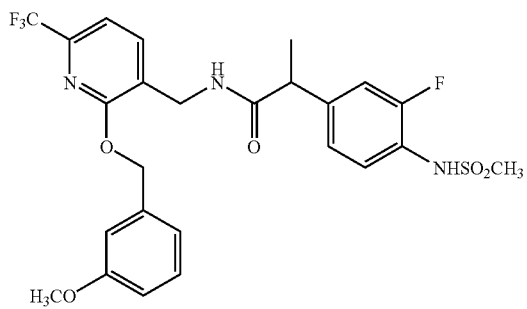

¹H NMR (300 MHz, CDCl₃) δ 7.62 (d, 1H, J=7.7 Hz), 7.46 (dd, 1H, J=8.3, 8.3 Hz), 7.31 (dd, 1H, J=8.1 Hz), 7.23 (d, 1H, J=7.4 Hz), 7.06-6.88 (m, 4H), 6.90 (m, 1H), 6.49 (bs, 1H), 5.99 (bt, 1H), 5.39 (m, 2H), 4.39 (m, 2H), 3.83 (s, 3H), 3.42 (q, 1H, J=7.1 Hz), 3.01 (s, 3H), 1.42 (d, 3H, J=7.1 Hz); IR (neat) 3294, 1656, 1600, 1512, 1417, 1349, 1267, 1157, 976, 910, 735 cm⁻¹; MS (FAB) m/z 556 (M+H)

Example 108

N-(2-butoxy-4-tert-butyl-benzyl)-2-(3-fluoro-4-methylsulfonamido-phenyl)-propionamide

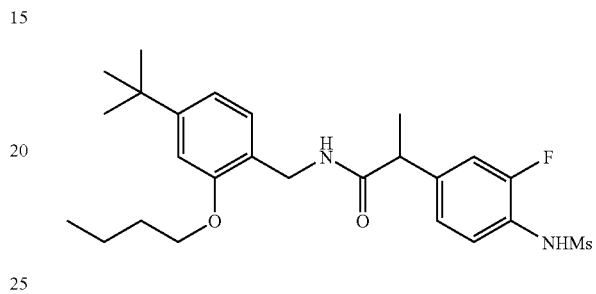

¹H NMR (300 MHz, CDCl₃) δ 7.48 (t, 1H, J=8.2 Hz), 7.16-7.04 (m, 3H), 6.92-6.85 (m, 2H), 6.59 (bs, 1H), 5.98 (bt, 1H), 4.45-4.29 (m, 2H), 3.98-3.90 (m, 2H), 3.46 (q, 1H, J=6.9 Hz), 3.01 (s, 3H), 1.75-1.65 (m, 2H), 1.48 (d, 3H, J=7.1 Hz), 1.30 (s, 9H), 0.97 (t, 3H, J=7.3 Hz); IR (KBr) 3289, 2961, 1650, 1510, 1413, 1334 cm⁻¹;

MS (FAB) m/z 479 (M+H)

Example 109

2-(3-fluoro-4-methylsulfonamido-phenyl)-N-[2-(4-phenyl-piperazin-1-yl)-6-trifluoromethyl-pyridin-3-ylmethyl]-propionamide

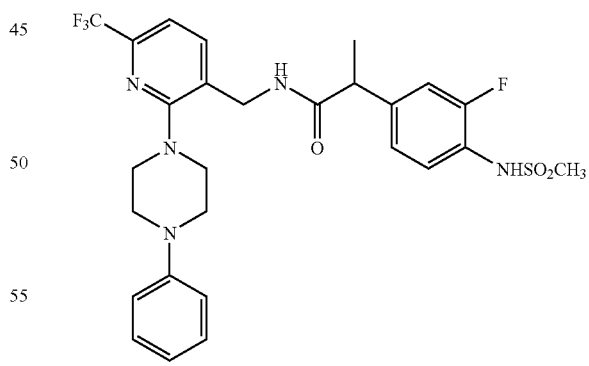

¹H NMR (300 MHz, CDCl₃) δ 7.54 (d, 1H, J=7.7 Hz), 7.48 (dd, 1H, J=8.2, 8.2 Hz), 7.31 (m, 3H), 7.13 (dd, 1H, J=11.0, 1.8 Hz), 7.08 (d, 1H, J=8.8 Hz), 6.96-6.89 (m, 3H), 6.33 (bs, 1H), 6.20 (bt, 1H), 4.54 (d, 2H, J=6.0 Hz), 3.57 (q, 1H, J=7.0 Hz), 3.32-3.29 (m, 8H), 2.99 (s, 3H), 1.53 (d, 3H, J=7.1 Hz); IR (neat) 3292, 1658, 1594, 1508, 1418, 1374, 1335, 1231, 1155, 968, 909, 834, 758, 694 cm⁻¹; MS (FAB) m/z 580 (M+H)

Example 110

2-(3-fluoro-4-methylsulfonamido-phenyl)-N-(2-phenylamino-6-trifluoromethyl-pyridin-3-ylmethyl)-propionamide

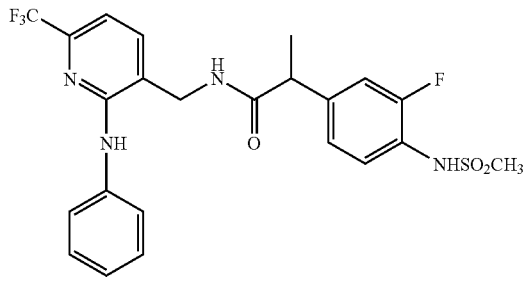

$^1$H NMR (300 MHz, CD$_3$OD) δ 7.67 (m, 2H), 7.59 (d, 1H, J=8.2 Hz), 7.34 (dd, 1H, J=8.2, 8.2 Hz), 7.19 (dd, 1H, J=10.9, 1.9 Hz), 7.11 (d, 1H, J=8.4 Hz), 7.06 (d, 1H, J=7.7 Hz), 7.02-6.95 (m, 3H), 4.45 (m, 2H), 3.67 (q, 1H, J=7.1 Hz), 2.89 (s, 3H), 1.47 (d, 3H, J=7.1 Hz); IR (neat) 3306, 2926, 1706, 1645, 1509, 1428, 1328, 1156, 968, 833 cm$^{-1}$; MS (FAB) m/z 511 (M+H)

Example 111

2-(3-fluoro-4-methylsulfonamido-phenyl)-N-(2-propoxy-6-trifluoromethyl-pyridin-3-ylmethyl)-propionamide

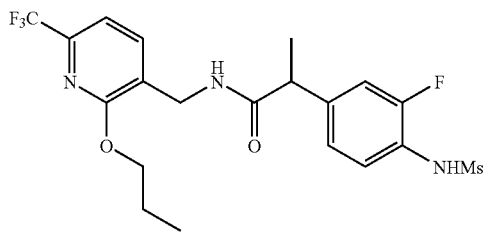

$^1$H NMR (CDCl$_3$) δ 7.58 (d, 1H, J=7.5 Hz), 7.52 (dd, 1H, J=8.2, 8.2 Hz), 7.19 (d, 1H, J=7.3 Hz), 7.12-7.05 (m, 2H), 6.50 (bs, NH), 5.97 (bt, NH), 4.39-4.23 (m, 4H), 3.52 (q, 1H, J=7.1 Hz), 3.03 (s, 3H), 1.74 (m, 2H), 0.99 (t, 3H, J=7.3 Hz); IR (neat) 3287, 2972, 1655, 1513, 1426, 1336, 1256, 976 cm$^{-1}$; MS (FAB) m/z 478 (M+H)

Example 112

2-(3-fluoro-4-methylsulfonamido-phenyl)-N-[2-(4-fluoro-phenylamino)-6-trifluoromethyl-pyridin-3-ylmethyl]-propionamide

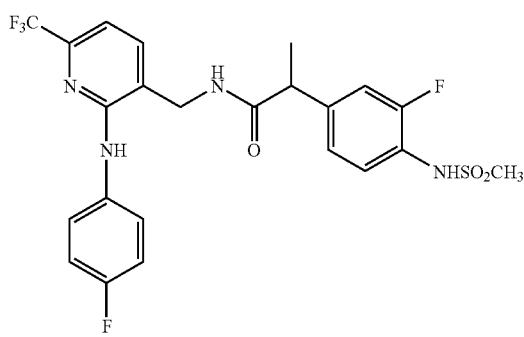

$^1$H NMR (300 MHz, CD$_3$OD) δ 7.90 (m, 2H), 7.59 (d, 1H, J=7.5 Hz), 7.33 (dd, 1H, J=8.3, 8.3 Hz), 7.24 (m, 1H), 7.21 (dd, 1H, J=11.4, 1.8 Hz), 7.11 (d, 1H, J=8.4 Hz), 7.06 (d, 1H, J=7.5 Hz), 6.59 (m, 1H), 4.46 (m, 2H), 3.68 (q, 1H, J=7.1 Hz), 2.87 (s, 3H), 1.47 (d, 3H, J=7.1 Hz); IR (neat) 3267, 2928, 1707, 1644, 1593, 1502, 1433, 1329, 1157, 969, 817, 755, 694 cm$^{-1}$; MS (FAB) m/z 529 (M+H)

Example 113

N-[2-(4-chloro-phenylamino)-6-trifluoromethyl-pyridin-3-ylmethyl]-2-(3-fluoro-4-methylsulfonamido-phenyl)-propionamide

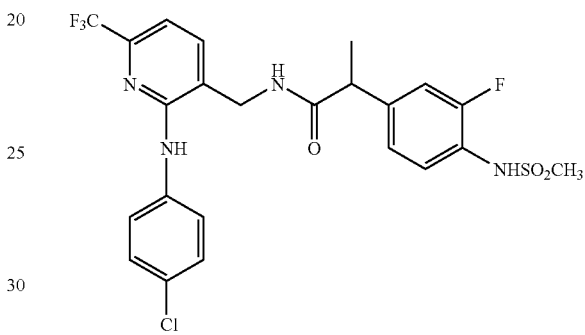

$^1$H NMR (300 MHz, CD$_3$OD) δ 7.10 (d, 2H, J=9.0 Hz,) 7.62 (d, 1H, J=7.5 Hz), 7.34 (dd, 1H, J=8.3, 8.3 Hz), 7.23 (d, 2H, J=9.0 Hz), 7.19 (dd, 1H, J=11.7, 2.0 Hz), 7.10 (d, 1H, J=8.3 Hz), 7.09 (d, 1H, J=7.5 Hz), 4.45 (m, 2H), 3.67 (q, 1H, J=7.0 Hz), 2.88 (s, 3H), 1.47 (d, 3H, J=7.1 Hz); IR (neat) 2922, 1645, 1496, 1466, 1334, 1151, 971, 819 cm$^{-1}$; MS (FAB) m/z 545 (M+H)

Example 114

2-(3-fluoro-4-methylsulfonamido-phenyl)-N-(2-fluoro-4-trifluoromethyl-benzyl)-propionamide

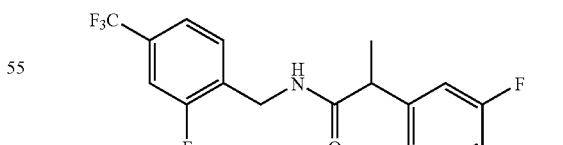

$^1$H NMR (300 MHz, CDCl$_3$) δ 7.50 (dd, 1H, J=8.0, 8.0 Hz), 7.41-7.26 (m, 3H), 7.13 (dd, 1H, J=11.0, 2.0 Hz), 7.07 (bd, 1H), 6.60 (bs, 1H), 6.00 (bt, 1H), 4.48 (m, 2H), 3.03 (s, 3H), 1.49 (d, 3H J=7.1 Hz); IR (KBr) 3288, 1657, 1588, 1512, 1430, 1332, 1220 cm$^{-1}$; MS (FAB) m/z 437 (M+H)

Example 115

N-(2-benzylamino-6-trifluoromethyl-pyridin-3-ylm-ethyl)-2-(3-fluoro-4-methylsulfonamido-phenyl)-propionamide

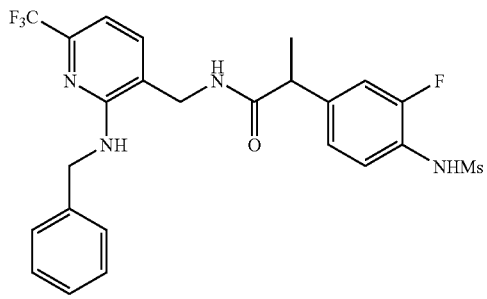

$^1$H NMR (300 MHz, CD$_3$OD) δ 7.42-7.14 (m, 8H), 6.82 (d, 1H, J=7.2 Hz), 6.69 (bt, 1H), 4.68-4.44 (m, 2H), 4.25 (m, 2H), 3.62 (q, 1H, J=7.1 Hz), 2.94 (s, 3H), 1.37 (d, 3H, J=7.3 Hz); IR (KBr) 3269, 2928, 2493, 1706, 1644, 1513, 1452 cm$^{-1}$; MS (FAB) m/z 525 (M+H)

Example 117

2-(3-fluoro-4-methylsulfonamido-phenyl)-N-((2-(4-tert-butylphenyl)-6-(trifluoromethyl)pyridin-3-ylm-ethyl)-propionamide

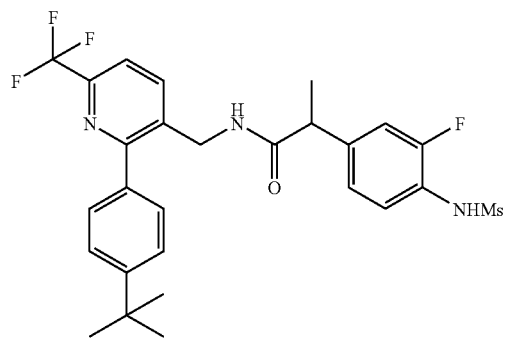

$^1$H NMR (300 MHz, CD$_3$OD) δ 7.77 (d, 1H, J=8.1 Hz), 7.66 (d, 1H, J=8.1 Hz), 7.50 (d, 2H, J=6.6 Hz), 7.40-7.45 (m, 3H), 7.06-7.19 (m, 3H), 4.40 (s, 2H), 3.65 (q, 1H, J=6.6 Hz), 2.96 (s, 3H), 1.40 (d, 3H, J=6.6 Hz), 1.35 (s, 9H); IR (KBr) 2927, 2856, 1619, 1511, 1455, 1339, 1274, 1158 cm$^{-1}$; MS (FAB) m/z 552 (M+H)

Example 118

2-(3-fluoro-4-methylsulfonamido-phenyl)-(N(2-(3-chloro-4-fluorophenyl)-6-(trifluoromethyl)pyridin-3-ylmethyl)-propionamide

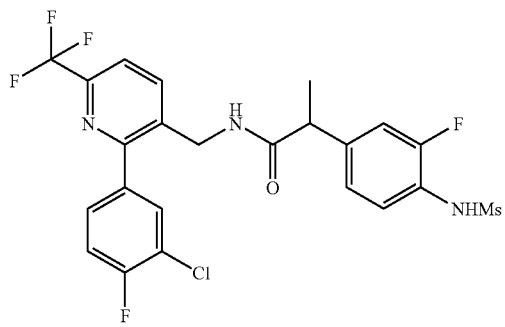

$^1$H NMR (300 MHz, CD$_3$OD) δ 7.75 (d, 1H, J=7.5 Hz), 7.63 (d, 1H, J=7.5 Hz), 7.56 (dd, 1H, J=2.1 Hz, 6.9 Hz), 7.34-7.49 (m, 3H), 7.23 (t, 1H, J=7.5 Hz), 7.05-7.14 (m, 2H), 4.41 (s, 2H), 3.56 (q, 1H, J=6.9 Hz), 2.98 (s, 3H), 1.40 (d, 3H, J=6.9 Hz); IR (KBr) 2919, 1651, 1508, 1409, 1338, 1150, 971, 829 cm$^{-1}$; MS (FAB) m/z 548 (M+H)

Example 122

2-(3-fluoro-4-methylsulfonamido-phenyl)-(N(2-(bu-tylthio)-6-(trifluoromethyl)pyridin-3-ylmethyl)-pro-pionamide

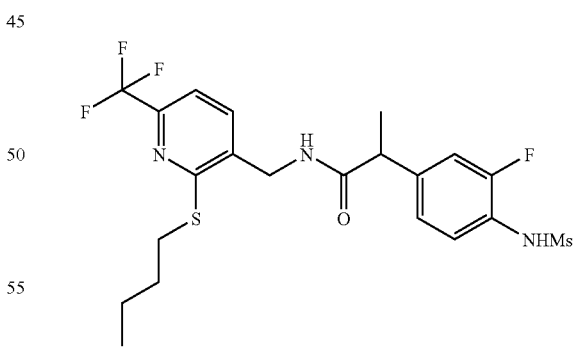

$^1$H NMR (300 MHz, CDCl$_3$) δ 7.42-7.50 (m, 2H), 7.27 (s, 1H), 7.13 (dd, 1H, J=8.1, 1.8 Hz), 7.07 (d, 1H, J=8.1 Hz), 6.98 (bs 1H), 6.33 (bt, 1H), 4.36 (m, 2H), 3.56 (q, 1H, J=6.9 Hz), 3.22 (t, 2H, J=7.5 Hz), 3.01 (s, 3H), 1.66 (m, 2H), 1.38-1.50 (m, 5H), 0.93 (t, 3H, J=7.2 Hz); IR (KBr) 3291, 2930, 2856, 1707, 1587, 1513, 1337, 1272, 1154, 1108, 898, 815 cm$^{-1}$; MS (FAB) m/z 508 (M+H)

Example 124

2-(3-fluoro-4-methylsulfonamido-phenyl)-N-[2-(2-methyl-cyclopropyl methoxy)-6-trifluoromethyl-pyridin-3-ylmethyl]-propionamide

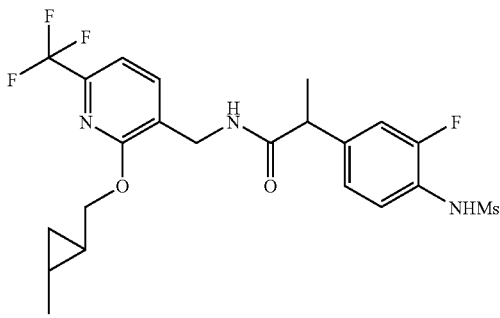

¹H NMR (300 MHz, CD₃OD) δ 7.48 (d, 1H, J=7.5 Hz), 7.43 (dd, 1H, J=8.1, 8.1 Hz), 7.15-7.23 (m, 3H), 4.34 (d, 2H, J=5.1 Hz), 4.20 (d, 2H, J=7.1 Hz), 3.73 (q, 1H, J=6.9 Hz), 2.98 (s, 3H), 1.46 (d, 3H, J=7.1 Hz), 1.04 (d, 3H, J=6.0 Hz), 0.95 (m, 1H), 0.78 (m, 1H), 0.51 (m, 1H), 0.31 (m, 1H); IR (KBr) 3280, 2928, 1654, 1512, 1450, 1427, 1339, 1267, 1158, 980 cm⁻¹; MS (FAB) m/z 504 (M+H)

Example 125

2-(3-fluoro-4-methylsulfonamido-phenyl)-(N-(2-(3,3-dimethylbutoxy)-6-(trifluoromethyl)pyridin-3-ylmethyl)-propionamide

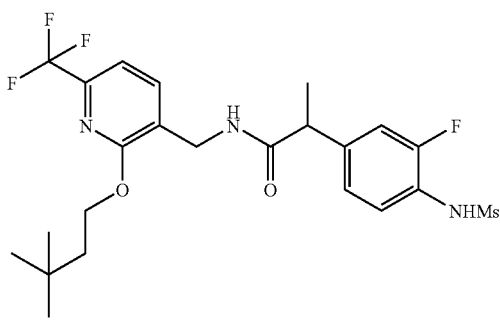

¹H NMR (300 MHz, CD₃OD) δ 7.40-7.48 (m, 2H), 7.13-7.22 (m, 3H), 4.42 (t, 2H, J=7.5 Hz), 4.31 (d, 2H, J=7.2 Hz), 3.72 (q, 1H, J=6.9 Hz), 2.97 (s, 3H), 1.68 (t, 2H, J=7.2 Hz), 1.45 (d, 3H, J=6.9 Hz), 0.97 (s, 9H); IR (KBr) 3352, 3077, 2950, 1655, 1545, 1510, 1427, 1366, 1331, 1150 cm⁻¹; MS (FAB) m/z 520 (M+H)

Example 126

2-(3-fluoro-4-methylsulfonamido-phenyl)-(N-(2-(cyclohexylthio)-6-(trifluoromethyl)pyridin-3-ylmethyl)-propionamide

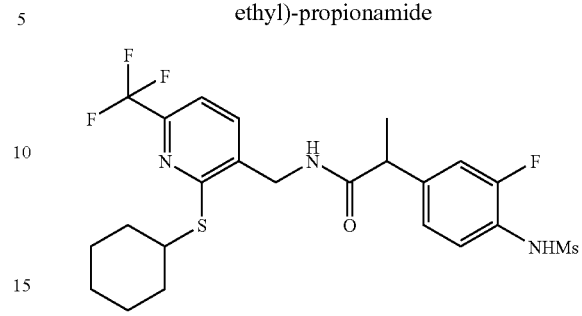

¹H NMR (300 MHz, CD₃OD) δ 7.35-7.48 (m, 3H), 7.26 (d, 1H, J=7.8 Hz), 7.16 (dd, 1H, J=1.8, 11.1 Hz), 7.10 (d, 1H, J=8.4 Hz), 6.13 (bs, 1H), 4.35 (d, 2H, J=5.7 Hz), 3.82 (m, 1H), 3.56 (q, 1H, J=7.2 Hz), 3.02 (s, 3H), 2.06 (m, 2H), 1.75 (m, 2H), 1.49 (d, 3H, J=7.2 Hz), 1.26-1.33 (m, 6H); IR (KBr) 3284, 2932, 2854, 1654, 1586, 1512, 1449, 1336, 1267 cm⁻¹; MS (FAB) m/z 534 (M+H)

Example 127

2-(4-methylsulfonamido-3-methyl-phenyl)-N-(6'-trifluoromethyl-3,4,5,6-tetrahydro-2H-[1,2']bipyridinyl-3'-ylmethyl)-propionamide

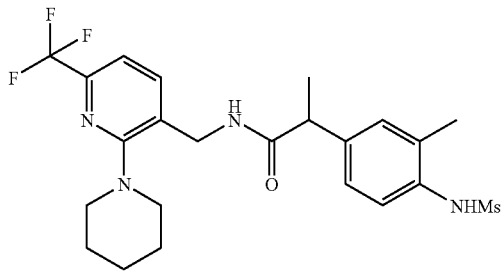

¹H NMR (300 MHz, CDCl₃) δ 7.46 (d, 1H, J=8.1 Hz), 7.39 (d, 1H, J=8.1 Hz), 7.11-7.20 (m, 3H), 6.33 (s, 1H), 6.25 (bs, 1H), 4.46 (d, 2H, J=5.7 Hz), 3.56 (q, 1H, J=7.5 Hz), 2.96-3.02 (m, 7H), 2.38 (s, 3H), 1.54-1.63 (m, 6H), 1.52 (d, 3H, J=7.5 Hz); IR (KBr) 3288, 2928, 2853, 1652, 1538, 1457, 1246, 970 cm⁻¹; MS (FAB) m/z 499 (M+H)

Example 128

N-(2-azocan-1-yl-6-trifluoromethyl-pyridin-3-ylmethyl)-2-(3-fluoro-4-methylsulfonamido-phenyl)-propionamide

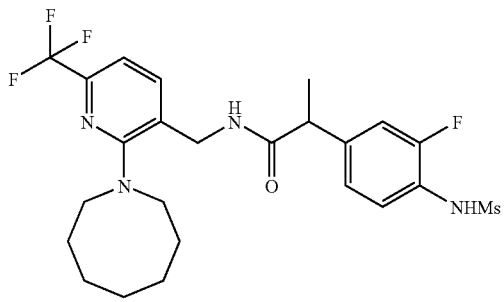

¹H NMR (300 MHz, CDCl₃) δ 7.48 (t, 1H, J=8.1 Hz), 7.36 (d, 1H, J=7.8 Hz), 7.14 (dd, 1H, J=2.1, 11.1 Hz), 7.07 (d, 1H, J=8.1 Hz), 6.96 (d, 1H, J=7.8 Hz), 6.94 (bs, 1H), 5.97 (bs, 1H), 4.39 (d, 2H, J=5.1 Hz), 3.59 (q, 1H, J=7.2 Hz), 3.46 (m, 4H), 3.01 (s, 3H), 1.68 (m, 4H), 1.51 (m, 6H); IR (KBr) 3275, 2926, 1652, 1594, 1509, 1454, 1421, 1334 cm⁻¹; MS (FAB) m/z 531 (M+H)

Example 129

2-(3-fluoro-4-methylsulfonamido-phenyl)-N-(2-pyrrolidin-1-yl-6-trifluoromethyl-pyridin-3-ylmethyl)-thiopropionamide

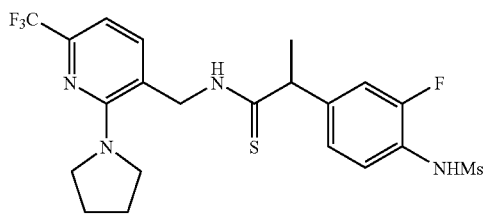

¹H NMR (300 MHz, CDCl₃) δ 7.97 (bs, 1H), 7.50 (dd, 1H, J=8.1, 8.1 Hz), 7.08-7.29 (m, 4H), 6.54 (bs, 1H), 4.85 (d, 2H, J=5.7 Hz), 4.01 (q, 1H, J=6.9 Hz), 3.09 (m, 4H), 3.01 (s, 3H), 1.87 (m, 4H), 1.62 (d, 3H, J=6.9 Hz); IR (KBr)) 3296, 2923, 1509, 1428, 1334, 1159, 1121, 978, 907, 733 cm⁻¹; MS (FAB) m/z 505 (M+H)

Example 130

2-(3-fluoro-4-methylsulfonamido-phenyl)-N-[2-(4-fluoro-phenyl)-6-trifluoromethyl-pyridin-3-ylmethyl]-thiopropionamide

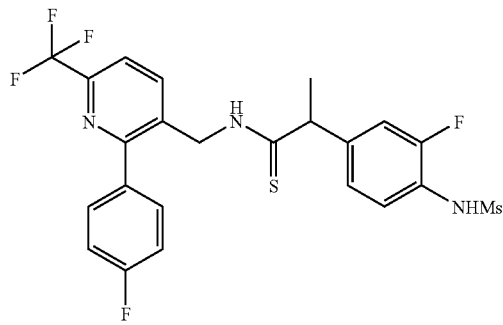

¹H NMR (300 MHz, CDCl₃) δ 7.76 (d, 1H, J=8.1 Hz), 7.60 (d, 1H, J=8.1 Hz), 7.42-7.47 (m, 3H), 7.00-7.19 (m, 5H), 6.54 (bs, 1H), 4.95 (d, 2H, J=5.7 Hz), 3.93 (q, 1H, J=6.9 Hz), 3.03 (s, 3H), 1.59 (d, 3H, J=6.9 Hz); IR (KBr)) 3300, 1512, 1409, 1340, 1155, 1047 cm⁻¹; MS (FAB) m/z 530 (M+H)

Example 131

2-(3-fluoro-4-methylsulfonamido-phenyl)-N-(4-methylpiperidin-1-yl-6-chlorodifluoromethyl-pyridin-3-ylmethyl)-propionamide

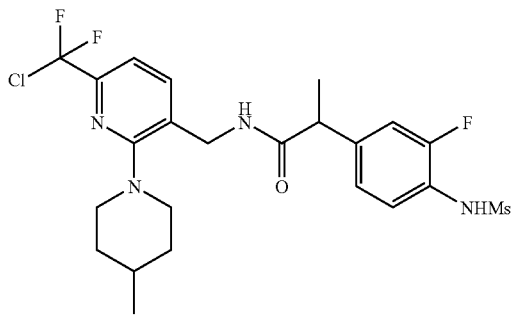

¹H NMR (300 MHz, CDCl₃) δ 7.45-7.53 (m, 2H), 7.07-7.18 (m, 3H), 6.72 (bs, 1H), 6.37 (bt, 1H), 4.46 (d, 2H, J=5.7 Hz), 3.56 (q, 1H, J=6.9 Hz), 3.32 (m, 2H), 3.02 (s, 3H), 2.82 (m, 2H), 1.71 (m, 2H), 1.53 (d, 3H, J=7.5 Hz), 1.23 (m, 3H), 0.97 (d, 3H, J=6.9 Hz); IR (KBr) 2924, 1653, 1590, 1512, 1453, 1334, 1157 cm⁻¹; MS (FAB) m/z 534 (M+H)

Example 132

N-[2-azepan-1-yl-6-(chloro-difluoro-methyl)-pyridin-3-ylmethyl]-2-(3-fluoro-4-methylsulfonamido-phenyl)-propionamide

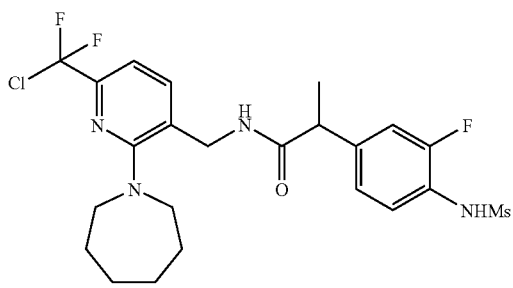

¹H NMR (300 MHz, CDCl₃) δ 7.52 (dd, 1H, J=8.1, 8.1 Hz), 7.38 (d, 1H, J=7.5 Hz), 7.17 (dd, 1H, J=1.8, 11.1 Hz), 7.08 (d, 1H, J=8.1 Hz), 6.99 (d, 1H, J=7.5 Hz), 6.57 (bs, 1H), 5.87 (bt, 1H), 4.42 (d, 2H, J=5.7 Hz), 3.56 (q, 1H, J=6.9 Hz), 3.39 (t, 4H, J=6.0 Hz), 3.02 (s, 3H), 1.75 (m, 4H), 1.56 (m, 4H), 1.52 (d, 3H, J=6.9 Hz); IR (KBr) 3286, 2929, 1652, 1592, 1511, 1452, 1421, 1333, 1159 cm⁻¹; MS (FAB) m/z 534 (M+H)

Example 134

2-(3-fluoro-4-methylsulfonamido-phenyl)-N-[2-(4-methyl-piperazin-1-yl)-6-trifluoromethyl-pyridin-3-ylmethyl]-propionamide

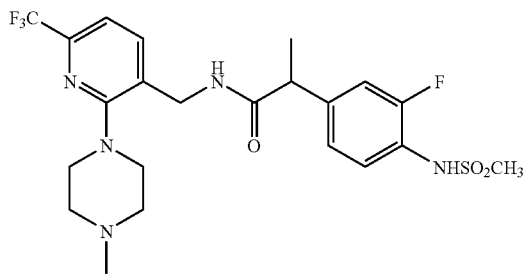

¹H NMR (300 MHz, CDCl₃) δ 7.54 (dd, 1H, J=8.4, 8.4 Hz), 7.50 (d, 1H, J=8.1 Hz), 7.23 (d, 1H, J=7.7 Hz), 7.14 (dd, 1H, J=11.2, 1.9 Hz), 7.09 (d, 1H, J=8.2 Hz), 6.21 (bt, 1H), 4.47 (m, 2H), 3.57 (q, 1H, J=7.1 Hz), 3.19-3.15 (m, 4H), 3.04 (s, 3H), 2.53-2.49 (m, 4H), 2.34 (s, 3H), 1.54 (d, 3H, J=7.1 Hz); IR (neat) 2935, 1655, 1591, 1511, 1457, 1417, 1334, 1149, 966, 757 cm⁻¹; MS (FAB) m/z 518 (M+H)

Example 135

N-[2-(3,4-dimethyl-phenylamino)-6-trifluoromethyl-pyridin-3-ylmethyl]-2-(3-fluoro-4-methylsulfonamido-phenyl)-propionamide

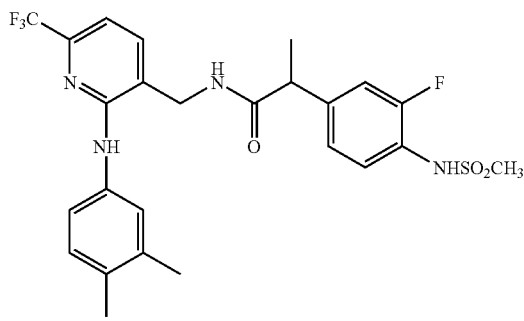

¹H NMR (300 MHz, CDCl₃) δ 7.56 (m, 2H), 7.43 (dd, 1H, J=8.4, 8.4 Hz), 7.39 (d, 1H, J=7.8 Hz), 7.14 (dd, 1H, J=11.0, 2.2 Hz), 7.06 (d, 1H, J=8.7 Hz), 7.03 (d, 1H, J=7.7 Hz), 6.95 (d, 1H, J=7.5 Hz), 6.41 (bs, 1H), 5.85 (bt, 1H), 4.47 (d, 2H, J=6.4 Hz), 3.52 (q, 1H, J=7.1 Hz), 2.96 (s, 3H), 2.27 (s, 3H), 2.23 (s, 3H), 1.52 (d, 3H, J=7.1 Hz); IR (neat) 3363, 2922, 1646, 1538, 1509, 1428, 1328, 1156, 970, 814 cm⁻¹; MS (FAB) m/z 539 (M+H)

Example 136

N-[2-(5-chloro-2-methyl-phenylamino)-6-trifluoromethyl-pyridin-3-ylmethyl]-2-(3-fluoro-4-methyl-sulfonamido-phenyl)-propionamide

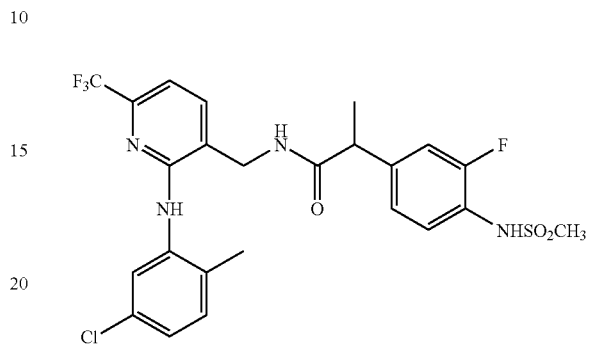

¹H NMR (300 MHz, CDCl₃) δ 7.68 (d, 1H, J=2.2 Hz), 7.45 (d, 1H, J=7.5 Hz), 7.42 (dd, 1H, J=8.3, 8.3 Hz), 7.11 (d, 1H, J=7.7 H), 7.08 (dd, 1H, J=9.0, 2.2 Hz), 7.03-7.00 (m, 3H), 6.43 (bs, 1H), 5.87 (bt, 1H), 4.49 (m, 2H), 3.51 (q, 1H, J=7.1 Hz), 3.02 (s, 3H), 2.25 (s, 3H), 1.48 (d, 3H, J=7.1 Hz); IR (neat) 3293, 1706, 1651, 1595, 1517, 1423, 1334, 1156, 969, 904, 819 cm⁻¹; MS (FAB) m/z 559 (M+H)

Example 137

N-(2-azocan-1-yl-6-trifluoromethyl-pyridin-3-ylmethyl)-2-(3-fluoro-4-methylsulfonamido-phenyl)-propionamide

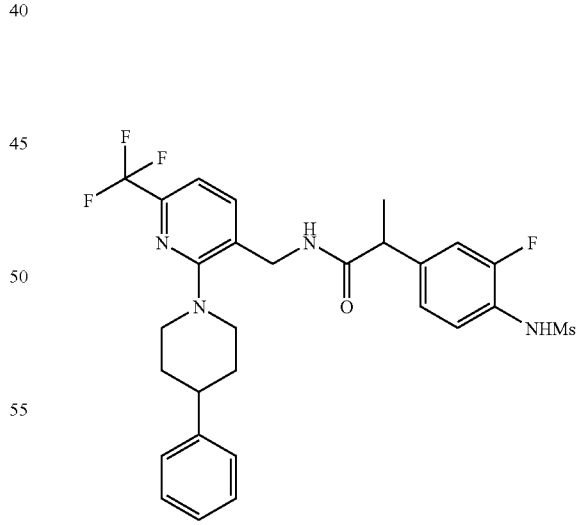

¹H NMR (300 MHz, CDCl₃) δ 7.48-7.51 (m, 2H), 7.08-7.36 (m, 8H), 6.52 (s, 1H), 6.23 (bs, 1H), 4.53 (d, 2H, J=5.1 Hz), 3.56 (q, 1H, J=7.2 Hz), 3.46 (m, 2H), 2.95-3.00 (m, 5H), 2.03 (m, 2H), 1.82 (m, 2H), 1.54 (d, 3H, J=7.2 Hz); IR (KBr) 2933, 1655, 1592, 1512, 1419, 1374, 1336, 1224, 1158, 957, 834, 758, 701 cm⁻¹; MS (FAB) m/z 579 (M+H)

Example 138

2-(3-fluoro-4-methylsulfonamido-phenyl)-N-(4-fluoro-6'-trifluoromethyl-3,4,5,6-tetrahydro-2H-[1,2']bipyridinyl-3'-ylmethyl)-propionamide

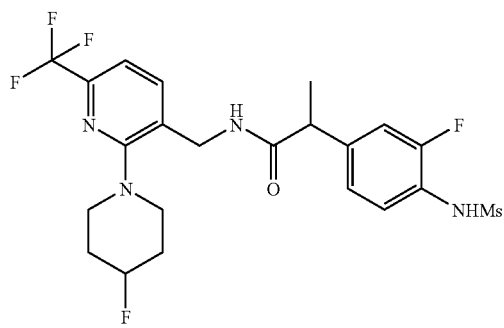

$^1$H NMR (300 MHz, CD$_3$OD) δ 7.50 (d, 1H, J=8.1 Hz), 7.43 (t, 1H, J=8.1 Hz), 7.14-7.26 (m, 3H), 4.75 (dm, 1H, J=50 Hz), 4.38 (d, 2H, J=5.7 Hz) 3.71 (q, 1H, J=7.2 Hz), 3.30 (m, 2H), 3.03 (m, 2H), 2.96 (s, 3H), 1.88 (m, 4H), 1.46 (d, 3H, J=7.2 Hz); IR (KBr) 2926, 2854, 1656, 1591, 1512, 1418 cm$^{-1}$; MS (FAB) m/z 521 (M+H)

Example 139

2-(3-fluoro-4-methylsulfonamido-phenyl)-N-(6'-trifluoromethyl-3,6-dihydro-2H-[1,2']bipyridinyl-3'-ylmethyl)-propionamide

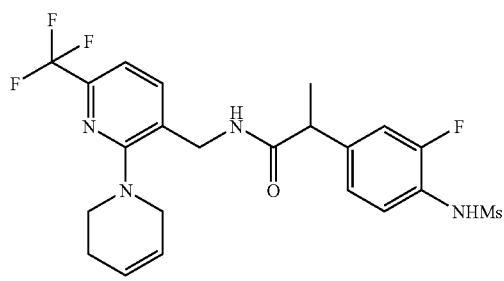

$^1$H NMR (300 MHz, CDCl$_3$) δ 7.47-7.52 (m, 2H), 7.06-7.22 (m, 4H), 6.68 (bs, 1H), 6.40 (bt, 1H), 5.79-5.83 (m, 2H), 4.49 (d, 2H, J=5.7 Hz), 3.69 (m, 2H), 3.56 (q, 1H, J=7.2 Hz), 3.21 (m, 2H), 3.02 (s, 3H), 2.27 (m, 2H), 1.52 (d, 3H, J=7.2 Hz); IR (KBr) 3286, 2924, 1654, 1592, 1512, 1423, 1337, 1271, 1158, 972, 833, 737 cm$^{-1}$;

MS (FAB) m/z 501 (M+H)

Example 142

2-(3-fluoro-4-methylsulfonamido-phenyl)-N-(2-pentyl-6-trifluoromethyl-pyridin-3-ylmethyl)-propionamide

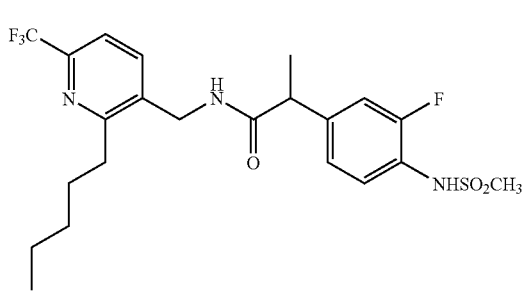

$^1$H NMR (300 MHz, CDCl$_3$) δ 7.54 (d, 1H, J=7.7 Hz), 7.43 (dd, 1H, J=8.0, 8.0 Hz), 7.41 (d, 1H, 7.9 Hz), 7.15 (dd, 1H, J=11.2, 1.8 Hz), 7.06 (d, 1H, J=1.4 Hz), 6.20 (bt, 1H), 4.41-4.55 (m, 2H), 3.60 (q, 1H, J=7.0 Hz), 3.01 (s, 3H), 2.75 (t, 2H, J=7.9 Hz), 1.61-1.71 (m, 2H), 1.51 (d, 3H, J=7.1 Hz), 1.18-1.35 (m, 4H), 0.85-0.90 (m, 3H); IR (KBr) 3289, 2930, 1655, 1521, 1459, 1340, 1157, 973, 911, 732 cm$^{-1}$;

MS (FAB) m/z 490 (M+H)

Example 147

N-[2-(4-chloro-phenyl)-6-trifluoromethyl-pyridin-3-ylmethyl]-2-(3-fluoro-4-methylsulfonamido-phenyl)-propionamide

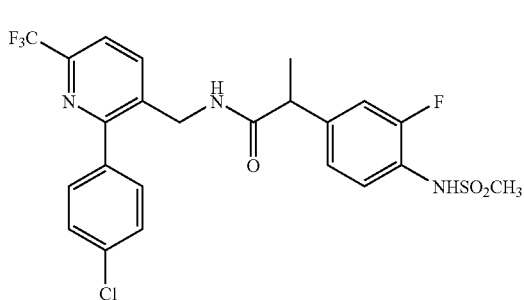

$^1$H NMR (300 MHz, CDCl$_3$) δ 7.79 (d, 1H, J=8.2 Hz), 7.62 (d, 1H, J=8.1 Hz), 7.53 (m, 1H), 7.37-7.45 (m, 4H), 7.06 (m, 1H), 7.02 (d, 1H, J=7.9 Hz), 5.59 (bt, 1H), 4.50 (d, 2H, J=6.0 Hz), 3.48 (q, 1H, J=7.3 Hz), 3.04 (s, 3H), 1.47 (d, 3H, J=7.1 Hz); IR (KBr) 3290, 1657, 1512, 1456, 1409, 1339, 1154, 972, 910, 835, 732 cm$^{-1}$;

MS (FAB) m/z 530 (M+H)

Example 148

2-(3-fluoro-4-methylsulfonamido-phenyl)-N-[2-(3-fluoro-phenyl)-6-trifluoromethyl-pyridin-3-ylmethyl]-propionamide

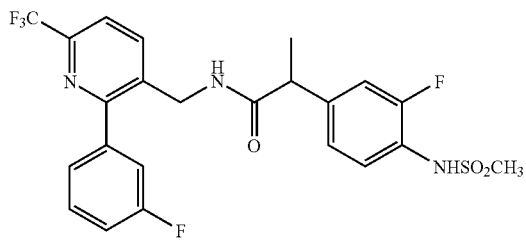

$^1$H NMR (300 MHz, CDCl$_3$) δ 7.79 (d, 1H, J=8.1 Hz), 7.62 (d, 1H, J=8.1 Hz), 7.36-7.44 (m, 2H), 6.97-7.19 (m, 5H), 6.90 (bs, 1H), 6.01 (bt, 1H), 4.37-4.51 (m, 2H), 3.50 (q, 1H, J=7.1 Hz), 3.00 (s, 3H), 1.45 (d, 3H, J=7.1 Hz); IR (KBr) 3239, 1655, 1586, 1512, 1448, 1340, 1154, 972, 912 cm$^{-1}$; MS (FAB) m/z 514 (M+H)

Example 149

N-[2-(3-chloro-phenyl)-6-trifluoromethyl-pyridin-3-ylmethyl]-2-(3-fluoro-4-methylsulfonamido-phenyl)-propionamide

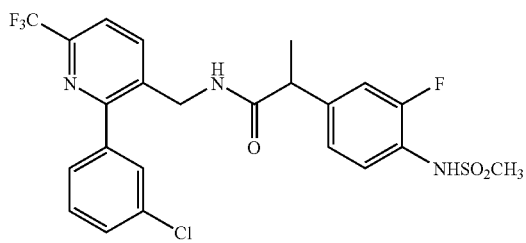

$^1$H NMR (300 MHz, CDCl$_3$) δ 7.82 (d, 1H, J=8.3 Hz), 7.62 (d, 1H, J=8.0 Hz), 7.52 (dd, 1H, J=8.3, 8.3 Hz), 7.40-7.42 (m, 3H), 7.31 (m, 1H), 7.07 (m, 1H), 7.01 (m, 1H), 4.48 (d, 2H, J=6.6 Hz), 3.48 (q, 1H, J=7.0 Hz), 3.04 (s, 3H), 1.47 (d, 3H, J=7.1 Hz); IR (KBr) 3293, 2927, 1655, 1512, 1340, 1153, 732 cm$^{-1}$; MS (FAB) m/z 530 (M+H)

Example 150

2-(3-fluoro-4-methylsulfonamido-phenyl)-N-[2-(2-fluoro-phenyl)-6-trifluoromethyl-pyridin-3-ylmethyl]-propionamide

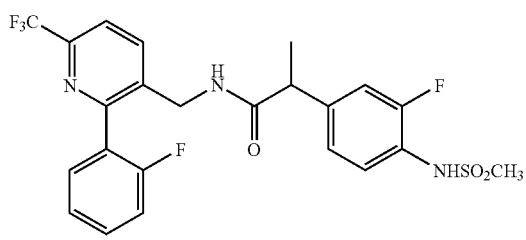

$^1$H NMR (300 MHz, CDCl$_3$) δ 7.86 (d, 1H, J=8.1 Hz), 7.66 (d, 1H, J=8.0 Hz), 7.36-7.51 (m, 3H), 7.28 (m, 1H), 7.01-7.16 (m, 3H), 6.68 (bs, 1H), 5.84 (bt, 1H), 4.29-4.44 (m, 2H), 3.49 (q, 1H, J=7.0 Hz), 3.02 (s, 3H), 1.47 (d, 3H, J=7.1 Hz); IR (KBr) 3292, 1658, 1512, 1340, 1156, 973, 732 cm$^{-1}$; MS (FAB) m/z 514 (M+H)

Example 151

2-(3-fluoro-4-methylsulfonamido-phenyl)-N-[2-(4-methoxy-phenyl)-6-trifluoromethyl-pyridin-3-ylmethyl]-propionamide

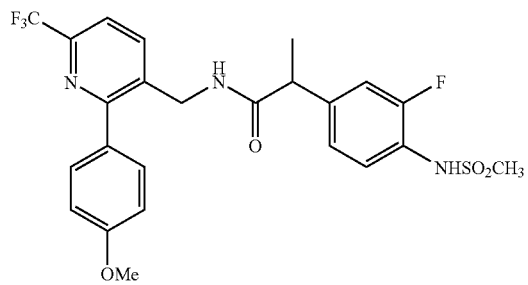

$^1$H NMR (300 MHz, CDCl$_3$) δ 7.77 (d, 1H, J=7.9 Hz), 7.57 (d, 1H, J=8.1 Hz), 7.50 (dd, 1H, J=8.3, 8.3 Hz), 7.38 (d, 2H, J=8.8 Hz), 7.01-7.06 (m, 2H), 6.96 (d, 2H, J=8.9 Hz), 6.50 (bs, 1H), 5.57 (bs, 1H), 4.53 (d, 2H, J=5.3 Hz), 3.86 (s, 3H), 3.46 (q, 1H, J=7.0 Hz), 3.03 (s, 3H), 1.46 (d, 3H, J=7.1 Hz); IR (KBr) 2928, 1655, 1514, 1340, 1251, 1155, 973, 837, 732 cm$^{-1}$; MS (FAB) m/z 526 (M+H)

Example 152

N-[4-tert-butyl-2-(2,2-dimethyl-propoxy)-benzyl]-2-(3-fluoro-4-methylsulfonamido-phenyl)-propionamide

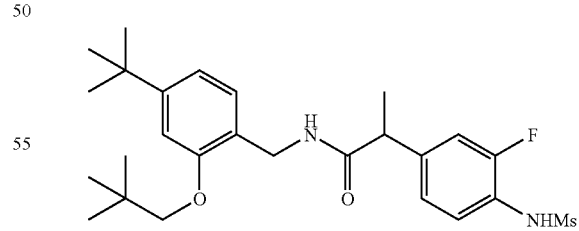

$^1$H NMR (300 MHz, CDCl$_3$) δ 7.47 (t, 1H, J=8.2 Hz), 7.16-7.11 (m, 2H), 7.04 (d, 1H, J=8.2 Hz), 6.93-6.84 (m, 2H), 6.52 (bs, 1H), 5.90 (bt, 1H), 4.50-4.31 (m, 2H), 3.63-3.57 (m, 2H), 3.44 (q, 1H, J=6.9 Hz), 3.01 (s, 3H), 1.47 (d, 3H, J=6.9 Hz), 1.31 (s, 9H), 1.0 (s, 9H); IR (KBr) 3292, 2960, 1649, 1511, 1457, 1408 cm$^{-1}$; MS (FAB) m/z 493 (M+H)

Example 153

N-(4-tert-butyl-2-pentyloxy-benzyl)-2-(3-fluoro-4-methylsulfonamido-phenyl)-propionamide

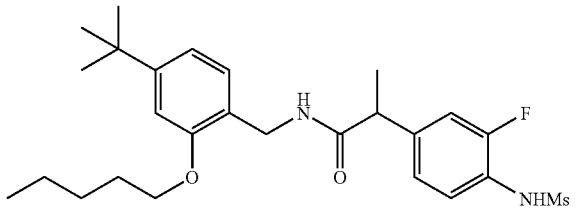

$^1$H NMR (300 MHz, CDCl$_3$) δ 7.49 (t, 1H, J=8.2 Hz), 7.16-7.04 (m, 3H), 6.92-6.85 (m, 2H) 6.52 (bs, 1H), 5.99 (bt, 1H), 4.45-4.29 (m, 2H), 4.01-3.89 (m, 2H), 3.46 (q, 1H, J=7.1 Hz), 3.01 (s, 3H), 1.77-1.68 (m, 2H), 1.48 (d, 3H, J=7.1 Hz), 1.43-1.39 (m, 4H), 1.30 (s, 9H), 0.93 (t, 3H, J=7.1 Hz); IR (KBr) 3288, 2959, 2868, 1650, 1510, 1455 cm$^{-1}$; MS (FAB) m/z 493 (M+H)

Example 154

N-(4-tert-butyl-2-cyclohexyloxy-benzyl)-2-(3-fluoro-4-methylsulfonamido-phenyl)-propionamide

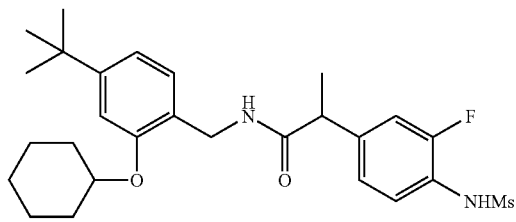

$^1$H NMR (300 MHz, CDCl$_3$) δ 7.50 (t, 1H, J=8.4 Hz), 7.17-6.86 (m, 5H), 6.44 (bs, 1H), 6.01 (bt, 1H), 4.45-4.30 (m, 3H), 3.47 (q, 1H, J=6.9 Hz), 3.01 (s, 3H), 1.95-1.25 (m, 10H), 1.48 (d, 3H, J=7.1 Hz), 1.29 (s, 9H); IR (KBr) 3292, 2935, 2859, 1650, 1509, 1454 cm$^{-1}$; MS (FAB) m/z 505 (M+H)

Example 155

N-(4-tert-butyl-2-cyclopentyloxy-benzyl)-2-(3-fluoro-4-methylsulfonamido-phenyl)-propionamide

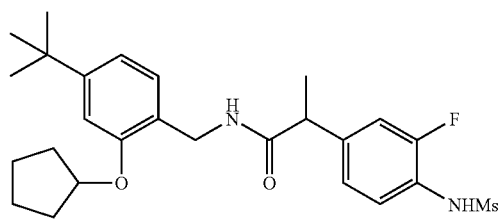

$^1$H NMR (300 MHz, CDCl$_3$) δ 7.49 (t, 1H, J=8.2 Hz), 7.16-7.04 (m, 3H), 6.90-6.86 (m, 2H), 6.51 (bs, 1H), 5.94 (bt, 1H), 4.78-4.76 (m, 1H), 4.41-4.25 (m, 2H), 3.46 (q, 1H, J=7.1 Hz), 3.01 (s, 3H), 1.90-1.61 (m, 8H), 1.48 (d, 3H, J=7.1 Hz), 1.29 (s, 9H); IR (KBr) 3289, 2962, 2870, 1650, 1509, 1411 cm$^{-1}$; MS (FAB) m/z 491 (M+H)

Example 156

N-(2-cyclobutoxy-6-trifluoromethyl-pyridin-3-ylmethyl)-2-(3-fluoro-4-methylsulfonamido-phenyl)-propionamide

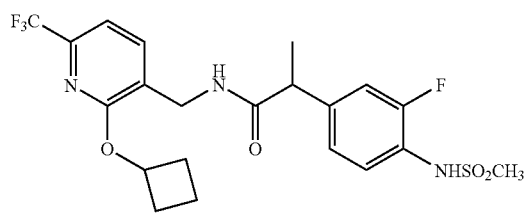

$^1$H NMR (CDCl$_3$) δ 7.58-7.51 (m, 2H), 7.18 (d, 1H, J=7.3 Hz), 7.13-7.07 (m, 2H), 6.50 (bs, NH), 6.00 (bt, NH), 5.20 (m, 1H), 4.37 (d, 2H, J=6.2 Hz), 3.56 (q, 1H, J=7.0 Hz), 3.03 (s, 3H), 2.50-2.40 (m, 2H), 2.05-1.65 (m, 4H), 1.50 (d, 3H, J=7.1 Hz); IR (neat) 3290, 2987, 1655, 1513, 1421, 1340, 1275, 1157, 1071, 962 cm$^{-1}$; MS (FAB) m/z 490 (M+H)

Example 157

2-(3-fluoro-4-methylsulfonamido-phenyl)-N-[2-(4-methyl-cyclohexyloxy)-6-trifluoromethyl-pyridin-3-ylmethyl]-propionamide

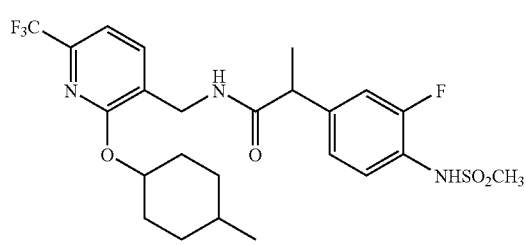

$^1$H NMR (CDCl$_3$) δ 7.57-7.49 (m, 2H), 7.16 (d, 1H, J=7.3 Hz), 7.12-7.05 (m, 2H), 6.48 (bs, NH), 5.99 (bt, NH), 5.00 (m, 1H), 4.34 (d, 2H, J=5.8 Hz), 3.51 (q, 1H, J=6.8 Hz), 3.03 (s, 3H), 2.12-2.00 (m, 2H), 1.80-1.72 (m, 2H), 1.50-1.10 (m, 5H), 1.48 (d, 3H, J=7.1 Hz), 0.94 (d, 3H, J=6.6 Hz); IR (neat) 3287, 2931, 1655, 1513, 1422, 1336, 1271, 1158, 914, 734 cm$^{-1}$; MS (FAB) m/z 532 (M+H)

Example 158 acetic acid 3'-{[2-(3-fluoro-4-methylsulfonamido-phenyl)-propionylamino]-methyl}-6'-trifluoromethyl-3,4,5,6-tetrahydro-2H-[1,2']bipyridinyl-4-yl ester

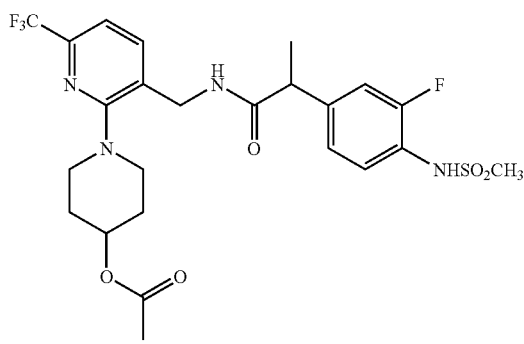

¹H NMR (CDCl₃) δ 7.57-7.48 (m, 2H), 7.24 (d, 1H, J=8.1 Hz), 7.17-7.09 (m, 2H), 6.47 (bs, NH), 6.05 (bt, NH), 4.93 (m, 1H), 4.47 (d, 2H, J=5.7 Hz), 3.57 (q, 1H, J=7.0 Hz), 3.35-3.25 (m, 2H), 3.07-2.97 (m, 2H), 3.04 (s, 3H), 2.08 (s, 3H), 2.02-1.92 (m, 2H), 1.80-1.70 (m, 2H), 1.54 (d, 3H, J=7.3 Hz); IR (neat) 3362, 2910, 1726, 1657, 1512, 1419, 1335, 1260, 1157, 1033, 758 cm⁻¹; MS (FAB) m/z 561 (M+H)

Example 159

2-(3-fluoro-4-methylsulfonamido-phenyl)-N-(4-methoxy-6'-trifluoromethyl-3,4,5,6-tetrahydro-2H-[1,2']bipyridinyl-3'-ylmethyl)-propionamide

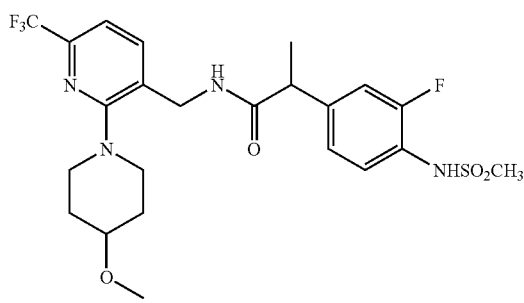

¹H NMR (CDCl₃) δ 7.53-7.47 (m, 2H), 7.22 (d, 1H, J=7.7 Hz), 7.15-7.07 (m, 2H), 6.77 (bs, NH), 6.32 (bt, NH), 4.47 (d, 2H, J=5.7 Hz), 3.58 (q, 1H, J=7.1 Hz), 3.40-3.25 (m, 3H), 3.37 (s, 3H), 3.03 (s, 3H), 2.95-2.86 (m, 2H), 2.04-1.95 (m, 2H), 1.63-1.50 (m, 2H), 1.53 (d, 3H, J=7.0 Hz); IR (neat) 3289, 2932, 1656, 1592, 1512, 1457, 1418, 1335, 1275, 1158, 733 cm⁻¹; MS (FAB) m/z 533 (M+H)

Example 160

N-(4-butoxy-6'-trifluoromethyl-3,4,5,6-tetrahydro-2H-[1,2']bipyridinyl-3'-ylmethyl)-2-(3-fluoro-4-methylsulfonamido-phenyl)-propionamide

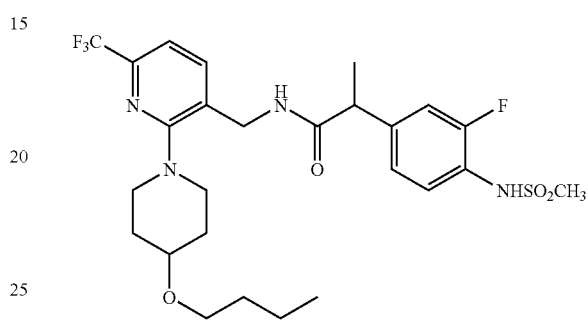

¹H NMR (CDCl₃) δ 7.54-7.48 (m, 2H), 7.21 (d, 1H, J=7.5 Hz), 7.14-7.07 (m, 2H), 6.64 (bs, NH), 6.26 (bt, NH), 4.47 (d, 2H, J=5.7 Hz), 3.57 (q, 1H, J=7.1 Hz), 3.50-3.26 (m, 5H), 3.03 (s, 3H), 2.94-2.86 (m, 2H), 2.02-1.95 (m, 2H), 1.62-1.50 (m, 7H), 1.45-1.33 (m, 2H), 0.93 (t, 3H, J=7.3 Hz); IR (neat) 3295, 2931, 1654, 1513, 1458, 1420, 1335, 1157 cm⁻¹; MS (FAB) m/z 575 (M+H)

Example 161

N-(2-cyclopentylmethoxy-6-trifluoromethyl-pyridin-3-ylmethyl)-2-(3-fluoro-4-methylsulfonamido-phenyl)-propionamide

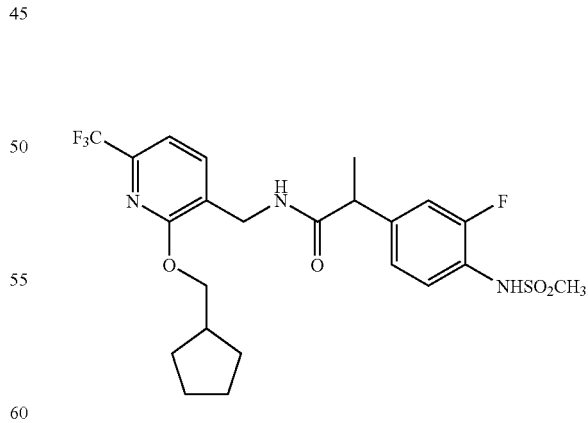

¹H NMR (CDCl₃) δ 7.58 (d, 1H, J=7.3 Hz), 7.51 (dd, 1H, J=8.4, 8.4 Hz), 7.19 (d, 1H, J=7.3 Hz), 7.11-7.04 (m, 2H), 6.54 (bs, NH), 6.00 (bt, NH), 4.38 (m, 2H), 4.20 (m, 2H), 3.50 (q, 1H, J=7.1 Hz), 3.03 (s, 3H), 2.29 (m, 1H), 1.80-1.70 (m, 2H), 1.70-1.55 (m, 4H), 1.48 (d, 3H, J=7.1 Hz), 1.37-1.27 (m,

2H); IR (neat) 3293, 2952, 1655, 1513, 1424, 1338, 1158 cm$^{-1}$; MS (FAB) m/z 518 (M+H)

Example 162

2-(3-fluoro-4-methylsulfonamido-phenyl)-N-(4-isopropoxy-6'-trifluoromethyl-3,4,5,6-tetrahydro-2H-[1,2']bipyridinyl-3'-ylmethyl)-propionamide

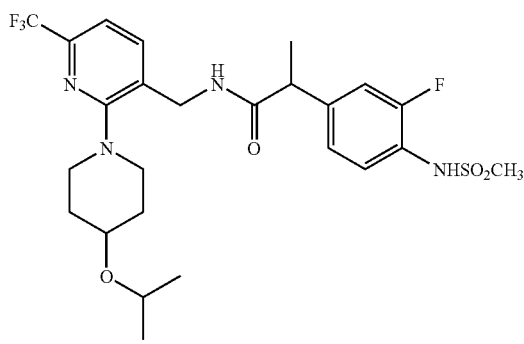

$^1$H NMR (CDCl$_3$) δ 7.55-7.48 (m, 2H), 7.22 (d, 1H, J=7.7 Hz), 7.15-7.08 (m, 2H), 6.56 (bs, NH), 6.23 (bt, NH), 4.47 (d, 2H, J=5.9 Hz), 3.74 (m, 1H), 3.60-3.45 (m, 2H), 3.37-3.33 (m, 2H), 3.04 (s, 3H), 2.94-2.85 (m, 2H), 1.98-1.90 (m, 2H), 1.62-1.50 (m, 2H), 1.53 (d, 3H, J=7.0 Hz), 1.18 (d, 6H, J=6.1 Hz); IR (neat) 3289, 2925, 1655, 1593, 1513, 1335, 1155 cm$^{-1}$; MS (FAB) m/z 561 (M+H)

Example 163

N-(2-ethoxy-6-trifluoromethyl-pyridin-3-ylmethyl)-2-(3-fluoro-4-methylsulfonamido-phenyl)-propionamide

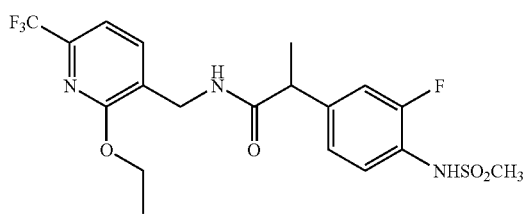

$^1$H NMR (CDCl$_3$) δ 7.58 (d, 1H, J=7.3 Hz), 7.51 (dd, 1H, J=8.2, 8.2 Hz), 7.19 (d, 1H, J=7.3 Hz), 7.12-7.05 (m, 2H), 6.58 (bs, NH), 6.02 (bt, NH), 4.44-4.36 (m, 4H), 3.53 (q, 1H, J=7.0 Hz), 3.03 (s, 3H), 1.49 (d, 3H, J=7.1 Hz), 1.34 (t, 3H, J=7.1 Hz); IR (neat) 3294, 1654, 1513, 1425, 1342, 1156 cm$^{-1}$; MS (FAB) m/z 464 (M+H)

Example 164

2-(3-fluoro-4-methylsulfonamido-phenyl)-N-(6''-trifluoromethyl-3,4,5,6,3',4',5',6'-octahydro-2H,2'H-[1,4';1',2'']terpyridin-3''-ylmethyl)-propionamide

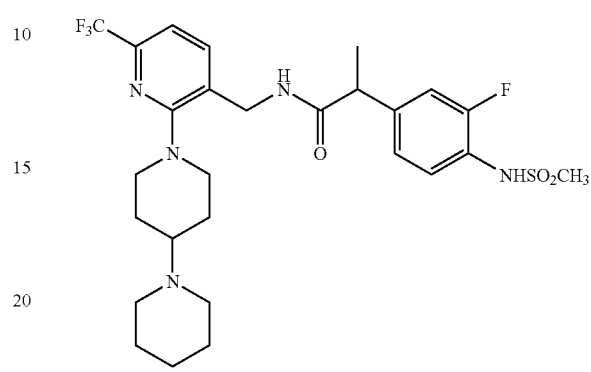

$^1$H NMR (300 MHz, CD$_3$OD) δ 7.51 (d, 1H, J=7.7 Hz), 7.42 (dd, 1H, J=8.2, 8.2 Hz), 7.53 (d, 1H, J=7.7 Hz), 7.13-7.21 (m, 2H), 4.30-4.47 (m, 2H), 3.71 (q, 1H, J=7.0 Hz), 3.48-3.52 (m, 2H), 2.97 (s, 3H), 2.80-2.84 (m, 2H), 2.55-2.75 (m, 5H), 1.88-2.00 (m, 2H), 1.60-1.75 (m, 6H), 1.50-1.55 (m, 2H), 1.46 (d, 3H, J=7.0 Hz); IR (KBr) 2924, 1649, 1509, 1456, 1419, 1334, 1124, 961 cm$^{-1}$; MS (FAB) m/z 586 (M+H)

Example 165

2-(3-fluoro-4-methylsulfonamido-phenyl)-N-(4-pyrrolidin-1-yl-6'-trifluoromethyl-3,4,5,6-tetrahydro-2H-[1,2']bipyridinyl-3'-ylmethyl)-propionamide

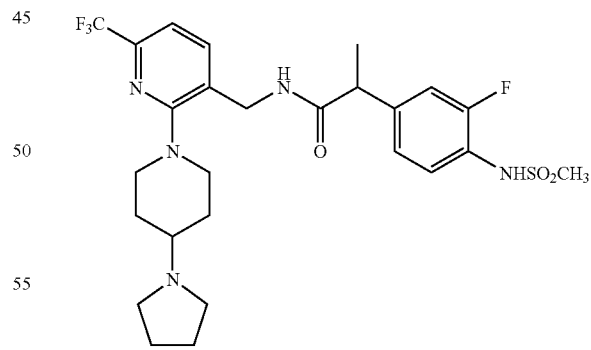

$^1$H NMR (300 MHz, CD$_3$OD) δ 7.50 (d, 1H, J=7.7 Hz), 7.42 (dd, 1H, J=8.3, 8.3 Hz), 7.25 (d, 1H, J=7.7 Hz), 7.10-7.22 (m, 2H), 4.29-4.45 (m, 2H), 3.72 (q, 1H, J=7.1 Hz), 3.40-3.50 (m, 2H), 2.70-2.92 (m, 6H), 2.40 (m, 1H), 1.95-2.10 (m, 2H), 1.81-2.10 (m, 4H), 1.57-1.74 (m, 2H), 1.46 (d, 3H, J=7.0 Hz) IR (KBr) 3296, 2926, 1651, 1580, 1420, 1333, 1126, 980, 832 cm$^{-1}$; MS (FAB) m/z 572 (M+H)

Example 166

N-[6-(chloro-difluoro-methyl)-2-cyclopentyloxy-pyridin-3-ylmethyl]-2-(3-fluoro-4-methylsulfonamido-phenyl)-propionamide

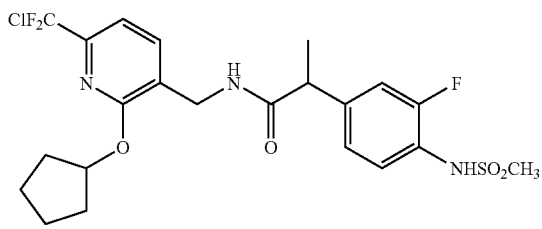

¹H NMR (300 MHz, CDCl₃) δ 7.48-7.57 (m, 2H), 7.03-7.15 (m, 3H), 6.56 (bs, 1H), 5.96 (bt, 1H), 5.46 (m, 1H), 4.27-4.42 (m, 2H), 3.52 (q, 1H, J=7.1 Hz), 3.03 (s, 3H), 1.19-2.08 (m, 2H), 1.56-1.78 (m, 6H), 1.49 (d, 3H, J=7.1 Hz); IR (KBr) 3288, 2967, 1655, 1512, 1419, 1339, 1159, 1112, 989, 889 cm⁻¹; MS (FAB) m/z 520 (M+H)

Example 167

N-[2-(butyl-methyl-amino)-6-trifluoromethyl-pyridin-3-ylmethyl]-2-(3-fluoro-4-methylsulfonamido-phenyl)-propionamide

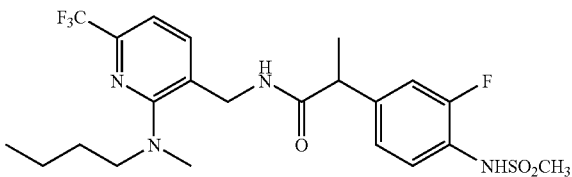

¹H NMR (300 MHz, CDCl₃) δ 7.53 (dd, 1H, J=8.3, 8.3 Hz), 7.45 (d, 1H, J=7.9 Hz), 7.05-7.19 (m, 3H), 6.52 (bs, 1H), 6.13 (bt, 1H), 4.46 (d, 2H, J=5.9 Hz), 3.56 (q, 1H, J=7.1 Hz), 3.05-3.12 (m, 2H), 3.04 (s, 3H), 2.80 (s, 3H), 1.42-1.58 (m, 5H), 1.20-1.38 (m, 2H), 0.90 (t, 3H, J=7.3 Hz); IR (KBr) 3280, 2932, 1653, 1511, 1460, 1400, 1335, 1159, 971 cm⁻¹; MS (FAB) m/z 505 (M+H)

Example 168

N-[6-(chloro-difluoro-methyl)-2-cyclohexyloxy-pyridin-3-ylmethyl]-2-(3-fluoro-4-methylsulfonamido-phenyl)-propionamide

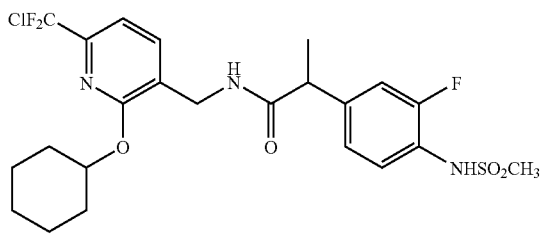

¹H NMR (300 MHz, CDCl₃) δ 7.48-7.59 (m, 2H), 7.02-7.14 (m, 3H), 6.49 (bs, 1H), 6.01 (bt, 1H), 5.13 (m, 1H), 4.29-4.47 (m, 2H), 3.52 (q, 1H, J=7.3 Hz), 3 H), 1.85-1.99 (m, 2H), 1.62-1.77 (m, 2H), 1.38-1.52 (m, 9H); IR (KBr) 3288, 2935, 2857, 1653, 1512, 1420, 1335, 1266, 1158, 1114, 987, 882 cm⁻¹; MS (FAB) m/z 534 (M+H)

Example 169

N-[2-benzyloxy-6-(chloro-difluoro-methyl)-pyridin-3-ylmethyl]-2-(3-fluoro-4-methylsulfonamido-phenyl)-propionamide

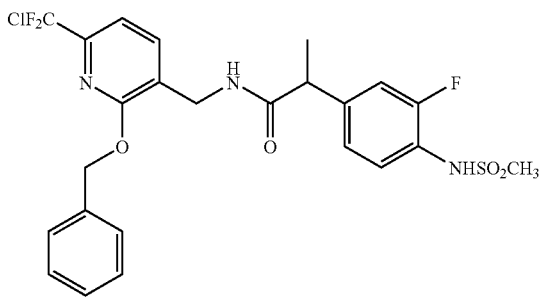

¹H NMR (300 MHz, CDCl₃) δ 7.59 (d, 1H, J=7.3 Hz), 7.30-7.50 (m, 6H), 7.20 (d, 1H, J=7.8 Hz), 7.05 (dd, 1H, J=11.2, 2.0 Hz), 6.97 (d, 1H, J=7.9 Hz), 6.52 (bs, 1H), 6.00 (bt, 1H), 5.36-5.49 (m, 2H), 4.30-4.46 (m, 2H), 3.42 (q, 1H, J=7.1 Hz), 3.00 (s, 3H), 1.43 (d, 3H, J=7.1 Hz); IR (KBr) 3286, 1653, 1511, 1417, 1334, 1267, 1157, 1114, 971, 883, 756 cm⁻¹; MS (FAB) m/z 542 (M+H)

Example 170

N-[2-(4-tert-butyl-cyclohexyloxy)-6-trifluoromethyl-pyridin-3-ylmethyl]-2-(3-fluoro-4-methylsulfonamido-phenyl)-propionamide

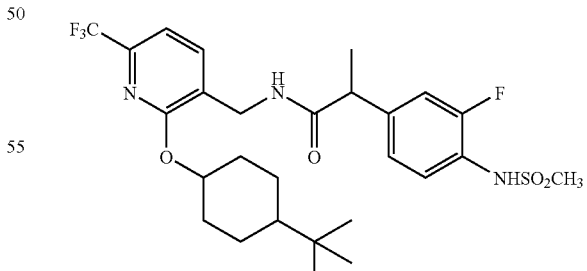

¹H NMR (CDCl₃) δ 7.57-7.50 (m, 2H), 7.16 (d, 1H, J=7.3 Hz), 7.12-7.05 (m, 2H), 6.46 (bs, NH), 5.98 (bt, NH), 4.96 (m, 1H), 4.34 (m, 2H), 3.51 (q, 1H, J=7.1 Hz), 3.03 (s, 3H), 2.20-2.10 (m, 2H), 1.88-1.80 (m, 2H), 1.49 (d, 3H, J=7.1 Hz), 1.30-1.00 (m, 5H), 0.89 (s, 9H); IR (neat) 3291, 2950, 2866, 1654, 1513, 1422, 1338, 1268, 1158 cm$^{-1}$; MS (FAB) m/z 574 (M+H)

Example 171

N-[2-(4-ethyl-cyclohexyloxy)-6-trifluoromethyl-pyridin-3-ylmethyl]-2-(3-fluoro-4-methylsulfonamido-phenyl)-propionamide

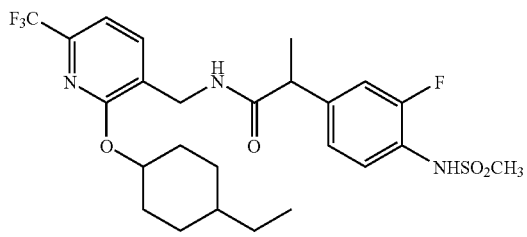

$^1$H NMR (CDCl$_3$) δ 7.57-7.50 (m, 2H), 7.16 (d, 1H, J=7.3 Hz), 7.12-7.05 (m, 2H), 6.47 (bs, NH), 5.99 (bt, NH), 5.00 (m, 1H), 4.34 (m, 2H), 3.52 (q, 1H, J=7.5 Hz), 3.03 (s, 3H), 2.13-2.03 (m, 2H), 1.87-1.80 (m, 2H), 1.49 (d, 3H, J=7.1 Hz), 1.32-1.04 (m, 7H), 0.91 (t, 3H, J=7.1 Hz); IR (neat) 3287, 2935, 2858, 1655, 1513, 1421, 1337, 1269, 1159 cm$^{-1}$; MS (FAB) m/z 546 (M+H)

Example 172

2-(3-fluoro-4-methylsulfonamido-phenyl)-N-[2-(4-methyl-benzyloxy)-6-trifluoromethyl-pyridin-3-ylmethyl]-propionamide

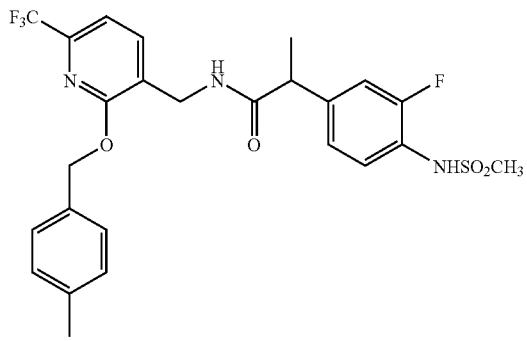

$^1$H NMR (300 MHz, CDCl$_3$) δ 7.61 (d, 1H, J=7.4 Hz), 7.47 (dd, 1H, J=8.1, 8.1 Hz), 7.31 (d, 2H, J=8.0 Hz), 7.22 (d, 1H, J=7.2 Hz), 7.20 (d, 2H, J=7.9 Hz), 7.03 (dd, 1H, J=11.5, 1.9 Hz), 6.96 (d, 1H, J=8.6 Hz), 6.46 (bs, 1H), 5.98 (bt, 1H), 5.36 (m, 2H), 4.37 (m, 2H), 3.40 (q, 1H, J=7.1 Hz), 3.01 (s, 3H), 2.28 (s, 3H), 1.42 (d, 3H, J=7.0 Hz); IR (neat) 3289, 2925, 1654, 1513, 1458, 1422, 1137, 1267, 1158, 976, 933, 808 cm$^{-1}$; MS (FAB) m/z 540 (M+H)

Example 173

N-[2-(4-chloro-benzylamino)-6-trifluoromethyl-pyridin-3-ylmethyl]-2-(3-fluoro-4-methylsulfonamido-phenyl)-propionamide

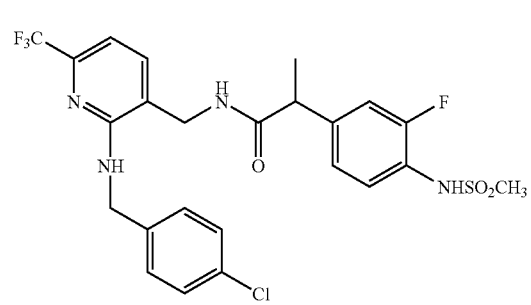

$^1$H NMR (300 MHz, CDCl$_3$) δ 7.48 (dd, 1H, J=8.3, 8.3 Hz), 7.33 (d, 2H, J=8.6 Hz), 7.25 (d, 2H, J=8.6 Hz), 7.24 (d, 1H, J=7.5 Hz), 7.07 (dd, 1H, J=11.2, 2.0 Hz), 6.99 (d, 1H, J=8.4 Hz), 6.81 (d, 1H, J=7.5 Hz), 6.71 (bt, 1H), 6.47 (bs, 1H), 5.72 (bs, 1H), 4.58 (m, 2H), 4.32 (m, 2H), 3.44 (q, 1H, J=7.1 Hz), 3.03 (s, 3H), 1.42 (d, 3H, J=7.1 Hz); IR (neat) 3343, 2929, 1706, 16347, 1610, 1514, 1454, 1334, 1158, 1016, 973, 909, 833, 760 cm$^{-1}$; MS (FAB) m/z 559 (M+H)

Example 174

N-(2-azepan-1-yl-4-trifluoromethyl-benzyl)-2-(3-fluoro-4-methylsulfonamido-phenyl)-propionamide

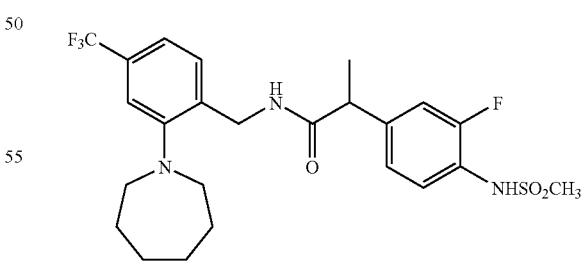

$^1$H NMR (300 MHz, CDCl$_3$) δ 7.51 (dd, 1H, J=8.2, 8.2 Hz), 7.32 (s, 1H), 7.23 (s, 2H), 7.14 (dd, 1H, J=11.3, 1.9 Hz), 7.08 (d, 1H, J=8.2 Hz), 6.52 (bs, 1H), 6.43 (bt, 1H), 4.53 (m, 2H), 3.54 (q, 1H, J=7.0 Hz), 3.04-3.00 (m, 7H), 1.72-1.64 (m, 8H), 1.52 (d, 3H, J=7.0 Hz); IR (neat) 3273, 2930, 2854, 1650, 1510, 1424, 1335, 1159, 1121, 972, 901, 737 cm$^{-1}$; MS (FAB) m/z 516 (M+H)

Example 175

N-[2-(4-fluoro-benzyloxy)-6-trifluoromethyl-pyridin-3-ylmethyl]-2-(3-fluoro-4-methylsulfonamido-phenyl)-propionamide

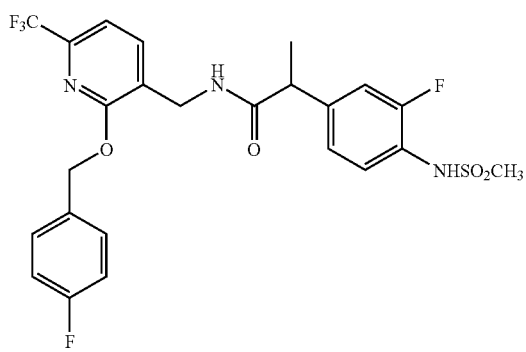

$^1$H NMR (300 MHz, CDCl$_3$) δ 7.59 (d, 1H, J=7.3 Hz), 7.48 (dd, 1H, J=8.3, 8.3 Hz) 7.41 (m, 2H), 7.23 (d, 1H, J=7.5 Hz), 7.06 (m, 3H), 6.99 (d, 1H, J=8.0 Hz), 6.51 (bs, 1H), 5.93 (bt, 1H), 5.37 (m, 2H), 4.38 (m, 2H), 3.45 (q, 1H, J=7.1 Hz), 3.02 (s, 3H), 1.44 (d, 3H, J=7.1 Hz); IR (neat) 2925, 1654, 1603, 1512, 1423, 1337, 1268, 1225, 1158, 975, 931, 759 cm$^{-1}$; MS (FAB) m/z 544 (M+H)

Example 176

2-(3-fluoro-4-methylsulfonamido-phenyl)-N-[2-(4-pyridin-4-yl-piperazin-1-yl)-6-trifluoromethyl-pyridin-3-ylmethyl]-propionamide

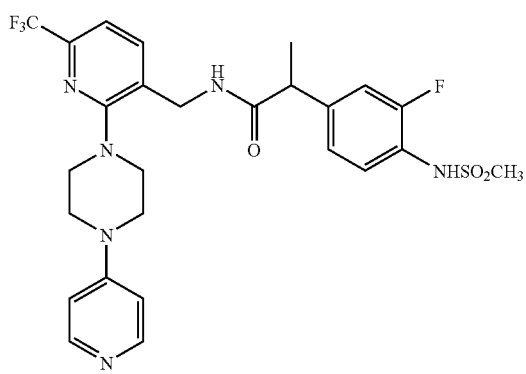

$^1$H NMR (300 MHz, CDCl$_3$) δ 8.28 (d, 2H, J=6.4 Hz), 7.55 (d, 1H, J=7.9 Hz), 7.50 (dd, 1H, J=8.2, 8.2 Hz), 7.29 (d, 1H, J=7.9 Hz), 7.14 (dd, 1H, J=11.4, 2.0 Hz), 7.09 (d, 1H, J=8.3 Hz), 6.69 (d, 2H, J=6.6 Hz), 6.26 (bt, 1H), 4.52 (d, 2H, J=5.7 Hz), 3.60 (q, 1H, J=7.0 Hz), 3.43-3.38 (m, 4H), 3.29-3.25 (m, 4H), 3.02 (s, 3H), 1.54 (d, 3H, J=7.1 Hz); IR (neat) 2848, 1650, 1597, 1512, 1454, 1416, 1333, 1238, 1152, 994, 966, 808, 735 cm$^{-1}$; MS (FAB) m/z 581 (M+H)

Example 177

2-(3-fluoro-4-methylsulfonamido-phenyl)-N-[2-(pyridin-4-ylmethoxy)-6-trifluoromethyl-pyridin-3-ylmethyl]-propionamide

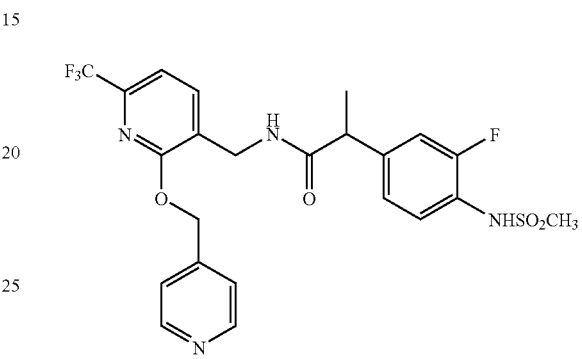

$^1$H NMR (300 MHz, CDCl$_3$) δ 8.49 (d, 2H, J=6.2 Hz), 7.61 (d, 1H, J=7.4 Hz), 7.49 (d, 2H, J=6.2 Hz), 7.40 (dd, 1H, J=8.3, 8.3 Hz), 7.32 (d, 1H, J=7.4 Hz), 7.19 (dd, 1H, J=11.5, 2.0 Hz), 7.14 (d, 1H, J=8.4 Hz), 5.49 (s, 2H), 4.35 (m, 2H), 3.72 (q, 1H, J=6.9 Hz), 2.96 (s, 3H), 1.45 (d, 3H, J=7.0 Hz); IR (neat) 3735, 3264, 1640, 1514, 1462, 1419, 1335, 1270 1154, 970, 827 cm$^{-1}$; MS (FAB) m/z 527 (M+H)

Example 178

2-(3-fluoro-4-methylsulfonamido-phenyl)-N-(2-phenethyloxy-6-trifluoromethyl-pyridin-3-ylmethyl)-propionamide

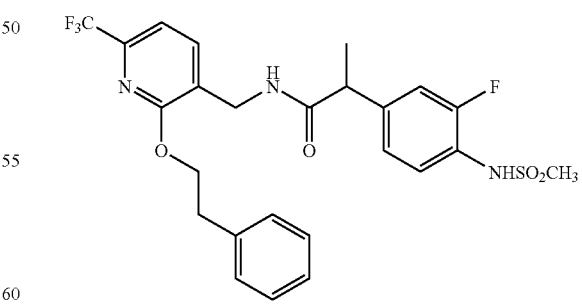

$^1$H NMR (300 MHz, CDCl$_3$) δ 7.60 (d, 1H, J=7.4 Hz), 7.46 (dd, 1H, J=8.3, 8.3 Hz), 7.33 (m, 5H), 7.19 (d, 1H, J=7.3 Hz), 6.97 (dd, 1H, J=11.3, 1.8 Hz), 6.89 (d, 1H, J=8.9 Hz), 6.43 (bs, 1H), 5.70 (bt, 1H), 4.66 (m, 1H), 4.50 (m, 1H), 4.28 (d, 2H, J=6.2 Hz), 3.14-3.05 (m, 3H), 2.99 (s, 3H), 1.36 (d, 3H,

J=7.1 Hz); IR (neat) 3296, 2925, 1659, 1602, 1511, 1424, 1337, 1269, 1158, 973, 755, 701 cm$^{-1}$; MS (FAB) m/z 539 (M+H)

Example 179

2-(3-fluoro-4-methylsulfonamido-phenyl)-N-{2-[4-(4-fluoro-phenyl)-piperazin-1-yl]-6-trifluoromethyl-pyridin-3-ylmethyl}-propionamide

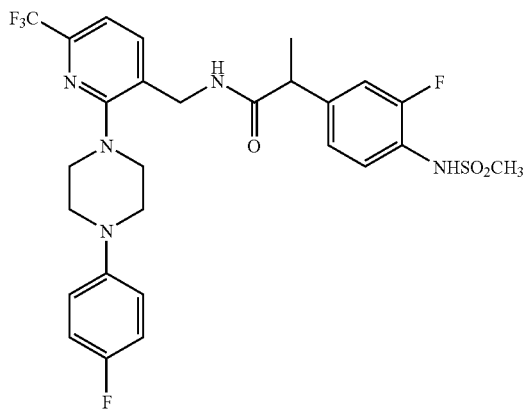

$^1$H NMR (300 MHz, CDCl$_3$) δ 7.53 (d, 1H, J=7.5 Hz), 7.49 (dd, 1H, J=7.9, 7.9 Hz), 7.27 (d, 1H, J=7.5 Hz), 7.14 (d, 1H, J=11.0 Hz), 7.08 (d, 1H, J=8.4 Hz), 6.99 (m, 2H), 6.90 (m, 2H), 6.58 (bs, 1H), 6.17 (bt, 1H), 4.52 (d, 2H, J=5.7 H), 3.58 (q, 1H, J=6.8 Hz), 3.29-3.25 (m, 4H), 3.22-3.18 (m, 4H), 3.01 (s, 3H), 1.53 (d, 3H, J=7.1 Hz); IR (neat) 3296, 2925, 2851, 1658, 1591, 1510, 1418, 1335, 1232, 1156, 968, 828, 758 cm$^{-1}$; MS (FAB) m/z 598 (M+H)

Example 180

N-[6-(chloro-difluoro-methyl)-2-hexyloxy-pyridin-3-ylmethyl]-2-(3-fluoro-4-methylsulfonamido-phenyl)-propionamide

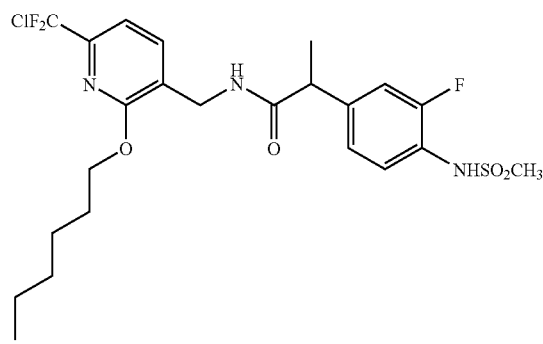

$^1$H NMR (400 MHz, CDCl$_3$) δ 7.47-7.58 (m, 2H), 7.03-7.17 (m, 3H), 6.50 (bs, 1H), 5.98 (bt, 1H), 4.25-4.43 (m, 4H), 3.51 (q, 1H, J=6.8 Hz), 3.03 (s, 3H), 1.67-1.78 (m, 2H), 1.49 (d, 3H, J=6.8 Hz), 1.27-1.46 (m, 6H), 0.87-0.94 (m, 3H); IR (KBr) 3291, 2930, 1654, 1512, 1424, 1337, 1267, 1158, 1113, 974, 880 cm$^{-1}$; MS (FAB) m/z 536 (M+H)

Example 181

N-[6-(chloro-difluoro-methyl)-2-(pyridin-3-yl-methoxy)-pyridin-3-ylmethyl]-2-(3-fluoro-4-methyl-sulfonamido-phenyl)-propionamide

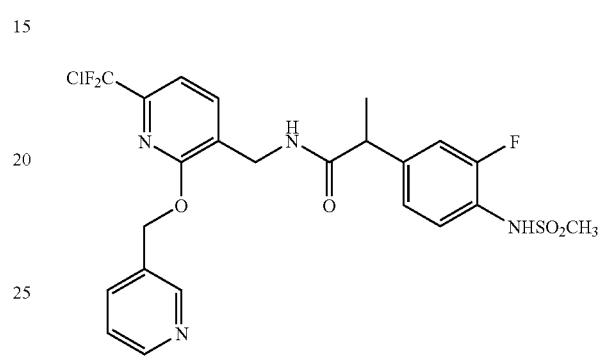

$^1$H NMR (400 MHz, CDCl$_3$) δ 8.56-8.61 (m, 2H), 7.77 (m, 1H), 7.62 (d, 1H, J=7.6 Hz), 7.48 (dd, 1H, J=8.0, 8.0 Hz), 7.31 (m, 1), 7.21 (d, 1H, J=7.6 Hz), 6.92-7.09 (m, 2H), 5.88 (bt, 1H), 5.37-5.47 (m, 2H), 4.30-4.43 (m, 2H), 3.49 (q, 1H J=6.8 Hz), 3.03 (s, 3H), 1.28 (d, 3H, J=6.8 Hz); IR (KBr) 2964, 1656, 1597, 1511, 1414, 1332, 1262, 1155, 1094, 1020, 800, 732 cm$^{-1}$; MS (FAB) m/z 543 (M+H)

Example 182

N-[6-(chloro-difluoro-methyl)-2-(pyridin-2-yl-methoxy)-pyridin-3-ylmethyl]-2-(3-fluoro-4-methyl-sulfonamido-phenyl)-propionamide

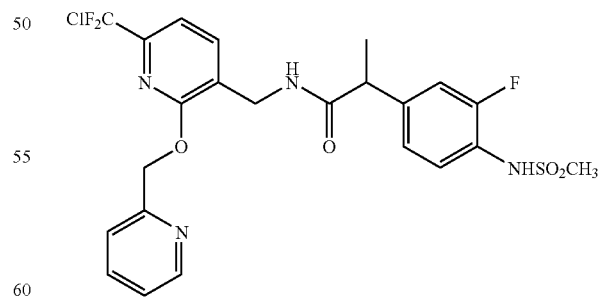

$^1$H NMR (400 MHz, CDCl$_3$) δ 8.62 (d, 1H, J=4.4 Hz), 7.75 (dd, 1H, J=7.6, 7.6 Hz), 7.67 (d, 1H, J=7.2 Hz), 7.40-7.51 (m, 2H), 7.19-7.27 (m, 2H), 7.13 (dd, 1H, J=11.2, 1.6 Hz), 7.04 (d, 1H, J=8.4 Hz), 6.50 (bs, 1H), 5.48-5.63 (m, 2H), 4.40-4.61 (m, 2H), 3.60 (q, 1H, J=7.2 Hz), 3.05 (s, 3H), 1.49 (d, 3H,

J=7.2 Hz); IR (KBr) 3287, 1659, 1596, 1511, 1454, 1415, 1334, 1270, 1157, 1117, 971, 882, 828, 758 cm⁻¹; MS (FAB) m/z 543 (M+H)

Example 183

N-(2-dibutylamino-6-trifluoromethyl-pyridin-3-ylmethyl)-2-(3-fluoro-4-methylsulfonamido-phenyl)-propionamide

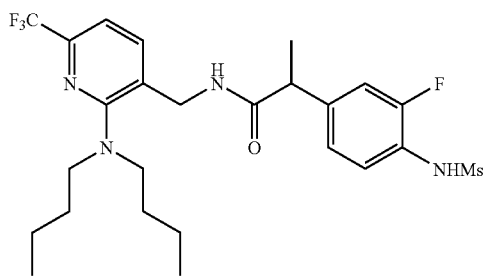

¹H NMR (300 MHz, CDCl₃) δ 7.51-7.43 (m, 2H), 7.19-7.07 (m, 3H), 6.96 (bs, 1H), 6.40 (bt, 1H), 4.50 (m, 2H), 3.56 (q, 1H, J=7.1 Hz), 3.13 (m, 4H), 3.02 (s, 3H), 1.52 (d, 3H, J=7.1 Hz) 1.50 (m, 4H), 1.31-1.10 (m, 4H), 0.87 (t, 6H, J=7.1 Hz); IR (KBr) 3294, 2960, 1655, 1593, 1513, 1462, 1419 cm⁻¹; MS (FAB) m/z 547 (M+H)

Example 184

2-(3-fluoro-4-methylsulfonamido-phenyl)-N-[6'-(4-fluoro-phenyl)-4-methyl-3,4,5,6-tetrahydro-2H-[1,2']bipyridinyl-3'-ylmethyl]-propionamide

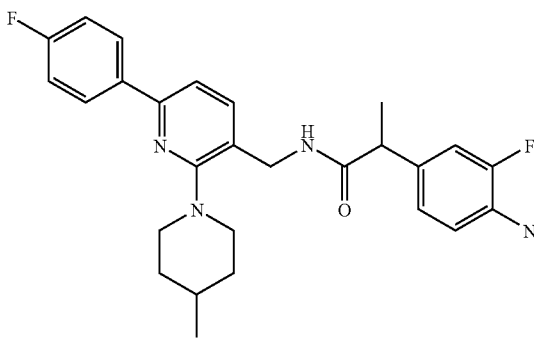

¹H NMR (300 MHz, CDCl₃) δ 7.49-7.54 (m, 2H), 7.51 (dd, 1H, J=8.1, 8.1 Hz), 7.43 (d, 1H, 7.8 Hz), 7.29 (d, 1H, J=7.8 Hz), 7.09-7.17 (m, 4H), 6.64 (bt, 1H), 4.48 (d, 2H, J=5.7 Hz), 3.52 (q, 1H, J=6.9 Hz), 3.30 (m, 2H), 3.03 (s, 3H), 2.88 (m, 2H), 1.76 (m, 2H), 1.51 (d, 3H, J=6.9 Hz), 1.24 (m, 3H), 0.99 (d, 3H, J=6.6 Hz); IR (KBr) 3292, 2962, 1653, 1512, 1457, 1423, 1335, 1267, 1158, 1113, 977, 889, 824 cm⁻¹; MS (FAB) m/z 508 (M+H)

Example 185

2-(3-fluoro-4-methylsulfonamido-phenyl)-N-[6'-(4-fluoro-phenyl)-4-methyl-3,4,5,6-tetrahydro-2H-[1,2']bipyridinyl-3'-ylmethyl]-propionamide

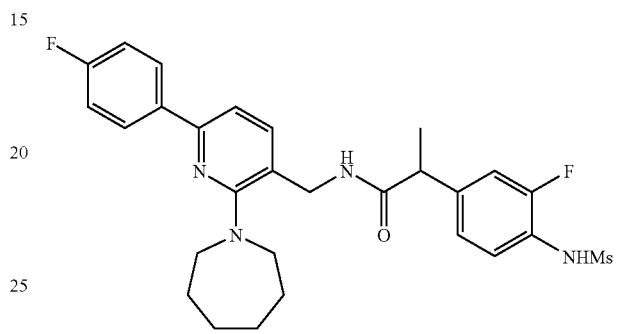

¹H NMR (300 MHz, CDCl₃) δ 7.95-8.00 (m, 2H), 7.52 (dd, 1H, J=8.1, 8.1 Hz), 7.37 (d, 1H J=7.5 Hz), 7.08-7.18 (m, 5H), 6.43 (bs, 1H), 6.07 (bt, 1H), 4.44 (d, 2H, J=5.7 Hz), 3.54 (q, 1H, J=7.2 Hz), 3.40 (m, 2H), 3.00 (s, 3H), 1.78 (m, 4H), 1.61 (m, 4H), 1.52 (d, 3H, J=7.2 Hz); IR (KBr) 3287, 2927, 1649, 1509, 1448, 1333, 1228, 1157, 972, 909, 813, 732 cm⁻¹; MS (FAB) m/z 508 (M+H)

Example 186

N-[6-(chloro-difluoro-methyl)-2-dipropylamino-pyridin-3-ylmethyl]-2-(3-fluoro-4-methylsulfonamido-phenyl)-propionamide

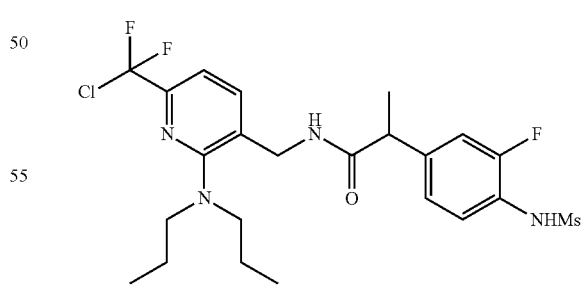

¹H NMR (300 MHz, CDCl₃) δ 7.53 (dd, 1H, J=8.1, 8.1 Hz), 7.43 (d, 1H, J=7.8 Hz), 7.16 (dd, 1H, J=2.1, 10.8 Hz), 7.08-7.12 (m, 2H), 6.46 (bs, 1H), 6.15 (bt, 1H), 4.44 (d, 2H, J=5.7 Hz), 3.53 (q, 1H, J=6.9 Hz), 3.10 (m, 4H), 3.02 (s, 3H), 1.44-1.54 (m, 4H), 0.83 (t, 6H, J=7.2 Hz); IR (KBr) 3288, 2965, 1652, 1591, 1511, 1456, 1419, 1334, 1158, 1110, 974, 938, 820, 734 cm$^{-1}$; MS (FAB) m/z 535 (M+H)

Example 187

N-[6'-(chloro-difluoro-methyl)-3,5-dimethyl-3,4,5,6-tetrahydro-2H-[1,2']bipyridinyl-3'-ylmethyl]-2-(3-fluoro-4-methylsulfonamido-phenyl)-propionamide

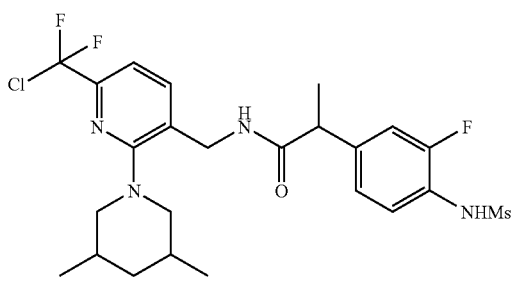

$^1$H NMR (300 MHz, CDCl$_3$) δ 7.45-7.54 (m, 2H), 7.06-7.15 (m, 3H), 6.62 (bs, 1H), 6.31 (bt, 1H), 4.46 (d, 2H, J=5.7 Hz), 3.54 (q, 1H, J=7.2 Hz), 3.25 (m, 2H), 3.02 (s, 3H), 2.36 (m, 2H), 2.03 (m, 1H), 1.53-1.65 (m, 3H), 1.52 (d, 3H, J=7.2 Hz) 0.92 (d, 3H, J=6.6 Hz), 0.88 (d, 3H, J=6.6 Hz); IR (neat) 2926, 1653, 1591, 1511, 145, 1334, 1253, 1017, 967, 733 cm$^{-1}$; MS (FAB) m/z 548 (M+H)

Example 188

N-[2-(1,3-dihydro-isoindol-2-yl)-6-trifluoromethyl-pyridin-3-ylmethyl]-2-(3-fluoro-4-methylsulfonamido-phenyl)-propionamide

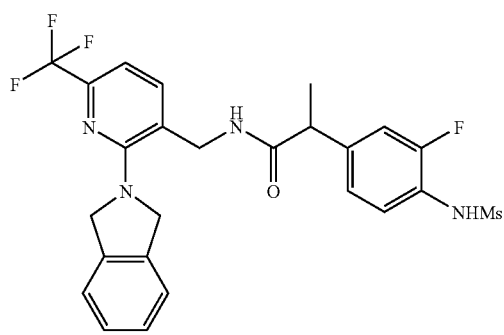

$^1$H NMR (300 MHz, CDCl$_3$) δ 7.46 (d, 1H, J=7.5 Hz), 7.25-7.37 (m, 5H), 7.01-7.10 (m, 3H), 6.24 (bs, 1H), 5.75 (bt, 1H), 4.84 (s, 4H), 4.59 (d, 2H, J=5.7 Hz), 3.52 (q, 1H, J=7.2

Hz), 2.94 (s, 3H), 1.49 (d, 3H, J=7.2 Hz); IR (KBr) 3298, 2922, 1650, 1512, 1457, 1425, 1334, 1155, 747 cm$^{-1}$; MS (FAB) m/z 537 (M+H)

Example 189

3'-{[2-(3-fluoro-4-methylsulfonamido-phenyl)-propionylamino]-methyl}-4-phenyl-6'-trifluoromethyl-3,4,5,6-tetrahydro-2H-[1,2']bipyridinyl-4-carbonic acid ethyl ester

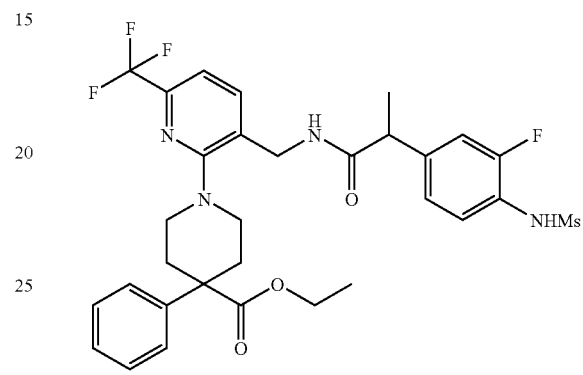

$^1$H NMR (300 MHz, CDCl$_3$) δ 7.28-7.50 (m, 7H), 7.21 (d, 1H, 7.8 Hz), 7.12 (dd, 1H, J=7.8, 2.1 Hz), 7.04 (d, 1H, J=8.1 Hz), 6.44 (bs, 1H), 6.13 (bt, 1H), 4.47 (d, 2H, J=5.7 Hz), 4.14 (q, 2H, J=7.2 Hz), 3.52 (q, 1H, J=6.9 Hz), 3.37 (m, 2H), 2.98-3.05 (m, 5H), 2.66 (m, 2H), 1.99 (m, 2H), 1.52 (d, 3H, J=7.2 Hz), 1.18 (t, 3H, 6.9 Hz); IR (neat) 2927, 1721, 1654, 1512, 1455, 1336, 1159, 968 cm$^{-1}$; MS (FAB) m/z 651 (M+H)

Example 190

N-(4,6'-bis-trifluoromethyl-3,4,5,6-tetrahydro-2H-[1,2']bipyridinyl-3'-ylmethyl)-2-(3-fluoro-4-methylsulfonamido-phenyl)-propionamide

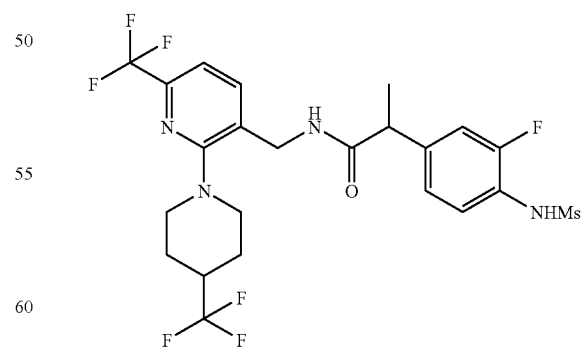

$^1$H NMR (300 MHz, CDCl$_3$) δ 7.47-7.51 (m, 2H), 7.25 (d, 1H, J=7.8 Hz), 7.08-7.15 (m, 2H), 6.34 (bs 1H), 6.04 (bt, 1H), 4.47 (d, 2H, J=5.7 Hz), 3.61 (q, 1H, J=6.9 Hz), 3.43 (m, 2H), 3.01 (s, 3H), 2.84 (t, 2H, J=11.1 Hz), 1.95 (m, 2H), 1.66 (m,

Example 195

N-(4,6'-bis-trifluoromethyl-3,4,5,6-tetrahydro-2H-[1,2']bipyridinyl-3'-ylmethyl)-2-(4-methylsulfonamido-3-methyl-phenyl)-propionamide

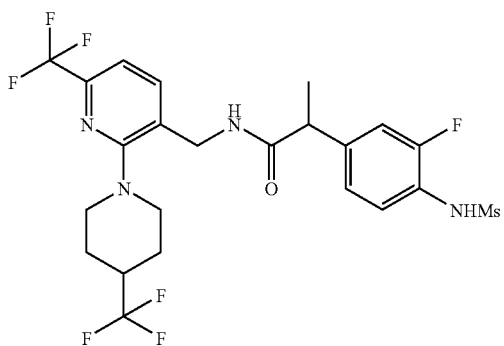

$^1$H NMR (300 MHz, CDCl$_3$) δ 7.48 (d, 1H, J=7.8 Hz), 7.38 (d, 1H, J=8.1 Hz), 7.23 (d, 1H, J=7.8 Hz), 7.11-7.15 (m, 2H), 6.60 (bs, 1H), 6.12 (bt, 1H), 4.45 (d, 2H, J=5.7 Hz), 3.58 (q, 1H, J=6.9 Hz), 3.40 (m, 2H), 3.01 (s, 3H), 2.80 (m, 2H), 2.30 (s, 3H), 2.19 (m 1H), 1.94 (m, 2H), 1.62 (m, 2H), 1.52 (d, 3H, J=6.9 Hz); IR (KBr) 2929, 1655, 1504, 1420, 1335, 1254, 1147, 1083, 959 cm$^{-1}$; MS (FAB) m/z 567 (M+H)

Example 196

2-(4-methylsulfonamido-3-methyl-phenyl)-N-(4-methyl-6'-trifluoromethyl-3,4,5,6-tetrahydro-2H-[1,2']bipyridinyl-3'-ylmethyl)-propionamide

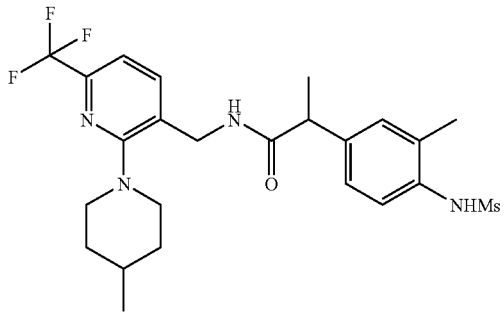

$^1$H NMR (300 MHz, CDCl$_3$) δ 7.46 (d, 1H, J=7.5 Hz), 7.39 (d, 1H, J=7.8 Hz), 7.18 (d, 1H, J=7.8 Hz), 7.11-7.14 (m, 2H), 6.37 (bs, 1H), 6.21 (bt, 1H), 4.45 (d, 2H, J=5.7 Hz), 3.56 (q, 1H, J=6.9 Hz), 3.29 (m, 2H), 3.01 (s, 3H), 2.79 (m, 2H), 2.29 (s, 3H), 2.19 (m 1H), 2.05 (m, 2H), 1.69 (m, 2H), 1.52 (d, 3H, J=6.9 Hz); 1.53 (d, 3H, J=6.9 Hz); IR (KBr) 2934, 1655, 1591, 1512, 1420, 1337, 1255, 1146, 1083, 960, 908 cm$^{-1}$; MS (FAB) m/z 571 (M+H)

Example 197

N-(4-ethyl-6'-trifluoromethyl-3,4,5,6-tetrahydro-2H-[1,2']bipyridinyl-3'-ylmethyl)-2-(3-fluoro-4-methyl-sulfonamido-phenyl)-propionamide

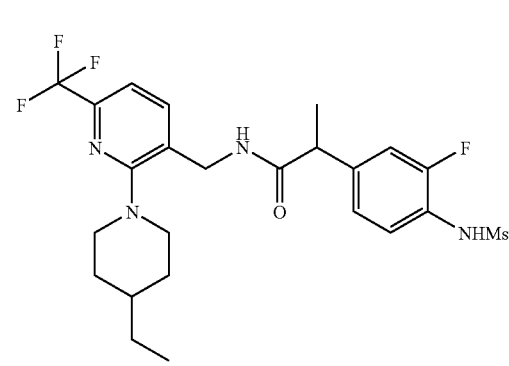

$^1$H NMR (300 MHz, CD$_3$OD) δ 7.47-7.52 (m, 2H), 7.19 (d, 1H, J=7.8 Hz), 7.06-7.14 (m, 2H), 6.69 (bs, 1H), 6.37 (bt, 1H), 4.47 (d, 2H, J=5.7 Hz), 3.56 (q, 1H, J=6.9 Hz), 3.33 (m, 2H), 3.02 (s, 3H), 2.80 (m, 2H), 1.76 (m, 2H), 1.52 (d, 3H, J=6.9 Hz), 1.21-1.32 (m, 5H), 0.91 (t, 3H, J=7.2 Hz); IR (KBr) 3288, 2929, 1655, 1591, 1512, 1419, 1336, 1275, 1158, 956, 910, 733 cm$^{-1}$; MS (FAB) m/z 531 (M+H)

Example 198

2-(3-fluoro-4-methylsulfonamido-phenyl)-N-(2-phenoxy-6-trifluoromethyl-pyridin-3-ylmethyl)-propionamide

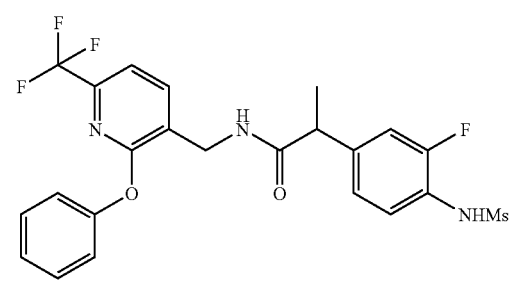

$^1$H NMR (300 MHz, CD$_3$OD) δ 7.75 (d, 1H, J=7.2 Hz), 7.00-7.49 (m, 9H, J=7.8 Hz), 6.26 (bt, 1H), 4.51 (d, 2H, J=5.7 Hz), 3.56 (q, 1H, J=6.9 Hz), 3.01 (s, 3H), 1.48 (d, 3H, J=6.9

Hz); IR (KBr) 3291, 2927, 1659, 1589, 1513, 1406, 1335, 1260, 1156, 972, 940, 835, 757 cm$^{-1}$; MS (FAB) m/z 512 (M+H)

Example 199

2-(3-fluoro-4-methylsulfonamido-phenyl)-N-(4-methoxymethyl-6'-trifluoromethyl-3,4,5,6-tetrahydro-2H-[1,2']bipyridinyl-3'-ylmethyl)-propionamide

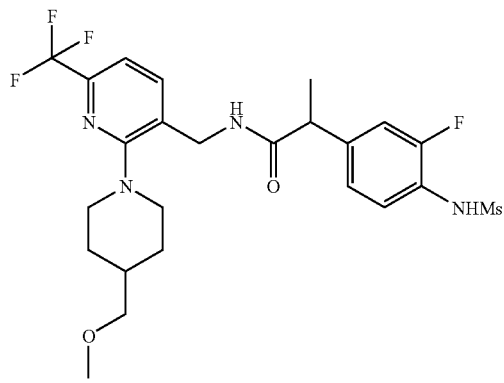

$^1$H NMR (300 MHz, CDCl$_3$) δ 7.46-7.52 (m, 2H), 7.20 (d, 1H, J=7.8 Hz), 7.07-7.15 (m, 2H), 6.82 (bs, 1H), 6.37 (bt, 1H), 4.46 (d, 2H, J=5.7 Hz), 3.58 (q, 1H, J=6.9 Hz), 3.26-3.38 (m, 5H), 3.02 (s, 3H), 2.82 (m, 2H), 1.79 (m, 3H), 1.51 (d, 3H, J=6.9 Hz), 1.25-1.30 (m, 4H); IR (KBr) 3289, 2927, 1657, 1592, 1512, 1455, 1420, 1375, 1335, 1275, 1157, 971, 832, 753 cm$^{-1}$; MS (FAB) m/z 547 (M+H)

Example 200

2-(3-fluoro-4-methylsulfonamido-phenyl)-N-[4-(4-fluoro-phenyl)-6'-trifluoromethyl-3,4,5,6-tetrahydro-2H-[1,2']bipyridinyl-3'-ylmethyl]-propionamide

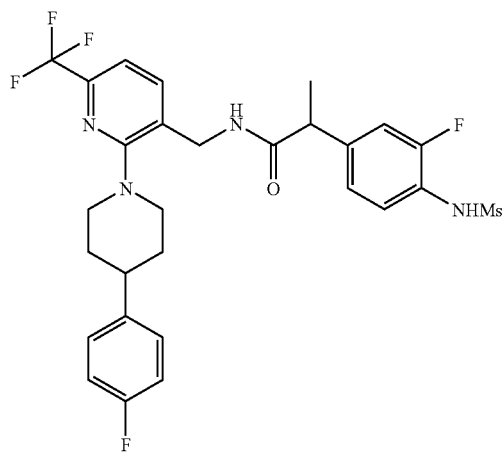

$^1$H NMR (300 MHz, CDCl$_3$) δ 7.46-7.51 (m, 2H), 6.97-7.25 (m, 7H), 6.72 (bs 1H), 6.24 (bt, 1H), 4.50 (d, 2H, J=5.7 Hz), 3.59 (q, 1H, J=6.9 Hz), 3.45 (m, 2H), 3.00 (s, 3H), 2.93 (m, 2H), 1.92 (m, 2H), 1.76 (m, 3H), 1.51 (d, 3H, J=6.9 Hz); IR (KBr) 2927, 1653, 1511, 1455, 1420, 1336, 1224, 1159, 959, 833, 732 cm$^{-1}$; MS (FAB) m/z 597 (M+H)

Example 201

2-(3-fluoro-4-methylsulfonamido-phenyl)-N-{2-[4-(2-fluoro-phenyl)-piperazin-1-yl]-6-trifluoromethyl-pyridin-3-ylmethyl}-propionamide

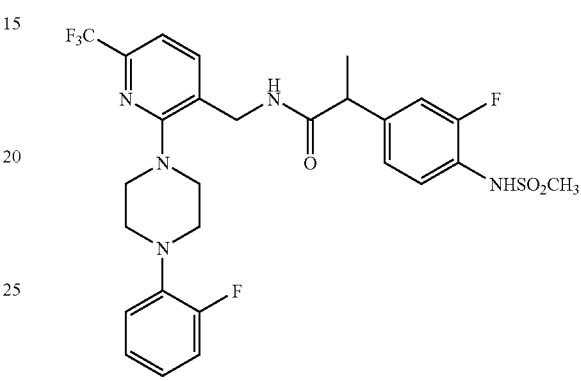

$^1$H NMR (300 MHz, CDCl$_3$) δ 7.53 (d, 1H, J=8.1 Hz), 7.52 (dd, 1H, J=8.3, 8.3 Hz), 7.27 (d, 1H, J=8.0 Hz), 7.11 (m, 4H), 6.98 (m, 2H), 6.40 (bs, 1H), 6.16 (bt, 1H), 4.53 (d, 2H, J=4.6 Hz), 3.58 (q, 1H, J=7.3 Hz), 3.32-3.28 (m, 4H), 3.18-3.15 (m, 4H), 3.01 (s, 3H), 1.54 (d, 3H, J=7.0 Hz); IR (neat) 2391, 2846, 1707, 1657, 1591, 1504, 1453, 1417, 1336, 1235, 1157, 968, 835, 757 cm$^{-1}$; MS (FAB) m/z 598 (M+H)

Example 202

2-(3-fluoro-4-methylsulfonamido-phenyl)-N-[2-(pyridin-2-ylmethoxy)-6-trifluoromethyl-pyridin-3-ylmethyl]-propionamide

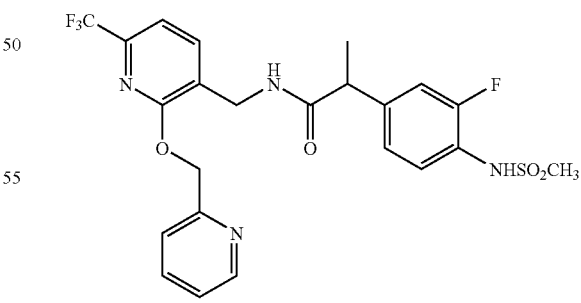

$^1$H NMR (300 MHz, CDCl$_3$) δ 8.61 (d, 1H, J=4.7 Hz), 7.74 (dd, 1H, J=7.6, 1.7 Hz), 7.67 (d, 1H, J=7.3 Hz), 7.42 (dd, 1H, J=8.2, 8.2 Hz), 7.43 (d, 1H, J=7.7 Hz), 7.33 (m, 1H), 7.24 (d, 1H, J=7.5 Hz), 7.09 (dd, 1H, J=11.4, 2.0 Hz), 7.01 (d, 1H, J=8.2 Hz), 6.54 (bs, 1H), 5.51 (m, 2H), 4.45 (d, 2H, J=5.7 Hz), 3.58 (q, 1H, J=7.0 Hz), 3.01 (s, 3H), 1.46 (d, 3H, J=7.0 Hz);

IR (neat) 3271, 1656, 1598, 1512, 1417, 1335, 1273, 1155, 973, 935, 835, 761 cm$^{-1}$; MS (FAB) m/z 527 (M+H)

Example 203

2-(4-methylsulfonamido-3-methyl-phenyl)-N-[2-(4-phenyl-piperazin-1-yl)-6-trifluoromethyl-pyridin-3-ylmethyl]-propionamide

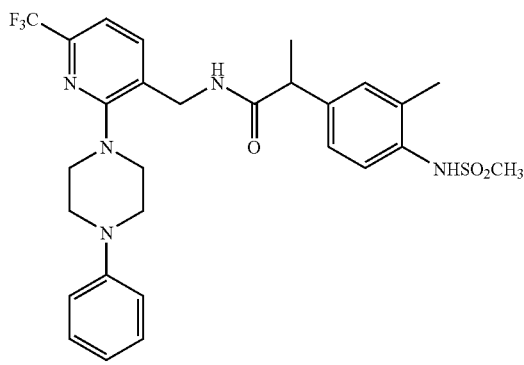

$^1$H NMR (300 MHz, CDCl$_3$) δ 7.53 (d, 1H, J=7.7 Hz), 7.32 (m, 4H), 7.14 (s, 1H), 7.13 (d, 1H, J=7.0 Hz), 6.92 (m, 3H), 6.18 (bt, 1H), 5.89 (bs, 1H), 4.53 (d, 2H, J=5.7 Hz), 3.56 (q, 1H, J=7.1 Hz), 3.27-3.15 (m, 8H), 2.98 (s, 3H), 2.23 (s, 3H), 1.51 (d, 3H, J=7.1 Hz); IR (neat) 2920, 1652, 1596, 1503, 1418, 1331, 1231, 1150, 967, 761 cm$^{-1}$; MS (FAB) m/z 576 (M+H)

Example 204

N-(2-benzyloxy-6-trifluoromethyl-pyridin-3-ylmethyl)-2-(4-methylsulfonamido-3-methyl-phenyl)-propionamide

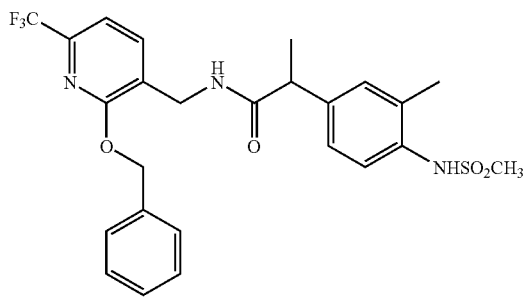

$^1$H NMR (300 MHz, CDCl$_3$) δ 7.60 (d, 1H, J=7.5 Hz), 7.39-7.33 (m, 6H), 7.22 (d, 1H, J=7.3 Hz), 7.05 (s, 1H), 7.04 (d, 1H, J=7.5 Hz), 6.10 (bs, 1H), 5.91 (bt, 1H), 5.37 (q, 2H, J=12.5 Hz), 4.37 (d, 2H, J=6.1 Hz), 3.43 (q, 1H, J=7.1 Hz), 3.00 (s, 3H), 2.24 (s, 3H), 1.43 (d, 3H, J=7.1 Hz); IR (neat)

3295, 2925, 1655, 1505, 1459, 1420, 1356, 1326, 1151, 977, 756 cm$^{-1}$; MS (FAB) m/z 522 (M+H)

Example 205

2-(3-fluoro-4-methylsulfonamido-phenyl)-N-[2-(methyl-phenyl-amino)-6-trifluoromethyl-pyridin-3-ylmethyl]-propionamide

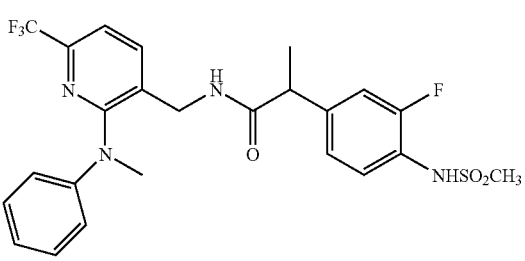

$^1$H NMR (300 MHz, CDCl$_3$) δ 7.55 (d, 1H, J=7.9 Hz), 7.53 (dd, 1H, J=8.2, 8.2 Hz) 7.29-7.23 (m, 3H), 7.10-7.01 (m, 3H), 6.83 (m, 2H), 6.48 (bs, 1H), 5.42 (bt, 1H), 3.88 (d, 2H, J=6.0 Hz), 3.38 (s, 3H), 3.37 (q, 1H, J=7.1 Hz), 3.04 (s, 3H), 1.43 (d, 3H, J=7.1 Hz); IR (neat) 2923, 1654, 1590, 1509, 1462, 1398, 1338, 1270, 1156, 973, 929, 758 cm$^{-1}$; MS (FAB) m/z 525 (M+H)

Example 206

2-(3-fluoro-4-methylsulfonamido-phenyl)-N-[6-trifluoromethyl-2-(4-trifluoromethyl-benzyloxy)-pyridin-3-ylmethyl]-propionamide

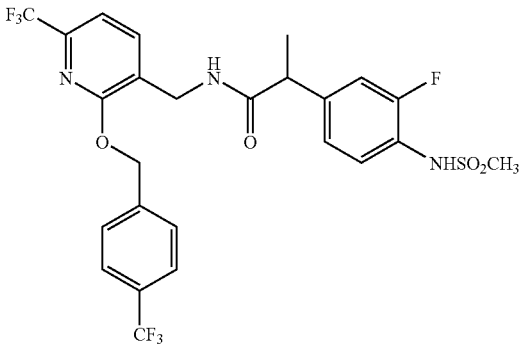

$^1$H NMR (300 MHz, CDCl$_3$) δ 7.64 (d, 1H, J=8.4 Hz), 7.61 (d, 2H, J=8.6 Hz), 7.55 (d, 2H, J=8.1 Hz), 7.49 (dd, 1H, J=8.2, 8.2 Hz), 7.25 (d, 1H, J=8.3 Hz), 7.07 (dd, 1H, J=11.2, 2.0 Hz), 7.01 (d, 1H, J=7.9 Hz), 6.43 (bs, 1H), 5.89 (bt, 1H), 5.46 (m, 2H), 4.42 (d, 2H, J=6.0 Hz), 3.48 (q, 1H, J=7.1 Hz), 3.02 (s,

3H), 1.45 (d, 3H, J=7.1 Hz); IR (neat) 3369, 1657, 1511, 1419, 1326, 1267, 1159, 1119, 1067, 975, 934, 826 cm⁻¹; MS (FAB) m/z 594 (M+H)

Example 207

N-{6-(chloro-difluoro-methyl)-2-[4-(1-vinyl-propenyl)-piperazin-1-yl]-pyridin-3-ylmethyl}-2-(3-fluoro-4-methylsulfonamido-phenyl)-propionamide

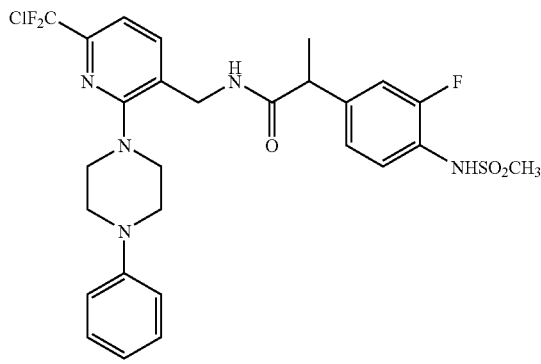

¹H NMR (300 MHz, CD₃OD) δ 8.60 (m, 1H), 7.58 (d, 1H, J=7.5 Hz), 7.25-7.47 (m, 4H), 7.00-7.25 (m, 4H), 4.35-4.57 (m, 2H), 3.73 (m, 1H, J=7.1 Hz), 3.32-3.45 (m, 8H), 2.95 (s, 3H), 1.47 (d, 3H, J=7.1 Hz); IR (KBr) 2919, 1646, 1592, 1506, 1446, 1332 cm⁻¹; MS (FAB) m/z 596 (M+H)

Example 208

N-[6-(chloro-difluoro-methyl)-2-isobutoxy-pyridin-3-ylmethyl]-2-(3-fluoro-4-methylsulfonamido-phenyl)-propionamide

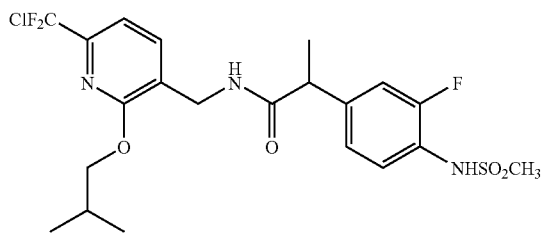

¹H NMR (300 MHz, CDCl₃) δ 7.48-7.58 (m, 2H), 7.16 (d, 1H, J=7.5 Hz), 7.11 (m, 1H), 7.06 (m, 1H), 6.46 (m, 1H), 5.95 (bt, 1H), 4.32-4.44 (m, 2H), 4.06-4.19 (m, 2H), 3.51 (q, 1H, J=7.1 Hz), 3.04 (s, 3H), 2.05 (m, 1H), 1.49 (d, 3H, J=7.1 Hz), 0.99 (d, 6H, J=6.8 Hz); IR (KBr) 3291, 2964, 1654, 1601, 1512, 1424, 1335, 1267, 1159, 1114, 1012, 971, 881, 824 cm⁻¹; MS (FAB) m/z 508 (M+H)

Example 209

N-(2-benzyloxy-4-trifluoromethyl-benzyl)-2-(3-fluoro-4-methylsulfonamido-phenyl)-propionamide

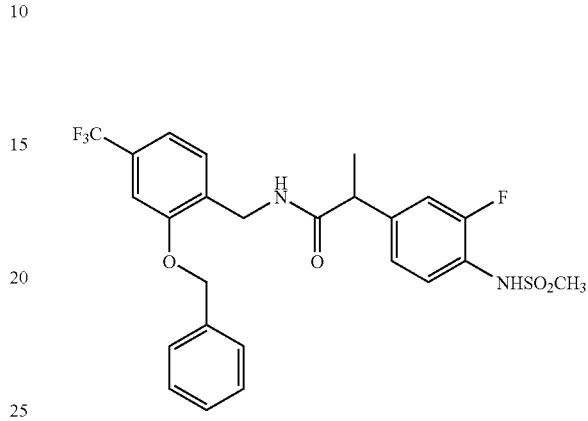

¹H NMR (300 MHz, CDCl₃) δ 7.44 (dd, 1H, J=8.4, 8.4 Hz), 7.41-7.34 (m, 5H), 7.33 (d, 1H, J=8.6 Hz), 7.19 (d, 1H, J=7.9 Hz), 7.14 (s, 1H), 7.05 (dd, 1H, J=11.3, 2.0 Hz), 6.95 (d, 1H, J=6.4 Hz), 6.41 (bs, 1H), 5.94 (bt, 1H), 5.08 (s, 2H), 4.46 (m, 2H), 3.41 (q, 1H, J=7.0 Hz), 2.99 (s, 3H), 1.43 (d, 3H, J=7.1 Hz); IR (neat) 3292, 1652, 1510, 1426, 1329, 1240, 1159, 1122, 907, 742 cm⁻¹; MS (FAB) m/z 525 (M+H)

Example 210

N-(4,4-dimethyl-6'-trifluoromethyl-3,4,5,6-tetrahydro-2H-[1,2']bipyridinyl-3'-ylmethyl)-2-(3-fluoro-4-methylsulfonamido-phenyl)-propionamide

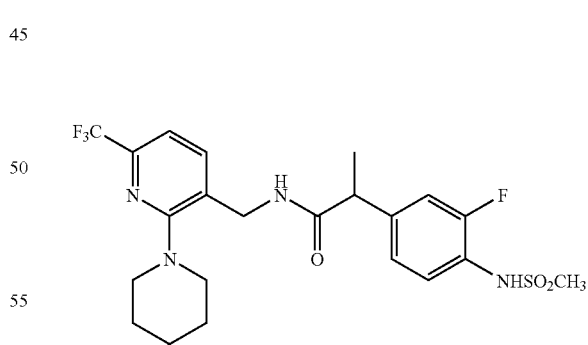

¹H NMR (300 MHz, CDCl₃) δ 7.53 (dd, 1H, J=8.4, 8.4 Hz), 7.48 (d, 1H, J=7.6 Hz), 7.21 (d, 1H, J=7.5 Hz), 7.14 (dd, 1H, J=11.4, 1.9 Hz), 7.09 (d, 1H, J=8.8 Hz), 6.47 (bs, 1H), 6.26 (bt, 1H), 4.47 (d, 2H, J=5.0 Hz), 3.56 (q, 1H, J=7.1 Hz), 3.08-3.04 (m, 4H), 3.03 (s, 3H), 1.53 (d, 3H, J=7.1 Hz), 1.48-1.43 (m, 4H), 0.99 (s, 6H); IR (neat) 3289, 2922, 1709, 1655, 1591, 1512, 1457, 1420, 1336, 1159, 957, 834, 763 cm⁻¹; MS (FAB) m/z 531 (M+H)

Example 211

2-(3-fluoro-4-methylsulfonamido-phenyl)-N-[2-(pyridin-3-ylmethoxy)-6-trifluoromethyl-pyridin-3-ylmethyl]-propionamide

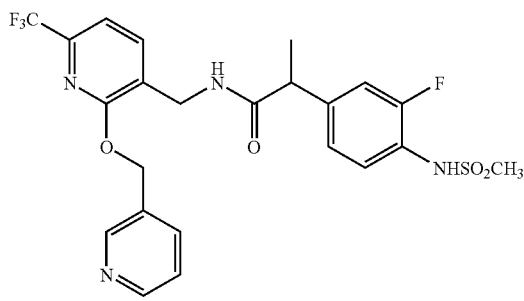

¹H NMR (300 MHz, CDCl₃) δ 8.69 (m, 2H), 7.79 (d, 1H, J=7.7 Hz), 7.64 (d, 1H, J=7.5 Hz), 7.48 (dd, 1H, J=8.1 Hz), 7.34 (m, 1H), 7.25 (d, 1H, J=7.5 Hz), 7.05 (dd, 1H, J=11.4, 1.9 Hz), 7.02 (d, 1H, J=8.4 Hz), 5.87 (bt, 1H), 5.41 (s, 2H), 4.38 (d, 2H, J=6.2 Hz), 3.49 (q, 1H, J=7.3 Hz), 3.04 (s, 3H), 1.46 (d, 3H, J=7.1 Hz); IR (neat) 3299, 1658, 1601, 1511, 1416, 1335, 1267, 1156, 974, 740 cm⁻¹; MS (FAB) m/z 527 (M+H)

Example 212

2-(3-fluoro-4-methylsulfonamido-phenyl)-N-{6-trifluoromethyl-2-[4-(3-trifluoromethyl-pyridin-2-yl)-piperazin-1-yl]-pyridin-3-ylmethyl}-propionamide

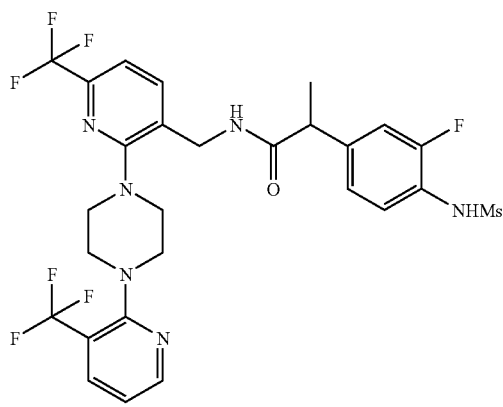

¹H NMR (300 MHz, CDCl₃) δ 8.50 (d, 1H, J=3.6 Hz), 7.91 (dd, 1H, J=7.8, 1.8 Hz), 7.54 (d, 1H, J=6.9 Hz), 7.49 (dd, 1H, J=8.1, 8.1 Hz), 7.05-7.17 (m, 4H), 6.40 (bt, 1H), 4.52 (d, 2H, J=5.7 Hz), 3.61 (q, 1H, J=6.9 Hz), 3.35 (m, 8H), 3.02 (s, 3H), 1.53 (d, 3H, J=6.9 Hz); IR (KBr) 3290, 2851, 1657, 1590,

Example 216

2-(3-fluoro-4-methylsulfonamido-phenyl)-N-[2-(4-phenyl-piperazin-1-yl)-4-trifluoromethyl-benzyl]-propionamide)

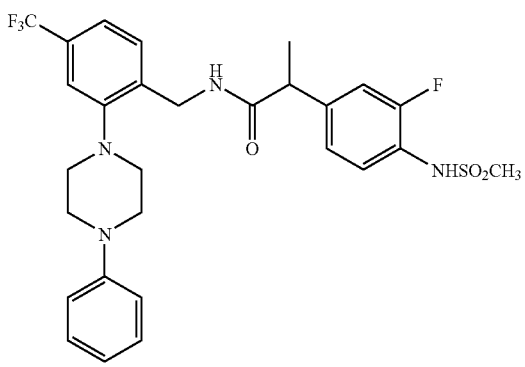

¹H NMR (300 MHz, CDCl₃) δ 7.46 (dd, 1H, J=8.4, 8.4 Hz), 7.28-7.35 (m, 5H), 7.13 (m, 1H), 7.07 (d, 1H, J=8.4 Hz), 6.89-6.99 (m, 3H), 6.32 (bt, 1H), 4.53-4.67 (m, 2H), 3.55 (q, 1H, J=7.1 Hz), 3.20-3.28 (m, 4H), 3.00-3.08 (m, 4H), 2.98 (s, 3H), 1.51 (d, 3H, J=6.9 Hz); IR (KBr) 2829, 1652, 1598, 1506, 1425, 1335, 1230, 1159, 1122, 962, 911, 733 cm⁻¹; MS (FAB) m/z 579 (M+H)

Example 217

N-(2-azocan-1-yl-4-trifluoromethyl-benzyl)-2-(3-fluoro-4-methylsulfonamido-phenyl)-propionamide

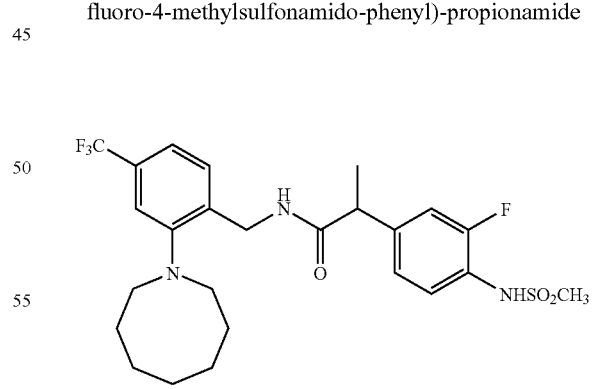

¹H NMR (300 MHz, CDCl₃) δ 7.52 (dd, 1H, J=8.3, 8.3 Hz), 7.38 (s, 1H), 7.22-7.25 (m, 2H), 7.15 (dd, 1H, J=11.2, 2.0 Hz), 7.11 (d, 1H, J=8.1 Hz), 6.51 (bs, 1H), 6.01 (bt, 1H), 4.55 (d, 2H, J=5.7 Hz), 3.55 (q, 1H, J=7.5 Hz), 3.00-3.05 (m, 7H), 1.62-1.72 (m, 10H), 1.53 (d, 3H, J=7.1 Hz); IR (KBr) 3289, 2926, 1651, 1510, 1420, 1334, 1214, 1160, 1122, 975, 908, 732 cm⁻¹; MS (FAB) m/z 530 (M+H)

Example 218

N-[2-(4,4-dimethyl-piperidin-1-yl)-4-trifluoromethyl-benzyl]-2-(3-fluoro-4-methylsulfonamido-phenyl)-propionamide

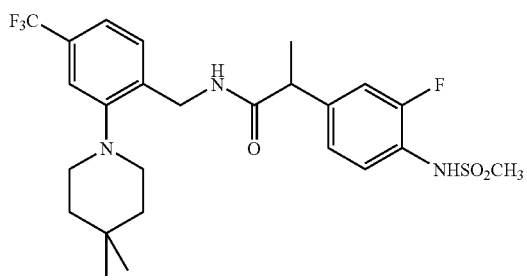

¹H NMR (300 MHz, CDCl₃) δ 7.51 (dd, 1H, J=8.3, 8.3 Hz), 7.32 (s, 1H), 7.21-7.30 (m, 2H), 7.14 (dd, 1H, J=11.2, 1.8 Hz), 7.08 (d, 1H, J=8.6 Hz), 6.52 (bs, 2H), 4.45-4.60 (m, 2H), 3.54 (q, 1H, J=7.1 Hz), 3.02 (s, 3H), 2.75-2.85 (m, 4H), 1.52 (d, 3H, J=7.1 Hz), 1.42-1.50 (m, 4H), 1.00 (s, 6H); IR (KBr) 3284, 2922, 1652, 1509, 1424, 1337, 1224, 1160, 1122, 1078, 973, 894, 827, 758 cm⁻¹; MS (FAB) m/z 530 (M+H)

Example 219

2-(3-fluoro-4-methylsulfonamido-phenyl)-N-[2-(4-p-tolyl-piperazin-1-yl)-6-trifluoromethyl-pyridin-3-ylmethyl]-propionamide

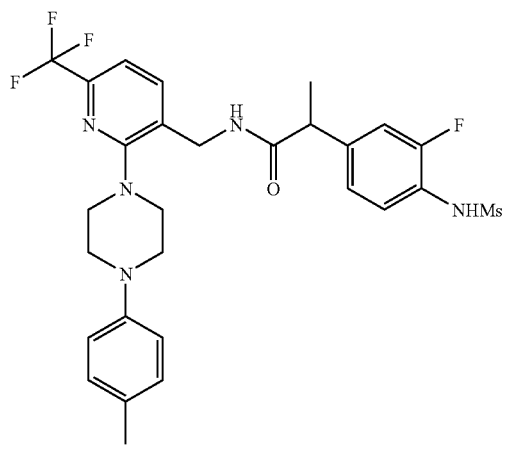

¹H NMR (300 MHz, CDCl₃) δ 7.55 (m, 1H), 7.41 (d, 1H, J=7.8 Hz), 7.24-7.32 (m, 2H), 6.96-7.12 (m, 4H), 6.78-6.81 (m, 3H), 4.40 (d, 2H, J=5.7 Hz), 3.56 (q, 1H, J=6.9 Hz), 3.12 (m, 8H), 2.86 (s, 3H), 2.18 (s, 3H), 1.40 (d, 3H, J=6.9 Hz); IR (KBr) 3292, 2923, 1659, 1591, 1514, 1418, 1374, 1335, 1235, 1155, 968, 817, 757 cm⁻¹;

MS (FAB) m/z 594 (M+H)

Example 220

2-(3-fluoro-4-methylsulfonamido-phenyl)-N-[2-(4-m-tolyl-piperazin-1-yl)-6-trifluoromethyl-pyridin-3-ylmethyl]-propionamide

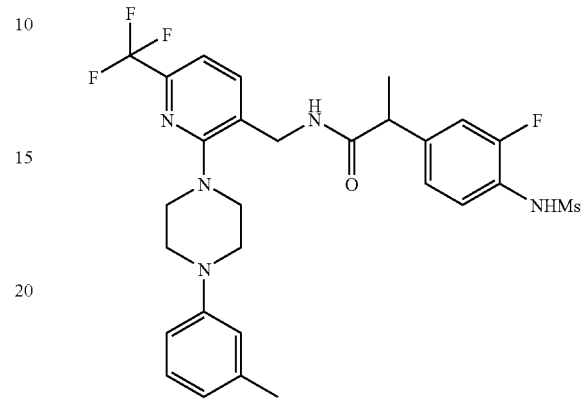

¹H NMR (300 MHz, CDCl₃) δ 7.45-7.54 (m, 2H), 7.06-7.28 (m, 4H), 6.73-6.76 (m, 3H), 6.28 (bs, 1H), 6.20 (bt, 1H), 4.52 (d, 2H, J=5.7 Hz), 3.56 (q, 1H, J=6.9 Hz), 3.24 (m, 8H), 2.98 (s, 3H), 2.35 (s, 3H), 1.52 (d, 3H, J=6.9 Hz); IR (KBr) 3292, 2923, 1659, 1591, 1514, 1418, 1374, 1335, 1235, 1155, 968, 817, 757 cm⁻¹; MS (FAB) m/z 594 (M+H)

Example 221

2-(3-fluoro-4-methylsulfonamido-phenyl)-N-{2-[4-(4-methoxy-phenyl)-piperazin-1-yl]-6-trifluoromethyl-pyridin-3-ylmethyl}-propionamide

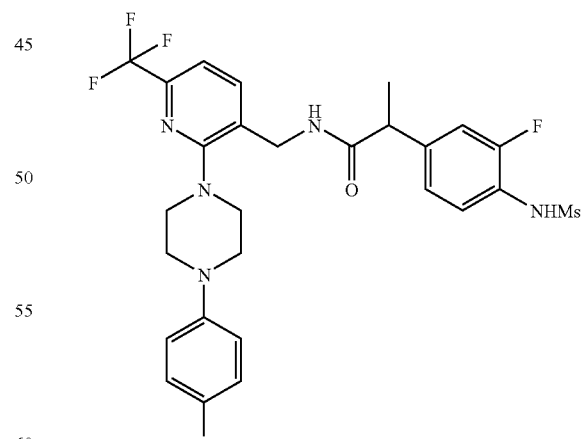

¹H NMR (300 MHz, CDCl₃) δ 7.45-7.54 (m, 2H), 7.26 (d, 1H, J=7.5 Hz), 7.06-7.14 (m, 2H), 6.85-6.93 (m, 4H), 6.41 (bs, 1H), 6.23 (bt, 1H), 4.53 (d, 2H, J=5.7 Hz), 3.79 (s, 3H), 3.56 (q, 1H, J=6.9 Hz), 3.79 (m, 4H), 3.12 (m, 4H), 2.99 (s, 3H), 1.51 (d, 3H, J=6.9 Hz); IR (KBr) 3294, 2839, 1659, 1591, 1511, 1418, 1335, 1242, 1155, 1034, 968, 828, 757 cm$^{-1}$; MS (FAB) m/z 610 (M+H)

Example 222

2-(3-fluoro-4-methylsulfonamido-phenyl)-N-{6-trifluoromethyl-2-[4-(4-trifluoromethyl-phenyl)-piperazin-1-yl]-pyridin-3-ylmethyl}propionamide

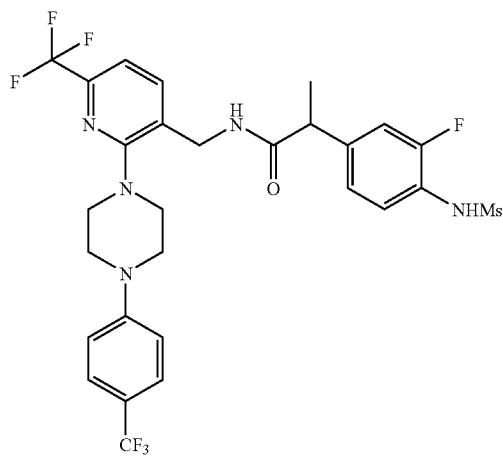

$^1$H NMR (300 MHz, CD$_3$OD) δ 7.39-7.52 (m, 5H), 7.27 (d, 1H, J=7.8 Hz), 7.11-7.20 (m, 2H), 4.46 (d, 2H, J=5.7 Hz), 3.67 (q, 1H, J=6.9 Hz), 3.33-3.38 (m, 8H), 3.00 (s, 3H), 1.53 (d, 3H, J=6.9 Hz); IR (KBr) 3295, 2922, 1647, 1616, 1514, 1416, 1331, 1234, 1156, 1115, 968, 829, 757 cm$^{-1}$; MS (FAB) m/z 648 (M+H)

Example 223

N-(2-benzyloxy-6-tert-butyl-4-hydroxymethyl-pyridin-3-ylmethyl)-2-(3-fluoro-4-methylsulfonamido-phenyl)-propionamide

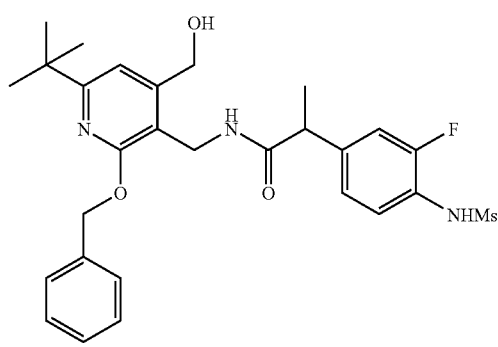

$^1$H NMR (300 MHz, CDCl$_3$) δ 7.35-7.52 (m, 6H), 6.88-6.99 (m, 3H), 6.54 (bs 1H), 6.32 (bt, 1H), 5.46 (d, 1H, J=16.3 Hz), 5.34 (d, 1H, J=16.3 Hz), 4.65 (m, 2H), 4.35 (d, 2H, J=5.7 Hz), 3.32 (q, 1H, J=6.9 Hz), 2.98 (s, 3H), 1.35 (d, 3H, J=6.9 Hz), 1.30 (s, 9H); IR (KBr) 3368, 2960, 1648, 1592, 1512, 1449, 1398, 1333, 1157, 1027, 973, 756 cm$^{-1}$; MS (FAB) m/z 544 (M+H)

Example 225

2-(3-fluoro-4-methylsulfonamido-phenyl)-N-(2-pentyloxy-6-trifluoromethyl-pyridin-3-ylmethyl)-propionamide

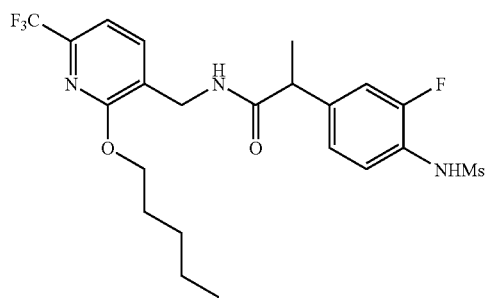

$^1$H NMR (CDCl$_3$) δ 7.57 (d, 1H, J=7.5 Hz), 7.52 (dd, 1H, J=8.2, 8.2 Hz), 7.19 (d, 1H, J=7.4 Hz), 7.12-7.05 (m, 2H), 6.45 (bs, NH), 5.98 (bt, NH), 4.38-4.29 (m, 4H), 3.51 (q, 1H, J=7.0 Hz), 3.03 (s, 3H), 1.77-1.67 (m, 2H), 1.49 (d, 3H, J=7.1 Hz), 1.43-1.35 (m, 4H), 0.93 (t, 3H, J=7.1 Hz); IR (neat) 3287, 2959, 1656, 1604, 1513, 1464, 1425, 1337, 1269, 1157, 977 cm$^{-1}$; Mass (FAB) m/z 506 [M+H]

Example 226

2,2-dimethyl-propionic acid 3'-{[2-(3-fluoro-4-methylsulfonamido-phenyl)-propionylamino]-methyl}-6'-trifluoromethyl-3,4,5,6-tetrahydro-2H-[1,2']bipyridinyl-4-yl ester

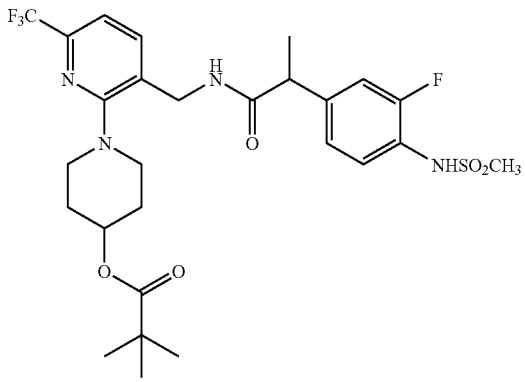

$^1$H NMR (CDCl$_3$) δ 7.54-7.47 (m, 2H), 7.22 (d, 1H, J=7.7 Hz), 7.15 (dd, 1H, J=11.0, 1.8 Hz), 7.10 (m, 1H), 6.49 (bs, NH), 6.01 (bt, NH), 4.94 (m, 1H), 4.47 (d, 2H, J=6.0 Hz), 3.58 (q, 1H, J=7.0 Hz), 3.32-3.22 (m, 2H), 3.13-3.03 (m, 2H), 3.04 (s, 3H), 2.00-1.90 (m, 2H), 1.82-1.70 (m, 2H), 1.55 (d, 3H,

J=7.1 Hz), 1.21 (s, 9H); IR (neat) 3300, 2973, 1715, 1656, 1513, 1420, 1336, 1284, 1163, 759 cm$^{-1}$; MS (FAB) m/z 603 (M+H)

Example 227

2-(3-fluoro-4-methylsulfonamido-phenyl)-N-(4-oxo-6'-trifluoromethyl-3,4,5,6-tetrahydro-2H-[1,2']bipyridinyl-3'-ylmethyl)-propionamide 3'-ylmethyl)-propionamide

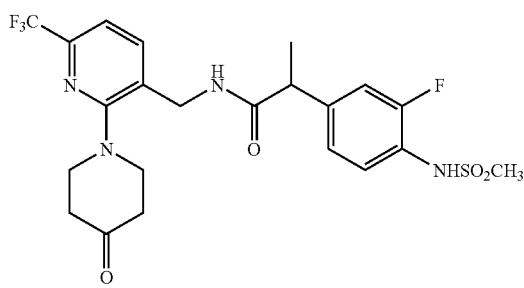

$^1$H NMR (CDCl$_3$) δ 7.55-7.49 (m, 2H), 7.29 (d, 1H, J=7.9 Hz), 7.17 (dd, 1H, J=11.2, 2.0 Hz), 7.11 (d, 1H, J=8.6 Hz), 6.70 (bs, NH), 6.04 (bt, NH), 4.54 (d, 2H, J=5.7 Hz), 3.61 (q, 1H, J=7.0 Hz), 3.49 (t, 4H, J=6.0 Hz), 3.04 (s, 3H), 2.55 (t, 4H, J=6.1 Hz), 1.55 (d, 3H, J=7.1 Hz); IR (neat) 3294, 1712, 1658, 1592, 1513, 1418, 1335, 1156, 733 cm$^{-1}$; MS (FAB) m/z 517 (M+H)

Example 228

N-(4-ethoxy-6'-trifluoromethyl-3,4,5,6-tetrahydro-2H-[1,2']bipyridinyl-3'-ylmethyl)-2-(3-fluoro-4-methylsulfonamido-phenyl)-propionamide

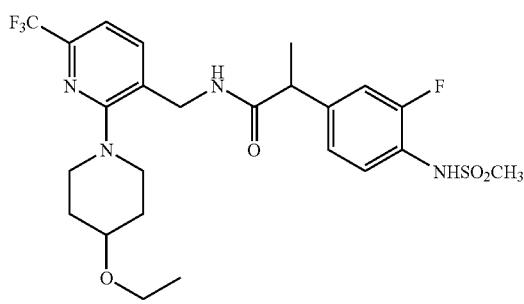

$^1$H NMR (CDCl$_3$) δ 7.55-7.48 (m, 2H), 7.23 (d, 1H, J=7.7 Hz), 7.15-7.08 (m, 2H), 6.54 (bs, NH), 6.23 (bt, NH), 4.48 (d, 2H), 3.58-3.23 (m, 6H), 3.04 (s, 3H), 2.94-2.86 (m, 2H), 2.05-1.95 (m, 2H), 1.63-1.50 (m, 2H), 1.53 (d, 3H, J=7.1 Hz), 1.24 (t, 3H, J=7.0 Hz); IR (neat) 3290, 2929, 1655, 1513, 1419, 1335, 1158 cm$^{-1}$; MS (FAB) m/z 547 (M+H)

Example 229

N-[2-(4-ethyl-piperidin-1-yl)-4-trifluoromethyl-benzyl]-2-(3-fluoro-4-methylsulfonamido-phenyl)-propionamide

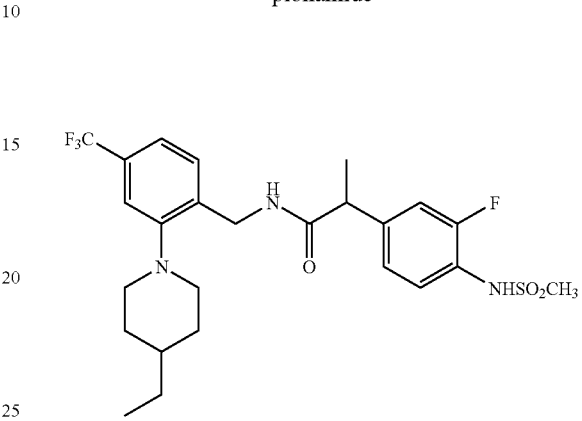

$^1$H NMR (300 MHz, CDCl$_3$) δ 7.51 (dd, 1H, J=8.3, 8.3 Hz), 7.29 (s, 1H), 7.21-7.27 (m, 2H), 7.14 (m, 1H), 7.08 (d, 1H, J=8.4 Hz), 6.48-6.59 (m, 2H), 4.46-4.60 (m, 2H), 3.53 (q, 1H, J=6.9 Hz), 2.91-3.07 (m, 5H), 2.58-2.61 (m, 2H), 1.75-1.86 (m, 2H), 1.52 (d, 3H, J=7.1 Hz), 1.10-1.37 (m, 5H), 0.93 (t, 3H, J=7.0 Hz); IR (KBr) 3285, 2930, 1652, 1509, 1423, 1336, 1160, 1122, 973, 910, 733 cm$^{-1}$; MS (FAB) m/z 530 (M+H)

Example 230

2-(3-fluoro-4-methylsulfonamido-phenyl)-N-[4-trifluoromethyl-2-(4-trifluoromethyl-piperidin-1-yl)-benzyl]-propionamide

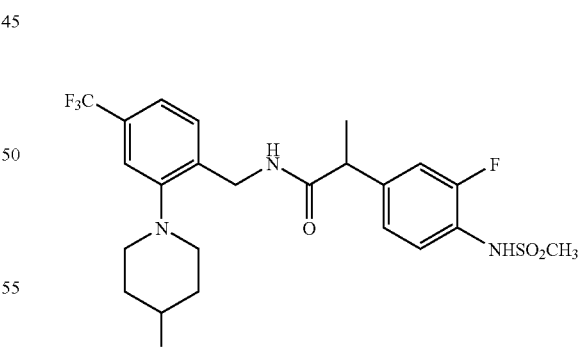

$^1$H NMR (300 MHz, CDCl$_3$) δ 7.52 (dd, 1H, J=8.2, 8.2 Hz), 7.22-7.32 (m, 3H), 7.12-7.19 (m, 1H), 7.09 (d, 1H, J=8.3 Hz), 6.52 (bs, 1H), 6.12 (bt, 1H), 4.52 (d, 2H, J=5.9 Hz), 3.56 (q, 1H, J=7.1 Hz), 3.05-3.15 (m, 2H), 3.03 (bs, 3H), 2.62-2.77 (m, 2H), 2.08-2.24 (m, 1H), 1.93-2.02 (m, 2H), 1.61-1.74 (m, 2H), 1.54 (d, 3H, J=7.1 Hz); IR (KBr) 3289, 2936, 1653, 1510, 1425, 1334, 1254, 1158, 1081, 972, 907, 825, 733 cm$^{-1}$; MS (FAB) m/z 570 (M+H)

Example 231

N-[2-(4-benzyl-piperidin-1-yl)-4-trifluoromethyl-benzyl]-2-(3-fluoro-4-methylsulfonamido-phenyl)-propionamide

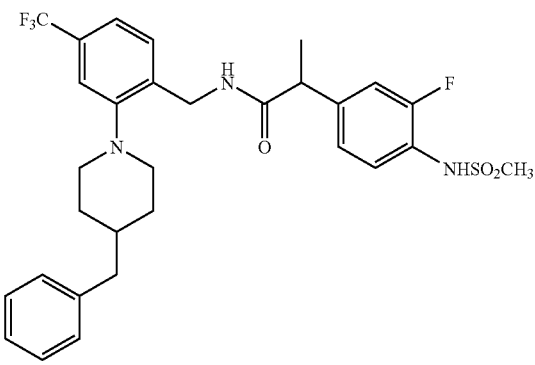

$^1$H NMR (300 MHz, CDCl$_3$) δ 7.52 (dd, 1H, J=8.2, 8.2 Hz), 7.27-7.35 (m, 3H), 7.20-7.26 (m, 2H), 7.11-7.19 (m, 4H), 7.08 (d, 1H, J=8.2 Hz), 6.38-6.46 (m, 2H), 4.51 (d, 2H, J=5.7 Hz), 3.52 (q, 1H, J=7.1 Hz), 2.85-3.05 (m, 5H), 2.55-2.70 (m, 4H), 1.60-1.80 (m, 3H), 1.52 (d, 3H, J=7.1 Hz), 1.21-1.38 (m, 2H); IR (KBr) 3292, 2923, 1652, 1509, 1424, 1336, 1160, 1121, 973, 909, 734, 701 cm$^{-1}$; MS (FAB) m/z 592 (M+H)

Example 233

N-(6-tert-butyl-2-cyclohexyloxy-pyridin-3-ylmethyl)-2-(3-fluoro-4-methylsulfonamido-phenyl)-propionamide

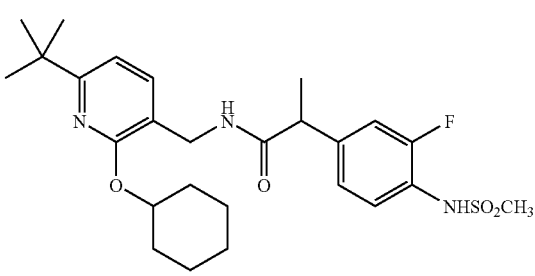

$^1$H NMR (CDCl$_3$) δ 7.50 (dd, 1H, J=8.3, 8.3 Hz), 7.36 (d, 1H, J=7.3 Hz), 7.14-7.05 (m, 2H), 6.77 (d, 1H, J=7.5 Hz), 6.70 (bs, NH), 6.14 (bt, NH), 5.10 (m, 1H), 4.39-4.23 (m, 2H), 3.49 (q, 1H, J=7.1 Hz), 3.02 (s, 3H), 1.92 (m, 2H), 1.71 (m, 2H), 1.60-1.25 (m, 6H), 1.48 (d, 1H, J=7.1 Hz), 1.28 (s, 9H); IR (neat) 3288, 2935, 2859, 1652, 1585, 1513, 1451, 1406, 1335, 1254, 1159, 733 cm$^{-1}$; MS (FAB) m/z 506 (M+H)

Example 234

N-(6-tert-butyl-2-cyclopentyloxy-pyridin-3-ylmethyl)-2-(3-fluoro-4-methylsulfonamido-phenyl)-propionamide

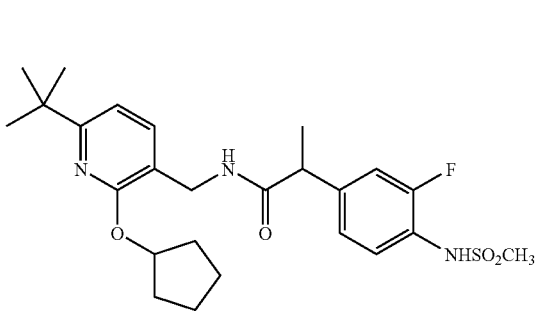

$^1$H NMR (CDCl$_3$) δ 7.50 (dd, 1H, J=8.3, 8.3 Hz), 7.35 (d, 1H, J=7.7 Hz), 7.14-7.05 (m, 2H), 6.77 (d, 1H, J=7.5 Hz), 6.59 (bs, NH), 6.03 (bt, NH), 5.44 (m, 1H), 4.36-4.21 (m, 1H), 3.48 (q, 1H, J=6.8 Hz), 3.02 (s, 3H), 1.96 (m, 2H), 1.75-1.60 (m, 6H), 1.48 (d, 3H, J=7.1 Hz), 1.29 (s, 9H); IR (neat) 3291, 2962, 1652, 1513, 1452, 1406, 1337, 1255, 1159, 982 cm$^{-1}$; MS (FAB) m/z 492 (M+H)

Example 235

N-(2-butoxy-6-tert-butyl-pyridin-3-ylmethyl)-2-(3-fluoro-4-methylsulfonamido-phenyl)-propionamide

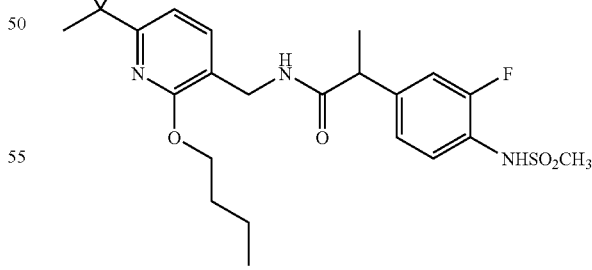

$^1$H NMR (CDCl$_3$) δ 7.50 (dd, 1H, J=8.4, 8.4 Hz), 7.36 (d, 1H, J=7.5 Hz), 7.15-7.05 (m, 2H), 6.79 (d, 1H, J=7.5 Hz), 6.59 (bs, NH), 6.06 (bt, NH), 4.39-4.23 (m, 4H), 3.48 (q, 1H, J=7.3 Hz), 3.02 (s, 3H), 1.69 (m, 2H), 1.48 (d, 3H, J=7.1 Hz), 1.43 (m, 2H), 1.29 (s, 9H), 0.97 (t, 3H, J=7.3 Hz); IR (neat)

3289, 2959, 1651, 1585, 1513, 1455, 1410, 1337, 1254, 1159 cm⁻¹; MS (FAB) m/z 480 (M+H)

Example 236

N-(6-tert-butyl-2-hexyloxy-pyridin-3-ylmethyl)-2-(3-fluoro-4-methylsulfonamido-phenyl)-propionamide

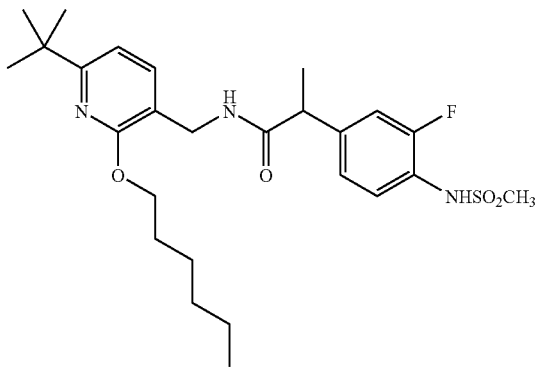

¹H NMR (CDCl₃) δ 7.50 (dd, 1H, J=8.4, 8.4 Hz), 7.36 (d, 1H, J=7.5 Hz), 7.15-7.05 (m, 2H), 6.79 (d, 1H, J=7.5 Hz), 6.58 (bs, NH), 6.07 (bt, NH), 4.39-4.24 (m, 4H), 3.48 (q, 1H, J=7.0 Hz), 3.02 (s, 3H), 1.71 (m, 2H), 1.48 (d, 3H, J=7.1 Hz), 1.45-1.25 (m, 6H), 1.29 (s, 9H), 0.91 (m, 3H); IR (neat) 3289, 2957, 1651, 1585, 1513, 1455, 1411, 1338, 1254, 1159, 973 cm⁻¹; MS (FAB) m/z 508 (M+H)

Example 237

N-(2-benzyloxy-6-tert-butyl-pyridin-3-ylmethyl)-2-(3-fluoro-4-methylsulfonamido-phenyl)-propionamide

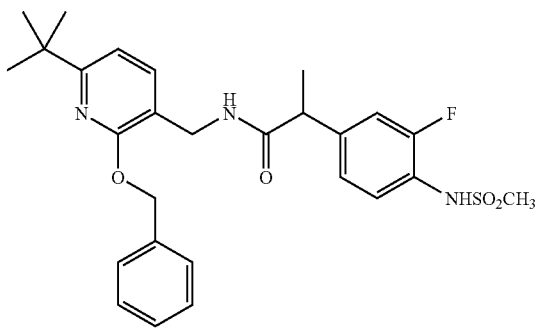

¹H NMR (CDCl₃) δ 7.46-7.30 (m, 7H), 7.06 (dd, 1H, J=11.2, 1.8 Hz), 6.95 (d, 1H, J=8.4 Hz), 6.84 (d, 1H, J=7.5 Hz), 6.53 (bs, NH), 6.06 (bt, NH), 5.42 (m, 2H), 4.42-4.26 (m, 2H), 3.38 (q, 1H, J=7.1 Hz), 2.98 (s, 3H), 1.41 (d, 3H, J=7.1 Hz), 1.30 (s, 9H); IR (neat) 3291, 2959, 1652, 1512, 1452, 1405, 1338, 1254, 1158 cm⁻¹; MS (FAB) m/z 514 (M+H)

Example 238

N-(2-cyclohexyloxy-4-trifluoromethyl-benzyl)-2-(3-fluoro-4-methylsulfonamido-phenyl)-propionamide

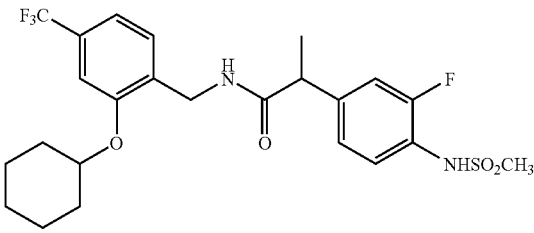

¹H NMR (300 MHz, CDCl₃) δ 7.51 (dd, 1H, J=8.4, 8.4 Hz), 7.30 (m, 1H), 7.09-7.10 (m, 2H), 7.06 (d, 1H, J=8.3 Hz), 7.02 (bs, 1H), 6.47 (bs, 1H), 5.53 (m, 1H), 4.27-4.50 (m, 3H), 3.50 (q, 1H, J=7.0 Hz), 3.02 (s, 3H), 1.84-1.96 (m, 2H), 1.64-1.78 (m, 2H), 1.25-1.63 (m, 9H); IR (KBr) 3289, 2937, 2859, 1653, 1510, 1427, 1330, 1236, 1160, 1124, 1043, 973, 906, 733 cm⁻¹; MS (FAB) m/z 517 (M+H)

Example 240

N-(6-tert-butyl-2-pyrrolidin-1-yl-pyridin-3-ylmethyl)-2-(3-fluoro-4-methansulfonylamino-phenyl)-propionamide

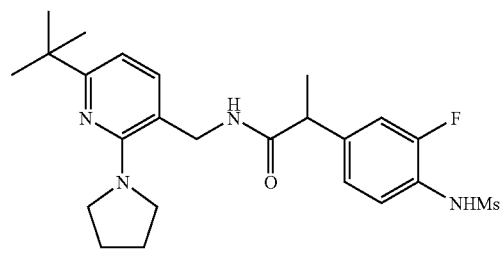

¹H NMR (300 MHz, CDCl₃) δ 7.51 (dd, 1H, J=8.3, 8.3 Hz), 7.24 (d, 1H, J=7.7 Hz), 7.20 (dd, 1H, J=11.0, 2.0 Hz), 7.08 (d, 1H, J=8.8 Hz), 6.67 (d, 1H, J=7.7 Hz), 6.50 (bs, 1H), 5.90 (bs, 1H), 4.4 (d, 2H, J=4.6 Hz), 3.5 (q, 1H, J=7.0 Hz), 3.41-3.36 (m, 4H), 3.00 (s, 3H), 1.85-1.80 (m, 4H), 1.50 (d, 3H, J=7.1 Hz), 1.30 (s, 9 H); IR (KBr) 3289, 2962, 2868, 1650, 1513, 1450, 1411 cm⁻¹; MS (FAB) m/z 477 (M+H)

Example 241

N-(6'-tert-butyl-4-methyl-3,4,5,6-tetrahydro-2H-[1,2']bipyridinyl-3'-ylmethyl)-2-(3-fluoro-4-methylsulfonamido-phenyl)-propionamide

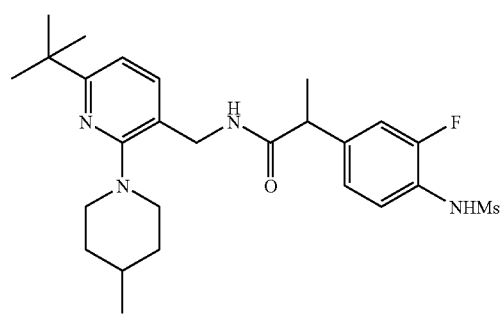

¹H NMR (300 MHz, CDCl₃) δ 7.51 (dd, 1H, J=8.3, 8.3 Hz), 7.30 (d, 1H, J=7.7 Hz), 7.20-7.00 (m, 2H), 6.90 (d, 1H, J=7.7 Hz), 4.45 (m, 2H), 3.52 (q, 1H, J=7.0 Hz), 3.30 (m, 2H), 3.00 (s, 3H), 2.78 (m, 2H), 1.70-1.50 (m, 5H), 1.50 (d, 3H, J=7.1 Hz), 1.30 (s, 9H), 0.97 (d, 3H, J=6.6 Hz); IR (KBr) 3291, 2922, 1651, 1513, 1452, 1400, 1335 cm⁻¹; MS (FAB) m/z 505 (M+H)

Example 243

N-[2-(4-butyl-benzyloxy)-6-trifluoromethyl-pyridin-3-ylmethyl]-2-(3-fluoro-4-methylsulfonamido-phenyl)-propionamide

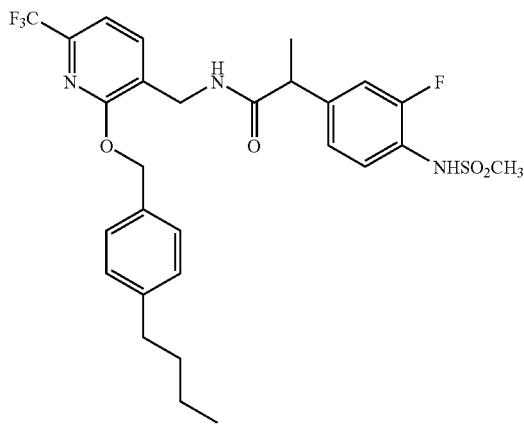

¹H NMR (300 MHz, CDCl₃) δ 7.61 (d, 1H, J=7.5 Hz), 7.48 (dd, 1H, J=8.2, 8.2 Hz), 7.33 (d, 2H, J=8.1 Hz), 7.23 (d, 1H, J=7.3 Hz), 7.10 (d, 2H, J=7.9 Hz), 7.04 (dd, 1H, J=11.2, 2.0 Hz), 6.97 (d, 1H, J=8.6 Hz), 6.41 (bs, 1H), 5.94 (bt, 1H), 5.38 (m, 2H), 4.37 (m, 2H), 3.39 (q, 1H, J=7.0 Hz), 3.01 (s, 3H), 2.63 (t, 2H, J=7.9 Hz), 1.61 (m, 2H), 1.41 (d, 3H, J=7.1 Hz), 1.38 (m, 2H), 0.93 (t, 3H, J=7.3 Hz); IR (neat) 3289, 2930, 1655, 1602, 1512, 1463, 1420, 1352, 1267, 1158, 975, 933, 831, 761 cm⁻¹; MS (FAB) m/z 582 (M+H)

Example 244

N-[2-(4-tert-butyl-benzyloxy)-6-trifluoromethyl-pyridin-3-ylmethyl]-2-(3-fluoro-4-methylsulfonamido-phenyl)-propionamide

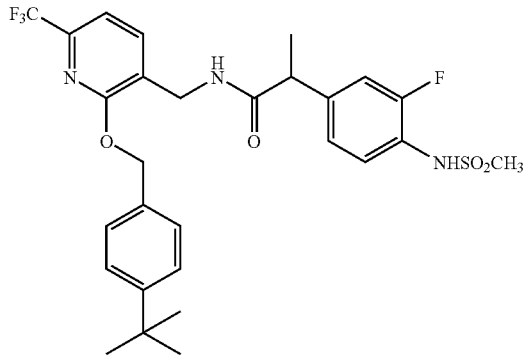

¹H NMR (300 MHz, CDCl₃) δ 7.61 (d, 1H, J=7.1 Hz), 7.48 (dd, 1H, J=8.3, 8.3 Hz), 7.45-7.37 (m, 4H), 7.23 (d, 1H, J=7.3 Hz), 7.04 (dd, 1H, J=11.2, 1.9 Hz), 6.97 (d, 1H, J=8.1 Hz), 6.42 (bs, 1H), 5.98 (bt, 1H), 5.39 (m, 2H), 4.38 (m, 2H), 3.40 (q, 1H, J=7.3 Hz), 3.00 (s, 3H), 1.41 (d, 3H, J=7.1 Hz), 1.34 (s, 9H); IR (neat) 3293, 2964, 1656, 1601, 1513, 1462, 1422, 1348, 1267, 1156, 976, 833, 758 cm⁻¹; MS (FAB) m/z 582 (M+H)

Example 245

2-(3-fluoro-4-methylsulfonamido-phenyl)-N-[2-(indan-2-yloxy)-6-trifluoromethyl-pyridin-3-ylmethyl]-propionamide

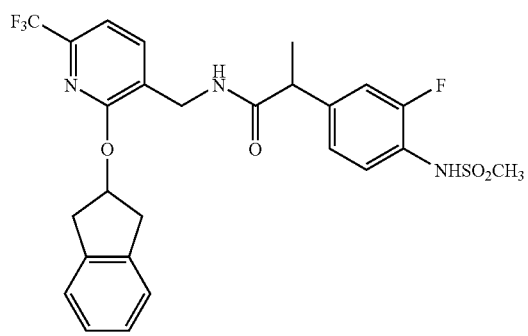

¹H NMR (300 MHz, CDCl₃) δ 7.59 (d, 1H, J=7.3 Hz), 7.46 (dd, 1H, J=8.2, 8.2 Hz), 7.29-7.24 (m, 5H), 6.99 (dd, 1H, J=11.2, 2.0 Hz), 6.91 (d, 1H, J=8.8 Hz), 6.35 (bs, 1H), 5.89 (m, 1H), 5.79 (bt, 1H), 4.27 (m, 2H), 3.43 (dd, 2H, J=17.2, 5.5 Hz), 3.08-3.04 (m, 3H), 3.00 (s, 3H), 1.31 (d, 3H, J=7.1 Hz) IR (neat) 3291, 2927, 1658, 1600, 1511, 1418, 1339, 1268, 1157, 1015, 970, 933, 747 cm⁻¹; MS (FAB) m/z 552 (M+H)

Example 246

2-(3-fluoro-4-methylsulfonamido-phenyl)-N-[2-(4-p-tolyl-piperazin-1-yl)-4-trifluoromethyl-benzyl]-propionamide

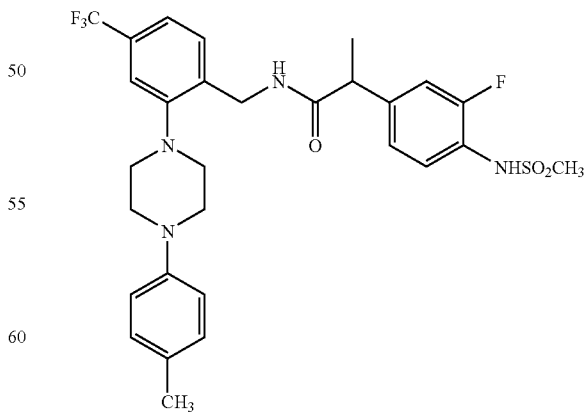

¹H NMR (300 MHz, CDCl₃) δ 7.46 (dd, 1H, J=8.2, 8.2 Hz), 7.34 (s, 1H), 7.33 (d, 1H, J=7.5 Hz), 7.31 (d, 1H, J=7.0 Hz), 7.13 (d, 2H, J=8.1 Hz), 7.14 (dd, 1H, J=11.2, 2.0 Hz), 7.08 (d,

1H, J=10.0 Hz), 6.86 (d, 2H, J=8.6 Hz), 6.35 (bt, 2H), 6.22 (bs, 1H), 4.57 (m, 2H), 3.54 (q, 1H, J=7.0 Hz), 3.18-3.12 (m, 4H), 3.05-3.01 (m, 4H), 2.97 (s, 3H), 2.31 (s, 3H), 1.51 (d, 3H, J=7.1 Hz); IR (neat) 2923, 1655, 1513, 1425, 1334, 1221, 1159, 1123, 963, 816, 757 cm⁻¹; MS (FAB) m/z 593 (M+H)

Example 247

2-(3-fluoro-4-methylsulfonamido-phenyl)-N-[2-(4-m-tolyl-piperazin-1-yl)-4-trifluoromethyl-benzyl]-propionamide

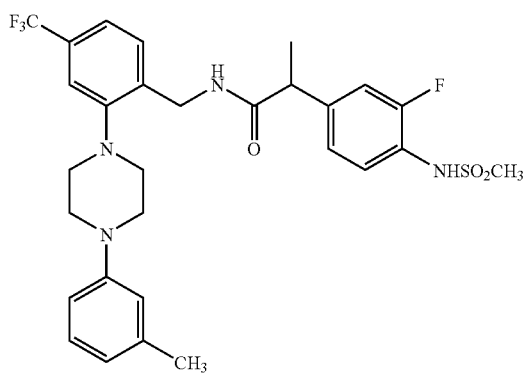

$^1$H NMR (300 MHz, CDCl$_3$) δ 7.46 (dd, 1H, J=8.2 Hz), 7.36-7.26 (m, 3H), 7.21 (m, 1H), 7.13 (dd, 1H, J=11.2, 2.0 Hz), 7.07 (d, 1H, J=8.1, 8.1 Hz), 6.79-6.74 (m, 3H), 6.33 (bt, 2H), 6.25 (bs, 1H), 4.57 (m, 2H), 3.54 (q, 1H, J=7.1 Hz), 3.24-3.18 (m, 4H), 3.08-3.01 (m, 4H), 2.97 (s, 3H), 2.36 (s, 3H), 1.51 (d, 3H, J=7.1 Hz); IR (neat) 3294, 2921, 1653, 1603, 1509, 1425, 1335, 1249, 1159, 1122, 965, 775 cm⁻¹; MS (FAB) m/z 593 (M+H)

Example 248

2-(3-fluoro-4-methylsulfonamido-phenyl)-N-{4-trifluoromethyl-2-[4-(4-trifluoromethyl-phenyl)-piperazin-1-yl]-benzyl}-propionamide

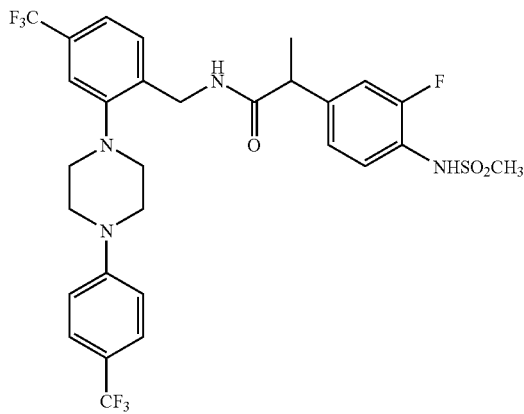

$^1$H NMR (300 MHz, CDCl$_3$) δ 7.53 (d, 2H, J=8.6 Hz), 7.50 (dd, 1H, J=8.3, 8.3 Hz), 7.33 (s, 1H), 7.30 (d, 2H, J=8.2 Hz), 7.14 (dd, 1H, J=11.2, 2.0 Hz), 7.08 (d, 1H, J=10.0 Hz), 6.97 (d, 2H, J=8.9 Hz), 6.23 (bt, 1H), 4.58 (d, 2H, J=6.4 Hz), 3.54 (q, 1H, J=7.1 Hz), 3.39-3.31 (m, 4H), 3.04-2.98 (m, 4H), 3.01 (s, 3H), 1.53 (d, 3H, J=7.1 Hz); IR (neat) 2923, 1652, 1615, 1511, 1423, 1331, 1237, 1159, 1117, 961, 827 cm⁻¹; MS (FAB) m/z 647 (M+H)

Example 249

2-(3-fluoro-4-methylsulfonamido-phenyl)-N-{2-[4-(4-methoxy-phenyl)-piperazin-1-yl]-4-trifluoromethyl-benzyl}-propionamide

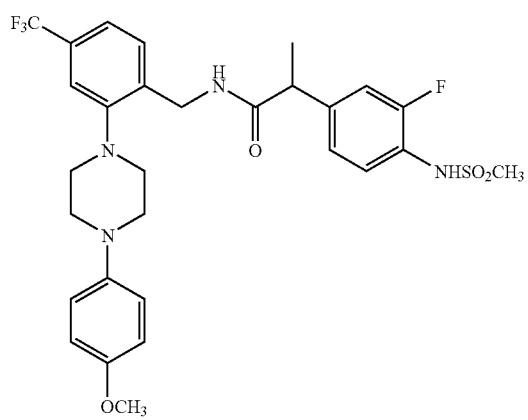

$^1$H NMR (300 MHz, CDCl$_3$) δ 7.47 (dd, 1H, J=8.2, 8.2 Hz), 7.33 (d, 2H, J=10.1 Hz), 7.29 (s, 1H), 7.13 (dd, 1H, J=11.2, 2.0 Hz), 7.07 (d, 1H, J=8.3 Hz), 6.98-6.85 (m, 4H), 6.35 (bs, 1H), 6.33 (bt, 1H), 4.59 (m, 2H), 3.80 (s, 3H), 3.54 (q, 1H, J=7.1 Hz), 3.15-3.08 (m, 4H), 3.05-2.98 (m, 4H), 2.98 (s, 3H), 1.51 (d, 3H, J=7.1 Hz); IR (neat) 2929, 1657, 1511, 1425, 1335, 1244, 1159, 1122, 1036, 963, 827, 757 cm⁻¹; MS (FAB) m/z 609 (M+H)

Example 255

2-(3-fluoro-4-methylsulfonamido-phenyl)-N-{2-[4-(4-fluoro-phenyl)-piperidin-1-yl]-4-trifluoromethyl-benzyl}-propionamide

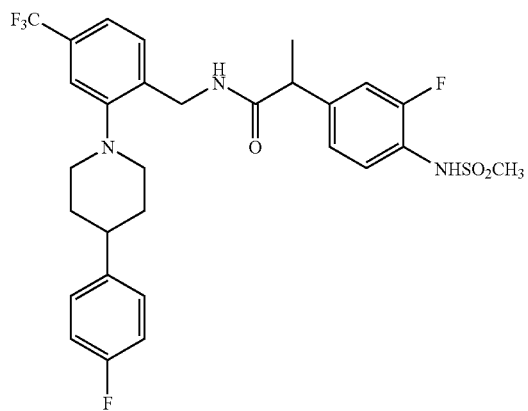

$^1$H NMR (300 MHz, CDCl$_3$) δ 7.50 (dd, 1H, J=8.3 Hz), 7.30-7.26 (m, 3H), 7.23-7.18 (m, 2H), 7.15 (dd, 1H, J=11.8, 2.0 Hz), 7.08 (d, 1H, J=10.0 Hz), 7.03 (m, 2H), 6.46 (bs, 1H), 6.24 (bt, 1H), 4.56 (d, 2H, J=5.7 Hz), 3.56 (q, 1H, J=7.1 Hz), 3.09 (m, 2H), 3.00 (s, 3H), 2.83 (m, 2H), 2.64 (m, 1H), 1.94 (m, 2H), 1.78 (m, 2H), 1.54 (d, 3H, J=6.9 Hz); IR (neat) 3320, 2922, 1652, 1509, 1423, 1332, 1222, 1159, 1120, 971, 888, 834, 763 cm$^{-1}$; MS (FAB) m/z 596 (M+H)

Example 256

N-(2-butoxy-6-trifluoromethyl-pyridin-3-ylmethyl)-2-(4-methylsulfonamido-3-methyl-phenyl)-propionamide

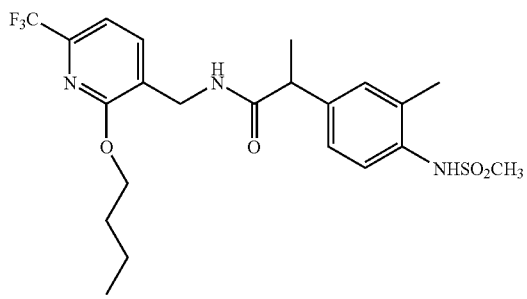

$^1$H NMR (300 MHz, CDCl$_3$) δ 7.55 (d, 1H, J=7.5 Hz), 7.40 (d, 1H, J=8.8 Hz), 7.17 (d, 1H, J=7.3 Hz), 7.11 (d, 1H, J=6.9 Hz), 7.10 (s, 1H), 6.21 (bs, 1H), 5.93 (bt, 1H), 4.36 (d, 2H, J=6.4 Hz), 4.31 (m, 2H), 3.51 (q, 1H, J=7.1 Hz), 3.03 (s, 3H), 2.28 (s, 3H), 1.69 (m, 2H), 1.48 (d, 3H, J=7.1 Hz), 1.41 (m, 2H), 0.96 (t, 3H, J=7.3 Hz); IR (neat) 3291, 2963, 1654, 1605, 1537, 1463, 1425, 1326, 1151, 972, 932, 834 cm$^{-1}$; MS (FAB) m/z 488 (M+H)

Example 257

N-(2-hexyloxy-6-trifluoromethyl-pyridin-3-ylmethyl)-2-(4-methylsulfonamido-3-methyl-phenyl)-propionamide

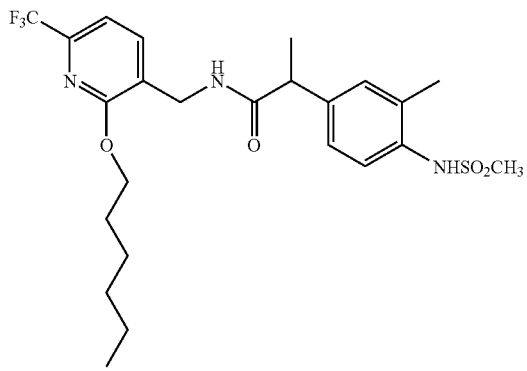

$^1$H NMR (300 MHz, CDCl$_3$) δ 7.54 (d, 1H, J=7.5 Hz), 7.39 (d, 1H, J=9.0 Hz), 7.17 (d, 1H, J=7.3 Hz), 7.11 (d, 1H, J=7.0 Hz), 7.09 (s, 1H), 6.21 (bs, 1H), 5.94 (bt, 1H), 4.36 (d, 2H, J=6.2 Hz), 4.30 (m, 2H), 3.51 (q, 1H, J=7.1 Hz), 3.03 (s, 3H), 2.28 (s, 3H), 1.69 (m, 2H), 1.48 (d, 3H, J=7.1 Hz), 1.39-1.26 (m, 6H), 0.91 (t, 3H, J=6.6 Hz); IR (neat) 3290, 2931, 1655, 1604, 1504, 1464

Example 258

N-[2-(4-chloro-benzyloxy)-6-trifluoromethyl-pyridin-3-ylmethyl]-2-(3-fluoro-4-methylsulfonamido-phenyl)-propionamide

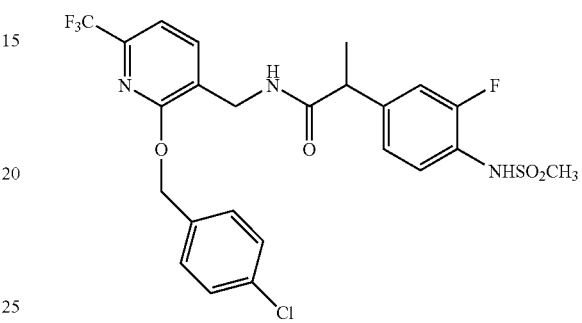

$^1$H NMR (300 MHz, CDCl$_3$) δ 7.60 (d, 1H, J=7.5 Hz), 7.48 (dd, 1H, J=8.3, 8.3 Hz), 7.39-7.28 (m, 4H), 7.24 (d, 1H, J=7.5 Hz), 7.05 (dd, 1H, J=11.2, 2.0 Hz), 7.00 (d, 1H, J=8.3 Hz), 6.48 (bs, 1H), 5.91 (bt, 1H), 5.37 (d, 2H, J=4.7 Hz), 4.39 (m, 2H), 3.45 (q, 1H, J=7.1 Hz), 3.02 (s, 3H), 1.44 (d, 3H, J=7.0 Hz); IR (neat) 3299, 2929, 1658, 1601, 1512, 1461, 1423, 1350, 1267, 7756, 975, 934, 808 cm$^{-1}$; MS (FAB) m/z 560 (M+H)

Example 259

N-(4-dimethylaminomethyl-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide

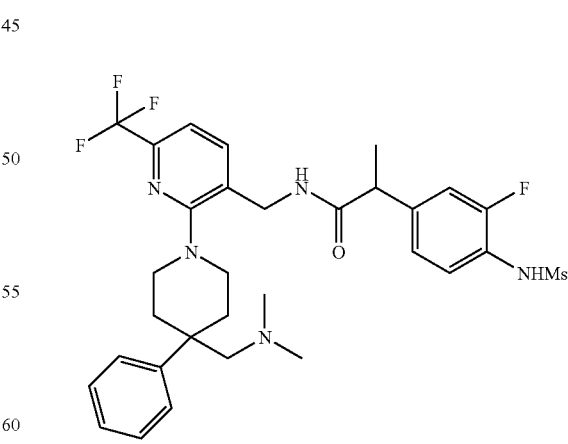

$^1$H NMR (300 MHz, CDCl$_3$) δ 7.45-7.50 (m, 2H), 7.36 (m, 4H), 7.21 (m, 1H), 7.18 (d, 1H, J=8.1 Hz), 7.13 (dd, 1H, J=11.1, 1.8 Hz), 7.06 (d, 1H, J=8.1 Hz), 6.37 (bt, 1H), 4.46 (d, 2H, J=5.7 Hz), 3.58 (q, 1H, J=6.9 Hz), 3.17 (m, 2H), 3.01 (s, 3H), 2.98 (m, 2H), 2.52 (s, 2H), 2.18 (m, 2H), 1.98 (s, 6H),

Example 260

N-[2-(4-cyclohexyl-piperazin-1-yl)-6-trifluoromethyl-pyridin-3-ylmethyl]-2-(3-fluoro-4-methylsulfonamido-phenyl)-propionamide

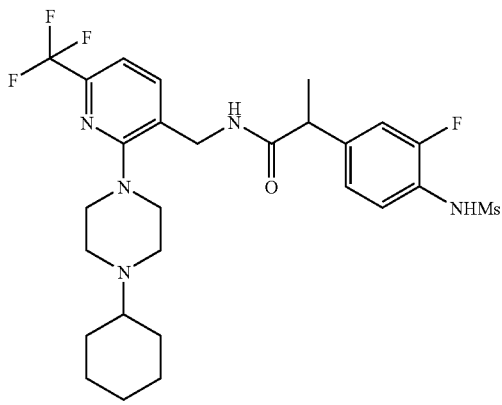

$^1$H NMR (300 MHz, CDCl$_3$) δ 7.47-7.53 (m, 2H), 7.23 (d, 1H, J=7.8 Hz), 7.07-7.15 (m, 2H), 6.26 (bt, 1H), 4.44 (d, 2H, J=5.7 Hz), 3.58 (q, 1H, J=6.9 Hz), 3.27 (m, 4H), 3.03 (s, 3H), 2.84 (m, 4H), 2.50 (m, 1H), 1.94 (m, 2H), 1.85 (m, 2H), 1.51 (d, 3H, J=6.9 Hz), 1.25-1.30 (m, 6H); IR (KBr)) 2934, 2857, 1657, 1591, 1502, 1459, 1418, 1334, 1271, 1152, 979, 757 cm$^{-1}$; MS (FAB) m/z 586 (M+H)

Example 261

N-(6-tert-butyl-2-cyclopentyloxy-4-hydroxymethyl-pyridin-3-ylmethyl)-2-(3-fluoro-4-methylsulfonamido-phenyl)-propionamide

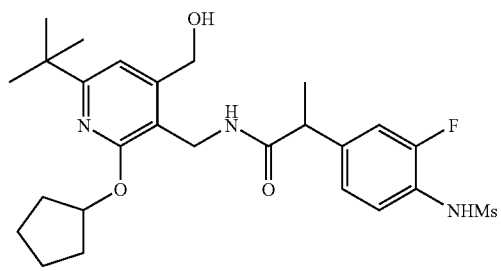

$^1$H NMR (300 MHz, CDCl$_3$) δ 7.48 (dd, 1H, J=8.1, 8.1 Hz), 6.99-7.05 (m, 2H), 6.82 (s, 1H), 6.32 (bt, 1H), 5.40 (m, 1H), 4.63 (d, 2H, J=5.7 Hz), 4.37 (m, 2H), 3.47 (q, 1H, J=6.9 Hz), 3.03 (s, 3H), 1.94 (m, 2H), 1.63 (m, 6H), 1.45 (d, 3H, J=6.9 Hz), 1.29 (s, 9H); IR (KBr) 3369, 2962, 1651, 1592, 1513, 1452, 1397, 1336, 1158, 1026, 974, 758 cm$^{-1}$; MS (FAB) m/z 522 (M+H)

Example 262

2-(4-methylsulfonamido-phenyl)-N-(4-methyl-6'-trifluoromethyl-3,4,5,6-tetrahydro-2H-[1,2']bipyridinyl-3'-ylmethyl)-propionamide

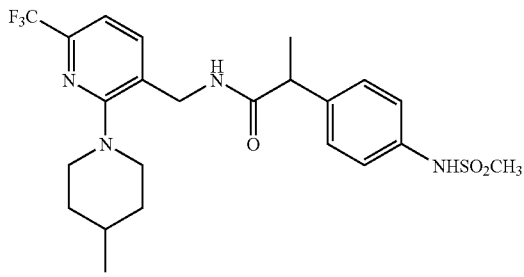

$^1$H NMR (300 MHz, CDCl$_3$) δ 7.46 (d, 1H, J=7.5 Hz), 7.23-7.31 (m, 2H), 7.14-7.22 (m, 3H), 6.60 (bs, 1H), 6.20 (bt, 1H), 4.46 (d, 2H, J=5.9 Hz), 3.59 (q, 1H, J=7.1 Hz), 3.19-3.38 (m, 2H), 3.01 (s, 3H), 2.75-2.87 (m, 2H), 1.65-1.79 (m, 2H), 1.48-1.56 (m, 4H), 1.14-1.32 (m, 2H), 0.97 (d, 3H, J=6.6 Hz); IR (KBr) 3287, 2921, 1646, 1512, 1458, 1423, 1335, 1233, 1145, 970, 840 cm$^{-1}$; MS (FAB) m/z 499 (M+H)

Example 263

N-[2-(3,3-dimethyl-butyl)-6-trifluoromethyl-pyridin-3-ylmethyl]-2-(3-fluoro-4-methylsulfonamido-phenyl)-propionamide

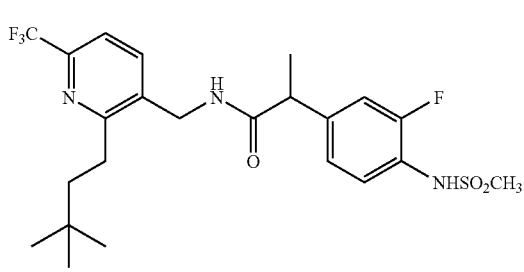

$^1$H NMR (300 MHz, CDCl$_3$) δ 7.49-7.58 (m, 2H), 7.43 (d, 1H, J=7.9 Hz), 7.17 (dd, 1H, J=11.2, 1.8 Hz), 7.11 (d, 1H, J=8.6 Hz), 6.48 (bs, 1H), 5.70 (bt, 1H), 4.41-4.56 (m, 2H), 3.58 (q, 1H, J=7.3 Hz), 3.04 (s, 3H), 2.71-2.79 (m, 2H), 1.51-1.60 (m, 5H), 0.96 (s, 9H); IR (KBr) 3292, 2957, 1656, 1512, 1463, 1408, 1340, 1277, 1157, 972, 906, 758 cm$^{-1}$; MS (FAB) m/z 504 (M+H)

Example 264

2-(3-fluoro-4-methylsulfonamido-phenyl)-N-[2-(2-p-tolyl-ethyl)-6-trifluoromethyl-pyridin-3-ylmethyl]-propionamide

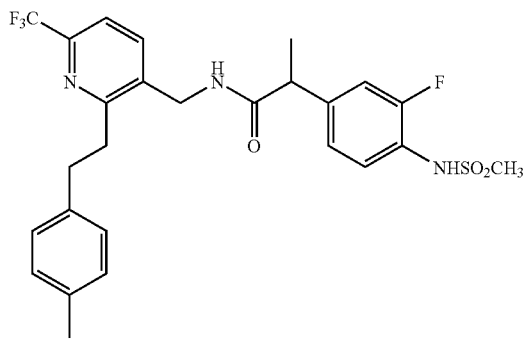

$^1$H NMR (300 MHz, CDCl$_3$) δ 7.48-7.59 (m, 2H), 7.46 (m, 1H), 7.12 (dd, 1H, J=11.2, 2.0 Hz), 6.96-7.10 (m, 5H), 6.41 (bs, 1H), 5.26 (bt, 1H), 4.20-4.39 (m, 2H), 3.35 (q, 1H, J=7.1 Hz), 3.05-3.15 (m, 4H), 3.05 (s, 3H), 2.31 (s, 3H), 1.47 (d, 3H, J=7.1 Hz); IR (KBr) 3298, 2925, 1658, 1589, 1513, 1408, 1339, 1279, 1157, 973, 912, 813, 733 cm$^{-1}$; MS (FAB) m/z 538 (M+H)

Example 267

2-(3-fluoro-4-methylsulfonamido-phenyl)-N-(2-hexyl-6-trifluoromethyl-pyridin-3-ylmethyl)-propionamide

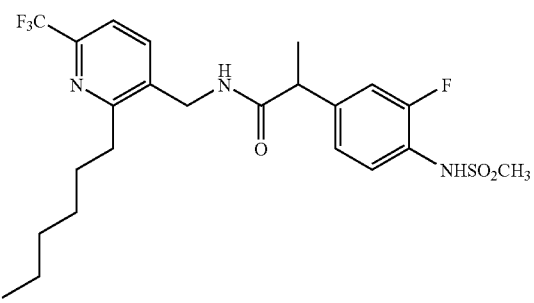

$^1$H NMR (300 MHz, CDCl$_3$) δ 7.50-7.59 (m, 2H), 7.44 (d, 1H, J=8.1 Hz), 7.16 (dd, 1H, J=11.2, 2.0 Hz), 7.10 (d, 1H, J=8.4 Hz), 6.43 (bs, 1H), 5.70 (bt, 1H), 4.41-4.58 (m, 2H), 3.57 (q, 1H, J=7.1 Hz), 3.04 (bs, 3H), 2.78 (t, 2H, J=7.9 Hz), 1.61-1.74 (m, 2H), 1.53 (d, 3H, J=7.1 Hz), 1.21-1.43 (m, 6H), 0.88 (m, 3H); IR (KBr) 3289, 2929, 2857, 1658, 1589, 1512, 1462, 1408, 1341, 1277, 1158, 973, 908 cm$^{-1}$; MS (FAB) m/z 504 (M+H)

Example 268

2-(3-fluoro-4-methylsulfonamido-phenyl)-N-[2-(4-methyl-pentyl)-6-trifluoromethyl-pyridin-3-ylmethyl]-propionamide

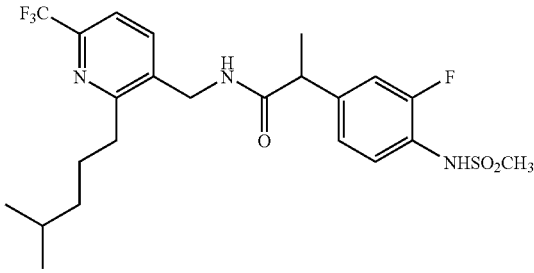

$^1$H NMR (300 MHz, CDCl$_3$) δ 7.51-7.58 (m, 2H), 7.44 (d, 1H, J=8.0 Hz), 7.17 (dd, 1H, J=11.2, 2.0 Hz), 7.10 (d, 1H, J=8.4 Hz), 6.48 (bs, 1H), 5.70 (bt, 1H), 4.41-4.57 (m, 2H), 3.57 (q, 1H, J=7.0 Hz), 3.04 (s, 3H), 2.76 (t, 2H, J=8.0 Hz), 1.61-1.76 (m, 2H), 1.58 (m, 1H), 1.54 (d, 3H, J=7.1 Hz), 1.19-1.27 (m, 2H), 0.87 (d, 6H, J=6.6 Hz); IR (KBr) 3290, 2956, 1656, 1589, 1512, 1462, 1408, 1339, 1279, 1158, 972, 906 cm$^{-1}$; MS (FAB) m/z 504 (M+H)

Example 269

2-(3-fluoro-4-methylsulfonamido-phenyl)-N-(4-hydroxy-6'-trifluoromethyl-3,4,5,6-tetrahydro-2H-[1,2']bipyridinyl-3'-ylmethyl)-propionamide

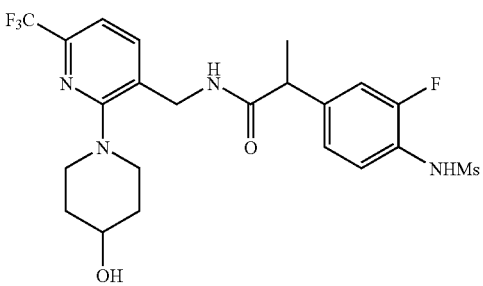

$^1$H NMR (CDCl$_3$) δ 7.54-7.49 (m, 2H), 7.23 (d, 1H, J=7.7 Hz), 7.16-7.09 (m, 2H), 6.69 (bs, NH), 6.25 (bt, NH), 4.48 (m, 2H), 3.84 (m, 1H), 3.58 (q, 1H, J=7.3 Hz), 3.38-3.26 (m, 2H), 3.04 (s, 3H), 2.97-2.88 (m, 2H), 2.02-1.92 (m, 2H), 1.75 (s,

OH), 1.53 (d, 3H, J=7.1 Hz); IR (neat) 3294, 2934, 1658, 1592, 1512, 1418, 1334, 1155, 732 cm⁻¹; Mass (FAB) m/z 519 [M+H]

Example 270

N-(2-cyclohexylmethoxy-6-trifluoromethyl-pyridin-3-ylmethyl)-2-(3-fluoro-4-methylsulfonamido-phenyl)-propionamide

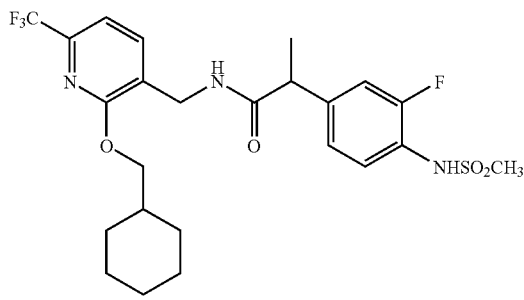

¹H NMR (CDCl₃) δ 7.56 (d, 1H, J=7.3 Hz), 7.51 (dd, 1H, J=8.3, 8.3 Hz), 7.18 (d, 1H, J=7.3 Hz), 7.12-7.04 (m, 2H), 6.57 (bs, NH), 5.99 (bt, NH), 4.38 (m, H), 4.16 (m, H) 4.16 (m, 2H), 3.51 (q, 1H, J=7.1 Hz), 3.03 (s, 3H), 1.82-1.67 (m, 5H), 1.49 (d, 3H, J=7.1 Hz), 1.32-1.00 (m, 6H); IR (neat) 3292, 2928, 2854, 1656, 1513, 1425, 1338, 1269, 1158 cm⁻¹; MS (FAB) m/z 532 (M+H)

Example 271

2-(3-fluoro-4-methylsulfonamido-phenyl)-N-[2-(4-methyl-cyclohexylmethoxy)-6-trifluoromethyl-pyridin-3-ylmethyl]-propionamide

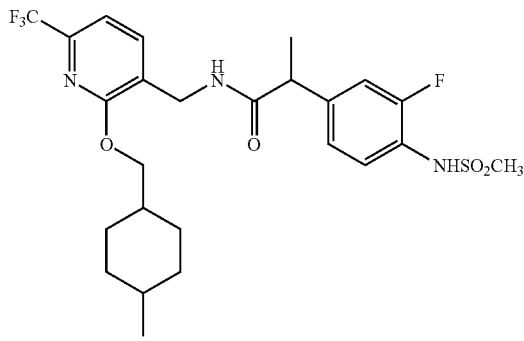

¹H NMR (CDCl₃) δ 7.56 (d, 1H, J=7.3 Hz), 7.50 (dd, 1H, J=8.2, 8.2 Hz), 7.18 (d, 1H, J=7.5 Hz), 7.12-7.04 (m, 2H), 6.59 (bs, NH), 6.00 (bt, NH), 4.45-4.11 (m, 4H), 3.51 (q, 1H, J=7.1 Hz), 3.03 (s, 3H), 1.95-1.25 (m, 12H), 1.10-0.90 (m, 4H); IR (neat) 3295, 2924, 1655, 1513, 1425, 1337, 1268, 1158 cm⁻¹; MS (FAB) m/z 546 (M+H)

Example 279

N-[2-(2,2-dimethyl-cyclopropylmethoxy)-6-trifluoromethyl-pyridin-3-ylmethyl]-2-(3-fluoro-4-methylsulfonamido-phenyl)-propionamide

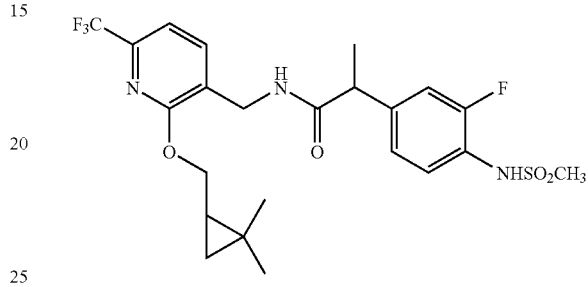

¹H NMR (CDCl₃) δ 7.58 (d, 1H, J=7.3 Hz), 7.51 (dd, 1H, J=8.4, 8.4 Hz), 7.19 (d, 1H, J=7.3 Hz), 7.14-7.05 (m, 2H), 6.54 (bs, NH), 6.07 (bt, NH), 4.57-4.33 (m, 3H), 4.24-4.15 (m, 1H), 3.51 (q, 1H, J=7.1 Hz), 3.03 (s, 3H), 1.49 (dd, 3H, J=7.0, 1.7 Hz), 1.13 (d, 3H, J=1.5 Hz), 1.09 (s, 3H), 1.06-0.95 (m, 1H), 0.57 (dd, 1H, J=8.4, 4.4 Hz), 0.28 (m, 1H); IR (neat) 3293, 2928, 1655, 1514, 1427, 1339, 1266, 1158, 980 cm⁻¹; MS (FAB) m/z 518 (M+H)

Example 282

2-(3-fluoro-4-methylsulfonamido-phenyl)-N-(3-methyl-6'-trifluoromethyl-3,4,5,6-tetrahydro-2H-[1,2']bipyridinyl-3'-ylmethyl)-propionamide

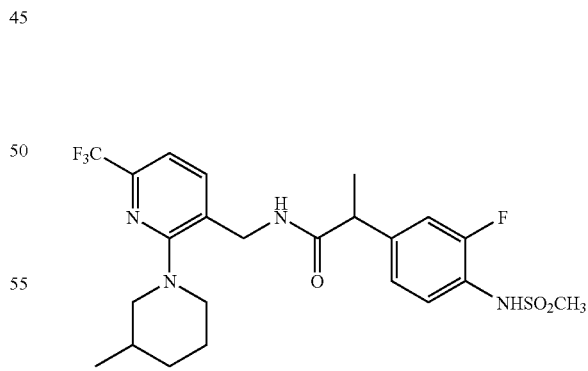

¹H NMR (CDCl₃) δ 7.54-7.47 (m, 2H), 7.21 (d, 1H, J=7.7 Hz), 7.15-7.07 (m, 2H), 6.64 (bs, NH), 6.34 (bt, NH), 4.48 (d, 2H, J=5.9 Hz), 3.56 (q, 1H, J=7.0 Hz), 3.32-3.17 (m, 2H), 3.03 (s, 3H), 2.74 (m, 1H), 2.46 (m, 1H), 1.82-1.61 (m, 4H), 1.53 (d, 3H, J=7.1 Hz), 1.13-1.01 (m, 1H), 0.91 (m, 3H); IR

Example 283

2-(3-fluoro-4-methylsulfonamido-phenyl)-N-(2-methyl-6'-trifluoromethyl-3,4,5,6-tetrahydro-2H-[1,2']bipyridinyl-3'-ylmethyl)-propionamide

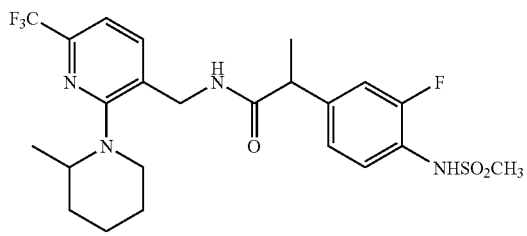

$^1$H NMR (CDCl$_3$) δ 7.62-7.48 (m, 2H), 7.30 (m, 1H), 7.18-7.07 (m, 2H), 6.71 (bt, NH), 6.58 (bs, NH), 4.67-4.57 (m, 1H), 4.35 (m, 1H), 3.56-3.46 (m, 2H), 3.03 & 3.02 (s, 3H), 3.01-2.95 (m, 1H), 2.79 (m, 1H), 1.80-1.50 (m, 9H), 0.90 & 0.85 (d, 3H); IR (neat) 3289, 2933, 2853, 1655, 1512, 1456, 1411, 1335, 1158 cm$^{-1}$; MS (FAB) m/z 517 (M+H)

Example 284

2-(3-fluoro-4-methylsulfonamido-phenyl)-N-[2-(4-methyl-6'-trifluoromethyl-3,4,5,6-tetrahydro-2H-[1,2']bipyridinyl-3'-yl)-ethyl]-propionamide

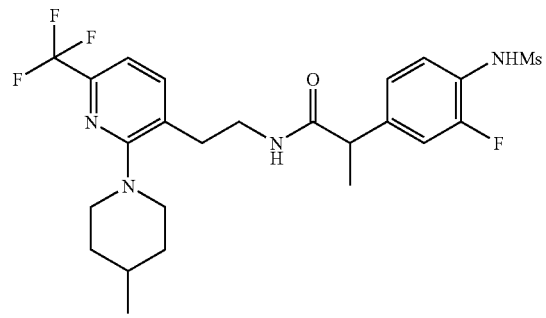

$^1$H NMR (300 MHz, CDCl$_3$) δ 7.44-7.50 (m, 2H), 7.19 (d, 1H, J=7.8 Hz), 6.96-7.06 (m, 2H), 5.79 (bt, 1H), 3.54 (q, 2H, J=6.3 Hz), 3.25-3.40 (m, 3H), 3.03 (s, 3H), 2.78-2.87 (m, 4H), 1.76 (m, 2H), 1.60 (m, 3H), 1.42 (d, 3H, J=6.9 Hz), 0.99 (d, 3 H, J=6.6 Hz); IR (KBr) 2920, 1646, 1537, 1455, 1415, 1325, 1153, 832 cm$^{-1}$; MS (FAB) m/z 531 (M+H)

Example 285

N-(4-cyano-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide

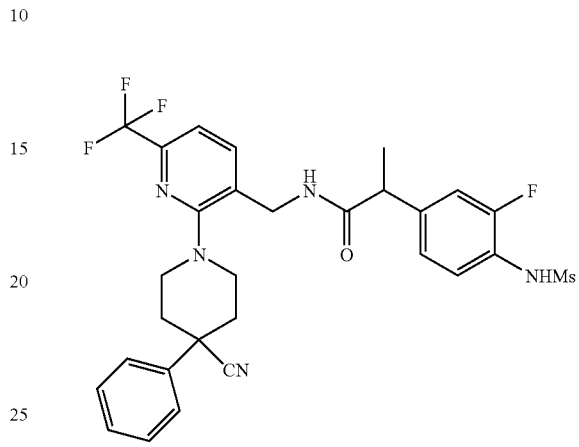

$^1$H NMR (300 MHz, CDCl$_3$) δ 7.28-7.52 (m, 8H), 7.08-7.17 (m, 2H), 6.04 (bt, 1H), 4.49 (d, 2H, J=5.7 Hz), 3.58 (q, 1H, J=6.9 Hz), 3.36-3.60 (m, 5H), 3.02 (s, 3H), 2.17 (m, 4H), 1.54 (d, 3H, J=6.9 Hz); IR (KBr) 2931, 1657, 1590, 1509, 1455, 1324, 1241, 1154, 966, 758, 702 cm$^{-1}$; MS (FAB) m/z 604 (M+H)

Example 287

2-(4-ethanesulfonylamino-3-fluoro-phenyl)-N-(4-methyl-6'-trifluoromethyl-3,4,5,6-tetrahydro-2H-[1,2']bipyridinyl-3'-ylmethyl)-propionamide

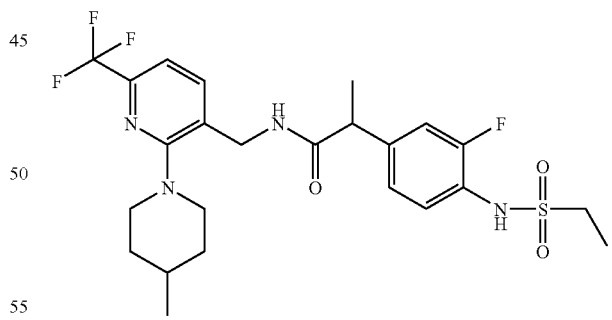

$^1$H NMR (300 MHz, CDCl$_3$) δ 7.53 (dd, 1H, J=8.1, 8.1 Hz), 7.47 (d, 1H, J=7.5 Hz), 7.19 (d, 1H, J=7.5 Hz), 7.11 (d, 1H, J=11.4, 1.8 Hz), 7.06 (d, 1H, 8.4 Hz), 6.55 (bs, 1H), 6.30 (bt, 1H), 4.46 (d, 2H, J=5.7 Hz), 3.55 (q, 1H, J=6.9 Hz), 3.29 (m, 2H), 3.11 (q, 2H, J=7.5 Hz), 2.80 (m, 2H), 1.67-1.70 (m, 3H), 1.52 (d, 3H, J=6.9 Hz), 1.38 (t, 3H, J=7.5 Hz), 1.22 (m, 2H), 0.97 (d, 3H, J=6.3 Hz); IR (KBr) 3290, 2926, 2658, 1592, 1511, 1456, 1418, 1374, 1335, 1275, 1148, 942, 832, 757 cm$^{-1}$;

MS (FAB) m/z 531 (M+H)

Example 288

2-(4-dimethylaminsulfonylamino-3-fluoro-phenyl)-N-(4-methyl-6'-trifluoromethyl-3,4,5,6-tetrahydro-2H-[1,2']bipyridinyl-3'-ylmethyl)-propionamide

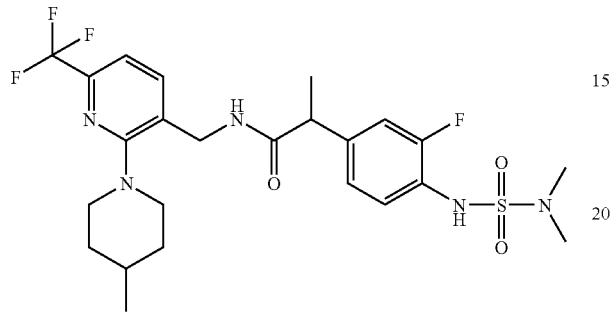

$^1$H NMR (300 MHz, CDCl$_3$) δ 7.45-7.52 (m, 2H), 7.18 (d, 1H, J=7.5 Hz), 7.02-7.10 (m, 2H), 6.26 (bs, 1H), 4.46 (d, 2H, J=5.7 Hz), 4.55 (q, 1H, J=6.9 Hz), 3.30 (m, 2H), 2.77-2.83 (m, 9H), 1.72 (m, 2H), 1.52 (d, 3H, J=6.9 Hz), 1.19-1.26 (m, 3H), 0.97 (d, 3H, J=6.0 Hz); IR (KBr) 3293, 2923, 1658, 1592, 1512, 1456, 1420, 1339, 1272, 1152, 959, 758 cm$^{-1}$; MS (FAB) m/z 546 (M+H)

Example 289

2-(4-methylsulfonamido-3-methoxy-phenyl)-N-(4-methyl-6'-trifluoromethyl-3,4,5,6-tetrahydro-2H-[1,2']bipyridinyl-3'-ylmethyl)-propionamide

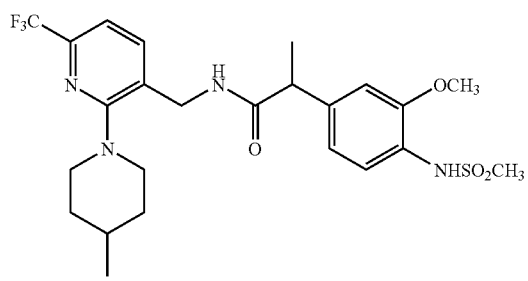

$^1$H NMR (CDCl$_3$) δ 7.48-7.45 (m, 2H), 7.18 (d, 1H, J=7.7 Hz), 6.89-6.83 (m, 2H), 6.75 (bs, NH), 6.25 (bt, NH), 4.46 (d, 2H, J=5.7 Hz), 3.83 (s, 3H), 3.57 (q, 1H, J=7.0 Hz), 3.33-3.21 (m, 2H), 2.95 (s, 3H), 2.84-2.76 (m, 2H), 1.75-1.63 (m, 3H), 1.54 (d, 3H, J=7.1 Hz), 1.30-1.13 (m, 2H), 0.97 (d, 3H, J=6.4 Hz); IR (neat) 3297, 2925, 1656, 1594, 1512, 1459, 1419, 1336, 1130 cm$^{-1}$; MS (FAB) m/z 529 (M+H)

Example 290

2-(3-fluoro-4-methylsulfonamido-phenyl)-N-(4-phenylamino-6'-trifluoromethyl-3,4,5,6-tetrahydro-2H-[1,2']bipyridinyl-3'-ylmethyl)-propionamide

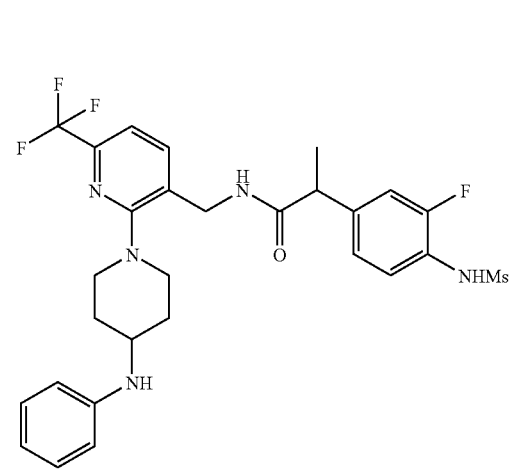

$^1$H NMR (300 MHz, CDCl$_3$) δ 7.49-7.54 (m, 2H), 7.08-7.25 (m, 6H), 6.72 (t, 1H, J=7.2 Hz), 6.63 (d, 2H, J=8.1 Hz), 6.21 (bt, 1H), 4.48 (d, 2H, J=5.7 Hz), 3.57 (q, 1H, J=6.9 Hz), 3.35-3.46 (m, 3H), 3.01-3.04 (m, 5H), 2.60 (m, 2H), 2.17 (m, 2H), 1.52 (d, 3H, J=6.9 Hz); IR (KBr) 2927. 1655. 1597. 1511. 1456. 1420. 1375. 1334. 1155. 972. 756 cm$^{-1}$; MS (FAB) m/z 594 (M+H)

Example 291

N-(2-cyclohexyl-6-trifluoromethyl-pyridin-3-ylmethyl)-2-(3-fluoro-4-methylsulfonamido-phenyl)-propionamide

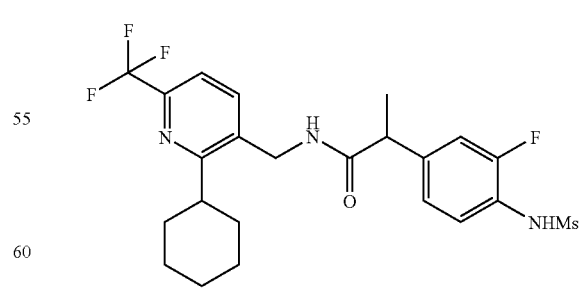

$^1$H NMR (300 MHz, CDCl$_3$) δ 7.48-7.54 (m, 2H), 7.38 (d, 1H, J=8.1 Hz), 7.14 (dd, 1H, J=11.1, 1.8 Hz) 7.08 (d, 1H, J=8.1 Hz), 5.78 (bt, 1H), 4.49 (d, 2H, J=5.7 Hz), 3.57 (q, 1H, J=6.9 Hz), 3.02 (s, 3H), 2.76 (m, 1H), 1.62-1.81 (m, 6H), 1.52

(d, 3H, J=6.9 Hz), 1.25-1.31 (m, 4H); IR (KBr) 3300, 2927, 2855, 1643, 1512, 1453, 1336, 1151, 973, 753 cm⁻¹; MS (FAB) m/z 502 (M+H)

Example 292

2-(3-fluoro-4-methylsulfonamido-phenyl)-N-(4-phenyl-6-trifluoromethyl-pyridin-3-ylmethyl)-propionamide

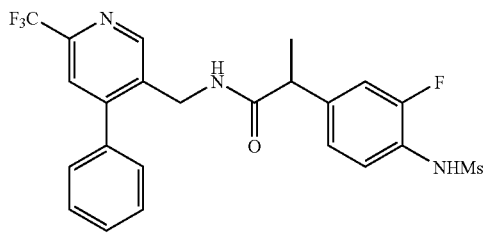

¹H NMR (300 MHz, CDCl₃) δ 8.55 (s, 1H), 7.46-7.53 (m, 5H), 7.24-7.27 (m, 2H), 7.05 (dd, 1H, J=11.1, 1.8 Hz), 6.99 (d, 1H, J=8.1 Hz), 6.62 (bs 1H), 5.67 (bt, 1H), 4.49 (d, 2H, J=5.7 Hz), 3.45 (q, 1H, J=6.9 Hz), 3.04 (s, 3H), 1.45 (d, 3H, J=6.9 Hz); IR (neat) 3296, 2937, 1715, 1646, 1592, 1505, 1457, 1416, 1361, 1277, 1159, 963, 758 cm⁻¹; MS (FAB) m/z 496 (M+H)

Example 293

2-(3-fluoro-4-methylsulfonamido-phenyl)-N-(4-methyl-6'-trifluoromethyl-3,4,5,6-tetrahydro-2H-[1,2']bipyridinyl-3'-ylmethyl)-thiopropionamide

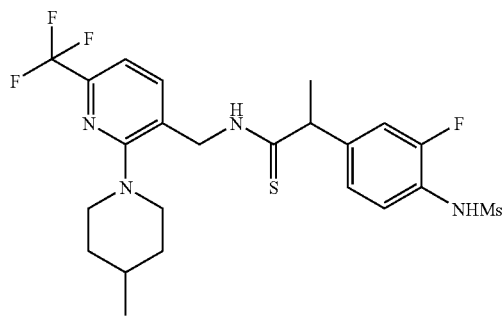

¹H NMR (300 MHz, CDCl₃) δ 8.25 (bs, 1H), 7.48-7.54 (m, 2H), 7.10-7.25 (m, 3H), 4.93 (d, 2H, J=5.7 Hz), 4.02 (q, 1H, J=6.9 Hz), 3.29 (m, 2H), 3.02 (s, 3H), 2.84 (m, 2H), 1.70 (m, 2H), 1.67 (d, 3H, J=6.9 Hz), 1.50 (m, 1H), 1.24 (m, 2H), 0.98

(d, 3H, J=6.6 Hz); IR (KBr) 3268, 2924, 1592, 1512, 1418, 1333, 1157, 1045, 970, 833, 758 cm⁻¹; MS (FAB) m/z 533 (M+H)

Example 296

N-(2-azepan-1-yl-6-tert-butyl-pyridin-3-ylmethyl)-2-(3-fluoro-4-methansulfonyl amino-phenyl)-propionamide

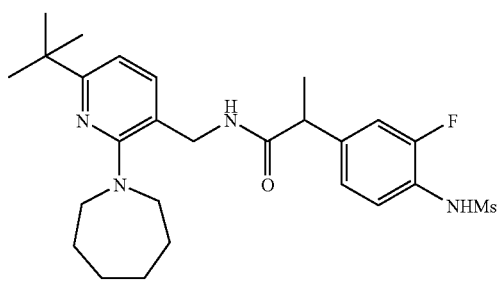

¹H NMR (300 MHz, CDCl₃) δ 7.52 (dd, 1H, J=8.4, 8.4 Hz), 7.24 (d, 1H, J=7.7 Hz), 7.16 (dd, 1H, J=11.3, 2.0 Hz), 7.08 (d, 1H, J=8.8 Hz), 6.74 (d, 1H, J=7.7 Hz), 6.16 (bs, 1H), 4.37 (m, 2H), 3.51 (q, 1H, J=7.1 Hz), 3.34-3.30 (m, 4H), 3.02 (s, 3H), 1.80-1.60 (m, 4H), 1.58-1.49 (m, 4H), 1.51 (d, 3H, J=7.1 Hz), 1.29 (s, 9H); IR (KBr) 3275, 2926, 1650, 1588, 1513, 1448, 1335 cm⁻¹; MS (FAB) m/z 505 (M+H)

Example 297

N-(6-tert-butyl-2-dipropylamino-pyridin-3-ylmethyl)-2-(3-fluoro-4-methylsulfonamido-phenyl)-propionamide

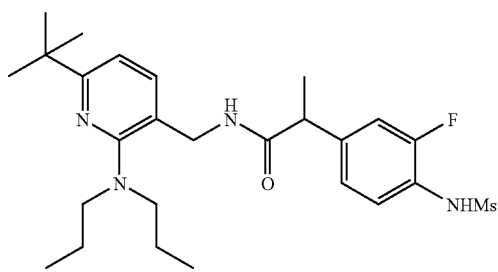

¹H NMR (300 MHz, CDCl₃) δ 7.51 (dd, 1H, J=8.3, 8.3 Hz), 7.29 (d, 1H, J=7.7 Hz), 7.17 (dd, 1H, J=11.3 Hz, 1.8 Hz), 7.08 (d, 1H, J=8.4 Hz), 6.85 (d, 1H, J=7.7 Hz), 6.74 (bs, 1H), 6.47 (bs, 1H), 4.47-4.33 (m, 2H), 3.49 (q, 1H, J=7.0 Hz), 3.07-2.96 (m, 7H), 1.52-1.34 (m, 7H), 1.29 (s, 9H), 0.82 (t, 6H, J=7.4

Hz); IR (KBr) 3290, 2961, 2871, 1650, 1513, 1456, 1335 cm$^{-1}$; MS (FAB) m/z 507 (M+H)

Example 298

N-(2-but-2-enyloxy-6-trifluoromethyl-pyridin-3-ylmethyl)-2-(3-fluoro-4-methylsulfonamido-phenyl)-propionamide

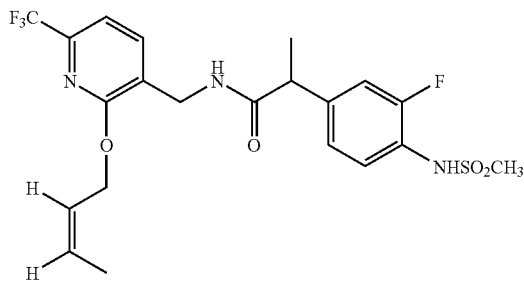

$^1$H NMR (300 MHz, CDCl$_3$) δ 7.59 (d, 1H, J=8.2 Hz), 7.52 (dd, 1H, J=8.3, 8.3 Hz), 7.20 (d, 1H, J=7.5 Hz), 7.09 (dd, 1H, J=11.5, 1.8 Hz), 7.06 (d, 1H, J=9.1 Hz), 6.48 (bs, 1H), 6.01 (bt, 1H), 5.76 (m, 1H), 5.58 (m, 1H), 4.94 (d, 2H, J=6.8 Hz), 4.37 (d, 2H, J=6.0 Hz), 3.50 (q, 1H, J=7.0 Hz), 3.02 (s, 3H), 1.77 (d, 3H, J=7.0 Hz), 1.48 (d, 3H, J=7.1 Hz); IR (neat) 3289, 2928, 1655, 1602, 1512, 1462, 1422, 1373, 1334, 1265, 1156, 973, 904, 833 cm$^{-1}$; MS (FAB) m/z 490 (M+H)

Example 299

2-(3-fluoro-4-methylsulfonamido-phenyl)-N-(2-pent-2-enyloxy-6-trifluoromethyl-pyridin-3-ylmethyl)-propionamide

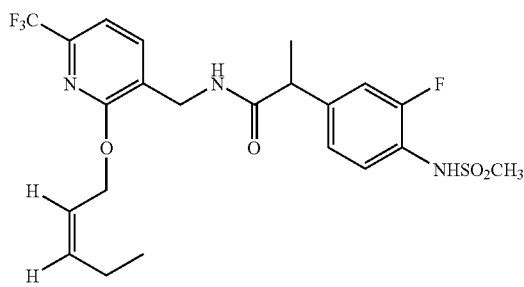

$^1$H NMR (300 MHz, CDCl$_3$) δ 7.59 (d, 1H, J=7.4 Hz), 7.51 (dd, 1H, J=8.4, 8.4 Hz), 7.20 (d, 1H, J=8.4 Hz), 7.09 (dd, 1H, J=11.5, 1.8 Hz), 7.06 (d, 1H, J=9.2 Hz), 6.49 (s, 1H), 6.01 (bt, 1H), 5.67 (m, 1H), 5.52 (m, 1H), 4.92 (d, 2H, J=4.7 Hz), 4.37 (d, 2H, J=6.4 Hz), 3.50 (q, 1H, J=6.8 Hz), 3.03 (s, 3H), 2.20 (m, 2H), 1.48 (d, 3H, J=7.1 Hz), 1.02 (t, 3H, J=7.5 Hz); IR (neat) 3292, 2971, 1656, 1601, 1512, 1462, 1422, 1338, 1266, 1157, 977, 903, 759 cm$^{-1}$; MS (FAB) m/z 504 (M+H)

Example 300

2-(3-fluoro-4-methylsulfonamido-phenyl)-N-(2-pent-1-enyl-6-trifluoromethyl-pyridin-3-ylmethyl)-propionamide

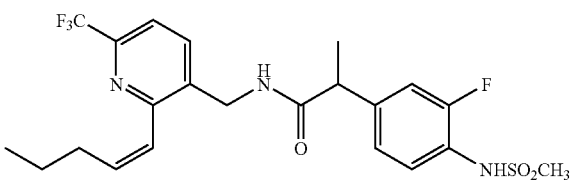

$^1$H NMR (300 MHz, CDCl$_3$) δ 7.62 (d, 1H, J=8.1 Hz), 7.53 (dd, 1H, J=8.3, 8.3 Hz), 7.45 (d, 1H, J=7.9 Hz), 7.14 (dd, 1H, J=11.2, 2.0 Hz), 7.08 (d, 1H, J=8.4 Hz), 6.52 (bs, 1H), 5.73 (bt, 1H), 6.41 (dt, 1H, J=11.6 Hz), 6.05 (m, 1H), 5.73 (bt, 1H), 4.47 (m, 2H), 3.53 (q, 1H, J=7.1 Hz), 3.03 (s, 3H), 2.44 (m, 2H), 1.51 (d, 3H, J=7.1 Hz), 1.47 (m, 2H), 0.92 (t, 3H, J=7.3 Hz); IR (neat) 3296, 2927, 1652, 1513, 1458, 1339, 1280, 1156, 973 cm$^{-1}$; MS (FAB) m/z 488 (M+H)

Example 301

2-(3-fluoro-4-methylsulfonamido-phenyl)-N-(2-pent-1-enyl-6-trifluoromethyl-pyridin-3-ylmethyl)-propionamide

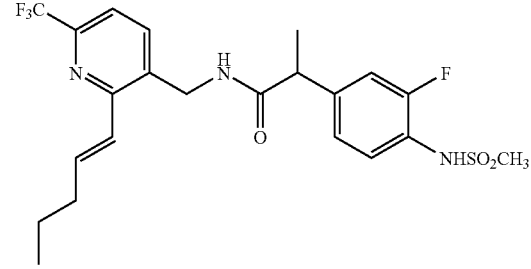

$^1$H NMR (300 MHz, CDCl$_3$) δ 7.58 (d, 1H, J=7.9 Hz), 7.52 (dd, 1H, J=8.3, 8.3 Hz), 7.41 (d, 1H, J=7.9 Hz), 7.15 (dd, 1H, J=11.2, 2.0 Hz), 7.08 (d, 1H, J=7.9 Hz), 6.51 (dt, 2H, J=15.0 Hz), 5.64 (bt, 1H), 4.52 (m, 1H), 3.53 (q, 1H, J=7.4 Hz), 3.03 (s, 3H), 2.24 (m, 2H), 1.59-1.45 (m, 5H), 0.97 (t, 3H, J=7.3 Hz); IR (neat) 3291, 2930, 1652, 1587, 1513, 1456, 1412, 1339, 1278, 1156, 973, 936, 838 cm$^{-1}$;

MS (FAB) m/z 488 (M+H)

Example 302

2-(3-fluoro-4-methylsulfonamido-phenyl)-N-(4-methyl-2-pentyloxy-6-trifluoromethyl-pyridin-3-ylmethyl)-propionamide

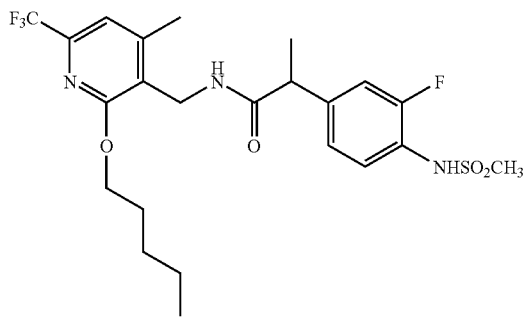

¹H NMR (300 MHz, CDCl₃) δ 7.50 (dd, 1H, J=8.3, 8.3 Hz), 7.13-7.01 (m, 3H), 3H), 6.03 (bt, 1H), 4.42 (m, 2H), 4.29 (m, 2H), 3.45 (q, 1H, J=7.0 Hz), 3.02 (s, 3H), 2.49 (s, 3H), 1.69 (m, 2H), 1.45 (d, 3H, J=7.1 Hz), 1.35 (m, 2H), 1.25 (m, 2H), 0.98-0.87 (m, 5H); IR (neat) 3291, 2926, 1649, 1512, 1459, 1409, 1341, 1291, 1245, 1158, 972, 912, 766 cm⁻¹; MS (FAB) m/z 520 (M+H)

Example 303

2-(3-fluoro-4-methylsulfonamido-phenyl)-N-{2-[2-(4-fluoro-phenyl)-ethyl]-6-trifluoromethyl-pyridin-3-ylmethyl}-propionamide

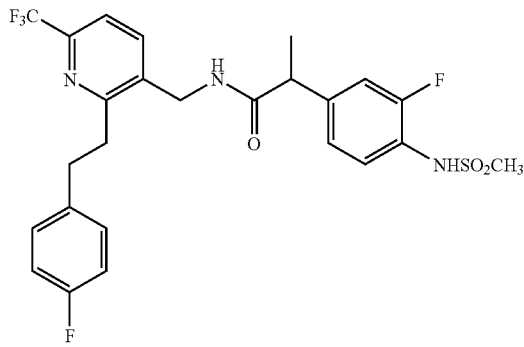

¹H NMR (300 MHz, CDCl₃) δ 7.35-7.56 (m, 3H), 7.02-7.17 (m, 4H), 6.88-6.97 (m, 2H), 6.54 (bs, 1H), 5.49 (bt, 1H), 4.24-4.40 (m, 2H), 3.46 (q, 1H, J=7.0 Hz), 3.00-3.12 (m, 7H), 1.49 (d, 3H, J=7.1 Hz); IR (KBr) 3296, 1652, 1511, 1456, 1338, 1157, 972, 911, 832, 734 cm⁻¹; MS (FAB) m/z 542 (M+H)

Example 304

N-(4-acetyl-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide

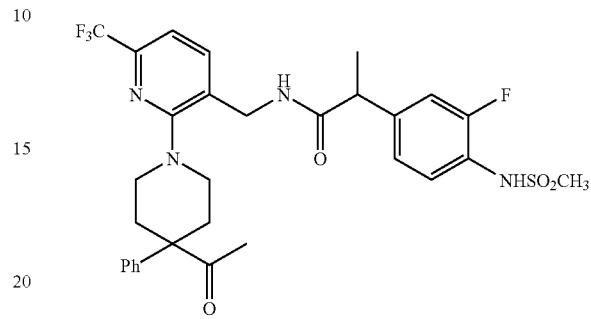

¹H NMR (300 MHz, CDCl₃) δ 7.44-7.53 (m, 2H), 7.27-7.43 (m, 5H), 7.21 (d, 1H, J=7.7 Hz), 7.11 (m, 1H), 7.05 (d, 1H, J=8.6 Hz), 6.50 (bs, 1H), 6.12 (bt, 1H), 4.46 (d, 2H, J=5.7 Hz), 3.55 (q, 1H, J=7.0 Hz), 3.19-3.32 (m, 2H), 2.97-3.10 (m, 5H), 2.41-2.54 (m, 2H), 2.05-2.20 (m, 2H), 1.95 (s, 3H), 1.52 (d, 3H, J=7.0 Hz); IR (KBr) 2928, 1699, 1652, 1592, 1512, 1455, 1420, 1336, 1159, 965, 910, 733 cm⁻¹;

MS (FAB) m/z 621 (M+H)

Example 307

2-(3-fluoro-4-methylsulfonamido-phenyl)-N-[4-(phenyl-propionyl-amino)-6'-trifluoromethyl-3,4,5,6-tetrahydro-2H-[1,2']bipyridinyl-3'-ylmethyl]-propionamide

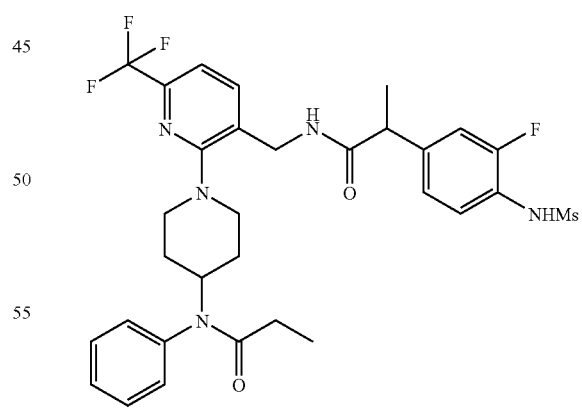

¹H NMR (300 MHz, CDCl₃) δ 7.42-7.52 (m, 6H), 7.05-7.19 (m, 4H), 6.99 (d, 1H, J=8.1 Hz), 6.16 (bt, 1H), 4.75 (m, 1H), 4.36 (d, 2H, J=5.7 Hz), 4.12 (q, 2H, J=7.2 Hz), 3.48 (q, 1H, J=6.9 Hz), 3.34 (m, 2H), 3.02 (s, 3H), 2.92 (m, 2H), 1.90 (m, 2H), 1.46 (d, 3H, J=6.9 Hz), 1.25 (t, 3H, J=7.2 Hz); IR (KBr) 2927, 1639, 1592, 1509, 1456, 1414, 1373, 1337, 1275, 1158, 959, 705 cm⁻¹; MS (FAB) m/z 650 (M+H)

Example 308

N-[2-(4-dimethylamino-phenyl)-6-trifluoromethyl-pyridin-3-ylmethyl]-2-(3-fluoro-4-methylsulfonamido-phenyl)-propionamide

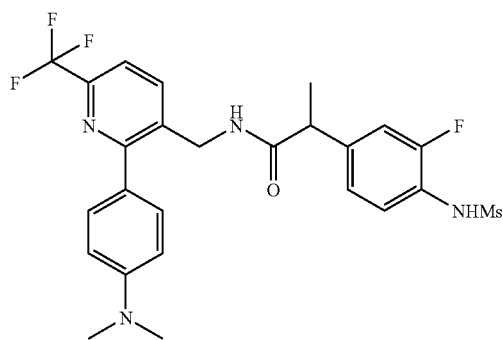

$^1$H NMR (300 MHz, CDCl$_3$) δ 7.74 (d, 1H, J=7.8 Hz), 7.53 (dd, 1H, J=8.1, 8.1 Hz), 7.48 (d, 2H, J=8.7 Hz), 7.31 (d, 1H, J=7.8 Hz), 7.02 (dd, 1H, J=11.1, 1.8 Hz), 6.97 (d, 1H, J=8.1 Hz), 6.72 (d, 1H, 8.7 Hz) (m, 6H), 6.58 (bs, 1H), 5.58 (bt, 1H), 4.57 (d, 2H, J=5.7 Hz), 3.44 (q, 1H, J=6.9 Hz), 3.01 (s, 6H), 2.96 (s, 3H), 1.44 (d, 3H, J=6.9 Hz); IR (KBr) 3291, 2926, 1658, 1611, 1514, 1454, 1403, 1339, 1265, 1157, 972, 825, 736 cm$^{-1}$; MS (FAB) m/z 539 (M+H)

Example 309

2-[3-fluoro-4-(propan-2-sulfonylamino)-phenyl]-N-(4-methyl-6'-trifluoromethyl-3,4,5,6-tetrahydro-2H-[1,2']bipyridinyl-3'-ylmethyl)-propionamide

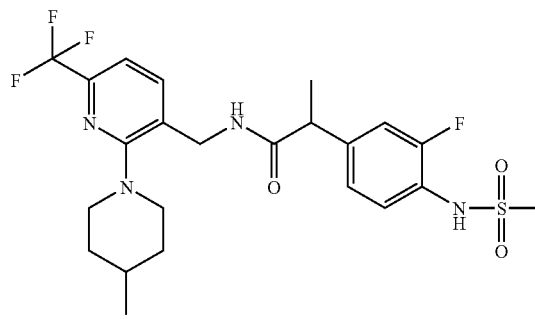

$^1$H NMR (300 MHz, CDCl$_3$) δ 7.56 (dd, 1H, J=8.1, 8.1 Hz), 7.6 (d, 1H, J=7.5 Hz), 7.18 (d, 1H, J=7.5 Hz), 7.07 (dd, 1H, J=11.1, 1.8 Hz), 7.05 (d, 1H, J=8.1 Hz), 6.56 (bs, 1H), 6.33 (bt, 1H), 4.46 (d, 1H, J=5.7 Hz), 3.55 (q, 1H, J=6.9 Hz), 3.20-3.34 (m, 3H), 2.81 (m, 2H), 1.71 (m, 3H), 1.50 (d, 3H, J=6.9 Hz), 1.39 (d, 6H, J=6.9 Hz), 0.97 (d, 3H, J=6.3 Hz); IR (KBr) 3273, 2923, 1657, 1592, 1511, 1458, 1419, 1332, 1270, 1142, 909, 732 cm$^{-1}$; MS (FAB) m/z 545 (M+H)

Example 310

2-[3-fluoro-4-(2,2,2-trifluoro-ethansulfonylamino)-phenyl]-N-(4-methyl-6'-trifluoromethyl-3,4,5,6-tetrahydro-2H-[1,2']bipyridinyl-3'-ylmethyl)-propionamide

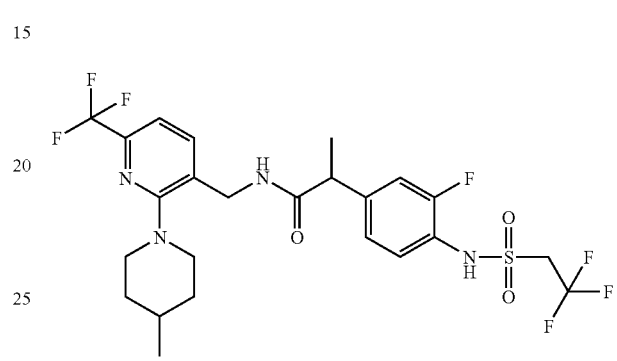

$^1$H NMR (300 MHz, CDCl$_3$) δ 7.48-7.53 (m, 2H), 7.21 (d, 1H, J=7.5 Hz), 7.16 (d, 1H, J=11.1 Hz), 7.09 (d, 1H, J=8.1 Hz), 6.41 (bt, 1H), 4.48 (d, 2H, J=5.7 Hz), 3.84 (m, 2H), 3.67 (q, 1H, J=6.9 Hz), 3.30 (m, 2H), 2.82 (m, 2H), 1.72 (m, 3H), 1.53 (d, 3H, J=6.9 Hz), 1.25 (m, 2H), 0.98 (d, 3H, J=6.6 Hz); IR (neat) 2924, 1657, 1592, 1512, 1456, 1418, 1358, 1253, 1169, 1134, 1086, 944 cm$^{-1}$; MS (FAB) m/z 585 (M+H)

Example 311

N-[2-(2,6-dimethyl-morpholin-4-yl)-6-trifluoromethyl-pyridin-3-ylmethyl]-2-(3-fluoro-4-methylsulfonamido-phenyl)-propionamide

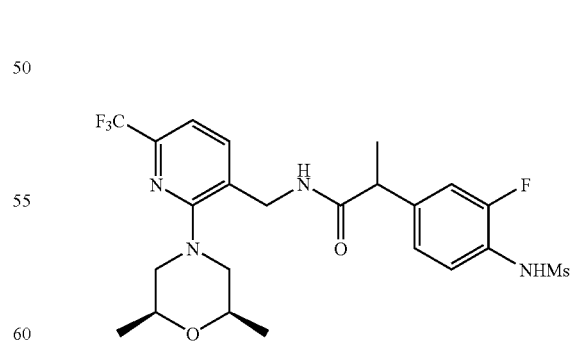

$^1$H NMR (300 MHz, CDCl$_3$) δ 7.48-7.52 (m, 2H), 7.10-7.25 (m, 3H), 6.52 (bs, 1H), 6.06 (bt, 1H), 4.47 (d, 2H, J=5.7 Hz), 3.70 (m, 2H), 3.58 (q, 1H, J=6.9 Hz), 3.16 (m, 2H), 3.04 (s, 3H), 2.64 (m, 2H), 1.55 (d, 3H, J=6.9 Hz), 1.19 (d, 6H,

Example 312

2-(3-fluoro-4-trifluoromethylsulfonamido-phenyl)-N-(4-methyl-6'-trifluoromethyl-3,4,5,6-tetrahydro-2H-[1,2']bipyridinyl-3'-ylmethyl)-propionamide

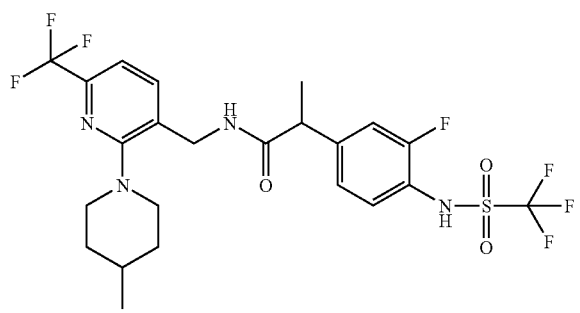 [SMILES: CC1CCN(c2nc(C(F)(F)F)ccc2CNC(=O)C(C)c2ccc(NS(=O)(=O)C(F)(F)F)c(F)c2)CC1]

$^1$H NMR (300 MHz, CDCl$_3$) δ 7.28-7.51 (m, 2H), 7.10-7.23 (m, 3H), 6.56 (bs, 1H), 6.06 (bt, 1H), 4.50 (d, 2H, J=5.7 Hz), 3.57 (q, 1H, J=6.9 Hz), 3.33 (m, 2H), 2.84 (m, 2H), 1.73 (m, 2H), 1.53 (d, 3H, J=6.9 Hz), 1.25 (m, 3H), 0.98 (d, 3H, J=6.0 Hz); IR (neat) 2924, 1656, 1593, 1512, 1456, 1423, 1377, 1338, 1232, 1203, 1142, 956, 738 cm$^{-1}$; MS (FAB) m/z 571 (M+H)

Example 313

2-(3-fluoro-4-aminosulfonylamino-phenyl)-N-(4-methyl-6'-trifluoromethyl-3,4,5,6-tetrahydro-2H-[1,2']bipyridinyl-3'-ylmethyl)-propionamide

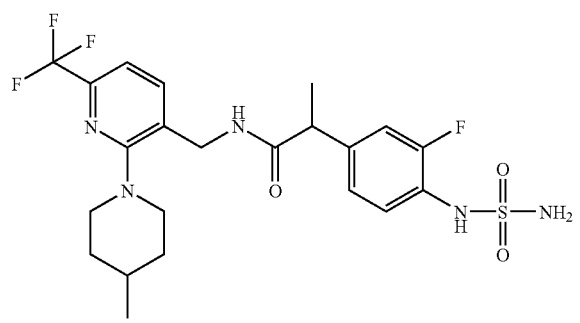 [SMILES: CC1CCN(c2nc(C(F)(F)F)ccc2CNC(=O)C(C)c2ccc(NS(N)(=O)=O)c(F)c2)CC1]

$^1$H NMR (300 MHz, CDCl$_3$) δ 7.46-7.51 (m, 2H), 7.19 (d, 1H, J=7.2 Hz), 7.05-7.10 (m, 2H), 6.83 (bs, 1H), 6.50 (bt, 1H), 5.04 (s, 2H), 4.46 (d, 2H, J=5.7 Hz), 3.57 (q, 1H, J=6.9 Hz), 3.27 (m, 2H), 2.81 (m, 2H), 1.78 (m, 2H), 1.51 (d, 3H, J=6.9 Hz), 1.25 (m, 3H), 0.97 (d, 3H, J=6.0 Hz); IR (KBr) 3292, 2924, 1653, 1592, 1514, 1455, 1418, 1339, 1169, 944, 833, 736 cm$^{-1}$; MS (FAB) m/z 571 (M+H)

Example 314

N-[2-(1,1-dioxo-1l6-thiomorpholin-4-yl)-6-trifluoromethyl-pyridin-3-ylmethyl]-2-(3-fluoro-4-methylsulfonamido-phenyl)-propionamide

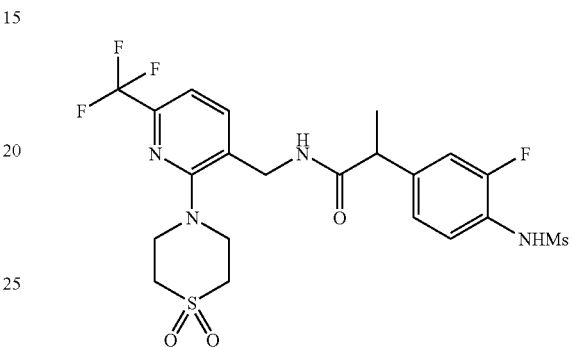

$^1$H NMR (300 MHz, CDCl$_3$) δ 7.50-7.56 (m, 2H), 7.33 (d, 1H, J=7.5 Hz), 7.09-7.17 (m, 2H), 5.94 (bt, 1H), 4.46 (d, 2H, J=5.7 Hz), 3.72 (m, 4H), 3.60 (q, 1H, J=6.9 Hz), 3.16 (m, 4H), 3.02 (s, 3H), 1.54 (d, 3H, J=6.9 Hz); IR (KBr) 3369, 2933, 1659, 1590, 1514, 1462, 1415, 1333, 1278, 1124, 974, 912, 732 cm$^{-1}$; MS (FAB) m/z 553 (M+H)

Example 315

N-(6'-difluoromethyl-4-methyl-3,4,5,6-tetrahydro-2H-[1,2']bipyridinyl-3'-ylmethyl)-2-(3-fluoro-4-methylsulfonamido-phenyl)-propionamide

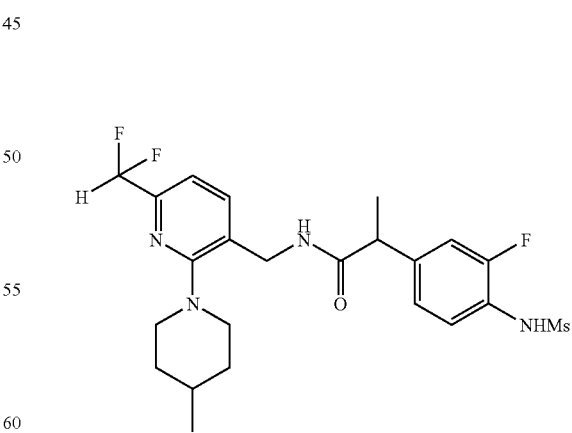

$^1$H NMR (300 MHz, CDCl$_3$) δ 7.47-7.54 (m, 2H), 7.06-7.19 (m, 3H), 6.48 (t, 1H, J=55.0 Hz), 6.41 (bs, 1H), 6.06 (bt, 1H), 4.46 (d, 2H, J=5.7 Hz), 3.55 (q, 1H, J=6.9 Hz), 3.25 (m, 2H), 3.02 (s, 3H), 2.79 (m, 2H), 1.71 (m, 2H), 1.52 (d, 3H, J=6.9 Hz), 1.25 (m, 3H), 0.97 (d, 6H, J=6.0 Hz); IR (KBr)

3291, 2922, 1652, 1589, 1512, 1421, 1334, 1158, 1087, 1041, 970, 795 cm$^{-1}$; MS (FAB) m/z 499 (M+H)

Example 316

N-(4,6'-dimethyl-3,4,5,6-tetrahydro-2H-[1,2']bipyridinyl-3'-ylmethyl)-2-(3-fluoro-4-methylsulfonamido-phenyl)-propionamide

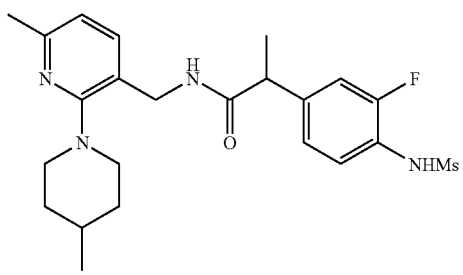

$^1$H NMR (300 MHz, CDCl$_3$) δ 7.50 (dd, 1H, J=8.1, 8.1 Hz), 7.28 (d, 1H, J=7.5 Hz), 7.13 (dd, 1H, J=8.1, 1.8 Hz), 7.07 (d, 1H, J=8.1 Hz), 6.75 (d, 1H, J=7.5 Hz), 6.72 (bs, 1H), 6.46 (bt, 1H), 4.40 (d, 2H, J=5.7 Hz), 3.51 (q, 1H, J=6.9 Hz), 3.18 (m, 2H), 3.02 (s, 3H), 2.77 (m, 2H), 2.42 (s, 3H), 1.72 (m, 2H), 1.50 (d, 3H, J=6.9 Hz), 1.26 (m, 3H), 0.97 (d, 6H, J=6.0 Hz); IR (KBr) 3289, 2922, 1651, 1584, 1511, 1453, 1374, 1333, 1157, 1115, 971, 735 cm$^{-1}$; MS (FAB) m/z 463 (M+H)

Example 317

2-(3-fluoro-4-methylsulfonamido-phenyl)-N-(4-phenyl-6'-trifluoromethyl-3,6-dihydro-2H-[1,2']bipyridinyl-3'-ylmethyl)-propionamide

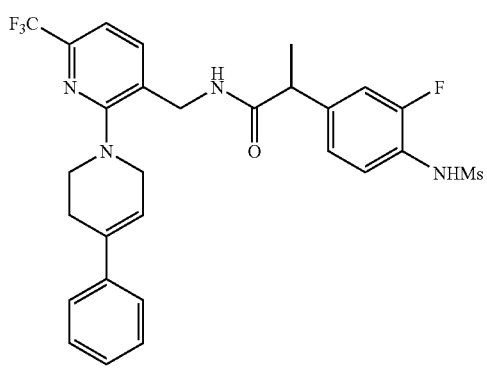

$^1$H NMR (300 MHz, CDCl$_3$) δ 7.21-7.54 (m, 7H), 7.02-7.16 (m, 3H), 6.63 (bs, 1H), 6.35 (bt, 1H), 6.18 (m, 1H), 4.52 (d, 2H, J=5.7 Hz), 3.87 (d, 2H, J=2.7 Hz), 3.36-3.59 (m, 3H), 2.99 (s, 3H), 2.67 (m, 2H), 1.52 (d, 3H, J=6.9 Hz) IR (KBr)

3293, 2930, 1656, 1592, 1512, 1421, 1336, 1274, 1229, 1157, 970, 833, 755, 697 cm$^{-1}$; MS (FAB) m/z 577 (M+H)

Example 318

N-(4,4'-dimethyl-6'-trifluoromethyl-3,4,5,6-tetrahydro-2H-[1,2']bipyridinyl-3'-ylmethyl)-2-(3-fluoro-4-methylsulfonamido-phenyl)-propionamide

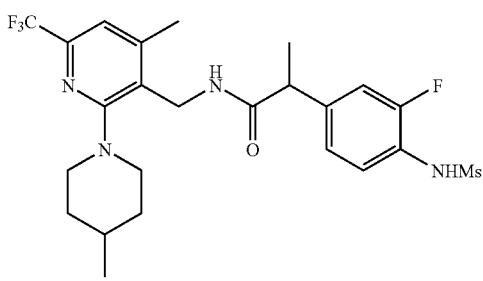

$^1$H NMR (300 MHz, CDCl$_3$) δ 7.48 (dd, 1H, J=8.1, 8.1 Hz), 7.14 (s, 1H), 7.02-7.07 (m, 2H), 6.80 (bs, 1H), 4.52 (d, 2H, J=5.7 Hz), 3.48 (q, 1H, J=6.9 Hz), 3.17 (m, 1H), 2.01-3.04 (m, 4H), 2.79 (m, 2H), 2.38 (m, 2H), 1.70 (m, 2H), 1.47 (d, 3H, J=6.9 Hz), 1.13-1.25 (m, 3H), 0.97 (d, 3H, J=6.3 Hz); IR (KBr) 3302, 2923, 1644, 1512, 1451, 1408, 1333, 1280, 1159, 975, 759 cm$^{-1}$; MS (FAB) m/z 531 (M+H)

Example 319

N-[2-(4-cyclohexyl-piperazin-1-yl)-4-trifluoromethyl-benzyl]-2-(3-fluoro-4-methylsulfonamido-phenyl)-propionamide

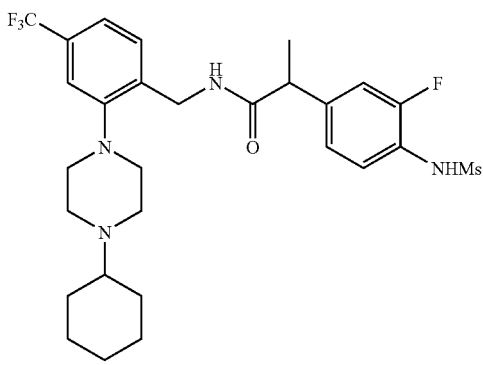

$^1$H NMR (300 MHz, CDCl$_3$) δ 7.52 (t, 1H, J=8.2 Hz), 7.31 (s, 1H), 7.26~7.28 (m, 2H), 7.08~7.16 (m, 2H), 6.42 (bs, 1H), 4.52 (d, 2H, J=5.9), 3.54 (q, 1H, J=7.1 Hz), 3.0 (s, 3H), 2.88~2.95 (m, 4H), 2.67 (s, 3H), 1.81~1.90 (m, 3H), 1.64 (m, 2H), 1.52 (d, 3H, J=7.0 Hz), 1.20~1.30 (m, 5H), 0.89~0.92

Example 320

N-(4'-tert-butyl-5-trifluoromethyl-biphenyl-2-ylmethyl)-2-(3-fluoro-4-methylsulfonamido-phenyl)-propionamide

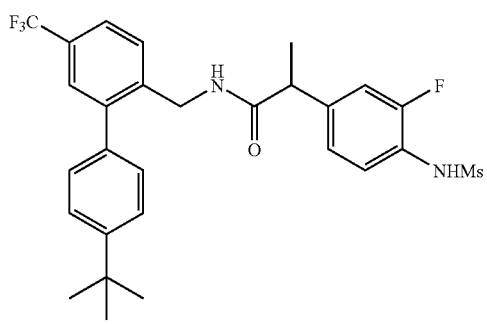

$^1$H NMR (300 MHz, CDCl$_3$) δ 7.28~7.55 (m, 6H), 7.16 (d, 2H, J=7.4 Hz), 7.07 (dd, 1H, J=11.2, 1.8 Hz), 6.97~7.02 (m, 1H), 5.51 (bt, 1H), 4.41~4.51 (m, 2H), 3.43 (q, 1H, J=7.1 Hz), 3.0 (s, 3H), 1.44 (d, 3H, J=7.1 Hz), 1.36 (s, 9H); IR (KBr) 2965, 1460, 1259, 1078, 979, 908, 836, 734 cm$^{-1}$; MS (FAB) m/z 551 (M+H)

Example 321

2-(3-fluoro-4-methylsulfonamido-phenyl)-N-(4'-methoxy-5-trifluoromethyl-biphenyl-2-ylmethyl)-propionamide

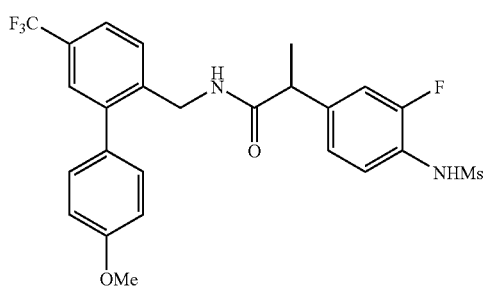

$^1$H NMR (300 MHz, CDCl$_3$) δ 7.46~7.54 (m, 3H), 7.39 (d, 1H, J=8.0 Hz), 7.14 (dd, 2H, J=6.4, 2.0 Hz), 7.05 (dd, 1H, J=11.0, 1.8 Hz), 6.99 (d, 1H, J=8.3 Hz), 6.93 (dd, 2H, J=6.8, 2.2 Hz), 5.46 (bt, 1H), 4.43 (t, 2H, J=3.7 Hz), 3.86 (s, 3H), 3.43 (q, 1H, J=7.5 Hz), 3.02 (s, 3H), 1.44 (d, 3H, J=7.0 Hz); IR (KBr) 3295, 1422, 1252, 1042, 973, 907, 835, 732 cm$^{-1}$; MS (FAB) m/z 525 (M+H)

Example 322

N-(3'-chloro-5-trifluoromethyl-biphenyl-2-ylmethyl)-2-(3-fluoro-4 methylsulfonamido-phenyl)-propionamide

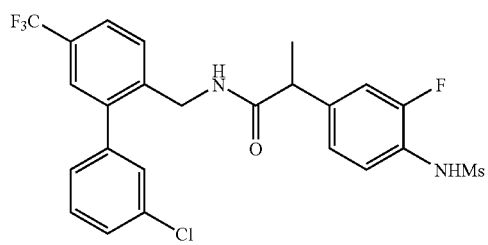

$^1$H NMR (300 MHz, CDCl$_3$) δ 7.58~7.32 (m, 6H), 7.23 (m, 1H), 7.14~7.00 (m, 3H), 5.61 (b t, 1H), 4.39 (t, 2H, J=5.5 Hz), 3.46 (q, 1H, J=7.1 Hz), 3.0 (s, 3H), 1.45 (d, 3H, J=7.1 Hz); IR (KBr) 3290, 1651, 1421, 1078, 1041, 974, 908, 732 cm$^{-1}$; MS (FAB) m/z 528 (M+H)

Example 323

2-(3-fluoro-4-methylsulfonamido-phenyl)-N-(3'-fluoro-5-trifluoromethyl-biphenyl-2-ylmethyl)-propionamide

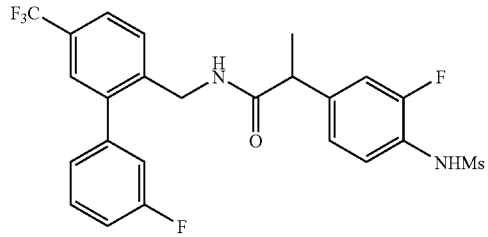

$^1$H NMR (300 MHz, CDCl$_3$) δ 7.38~7.59 (m, 5H), 7.00~7.09 (m, 4H), 6.93 (d, 1H, J=10.4 Hz) 4.39 (m, 2H), 3.45 (q, 1H, J=7.3 Hz), 3.03 (s, 3H), 1.46 (d, 3H, J=7.1 Hz); IR (KBr) 3289, 1586, 1446, 1277, 1078, 973, 907, 733 cm$^{-1}$; MS (FAB) m/z 513 (M+H)

Example 324

N-(3'-chloro-4'-fluoro-5-trifluoromethyl-biphenyl-2-ylmethyl)-2-(3-fluoro-4-methylsulfonamido-phenyl)-propionamide

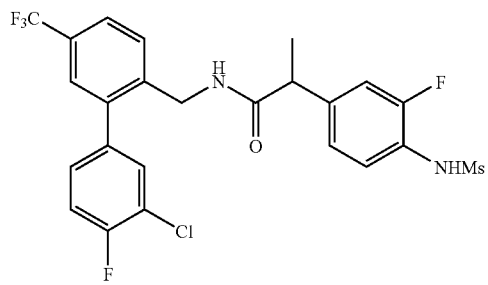

¹H NMR (300 MHz, CDCl₃) δ 7.49~7.59 (m, 2H), 7.37~7.44 (m, 2H), 7.02~7.22 (m, 5H), 5.54 (bt, 1H), 4.38 (d, 2H, J=6.0 Hz), 3.49 (q, 1H, J=7.0 Hz), 3.04 (s, 3H), 1.47 (d, 3H, J=7.1 Hz); IR (KBr) 3246, 1420, 1265, 1077, 973, 908, 828, 732 cm⁻¹;

MS (FAB) m/z 548 (M+H)

Example 325

N-(3',4'-dimethoxy-5-trifluoromethyl-biphenyl-2-ylmethyl)-2-(3-fluoro-4-methylsulfonamido-phenyl)-propionamide

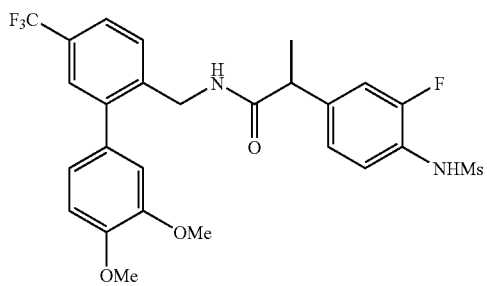

¹H NMR (300 MHz, CDCl₃) δ 7.43~7.53 (m, 3H), 7.38 (d, 1H, J=8.1 Hz), 7.07 (dd, 1H, J=11.3, 2.0 Hz), 7.0 (d, 1H, J=8.2 Hz), 6.90 (d, 1H, J=8.2 Hz), 6.74~6.77 (m, 2H), 5.72 (bs, 1H), 4.44 (m, 2H), 3.92 (s, 3H), 3.86 (s, 3H), 3.46 (q, 1H, J=7.1 Hz), 3.01 (s, 3H), 1.44 (d, 3H, J=7.1 Hz); IR (KBr) 2936, 1423, 1078, 1025, 974, 908, 765, 732 cm⁻¹; MS (FAB) m/z 555 (M+H)

Example 326

N-[2-(3,4-dimethoxy-phenyl)-6-trifluoromethyl-pyridin-3-ylmethyl]-2-(3-fluoro-4-methylsulfonamido-phenyl)-propionamide

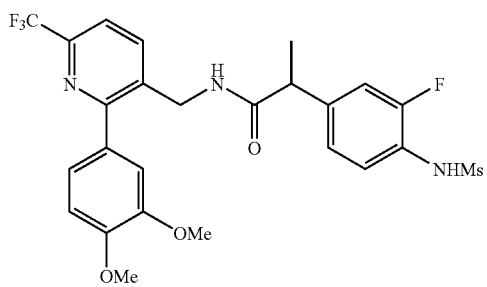

¹H NMR (300 MHz, CDCl₃) δ 7.76 (d, 1H, J=8.1 Hz), 7.57 (d, 1H, J=8.0 Hz), 7.45 (t, 1H, J=8.3 Hz), 6.79~7.08 (m, 5H), 5.90 (bt, 1H), 4.53 (d, 2H, J=5.5 Hz), 3.91 (s, 3H), 3.88 (s, 3H), 3.49 (q, 1H, J=6.9 Hz), 3.02 (s, 3H), 1.43 (d, 3H, J=7.2 Hz); IR (KBr) 3271, 2937, 1587, 1416, 1025, 972, 913 cm⁻¹; MS (FAB) m/z 556 (M+H)

Example 327

4-(3-{[2-(3-fluoro-4-methylsulfonamido-phenyl)-propionylamino]-methyl}-6-trifluoromethyl-pyridin-2-yloxymethyl)-piperidine-1-carbonic acid tert-butyl ester

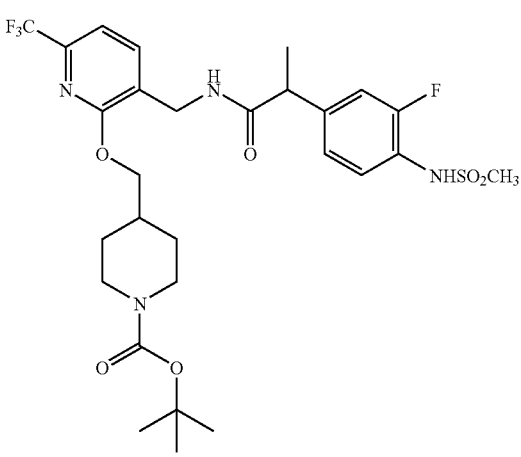

¹H NMR (CDCl₃) δ 7.60 d, 1H, J=7.5 Hz), 7.52 (dd, 1H, J=8.4, 8.4 Hz), 7.21 (d, 1H, J=7.5 Hz), 7.12-7.05 (m, 2H), 5.83 (bs, N H), 4.37 (d, 2H, J=5.9 Hz), 4.25-4.07 (m, 4H), 3.53 (q, 1H, J=6.4 Hz), 3.04 (s, 3H), 2.78-2.63 (m, 2H), 1.90 (m, 1H), 1.68-1.55 (m, 2H), 1.48 (s, 9H), 1.25-1.05 (m, 2H); IR (neat) 3303, 2935, 1665, 1426, 1359, 1271, 1157, 757 cm⁻¹; MS (FAB) m/z 633 (M+H)

Example 331

N-(2-dipropylamino-6-trifluoromethyl-pyridin-3-yl methyl)-2-(4-methylsulfonamido-3-methyl-phenyl)-propionamide

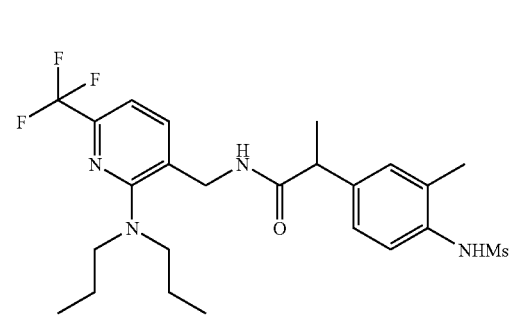

¹H NMR (300 MHz, CDCl₃) δ 7.36-7.41 (m, 2H), 7.08-7.18 (m, 4H), 6.29 (bt, 1H), 4.42 (d, 2H, J=5.7 Hz), 3.56 (q, 1H, J=6.9 Hz), 3.09 (t, 4H, J=7.5 Hz), 2.99 (s, 3H), 2.32 (s, 3H), 2.82 (m, 2H), 1.52 (d, 3H, J=6.9 Hz), 1.43 (m, 4H), 0.82

(t, 6H, J=7.5 Hz); IR (neat) 3272, 2965, 1655, 1594, 1503, 1460, 1419, 1331, 1152, 1027, 895, 825, 762 cm⁻¹; MS (FAB) m/z 563 (M+H)

Example 339

2-(3-fluoro-4-methylsulfonamido-phenyl)-N-[6-trifluoromethyl-2-(4-trifluoromethyl-cyclohexyloxy)-pyridin-3-ylmethyl]-propionamide

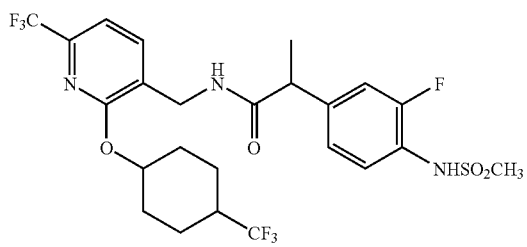

$^1$H NMR (CDCl$_3$) δ 7.59 (d, 1H, J=7.0 Hz), 7.51 (dd, 1H, J=8.2, 8.2 Hz), 7.20 (d, 1H, J=7.5 Hz), 7.13-7.05 (m, 2H), 6.50 (bs, NH), 5.91 (bt, NH), 5.43 (m, 1H), 4.39 (m, 2H), 3.51 (q, 1H, J=6.6 Hz), 3.03 (s, 3H), 2.20-2.08 (m, 3H), 1.85-1.77 (m, 2H), 1.63-1.50 (m, 4H), 1.49 (d, 3H, J=7.1 Hz); IR (neat) 3293, 2953, 1658, 1513, 1422, 1343, 1264, 1141, 970 cm⁻¹; MS (FAB) m/z 586 (M+H)

Example 340

2-(3-fluoro-4-methylsulfonamido-phenyl)-N-[6-trifluoromethyl-2-(4-trifluoromethyl-cyclohexyloxy)-pyridin-3-ylmethyl]-propionamide

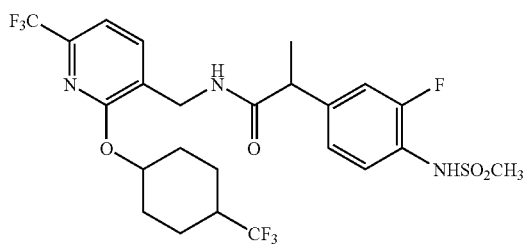

$^1$H NMR (CDCl$_3$) δ 7.57-7.50 (m, 2H), 7.19 (d, 1H, J=7.3 Hz), 7.13-7.06 (m, 2H), 5.90 (bt, NH), 5.03 (m, 1H), 4.36 (m, 2H), 3.53 (q, 1H, J=7.4 Hz), 3.05 (s, 3H), 2.28-2.00 (m, 4H), 1.62-1.25 (m, 5H), 1.50 (d, 3H, J=7.1 Hz); IR (neat) 3288, 2952, 1658, 1512, 1422, 1365, 1338, 1275, 1156, 975 cm⁻¹; MS (FAB) m/z 586 (M+H)

Example 341

4-(3-{[2-(3-fluoro-4-methylsulfonamido-phenyl)-propionylamino]-methyl}-6-trifluoromethyl-pyridin-2-yloxy)-piperidine-1-carbonic acid tert-butyl ester

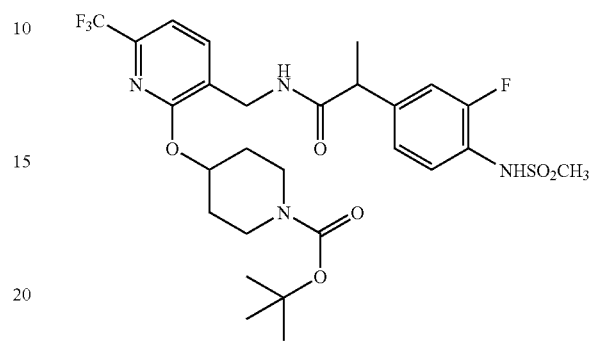

$^1$H NMR (CDCl$_3$) δ 7.60 (d, 1H, J=7.3 Hz), 7.50 (dd, 1H, J=8.2, 8.2 Hz), 7.20 (d, 1H, J=7.3 Hz), 7.13-7.04 (m, 2H), 5.87 (bt, NH), 5.24 (m, 1H), 4.36 (d, 2H), 3.70-3.62 (m, 2H), 3.54 (q, 1H, J=7.7 Hz), 3.28-3.17 (m, 2H), 3.04 (s, 3H), 1.98-1.88 (m, 2H), 1.54-1.40 (m, 2H), 1.51 (d, 3H), 1.50 (s, 9H); IR (neat) 3301, 2977, 1665, 1420, 1337, 1276, 1163, 1027 cm⁻¹; MS (FAB) m/z 619 (M+H)

Example 342

4-[(3-{[2-(3-fluoro-4-methylsulfonamido-phenyl)-propionylamino]-methyl}-6-trifluoromethyl-pyridin-2-ylamino)-methyl]-piperidine-1-carbonic acid tert-butyl ester

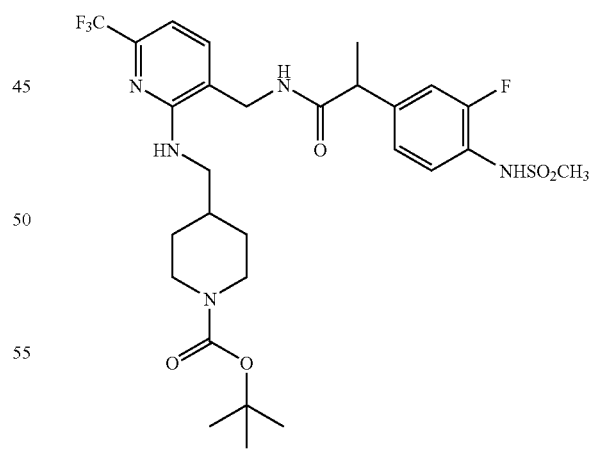

$^1$H NMR (CDCl$_3$) δ 7.48 (dd, 1H, J=8.2, 8.2 Hz), 7.25 (d, 1H), 7.16 (d, 1H), 7.06 (d, 1H), 6.77 (d, 1H, J=7.3 Hz), 6.21 (bs, NH), 5.93 (bs, NH), 4.32 (m, 2H), 4.06 (m, 2H), 3.49 (q, 1H, J=7.3 Hz), 3.32 (m, 2H), 2.66 (m, 2H), 1.76 (m, 2H), 1.51 (d, 3H, J=7.0 Hz), 1.46 (s, 9H); IR (neat) 3303, 2927, 1658, 1611, 1515, 1428, 1335, 1161, 734 cm⁻¹; MS (FAB) m/z 632 (M+H)

Example 343

2-(3-fluoro-4-methylsulfonamido-phenyl)-N-[2-(piperidin-4-ylmethoxy)-6-trifluoromethyl-pyridin-3-ylmethyl]-propionamide

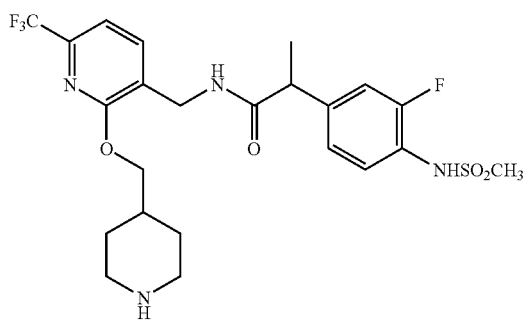

$^1$H NMR (CDCl$_3$) δ 7.58 (d, 1H, J=7.9 Hz), 7.43 (dd, 1H, J=8.3, 8.3 Hz), 7.29 (d, 1H, J=7.4 Hz), 7.22-7.15 (m, 2H), 4.47-4.23 (m, 4H), 3.73 (q, 1H, J=7.1 Hz), 3.43-3.36 (m, 2H), 3.05-2.93 (m, 2H), 3.00 (s, 3H), 2.04-1.96 (m, 3H), 1.53-1.45 (m, 2H), 1.46 (d, 3H, J=7.1 Hz); IR (neat) 3405, 2923, 1674, 1512, 1425, 1334, 1270, 1153 cm$^{-1}$; MS (FAB) m/z 533 (M+H)

Example 344

2-(3-fluoro-4-methylsulfonamido-phenyl)-N-[2-(piperidin-4-yloxy)-6-trifluoromethyl-pyridin-3-ylmethyl]-propionamide

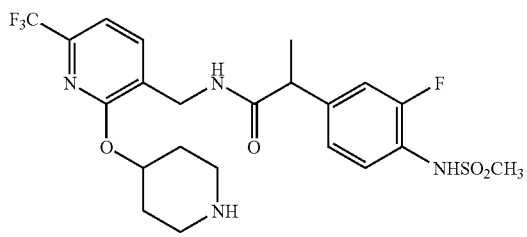

$^1$H NMR (CDCl$_3$) δ 7.58 (d, 1H, J=7.5 Hz), 7.41 (dd, 1H, J=8.3, 8.3 Hz), 7.27 (d, 1H, J=7.5 Hz), 7.19-7.11 (m, 2H), 5.29 (m, 1H), 4.36 (m, 2H), 3.71 (q, 1H, J=7.0 Hz), 3.20 (m, 2H), 3.01-2.90 (m, 2H), 2.97 (s, 3H), 2.06 (m, 2H), 1.81 (m, 2H), 1.45 (d, 3H, J=7.1 Hz); IR (neat) 3397, 2923, 1657, 1505, 1421, 1292, 1115, 987 cm$^{-1}$; MS (FAB) m/z 519 (M+H)

Example 345

2-(3-fluoro-4-methylsulfonamido-phenyl)-N-(2-p-tolyloxy-6-trifluoromethyl-pyridin-3-ylmethyl)-propionamide

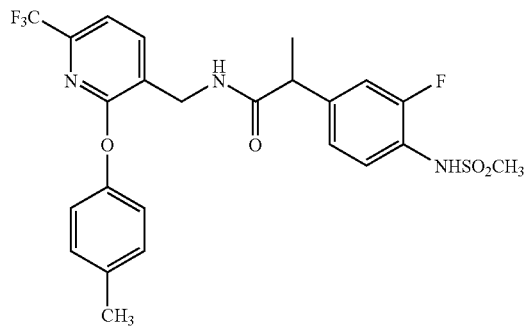

$^1$H NMR (300 MHz, CDCl$_3$) δ 7.74 (J=7.5 Hz), 7.47 (dd, 1H, J=8.4, 8.4 Hz), 7.31 (d, 1H, J=7.9 Hz), 7.18 (d, 2H, J=8.8 Hz), 7.01 (m, 2H), 6.91 (m, 2H), 4.49 (m, 2H), 3.58 (q, 1H, J=7.0 Hz), 2.94 (s, 3H), 1.49 (d, 3H, J=7.1 Hz); IR (neat) 3292, 1655, 1593, 1509, 1465, 1406, 1336, 1260, 1156, 972, 940, 831 cm$^1$; MS (FAB) m/z 526 (M+H)

Example 346

N-[2-(2-cyclohexyl-vinyl)-6-trifluoromethyl-pyridin-3-ylmethyl]-2-(3-fluoro-4-methylsulfonamido-phenyl)-propionamide

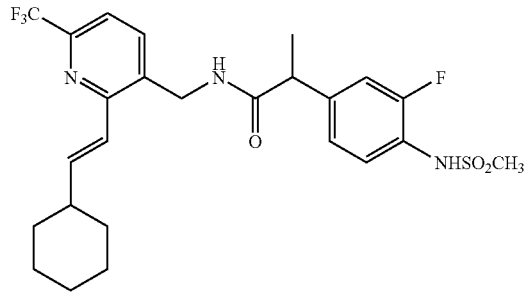

$^1$H NMR (300 MHz, CDCl$_3$) δ 7.57 (d, 1H, J=7.9 Hz), 7.52 (dd, 1H, J=8.3, 8.3 Hz), 7.41 (d, 1H, J=7.9 Hz), 7.15 (dd, 1H, J=11.3, 2.0 Hz), 7.08 (d, 1H, J=7.0 Hz), 6.49 (m, 2H), 5.64 (bt, 1H), 4.52 (m, 2H), 3.53 (q, 1H, J=7.0 Hz), 3.03 (s, 3H), 2.17 (m, 1H), 1.85-1.73 (m, 4H), 1.52 (d, 3H, J=7.1 Hz), 1.34-1.23 (m, 6H); IR (neat) 3292, 2927, 2853, 1651, 1588, 1513, 1452, 1412, 1340, 1157, 973, 843 cm$^{-1}$;

MS (FAB) m/z 528 (M+H)

Example 347

2-(3-fluoro-4-methylsulfonamido-phenyl)-N-(4-methyl-6'-trifluoromethyl-3,4,5,6-tetrahydro-2H-[1,2']bipyridinyl-3'-ylmethyl)-butyramide

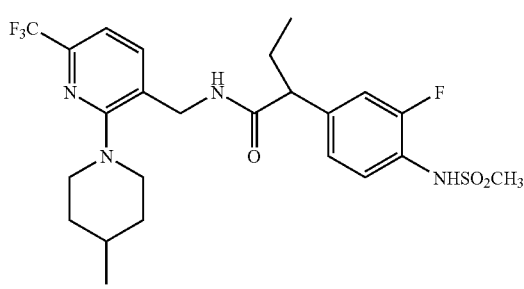

$^1$H NMR (300 MHz, CDCl$_3$) δ 7.51 (dd, 1H, J=8.3, 8.3 Hz), 7.49 (d, 1H, J=8.3 Hz), 7.18 (m, 2H), 7.08 (d, 1H, J=8.3 Hz), 6.51 (bs, 1H), 6.34 (bt, 1H), 4.47 (m, 2H), 3.31 (m, 2H), 3.21 (t, 1H, J=7.7 Hz), 3.03 (s, 3H), 2.83 (m, 2H), 2.16 (m, 1H), 1.80 (m, 1H), 1.73 (m, 2H), 1.55 (m, 1H), 1.26 (m, 2H), 0.98 (d, 3H, J=6.6 Hz), 0.91 (t, 3H, J=7.5 Hz); IR (neat) 3291, 2925, 1652, 1592, 1512, 1456, 1419, 1335, 1272, 1157, 969, 832 cm$^{-1}$; MS (FAB) m/z 531 (M+H)

Example 348

N-[2-(3,5-dimethoxy-phenyl)-6-trifluoromethyl-pyridin-3-ylmethyl]-2-(3-fluoro-4-methylsulfonamido-phenyl)-propionamide

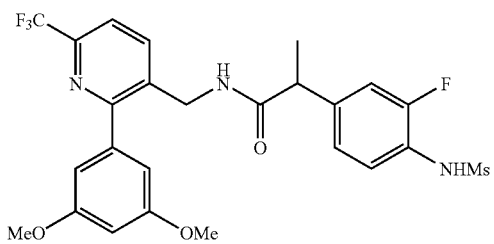

$^1$H NMR (300 MHz, CDCl$_3$) δ 7.81 (d, 1H, J=8.0 Hz), 7.61 (d, 1H, J=8.0 Hz), 7.49 (t, 1H, J=8.4 Hz), 6.98~7.07 (m, 2H), 6.51 (s, 3H), 5.64 (bt, 1H), 4.49 (d, 2H, J=3.8 Hz), 3.81 (s, 6H), 3.46 (q, 1H, J=7.1 Hz), 3.03 (s, 3H), 1.45 (d, 3H, J=7.1 Hz); IR (KBr) 3293, 2931, 1655, 1458, 1402, 973, 911, 732 cm$^{-1}$; MS (FAB) m/z 556 (M+H)

Example 349

N-(2-cyclopentyloxy-4-methyl-6-trifluoromethyl-pyridin-3-ylmethyl)-2-(3-fluoro-4-methylsulfonamido-phenyl)-propionamide)

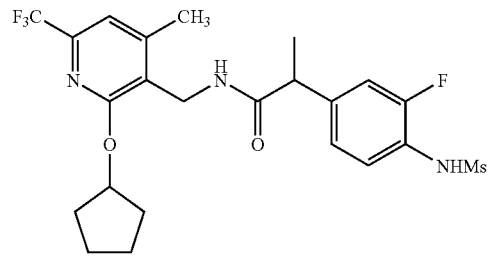

$^1$H NMR (300 MHz, CDCl$_3$) δ 7.49 (m, 1H), 7.00~7.07 (m, 3H), 6.05 (bt, 1H), 5.43 (m, 1H), 4.39 (m, 2H), 3.47 (q, 1H, J=7.1 Hz), 3.02 (s, 3H), 2.47 (s, 3H), 1.96 (m, 2H), 1.58~1.65 (m, 6H), 1.45 (d, 3H, J=7.1 Hz); IR (KBr) 3271, 2967, 1290, 1246, 1093, 973, 911, 731 cm$^{-1}$; MS (FAB) m/z 518 (M+H)

Example 350

N-(3',5'-dimethoxy-5-trifluoromethyl-biphenyl-2-ylmethyl)-2-(3-fluoro-4-methylsulfonamido-phenyl)-propionamide

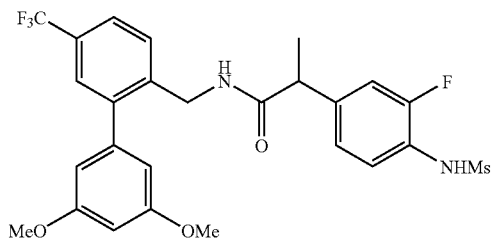

$^1$H NMR (300 MHz, CDCl$_3$) δ 7.40~7.56 (m, 4H), 6.98~7.08 (m, 2H), 6.48 (t, 1H, J=2.4 Hz), 6.35 (d, 2H, J=2.2 Hz), 5.56 (bt, 1H), 4.43 (t, 2H, J=5.5 Hz), 3.81 (s, 6H), 3.43 (q, 1H, J=7.2 Hz), 3.02 (s, 3H), 1.44 (d, 3H, J=7.1 Hz); IR (KBr) 3298, 1651, 1512, 1455, 1207, 1078, 907 cm$^{-1}$; MS (FAB) m/z 555 (M+H)

Example 351

5-{[2-(3-fluoro-4-methylsulfonamido-phenyl)-propionylamino]-methyl}-4-(4-methyl-piperidin-1-yl)-2-trifluoromethyl-benzoic acid ethyl ester

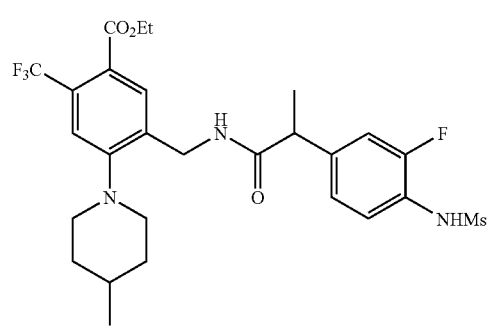

¹H NMR (300 MHz, CDCl₃) δ 7.74 (s, 1H), 7.48 (t, 1H, J=8.4 Hz), 7.11~7.20 (m, 2H), 4.38~4.31 (m, 4H), 3.68~3.59 (m, 3H), 3.02 (s, 3H), 2.83~2.92 (m, 2H), 1.74~1.52 (m, 3H), 1.53 (d, 3H, J=7.1 Hz), 1.36 (t, 3H, J=7.1 Hz), 1.29~1.26 (m, 2H), 0.97 (d, 3H, J=6.4 Hz); IR (KBr) 3364, 2927, 1725, 1373, 1031, 916, 796, 732 cm⁻¹; MS (FAB) m/z 589 (M+H)

Example 352

N-[2-(1-butyl-pentyloxy)-6-trifluoromethyl-pyridin-3-ylmethyl]-2-(3-fluoro-4-methylsulfonamido-phenyl)-propionamide

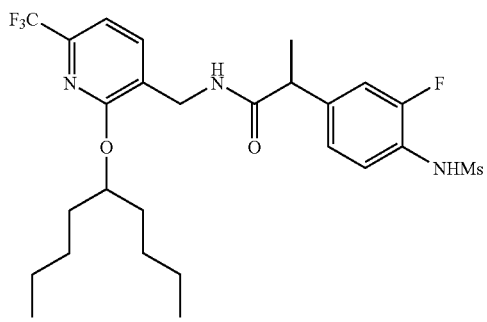

¹H NMR (300 MHz, CDCl₃) δ 7.49~7.56 (m, 2H), 7.15 (d, 1H, J=7.7 Hz), 7.08 (t, 1H, J=5.9 Hz), 6.47 (bs, 1H), 5.98 (bt, 1H), 5.29 (m, 1H), 4.37 (m, 2H), 3.49 (q, 1H, J=7.0 Hz), 3.03 (s, 3H), 1.57 (m, 2H), 1.49 (d, 3H, J=7.0 Hz), 1.24~1.31 (m, 8H), 0.88~0.90 (m, 6H); IR (neat) 3295, 2933, 2865, 1601, 1513, 1463, 1269, 974 cm⁻¹; MS (FAB) m/z 562 (M+H)

Example 353

N-(6-tert-butyl-2-isobutoxy-pyridin-3-ylmethyl)-2-(3-fluoro-4-methylsulfonamido-phenyl)-propionamide

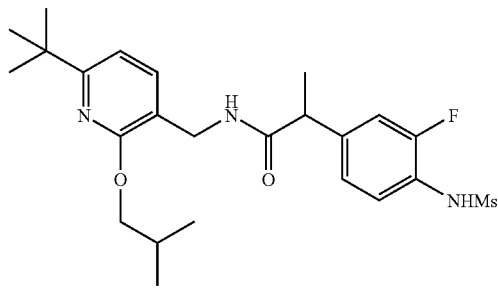

¹H NMR (300 MHz, CDCl₃) δ 7.49 (t, 1H, J=8.4 Hz), 7.36 (d, 1H, J=7.5 Hz), 7.04~7.15 (m, 2H), 6.79 (d, 1H, J=7.5 Hz), 6.06 (bt, 1H), 4.32 (m, 2H), 4.05~4.16 (m, 3H), 3.48 (q, 1H, J=7.1 Hz), 3.02 (s, 3H), 1.48 (d, 3H, J=7.1 Hz), 1.29 (s, 9H), 0.97 (d, 6H, J=6.6 Hz); IR (KBr) 3291, 1585, 1410, 1254, 1119, 1019, 972, 732 cm⁻¹; MS (FAB) m/z 480 (M+H)

Example 354

2-(3-fluoro-4-methylsulfonamido-phenyl)-N-(2-phenylethynyl-6-trifluoromethyl-pyridin-3-ylmethyl)-propionamide

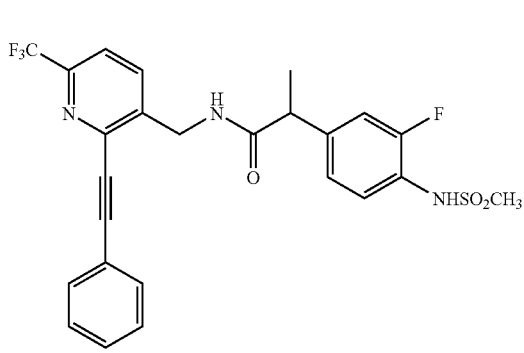

¹H NMR (300 MHz, CDCl₃) δ 7.80 (d, 1H, J=8.0 Hz), 7.58 (d, 1H, J=8.1 Hz), 7.49-7.55 (m, 2H), 7.35-7.48 (m, 4H), 7.00-7.11 (m, 2H), 6.08 (bt, 1H), 4.65 (d, 2H, J=6.0 Hz), 3.56 (q, 1H, J=7.0 Hz), 3.00 (s, 3H), 1.49 (d, 3H, J=7.1 Hz); IR (KBr) 3297, 2220, 1657, 1513, 1454, 1405, 1340, 1153, 1115, 972, 912, 759, 731 cm⁻¹; MS (FAB) m/z 520 (M+H)

Example 355

2-(3-fluoro-4-methylsulfonamido-phenyl)-N-[2-(3-methoxy-propoxy)-6-trifluoromethyl-pyridin-3-ylmethyl]-propionamide (SJS-284)

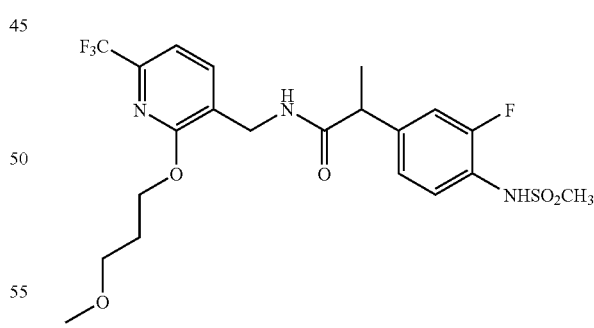

¹H NMR (300 MHz, CDCl₃) δ 7.61 (d, 1H, J=7.3 Hz), 7.49 (dd, 1H, J=8.1, 8.1 Hz), 7.20 (d, 1H, J=7.3 Hz), 7.02-7.11 (m, 2H), 6.44 (bt, 1H), 4.47-4.50 (m, 2H), 4.34 (d, 2H, J=6.0 Hz), 3.42-3.61 (m, 3H), 3.36 (s, 3H), 3.03 (s, 3H), 1.89-2.01 (m, 2H), 1.47 (d, 3H, J=7.1 Hz); IR (KBr) 3296, 2924, 1656, 1603, 1513, 1425, 1338, 1269, 1157, 975, 908 cm⁻¹; MS (FAB) m/z (M+H)

Example 356

N-(4-benzyl-4'-methyl-6'-trifluoromethyl-3,4,5,6-tetrahydro-2H-[1,2']bipyridinyl-3'-ylmethyl)-2-(3-fluoro-4-methylsulfonamido-phenyl)-propionamide

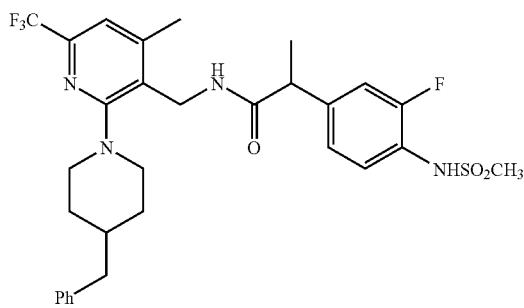

$^1$H NMR (300 MHz, CDCl$_3$) δ 7.49 (dd, 1H, J=8.3, 8.3 Hz), 7.27-7.35 (m, 2H), 7.11-7.25 (m, 4H), 6.89-7.10 (m, 2H), 6.70 (bt, 1H), 4.42-4.58 (m, 2H), 3.45 (q, 1H, J=7.1 Hz), 3.02-3.21 (m, 2H), 2.99 (s, 3H), 2.68-2.83 (m, 2H), 2.58 (d, 2H, J=6.6 Hz), 2.37 (s, 3H), 1.64-1.80 (m, 3H), 1.47 (d, 3H, J=7.1 Hz), 1.18-1.32 (m, 2H)

Example 357

2-(3-fluoro-4-methylsulfonamido-phenyl)-N-(4-methylene-6'-trifluoromethyl-3,4,5,6-tetrahydro-2H-[1,2']bipyridinyl-3'-ylmethyl)-propionamide

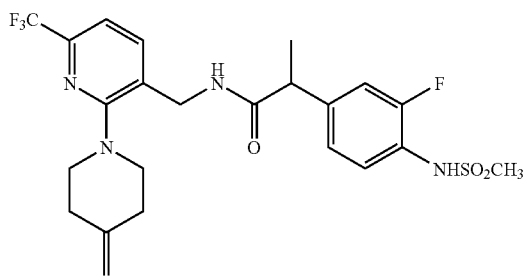

$^1$H NMR (CDCl$_3$) δ 7.53-7.48 (m, 2H), 7.22 (d, 1H, J=7.7 Hz), 7.16-7.08 (m, 2H), 6.52 (bs, NH), 6.19 (bt, NH), 4.76 (s, 2H), 4.50 (d, 2H, J=5.7 Hz), 3.57 (q, 1H, J=7.0 Hz), 3.13 (m, 4H), 3.03 (s, 3H), 2.30 (m, 4H), 1.54 (d, 3H, J=7.1 Hz); IR (neat) 3293, 2931, 1720, 1657, 1593, 1513, 1458, 1419, 1335, 1158 cm$^{-1}$; MS (FAB) m/z 515 (M+H)

Example 358

N-[2-(6-aza-spiro[2.5]oct-6-yl)-6-trifluoromethyl-pyridin-3-ylmethyl]-2-(3-fluoro-4-methylsulfonamido-phenyl)-propionamide

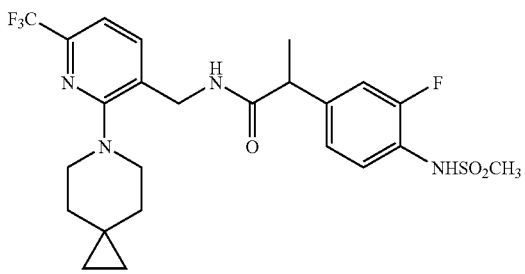

$^1$H NMR (CDCl$_3$) δ 7.55-7.49 (m, 2H), 7.22 (d, 1H, J=7.7 Hz), 7.17-7.08 (m, 2H), 6.52 (bs, NH), 6.35 (bt, NH), 4.50 (d, 2H, J=5.7 Hz), 3.56 (q, 1H), 3.12 (m, 4H), 3.03 (s, 3H), 1.53 (d, 3H, J=7.1 Hz), 1.45 (m, 4H), 0.35 (s, 4H); IR (neat) 3292, 2926, 1656, 1593, 1513, 1420, 1335, 1158, 734 cm$^{-1}$; MS (FAB) m/z 529 (M+H)

Example 359

2-(3-fluoro-4-methylsulfonamido-phenyl)-N-[2-(3-methyl-but-2-enyloxy)-6-trifluoromethyl-pyridin-3-ylmethyl]-propionamide

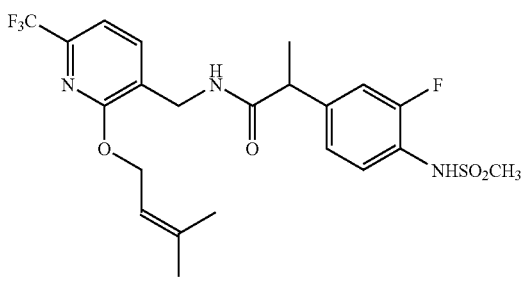

$^1$H NMR (CDCl$_3$) δ 7.58 (d, 1H, J=7.3 Hz), 7.51 (m, 1H), 7.18 (d, 1H, J=7.5 Hz), 7.12-7.05 (m, 2H), 6.07 (bt, NH), 5.38 (m, 1H), 4.87 (m, 2H), 4.37 (m, 2H), 3.51 (q, 1H, J=7.1 Hz), 3.03 (s, 3H), 1.78 (s, 6H), 1.48 (d, 3H, J=7.1 Hz); IR (neat 3289, 2935, 1656, 1603, 1513, 1420, 1333, 1262, 1158, 977 cm$^{-1}$; MS (FAB) m/z 503 (M+H)

Example 360

N-[2-(3-cyclohexyl-propyl)-6-trifluoromethyl-pyridin-3-ylmethyl]-2-(3-fluoro-4-methylsulfonamido-phenyl)-propionamide

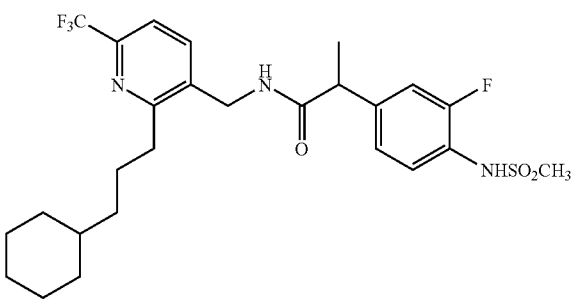

$^1$H NMR (300 MHz, CDCl$_3$) δ 7.50-7.57 (m, 2H), 7.44 (d, 1H, J=7.9 Hz), 7.17 (dd, 1H, J=11.0, 2.0 Hz), 7.10 (d, 1H, J=8.3 Hz), 6.47 (bs, 1H), 5.69 (bt, 1H), 4.40-4.57 (m, 2H), 3.57 (q, 1H, J=7.1 Hz), 3.05 (bs, 3H), 2.75 (t, 2H, J=7.7 Hz), 1.60-1.74 (m, 8H), 1.53 (d, 3H, J=7.1 Hz), 1.09-1.30 (m, 5H), 0.79-0.91 (m, 2H); IR (KBr) 3292, 2924, 2851, 1654, 1512, 1454, 1408, 1340, 1278, 1158, 972, 909, 733 cm$^{-1}$;

MS (FAB) m/z 544 (M+H)

Example 361

N-[2-(3-ethoxy-propoxy)-6-trifluoromethyl-pyridin-3-ylmethyl]-2-(3-fluoro-4-methylsulfonamido-phenyl)-propionamide

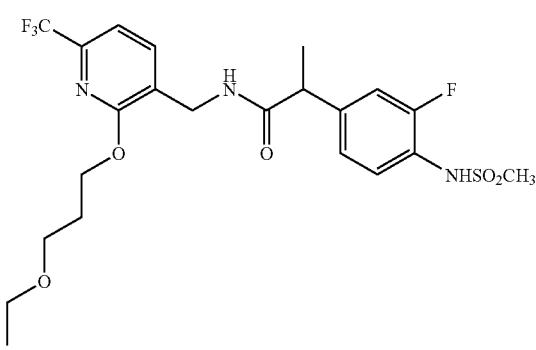

$^1$H NMR (300 MHz, CDCl$_3$) δ 7.61 (d, 1H, J=7.5 Hz) 7.50 (dd, 1H, J=8.3, 8.3 Hz), 7.20 (d, 1H, J=7.5 Hz), 7.01-7.12 (m, 2H), 6.35 (bt, 1H), 4.37-4.50 (m, 2H), 4.35 (d, 2H, J=6.0 Hz), 3.47-3.60 (m, 5H), 3.03 (s, 3H), 1.90-2.01 (m, 2H), 1.47 (d, 3H, J=7.0 Hz), 1.20 (t, 3H, J=7.1 Hz); IR (KBr) 3296, 2923, 1657, 1512, 1425, 1338, 1269, 1157, 972 cm$^{-1}$; MS (FAB) m/z (M+H)

Example 362

2-(3-fluoro-4-methylsulfonamido-phenyl)-N-[2-(2-phenoxy-ethoxy)-6-trifluoromethyl-pyridin-3-ylmethyl]-propionamide

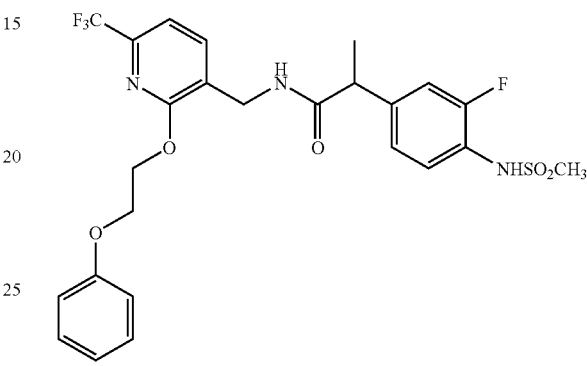

$^1$H NMR (300 MHz, CDCl$_3$) δ 7.66 (d, 1H, J=7.3 Hz), 7.41 (dd, 1H, J=8.4, 8.4 Hz), 7.22-7.35 (m, 3H), 6.88-7.05 (m, 5H), 6.42 (bs, 1H), 6.21 (bt, 1H), 4.63-4.82 (m, 2H), 4.27-4.42 (m, 4H), 3.34 (q, 1H, J=7.1 Hz), 2.99 (s, 3H), 1.38 (d, 3H, J=7.0 Hz); IR (KBr) 3295, 2924, 1657, 1598, 1510, 1423, 1339, 1244, 1157, 967, 910, 756 cm$^{-1}$; MS (FAB) m/z (M+H)

Example 363

N-[2-(3,5-dimethoxy-benzyloxy)-6-trifluoromethyl-pyridin-3-ylmethyl]-2-(3-fluoro-4-methylsulfonamido-phenyl)-propionamide

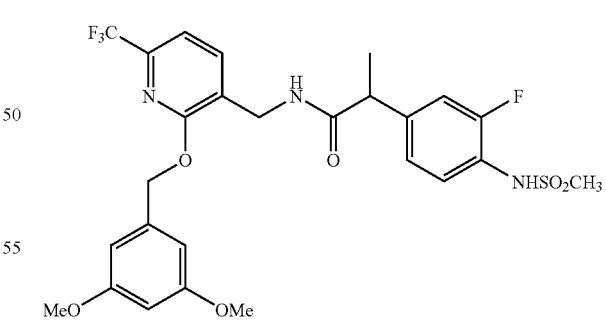

$^1$H NMR (300 MHz, CDCl$_3$) δ 7.63 (d, 1H, J=7.3 Hz) 7.45 (dd, 1H, J=8.3, 8.3 Hz), 7.24 (d, 1H, J=7.5 Hz), 7.04 (dd, 1H, J=11.2, 2.0 Hz), 6.98 (d, 1H, J=8.8 Hz), 6.59 (d, 2H, J=2.2 Hz), 6.45 (t, 1H, J=2.4 Hz), 6.00 (bt, 1H), 5.26-5.41 (m, 2H), 4.30-4.48 (m, 2H), 3.81 (s, 6H), 3.43 (q, 1H, J=7.3 Hz), 3.01 (s, 3H), 1.43 (d, 3H, J=7.1 Hz); IR (KBr) 1656, 1601, 1512, 1463, 1419, 1353, 1156, 1068, 976, 835 cm$^{-1}$; MS (FAB) m/z (M+H)

Example 364

2-(3-fluoro-4-methylsulfonamido-phenyl)-N-(4-hydroxymethyl-6'-trifluoromethyl-3,4,5,6-tetrahydro-2H-[1,2']bipyridinyl-3'-ylmethyl)-propionamide

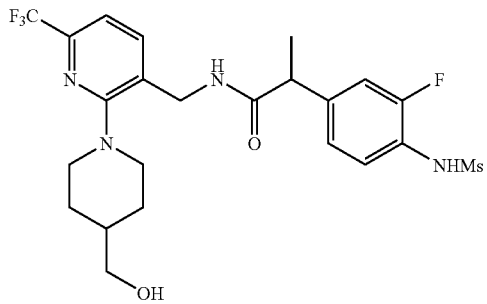

$^1$H NMR (300 MHz, CDCl$_3$) δ 7.54 (d, 1H, J=8.3 Hz), 7.51 (d, 1H, J=8.3 Hz), 7.23 (d, 1H, J=7.7 Hz), 7.16-7.08 (m, 2H), 6.24 (bs, 1H), 4.48 (m, 2H), 3.57-3.54 (m, 3H), 3.28 (m, 2H), 3.05 (s, 3H), 2.85 (m, 2H), 1.80 (m, 1H), 1.57-1.51 (m, 5H), 1.29 (m, 2H); IR (KBr) 3294, 2925, 1655, 1593, 1513, 1419, 1334 cm$^{-1}$; MS (FAB) m/z 533 (M+H)

Example 365

N-(6'-tert-butyl-4-phenyl-3,4,5,6-tetrahydro-2H-[1,2']bipyridinyl-3'-ylmethyl)-2-(3-fluoro-4-methylsulfonamido-phenyl)-propionamide

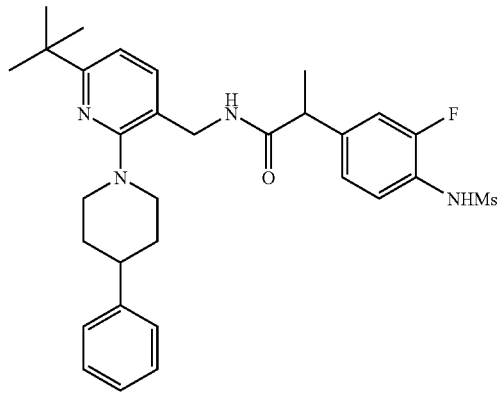

$^1$H NMR (300 MHz, CDCl$_3$) δ 7.47 (dd, 1H, J=8.3, 8.3 Hz), 7.37-7.14 (m, 7H), 7.09 (d, 1H, J=8.6 Hz), 6.92 (d, 1H, J=7.7 Hz), 6.72 (bs, 1H), 4.47 (m, 2H), 3.55 (q, 1H, J=7.1 Hz), 3.40 (m, 2H), 3.01-2.89 (m, 5H), 2.68 (m, 1H), 1.93-1.68 (m, 4H), 1.52 (d, 3H, J=7.1 Hz), 1.32 (s, 9H); IR (KBr) 3289, 2958, 1651, 1512, 1449, 1401, 1335 cm$^{-1}$; MS (FAB) m/z 567 (M+H)

Example 366

N-{6-tert-butyl-2-[4-(4-fluoro-phenyl)-piperazin-1-yl]-pyridin-3-ylmethyl}-2-(3-fluoro-4-methylsulfonamido-phenyl)-propionamide

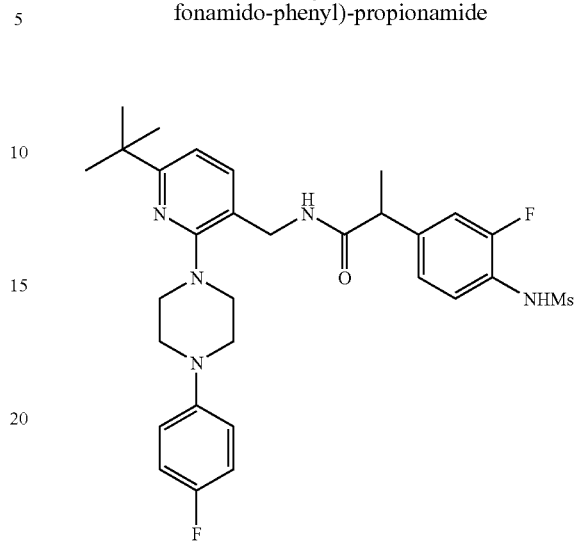

$^1$H NMR (300 MHz, CDCl$_3$) δ 7.47 (dd, 1H, J=8.2, 8.2 Hz), 7.34 (d, 1H, J=7.9 Hz), 7.17-6.87 (m, 7H), 6.51 (bs, 1H), 4.47 (m, 2H), 3.53 (q, 1H, J=6.9 Hz), 3.20-3.10 (m, 8H), 2.98 (s, 3H), 1.51 (d, 3H, J=6.9 Hz), 1.30 (s, 9H); IR (KBr) 3291, 2961, 1562, 1510, 1449, 1400, 1335 cm$^{-1}$; MS (FAB) m/z 586 (M+H)

Example 367

2-(4-methylsulfonamido-3-methyl-phenyl)-N-(2-pyrrolidin-1-yl-6-trifluoromethyl-pyridin-3-ylmethyl)-propionamide

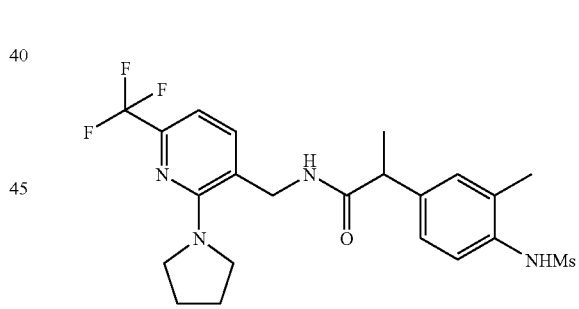

$^1$H NMR (300 MHz, CDCl$_3$) δ 7.74 (d, 1H, J=8.1 Hz), 7.39 (d, 1H, J=7.8 Hz), 7.35 (d, 1H, J=7.8 Hz), 7.32 (d, 1H, J=7.8 Hz), 7.12-7.14 (m, 2H), 6.92 (d, 1H, J=7.5 Hz), 6.26 (s, 1H), 5.68 (bs, 1H), 4.45 (d, 2H, J=5.7 Hz), 3.53 (q, 1H, J=7.2 Hz), 3.41 (m, 4H), 3.05 (s, 3H), 2.32 (s, 3H), 1.85 (m, 4H), 1.50 (d, 3H, J=7.2 Hz); IR (KBr) 3292, 2926, 1651, 1599, 1537, 1458, 1330, 1153 cm$^{-1}$; MS (FAB) m/z 485 (M+H)

---

| | | |
|---|---|---|
| 83 | (S)-2-(3-fluoro-4-methylsulfonamido-phenyl)-N-[2-(4-methyl-piperidin-1-yl)-4-trifluoromethyl-benzyl]-propionamide | |
| 84 | (R)-2-(3-fluoro-4-methylsulfonamido-phenyl)-N-[2-(4-methyl-piperidin-1-yl)-4-trifluoromethyl-benzyl]-propionamide | |
| 93 | (S)-2-(3-fluoro-4-methylsulfonamido-phenyl)-N-(2-hexyloxy-6-trifluoromethyl-pyridin-3-ylmethyl)-propionamide | |
| 94 | (R)-2-(3-fluoro-4-methylsulfonamido-phenyl)-N-(2-hexyloxy-6-trifluoromethyl-pyridin-3-ylmethyl)-propionamide | |

-continued

| | |
|---|---|
| 96 | (S)-2-(3-fluoro-4-methylsulfonamido-phenyl)-N-(2-isobutoxy-6-trifluoromethyl-pyridin-3-ylmethyl)-propionamide |
| 97 | (R)-2-(3-fluoro-4-methylsulfonamido-phenyl)-N-(2-isobutoxy-6-trifluoromethyl-pyridin-3-ylmethyl)-propionamide |
| 98 | 2-(3-fluoro-4-methylsulfonamido-phenyl)-N-(2-isobutoxy-4-trifluoromethyl-benzyl)-propionamide |
| 99 | (R)-2-(3-fluoro-4-methylsulfonamido-phenyl)-N-(2-isobutoxy-4-trifluoromethyl-benzyl)-propionamide |
| 111 | 2-(3-fluoro-4-methylsulfonamido-phenyl)-N-(2-propoxy-6-trifluoromethyl-pyridin-3-ylmethyl)-propionamide |
| 116 | N-(2-butylamino-6-trifluoromethyl-pyridin-3-ylmethyl)-2-(3-fluoro-4-methylsulfonamido-phenyl)-propionamide |
| 120 | (S)-N-[2-(3-chloro-4-fluoro-phenyl)-6-trifluoromethyl-pyridin-3-ylmethyl]-2-(3-fluoro-4-methylsulfonamido-phenyl)-propionamide |
| 121 | (R)-N-[2-(3-chloro-4-fluoro-phenyl)-6-trifluoromethyl-pyridin-3-ylmethyl]-2-(3-fluoro-4-methylsulfonamido-phenyl)-propionamide |
| 123 | 2-(3-fluoro-4-methylsulfonamido-phenyl)-N-[2-(3-methyl-butoxy)-6-trifluoromethyl-pyridin-3-ylmethyl]-propionamide |
| 133 | N-(4-tert-butyl-2-isobutoxy-benzyl)-2-(3-fluoro-4-methylsulfonamido-phenyl)-propionamide |
| 134 | 2-(3-fluoro-4-methylsulfonamido-phenyl)-N-[2-(4-methyl-piperazin-1-yl)-6-trifluoromethyl-pyridin-3-ylmethyl]-propionamide |
| 140 | N-[2-butoxy-6-(chlor-difluor-methyl)-pyridin-3-ylmethyl]-2-(3-fluoro-4-methylsulfonamido-phenyl)-propionamide |
| 144 | (S)-2-(3-fluoro-4-methylsulfonamido-phenyl)-N-(2-pentyl-6-trifluoromethyl-pyridin-3-ylmethyl)-propionamide |
| 145 | (R)-2-(3-fluoro-4-methylsulfonamido-phenyl)-N-(2-pentyl-6-trifluoromethyl-pyridin-3-ylmethyl)-propionamide |
| 191 | 2-(3-fluoro-4-(methylsulfonamido)phenyl)-N-((2-styryl-6-(trifluoromethyl)pyridin-3-yl)methyl)propanamide |
| 192 | 2-(3-fluoro-4-methylsulfonamido-phenyl)-N-(2-phenethyl-6-trifluoromethyl-pyridin-3-ylmethyl)-propionamide |
| 193 | N-{2-[4-(3-chloro-pyridin-2-yl)-piperazin-1-yl]-6-trifluoromethyl-pyridin-3-ylmethyl}-2-(3-fluoro-4-methylsulfonamido-phenyl)-propionamide |
| 194 | N-{2-[4-(3-chloro-pyridin-2-yl)-2-methyl-piperazin-1-yl]-6-trifluoromethyl-pyridin-3-ylmethyl}-2-(3-fluoro-4-methylsulfonamido-phenyl)-propionamide |
| 213 | 2-(3-fluoro-4-methylsulfonamido-phenyl)-N-{6-trifluoromethyl-2-[4-(3-trifluoromethyl-pyridin-2-yl)-piperazin-1-yl]-pyridin-3-ylmethyl}-propionamide |
| 214 | 2-(3-fluoro-4-methylsulfonamido-phenyl)-N-[2-(4-pyridin-2-yl-piperazin-1-yl)-6-trifluoromethyl-pyridin-3-ylmethyl]-propionamide |
| 215 | 2-(3-fluoro-4-methylsulfonamido-phenyl)-N-(6-trifluoromethyl-pyridin-3-ylmethyl)-propionamide |
| 239 | (R)-N-(2-cyclohexyloxy-4-trifluoromethyl-benzyl)-2-(3-fluoro-4-methylsulfonamido-phenyl)-propionamide |
| 242 | N-[2-(4-ethyl-benzyloxy)-6-trifluoromethyl-pyridin-3-ylmethyl]-2-(3-fluoro-4-methylsulfonamido-phenyl)-propionamide |
| 250 | N-[2-(3,4-dichloro-phenyl)-6-trifluoromethyl-pyridin-3-ylmethyl]-2-(3-fluoro-4-methylsulfonamido-phenyl)-propionamide |
| 251 | N-[2-(3-tert-butyl-1-oxa-2,8-diaza-spiro[4.5]dec-2-en-8-yl)-6-trifluoromethyl-pyridin-3-ylmethyl]-2-(3-fluoro-4-methylsulfonamido-phenyl)-propionamide |
| 252 | 2-(3-fluoro-4-methylsulfonamido-phenyl)-N-[2-(3-phenyl-1-oxa-2,8-diaza-spiro[4.5]dec-2-en-8-yl)-6-trifluoromethyl-pyridin-3-ylmethyl]-propionamide |
| 253 | 2-(3-fluoro-4-(pentafluorsulfanylsulfonamido)phenyl)-N-p-tolylpropanamide |
| 254 | 2-(3-fluoro-4-methylsulfonamido-phenyl)-N-[2-(3-fluoro-4-methoxy-phenyl)-6-trifluoromethyl-pyridin-3-ylmethyl]-propionamide |
| 265 | N-[2-(2,3-dihydro-benzo[1,4]dioxin-6-yl)-6-trifluoromethyl-pyridin-3-ylmethyl]-2-(3-fluoro-4-methylsulfonamido-phenyl)-propionamide |
| 266 | N-(2-benzo[1,3]dioxol-5-yl-6-trifluoromethyl-pyridin-3-ylmethyl)-2-(3-fluoro-4-methylsulfonamido-phenyl)-propionamide |
| 272 | 2-(3-fluoro-4-methylsulfonamido-phenyl)-N-[2-(3-methylsulfonamido-phenyl)-6-trifluoromethyl-pyridin-3-ylmethyl]-propionamide |
| 273 | 2-(3-fluoro-4-methylsulfonamido-phenyl)-N-[2-(2-methyl-propenyl)-6-trifluoromethyl-pyridin-3-ylmethyl]-propionamide |
| 274 | N-[2-(3,3-dimethyl-but-1-enyl)-6-trifluoromethyl-pyridin-3-ylmethyl]-2-(3-fluoro-4-methylsulfonamido-phenyl)-propionamide |
| 275 | 2-(3-fluoro-4-methylsulfonamido-phenyl)-N-[2-(1H-indol-6-yl)-6-trifluoromethyl-pyridin-3-ylmethyl]-propionamide |
| 276 | 2-(3-fluoro-4-methylsulfonamido-phenyl)-N-[2-(1H-indol-5-yl)-6-trifluoromethyl-pyridin-3-ylmethyl]-propionamide |
| 277 | N-[2-(4-chloro-3-fluoro-phenyl)-6-trifluoromethyl-pyridin-3-ylmethyl]-2-(3-fluoro-4-methylsulfonamido-phenyl)-propionamide |
| 278 | 2-(3-fluoro-4-methylsulfonamido-phenyl)-N-[2-(4-fluoro-3-methyl-phenyl)-6-trifluoromethyl-pyridin-3-ylmethyl]-propionamide |
| 294 | N-(2-cyclohexylsulfanyl-6-trifluoromethyl-pyridin-3-ylmethyl)-2-(3-fluoro-4-methylsulfonamido-phenyl)-propionamide |
| 295 | 2-(3-fluoro-4-methylsulfonamido-phenyl)-N-(4-phenyl-6'-trifluoromethyl-3,4,5,6-tetrahydro-2H-[1,2']bipyridinyl-3'-ylmethyl)-propionamide |
| 328 | N-(6-tert-butyl-2-pentyloxy-pyridin-3-ylmethyl)-2-(3-fluoro-4-methylsulfonamido-phenyl)-propionamide |
| 329 | N-[6-tert-butyl-2-(3-methyl-butoxy)-pyridin-3-ylmethyl]-2-(3-fluoro-4-methylsulfonamido-phenyl)-propionamide |

-continued

330 N-(4-dimethylamino-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide
332 2-(3-fluoro-4-methylsulfonamido-phenyl)-N-[4-(4-fluoro-phenyl)-6'-trifluoromethyl-3,6-dihydro-2H-[1,2']bipyridinyl-3'-ylmethyl]-propionamide
334 N-(2-cyclohex-1-enyl-6-trifluoromethyl-pyridin-3-ylmethyl)-2-(3-fluoro-4-methylsulfonamido-phenyl)-propionamide
335 N-[2-(1-ethyl-propoxy)-6-trifluoromethyl-pyridin-3-ylmethyl]-2-(3-fluoro-4-methylsulfonamido-phenyl)-propionamide
336 2-(3-fluoro-4-methylsulfonamido-phenyl)-N-[2-(1-propyl-butoxy)-6-trifluoromethyl-pyridin-3-ylmethyl]-propionamide
337 2-(3-fluoro-4-methylsulfonamido-phenyl)-N-[2-(1-isobutyl-3-methyl-butoxy)-6-trifluoromethyl-pyridin-3-ylmethyl]-propionamide
338 N-[2-(4,4-dimethyl-cyclohexyloxy)-6-trifluoromethyl-pyridin-3-ylmethyl]-2-(3-fluoro-4-methylsulfonamido-phenyl)-propionamide
[368] N-((2-(1H-indol-4-yl)-6-(trifluoromethyl)pyridin-3-yl)methyl)-2-(3-fluoro-4-(methylsulfonamido)phenyl)propanamide,
[369] N-((6-tert-butyl-2-propoxypyridin-3-yl)methyl)-2-(3-fluoro-4-(methylsulfonamido)phenyl)propanamide,
[370] N-((6-tert-butyl-2-(3-methoxypropoxy)pyridin-3-yl)methyl)-2-(3-fluoro-4-(methylsulfonamido)phenyl)propanamide,
[371] N-((6-tert-butyl-2-(4-(dimethylamino)-4-phenylpiperidin-1-yl)pyridin-3-yl)methyl)-2-(3-fluoro-4-(methylsulfonamido)phenyl)propanamide,
[372] N-((6-tert-butyl-2-methoxypyridin-3-yl)methyl)-2-(3-fluoro-4-(methylsulfonamido)phenyl)propanamide,
[373] N-((6-tert-butyl-2-ethoxypyridin-3-yl)methyl)-2-(3-fluoro-4-(methylsulfonamido)phenyl)propanamide,
[374] N-((6-tert-butyl-2-isopropoxypyridin-3-yl)methyl)-2-(3-fluoro-4-(methylsulfonamido)phenyl)propanamide,
[375] 2-(3-fluoro-4-(methylsulfonamido)phenyl)-N-((2-(pentyloxy)-6-(trifluoromethyl)pyridin-3-yl)methyl)propanamide,
[376] 2-(3-fluoro-4-(methylsulfonamido)phenyl)-N-((2-(hexyloxy)-6-(trifluoromethyl)pyridin-3-yl)methyl)propanamide,
[377] N-((2-(3,5-dimethylcyclohexyloxy)-6-(trifluoromethyl)pyridin-3-yl)methyl)-2-(3-fluoro-4-(methylsulfonamido)phenyl)propanamide,
[378] N-((6-tert-butyl-2-(2-ethoxyethoxy)pyridin-3-yl)methyl)-2-(3-fluoro-4-(methylsulfonamido)phenyl)propanamide, Pharmacological Data The affinity of the compounds according to the invention for the vanilloid receptor 1 (VR1/TRPV1 receptor) was determined as described above (pharmacological methods I or II).

The compounds according to the invention of the above-stated formula I exhibit excellent affinity for the VR1/TRPV1 receptor (table 2).

TABLE 2

| Compound according to Example | $K_i$ (rat) [nM] | $K_i$ (human) [nM] | $IC_{50}$ (human) [nM] after pH stimulus |
|---|---|---|---|
| 1 | 684 | 387 | |
| 2 | 3.5 | 0.4 | 218 |
| 3 | 2.6 | 1.7 | 135 |
| 6 | 95 | 169 | 2613 |
| 10 | 1.1 | 0.3 | 64 |
| 11 | 1.1 | 0.3 | 46.7 |
| 12 | 4.3 | 1.3 | 169 |
| 13 | 3.8 | 0.6 | 211 |
| 18 | 47 | 68.9 | 2711 |
| 19 | 1.0 | 0.3 | 31 |
| 20 | 5.4 | 2.1 | 93 |
| 21 | 1.3 | 0.9 | 29 |
| 22 | 4.9 | 6.4 | 62 |
| 31 | 0.5 | 0.6 | 50 |
| 33 | 4.8 | 7.2 | 1376 |
| 34 | 2.5 | 2.3 | 121 |
| 64 | 6.3 | 2.3 | |
| 65 | 36.5 | 4.2 | |
| 66 | 3.7 | 2.9 | |
| 67 | 5.1 | 3.2 | |
| 69 | 2.4 | 1.7 | |
| 70 | 9 | 15.5 | 1490 |
| 71 | 0.8 | 1.3 | 22.4 |
| 72 | 124 | 32.6 | 1660 |
| 73 | 6.6 | 8.8 | 634 |

TABLE 2-continued

| Compound according to Example | $K_i$ (rat) [nM] | $K_i$ (human) [nM] | $IC_{50}$ (human) [nM] after pH stimulus |
|---|---|---|---|
| 75 | 12.9 | 4.0 | 1212 |
| 76 | 1.5 | 1.3 | 43.4 |

The compounds of the present invention are particularly suitable for the inhibition of capsaicin induced hypothermie (table 3).

TABLE 3

| Compound according to example | Inhibition of capsaicin induced hypothermie[1] |
|---|---|
| 2 | 73 |
| 3 | 55 |
| 10 | 49 |
| 12 | 36 |
| 13 | 7 |
| 19 | 71 |
| 20 | 31 |
| 21 | 32 |
| 31 | 88 |
| 34 | 84 |
| 71 | 79 |
| 76 | 48 |

[1]in comparison to vehicle control at maximum effect 15 min after application of capsaicin; n = 5 (number of measurements)

The following table 4. includes the pharmacological data for example compounds 14 to 378.

| Example | $K_i$ (rat) Cap. [nM] | $K_i$ (human) Cap. [nM] | $IC_{50}$ (human) [nM] after pH stimulus | inhibition hypothermie (n = 5) | inhibition formaldehyde test (n = 10) | inhibition Bennet model (n = 10) |
|---|---|---|---|---|---|---|
| 14 | 67.9 | 19.1 | 2386.0 | | | |
| 15 | 12.0 | 3.5 | 148.0 | | | |
| 16 | 0.8 | 0.2 | 14.7 | 0.3 po 12% | | |
| 32 | 2.6 | 1.7 | 135.4 | 0.3 po 55% | | |
| 34 | | | | | 0.1 po 6% 0.3 po 51% | |
| 37 | 1.8 | 0.3 | 26.2 | | | |
| 40 | 0.4 | 1.0 | 48 | | | |
| 42 | 0.5 | 0.6 | 26 | | | |
| 46 | | 59.4 | 40% @ 5 μM 5% @ 1 μM | | | |
| 61 | ne @ 1 μM | ne @ 1 μM | 47% @ 10 μM | | | |
| 62 | ne @ 1 μM | ne @ 1 μM | ne @ 1 μM | | | |
| 63 | 23.9 | 28.6 | 70% @ 1 μM | | | |
| 71 | | | | | 0.3 po 0% 1 po 3% | |
| 74 | 70% @ 10 μM | 71% @ 10 μM | 35% @ 10 μM | | | |
| 76 | | | | | 0.3 po 12% | |
| 77 | 57% @ 10 μM | 21% @ 10 μM | ne @ 1 μM | | | |
| 78 | 19% @ 1 μM | 15% @ 1 μM | 36% @ 10 μM | | | |
| 79 | 0.8 | 0.7 | 25.6 | | | |
| 80 | 0.6 | 0.3 | 5.4 | 0.3 po 66% | 0.3 po 58% | |
| 81 | 2.4 | 0.8 | 25.1 | 0.3 po 21% | | |
| 82 | 0.7 | 0.9 | 16.2 | 0.3 po 53% | 0.3 po 39% 1 po 43% | |
| 85 | 67.9 | 19.1 | 2386 | | | |
| 87 | 143 | 36.1 | 2574 | 0.3 po 0% | | |
| 88 | 5 | 0.3 | 57.1 | 0.3 po 38% | 0.3 po 4% 1 po 16% | |
| 89 | 1.2 | 0.4 | 130.8 | 0.3 po 1% | | |
| 90 | 47 | 20.4 | 260 | 0.3 po 81% | 0.3 po 46% 1 po 37% | |
| 91 | 0.5 | 0.5 | 29.9 | | | 0.1 po 30% 1 po 46% 10 po 43% |
| 93 | 0.2 | 0.4 | 12.3 | 0.3 po 4% | | |
| 94 | | | | 0.3 po 0% | | |
| 95 | 0.8 | 0.5 | 52.6 | | | |
| 96 | | 0.5 | 30 | | | |
| 97 | | 44.5 | 2155 | | | |
| 98 | | 1.5 | 41 | | | |
| 99 | | 5.8 | 419 | 0.3 po 1% | | |
| 100 | 1.2 | 1.1 | 115.2 | 0.3 po 26% | | |
| 101 | 1 | 0.3 | 40.5 | | | |
| 102 | 7.4 | 4.2 | 18% @ 10 μM | | | |
| 103 | 4.9 | 2.8 | 16 @ 10 μM | 0.3 po 39% | 0.3 po 36% 1 po 50% | |
| 104 | 0.2 | 0.2 | 40 | | | 0.0001 po 20% 0.001 po 45% 0.01 po 49% 0.1 po 35% |
| 106 | 0.5 | 0.5 | 18.6 | 0.1 po 24% 0.3 po 21% 1 po 22% 10 po 84% | | |
| 107 | 1 | 0.8 | 43.7 | 0.3 po 21% | | |
| 108 | 0.6 | 1.4 | 114.1 | 0.3 po 38% | 0.3 po 15% 1 po 24% | |
| 109 | 0.6 | 0.7 | 30.7 | | | |
| 110 | 63.1 | 59.6 | 1395 | 0.3 po 13% | | |
| 111 | 3.5 | 0.9 | 90.1 | | | |
| 112 | 31.8 | 39.2 | 64% @ 10 μM 26% @ 1 μM | | | |
| 112 | 236.4 | 15% @ 1 μM | 67% @ 25 μM 39% @ 10 μM | | | |
| 114 | 28.1 | 68.7 | 2357 | | | |
| 115 | 10.9 | 15.8 | 203 | | | |
| 116 | 6.6 | 9.1 | 293 | 0.3 po 21% | 0.1 po 39% 0.3 po 57% | |
| 117 | 0.5 | 0.5 | 23.5 | 0.3 po 70% | 0.3 po 5% 1 po 41% | |
| 118 | 0.2 | 0.2 | 7.6 | | | |
| 120 | 0.4 | 0.7 | 51% @ 1 μM 41% @ 0.1 μM | | | |
| 121 | 5.8 | 13.2 | 56% @ 10 μM 32% @ 1 μM | 0.3 po 12% | | |

-continued

| Example | $K_i$ (rat) Cap. [nM] | $K_i$ (human) Cap. [nM] | $IC_{50}$ (human) [nM] after pH stimulus | inhibition hypothermie (n = 5) | inhibition formaldehyde test (n = 10) | inhibition Bennet model (n = 10) |
|---|---|---|---|---|---|---|
| 122 | 0.6 | 0.7 | 40.4 | 0.3 po 33% | | |
| 123 | 0.6 | 0.8 | 15.1 | 0.3 po 47% | | |
| 124 | 0.4 | 0.3 | 5.1 | 0.3 po 39% | | |
| 125 | 1 | 0.9 | 23.8 | 0.1 po 5%<br>0.3 po 37%<br>1 po 32%<br>3 po 65% | 0.3 po 24%<br>1 po 19% | 0.01 po 17%<br>0.1 po 30%<br>1 po 46%<br>3 po 40%<br>10 po 50% |
| 126 | 1.2 | 0.9 | 101 | 0.3 po 0% | 0.1 po 20%<br>0.3 po 69% | |
| 127 | 0.6 | 0.5 | 15.4 | 0.3 po 6% | 0.3 po 22%<br>1 po 25% | |
| 128 | 1 | 0.7 | 27.8 | | | |
| 129 | 1.6 | 1.8 | 77.2 | 0.3 po 10% | 0.3 po 5%<br>1 po 3% | |
| 130 | 4.5 | 2.1 | 34.3 | 0.3 po 58% | 0.3 po 41%<br>1 po 55% | |
| 131 | 0.4 | 0.3 | 5.9 | 0.3 po 26% | | |
| 132 | 0.7 | 0.5 | 14.7 | 0.3 po 0% | | |
| 133 | 0.7 | 2.1 | 62% @ 1 µM<br>38% @ 0.1 µM | | | |
| 134 | 335 | 146 | 69% @ 25 µM<br>15% @ 1 µM | | | |
| 135 | 48.9 | 39.3 | 1160 | | | |
| 136 | 8.3 | 14 | 140 | 0.3 po 43% | | 0.01 po 13%<br>0.1 po 33%<br>1 po 47%<br>10 po 63% |
| 137 | 1.9 | 0.7 | 12.5 | 0.3 po 9% | | |
| 138 | 1.2 | 0.5 | 19.8 | 0.3 po 0% | | |
| 139 | 0.9 | 0.3 | 12.1 | 0.3 po 43% | | |
| 140 | 0.4 | 0.7 | 9.2 | | 0.1 po 56%<br>0.3 po 73% | |
| 142 | 1.2 | 1 | 8.9 | | | |
| 144 | | 1 | 146 | | | |
| 145 | | 78 | 49% @ 10 µM<br>39% @ 5 µM<br>2% @ 1 µM | | | |
| 147 | 1 | 0.7 | 10.4 | 0.3 po 3% | | |
| 148 | 1.1 | 1.3 | 63.6 | 0.3 po 45% | 0.3 po 44%<br>1 po 46% | |
| 149 | 0.7 | 0.5 | 9.7 | | | |
| 150 | 22.4 | 63.3 | 1320 | | 0.3 po 17% | |
| 151 | 1.4 | 1 | 92.3 | | | |
| 152 | 2.2 | 3.8 | | 63% @ 10 µM<br>45% @ 1 µM | 0.3 po 33%<br>1 po 24% | |
| 153 | 0.7 | 2.2 | 92.4 | | | |
| 154 | 1.7 | 8.1 | 534 | 0.3 po 12% | | |
| 155 | 0.8 | 1.8 | 145 | | | |
| 156 | 1.7 | 1.4 | 69.8 | | | |
| 157 | 1.3 | 2.9 | 43.1 | | | |
| 158 | 12.6 | 4 | 139 | | | |
| 159 | 21.4 | 2.4 | 280 | 0.3 po 28% | 0.3 po 10%<br>1 po 14% | |
| 160 | 3 | 3.5 | 28.2 | 0.3 po 28% | 0.3 po 10%<br>1 po 14% | |
| 161 | 0.7 | 0.4 | 11.6 | | | |
| 162 | 1.6 | 3 | 58% @ 1 µM<br>31% @ 0.1 µM | | | |
| 163 | 8.5 | 12.7 | 277 | | | |
| 164 | 85% @10 µM;<br>1.5% @1 µM | 84% @ 10 µM;<br>20% @1 µM | 28% @25 µM; 30% @10 µM | | | |
| 165 | 82% @ 25 µM;<br>4% @ 10 µM | 76% @ 25 µM;<br>0.5% @ 10 µM | 40% @25 µM; 28% @10 µM | 0.3 po 41% | 0.3 po 29%<br>1 po 15% | |
| 166 | 1.1 | 0.5 | 18.5 | 0.3 po 28% | 0.3 po 48%<br>1 po 72% | |
| 167 | 2.8 | 0.8 | 21.3 | 0.3 po 19% | 0.1 po 62%<br>0.3 po 56% | |
| 168 | 1.4 | 0.9 | 17.6 | 0.3 po 21% | 0.3 po 1% | |
| 169 | 0.6 | 0.9 | 40.5 | | | |
| 170 | 5.1 | 7.7 | 242 | | | |
| 171 | 2.4 | 4.8 | 125 | 0.3 po 32% | 0.3 po 45%<br>1 po 46% | |
| 172 | 0.4 | 1.5 | 53 | | | |
| 173 | 78.4 | 65.7 | 414 | 0.3 po 36% | 0.3 po 0% | |

-continued

| Example | $K_i$ (rat) Cap. [nM] | $K_i$ (human) Cap. [nM] | $IC_{50}$ (human) [nM] after pH stimulus | inhibition hypothermie (n = 5) | inhibition formaldehyde test (n = 10) | inhibition Bennet model (n = 10) |
|---|---|---|---|---|---|---|
| 174 | 1.4 | 1.6 | 64.5 | 0.3 po 39% | 0.3 po 5% 1 po 49% | |
| 175 | 1.2 | 2.5 | 25 | | | |
| 176 | 60% @10 µM 8% @1 µM | 63% @ 10 µM 7.2% @ 1 µM | 43% @10 µM. 13% @1 µM | | | |
| 177 | 34% @1 µM 9% @0.1 µM | 51 | 1290 | 0.3 po 14% | 0.3 po 31% 1 po 24% | |
| 178 | 1.9 | 0.5 | 27.6 | 0.3 po 42% | 0.3 po 16% 1 po 28% | |
| 179 | 1 | 1.1 | 23.1 | 0.3 po 57% | 0.3 po 5% 1 po 22% | |
| 180 | 0.3 | 0.8 | 22.8 | | | |
| 181 | 5.6 | 14.6 | 1074 | | | |
| 182 | 7.3 | 4.2 | 637 | 0.3 po 45% | 0.3 po 1% 1 po 8% | |
| 183 | 0.7 | 0.6 | 10.5 | | | |
| 184 | 77 | 59 | ne @ 1 µM | | | |
| 185 | 49.1 | 425 | ne @ 1 µM | | | |
| 186 | 0.8 | 0.6 | 37.6 | | | |
| 187 | 0.5 | 1 | 39.6 | | | |
| 188 | 5 | 5 | 192 | 0.3 po 0% | | |
| 189 | 3 | 4.7 | 166 | | | |
| 190 | 0.4 | 0.6 | 31 | | | |
| 191 | 2 | 2.2 | 85 | | | |
| 192 | 2.4 | 1.4 | 47 | | | |
| 193 | 3.2 | 2.1 | 69% @1 µM 58% @0.1 µM 8% @0.01 µM | | | |
| 194 | 3.8 | 4.1 | 21% @ 1 µM 0% @ 0.1 µM | 0.3 po 14% | | |
| 195 | 0.4 | 1.1 | 61 | | | |
| 196 | 0.4 | 0.6 | 41% @1 µM 48% @0.1 µM 6% @0.01 µM | | | |
| 197 | 0.4 | 1.5 | 97.3 | | | |
| 198 | 0.9 | 6.4 | 31% @1 µM 11% @0.1 µM | | | |
| 199 | 1.6 | 1.4 | 31 | | | |
| 200 | 3.4 | 4.2 | 81 | | | |
| 201 | 1.2 | 2.4 | 34 | | | |
| 202 | 24.8 | 29.5 | 30% @1 µM 16% @0.1 µM | | | |
| 203 | 3.3 | 3 | 24% @1 µM 0% @0.1 µM | | | |
| 204 | 1.6 | 4 | 148.1 | | | |
| 205 | 11.4 | 0.9 | 57.4 | | | |
| 206 | 0.7 | 3.2 | 66.1 | | | |
| 207 | 0.8 | 0.8 | 38.6 | | | |
| 208 | 0.5 | 0.6 | 38.6 | | | |
| 209 | 0.2 | 0.9 | 34.9 | 3 po 46% | | |
| 210 | 0.2 | 0.3 | 8 | | | |
| 211 | 30.3 | 142 | 3441 | | | |
| 212 | 3.6 | 4.2 | 33% @1 µM 11% @0.1 µM | | | |
| 213 | 2.0 | 2.8 | 49% @10 µM 37% @1 µM | | | |
| 214 | 1.5 | 1.4 | 108.2 | | | |
| 215 | 48% @10 µM 4% @1 µM | 37% @10 µM | 15% @25 µM | | | |
| 216 | 0.5 | 2.0 | 64.7 | 0.3 po 4% | | |
| 217 | 1.1 | 2.8 | 36.5 | 0.1 po 40% 0.3 po 97% | 0.3 po 9% 1 po 37% | |
| 218 | 0.4 | 1.3 | 13.8 | | | |
| 219 | 2.4 | 3.3 | 38.3 | | | |
| 220 | 2.4 | 3.4 | 39.2 | | | |
| 221 | 1.9 | 2.5 | 44.5 | 0.3 po 18% | | |
| 222 | 2.4 | 3.4 | 39.2 | | | |
| 223 | 53% @1 µM | 38% @1 µM 4% @0.1 µM | ne @ 1 µM | | | |
| 225 | 0.5 | 0.7 | 27.3 | 0.3 po 20% | | |
| 226 | 1.5 | 2 | 45.2 | | | |
| 227 | 348 | 91 | 51% @10 µM 7% @1 µM | | | |
| 228 | 2.5 | 1.3 | 612 | | | |
| 229 | 0.7 | 0.7 | 17.7 | | | |
| 230 | 0.6 | 0.4 | 20.1 | | | |
| 231 | 0.8 | 1.4 | 37.6 | | | |
| 233 | 1.4 | 2.5 | 63% @ 10 µM 50% @1µ | | | |
| 234 | 1.0 | 1.5 | 85.3 | 0.1 po 19% 0.3 po 31% | 0.03 po 5% 0.1 po 28% 0.3 po 41% 1 po 44% | 0.001 po 26% 0.01 po 48% 0.1 po 53% 1 po 65% |
| 235 | 0.6 | 0.9 | 55 | | | |

-continued

| Example | $K_i$ (rat) Cap. [nM] | $K_i$ (human) Cap. [nM] | IC$_{50}$ (human) [nM] after pH stimulus | inhibition hypothermie (n = 5) | inhibition formaldehyde test (n = 10) | inhibition Bennet model (n = 10) |
|---|---|---|---|---|---|---|
| 236 | 1.4 | 2.7 | 69% @ 10 μM 76% @1 μM 2% @0.1 μM | | | |
| 237 | 2.0 | 4.4 | 70% @ 1 μM | | | |
| 238 | 0.6 | 0.7 | 55% @ 1 μM; 39% @ 0.1 μM 3% @ 0.01 μM | | | |
| 240 | 5.3 | 1.2 | 43% @ 1 μM 12% @0.1 μM | | | |
| 241 | 0.5 | 1.9 | 79% @1 μM 34% @0.1 μM | | | |
| 242 | 1.2 | 3.7 | 165 | | | |
| 243 | 5.1 | 16 | 337 | | | |
| 244 | 1.1 | 2.1 | 182 | | | |
| 245 | 1.7 | 2.7 | 74% @1 μM 21% @0.1 μM | | | |
| 246 | 0.5 | 0.7 | 87 | | | |
| 247 | 0.5 | 1.8 | 69% @1 μM 36% @0.1 μM | | | |
| 248 | 0.9 | 3.9 | 74% @25 μM 66% @10 μM 63% @1 μM | | | |
| 249 | 0.2 | 1.6 | 70% @1 μM 31% @0.1 μM | | | |
| 250 | 0.9 | 0.9 | 68% @ 10 μM 51% @ 1 μM 24% @ 0.1 μM | | | |
| 251 | 8.7 | 3.8 | 281 | | | |
| 252 | 17.9 | 6.1 | 289 | | | |
| 254 | 1.3 | 4.2 | 63% @ 1 μM 19% @0.1 μM | | | |
| 255 | 1.3 | 0.9 | 101 | | | |
| 256 | 0.3 | 0.6 (1.5) | 59% @1 μM 43% @0.1 μM 15% @0.01 μM | | | |
| 257 | 0.3 | 0.6 | 67% @1 μM 63% @0.1 μM 11% @0.01 μM | | | |
| 258 | 1.3 | 2.5 | 132 | | | |
| 259 | 22.8 | 15.4 | 47% @10 μM 51% @ 1 μM 0% @0.1 μM | | | |
| 260 | 25.3 | 21.6 | 66% @10 μM 51% @ 1 μM 8.5% @ 0.1 μM | | | |
| 261 | | | ne @ 1 μM | | | |
| 262 | 1.7 | 1.2 | 58% @1 μM 6% @0.1 μM | | | |
| 263 | 0.7 | 0.6 | 63% @1 μM 52% @0.1 μM 4% @0.01 μM | | | |
| 264 | 0.9 | 0.6 | 15.9 | | | |
| 265 | 2.5 | 5 | 33% @ 1 μM 17% @0.1 μM | | | |
| 266 | | 3.4 | ne @ 1 μM | | | |
| 267 | 1.7 | 1.6 | 24 | | | |
| 268 | 0.8 | 0.9 | 17 | | | |
| 269 | ne @ 1 μM | ne @ 1 μM | ne @ 1 μM | | | |
| 270 | 0.5 | 0.7 | 19.7 | | | |
| 271 | 1.1 | 1.0 | 44.4 | | | |
| 273 | | 11.5 | 1605 | | | |
| 274 | | 0.7 | 63 | | | |
| 275 | | 20.3 | 1189 | | | |
| 276 | | 78% @ 5 μM 35% @1 μM 14% @ 0.1 μM | 43% @5 μM 11% @1 μM 11% @ 0.1 μM | | | |
| 278 | | 0.4 | 76 | | | |
| 279 | 1.7 | 1.1 | 161 | | | |
| 282 | 1.2 | 0.8 | 62% @10 μM 57% @1 μM 55% @0.1 μM 12% @0.01 μM | | | |
| 283 | 4.5 | 2.9 | 51% @10 μM 51% @1 μM 43% @0.1 μM 11% @0.01 μM | | | |
| 284 | 48 | 54.9 | ne @ 1 μM | | | |
| 285 | 4.5 | 3.5 | 377 | | | |
| 287 | 3.5 | 4.4 | 189 | | | |
| 288 | 41 | 42 | ne @ 1 μM | | | |
| 289 | 3.3 | 2.5 | ne @ 1 μM | | | |
| 290 | | 4.4 | 480 | 0.1 po 24% 0.3 po 78% 1 po 68% | | |
| 291 | | 0.6 | 43.4 | | | |
| 292 | | 32.7 | 63% @ 5 μM; 6% @ 1 μM | | | |
| 293 | | 1.4 | 129 | | | |
| 294 | | 1.9 | 304 | | | |
| 295 | | 0.6 | 25 | | | |
| 296 | | 0.9 | 154 | | | |
| 297 | | 2.5 | 179 | | | |
| 298 | | 1.6 | 183 | | | |
| 299 | | 1 | 43 | | | |
| 300 | | 2.1 | 59.5 | | | |
| 301 | | 0.9 | 102 | | | |
| 302 | | 100.1 | 1182 | | | |
| 303 | | 1.8 | 76.2 | | | |

-continued

| Example | $K_i$ (rat) Cap. [nM] | $K_i$ (human) Cap. [nM] | IC$_{50}$ (human) [nM] after pH stimulus | inhibition hypothermie (n = 5) | inhibition formaldehyde test (n = 10) | inhibition Bennet model (n = 10) |
|---|---|---|---|---|---|---|
| 304 | | 0.71 | 35.4 | | | |
| 307 | | 5.0 | 456 | | | |
| 308 | | 3.2 | 414.5 | | | |
| 309 | | 8.7 | 20% bei 5 μM | | | |
| 310 | | 43.7 | 27% bei 5 μM | | | |
| 311 | | 1.43 | 1092.0 | | | |
| 312 | | 68% @ 5 μM 7% @ 1 μM | ne @ 1 μM | | | |
| 313 | | 2.7 | ne @ 1 μM | | | |
| 314 | | 46% @ 5 μM 12% @ 1 μM | 31% @10 μM 14% @5 μM | | | |
| 315 | | 1 | 295 | | | |
| 316 | | 72.1 | ne @ 1 μM | | | |
| 317 | | 1.7 | 43 | | | |
| 318 | | 17.5 | 32% @10 μM 4% @5 μM | | | |
| 319 | | 13.8 | 54% @10 μM 38% @5 μM 4% @1 μM | | | |
| 320 | | 1.1 | 36 | | | |
| 321 | | 0.8 | 38 | | | |
| 322 | | 1 | 54% @ 1 μM 25% @ 0.1 μM | | | |
| 323 | | 1.9 | 41% @ 1 μM 15% @ 0.1 μM | | | |
| 324 | | 0.6 | 33 | | | |
| 325 | | 8.6 | 716 | | | |
| 326 | | 25.6 | 66% @ 10 μM 32% @ 5 μM 8% @ 1 μM | | | |
| 327 | | 3.4 | 342 | | | |
| 328 | | 0.8 | 128 | | | |
| 329 | | 0.8 | 179 | 1 po 7% | 1 po 54% | |
| 330 | | 31.3 | 806 | 1 po 7% 1 iv 7% | 1 po 54% | |
| 331 | | 0.7 | 31% @ 10 μM 22% @ 5 μM 26% @ 1 μM 18% @ 0.1 μM | | | |
| 332 | | 2.4 | 159 | | | |
| 334 | | 0.7 | 99 | | | |
| 335 | | 1.1 | ne @ 1 μM | | | |
| 336 | | 0.7 | 50% @ 1 μM 35% @ 0.1 μM 28% @ 0.05 μM | | | |
| 337 | | 0.7 | 30% @ 10 μM 6% @ 5 μM | | | |
| 338 | | 0.9 | 140 | | | |
| 339 | | 0.3 | 14 | | | |
| 340 | | 1.2 | 279 | | | |
| 341 | | 1.3 | 293 | | | |
| 342 | | 19.3 | 1139 | | | |
| 343 | | 55% @ 5 μM 8% @ 1 μM | ne @ 1 μM | | | |
| 344 | | 34% @ 5 μM 3% @ 1 μM | ne @ 1 μM | | | |
| 345 | | 2.8 | 45% @ 5 μM 38% @ 1 μM 3% @ 0.1 μM | | | |
| 346 | | 0.7 | 66 | | | |
| 347 | | 1.6 | | | | |
| 349 | | 44 | ne @ 1 μM | | | |
| 350 | | 5.8 | 52% @ 1 μM 4% @ 0.1 μM | | | |
| 351 | | 44 | ne @ 1 μM | | | |
| 352 | | 0.5 | 61% @ 10 μM 34% @ 5 μM 27% @ 1 μM | | | |
| 353 | | 0.6 | 25% @ 1 μM 28% @ 0.1 μM 18% @ 0.05 μM | | | |
| 354 | | 0.8 | 85 | | | |
| 355 | | 15.3 | 2205 | | | |
| 356 | | 9.2 | ne @ 1 μM | | | |
| 361 | | 9.7 | 462 | | | |
| 362 | | 1.5 | 161 | | | |
| 363 | | 0.7 | 76 | | | |
| 369 | | 1.7 | 182 | | | |
| 370 | | 5.6 | 250 | | | |
| 371 | | 3.7 | 368 | | | |
| 372 | | 14.3 | 52% @ 1 μM | | | |
| 373 | | 14.8 | 492 | | | |
| 374 | | 2.3 | 314 | | | |
| 375 | | 0.7 | 30 | | | |
| 376 | | 0.8 | 20 | | | |

| Example | $K_i$ (rat) Cap. [nM] | $K_i$ (human) Cap. [nM] | $IC_{50}$ (human) [nM] after pH stimulus | inhibition hypothermie (n = 5) | inhibition formaldehyde test (n = 10) | inhibition Bennet model (n = 10) |
|---|---|---|---|---|---|---|
| 377 | | 3 | | | | |
| 378 | | 23.9 | 325 | | | |

The dosis is in each case given in mg/kg body weight; wherein po describes peroral administration and iv intravenous administration. ne denotes in each case "no effect", d. h. no reaction was observed.
The value given after the symbol "@" denotes the concentration at which the inhibition (given in percent) was determined in each case.

The invention claimed is:

1. A compound of formula A,

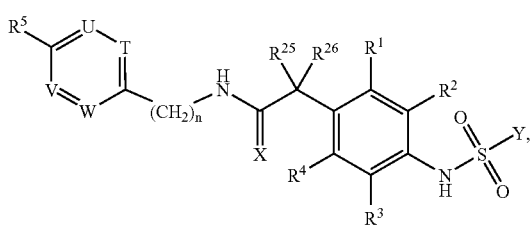

A in which
X denotes O;
Y denotes a linear or branched, saturated or unsaturated, unsubstituted or at least monosubstituted aliphatic $C_{1-10}$ residue;
n denotes 1;
$R^1$ and $R^4$ are H,
$R^2$ and $R^3$, mutually independently, in each case denote H; F; Cl; Br; I, or a linear or branched, saturated or unsaturated, unsubstituted or at least monosubstituted aliphatic $C_{1-10}$ residue;
$R^5$ denotes H; F; Cl; Br; I; $-NH_2$; $-OH$; $-SH$; $-NHR^{11}$; $-NR^{12}R^{13}$; $-OR^{14}$; $-SR^{15}$; or a linear or branched, unsaturated or saturated, unsubstituted or at least monosubstituted aliphatic $C_{1-10}$ residue;
T denotes C—$R^6$ and U denotes C—$R^7$ and V denotes N and W denotes C—$R^8$;
$R^6$ and $R^7$, mutually independently, in each case denote H; F; Cl; Br; I; or a linear or branched, saturated or unsaturated, unsubstituted or at least monosubstituted aliphatic $C_{1-10}$ residue;
$R^8$ denotes H; F; Cl; Br; I; $-NH_2$; $-OH$; $-SH$; $-NHR^{11}$; $-NR^{12}R^{13}$; $-OR^{14}$; $-SR^{15}$; or a linear or branched, saturated or unsaturated, unsubstituted or at least monosubstituted aliphatic $C_{1-10}$ residue;
denotes an unsaturated or saturated, unsubstituted or at least monosubstituted 3-, 4-, 5-, 6-, 7-, 8- or 9-membered cycloaliphatic residue which residue is in each case one or more of (i) attached to the parent structure via a carbon atom in the ring of the cycloaliphatic residue and may be fused with a saturated or unsaturated, unsubstituted or at least monosubstituted mono- or polycyclic ring system and (ii) attached via a linear or branched, unsubstituted or at least monosubstituted $C_{1-6}$ alkylene group or $C_{2-6}$ alkenylene group or $C_{2-6}$ alkynylene group;
or denotes an unsubstituted or at least monosubstituted 5- to 14-membered aryl or heteroaryl residue, which may be one or more of (i) fused with a saturated or unsaturated, unsubstituted or at least monosubstituted mono- or polycyclic ring system and (ii) attached via a linear or branched, unsubstituted or at least monosubstituted $C_{1-6}$ alkylene group or $C_{2-6}$ alkenylene group or $C_{2-6}$ alkynylene group;
$R^{11}$, $R^{12}$, $R^{13}$, $R^{14}$, $R^{15}$, and $R^{22}$, mutually independently, in each case denote a linear or branched, saturated or unsaturated, unsubstituted or at least monosubstituted aliphatic $C_{1-10}$ residue;
denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be one or more of (i) fused with a saturated or unsaturated, unsubstituted or at least monosubstituted mono- or polycyclic ring system and (ii) attached via a linear or branched, unsubstituted or at least monosubstituted $C_{1-6}$ alkylene group or 2- to 6-membered heteroalkylene group;
or denote an unsubstituted or at least monosubstituted 5- to 14-membered aryl or heteroaryl residue, which may be one or more of (i) fused with a saturated or unsaturated, unsubstituted or at least monosubstituted mono- or polycyclic ring system and (ii) attached via a linear or branched, unsubstituted or at least monosubstituted $C_{1-6}$ alkylene group or 2- to 6-membered heteroalkylene group;
or
$R^{12}$ and $R^{13}$, in each case together with the nitrogen atom joining them together as a ring member, form a saturated or unsaturated, unsubstituted or at least monosubstituted 4-, 5-, 6-, 7-, 8- or 9-membered heterocycloaliphatic residue optionally comprising at least one further heteroatom as ring member, which may be fused with a saturated or unsaturated, unsubstituted or at least monosubstituted mono- or polycyclic ring system;
and
$R^{25}$ and $R^{26}$, mutually independently, in each case denote a hydrogen residue; or denote a linear or branched, saturated or unsaturated, unsubstituted or at least monosubstituted aliphatic $C_{1-10}$ residue;
providing that $R^{25}$ and $R^{26}$ do not in each case denote a hydrogen residue;
wherein unless otherwise stated, the above-stated aliphatic $C_{1-10}$ residues may optionally in each case be substituted with 1, 2, 3, 4, 5, 6, 7, 8 or 9 substituents mutually independently selected from the group consisting of F, Cl, Br, I, $-CN$, $-NO_2$, $-OH$, $-NH_2$, $-SH$, $-O(C_{1-5}$-alkyl), $-S(C_{1-5}$-alkyl), $-NH(C_{1-5}$-alkyl), $-N(C_{1-5}$-alkyl)$(C_{1-5}$-alkyl), $-C(=O)-O-C_{1-5}$-alkyl, $-O-C(=O)-C_{1-5}$-alkyl, $-O$-phenyl, phenyl, $-OCF_3$ and $-SCF_3$;
the above-stated 2- to 6-membered heteroalkylene groups, $C_{1-6}$-alkylene groups, $C_{2-6}$-alkenylene groups and $C_{2-6}$-alkynylene groups may optionally in each case be substituted with 1, 2, 3, 4, 5, 6, 7, 8 or 9 substituents mutually independently selected from the group consisting of F, Cl, Br, I, $-CN$, $-NO_2$, $-OH$, $-NH_2$, $-SH$, —O($C_{1-5}$-alkyl), —S($C_{1-5}$-alkyl), —NH($C_{1-5}$-alkyl), —N($C_{1-5}$-alkyl)($C_{1-5}$-alkyl), —OCF$_3$ and —SCF$_3$;

the above-stated (hetero)cycloaliphatic residues may optionally in each case be substituted with 1, 2, 3, 4 or 5 substituents mutually independently selected from the group consisting of —$C_{1-6}$-alkylene-OH, =CH$_2$, —O—$C_{1-5}$-alkylene-oxetanyl, —$C_{1-5}$-alkylene —O—$C_{1-5}$-alkylene-oxetanyl, —CH$_2$—NH—$C_{1-5}$-alkyl, —CH$_2$—N($C_{1-5}$-alkyl)$_2$, —N[C(=O)—$C_{1-5}$-alkyl]-phenyl, —CH$_2$—O—$C_{1-5}$-alkyl, oxo (=O), thioxo (=S), F, Cl, Br, I, —CN, —CF$_3$, —SF$_5$, —OH, —O—$C_{1-5}$-alkyl, —O—C(=O)—$C_{1-5}$-alkyl, —NH$_2$, —NO$_2$, —O—CF$_3$, —S—CF$_3$, —SH, —S—$C_{1-5}$-alkyl, —$C_{1-5}$-alkyl, —C(=O)—$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —NH-phenyl, —N($C_{1-5}$-alkyl)-phenyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —(CH$_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N[C(=O)—$C_{1-5}$-alkyl]-phenyl, —NH-phenyl, —N($C_{1-5}$-alkyl)-phenyl, —(CH$_2$)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —$C_{1-5}$-alkyl, —O—$C_{1-5}$-alkyl, —O—CF$_3$, —S—CF$_3$, phenyl and —O-benzyl;

the rings of the above-stated mono- or polycyclic ring systems may optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—$C_{1-5}$-alkyl, —NH$_2$, —NO$_2$, —O—CF$_3$, —S—CF$_3$, —SH, —S—$C_{1-5}$-alkyl, —$C_{1-5}$-alkyl, —C(=O)—$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —$C_{1-5}$-alkyl, —O—$C_{1-5}$-alkyl, —O—CF$_3$, —S—CF$_3$, phenyl and —O-benzyl, and the above-stated aryl or heteroaryl residues may optionally in each case be substituted with 1, 2, 3, 4 or 5 substituents mutually independently selected from the group consisting of F, Cl, Br, I, —CN, —CF$_3$, —SF$_5$, —OH, —O—$C_{1-5}$-alkyl, —NH$_2$, —NO$_2$, —O—CF$_3$, —S—CF$_3$, —SH, —S—$C_{1-5}$-alkyl, —$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —NH—S(=O)$_2$—$C_{1-5}$-alkyl, —NH—C(=O)—O—$C_{1-5}$-alkyl, —C(=O)—H, —C(=O)—$C_{1-5}$-alkyl, —C(=O)—NH$_2$, —C(=O)—NH—$C_{1-5}$-alkyl, —C(=O)—N—($C_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —$C_{1-5}$-alkyl, —O—$C_{1-5}$-alkyl, —O—CF$_3$, —S—CF$_3$, phenyl and —O-benzyl, and the above-stated heteroalkylene groups in each case comprise 1, 2 or 3 heteroatom(s) mutually independently selected from the group consisting of oxygen, nitrogen (NH) and sulfur, the above-stated (hetero)cycloaliphatic residues may in each case optionally comprise 1, 2 or 3 heteroatom(s) mutually independently selected from the group consisting of oxygen, nitrogen and sulfur, the rings of the above-stated mono- or polycyclic ring systems are in each case 5-, 6- or 7-membered and may in each case optionally comprise 1, 2, 3, 4 or 5 heteroatom(s) as ring member(s), which are mutually independently selected from the group consisting of oxygen, nitrogen and sulfur, the above-stated heteroaryl residues in each case optionally comprise 1, 2, 3, 4 or 5 heteroatom(s) mutually independently selected from the group consisting of oxygen, nitrogen and sulfur as ring member(s);

a stereoisomer thereof, a diastereoisomer thereof, an enantiomer thereof, a racemate thereof or a salt thereof.

2. The compound according to claim 1, wherein
X denotes O;
n denotes 1;
$R^1$, $R^3$ and $R^4$ in each case denote H;
$R^2$ denote methyl; F; Cl; Br or I;
and
$R^{25}$ denotes an alkyl residue selected from the group consisting of —CH$_2$—OH, —CH$_2$—CH$_2$—OH, methyl, ethyl and n-propyl or denotes a residue selected from the group consisting of benzyl, phenyl, phenethyl, cyclopropyl, cyclobutyl, cyclopentyl and cyclohexyl;
$R^{26}$ denote a hydrogen residue or denote a residue selected from the group consisting of methyl, ethyl and n-propyl;
or
$R^{25}$ and $R^{26}$ in each case together with the carbon atom joining them together as a ring member, form a residue selected from the group consisting of cyclopropyl, cyclobutyl, cyclopentyl and cyclohexyl;
in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

3. The compound of claim 1 having the formula Ia1

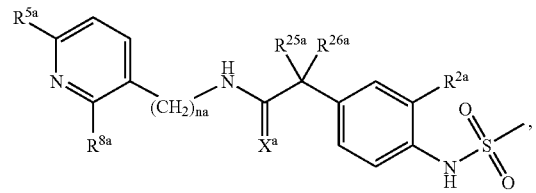

Ia1 in which
$X^a$ denotes O;
na denotes 1;
$R^{2a}$ denotes F; Cl; Br; I;
$R^{5a}$ denotes F; Cl; Br; I;
or denotes a residue selected from the group consisting of cyclopropyl, cyclobutyl, cyclopentyl, cyclohexyl, cyclopentenyl and cyclohexenyl;

R$^{8a}$ denotes H; F; Cl; Br; I; —OH; —NH$_2$; NHR$^{11a}$; —NR$^{12a}$R$^{13a}$; —OR$^{14a}$; —SR$^{15a}$;

or denotes a residue selected from the group consisting of methyl, ethyl, n-propyl, isopropyl, sec-butyl, isobutyl, tert-butyl, n-butyl, 3-methyl-but-1-yl, 4-methyl-pent-1-yl, n-pentyl, n-hexyl, (3,3)-dimethyl-but-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH═CH)—, —C≡C— or —C≡C—CH$_2$-group R$^{11a}$, R$^{12a}$, R$^{13a}$, R$^{14a}$, R$^{15a}$ and R$^{22a}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, piperidinyl, pyrrolidinyl, cyclopropyl, cyclobutyl, cyclopentyl and cyclohexyl, which may in each case be attached via a —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl;

or denote a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which may optionally be substituted with 1, 2, 3, 4 or 5 substituents mutually independently selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or

R$^{12a}$ and R$^{13a}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which may optionally in each case be substituted with 1 or 2 substituents mutually independently selected from the group consisting of —CH$_2$—O—CH$_2$-oxetanyl, —O—CH$_2$-oxetanyl, —CH$_2$—OH, —CH$_2$—CH$_2$—OH, ═CH$_2$, —C(═O)—O—CH$_3$, —C(═O)—O—C$_2$H$_5$, —C(═O)—O—C(CH$_3$)$_3$, —C(═O)—CH$_3$, —C(═O)—C$_2$H$_5$, —C(═O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(═O)—C$_2$H$_5$]-phenyl, —N—[C(═O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (═O), thioxo (═S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(═O)—CH$_3$, —O—C(═O)—C$_2$H$_5$, —O—C(═O)—C(CH$_3$)$_3$, —(CH$_2$)-pyridinyl, pyridinyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(═O)—C$_2$H$_5$]-phenyl, —N—[C(═O)—CH$_3$]-phenyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

R$^{25a}$ and R$^{26a}$, mutually independently, in each case denote a hydrogen residue; denote a residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

providing that R$^{25a}$ and R$^{26a}$ do not in each case denote a hydrogen residue;

or

R$^{25a}$ and R$^{26a}$ in each case together with the carbon atom joining them together as a ring member, form a residue selected from the group consisting of cyclopropyl, cyclobutyl, cyclopentyl, cyclohexyl and cycloheptyl.

4. The compound of formula Ia

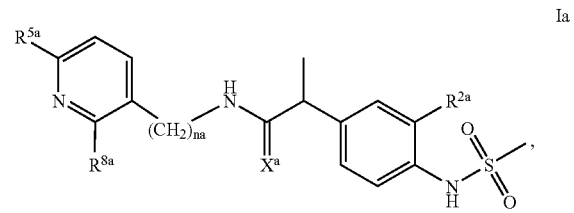

in which X$^a$, na, R$^{5a}$, R$^{8a}$ and R$^{2a}$ have the meaning as defined in claim 3.

5. The compound according to claim 4, wherein

R$^{2a}$ denotes F; Cl; Br; I;

R$^{5a}$ denotes F; Cl; Br; I;

or denotes a residue selected from the group consisting of cyclopropyl, cyclobutyl, cyclopentyl, cyclohexyl, cyclopentenyl and cyclohexenyl;

R$^{8a}$ denotes H; F; Cl; Br; I; —OH; —NH$_2$; —NHR$^{11a}$; —NR$^{12a}$R$^{13a}$; —OR$^{14a}$; SR$^{15a}$;

or denotes a residue selected from the group consisting of methyl, ethyl, n-propyl, isopropyl, sec-butyl, isobutyl, tert-butyl, n-butyl, 3-methyl-but-1-yl, 4-methyl-pent-1-yl, n-pentyl, n-hexyl, (3,3)-dimethyl-but-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

or denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, (2,3)-dihydrothieno[3,4-b][1,4]dioxinyl, benzo[b]furanyl, indolyl, phenyl, naphthyl, oxazolyl, thiazolyl, imidazolyl, pyrimidinyl, thiophenyl, furanyl and pyridinyl, which may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH3, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

$R^{11a}$, $R^{12a}$, $R^{13a}$, $R^{14a}$, $R^{15a}$ and $R^{22a}$, mutually independently, in each case denote a radical from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a radical selected from the group consisting of 2,3-dihydro-1H-indenyl, piperidinyl, pyrrolidinyl, cyclopropyl, cyclobutyl, oxetanyl, cyclopentyl and cyclohexyl, which may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or $R^{12a}$ and $R^{13a}$ in each case together with the nitrogen atom joining them together as a ring member, form a residue selected from the group consisting of

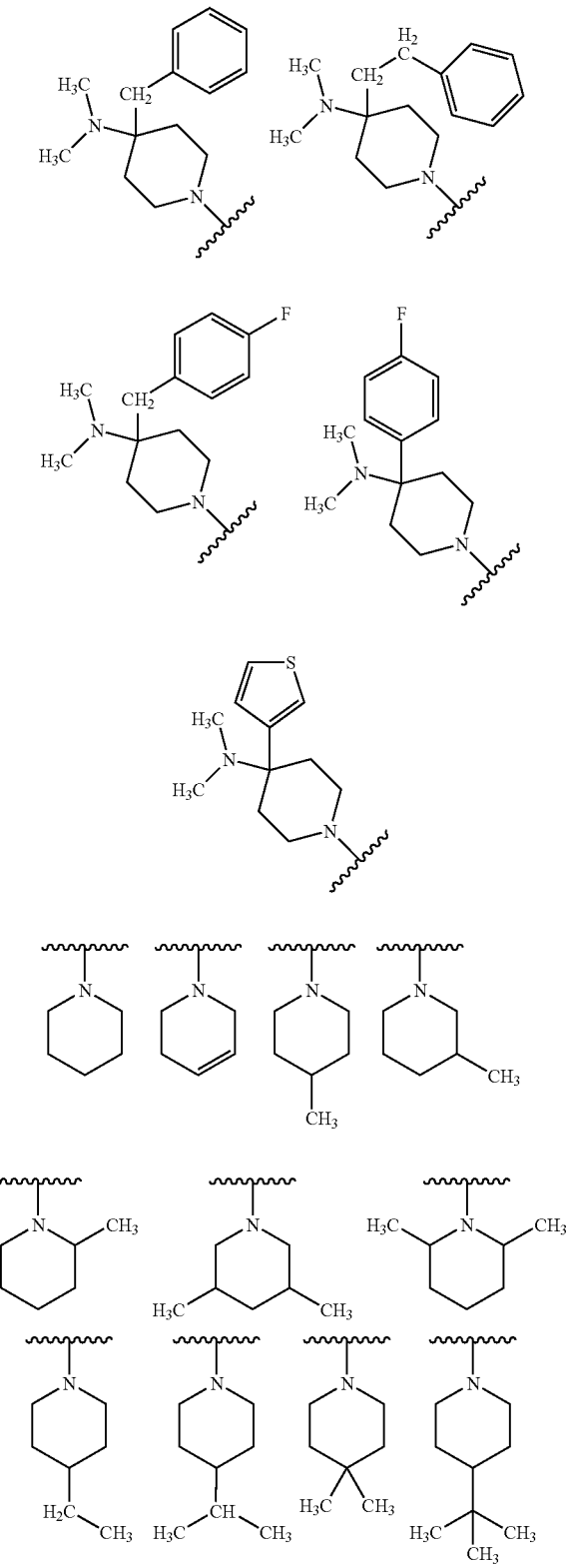

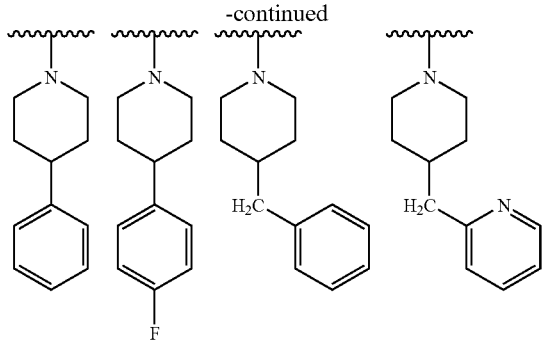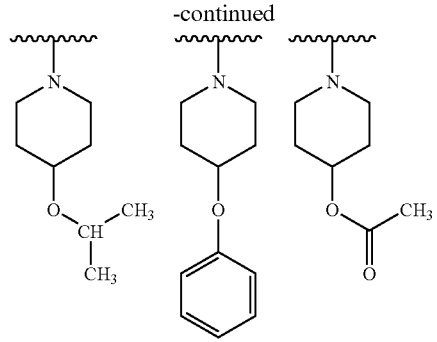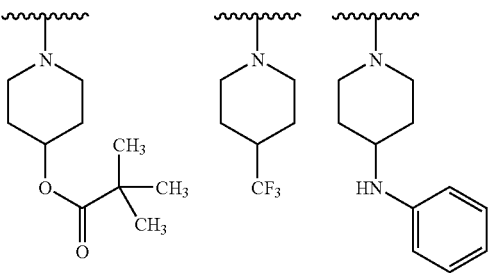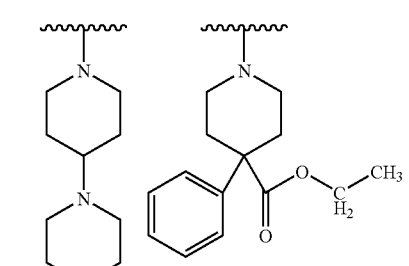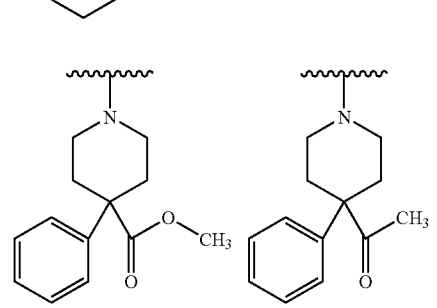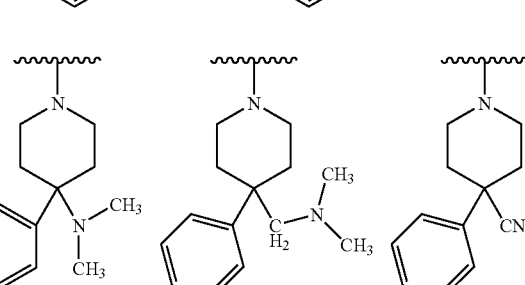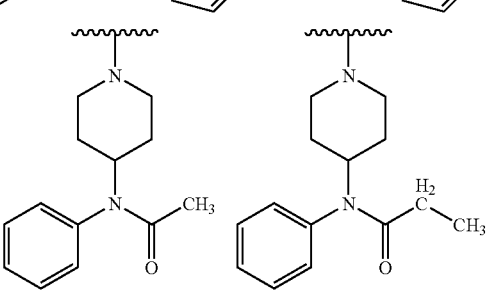

-continued
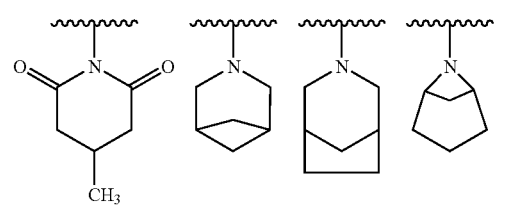
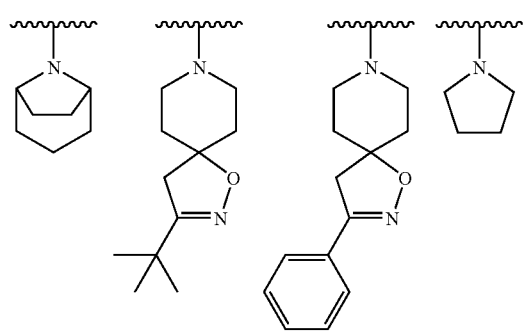
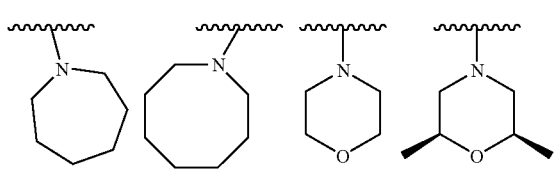
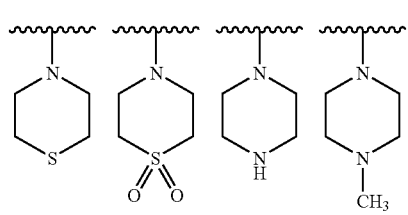
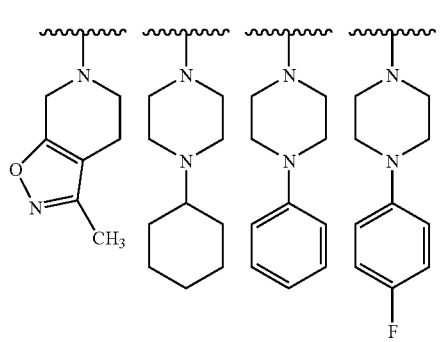
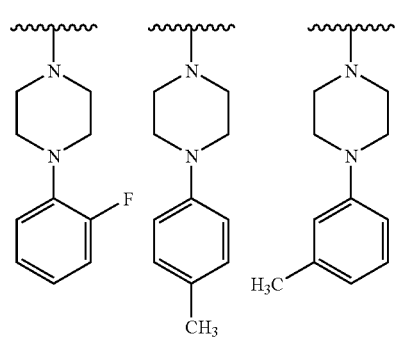
-continued
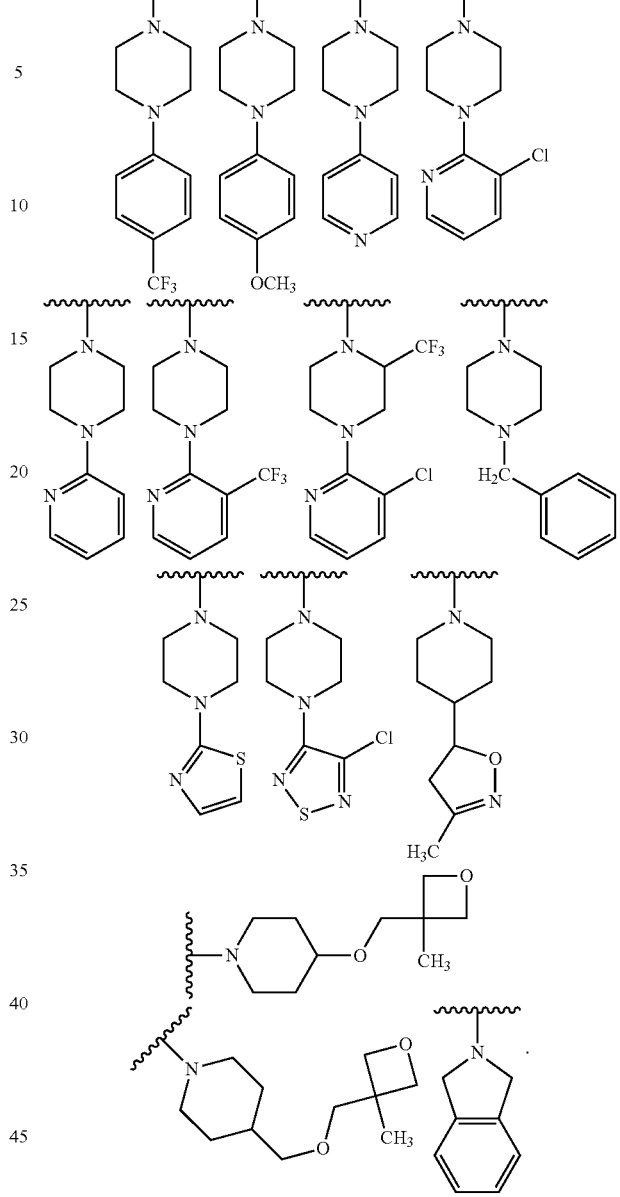
6. The compound of claim 3 having the formula C1
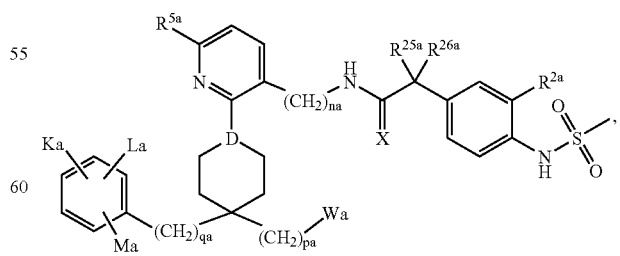
in which
D denotes CH or N;
pa denotes 0, qa denotes 0, 1 or 2;

Ka, La and Ma, mutually independently, in each case denote H, —CF$_3$, —OH, —O—CH$_3$, —O—C$_2$H$_5$, F, Cl, Br, methyl, ethyl, isopropyl, n-propyl, n-butyl, tert-butyl or sec-butyl;

Wa denotes —NR$^{34a}$R$^{35a}$, —CN, —C(=O)—R$^{36a}$ or —C(=O)—OR$^{37a}$;

and R$^{34a}$, R$^{35a}$, R$^{36a}$ and R$^{37a}$, mutually independently, in each case denote H or denote a residue selected from the group consisting of methyl, ethyl, n-propyl, isopropyl, n-butyl, sec-butyl and isobutyl.

7. The compound of claim 4, having the formula C2

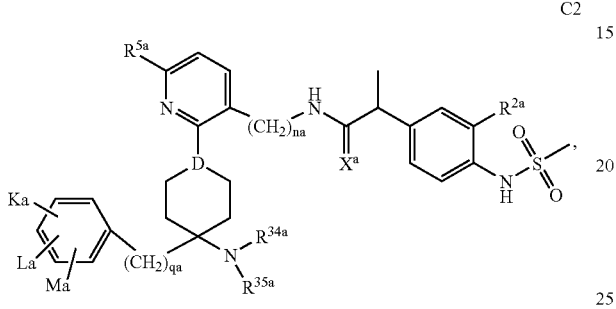

C2 in which

D denotes CH or N;

qa denotes 0, 1 or 2;

Ka, La and Ma, mutually independently, in each case denote H, —CF$_3$, —OH, —O—CH$_3$, —O—C$_2$H$_5$, F, Cl, Br, methyl, ethyl, isopropyl, n-propyl, n-butyl, tert-butyl or sec-butyl;

and R$^{34a}$ and R$^{35a}$, mutually independently, in each case denote H or denote a residue selected from the group consisting of methyl, ethyl, n-propyl, isopropyl, n-butyl, sec-butyl and isobutyl.

8. The compound of claim 1 having the formula Ib1

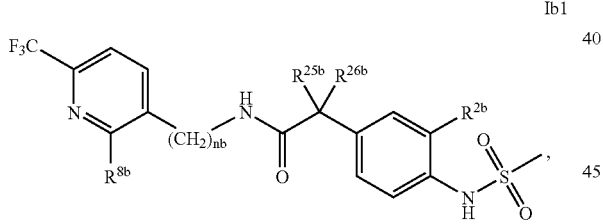

Ib1 in which nb denotes 0, 1 or 2;

R$^{2b}$ denotes methyl; —O—CH$_3$; F; Cl; Br or I;

R$^{8b}$ denotes H; F; Cl; Br; I; —OH; —NH$_2$; —NHR$^{11b}$; NR$^{12b}$R$^{13b}$; —OR$^{14b}$; —SR$^{15b}$;

denotes a residue selected from the group consisting of methyl, ethyl, n-propyl, isopropyl, sec-butyl, isobutyl, tert-butyl, n-butyl, n-pentyl, n-hexyl, (3,3)-dimethyl-but-1-yl, 3-methyl-but-1-yl, 4-methyl-pent-1-yl, (3,3)-dimethyl-but-1-ynyl, 4-methyl-pent-1-ynyl, 1-hexynyl, propynyl, ethynyl, butynyl, pentynyl, 2-methyl-propen-1-yl, 3-methyl-but-2-en-1-yl, 1-pentenyl, 1-octenyl, 1-heptenyl, 1-hexenyl and (3,3)-dimethyl-but-1-enyl;

denotes a residue from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and may optionally in each case be substituted with 1, 2, 3, 4 or 5 substituents mutually independently selected from the group consisting —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, which may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH3, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11b}$, R$^{12b}$, R$^{13b}$, R$^{14b}$ and R$^{15b}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, which may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which may optionally be substituted in each case with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or

R$^{12b}$ and R$^{13b}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo

[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which may optionally in each case be substituted with 1 or 2 substituents mutually independently selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, (4,5)-dihydroisoxazolyl, thiazolyl, (1,2,5)-thiadiazolyl, thiophenyl, phenethyl, cyclohexyl, cyclopentyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—C$_2$H$_5$]-phenyl, —N—[C(=O)—CH$_3$]-phenyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

$R^{25b}$ and $R^{26b}$, mutually independently, in each case denote a hydrogen residue; denote an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

providing that $R^{25b}$ and $R^{26b}$ do not in each case denote a hydrogen residue;

or $R^{25b}$ and $R^{26b}$ in each case together with the carbon atom joining them together as a ring member, form a residue selected from the group consisting of cyclopropyl, cyclobutyl, cyclopentyl, cyclohexyl and cycloheptyl.

9. The compound of claim 1 having formula Id1

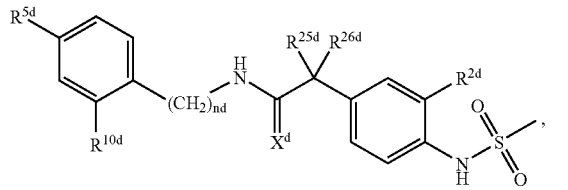

in which
$X^d$ denotes O;
nd denotes 1;

$R^{2d}$ denotes F; Cl; Br; I;
$R^{5d}$ denotes F; Cl; Br; I;
denotes a residue selected from the group consisting of methyl, ethyl, tert-butyl,
or denotes a residue selected from the group consisting of cyclopropyl, cyclobutyl, cyclopentyl, cyclohexyl, cyclopentenyl and cyclohexenyl;
$R^{10d}$ denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and in each case may optionally be substituted with 1, 2, 3, 4 or 5 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;
or denotes a residue selected from the group consisting of tetrazolyl, (1,3)-benzodioxolyl, (1,4)-benzodioxanyl, (2,3)-dihydrothieno[3,4-b][1,4]dioxinyl, benzo[b]furanyl, indolyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, NH—S(=O)$_2$—CH3, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;
$R^{11d}$, $R^{12d}$, $R^{13d}$, $R^{14d}$, $R^{15d}$ and $R^{22d}$, mutually independently, in each case
denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;
denote a residue selected from the group consisting of 2,3-dihydro-1H-indenyl, piperidinyl, pyrrolidinyl, cyclopropyl, cyclobutyl, oxetanyl, cyclopentyl and cyclohexyl, wherein the residue may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of —(CH$_2$)-pyridinyl, —(CH$_2$)$_2$-pyridinyl, phenyl, naphthyl, thiophenyl, furanyl, pyrrolyl and pyridinyl, which in each case may optionally be substituted with 1, 2, 3, 4 or 5 substituents selected from the group consisting of —CF$_3$, F, Cl, Br, —O—CH$_3$, —O—C$_2$H$_5$, methyl, ethyl, n-propyl, isopropyl, n-butyl, sec-butyl, isobutyl and tert-butyl;

or

R$^{12d}$ and R$^{13d}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, —N—[C(=O)—C$_2$H$_5$]-phenyl, —N—[C(=O)—CH$_3$]-phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

R$^{25d}$ and R$^{26d}$, mutually independently, in each case denote a hydrogen residue; or denote an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—OH, isopropyl, n-butyl, sec-butyl, isobutyl, methyl, ethyl and n-propyl;

providing that R$^{25d}$ and R$^{26d}$ do not in each case denote a hydrogen residue;

or

R$^{25d}$ and R$^{26d}$ in each case together with the carbon atom joining them together as a ring member, form a residue selected from the group consisting of cyclopropyl, cyclobutyl, cyclopentyl, cyclohexyl and cycloheptyl.

10. The compound of claim 9 having the formula Id

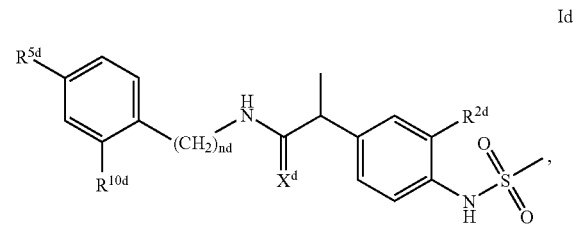

11. The compound of claim 1 having the formula Ie1

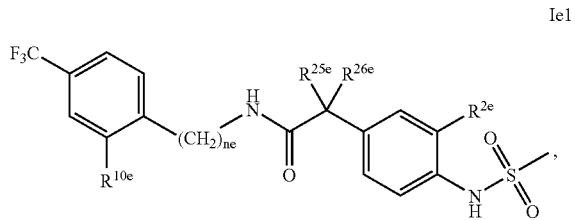

in which ne denotes 1;

R$^{2e}$ denotes methyl; F; Cl; Br or I;

R$^{10e}$ denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and in each case may optionally be substituted with 1, 2, 3, 4 or 5 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH$_3$, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11e}$, R$^{12e}$, R$^{13e}$, R$^{14e}$ and R$^{15e}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, wherein the residue may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF3, F, Cl, Br, —O—CH$_3$, —O—C$_2$H$_5$, methyl, ethyl, n-propyl, isopropyl, n-butyl, sec-butyl, isobutyl and tert-butyl;

or

R$^{12e}$ and R$^{13e}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, —N—[C(=O)—C$_2$H$_5$]-phenyl, —N—[C(=O)—CH$_3$]-phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

R$^{25e}$ and R$^{26e}$, mutually independently, in each denote a hydrogen residue;

or denote an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

providing that R$^{25e}$ and R$^{26e}$ do not in each case denote a hydrogen residue;

or

R$^{25e}$ and R$^{26e}$ each case together with the carbon atom joining them together as a ring member, form a residue selected from the group consisting of cyclopropyl, cyclobutyl, cyclopentyl, cyclohexyl and cycloheptyl.

12. The compound of claim 11 having the formula Ie

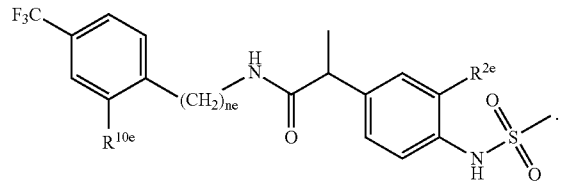

Ie

13. The compound according to claim 12, wherein
R$^{2e}$ denotes F;
R$^{10e}$
denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH$_2$-group and in each case may optionally be substituted with 1, 2, 3, 4 or 5 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of tetrazolyl, (1,3)-benzodioxolyl, (1,4)-benzodioxanyl, indolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, —NH$_2$, —N(CH$_3$)$_2$, —N(C$_2$H$_5$)$_2$, —NH—S(=O)$_2$—CH$_3$, —NH—S(=O)$_2$—C$_2$H$_5$, —NH—S(=O)$_2$—CH(CH$_3$)$_2$, —NO$_2$, —O—CF$_3$, —S—CF$_3$, —SH, —S—CH₃, —S—C₂H₅, —S—CH(CH₃)₂, —S—C(CH₃)₃, methyl, ethyl, n-propyl, isopropyl, n-butyl, sec-butyl, isobutyl and tert-butyl;

$R^{11e}, R^{12e}, R^{13e}, R^{14e}$ and $R^{15e}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH₂—CH₂—O—CH₃, —CH₂—CH₂—O—C₂H₅, —CH₂—CH₂—O-phenyl, —CH₂—CH₂—CH₂—O—CH₃, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, wherein the residue may in each case be attached via a —CH₂—O—, —CH₂—CH₂—O—, —CH₂—CH₂—O—CH₂—, —CH₂—CH(CH₃)—O—CH₂—, —(CH₂)—, —(CH₂)₂— or —(CH₂)₃-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH₃, —C(=O)—O—C₂H₅, —C(=O)—O—CH(CH₃)₂ and —C(=O)—O—C(CH₃)₃;

or denote a residue selected from the group consisting of —(CH₂)-pyridinyl, —(CH₂)₂-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF3, F, Cl, Br, —O—CH₃, —O—C₂H₅, methyl, ethyl, n-propyl, isopropyl, n-butyl, sec-butyl, isobutyl and tert-butyl;

or $R^{12e}$ and $R^{13e}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH₂—O—CH₂-oxetanyl, —O—CH₂-oxetanyl, —CH₂—OH, —CH₂—CH₂—OH, =CH₂, —C(=O)—O—CH₃, —C(=O)—O—C₂H₅, —C(=O)—O—C(CH₃)₃, —C(=O)—CH₃, —C(=O)—C₂H₅, —C(=O)—C(CH₃)₃, —CN, —CH₂—N(CH₃)₂, —CH₂—N(C₂H₅)₂, —CH₂—NH—CH₃, —CH₂—NH—C₂H₅, —N—[C(=O)—C₂H₅]-phenyl, —N—[C(=O)—CH₃]-phenyl, —CH₂—O—CH₃, —CH₂—O—CH₂—CH₃, —NH₂, —NH—CH₃, —NH—C₂H₅, —N(CH₃)₂, —N(C₂H₅)₂, —NH-phenyl, —N(CH₃)-phenyl, —N(C₂H₅)-phenyl, oxo (=O), thioxo (=S), —OH, F, Cl, Br, —CF₃, —O—CH₃, —O—C₂H₅, —O—C(CH₃)₃, —O—CH(CH₃)₂, —O—CH₂—CH₂—CH₂—CH₃, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH₃, —O—C(=O)—C₂H₅, —O—C(=O)—C(CH₃)₃, —(CH₂)-pyridinyl, pyridinyl, phenyl and benzyl, wherein in each case the cyclic moiety of the residues oxetanyl, N—[C(=O)—C₂H₅]-phenyl, —N—[C(=O)—CH₃]-phenyl, (4,5)-dihydroisoxazolyl, thiazolyl, (1,2,5)-thiadiazolyl, thiophenyl, phenethyl, —NH-phenyl, —N(CH₃)-phenyl, —N(C₂H₅)-phenyl, —(CH₂)-pyridinyl, pyridinyl, phenyl, —O-phenyl and benzyl may optionally be substituted with 1, 2, 3, 4 or 5 substituents mutually independently selected from the group consisting of —CF₃, —OH, —O—CH₃, —O—C₂H₅, F, Cl, Br, methyl, ethyl, isopropyl, n-propyl, n-butyl, tert-butyl and sec-butyl.

14. The compound of claim 1 having the formula If1

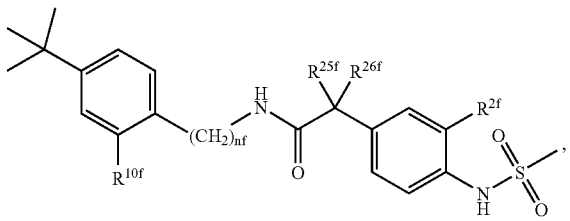

If1 in which nf denotes 1;

$R^{2f}$ denotes methyl; F; Cl; Br or I;

$R^{10f}$ denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a —(CH=CH)—, —C≡C— or —C≡C—CH₂-group and in each case may optionally be substituted with 1, 2, 3, 4 or 5 substituents selected from the group consisting of —C(=O)—O—CH₃, —C(=O)—O—C₂H₅, —C(=O)—O—C(CH₃)₃, —C(=O)—CH₃, —C(=O)—C₂H₅, —C(=O)—C(CH₃)₃, CN, —CH₂—N(CH₃)₂, —CH₂—N(C₂H₅)₂, —CH₂—NH—CH₃, —CH₂—NH—C₂H₅, —N—[C(=O)—C₂H₅]-phenyl, —N—[C(=O)—CH₃]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of (1,3)-benzodioxolyl, (1,4)-benzodioxanyl, indolyl, tetrazolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH₂)—, —(CH₂)₂— or —(CH₂)₃-group and/or in each case may optionally be substituted with 1, 2, 3, 4 or 5 substituents selected from the group consisting of F, Cl, Br, I, —CN, —CF₃, —SF₅, —OH, —O—CH₃, —O—C₂H₅, —NH₂, —N(CH₃)₂, —N(C₂H₅)₂, —NH—S(=O)₂—CH₃, —NH—S(=O₂)—C₂H₅, —NH—S(=O)₂—CH(CH₃)₂, —NO₂, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl and tert-butyl;

$R^{11f}, R^{12f}, R^{13f}, R^{14f}$ and $R^{15f}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, wherein the residue may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$-group and/or in each case may optionally be substituted with 1, 2, 3, 4 or 5 substituents selected from the group consisting of methyl, ethyl, n-propyl, isopropyl, n-butyl, sec-butyl, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of —(CH$_2$)-pyridinyl, —(CH$_2$)$_2$-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF3, F, Cl, Br, —O—CH$_3$, —O—C$_2$H$_5$, methyl, ethyl, n-propyl, isopropyl, n-butyl, sec-butyl, isobutyl and tert-butyl;

or

R$^{12f}$ and R$^{13f}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH$_2$—O—CH$_2$-oxetanyl, —O—CH$_2$-oxetanyl, —CH$_2$—OH, —CH$_2$—CH$_2$—OH, =CH$_2$, —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH$_2$, —NH—CH$_3$, —NH—C$_2$H$_5$, —N(CH$_3$)$_2$, —N(C$_2$H$_5$)$_2$, —NH-phenyl, —N(CH$_3$)-phenyl, —N(C$_2$H$_5$)-phenyl, oxo (=O), thioxo (=S), —OH, F, Cl, Br, —CF$_3$, —O—CH$_3$, —O—C$_2$H$_5$, —O—C(CH$_3$)$_3$, —O—CH(CH$_3$)$_2$, —O—CH$_2$—CH$_2$—CH$_2$—CH$_3$, methyl, ethyl, isopropyl, n-propyl, n-butyl, tert-butyl, sec-butyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —O-phenyl, —O—C(=O)—CH$_3$, —O—C(=O)—C$_2$H$_5$, —O—C(=O)—C(CH$_3$)$_3$, —(CH$_2$)-pyridinyl, pyridinyl, phenyl and benzyl, wherein in each case the cyclic moiety of the residues oxetanyl, —N—[C(=O)—C$_2$H$_5$]-phenyl, —N—[C(=O)—CH$_3$]-phenyl, (4,5)-dihydroisoxazolyl, thiazolyl, (1,2,5)-thiadiazolyl, thiophenyl, phenethyl, —NH-phenyl, —N(CH$_3$)-phenyl, —N(C$_2$H$_5$)-phenyl, —(CH$_2$)-pyridinyl, pyridinyl, phenyl, —O-phenyl and benzyl may optionally be substituted with 1, 2, 3, 4 or 5 substituents mutually independently selected from the group consisting of —CF$_3$, —OH, —O—CH$_3$, —O—C$_2$H$_5$, F, Cl, Br, methyl, ethyl, isopropyl, n-propyl, n-butyl, tert-butyl and sec-butyl;

R$^{25f}$ and R$^{26f}$, mutually independently, in each case denote a hydrogen residue;

or denote an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl and n-propyl;

providing that R$^{25f}$ f and R$^{26f}$ do not in each case denote a hydrogen residue;

or

R$^{25f}$ and R$^{26f}$ in each case together with the carbon atom joining them together as a ring member, form a residue selected from the group consisting of cyclopropyl, cyclobutyl, cyclopentyl, cyclohexyl and cycloheptyl.

15. The compound according to claim 14, wherein

R$^{2f}$ denotes F;

R$^{10f}$ denotes a residue selected from the group consisting of cyclopropyl, cyclobutyl, cyclopentyl, cyclohexyl, cyclohexenyl, pyrrolidinyl, piperidinyl, morpholinyl, piperazinyl, azepanyl, diazepanyl, azocanyl and thiomorpholinyl, which is in each case attached to the parent structure via a carbon atom of the rings of the above-stated residues or via a (CH=CH)—, —C≡C— or —C≡C—CH$_2$-group and in each case may optionally be substituted with 1, 2, 3, 4 or 5 substituents selected from the group consisting of —C(=O)—O—CH$_3$, —C(=O)—O—C$_2$H$_5$, —C(=O)—O—C(CH$_3$)$_3$, —C(=O)—CH$_3$, —C(=O)—C$_2$H$_5$, —C(=O)—C(CH$_3$)$_3$, —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), methyl, ethyl, n-propyl, isopropyl, n-butyl, sec-butyl, isobutyl, tert-butyl and n-pentyl;

or denotes a residue selected from the group consisting of (1,3)-benzodioxolyl, (1,4)-benzodioxanyl, indolyl, tetrazolyl, (2,3)-dihydrothieno[3,4-b][1,4]dioxinyl, benzo[b]furanyl, phenyl, naphthyl, oxazolyl, thiazolyl, imidazolyl, pyrimidinyl, thiophenyl, furanyl and pyridinyl, wherein the residue may in each case be attached via a —(CH=CH)—, —C≡C—, —(CH$_2$)—, —(CH$_2$)$_2$— or —(CH$_2$)$_3$-group and/or in each case may optionally be substituted with 1, 2, 3, 4 or 5 substituents selected from the group consisting of F, Cl, Br, I, —CN, —CF$_3$, —SF$_5$, —OH, —O—CH$_3$, —O—C$_2$H$_5$, NH$_2$, —N(CH$_3$)$_2$, —N(C$_2$H$_5$)$_2$, —NH—S(=O)$_2$—CH$_3$, —NH—S(=O$_2$)—C$_2$H$_5$, —NH—S(=O)$_2$—CH(CH$_3$)$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl and tert-butyl;

R$^{11f}$, R$^{12f}$, R$^{13f}$, R$^{14f}$ and R$^{15f}$, mutually independently, in each case denote a residue selected from the group consisting of methyl, ethyl, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl, (3,3)-dimethylbutyl, —CH$_2$—CH$_2$—O—CH$_3$, —CH$_2$—CH$_2$—O—C$_2$H$_5$, —CH$_2$—

CH₂—O-phenyl, —CH₂—CH₂—CH₂—O—CH₃, ethenyl, propenyl, 2-butenyl, 3-butenyl, 2-pentenyl and 3-pentenyl;

denote a residue selected from the group consisting of oxetanyl, 2,3-dihydro-1H-indenyl, piperidinyl, pyrrolidinyl, cyclopropyl, cyclobutyl, cyclopentyl and cyclohexyl, wherein the residue may in each case be attached via a —CH₂—O—, —CH₂—CH₂—O—, —CH₂—CH₂—O—CH₂—, —CH₂—CH(CH₃)—O—CH₂—, —(CH₂)—, —(CH₂)₂— or —(CH₂)₃-group and/or in each case may optionally be substituted with 1, 2, 3, 4 or 5 substituents selected from the group consisting of methyl, ethyl, n-propyl, isopropyl, n-butyl, sec-butyl, tert-butyl, n-pentyl, n-hexyl, —C(=O)—O—CH₃, —C(=O)—O—C₂H₅, —C(=O)—O—CH(CH₃)₂ and —C(=O)—O—C(CH₃)₃;

or denotes a residue selected from the group consisting of —(CH₂)-pyridinyl, —(CH₂)₂-pyridinyl, benzyl, phenethyl, phenyl, naphthyl, thiophenyl, furanyl, pyrrolyl and pyridinyl, which in each case may optionally be substituted with 1, 2, 3, 4 or 5 substituents selected from the group consisting of —CF₃, F, Cl, Br, —O—CH₃, —O—C₂H₅, methyl, ethyl, n-propyl, isopropyl, n-butyl, sec-butyl, isobutyl and tert-butyl;

or $R^{12f}$ and $R^{13f}$ in each case together with the nitrogen atom joining them together as a ring member, form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, (1,2,3,6)-tetrahydropyridinyl, piperazinyl, morpholinyl, azepanyl, diazepanyl and thiomorpholinyl, which in each case may optionally be substituted with 1 or 2 substituents selected from the group consisting of —CH₂—O—CH₂-oxetanyl, —O—CH₂-oxetanyl, —CH₂—OH, —CH₂—CH₂—OH, =CH₂, —C(=O)—O—CH₃, —C(=O)—O—C₂H₅, —C(=O)—O—C(CH₃)₃, —C(=O)—CH₃, —C(=O)—C₂H₅, —C(=O)—C(CH₃)₃, —CN, —CH₂—N(CH₃)₂, —CH₂—N(C₂H₅)₂, —CH₂—NH—CH₃, —CH₂—NH—C₂H₅, —N—[C(=O)—C₂H₅]-phenyl, —N—[C(=O)—CH₃]-phenyl, —CH₂—O—CH₃, —CH₂—O—CH₂—CH₃, —CH₂—O—CH₃, —NH₂, —NH—CH₃, —NH—C₂H₅, —N(CH₃)₂, —N(C₂H₅)₂, —NH-phenyl, —N(CH₃)-phenyl, —N(C₂H₅)-phenyl, oxo (=O), thioxo (=S), —OH, F, Cl, Br, —CF₃, —O—CH₃, —O—C₂H₅, —O—C(CH₃)₃, —O—CH(CH₃)₂, —O—CH₂—CH₂—CH₂—CH₃, methyl, ethyl, isopropyl, n-propyl, n-butyl, tert-butyl, sec-butyl, piperidinyl, pyrrolidinyl, —O-phenyl, —O—C(=O)—CH₃, —O—C(=O)—C₂H₅, —O—C(=O)—C(CH₃)₃, —(CH₂)-pyridinyl, cyclohexyl, cyclopentyl, (4,5)-dihydroisoxazolyl, thiazolyl, (1,2,5)-thiadiazolyl, thiophenyl, phenethyl, pyridinyl, phenyl and benzyl, wherein in each case the cyclic moiety of the residues oxetanyl, —N—[C(=O)—C₂H₅]-phenyl, —N—[C(=O)—CH₃]-phenyl, (4,5)-dihydroisoxazolyl, thiazolyl, (1,2,5)-thiadiazolyl, thiophenyl, phenethyl, —NH-phenyl, —N(CH₃)-phenyl, —N(C₂H₅)-phenyl, —(CH₂)-pyridinyl, pyridinyl, phenyl, —O-phenyl and benzyl may optionally be substituted with 1, 2, 3, 4 or 5 substituents mutually independently selected from the group consisting of —CF₃, —OH, —O—CH₃, —O—C₂H₅, F, Cl, Br, methyl, ethyl, isopropyl, n-propyl, n-butyl, tert-butyl and sec-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

16. The compound according to claim 1 selected from the group consisting of

[1] 2-(3-fluoro-4-(methylsulfonamido)phenyl)-N-((2-methyl-6-(trifluoromethyl)pyridin-3-yl)methyl)propanamide

[2] 2-(3-fluoro-4-(methylsulfonamido)phenyl)-N-((2-(piperidin-1-yl)-6-(trifluoromethyl)pyridin-3-yl)methyl)propanamide

[4] 2-(3-fluoro-4-(methylsulfonamido)phenyl)-N-((2-fluoro-6-(trifluoromethyl)pyridin-3-yl)methyl)propanamide

[5] N-((2-chloro-6-(trifluoromethyl)pyridin-3-yl)methyl)-2-(3-fluoro-4-(methylsulfonamido)phenyl)propanamide

[6] N-((-bromo2-bromo-6-(trifluoromethyl)pyridin-3-yl)methyl)-2-(3-fluoro-4-(methylsulfonamido)phenyl)propanamide

[7] 2-(3-fluoro-4-(methylsulfonamido)phenyl)-N-((2-iodo-6-(trifluoromethyl)pyridin-3-yl)methyl)propanamide

[8] N-((2-tert-butyl-6-(trifluoromethyl)pyridin-3-yl)methyl)-2-(3-fluoro-4-(methylsulfonamido)phenyl)propanamide

[10] (S)-2-(3-fluoro-4-(methylsulfonamido)phenyl)-N-((2-(piperidin-1-yl)-6-(trifluoromethyl)pyridin-3-yl)methyl)propanamide

[11] (R)-2-(3-fluoro-4-(methylsulfonamido)phenyl)-N-((2-(piperidin-1-yl)-6-(trifluoromethyl)pyridin-3-yl)methyl)propanamide

[12] 2-(3-fluoro-4-(methylsulfonamido)phenyl)-N-((2-morpholino-6-(trifluoromethyl)pyridin-3-yl)methyl)propanamide

[13] 2-(3-fluoro-4-(methylsulfonamido)phenyl)-N-((2-(pyrrolidin-1-yl)-6-(trifluoromethyl)pyridin-3-yl)methyl)propanamide

[14] N-((2-(dimethylamino)-6-(trifluoromethyl)pyridin-3-yl)methyl)-2-(3-fluoro-4-(methylsulfonamido)phenyl)propanamide

[15] N-((2-(diethylamino)-6-(trifluoromethyl)pyridin-3-yl)methyl)-2-(3-fluoro-4-(methylsulfonamido)phenyl)propanamide

[16] N-((2-(dipropylamino)-6-(trifluoromethyl)pyridin-3-yl)methyl)-2-(3-fluoro-4-(methylsulfonamido)phenyl)propanamide

[17] 2-(3-fluoro-4-(methylsulfonamido)phenyl)-N-((2-hydroxy-6-(trifluoromethyl)pyridin-3-yl)methyl)propanamide

[18] 2-(3-fluoro-4-(methylsulfonamido)phenyl)-N-((2-methoxy-6-(trifluoromethyl)pyridin-3-yl)methyl)propanamide

[19] N-((2-butoxy-6-(trifluoromethyl)pyridin-3-yl)methyl)-2-(3-fluoro-4-(methylsulfonamido)phenyl)propanamide

[20] 2-(3-fluoro-4-(methylsulfonamido)phenyl)-N-((2-isopropoxy-6-(trifluoromethyl)pyridin-3-yl)methyl)propanamide

[21] N-((2-cyclopentyloxy-6-(trifluoromethyl)pyridin-3-yl)methyl)-2-(3-fluoro-4-(methylsulfonamido)phenyl)propanamide
[22] 2-(3-fluoro-4-(methylsulfonamido)phenyl)-N-((2-phenyl-6-(trifluoromethyl)pyridin-3-yl)methyl)propanamide
[23] 2-(3-fluoro-4-(methylsulfonamido)phenyl)-N-((2-(4-fluoro-phenyl)-6-(trifluoromethyl)pyridin-3-yl)methyl)propanamide
[24] 2-(3-fluoro-4-(methylsulfonamido)phenyl)-N-((6-(trifluoromethyl)-2,2'-bipyridin-3-yl)methyl)propanamide
[25] 2-(3-fluoro-4-(methylsulfonamido)phenyl)-N-((6-(trifluoromethyl)-2,3'-bipyridin-3-yl)methyl)propanamide
[26] 2-(3-fluoro-4-(methylsulfonamido)phenyl)-N-((2-(pyrimidin-2-yl)-6-(trifluoromethyl)pyridin-3-yl)methyl)propanamide
[27] 2-(3-fluoro-4-(methylsulfonamido)phenyl)-N-((2-(thiazol-2-yl)-6-(trifluoromethyl)pyridin-3-yl)methyl)propanamide
[28] 2-(3-fluoro-4-(methylsulfonamido)phenyl)-N-((2-(oxazol-2-yl)-6-(trifluoromethyl)pyridin-3-yl)methyl)propanamide
[29] N-((2-(1H-imidazol-2-yl)-6-(trifluoromethyl)pyridin-3-yl)methyl)-2-(3-fluoro-4-(methylsulfonamido)phenyl)propanamide
[51] N-((6-tert-butyl-2-(piperidin-1-yl)pyridin-3-yl)methyl)-2-(3-fluoro-4-(methylsulfonamido)phenyl)propanamide
[57] 2-(3-fluoro-4-(methylsulfonamido)phenyl)-N-((2-piperidin-1-yl)-6-(trifluoromethyl)pyridin-3-yl)propanamide
[59] 2-(3-fluoro-4-(methylsulfonamido)phenyl)-N-(2-(2-(piperidin-1-yl)-6-(trifluoromethyl)pyridin-3-yl)ethyl)propanamide
[64] 2-(3-chloro-4-(methylsulfonamido)phenyl)-N-((2-(piperidin-1-yl)-6-(trifluoromethyl)pyridin-3-yl)methyl)propanamide
[65] 2-(3-chloro-4-(methylsulfonamido)phenyl)-N-((2-(pyrrolidin-1-yl)-6-(trifluoromethyl)pyridin-3-yl)methyl)propanamide
[67] 2-(3-bromo-4-(methylsulfonamido)phenyl)-N-((2-(piperidin-1-yl)-6-(trifluoromethyl)pyridin-3-yl)methyl)propanamide
[72] (S)-2-(3-fluoro-4-(methylsulfonamido)phenyl)-N-((2-morpholino-6-(trifluoromethyl)pyridin-3-yl)methyl)propanamide
[73] N-((2-(4-benzylpiperazin-1-yl)-6-(trifluoromethyl)pyridin-3-yl)methyl)-2-(3-fluoro-4-(methylsulfonamido)phenyl)propanamide
[74] 2-(3-fluoro-4-(methylsulfonamido)phenyl)-N-((2-piperazin-1-yl)-6-(trifluoromethyl)pyridin-3-yl)methyl)propanamide;
[76] N-((2-(cyclohexyloxy)-6-(trifluoromethyl)pyridin-3-yl)methyl-2-(3-fluoro-4-methylsulfonamido)phenyl)propanamide
[79] N-((2-(3,5-dimethylpiperidin-1-yl)-6-(trifluoromethyl)pyridin-3-yl)methyl)-2-(3-fluoro-4-(methylsulfonamido)phenyl)propanamide
[80] 2-(3-fluoro-4-(methylsulfonamido)phenyl)-N-((2-(4-methylpiperidin-1-yl)-6-(trifluoromethyl)pyridin-3-yl)methyl)propanamide
[81] N-((2-(azepan-1-yl)-6-(trifluoromethyl)pyridin-3-yl)methyl)-2-(3-fluoro-4-(methylsulfonamido)phenyl)propanamide 85 N-(2-dimethylamino-6-trifluoromethyl-pyridin-3-ylmethyl)-2-(3-fluoro-4-methylsulfonamido-phenyl)-propionamide
87 2-(3-fluoro-4-methylsulfonamido-phenyl)-N-(2-imidazol-1-yl-6-trifluoromethyl-pyridin-3-ylmethyl)-propionamide
88 2-(3-fluoro-4-methylsulfonamido-phenyl)-N-(2-thiophen-2-yl-6-trifluoromethyl-pyridin-3-ylmethyl)-propionamide
89 2-(3-fluoro-4-methylsulfonamido-phenyl)-N-[2-(4-fluoro-phenyl)-6-trifluoromethyl-pyridin-3-ylmethyl]-propionamide
90 N-(2-cyclohexylamino-6-trifluoromethyl-pyridin-3-yl-methyl)-2-(3-fluoro-4-methylsulfonamido-phenyl)-propionamide
91 2-(3-fluoro-4-methylsulfonamido-phenyl)-N-(2-hexyloxy-6-trifluoromethyl-pyridin-3-ylmethyl)-propionamide
93 (S)-2-(3-fluoro-4-methylsulfonamido-phenyl)-N-(2-hexyloxy-6-trifluoromethyl-pyridin-3-ylmethyl)-propionamide
94 (R)-2-(3-fluoro-4-methylsulfonamido-phenyl)-N-(2-hexyloxy-6-trifluoromethyl-pyridin-3-ylmethyl)-propionamide
95 2-(3-fluoro-4-methylsulfonamido-phenyl)-N-(2-isobutoxy-6-trifluoromethyl-pyridin-3-ylmethyl)-propionamide
96 (S)-2-(3-fluoro-4-methylsulfonamido-phenyl)-N-(2-isobutoxy-6-trifluoromethyl-pyridin-3-ylmethyl)-propionamide
97 (R)-2-(3-fluoro-4-methylsulfonamido-phenyl)-N-(2-isobutoxy-6-trifluoromethyl-pyridin-3-ylmethyl)-propionamide
100 N-(2-cyclopropylmethoxy-6-trifluoromethyl-pyridin-3-ylmethyl)-2-(3-fluoro-4-methylsulfonamido-phenyl)-propionamide
101 N-(2-cyclobutylmethoxy-6-trifluoromethyl-pyridin-3-ylmethyl)-2-(3-fluoro-4-methylsulfonamido-phenyl)-propionamide
102 2-(3-chloro-4-methylsulfonamido-phenyl)-N-(2-pyrrolidin-1-yl-6-trifluoromethyl-pyridin-3-ylmethyl)-propionamide
103 2-(3-bromo-4-methylsulfonamido-phenyl)-N-(2-pyrrolidin-1-yl-6-trifluoromethyl-pyridin-3-ylmethyl)-propionamide
104 N-(4-benzyl-6'-trifluoromethyl-3,4,5,6-tetrahydro-2H-[1,2']bipyridinyl-3'-ylmethyl)-2-(3-fluoro-4-methylsulfonamido-phenyl)-propionamide
106 N-(2-benzyloxy-6-trifluoromethyl-pyridin-3-ylmethyl)-2-(3-fluoro-4-methylsulfonamido-phenyl)-propionamide
107 2-(3-fluoro-4-methylsulfonamido-phenyl)-N-[2-(3-methoxy-benzyloxy)-6-trifluoromethyl-pyridin-3-ylmethyl]-propionamide
109 2-(3-fluoro-4-methylsulfonamido-phenyl)-N-[2-(4-phenyl-piperazin-1-yl)-6-trifluoromethyl-pyridin-3-ylmethyl]-propionamide
110 2-(3-fluoro-4-methylsulfonamido-phenyl)-N-(2-phenylamino-6-trifluoromethyl-pyridin-3-ylmethyl)-propionamide
111 2-(3-fluoro-4-methylsulfonamido-phenyl)-N-(2-propoxy-6-trifluoromethyl-pyridin-3-ylmethyl)-propionamide
112 2-(3-fluoro-4-methylsulfonamido-phenyl)-N-[2-(4-fluoro-phenylamino)-6-trifluoromethyl-pyridin-3-ylmethyl]-propionamide 113 N-[2-(4-chloro-phenylamino)-6-trifluoromethyl-pyridin-3-ylmethyl]-2-(3-fluoro-4-methylsulfonamido-phenyl)-propionamide 115 N-(2-benzylamino-6-trifluoromethyl-pyridin-3-ylmethyl)-2-(3-fluoro-4-methylsulfonamido-phenyl)-propionamide 116 N-(2-butylamino-6-trifluoromethyl-pyridin-3-ylmethyl)-2-(3-fluoro-4-methylsulfonamido-phenyl)-propionamide 117 N-[2-(4-tert-butyl-phenyl)-6-trifluoromethyl-pyridin-3-ylmethyl]-2-(3-fluoro-4-methylsulfonamido-phenyl)-propionamide 118 N-[2-(3-chloro-4-fluoro-phenyl)-6-trifluoromethyl-pyridin-3-ylmethyl]-2-(3-fluoro-4-methylsulfonamido-phenyl)-propionamide 120 (S)—N-[2-(3-chloro-4-fluoro-phenyl)-6-trifluoromethyl-pyridin-3-ylmethyl]-2-(3-fluoro-4-methylsulfonamido-phenyl)-propionamide 121 (R)—N-[2-(3-chloro-4-fluoro-phenyl)-6-trifluoromethyl-pyridin-3-ylmethyl]-2-(3-fluoro-4-methylsulfonamido-phenyl)-propionamide 122 N-(2-butylsulfanyl-6-trifluoromethyl-pyridin-3-ylmethyl)-2-(3-fluoro-4-methylsulfonamido-phenyl)-propionamide 123 2-(3-fluoro-4-methylsulfonamido-phenyl)-N-[2-(3-methyl-butoxy)-6-trifluoromethyl-pyridin-3-ylmethyl]-propionamide 124 2-(3-fluoro-4-methylsulfonamido-phenyl)-N-[2-(2-methyl-cyclopropylmethoxy)-6-trifluoromethyl-pyridin-3-ylmethyl]-propionamide 125 N-[2-(3,3-dimethyl-butoxy)-6-trifluoromethyl-pyridin-3-ylmethyl]-2-(3-fluoro-4-methylsulfonamido-phenyl)-propionamide 126 N-(2-cyclohexylsulfanyl-6-trifluoromethyl-pyridin-3-ylmethyl)-2-(3-fluoro-4-methylsulfonamido-phenyl)-propionamide 127 2-(4-methylsulfonamido-3-methyl-phenyl)-N-(6'-trifluoromethyl-3,4,5,6-tetrahydro-2H-[1,2']bipyridinyl-3'-ylmethyl)-propionamide 128 N-(2-azocan-1-yl-6-trifluoromethyl-pyridin-3-ylmethyl)-2-(3-fluoro-4-methylsulfonamido-phenyl)-propionamide 131 N-[6'-(chloro-difluoro-methyl)-4-methyl-3,4,5,6-tetrahydro-2H-[1,2']bipyridinyl-3'-ylmethyl]-2-(3-fluoro-4-methylsulfonamido-phenyl)-propionamide 132 N-[2-azepan-1-yl-6-(chlor-difluor-methyl)-pyridin-3-ylmethyl]-2-(3-fluoro-4-methylsulfonamido-phenyl)-propionamide 134 2-(3-fluoro-4-methylsulfonamido-phenyl)-N-[2-(4-methyl-piperazin-1-yl)-6-trifluoromethyl-pyridin-3-ylmethyl]-propionamide 135 N-[2-(3,4-dimethyl-phenylamino)-6-trifluoromethyl-pyridin-3-ylmethyl]-2-(3-fluoro-4-methylsulfonamido-phenyl)-propionamide 136 N-[2-(5-chloro-2-methyl-phenylamino)-6-trifluoromethyl-pyridin-3-ylmethyl]-2-(3-fluoro-4-methylsulfonamido-phenyl)-propionamide 137 2-(3-fluoro-4-methylsulfonamido-phenyl)-N-(4-phenyl-6'-trifluoromethyl-3,4,5,6-tetrahydro-2H-[1,2']bipyridinyl-3'-ylmethyl)-propionamide 138 2-(3-fluoro-4-methylsulfonamido-phenyl)-N-(4-fluoro-6'-trifluoromethyl-3,4,5,6-tetrahydro-2H-[1,2']bipyridinyl-3'-ylmethyl)-propionamide 139 2-(3-fluoro-4-methylsulfonamido-phenyl)-N-(6'-trifluoromethyl-3,6-dihydro-2H-[1,2']bipyridinyl-3'-ylmethyl)-propionamide 140 N-[2-butoxy-6-(chlor-difluor-methyl)-pyridin-3-ylmethyl]-2-(3-fluoro-4-methylsulfonamido-phenyl)-propionamide 142 2-(3-fluoro-4-methylsulfonamido-phenyl)-N-(2-pentyl-6-trifluoromethyl-pyridin-3-ylmethyl)-propionamide 144 (S)-2-(3-fluoro-4-methylsulfonamido-phenyl)-N-(2-pentyl-6-trifluoromethyl-pyridin-3-ylmethyl)-propionamide 145 (R)-2-(3-fluoro-4-methylsulfonamido-phenyl)-N-(2-pentyl-6-trifluoromethyl-pyridin-3-ylmethyl)-propionamide 147 N-[2-(4-chloro-phenyl)-6-trifluoromethyl-pyridin-3-ylmethyl]-2-(3-fluoro-4-methylsulfonamido-phenyl)-propionamide 148 2-(3-fluoro-4-methylsulfonamido-phenyl)-N-[2-(3-fluoro-phenyl)-6-trifluoromethyl-pyridin-3-ylmethyl]-propionamide 149 N-[2-(3-chloro-phenyl)-6-trifluoromethyl-pyridin-3-ylmethyl]-2-(3-fluoro-4-methylsulfonamido-phenyl)-propionamide 150 2-(3-fluoro-4-methylsulfonamido-phenyl)-N-[2-(2-fluoro-phenyl)-6-trifluoromethyl-pyridin-3-ylmethyl]-propionamide 151 2-(3-fluoro-4-methylsulfonamido-phenyl)-N-[2-(4-methoxy-phenyl)-6-tfifluoromethyl-pyridin-3-ylmethyl]-propionamide 156 N-(2-cyclobutoxy-6-trifluoromethyl-pyridin-3-ylmethyl)-2-(3-fluoro-4-methylsulfonamido-phenyl)-propionamide 157 2-(3-fluoro-4-methylsulfonamido-phenyl)-N-[2-(4-methyl-cyclohexyloxy)-6-trifluoromethyl-pyridin-3-ylmethyl]-propionamide 158 acetic acid-3'-{[2-(3-fluoro-4-methylsulfonamido-phenyl)-propionylamino]-methyl}-6'-trifluoromethyl-3,4,5,6-tetrahydro-2H-[1,2']bipyridinyl-4-yl ester 159 2-(3-fluoro-4-methylsulfonamido-phenyl)-N-(4-methoxy-6'-trifluoromethyl-3,4,5,6-tetrahydro-2H-[1,2']bipyridinyl-3'-ylmethyl)-propionamide 160 N-(4-butoxy-6'-trifluoromethyl-3,4,5,6-tetrahydro-2H-[1,2']bipyridinyl-3'-ylmethyl)-2-(3-fluoro-4-methylsulfonamido-phenyl)-propionamide 161 N-(2-cyclopentylmethoxy-6-trifluoromethyl-pyridin-3-ylmethyl)-2-(3-fluoro-4-methylsulfonamido-phenyl)-propionamide 162 2-(3-fluoro-4-methylsulfonamido-phenyl)-N-(4-isopropoxy-6'-trifluoromethyl-3,4,5,6-tetrahydro-2H-[1,2']bipyridinyl-3'-ylmethyl)-propionamide 163 N-(2-ethoxy-6-trifluoromethyl-pyridin-3-ylmethyl)-2-(3-fluoro-4-methylsulfonamido-phenyl)-propionamide 164 2-(3-fluoro-4-methylsulfonamido-phenyl)-N-(6"-trifluoromethyl-3,4,5,6,3'4'5',6'-octahydro-2H,2'H-[1,4';1',2"]terpyridin-3"-ylmethyl)-propionamide 165 2-(3-fluoro-4-methylsulfonamido-phenyl)-N-(4-pyrrolidin-1-yl-6'-trifluoromethyl-3,4,5,6-tetrahydro-2H-[1,2']bipyridinyl-3'-ylmethyl)-propionamide 166 N-[6-(chloro-difluoro-methyl)-2-cyclopentyloxy-pyridin-3-ylmethyl]-2-(3-fluoro-4-methylsulfonamido-phenyl)-propionamide 167 N-[2-(butyl-methyl-amino)-6-trifluoromethyl-pyridin-3-ylmethyl]-2-(3-fluoro-4-methylsulfonamido-phenyl)-propionamide 168 N-[6-(chloro-difluoro-methyl)-2-cyclohexyloxy-pyridin-3-ylmethyl]-2-(3-fluoro-4-methylsulfonamido-phenyl)-propionamide 169 N-[2-benzyloxy-6-(chlor-difluor-methyl)-pyridin-3-ylmethyl]-2-(3-fluoro-4-methylsulfonamido-phenyl)-propionamide
170 N-[2-(4-tert-butyl-cyclohexyloxy)-6-trifluoromethyl-pyridin-3-ylmethyl]-2-(3-fluoro-4-methylsulfonamido-phenyl)-propionamide
171 N-[2-(4-ethyl-cyclohexyloxy)-6-trifluoromethyl-pyridin-3-ylmethyl]-2-(3-fluoro-4-methylsulfonamido-phenyl)-propionamide
172 2-(3-fluoro-4-methylsulfonamido-phenyl)-N-[2-(4-methyl-benzyloxy)-6-trifluoromethyl-pyridin-3-ylmethyl]-propionamide
173 N-[2-(4-chloro-benzylamino)-6-trifluoromethyl-pyridin-3-ylmethyl]-2-(3-fluoro-4-methylsulfonamido-phenyl)-propionamide
175 N-[2-(4-fluoro-benzyloxy)-6-trifluoromethyl-pyridin-3-ylmethyl]-2-(3-fluoro-4-methylsulfonamido-phenyl)-propionamide
176 2-(3-fluoro-4-methylsulfonamido-phenyl)-N-[2-(4-pyridin-4-yl-piperazin-1-yl)-6-trifluoromethyl-pyridin-3-ylmethyl]-propionamide
177 2-(3-fluoro-4-methylsulfonamido-phenyl)-N-[2-(pyridin-4-ylmethoxy)-6-trifluoromethyl-pyridin-3-ylmethyl]-propionamide
178 2-(3-fluoro-4-methylsulfonamido-phenyl)-N-(2-phenethyloxy-6-trifluoromethyl-pyridin-3-ylmethyl)-propionamide
179 2-(3-fluoro-4-methylsulfonamido-phenyl)-N-{2-[4-(4-fluoro-phenyl)-piperazin-1-yl]-6-trifluoromethyl-pyridin-3-ylmethyl}-propionamide
180 N-[6-(chloro-difluoro-methyl)-2-hexyloxy-pyridin-3-ylmethyl]-2-(3-fluoro-4-methylsulfonamido-phenyl)-propionamide
181 N-[6-(chloro-difluoro-methyl)-2-(pyridin-3-ylmethoxy)-pyridin-3-ylmethyl]-2-(3-fluoro-4-methylsulfonamido-phenyl)-propionamide
182 N-[6-(chloro-difluoro-methyl)-2-(pyridin-2-ylmethoxy)-pyridin-3-ylmethyl]-2-(3-fluoro-4-methylsulfonamido-phenyl)-propionamide
183 N-(2-dibutylamino-6-trifluoromethyl-pyridin-3-ylmethyl)-2-(3-fluoro-4-methylsulfonamido-phenyl)-propionamide
184 2-(3-fluoro-4-methylsulfonamido-phenyl)-N-[6'-(4-fluoro-phenyl)-4-methyl-3,4,5,6-tetrahydro-2H-[1,2']bipyridinyl-3'-ylmethyl]-propionamide
186 N-[6-(chloro-difluoro-methyl)-2-dipropylamino-pyridin-3-ylmethyl]-2-(3-fluoro-4-methylsulfonamido-phenyl)-propionamide
187 N-[6'-(chloro-difluoro-methyl)-3,5-dimethyl-3,4,5,6-tetrahydro-2H-[1,2']bipyridinyl-3'-ylmethyl]-2-(3-fluoro-4-methylsulfonamido-phenyl)-propionamide
188 N-[2-(1,3-dihydro-isoindol-2-yl)-6-trifluoromethyl-pyridin-3-ylmethyl]-2-(3-fluoro-4-methylsulfonamido-phenyl)-propionamide
189 3'-{[2-(3-fluoro-4-methylsulfonamido-phenyl)-propionylamino]-methyl}-4-phenyl-6'-trifluoromethyl-3,4,5,6-tetrahydro-2H-[1,2']bipyridinyl-4-carbonic acid ethylester
190 N-(4,6'-bis-trifluoromethyl-3,4,5,6-tetrahydro-2H-[1,2']bipyridinyl-3'-ylmethyl)-2-(3-fluoro-4-methylsulfonamido-phenyl)-propionamide
191 2-(3-fluoro-4-(methylsulfonamido)phenyl)-N-((2-styryl-6-(trifluoromethyl)pyridin-3-yl)methyl)propanamide
192 2-(3-fluoro-4-methylsulfonamido-phenyl)-N-(2-phenethyl-6-trifluoromethyl-pyridin-3-ylmethyl)-propionamide
193 N-{2-[4-(3-chloro-pyridin-2-yl)-piperazin-1-yl]-6-trifluoromethyl-pyridin-3-ylmethyl}-2-(3-fluoro-4-methylsulfonamido-phenyl)-propionamide
194 N-{2-[4-(3-chloro-pyridin-2-yl)-2-methyl-piperazin-1-yl]-6-trifluoromethyl-pyridin-3-ylmethyl}-2-(3-fluoro-4-methylsulfonamido-phenyl)-propionamide
195 N-(4,6'-bis-trifluoromethyl-3,4,5,6-tetrahydro-2H-[1,2']bipyridinyl-3'-ylmethyl)-2-(4-methylsulfonamido-3-methyl-phenyl)-propionamide
196 2-(4-methylsulfonamido-3-methyl-phenyl)-N-(4-methyl-6'-trifluoromethyl-3,4,5,6-tetrahydro-2H-[1,2']bipyridinyl-3'-ylmethyl)-propionamide
197 N-(4-ethyl-6'-trifluoromethyl-3,4,5,6-tetrahydro-2H-[1,2']bipyridinyl-3'-ylmethyl)-2-(3-fluoro-4-methylsulfonamido-phenyl)-propionamide
198 2-(3-fluoro-4-methylsulfonamido-phenyl)-N-(2-phenoxy-6-trifluoromethyl-pyridin-3-ylmethyl)-propionamide
199 2-(3-fluoro-4-methylsulfonamido-phenyl)-N-(4-methoxymethyl-6'-trifluoromethyl-3,4,5,6-tetrahydro-2H-[1,2']bipyridinyl-3'-ylmethyl)-propionamide
200 2-(3-fluoro-4-methylsulfonamido-phenyl)-N-[4-(4-fluoro-phenyl)-6'-trifluoromethyl-3,4,5,6-tetrahydro-2H-[1,2']bipyridinyl-3'-ylmethyl]-propionamide
201 2-(3-fluoro-4-methylsulfonamido-phenyl)-N-{2-[4-(2-fluoro-phenyl)-piperazin-1-yl]-6-trifluoromethyl-pyridin-3-ylmethyl}-propionamide
202 2-(3-fluoro-4-methylsulfonamido-phenyl)-N-[2-(pyridin-2-ylmethoxy)-6-trifluoromethyl-pyridin-3-ylmethyl]-propionamide
203 2-(4-methylsulfonamido-3-methyl-phenyl)-N-[2-(4-phenyl-piperazin-1-yl)-6-trifluoromethyl-pyridin-3-ylmethyl]-propionamide
204 N-(2-benzyloxy-6-trifluoromethyl-pyridin-3-ylmethyl)-2-(4-methylsulfonamido-3-methyl-phenyl)-propionamide
205 2-(3-fluoro-4-methylsulfonamido-phenyl)-N-[2-(methyl-phenyl-amino)-6-trifluoromethyl-pyridin-3-ylmethyl]-propionamide
207 N-[6-(chloro-difluoro-methyl)-2-(4-phenyl-piperazin-1-yl)-pyridin-3-ylmethyl]-2-(3-fluoro-4-methylsulfonamido-phenyl)-propionamide
208 N-[6-(chloro-difluoro-methyl)-2-isobutoxy-pyridin-3-ylmethyl]-2-(3-fluoro-4-methylsulfonamido-phenyl)-propionamide
210 N-(4,4-dimethyl-6'-trifluoromethyl-3,4,5,6-tetrahydro-2H-[1,2']bipyridinyl-3'-ylmethyl)-2-(3-fluoro-4-methylsulfonamido-phenyl)-propionamide
212 2-(3-fluoro-4-methylsulfonamido-phenyl)-N-{6-trifluoromethyl-2-[4-(3-trifluoromethyl-pyridin-2-yl)-piperazin-1-yl]-pyridin-3-ylmethyl}-propionamide
213 2-(3-fluoro-4-methylsulfonamido-phenyl)-N-{6-trifluoromethyl-2-[4-(3-trifluoromethyl-pyridin-2-yl)-piperazin-1-yl]-pyridin-3-ylmethyl}-propionamide
214 2-(3-fluoro-4-methylsulfonamido-phenyl)-N-[2-(4-pyridin-2-yl-piperazin-1-yl)-6-trifluoromethyl-pyridin-3-ylmethyl]-propionamide
215 2-(3-fluoro-4-methylsulfonamido-phenyl)-N-(6-trifluoromethyl-pyridin-3-ylmethyl)-propionamide
219 2-(3-fluoro-4-methylsulfonamido-phenyl)-N-[2-(4-p-tolyl-piperazin-1-yl)-6-trifluoromethyl-pyridin-3-ylmethyl]-propionamide
220 2-(3-fluoro-4-methylsulfonamido-phenyl)-N-[2-(4-m-tolyl-piperazin-1-yl)-6-trifluoromethyl-pyridin-3-ylmethyl]-propionamide 221 2-(3-fluoro-4-methylsulfonamido-phenyl)-N-{2-[4-(4-methoxy-phenyl)-piperazin-1-yl]-6-trifluoromethyl-pyridin-3-ylmethyl}-propionamide
222 2-(3-fluoro-4-methylsulfonamido-phenyl)-N-{6-trifluoromethyl-2-[4-(4-trifluoromethyl-phenyl)-piperazin-1-yl]-pyridin-3-ylmethyl}-propionamide
223 N-(2-benzyloxy-4-hydroxymethyl-6-trifluoromethyl-pyridin-3-ylmethyl)-2-(3-fluoro-4-methylsulfonamido-phenyl)-propionamide
225 2-(3-fluoro-4-methylsulfonamido-phenyl)-N-(2-pentyloxy-6-trifluoromethyl-pyridin-3-ylmethyl)-propionamide
226 2,2-dimethyl-propionic acid-3'-{[2-(3-fluoro-4-methylsulfonamido-phenyl)-propionylamino]-methyl}-6'-trifluoromethyl-3,4,5,6-tetrahydro-2H-[1,2']bipyridinyl-4-yl ester
227 2-(3-fluoro-4-methylsulfonamido-phenyl)-N-(4-oxo-6'-trifluoromethyl-3,4,5,6-tetrahydro-2H-[1,2']bipyridinyl-3'-ylmethyl)-propionamide
228 N-(4-ethoxy-6'-trifluoromethyl-3,4,5,6-tetrahydro-2H-[1,2']bipyridinyl-3'-ylmethyl)-2-(3-fluoro-4-methylsulfonamido-phenyl)-propionamide
233 N-(6-tert-butyl-2-cyclohexyloxy-pyridin-3-ylmethyl)-2-(3-fluoro-4-methylsulfonamido-phenyl)-propionamide
234 N-(6-tert-butyl-2-cyclopentyloxy-pyridin-3-ylmethyl)-2-(3-fluoro-4-methylsulfonamido-phenyl)-propionamide
235 N-(2-butoxy-6-tert-butyl-pyridin-3-ylmethyl)-2-(3-fluoro-4-methylsulfonamido-phenyl)-propionamide
236 N-(6-tert-butyl-2-hexyloxy-pyridin-3-ylmethyl)-2-(3-fluoro-4-methylsulfonamido-phenyl)-propionamide
237 N-(2-benzyloxy-6-tert-butyl-pyridin-3-ylmethyl)-2-(3-fluoro-4-methylsulfonamido-phenyl)-propionamide
240 N-(6-tert-butyl-2-pyrrolidin-1-yl-pyridin-3-ylmethyl)-2-(3-fluoro-4-methylsulfonamido-phenyl)-propionamide
241 N-(6'-tert-butyl-4-methyl-3,4,5,6-tetrahydro-2H-[1,2']bipyridinyl-3'-ylmethyl)-2-(3-fluoro-4-methylsulfonamido-phenyl)-propionamide
242 N-[2-(4-ethyl-benzyloxy)-6-trifluoromethyl-pyridin-3-ylmethyl]-2-(3-fluoro-4-methylsulfonamido-phenyl)-propionamide
243 N-[2-(4-butyl-benzyloxy)-6-trifluoromethyl-pyridin-3-ylmethyl]-2-(3-fluoro-4-methylsulfonamido-phenyl)-propionamide
244 N-[2-(4-tert-butyl-benzyloxy)-6-trifluoromethyl-pyridin-3-ylmethyl]-2-(3-fluoro-4-methylsulfonamido-phenyl)-propionamide
245 2-(3-fluoro-4-methylsulfonamido-phenyl)-N-[2-(indan-2-yloxy)-6-trifluoromethyl-pyridin-3-ylmethyl]-propionamide
250 N-[2-(3,4-dichloro-phenyl)-6-trifluoromethyl-pyridin-3-ylmethyl]-2-(3-fluoro-4-methylsulfonamido-phenyl)-propionamide
251 N-[2-(3-tert-butyl-1-oxa-2,8-diaza-spiro[4.5]dec-2-en-8-yl)-6-trifluoromethyl-pyridin-3-ylmethyl]-2-(3-fluoro-4-methylsulfonamido-phenyl)-propionamide
252 2-(3-fluoro-4-methylsulfonamido-phenyl)-N-[2-(3-phenyl-1-oxa-2,8-diaza-spiro[4.5]dec-2-en-8-yl)-6-trifluoromethyl-pyridin-3-ylmethyl]-propionamide
254 2-(3-fluoro-4-methylsulfonamido-phenyl)-N-[2-(3-fluoro-4-methoxy-phenyl)-6-trifluoromethyl-pyridin-3-ylmethyl]-propionamide
255 2-(3-fluoro-4-methylsulfonamido-phenyl)-N-{2-[4-(4-fluoro-phenyl)-piperidin-1-yl]-4-trifluoromethyl-benzyl}-propionamide
256 N-(2-butoxy-6-trifluoromethyl-pyridin-3-ylmethyl)-2-(4-methylsulfonamido-3-methyl-phenyl)-propionamide
257 N-(2-hexyloxy-6-trifluoromethyl-pyridin-3-ylmethyl)-2-(4-methylsulfonamido-3-methyl-phenyl)-propionamide
258 N-[2-(4-chloro-benzyloxy)-6-trifluoromethyl-pyridin-3-ylmethyl]-2-(3-fluoro-4-methylsulfonamido-phenyl)-propionamide
259 N-(4-dimethylaminomethyl-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide
260 N-[2-(4-cyclohexyl-piperazin-1-yl)-6-trifluoromethyl-pyridin-3-ylmethyl]-2-(3-fluoro-4-methylsulfonamido-phenyl)-propionamide
261 N-(6-tert-butyl-2-cyclopentyloxy-4-hydroxymethyl-pyridin-3-ylmethyl)-2-(3-fluoro-4-methylsulfonamido-phenyl)-propionami de
262 2-(4-methylsulfonamido-phenyl)-N-(4-methyl-6'-trifluoromethyl-3,4,5,6-tetrahydro-2H-[1,2']bipyridinyl-3'-ylmethyl)-propionamide
263 N-[2-(3,3-dimethyl-butyl)-6-trifluoromethyl-pyridin-3-ylmethyl]-2-(3-fluoro-4-methylsulfonamido-phenyl)-propionamide
264 2-(3-fluoro-4-methylsulfonamido-phenyl)-N-[2-(2-p-tolyl-ethyl)-6-trifluoromethyl-pyridin-3-ylmethyl]-propionamide
265 N-[2-(2,3-dihydro-benzo[1,4]dioxin-6-yl)-6-trifluoromethyl-pyridin-3-ylmethyl]-2-(3-fluoro-4-methylsulfonamido-phenyl)-propionamide
266 N-(2-benzo[1,3]dioxol-5-yl-6-trifluoromethyl-pyridin-3-ylmethyl)-2-(3-fluoro-4-methylsulfonamido-phenyl)-propionamide
267 2-(3-fluoro-4-methylsulfonamido-phenyl)-N-(2-hexyl-6-trifluoromethyl-pyridin-3-ylmethyl)-propionamide
268 2-(3-fluoro-4-methylsulfonamido-phenyl)-N-[2-(4-methyl-pentyl)-6-trifluoromethyl-pyridin-3-ylmethyl]-propionamide
269 2-(3-fluoro-4-methylsulfonamido-phenyl)-N-(4-hydroxy-6'-trifluoromethyl-3,4,5,6-tetrahydro-2H-[1,2']bipyridinyl-3'-ylmethyl)-propionamide
270 N-(2-cyclohexylmethoxy-6-trifluoromethyl-pyridin-3-ylmethyl)-2-(3-fluoro-4-methylsulfonamido-phenyl)-propionamide
271 2-(3-fluoro-4-methylsulfonamido-phenyl)-N-[2-(4-methyl-cyclohexylmethoxy)-6-trifluoromethyl-pyridin-3-ylmethyl]-propionamide
272 2-(3-fluoro-4-methylsulfonamido-phenyl)-N-[2-(3-methylsulfonamido-phenyl)-6-trifluoromethyl-pyridin-3-ylmethyl]-propionamide
273 2-(3-fluoro-4-methylsulfonamido-phenyl)-N-[2-(2-methyl-propenyl)-6-trifluoromethyl-pyridin-3-ylmethyl]-propionamide
274 N-[2-(3,3-dimethyl-but-1-enyl)-6-trifluoromethyl-pyridin-3-ylmethyl]-2-(3-fluoro-4-methylsulfonamido-phenyl)-propionamide
275 2-(3-fluoro-4-methylsulfonamido-phenyl)-N-[2-(1H-indol-6-yl)-6-trifluoromethyl-pyridin-3-ylmethyl]-propionamide
276 2-(3-fluoro-4-methylsulfonamido-phenyl)-N-[2-(1H-indol-5-yl)-6-trifluoromethyl-pyridin-3-ylmethyl]-propionamide
277 N-[2-(4-chloro-3-fluoro-phenyl)-6-trifluoromethyl-pyridin-3-ylmethyl]-2-(3-fluoro-4-methylsulfonamido-phenyl)-propionamide 278  2-(3-fluoro-4-methylsulfonamido-phenyl)-N-[2-(4-fluoro-3-methyl-phenyl)-6-trifluoromethyl-pyridin-3-ylmethyl]-propionamide
279  N-[2-(2,2-dimethyl-cyclopropylmethoxy)-6-trifluoromethyl-pyridin-3-ylmethyl]-2-(3-fluoro-4-methylsulfonamido-phenyl)-propionamide
282  2-(3-fluoro-4-methylsulfonamido-phenyl)-N-(3-methyl-6'-trifluoromethyl-3,4,5,6-tetrahydro-2H-[1,2']bipyridinyl-3'-ylmethyl)-propionamide
283  2-(3-fluoro-4-methylsulfonamido-phenyl)-N-(2-methyl-6'-trifluoromethyl-3,4,5,6-tetrahydro-2H-[1,2']bipyridinyl-3'-ylmethyl)-propionamide
285  N-(4-cyano-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide
287  2-(4-ethanesulfonylamino-3-fluoro-phenyl)-N-(4-methyl-6'-trifluoromethyl-3,4,5,6-tetrahydro-2H-[1,2']bipyridinyl-3'-ylmethyl)-propionamide
288  2-(4-(N,N-dimethylsulfamoylamino)-3-fluorphenyl)-N-((2-(4-methylpiperidin-1-yl)-6-(trifluoromethyl)pyridin-3-yl)methyl)propanamide
289  2-(4-methylsulfonamido-3-methoxy-phenyl)-N-(4-methyl-6'-trifluoromethyl-3,4,5,6-tetrahydro-2H-[1,2']bipyridinyl-3'-ylmethyl)-propionamide
290  2-(3-fluoro-4-methylsulfonamido-phenyl)-N-(4-phenylamino-6'-trifluoromethyl-3,4,5,6-tetrahydro-2H-[1,2']bipyridinyl-3'-ylmethyl)-propionamide
291  N-(2-cyclohexyl-6-trifluoromethyl-pyridin-3-ylmethyl)-2-(3-fluoro-4-methylsulfonamido-phenyl)-propionamide
293  2-(3-fluoro-4-methylsulfonamido-phenyl)-N-(4-methyl-6'-trifluoromethyl-3,4,5,6-tetrahydro-2H-[1,2']bipyridinyl-3'-ylmethyl)-thiopropionamide
294  N-(2-cyclohexylsulfanyl-6-trifluoromethyl-pyridin-3-ylmethyl)-2-(3-fluoro-4-methylsulfonamido-phenyl)-propionamide
295  2-(3-fluoro-4-methylsulfonamido-phenyl)-N-(4-phenyl-6'-trifluoromethyl-3,4,5,6-tetrahydro-2H-[1,2']bipyridinyl-3'-ylmethyl)-propionamide
296  N-(2-azepan-1-yl-6-tert-butyl-pyridin-3-ylmethyl)-2-(3-fluoro-4-methylsulfonamido-phenyl)-propionamide
297  N-(6-tert-butyl-2-dipropylamino-pyridin-3-ylmethyl)-2-(3-fluoro-4-methylsulfonamido-phenyl)-propionamide
298  N-(2-but-2-enyloxy-6-trifluoromethyl-pyridin-3-ylmethyl)-2-(3-fluoro-4-methylsulfonamido-phenyl)-propionamide
299  2-(3-fluoro-4-methylsulfonamido-phenyl)-N-(2-pent-2-enyloxy-6-trifluoromethyl-pyridin-3-ylmethyl)-propionamide
300  2-(3-fluoro-4-methylsulfonamido-phenyl)-N-(2-pent-1-enyl-6-trifluoromethyl-pyridin-3-ylmethyl)-propionamide
301  2-(3-fluoro-4-methylsulfonamido-phenyl)-N-(2-pent-1-enyl-6-trifluoromethyl-pyridin-3-ylmethyl)-propionamide
302  2-(3-fluoro-4-methylsulfonamido-phenyl)-N-(2-hexyloxy-4-methyl-6-trifluoromethyl-pyridin-3-ylmethyl)-propionamide
303  2-(3-fluoro-4-methylsulfonamido-phenyl)-N-{2-[2-(4-fluoro-phenyl)-ethyl]-6-trifluoromethyl-pyridin-3-ylmethyl}-propionamide
304  N-(4-acetyl-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide
307  2-(3-fluoro-4-methylsulfonamido-phenyl)-N-[4-(phenyl-propionyl-amino)-6'-trifluoromethyl-3,4,5,6-tetrahydro-2H-[1,2']bipyridinyl-3'-ylmethyl]-propionamide
308  N-[2-(4-dimethylamino-phenyl)-6-trifluoromethyl-pyridin-3-ylmethyl]-2-(3-fluoro-4-methylsulfonamido-phenyl)-propionamide
309  2-[3-fluoro-4-(propan-2-sulfonylamino)-phenyl]-N-(4-methyl-6'-trifluoromethyl-3,4,5,6-tetrahydro-2H-[1,2']bipyridinyl-3'-ylmethyl)-propionamide
310  2-[3-fluoro-4-(2,2,2-trifluor-ethansulfonylamino)-phenyl]-N-(4-methyl-6'-trifluoromethyl-3,4,5,6-tetrahydro-2H-[1,2']bipyridinyl-3'-ylmethyl)-propionamide
311  N-[2-(2,6-dimethyl-morpholin-4-yl)-6-trifluoromethyl-pyridin-3-ylmethyl]-2-(3-fluoro-4-methylsulfonamido-phenyl)-propionamide
312  2-(3-fluoro-4-trifluormethylsulfonamido-phenyl)-N-(4-methyl-6'-trifluoromethyl-3,4,5,6-tetrahydro-2H-[1,2']bipyridinyl-3'-ylmethyl)-propionamide
314  N-[2-(1,1-dioxo-1l6-thiomorpholin-4-yl)-6-trifluoromethyl-pyridin-3-ylmethyl]-2-(3-fluoro-4-methylsulfonamido-phenyl)-propionamide
315  N-(6'-difluormethyl-4-methyl-3,4,5,6-tetrahydro-2H-[1,2']bipyridinyl-3'-ylmethyl)-2-(3-fluoro-4-methylsulfonamido-phenyl)-propionamide
316  N-(4,6'-dimethyl-3,4,5,6-tetrahydro-2H-[1,2']bipyridinyl-3'-ylmethyl)-2-(3-fluoro-4-methylsulfonamido-phenyl)-propionamide
317  2-(3-fluoro-4-methylsulfonamido-phenyl)-N-(4-phenyl-6'-trifluoromethyl-3,6-dihydro-2H-[1,2']bipyridinyl-3'-ylmethyl)-propionamide
318  N-(4,4'-dimethyl-6'-trifluoromethyl-3,4,5,6-tetrahydro-2H-[1,2']bipyridinyl-3'-ylmethyl)-2-(3-fluoro-4-methylsulfonamido-phenyl)-propionamide
326 N-[2-(3,4-dimethoxy-phenyl)-6-trifluoromethyl-pyridin-3-ylmethyl]-2-(3-fluoro-4-methylsulfonamido-phenyl)-propionamide
327  4-(3-{[2-(3-fluoro-4-methylsulfonamido-phenyl)-propionylamino]-methyl}-6-trifluoromethyl-pyridin-2-yloxymethyl)-piperidine-1-carbonic acid tert-butyl ester
328  N-(6-tert-butyl-2-pentyloxy-pyridin-3-ylmethyl)-2-(3-fluoro-4-methylsulfonamido-phenyl)-propionamide
329  N-[6-tert-butyl-2-(3-methyl-butoxy)-pyridin-3-ylmethyl]-2-(3-fluoro-4-methylsulfonamido-phenyl)-propionamide
330  N-(4-dimethylamino-4-phenyl-6'-trifluoromethyl-3,4,5,6-tetrahydro-2H-[1,2']bipyridinyl-3'-ylmethyl)-2-(3-fluoro-4-methylsulfonamido-phenyl)-propionamide
331  N-(2-dipropylamino-6-trifluoromethyl-pyridin-3-ylmethyl)-2-(4-methylsulfonamido-3-methyl-phenyl)-propionamide
332  2-(3-fluoro-4-methylsulfonamido-phenyl)-N-[4-(4-fluoro-phenyl)-6'-trifluoromethyl-3,6-dihydro-2H-[1,2']bipyridinyl-3'-ylmethyl]-propionamide
334  N-(2-cyclohex-1-enyl-6-trifluoromethyl-pyridin-3-ylmethyl)-2-(3-fluoro-4-methylsulfonamido-phenyl)-propionamide
335 N-[2-(1-ethyl-propoxy)-6-trifluoromethyl-pyridin-3-ylmethyl]-2-(3-fluoro-4-methylsulfonamido-phenyl)-propionamide
336  2-(3-fluoro-4-methylsulfonamido-phenyl)-N-[2-(1-propyl-butoxy)-6-trifluoromethyl-pyridin-3-ylmethyl]-propionamide 337 2-(3-fluoro-4-methylsulfonamido-phenyl)-N-[2-(1-isobutyl-3-methyl-butoxy)-6-trifluoromethyl-pyridin-3-ylmethyl]-propionamide
338 N-[2-(4,4-dimethyl-cyclohexyloxy)-6-trifluoromethyl-pyridin-3-ylmethyl]-2-(3-fluoro-4-methylsulfonamido-phenyl)-propionamide
339 2-(3-fluoro-4-methylsulfonamido-phenyl)-N-[6-trifluoromethyl-2-(4-trifluoromethyl-cyclohexyloxy)-pyridin-3-ylmethyl]-propionamide
340 2-(3-fluoro-4-methylsulfonamido-phenyl)-N-[6-trifluoromethyl-2-(4-trifluoromethyl-cyclohexyloxy)-pyridin-3-ylmethyl]-propionamide
341 4-(3-{[2-(3-fluoro-4-methylsulfonamido-phenyl)-propionylamino]-methyl}-6-trifluoromethyl-pyridin-2-yloxy)-piperidine-1-carbonic acid tert-butyl ester
342 4-[(3-{[2-(3-fluoro-4-methylsulfonamido-phenyl)-propionylamino]-methyl}-6-trifluoromethyl-pyridin-2-ylamino)-methyl]-piperidine-1-carbonic acid tert-butyl ester
343 2-(3-fluoro-4-methylsulfonamido-phenyl)-N-[2-(piperidin-4-ylmethoxy)-6-trifluoromethyl-pyridin-3-ylmethyl]-propionamide
344 2-(3-fluoro-4-methylsulfonamido-phenyl)-N-[2-(piperidin-4-yloxy)-6-trifluoromethyl-pyridin-3-ylmethyl]-propionamide
345 2-(3-fluoro-4-methylsulfonamido-phenyl)-N-(2-p-tolyloxy-6-trifluoromethyl-pyridin-3-ylmethyl)-propionamide
346 N-[2-(2-cyclohexyl-vinyl)-6-trifluoromethyl-pyridin-3-ylmethyl]-2-(3-fluoro-4-methylsulfonamido-phenyl)-propionamide
347 2-(3-fluoro-4-methylsulfonamido-phenyl)-N-(4-methyl-6'-trifluoromethyl-3,4,5,6-tetrahydro-2H-[1,2']bipyridinyl-3'-ylmethyl)-butyramide
348 N-[2-(3,5-dimethoxy-phenyl)-6-trifluoromethyl-pyridin-3-ylmethyl]-2-(3-fluoro-4-methylsulfonamido-phenyl)-propionamide
349 N-(2-cyclopentyloxy-4-methyl-6-trifluoromethyl-pyridin-3-ylmethyl)-2-(3-fluoro-4-methylsulfonamido-phenyl)-propionamide
351 ethyl 5-((2-(3-fluoro-4-(methylsulfonamido)phenyl)propanamido)methyl)-6-(4-methylpiperidin-1-yl)-2-(trifluoromethyl)nicotinat
352 2-(3-fluoro-4-(methylsulfonamido)phenyl)-N-((2-(nonan-5-yloxy)-6-(trifluoromethyl)pyridin-3-yl)methyl)propanamide
353 N-((6-tert-butyl-2-isobutoxypyridin-3-yl)methyl)-2-(3-fluoro-4-(methylsulfonamido)phenyl)propanamide
354 2-(3-fluoro-4-(methylsulfonamido)phenyl)-N-((2-(phenylethynyl)-6-(trifluoromethyl)pyridin-3-yl)methyl)propanamide
355 2-(3-fluoro-4-(methylsulfonamido)phenyl)-N-((2-(3-methoxypropoxy)-6-(trifluoromethyl)pyridin-3-yl)methyl)propanamide
356 N-((2-(4-benzylpiperidin-1-yl)-4-methyl-6-(trifluoromethyl)pyridin-3-yl)methyl)-2-(3-fluoro-4-(methylsulfonamido)phenyl)propanamide
357 2-(3-fluoro-4-methylsulfonamido-phenyl)-N-(4-methylene-6'-trifluoromethyl-3,4,5,6-tetrahydro-2H-[1,2']bipyridinyl-3'-ylmethyl)-propionamide
358 N-[2-(6-aza-spiro[2.5]oct-6-yl)-6-trifluoromethyl-pyridin-3-ylmethyl]-2-(3-fluoro-4-methylsulfonamido-phenyl)-propionamide
359 2-(3-fluoro-4-methylsulfonamido-phenyl)-N-[2-(3-methyl-but-2-enyloxy)-6-trifluoromethyl-pyridin-3-ylmethyl]-propionamide
360 N-[2-(3-cyclohexyl-propyl)-6-trifluoromethyl-pyridin-3-ylmethyl]-2-(3-fluoro-4-methylsulfonamido-phenyl)-propionamide
361 N-[2-(3-ethoxy-propoxy)-6-trifluoromethyl-pyridin-3-ylmethyl]-2-(3-fluoro-4-methylsulfonamido-phenyl)-propionamide
362 2-(3-fluoro-4-methylsulfonamido-phenyl)-N-[2-(2-phenoxy-ethoxy)-6-trifluoromethyl-pyridin-3-ylmethyl]-propionamide
363 N-[2-(3,5-dimethoxy-benzyloxy)-6-trifluoromethyl-pyridin-3-ylmethyl]-2-(3-fluoro-4-methylsulfonamido-phenyl)-propionamide
364 2-(3-fluoro-4-methylsulfonamido-phenyl)-N-(4-hydroxymethyl-6'-trifluoro methyl-3,4,5,6-tetrahydro-2H-[1,2']bipyridinyl-3'-ylmethyl)-propionamide
365 N-(6'-tert-butyl-4-phenyl-3,4,5,6-tetrahydro-2H-[1,2']bipyridinyl-3'-ylmethyl)-2-(3-fluoro-4-methylsulfonamido-phenyl)-propionamide
366 N-{6-tert-butyl-2-[4-(4-fluoro-phenyl)-piperazin-1-yl]-pyridin-3-ylmethyl}-2-(3-fluoro-4-methylsulfonamido-phenyl)-propionamide
367 2-(4-methylsulfonamido-3-methyl-phenyl)-N-(2-pyrrolidin-1-yl-6-trifluoromethyl-pyridin-3-ylmethyl)-propionamide
[368] N-((2-(1H-indol-4-yl)-6-(trifluoromethyl)pyridin-3-yl)methyl)-2-(3-fluoro-4-(methylsulfonamido)phenyl)propanamide,
[369] N-((6-tert-butyl-2-propoxypyridin-3-yl)methyl)-2-(3-fluoro-4-(methylsulfonamido)phenyl)propanamide,
[370] N-((6-tert-butyl-2-(3-methoxypropoxy)pyridin-3-yl)methyl)-2-(3-fluoro-4-(methylsulfonamido)phenyl)propanamide,
[371] N-((6-tert-butyl-2-(4-(dimethylamino)-4-phenylpiperidin-1-yl)pyridin-3-yl)methyl)-2-(3-fluoro-4-(methylsulfonamido)phenyl)propanamide,
[372] N-((6-tert-butyl-2-methoxypyridin-3-yl)methyl)-2-(3-fluoro-4-(methylsulfonamido)phenyl)propanamide,
[373] N-((6-tert-butyl-2-ethoxypyridin-3-yl)methyl)-2-(3-fluoro-4-(methylsulfonamido)phenyl)propanamide,
[374] N-((6-tert-butyl-2-isopropoxypyridin-3-yl)methyl)-2-(3-fluoro-4-(methylsulfonamido)phenyl)propanamide,
[375] 2-(3-fluoro-4-(methylsulfonamido)phenyl)-N-((2-(pentyloxy)-6-(trifluoromethyl)pyridin-3-yl)methyl)propanamide,
[376] 2-(3-fluoro-4-(methylsulfonamido)phenyl)-N-((2-(hexyloxy)-6-(trifluoromethyl)pyridin-3-yl)methyl)propanamide,
[377] N-((2-(3,5-dimethylcyclohexyloxy)-6-(trifluoromethyl)pyridin-3-yl)methyl)-2-(3-fluoro-4-(methylsulfonamido)phenyl)propanamide,
[378] N-((6-tert-butyl-2-(2-ethoxyethoxy)pyridin-3-yl)methyl)-2-(3-fluoro-4-(methylsulfonamido)phenyl)propanamide,
a stereoisomer thereof, an enantiomer thereof, a diastereomer thereof and a racemate thereof.

17. A pharmaceutical preparation containing at least one compound according to claim 1 and optionally one or more physiologically acceptable auxiliary substances.

18. The compound of claim 1, wherein
$R^2$ and $R^3$ are each independently selected from the group consisting of H, F, Cl, Br, I and a aliphatic $C_{1-10}$ residue;
$R^7$ is H;
$R^6$ is a saturated or unsaturated $C_{1-10}$ aliphatic residue.

19. A compound of formula A

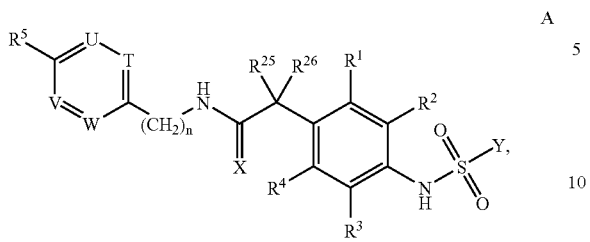

in which

X denotes O;

Y denotes a linear or branched, saturated or unsaturated aliphatic $C_{1-10}$ residue;

n denotes 1;

$R^1$ and $R^4$, mutually independently, in each case denote H;

$R^2$ $R^3$, mutually independently, in each case denote H; F; Cl; Br; I; or a linear or branched, saturated or unsaturated aliphatic $C_{1-10}$ residue;

$R^5$ denotes H, or a linear or branched, unsaturated aliphatic $C_{1-10}$ residue;

T denotes C—$R^6$ and U denotes C—$R^7$ and V denotes N and W denotes C—$R^8$ $R^6$ and $R^7$, mutually independently denotes H; F; Cl; Br; I; a linear or branched, saturated or unsaturated aliphatic $C_{1-10}$ residue; or a 6- or 10-membered aryl residue, which may be attached via a linear or branched $C_{1-6}$ alkylene group;

$R^8$ denotes H; F; Cl; Br; I; a saturated or unsaturated chain comprising 1 to 7 carbon atoms as chain members;

an unsaturated or saturated 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be attached via a linear or branched, unsubstituted or at least monosubstituted $C_{1-6}$ alkylene group or $C_{2-6}$ alkenylene group or $C_{2-6}$ alkynylene group; and $R^{25}$ and $R^{26}$, mutually independently, in each case denote a hydrogen residue; or a linear or branched, saturated or unsaturated aliphatic $C_{1-10}$ residue a steroisomer thereof, a diastereoisomer thereof, an enantiomer thereof, a racemate thereof or a salt thereof.

20. The compound of claim 1, wherein $R^5$ is an unsubstituted, saturated, branched or unbranched aliphatic $C_{1-10}$ residue;

$R^6$ is H or an unsubstituted, saturated, branched or unbranched aliphatic $C_{1-10}$ residue;

$R^7$ is H;

$R^8$ is selected from the group consisting of H, F, Cl, Br, I, an unsubstituted, saturated or unsaturated, branched or unbranched aliphatic $C_{1-10}$ residue, $OR^{15}$, $SR^{15}$, wherein $R^{15}$ is selected from the group consisting of H, a saturated or unsaturated, branched or unbranched aliphatic $C_{1-10}$ residue which may be substituted with one or more of OH, O-phenyl, cyclopropyl, cyclobutyl, cyclopentyl, cyclohexyl, benzoyl, phenyl, pyridyl, $NH_2$, piperidinyl, pyrrolidinyl, azepanyl, indolyl, thiophenyl, thiazolyl, imidazolyl, oxazolyl, pyrimidinyl, piperazinyl, morpholinyl and thiomorpholinyl.

21. A compound of formula A,

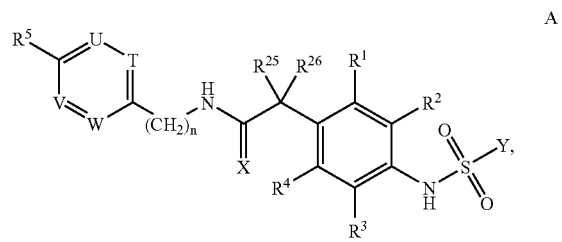

in which

X denotes O;

Y denotes a linear or branched, saturated or unsaturated, unsubstituted or at least monosubstituted aliphatic $C_{1-10}$ residue;

n denotes 1;

$R^1$ and $R^4$ are H;

$R^2$ and $R^3$, mutually independently, in each case denote H; F; Cl; Br; I; or a linear or branched, saturated or unsaturated, unsubstituted or at least monosubstituted aliphatic $C_{1-10}$ residue;

$R^5$ is an unsubstituted, saturated, branched or unbranched aliphatic $C_{1-10}$ residue;

T denotes C—$R^6$;

U denotes C—$R^7$;

V denotes N;

W denotes C—$R^8$;

$R^6$ is H or an unsubstituted, saturated, branched or unbranched aliphatic $C_{1-10}$ residue;

$R^7$ is H;

$R^8$ is selected from the group consisting of H, F, Cl, Br, I, an unsubstituted, saturated or unsaturated, branched or unbranched aliphatic $C_{1-10}$ residue, $OR^{15}$, $SR^{15}$, wherein $R^{15}$ is selected from the group consisting of H, a saturated or unsaturated, branched or unbranched aliphatic $C_{1-10}$ residue which may be substituted with one or more of OH, O-phenyl, cyclopropyl, cyclobutyl, cyclopentyl, cyclohexyl, benzoyl, phenyl, pyridyl, $NH_2$, piperidinyl, pyrrolidinyl, azepanyl, indolyl, thiophenyl, thiazolyl, imidazolyl, oxazolyl, pyrimidinyl, piperazinyl, morpholinyl and thiomorpholinyl;

$R^{15}$ denotes a linear or branched, saturated or unsaturated, unsubstituted or at least monosubstituted aliphatic $C_{1-10}$ residue;

denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be one or more of (i) fused with a saturated or unsaturated, unsubstituted or at least monosubstituted mono- or polycyclic ring system and (ii) attached via a linear or branched, unsubstituted or at least monosubstituted $C_{1-6}$ alkylene group or 2- to 6-membered heteroalkylene group;

or denote an unsubstituted or at least monosubstituted 5- to 14-membered aryl or heteroaryl residue, which may be one or more of (i) fused with a saturated or unsaturated, unsubstituted or at least monosubstituted mono- or polycyclic ring system and (ii) attached via a linear or branched, unsubstituted or at least monosubstituted $C_{1-6}$ alkylene group or 2- to 6-membered heteroalkylene group;

and $R^{25}$ and $R^{26}$, mutually independently, in each case denote a hydrogen residue; or denote a linear or branched, saturated or unsaturated, unsubstituted or at least monosubstituted aliphatic $C_{1-10}$ residue;
providing that $R^{25}$ and $R^{26}$ do not in each case denote a hydrogen residue;
wherein unless otherwise stated, the above-stated aliphatic $C_{1-10}$ residues may optionally in each case be substituted with 1, 2, 3, 4, 5, 6, 7, 8 or 9 substituents mutually independently selected from the group consisting of F, Cl, Br, I, —CN, —NO$_2$, —OH, —NH$_2$, —SH, —O(C$_{1-5}$-alkyl), —S(C$_{1-5}$-alkyl), —NH(C$_{1-5}$-alkyl), —N(C$_{1-5}$-alkyl)(C$_{1-5}$-alkyl), —C(=O)—O—C$_{1-5}$-alkyl, —O—C(=O)—C$_{1-5}$-alkyl, —O-phenyl, phenyl, —OCF$_3$ and —SCF$_3$;
the above-stated 2- to 6-membered heteroalkylene groups, $C_{1-6}$-alkylene groups, $C_{2-6}$-alkenylene groups and $C_{2-6}$-alkynylene groups may optionally in each case be substituted with 1, 2, 3, 4, 5, 6, 7, 8 or 9 substituents mutually independently selected from the group consisting of F, Cl, Br, I, —CN, —NO$_2$, —OH, —NH$_2$, —SH, —O(C$_{1-5}$-alkyl), —S(C$_{1-5}$-alkyl), —NH(C$_{1-5}$-alkyl), —N(C$_{1-5}$-alkyl)(C$_{1-5}$-alkyl), —OCF$_3$ and —SCF$_3$;
the above-stated (hetero)cycloaliphatic residues may optionally in each case be substituted with 1, 2, 3, 4 or 5 substituents mutually independently selected from the group consisting of —C$_{1-6}$-alkylene-OH, =CH$_2$, —O—C$_{1-5}$-alkylene-oxetanyl, —C$_{1-5}$-alkylene—O—C$_{1-5}$-alkylene-oxetanyl, —CH$_2$—NH—C$_{1-5}$-alkyl, —CH$_2$—N(C$_{1-5}$-alkyl)$_2$, —N[C(=O)—C$_{1-5}$-alkyl]-phenyl, —CH$_2$—O—C$_{1-5}$-alkyl, oxo (=O), thioxo (=S), F, Cl, Br, I, —CN, —CF$_3$, —SF$_5$, —OH, —O—C(=O)—C$_{1-5}$-alkyl, —NH$_2$, —NO$_2$, —O—CF$_3$, —S—CF$_3$, —SH, alkyl, —C$_{1-5}$-alkyl, —C(=O)—C$_{1-5}$-alkyl, —C(=O)—OH, —C(=O)—O—C$_{1-5}$-alkyl, alkyl, —N(C$_{1-5}$-alkyl)$_2$, —NH-phenyl, —N(C$_{1-5}$-alkyl)-phenyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —(CH$_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N[C(=O)—C$_{1-5}$-alkyl]-phenyl, —NH-phenyl, —N(C$_{1-5}$-alkyl)-phenyl, —(CH$_2$)-pyridinyl, pyridinyl, —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl;
the rings of the above-stated mono- or polycyclic ring systems may optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —C$_{1-5}$-alkyl, —C(=O)—C$_{1-5}$-alkyl, —C(=O)—OH, —C(=O)—O—C$_{1-5}$-alkyl, —N(C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl,
and the above-stated aryl or heteroaryl residues may optionally in each case be substituted with 1, 2, 3, 4 or 5 substituents mutually independently selected from the group consisting of F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —NH—S(=O)$_2$—C$_{1-5}$-alkyl, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, —C(=O)—N—(C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may optionally be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl,
and
the above-stated heteroalkylene groups in each case comprise 1, 2 or 3 heteroatom(s) mutually independently selected from the group consisting of oxygen, nitrogen (NH) and sulfur,
the above-stated (hetero)cycloaliphatic residues may in each case optionally comprise 1, 2 or 3 heteroatom(s) mutually independently selected from the group consisting of oxygen, nitrogen and sulfur,
the rings of the above-stated mono- or polycyclic ring systems are in each case 5-, 6- or 7-membered and may in each case optionally comprise 1, 2, 3, 4 or 5 heteroatom(s) as ring member(s), which are mutually independently selected from the group consisting of oxygen, nitrogen and sulfur,
the above-stated heteroaryl residues in each case optionally comprise 1, 2, 3, 4 or 5 heteroatom(s) mutually independently selected from the group consisting of oxygen, nitrogen and sulfur as ring member(s);
a steroisomer thereof, a diastereoisomer thereof, an enantiomer thereof, a racemate thereof or a salt thereof.

22. The compound of claim 20, wherein
$R^2$ and $R^3$, mutually independently, in each case denote H; F; Cl; Br; I; or a linear or branched, saturated or unsaturated, unsubstituted or at least monosubstituted aliphatic $C_{1-10}$ residue;
$R^5$ is an unsubstituted, saturated, branched or unbranched aliphatic $C_{1-10}$ residue;
T denotes C—$R^6$ and U denotes C—$R^7$ and V denotes N and W denotes C—$R^8$;
$R^6$ is H or an unsubstituted, saturated, branched or unbranched aliphatic $C_{1-10}$ residue;
$R^7$ is H;
$R^8$ is selected from the group consisting of H, F, Cl, Br, I, an unsubstituted, saturated or unsaturated, branched or unbranched aliphatic $C_{1-10}$ residue, $OR^{15}$, $SR^{15}$, wherein $R^{15}$ is selected from the group consisting of H, a saturated or unsaturated, branched or unbranched aliphatic $C_{1-10}$ residue which may be substituted with one or more of OH, O-phenyl, cyclopropyl, cyclobutyl, cyclopentyl, cyclohexyl, benzoyl, phenyl, pyridyl, NH$_2$, piperidinyl, pyrrolidinyl, azepanyl, indolyl, thiophenyl, thiazolyl, imidazolyl, oxazolyl, pyrimidinyl, piperazinyl, morpholinyl and thiomorpholinyl;
$R^{15}$ denotes a linear or branched, saturated or unsaturated, unsubstituted or at least monosubstituted aliphatic $C_{1-10}$ residue;

and $R^{25}$ and $R^{26}$, mutually independently, in each case denote a hydrogen residue; or denote a linear or branched, saturated or unsaturated, unsubstituted or at least monosubstituted aliphatic $C_{1-10}$ residue;

providing that $R^{25}$ and $R^{26}$ do not in each case denote a hydrogen residue.

* * * * *